United States Patent
Bennett et al.

(10) Patent No.: US 10,227,331 B2
(45) Date of Patent: Mar. 12, 2019

(54) METALLO-β-LACTAMASE INHIBITORS

(71) Applicant: Merck Sharp & Dohme Corp., Rahway, NJ (US)

(72) Inventors: Frank Bennett, Cranford, NJ (US); Jinlong Jiang, Scotch Plains, NJ (US); Alexander Pasternak, Princeton, NJ (US); Shuzhi Dong, Plainsboro, NJ (US); Xin Gu, Scotch Plains, NJ (US); Jack D. Scott, Scotch Plains, NJ (US); Haiqun Tang, Belle Mead, NJ (US); Zhiqiang Zhao, Scotch Plains, NJ (US); Yuhua Huang, Westfield, NJ (US); David Hunter, Hatfield, PA (US); Dexi Yang, Livingston, NJ (US); Katherine Young, Metuchen, NJ (US); Li Xiao, Cranbury, NJ (US); Zhibo Zhang, Beijing (CN); Jianmin Fu, Beijing (CN); Yunfeng Bai, Beijing (CN); Zhixiang Zheng, Beijing (CN); Xu Zhang, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/737,334

(22) PCT Filed: Jun. 24, 2016

(86) PCT No.: PCT/US2016/039185
§ 371 (c)(1),
(2) Date: Dec. 18, 2017

(87) PCT Pub. No.: WO2016/210234
PCT Pub. Date: Dec. 29, 2016

(65) Prior Publication Data
US 2018/0179190 A1    Jun. 28, 2018

(30) Foreign Application Priority Data
Jun. 26, 2015 (WO) ................ PCT/CN2015/082514

(51) Int. Cl.
*C07D 403/10* (2006.01)
*C07D 403/12* (2006.01)
(Continued)

(52) U.S. Cl.
CPC .......... *C07D 403/10* (2013.01); *A61K 31/198* (2013.01); *A61K 31/407* (2013.01); *A61K 31/41* (2013.01); *A61K 31/416* (2013.01); *A61K 31/4184* (2013.01); *A61K 31/4192* (2013.01); *A61K 31/4196* (2013.01); *A61K 31/421* (2013.01); *A61K 31/423* (2013.01); *A61K 31/428* (2013.01); *A61K 31/4245* (2013.01);
(Continued)

(58) Field of Classification Search
CPC .................................................... C07D 403/14
USPC ......................................................... 514/196
See application file for complete search history.

(56) References Cited

U.S. PATENT DOCUMENTS

| 4,746,353 A | 5/1988 | Levitt |
| 4,838,925 A | 6/1989 | Tseng |

(Continued)

FOREIGN PATENT DOCUMENTS

| CN | 1095549 | 11/1994 |
| CN | 103130686 | 6/2013 |

(Continued)

OTHER PUBLICATIONS

English language abstract for CN1095549, published Nov. 30, 1994.
(Continued)

*Primary Examiner* — Kahsay Habte
(74) *Attorney, Agent, or Firm* — Eric A. Meade; John C. Todaro

(57) ABSTRACT

The present invention relates to metallo-β-lactamase inhibitor compounds of Formula I: (I) and pharmaceutically acceptable salts thereof, wherein Z, $R^A$, $X_1$, $X_2$ and $R^B$ are as defined herein. The present invention also relates to compositions which comprise a metallo-β-lactamase inhibitor compound of the invention or a pharmaceutically acceptable salt thereof, and a pharmaceutically acceptable carrier, optionally in combination with a beta lactam antibiotic and/or a beta-lactamase inhibitor. The invention further relates to methods for treating a bacterial infection comprising administering to a patient a therapeutically effective amount of a compound of the invention, in combination with a therapeutically effective amount of one or more β-lactam antibiotics and optionally in combination with one or more beta-lactamase inhibitor compounds. The compounds of the invention are useful in the methods described herein for overcoming antibiotic resistance.

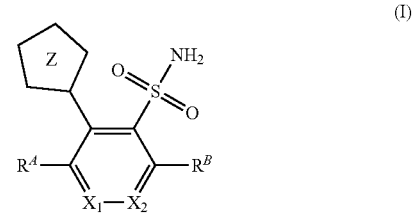

(I)

26 Claims, No Drawings

(51) Int. Cl.
*C07D 413/14* (2006.01)
*C07D 401/10* (2006.01)
*C07D 403/14* (2006.01)
*C07D 407/14* (2006.01)
*C07D 413/10* (2006.01)
*C07D 417/10* (2006.01)
*C07D 417/14* (2006.01)
*C07D 471/04* (2006.01)
*A61P 31/04* (2006.01)
*A61K 31/416* (2006.01)
*A61K 31/4184* (2006.01)
*A61K 31/423* (2006.01)
*A61K 31/428* (2006.01)
*A61K 31/437* (2006.01)
*A61K 31/4375* (2006.01)
*A61K 31/4439* (2006.01)
*A61K 31/454* (2006.01)
*A61K 31/4545* (2006.01)
*A61K 31/4709* (2006.01)
*A61K 31/4725* (2006.01)
*A61K 31/498* (2006.01)
*A61K 31/5025* (2006.01)
*A61K 31/506* (2006.01)
*A61K 31/517* (2006.01)
*A61K 31/5377* (2006.01)
*A61K 45/06* (2006.01)
*C07D 401/14* (2006.01)
*C07D 487/04* (2006.01)
*A61K 31/198* (2006.01)
*A61K 31/407* (2006.01)
*A61K 31/41* (2006.01)
*A61K 31/4192* (2006.01)
*A61K 31/4196* (2006.01)
*A61K 31/421* (2006.01)
*A61K 31/4245* (2006.01)
*A61K 31/431* (2006.01)
*A61K 31/439* (2006.01)
*A61K 31/496* (2006.01)
*A61K 31/541* (2006.01)
*A61K 31/546* (2006.01)
*C07D 405/14* (2006.01)
*C07D 453/02* (2006.01)
*C07D 487/10* (2006.01)
*C07D 493/04* (2006.01)
*C07D 493/08* (2006.01)
*C07D 495/08* (2006.01)

(52) U.S. Cl.
CPC .......... *A61K 31/431* (2013.01); *A61K 31/437* (2013.01); *A61K 31/439* (2013.01); *A61K 31/4375* (2013.01); *A61K 31/4439* (2013.01); *A61K 31/454* (2013.01); *A61K 31/4545* (2013.01); *A61K 31/4709* (2013.01); *A61K 31/4725* (2013.01); *A61K 31/496* (2013.01); *A61K 31/498* (2013.01); *A61K 31/506* (2013.01); *A61K 31/5025* (2013.01); *A61K 31/517* (2013.01); *A61K 31/5377* (2013.01); *A61K 31/541* (2013.01); *A61K 31/546* (2013.01); *A61K 45/06* (2013.01); *A61P 31/04* (2018.01); *C07D 401/10* (2013.01); *C07D 401/14* (2013.01); *C07D 403/12* (2013.01); *C07D 403/14* (2013.01); *C07D 405/14* (2013.01); *C07D 407/14* (2013.01); *C07D 413/10* (2013.01); *C07D 413/14* (2013.01); *C07D 417/10* (2013.01); *C07D 417/14* (2013.01); *C07D 453/02* (2013.01); *C07D 471/04* (2013.01); *C07D 487/04* (2013.01); *C07D 487/10* (2013.01); *C07D 493/04* (2013.01); *C07D 493/08* (2013.01); *C07D 495/08* (2013.01)

(56) References Cited

U.S. PATENT DOCUMENTS 4,927,453 A    5/1990    Gee
9,708,336 B2    7/2017    Mandal et al.

FOREIGN PATENT DOCUMENTS

| CN | 103191091 | 7/2013 |
| EP | 204513 | 12/1986 |
| EP | 244166 | 11/1987 |
| WO | WO2008039420 | 4/2008 |
| WO | WO2013103760 | 7/2013 |
| WO | WO2014198849 | 12/2014 |
| WO | 2015112441 A1 | 7/2015 |
| WO | WO2016210215 A1 | 12/2016 |

OTHER PUBLICATIONS

Fast and Sutton, Proteins and Proteomics, Biochimica et Biophysica Acta, NPL-FAST-2013-1834, p. 1834, 8.
Fast et al., Metallo-β-lactamase: inhibitors and reporter substrates, Biochimica et Biophysica Acta—Proteins and Proteomics, 2013, 1648-1659, 1834(8).
Green et al., Inhibition of bacterial peptide deformylase by biaryl acid analogs, Archives of Biochemistry and Biophysics, 2000, 355-358, 375(2).
International Search Report and Written Opinion of the International Searching Authority for PCT/US2016/039185 dated Sep. 13, 2016.
J. D. Buynak, Beta-Lactamase inhibitors: A review of the patent literature (2010-2013), Expert Opinion on Therapeutic Patents, Nov. 1, 2013, pp. 1469-1481, vol. 23, No. 11.
King, Dustin T., et al., Targeting metallo-b-lactamase enzymes in, Future Med. Chem., 2013, pp. 1243-1263, 5(11).
Olsen et al., Docking and scoring of metallo-beta-lactamases inhibitors, Journal of Computer-Aided Molecular Design, 2004, 287-302, 18(4).
Shen et al., Inhibitor Discovery of Full-Length New Delhi Metallo-b-Lactamase-1 (NDM-1), PLOS One, 2013, 1-7, 8(5) e62955.
Toney et al., Antibiotic sensitization using biphenyl tetrazoles as potent inhibitors of Bacteroides fragilis metallo-beta-lactamase, Chemistry & Biology, 1998, 185-196, 5(4).
Toney et al., Structure-activity relationships of biphenyl tetrazoles as metallo-beta-lactamase inhibitors, Bioorganic & Medicinal Chemistry Letters, 1999, 2741-2746, 18(9).
Yang, S.-K., et al., Azolylthioacetamide: A Highly Promising Scaffold for the Development of Metallo-beta-lactamase Inhibitors, ACS Medicinal Chemistry Letters, 2015, pp. 455-460, 6.
Zhang, Y.; et al., Diaryl-Substituted Azolylthioacetamides: Inhibitor, ChemMedChem, 2014, pp. 2445-2448, 9.
Gilchrist, T.L., "Five-Membered Ring Compounds With Two or More Heteroatoms", Heterocyclic Chemistry, 1985, pp. 187-188, Chapter 7.1, London.
Jones, Maitland Jr., Introduction to Amino Acids and Polyamino Acids (Peptides and Proteins), Organic Chemistry, 2000, pp. 1273-1275, Chapter 25.1.
English language abstract for CN103130686, published Jun. 5, 2013.
English language abstract for CN103191091, published on Jul. 10, 2013.
EP Search Report dated Dec. 11, 2018—EP Application No. 16815358.3-1116.

METALLO-β-LACTAMASE INHIBITORS

CROSS REFERENCE TO RELATED APPLICATIONS

This application is a U.S. National Phase application under 35 U.S.C. § 371 of PCT Application No. PCT/US2016/039185, filed Jun. 24, 2016, which claims priority under 35 U.S.C. § 119(e) from International Application No. PCT/CN2015/082514, filed. Jun. 26, 2015.

FIELD OF THE INVENTION

This invention relates to novel metallo-β-lactamase inhibitors and their uses. A preferred use of the metallo-β-lactamase inhibitors is for reducing bacterial beta-lactam antibiotic resistance.

BACKGROUND OF THE INVENTION

Bacterial antibiotic resistance has become one of the most serious threats to modern health care. Infections caused by resistant bacteria frequently result in longer hospital stays, higher mortality and increased cost of treatment. See, e.g., Cohen, *Science* 1992, 257:1051-1055. The need for new antibiotics will continue to escalate because bacteria have a remarkable ability to develop resistance to new agents, rendering them quickly ineffective. See, e.g., Neu, *Science* 1992, 257: 1064-1073. The spread of antibiotic resistance has been referred to as a pandemic. A solution to the growing public health threat will require an interdisciplinary approach. See, e.g., Anderson, *Nature America* 1999, 5: 147-149. See also Bush et al., *Nature Reviews in Microbiology* 2011, 9: 894-896; Levy and Marshall, *Nature Medicine* 2004, 10: S122-S129; Livermore, *Clinical Infectious Diseases* 2003, 36: S11-S23; and Roberts et al., *Clinical Infectious Diseases* 2009, 49: 1175-1184.

The present crisis has prompted various efforts to elucidate the mechanisms responsible for bacterial resistance. The widespread use of penicillins and cephalosporins has resulted in the emergence of β-lactamases, a family of bacterial enzymes that catalyze the hydrolysis of the β-lactam ring common to numerous presently used antibiotics. See, Coulton et al., *Progress in Medicinal Chemistry* 1994, 31: 297-349. This family of bacterial β-lactamases is further divided into four sub-families: A, C, and D families, which comprise β-lactamases that have a serine at the active site that catalyzes the hydrolysis of β-lactam antibiotics, and B family, which comprises β-lactamases that are zinc metalloenzymes. Resistance mediated by β-lactamases is a critical aspect at the core of the development of bacterial antibiotic resistance. See, Dudley, *Pharmacotherapy* 1995, 15: 9S-14S. Clavulanic acid, which is a metabolite of *Streptomyces clavuligerus*, and two semi-synthetic inhibitors, sulbactam and tazobactam, are currently available semi-synthetic or natural product β-lactamase inhibitors. Synthetic β-lactamase inhibitors have also been described. See, U.S. Pat. Nos. 5,698,577; 5,510,343; 6,472,406; Hubschwerlen et al., *J. Med. Chem.* 1998, 41: 3961; and Livermore et al., *J. Med. Chem.* 1997, 40: 335-343. Poole (*Cell. Mol. Life Sci.* 2004, 61: 2200-2223) provides a review of the resistance of bacterial pathogens to β-lactam antibiotics and approaches for overcoming resistance. For a review of inhibitors of metallo β-lactamases, see Fast and Sutton, *Biochimica et Biophysica Acta—Proteins and Proteomics* 2013, 1834(8): 1648-1659.

U.S. Patent Application Publication No. US 2003/0199541 discloses certain azabicyclic compounds including certain 7-oxo-6-diazabicyclic[3.2.1]octane-2-carboxamides and their use as anti-bacterial agents. U.S. Patent Application Publication No. US 2004/0157826 discloses heterobicyclic compounds including certain diazepine carboxamide and diazepine carboxylate derivatives and their use as anti-bacterials and 3-lactamase inhibitors. International Patent Application Publication No. WO 2008/039420 discloses 7-oxo-2,6-diazabicyclo[3.2.0]heptane-6-sulfooxy-2-carboxamides and their use as β-lactamase inhibitors.

Zheng et al. (*PLOS One* 2013, 8(5), e62955) disclose substituted 2,5-bis-tetrazolylmethyl-thiophenes and their use as β-lactamase inhibitors. Chinese Patent Application Publication No. CN103130686 A discloses N,N'-diarylureas and their use as inhibitors of metallo β-lactamases. Chinese Patent Application Publication No. CN103191091 A discloses substituted arylsulfonamides and their use as inhibitors of metallo β-lactamases.

U.S. Pat. Nos. 4,786,311; 4,746,353; 4,838,925; European Patent Application Publication Nos. EP204513; EP244166; and Chinese Patent Application Publication No. CN1095549A disclose substituted 2-(1H-tetrazol-5-yl)benzenesulfonamides and their use as herbicides.

International Patent Application Publication No. WO 2015/112441 discloses substituted 1H- and 2H-tetrazol-5-yl sulfonamide compounds as metallo β-lactamase inhibitors.

SUMMARY OF THE INVENTION

The present invention is directed to substituted 1H- and 2H-tetrazol-5-yl sulfonamide compounds and related compounds which are metallo-β-lactamase inhibitors. The compounds, and their pharmaceutically acceptable salts, are useful, for example, in combination with β-lactam antibiotics, and optionally serine β-lactamase inhibitors, for the treatment of bacterial infections, particularly antibiotic-resistant bacterial infections. More particularly, the present invention includes compounds of Formula I:

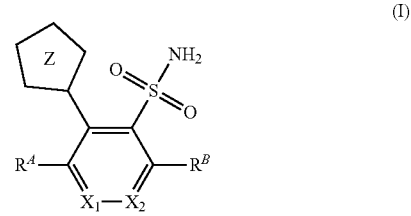

or a pharmaceutically acceptable salt thereof, wherein:
$X^1$ is N or CH;
$X^2$ is N or CH;
Z is tetrazolyl, wherein Z is linked through a carbon to carbon bond to the six-membered core ring having $X_1$ and $X_2$;
$R^A$ is $-(CH_2)_n$-AryA1, $-(CH_2)_n$-HetA1, $-(CH_2)_n-C_4-C_6$cycloalkyl, or $-(CH_2)_n-C_4-C_6$cycloalkenyl, wherein said $-(CH_2)_n-C_4-C_6$cycloalkyl and $-(CH_2)_n-C_4-C_6$cycloalkenyl are optionally substituted with 1, 2, or 3 substituents independently selected from $-NH_2$, $-OH$, $-F$, and $-NR^aC(O)C_1-C_6$alkyl optionally substituted with 1 or 2 substituents independently selected from $-F$, $-CF_3$, $-NR^aR^b$, and $-OR^a$;
$R^B$ is $-SR^1$, $-SOR^2$ or $-SO_2R^3$;
$R^1$ is HetB1, AryB1, or $-CH_3$;

$R^2$ is HetB1 or —$CH_3$;

$R^3$ is

1) $C_1$-$C_6$alkyl optionally substituted with 1, 2 or 3 substituents independently selected from F, —$NR^aR^b$, —$N^+R^aR^bH$, —$N^+R^aR^bCH_3$, —OH, and cyclopropyl;
2) $C_4$-$C_6$cycloalkyl optionally substituted with 1 or 2 substituents independently selected from F, —$NR^aR^b$, and —OH;
3) —OH;
4) —$(CH_2)_k$AryB1;
5) —$(CH_2)_k$HetB1;

AryA1 is an aromatic ring system selected from:
1) a 5-6 membered monocyclic ring with 0, 1, 2, or 3 heteroatom ring atoms independently selected from N, O, and S, optionally substituted with 1, 2, or 3 substituents independently selected from:
   a) halogen,
   b) —$C_1$-$C_6$alkyl,
   c) —CN,
   d) —$CH_2OH$,
   e) —$C(O)NR^aR^b$,
   f) —$C(O)NH(CH_2)_{2-4}NH_2$ optionally substituted with one or two substituents independently selected from —$NR^aR^b$ and —$(CH_2)_nOR^a$,
   g) —$C(O)OR^a$,
   h) —$(CH_2)_pNHR^a$ optionally substituted with one or two substituents independently selected from —$NR^aR^b$ or —$OR^a$,
   i) —$(CH_2)_pNR^aC(=NH)NH_2$,
   j) —$NR^aC(O)C_1$-$C_6$ alkyl optionally substituted with one or two substituents independently selected from —$NR^aR^b$ or —$OR^a$,
   k) —$NR^aSO_2$—$C_1$-$C_6$alkyl,
   l) —$NR^aSO_2$-cyclopropyl,
   m) —$OR^a$,
   n) oxo,
   o) —$SC_1$-$C_6$ alkyl optionally substituted with one or two substituents independently selected from —$NR^aR^b$ or —$OR^a$;
   p) —$SO_2R^a$,
   q) —$SO_2NR^aR^b$,
   r) —$SO_2NH$-cyclopropyl,
   s) -AryA2,
   t) —$(CH_2)_nNR^a$AryA2,
   u) —$C(O)NR^a$HetA2 and
   v) -HetA2, and
2) an 8- to 10-membered bicyclic ring with 1, 2, 3 or 4 heteroatom ring atoms selected from N, O and S, wherein an S atom optionally has one or two oxo substituents and a N atom is optionally in the form of an N-oxide, and wherein the ring is optionally substituted with 1 or 2 substituents independently selected from
   a) halogen;
   b) $C_1$-$C_6$alkyl optionally substituted with one to three substituents independently selected from —$NR^aR^b$, —$C(O)OR^a$, —$NR^aC(O)CF_3$, —F and —$OR^a$;
   c) —$(CH_2)_nCF_3$;
   d) —$C(=NH)NH_2$;
   e) —CN;
   f) —$C(O)CF_3$;
   g) —$C(O)NR^aR^b$;
   h) —$C(O)NHCH_2C(O)OR^a$;
   i) —$C(O)NH$—$C_2$-$C_4$alkyl-$NH_2$,
   j) —$C(O)OR^a$;
   k) —$NR^aR^b$;
   l) —$NHCH_2SO_3H$;
   m) —$(CH_2)_nNHC(=NH)NH_2$;
   n) —$NHC(O)C_1$-$C_6$alkyl;
   o) —$NHC(O)NH_2$;
   p) —$NHC(O)OR^a$;
   q) —$NHSO_2CH_3$;
   r) —$OR^a$;
   s) oxo;
   t) —$SO_2R^a$,
   u) —$CH_2$-phenyl-$OCH_3$; and
   v) -HetA2;

HetA1 is dihydrothiopyranyl, wherein the S atom is optionally substituted with 2 oxo, or tetrahydropyranyl;

AryA2 is a 5-6-membered aromatic monocyclic ring with 1, 2, 3, or 4 heteroatom ring atoms independently selected from N, N as a quaternary salt, and S, or 4 N ring atoms, optionally substituted with one or two substituents independently selected from: —$CH_2OH$, —COOH, —$CONH_2$, —$C(O)OC_1$-$C_6$alkyl, and —$(CH_2)_pNHR^a$ optionally substituted with one or two substituents independently selected from —$NR^aR^b$ and —$OR^a$;

HetA2 is a 4-6-membered saturated monocyclic ring with 1 or 2 heteroatom ring atoms independently selected from N, O and S, wherein the S is optionally substituted with two oxo groups, and wherein the ring is optionally substituted with 1 or 2 substituents independently selected from $C_1$-$C_6$alkyl, —CN, —OH, and oxo;

AryB1 is an aromatic ring selected from:
1) a 5-6 membered monocyclic aromatic ring with 0, 1, 2, or 3 N ring atoms, optionally substituted with 1 substituent selected from —$CF_3$, $C_1$-$C_6$ alkyl, —$(CH_2)_nNH_2$ and —$OCH_3$; and
2) a 9-membered bicyclic ring with 2 N ring atoms;

HetB1 is a saturated ring selected from:
1) a carbon-linked 4-6-membered saturated monocyclic ring with 1 or 2 heteroatom ring atoms independently selected from N, O and S, wherein the S is optionally substituted with one or two oxo groups, and wherein the ring is optionally substituted with 1 or 2 substituents independently selected from F, $C_1$-$C_6$ alkyl, $C_1$-$C_6$ hydroxyalkyl, —CN, —$C(O)C_1$-$C_6$ alkyl, —$(C_1$-$C_4$alkyl$)_n$-$NR^aR^b$, —$(CH_2)_nC(O)NR^aR^b$, —$C(O)NH$-cyclopropyl, —$C(O)OR^a$, —OH, oxo, and —$SO_2$—$C_1$-$C_6$ alkyl; and
2) a carbon-linked 6-10-membered bicyclic ring with 1, 2, 3 or 4 heteroatom ring atoms selected from N, O and S, optionally substituted with one to three substituents, independently selected from: —F, —$C_1$-$C_6$alkyl, —$NR^aR^b$, oxo, —$(CH_2)_{1-2}$ OH, —$CH_2NH_2$, —$SO_2CH_3$, —$CH_2C_3$-$C_6$cycloalkyl or —$NH_2$, wherein a ring sulfur atom is optionally substituted with one or two oxo groups, wherein the bicyclic ring may be bridged, fused or spirocyclic, and wherein the $C_3$-$C_6$cycloalkyl is optionally substituted with —$CH_2OH$;

$R^a$ and $R^b$ are independently H or $C_1$-$C_6$ alkyl;

k is 0, 1, 2, 3, or 4;

each n is independently 0 or 1; and each p is independently 0, 1, 2, or 3.

Compounds of Formula I inhibit metallo-β lactamases and can synergize the antibacterial effects of β lactam antibiotics (e.g., imipenem, ceftazidime, ceftolozane, and piperacillin) against microorganisms normally resistant to β lactam antibiotics as a result of the presence of the metallo-β lactamases. Compounds of the present invention are effective against metallo-β lactamases and their combination with a β-lactam antibiotic, such as imipenem, ceftazidime, ceftolozane, or piperacillin, can provide effective treatment of bacterial infections caused by metallo-β lactamase-producing microorganisms. Accordingly, in certain embodiments, the present invention provides compositions comprising a compound of Formula I, IA, or IB with a β-lactam antibiotic, and optionally one or more additional β-lactamase inhibitors, suitable for use against metallo-β lactamase producing bacteria such as *Pseudomonas* spp. and *Klebsiella* spp. In some embodiments, the additional one or more β-lactamase inhibitor(s) is a serine (Class A, C and D) β-lactamase inhibitor. The invention also includes compositions comprising a compound of Formula I, IA, or IB or a pharmaceutically acceptable salt thereof, and a pharmaceutically acceptable carrier. The invention further includes methods for treating bacterial infections and inhibiting bacterial growth by administration of a compound of Formula I, IA, or IB, or a pharmaceutically acceptable salt thereof, to a patient in need thereof, or by administration of a pharmaceutical composition comprising a compound of Formula I, IA, or IB or its salt and a pharmaceutically acceptable carrier.

Embodiments, sub-embodiments, aspects and features of the present invention are either further described in or will be apparent from the ensuing description, examples and appended claims.

DETAILED DESCRIPTION OF THE INVENTION

As noted above, the present invention includes compounds of Formula I, IA, and IB, wherein the compounds are metallo-β-lactamase inhibitors suitable for use in combination with β-lactam antibiotics and optionally class A, C, and D β-lactamase inhibitors for the treatment of bacterial infections.

The invention is based, in part, on the presence of a sulfur linker at the 6-position of the core ring as a sulfide, sulfoxide, or sulfone. The presence of a sulfur at this position results in improved enzyme potency compared to when the linker is carbon and also provides improved activity on difficult to penetrate *Pseudomonas* bacterial strains. The improved Pseudomonal activity is likely due to a decrease in efflux from the cells as a result of the sulfur linker.

In each of the various embodiments of the compounds of the invention described herein, each variable including those of Formulas I, IA and IB and the various embodiments thereof, is selected independently of the other variables unless otherwise indicated.

The present invention encompasses for each of the various embodiments of the compounds of the invention described herein, including those of Formulas I, IA and IB, and the various embodiments thereof and the compounds of the examples, all forms of the compounds such as, for example, any solvates, hydrates, stereoisomers, and tautomers of said compounds and of any pharmaceutically acceptable salts thereof, unless otherwise indicated. Additionally, in the examples described herein, the compounds of the invention may be depicted in the salt form. In such cases, it is to be understood that the compounds of the invention include the free acid or free base forms of such salts, and any pharmaceutically acceptable salt of said free acid or free base forms. In addition, in instances where an acidic group such as tetrazole and a basic group such as an amine are present within the same compound, these compounds may be drawn herein for convenience as the free acid and base forms but it should be understood that these can also be alternatively depicted in their zwitterionic forms in which the tetrazole bears a negative charge and the amine bears a positive charge, which are also included as compounds of the invention.

The Compounds of Formula (I):

In one aspect, the present invention includes compounds of Formula I:

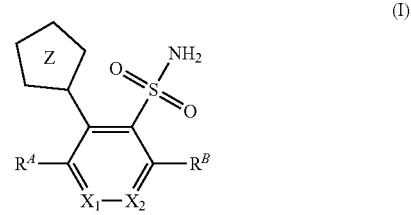

or a pharmaceutically acceptable salt thereof, wherein $X_1$, $X_2$, Z, $R^A$ and $R^B$ are as defined herein for the Compounds of Formula (I) (i.e. as defined in the Summary of the Invention); wherein the compounds may be suitable for use for the treatment of bacterial infections in combination with a β-lactam antibiotic.

A first embodiment of the invention (Embodiment E1) is a compound of Formula I, or a pharmaceutically acceptable salt thereof, wherein $X_1$, $X_2$, Z, $R^A$ and $R^B$ are as defined in Formula (I) in the Summary of the Invention.

A second embodiment (Embodiment E2) is a compound of Formula I, or a pharmaceutically acceptable salt thereof, wherein $X_1$ is CH, and all other variables are as defined in Embodiment E1.

A third embodiment (Embodiment E3) is a compound of Formula I, or a pharmaceutically acceptable salt thereof, wherein $X_1$ is N, and all other variables are as defined in Embodiment E1.

A fourth embodiment (Embodiment E4) is a compound of Formula I, or a pharmaceutically acceptable salt thereof, wherein $X_1$ is defined in Embodiment E2 or E3, $X_2$ is CH, and all other variables are as defined in Embodiment E1.

A fifth embodiment (Embodiment E5) is a compound of Formula I, or a pharmaceutically acceptable salt thereof, wherein $X_1$ is defined in Embodiment E2 or E3, $X_2$ is N, and all other variables are as defined in Embodiment E1.

A sixth embodiment (Embodiment E6) is a compound of Formula I, or a pharmaceutically acceptable salt thereof, wherein $X_1$ is defined in Embodiment E2 or E3, $X_2$ is defined in Embodiment E4 or E5, $R^A$ is —$(CH_2)_n$-AryA1 and all other variables are as defined in Embodiment E1.

A seventh embodiment (Embodiment E7) is a compound of Formula I, or a pharmaceutically acceptable salt thereof, wherein $X_1$ is defined in Embodiment E2 or E3, $X_2$ is defined in Embodiment E4 or E5, $R^A$ is —$(CH_2)_n$-HetA1 and all other variables are as defined in Embodiment E1.

An eighth embodiment (Embodiment E8) is a compound of Formula I, or a pharmaceutically acceptable salt thereof, wherein $X_1$ is defined in Embodiment E2 or E3, $X_2$ is defined in Embodiment E4 or E5, $R^A$ is —$(CH_2)_n$—$C_4$-$C_6$cycloalkyl, wherein said —$(CH_2)_n$—$C_4$-$C_6$cycloalkyl is optionally substituted with 1, 2, or 3 substituents independently selected from —$NH_2$, —OH, —F, and —$NR^aC(O)$ $C_1$-$C_6$alkyl optionally substituted with 1 or 2 substituents independently selected from —F, —$CF_3$, —$NR^aR^b$, and —$OR^a$ and all other variables are as defined in Embodiment E1.

In one sub-embodiment of Embodiment E8, —$(CH_2)_n$—$C_4$-$C_6$cycloalkyl is unsubstituted. In another sub-embodiment of Embodiment E8, —(CH$_2$)$_n$—C$_4$-C$_6$cycloalkyl is substituted with 1 substituent. In another sub-embodiment of Embodiment E8, —(CH$_2$)$_n$—C$_4$-C$_6$cycloalkyl is substituted with 2 substituents. In another sub-embodiment of Embodiment E8, —(CH$_2$)$_n$—C$_4$-C$_6$cycloalkyl is substituted with 3 substituents.

In another sub-embodiment of Embodiment E8 —(CH$_2$)$_n$—C$_4$-C$_6$cycloalkyl is substituted with at least one occurrence of NH$_2$.

In a further sub-embodiment of Embodiment E8 —(CH$_2$)$_n$—C$_4$-C$_6$cycloalkyl is substituted with at least one occurrence of —OH.

In yet another sub-embodiment of Embodiment E8 —(CH$_2$)$_n$—C$_4$-C$_6$cycloalkyl is substituted with at least one occurrence of —F.

In one sub-embodiment of Embodiment E8 —(CH$_2$)$_n$—C$_4$-C$_6$cycloalkyl is substituted with at least one occurrence of —NR$^a$C(O)C$_1$-C$_6$alkyl optionally substituted with 1 or 2 substituents independently selected from —F, —CF$_3$, —NR$^a$R$^b$, and —OR$^a$.

A ninth embodiment (Embodiment E9) is a compound of Formula I, or a pharmaceutically acceptable salt thereof, wherein X$_1$ is defined in Embodiment E2 or E3, X$_2$ is defined in Embodiment E4 or E5, R$^A$ is —(CH$_2$)$_n$—C$_4$-C$_6$cycloalkenyl, wherein —(CH$_2$)$_n$—C$_4$-C$_6$cycloalkenyl is optionally substituted with 1, 2, or 3 substituents independently selected from —NH$_2$, —OH, —F, and —NR$^a$C(O)C$_1$-C$_6$alkyl optionally substituted with 1 or 2 substituents independently selected from —F, —CF$_3$, —NR$^a$R$^b$, and —OR$^a$ and all other variables are as defined in Embodiment E1.

In one sub-embodiment of Embodiment E9, —(CH$_2$)$_n$—C$_4$-C$_6$cycloalkenyl is unsubstituted. In another sub-embodiment of Embodiment E9, —(CH$_2$)$_n$—C$_4$-C$_6$cycloalkenyl is substituted with 1 substituent. In another sub-embodiment of Embodiment E9, —(CH$_2$)$_n$—C$_4$-C$_6$cycloalkenyl is substituted with 2 substituents. In another sub-embodiment of Embodiment E9, —(CH$_2$)$_n$—C$_4$-C$_6$cycloalkenyl is substituted with 3 substituents.

In another sub-embodiment of Embodiment E9 —(CH$_2$)$_n$—C$_4$-C$_6$cycloalkenyl is substituted with at least one occurrence of NH$_2$.

In a further sub-embodiment of Embodiment E9 —(CH$_2$)$_n$ C$_4$-C$_6$cycloalkenyl is substituted with at least one occurrence of —OH.

In yet another sub-embodiment of Embodiment E9 —(CH$_2$)$_n$—C$_4$-C$_6$cycloalkenyl is substituted with at least one occurrence of —F.

In one sub-embodiment of Embodiment E9 —(CH$_2$)$_n$—C$_4$-C$_6$cycloalkenyl is substituted with at least one occurrence of —NR$^a$C(O)C$_1$-C$_6$alkyl optionally substituted with 1 or 2 substituents independently selected from —F, —CF$_3$, —NR$^a$R$^b$, and —OR$^a$.

A tenth embodiment (Embodiment E10) is a compound of Formula I, or a pharmaceutically acceptable salt thereof, wherein X$_1$ is defined in Embodiment E2 or E3, X$_2$ is defined in Embodiment E4 or E5, R$^A$ is AryA1 and all other variables are as defined in Embodiment E1.

An eleventh embodiment (Embodiment E11) is a compound of Formula I, or a pharmaceutically acceptable salt thereof, wherein X$_1$ is defined in Embodiment E2 or E3, X$_2$ is defined in Embodiment E4 or E5, R$^A$ is C$_4$-C$_6$cycloalkyl optionally substituted with —NH$_2$ or NHC(O)(CH$_2$)$_{1-3}$NH$_2$, and all other variables are as defined in Embodiment E1.

A twelfth embodiment (Embodiment E12) is a compound of Formula I, or a pharmaceutically acceptable salt thereof, wherein X$_1$ is defined in Embodiment E2 or E3, X$_2$ is defined in Embodiment E4 or E5, R$^A$ is C$_4$-C$_6$cycloalkenyl optionally substituted with —NH$_2$ or NHC(O)(CH$_2$)$_{1-3}$NH$_2$, and all other variables are as defined in Embodiment E1.

A thirteenth embodiment (Embodiment E13) is a compound of Formula I, or a pharmaceutically acceptable salt thereof, wherein X$_1$ is defined in Embodiment E2 or E3, X$_2$ is defined in Embodiment E4 or E5, R$^A$ is HetA1 and all other variables are as defined in Embodiment E1.

A fourteenth embodiment (Embodiment E14) is a compound of Formula I, or a pharmaceutically acceptable salt thereof, wherein X$_1$ is defined in Embodiment E2 or E3, X$_2$ is defined in Embodiment E4 or E5, R$^A$ is: selected from the group consisting of:

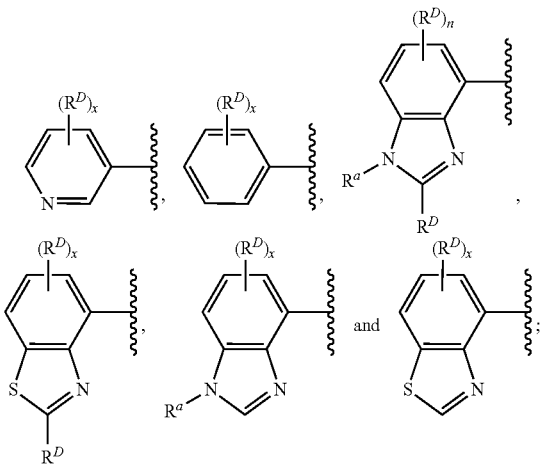

each R$^D$ is independently F, —C$_1$-C$_6$ alkyl, —CONH—C$_2$-C$_4$alkyl-NH$_2$, —NHR$^a$ or —(CH$_2$)$_x$NHR$^a$, each x is independently 0, 1, or 2, n is 0 or 1, and all other variables are as defined in Embodiment E1.

A fifteenth embodiment (Embodiment E15) is a compound of Formula I, or a pharmaceutically acceptable salt thereof, wherein X$_1$ is defined in Embodiment E2 or E3, X$_2$ is defined in Embodiment E4 or E5, R$^A$ is:

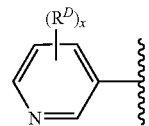

each R$^D$ is independently F, —C$_1$-C$_6$ alkyl, —CONH—C$_2$-C$_4$alkyl-NH$_2$, —NHR$^a$ or —(CH$_2$)$_x$NHR$^a$, each x is independently 0, 1, or 2, and all other variables are as defined in Embodiment E1.

A sixteenth embodiment (Embodiment E16) is a compound of Formula I, or a pharmaceutically acceptable salt thereof, wherein X$_1$ is defined in Embodiment E2 or E3, X$_2$ is defined in Embodiment E4 or E5, R$^A$ is:

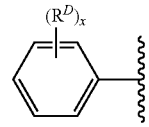

each $R^D$ is independently F, —$C_1$-$C_6$ alkyl, —CONH—$C_2$-$C_4$alkyl-$NH_2$, —$NHR^a$ or —$(CH_2)_x NHR^a$, each x is independently 0, 1, or 2, and all other variables are as defined in Embodiment E1.

A seventeenth embodiment (Embodiment E17) is a compound of Formula I, or a pharmaceutically acceptable salt thereof, wherein $X_1$ is defined in Embodiment E2 or E3, $X_2$ is defined in Embodiment E4 or E5, $R^4$ is:

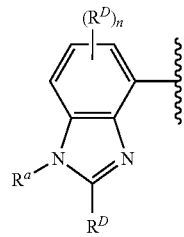

each $R^D$ is independently —F, —$C_1$-$C_6$ alkyl, —CONH—$C_2$-$C_4$alkyl-$NH_2$, —$NHR^a$ or —$(CH_2)_x NHR^a$, x is 0, 1, or 2, n is 0 or 1, and all other variables are as defined in Embodiment E1.

An eighteenth embodiment (Embodiment E18) is a compound of Formula I, or a pharmaceutically acceptable salt thereof, wherein $X_1$ is defined in Embodiment E2 or E3, $X_2$ is defined in Embodiment E4 or E5, $R^4$ is:

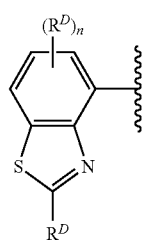

each $R^D$ is independently F, —$C_1$-$C_6$ alkyl, —CONH—$C_2$-$C_4$alkyl-$NH_2$, —$NHR^a$ or —$(CH_2)_x NHR^a$, x is 0, 1, or 2, n is 0 or 1, and all other variables are as defined in Embodiment E1.

In sub-embodiments of Embodiments E17 and E18, n is 0.

In other sub-embodiments of Embodiments E17 and E18, at least one occurrence of $R^D$ is $NH_2$. In other sub-embodiments of Embodiment E17 and E18, at least one occurrence of $R^D$ is —$(CH_2)_x NHR^a$. In further sub-embodiments of Embodiments E17 and E18, at least one occurrence of $R^D$ is methyl. In yet other sub-embodiments of Embodiments E17 and E18, at least one occurrence of $R^D$ is —$CH_2NH_2$. In further sub-embodiments of Embodiments E17 and E18, at least one occurrence of $R^D$ is —F. In yet further sub-embodiments of Embodiments E17 and E18, at least one occurrence of $R^D$ is —CONH—$C_2$-$C_4$alkyl-$NH_2$. In other sub-embodiments of Embodiments E17 and E18, at least one occurrence of $R^D$ is —$C_1$-$C_6$ alkyl.

A nineteenth embodiment (Embodiment E19) is a compound of Formula I, or a pharmaceutically acceptable salt thereof, wherein $X_1$ is defined in Embodiment E2 or E3, $X_2$ is defined in Embodiment E4 or E5, $R^4$ is:

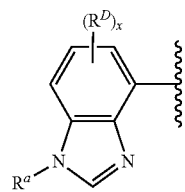

each $R^D$ is independently F, —$C_1$-$C_6$ alkyl, —CONH—$C_2$-$C_4$alkyl-$NH_2$, —$NHR^a$ or —$(CH_2)_x NHR^a$, each x is independently 0, 1, or 2, and all other variables are as defined in Embodiment E1.

A twentieth embodiment (Embodiment E20) is a compound of Formula I, or a pharmaceutically acceptable salt thereof, wherein $X_1$ is defined in Embodiment E2 or E3, $X_2$ is defined in Embodiment E4 or E5, $R^4$ is:

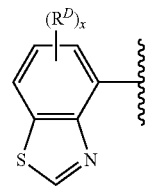

each $R^D$ is independently F, —$C_1$-$C_6$ alkyl, —CONH—$C_2$-$C_4$alkyl-$NH_2$, —$NHR^a$ or —$(CH_2)_x NHR^a$, each x is independently 0, 1, or 2, and all other variables are as defined in Embodiment E1.

A twenty-first embodiment (Embodiment E21) is a compound of Formula I, or a pharmaceutically acceptable salt thereof, wherein $X_1$ is defined in Embodiment E2 or E3, $X_2$ is defined in Embodiment E4 or E5, $R^4$ is:

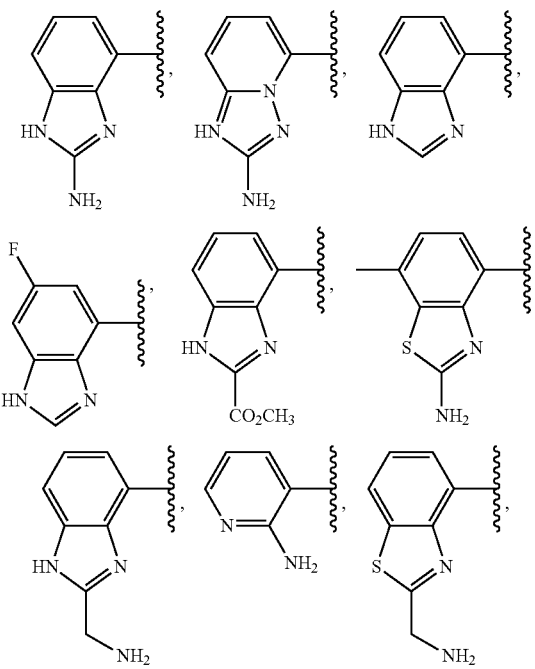

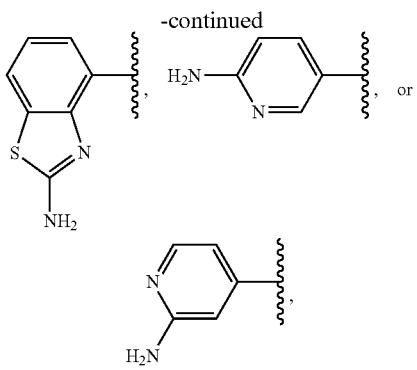

and all other variables are as defined in Embodiment E1.

A twenty-second embodiment (Embodiment E22) is a compound of Formula I, or a pharmaceutically acceptable salt thereof, wherein $X_1$ is defined in Embodiment E2 or E3, $X_2$ is defined in Embodiment E4 or E5, $R^A$ is a 5-6 membered aromatic monocyclic ring with 0, 1, 2, or 3 heteroatom ring atoms independently selected from N, O, and S, optionally substituted with 1, 2, or 3 substituents independently selected from: halogen, —$C_1$-$C_6$alkyl, —CN, —$CH_2$OH, —C(O)$NR^aR^b$, —C(O)NH($CH_2$)$_{2-4}NH_2$ optionally substituted with one or two substituents independently selected from —$NR^aR^b$ and —($CH_2$)$_n$$OR^a$, —C(O)$OR^a$, —($CH_2$)$_p$NH$R^a$ optionally substituted with one or two substituents independently selected from —$NR^aR^b$ or —$OR^a$,—($CH_2$)$_p$$NR^aC(=NH)NH_2$, —$NR^aC(O)C_1$-$C_6$ alkyl optionally substituted with one or two substituents independently selected from —$NR^aR^b$ or —$OR^a$, —$NR^aSO_2$—$C_1$-$C_6$alkyl, —$NR^aSO_2$-cyclopropyl, —$OR^a$, oxo, —$SC_1$-$C_6$ alkyl optionally substituted with one or two substituents independently selected from —$NR^aR^b$ or —$OR^a$; —$SO_2R^a$, —$SO_2NR^aR^b$, —$SO_2$NH-cyclopropyl, -AryA2, —($CH_2$)$_n$$NR^a$AryA2, —C(O)$NR^a$HetA2 and -HetA2, and all other variables are as defined in Embodiment E1.

A twenty-third embodiment (Embodiment E23) is a compound of Formula I, or a pharmaceutically acceptable salt thereof, wherein $X_1$ is defined in Embodiment E2 or E3, $X_2$ is defined in Embodiment E4 or E5, $R^A$ is an 8- to 10-membered bicyclic aromatic ring system with 1, 2, 3 or 4 heteroatom ring atoms selected from N, O and S, wherein an S atom optionally has one or two oxo substituents and a N atom is optionally in the form of an N-oxide, and wherein the ring is optionally substituted with 1 or 2 substituents independently selected from halogen; $C_1$-$C_6$alkyl optionally substituted with one to three substituents independently selected from —$NR^aR^b$, —C(O)$OR^a$, —$NR^aC(O)CF_3$, —F and —$OR^a$; —($CH_2$)$_n$$CF_3$; —C(=NH)$NH_2$; —CN; C(O)$CF_3$; —C(O)$NR^aR^b$; —C(O)NH$CH_2$C(O)$OR^a$; —C(O)NH—$C_2$-$C_4$alkyl-$NH_2$, —C(O)$OR^a$; —$NR^aR^b$; —NH$CH_2SO_3H$; —($CH_2$)$_n$NHC(=NH)$NH_2$; —NHC(O)$C_1$-$C_6$alkyl; —NHC(O)$NH_2$; —NHC(O)$OR^a$; —NH$SO_2CH_3$; —$OR^a$; oxo; —$SO_2R^a$, —$CH_2$-phenyl-$OCH_3$; and -HetA2; and all other variables are as defined in Embodiment E1.

A twenty-fourth embodiment (Embodiment E24) is a compound of Formula I, or a pharmaceutically acceptable salt thereof, wherein $X_1$ is defined in Embodiment E2 or E3, $X_2$ is defined in Embodiment E4 or E5, $R^A$ is dihydrothiopyranyl wherein the S atom is optionally substituted with 2 oxo, and all other variables are as defined in Embodiment E1.

A twenty-fifth embodiment (Embodiment E25) is a compound of Formula I, or a pharmaceutically acceptable salt thereof, wherein $X_1$ is defined in Embodiment E2 or E3, $X_2$ is defined in Embodiment E4 or E5, $R^A$ is tetrahydropyranyl, and all other variables are as defined in Embodiment E1.

A twenty-sixth embodiment (Embodiment E26) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SR^1$ and all other variables are as defined in Embodiment E1.

A twenty-seventh embodiment (Embodiment E27) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SOR^2$ and all other variables are as defined in Embodiment E1.

A twenty-eighth embodiment (Embodiment E28) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SO_2R^3$ and all other variables are as defined in Embodiment E1.

A twenty-ninth embodiment (Embodiment E29) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SR^1$, $R^1$ is HetB1 and all other variables are as defined in Embodiment E1.

A thirtieth embodiment (Embodiment E30) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SR^1$, $R^1$ is AryB1 and all other variables are as defined in Embodiment E1.

A thirty-first embodiment (Embodiment E31) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SR^1$, $R^1$ is —$CH_3$ and all other variables are as defined in Embodiment E1.

A thirty-second embodiment (Embodiment E32) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SOR^2$, $R^2$ is —$CH_3$ and all other variables are as defined in Embodiment E1.

A thirty-third embodiment (Embodiment E33) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SOR^2$, $R^2$ is -HetB1 and all other variables are as defined in Embodiment E1.

A thirty-fourth embodiment (Embodiment E34) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SO_2R^3$, $R^3$ is $C_1$-$C_6$alkyl optionally substituted with 1, 2 or 3 substituents independently selected from F, —$NR^aR^b$, —$N^+R^aR^bCH_3$, —$N^+R^aR^b$H, —OH, and cyclopropyl, and all other variables are as defined in Embodiment E1.

A thirty-fifth embodiment (Embodiment E35) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^B$ is $SO_2R^3$, $R^3$ is $C_4$-$C_6$cycloalkyl optionally substituted with 1 or 2 substituents independently selected from F, —NR$^a$R$^b$ and —OH, and all other variables are as defined in Embodiment E1.

A thirty-sixth embodiment (Embodiment E36) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^B$ is SO$_2$R$^3$, R$^3$ is —OH, and all other variables are as defined in Embodiment E1.

A thirty-seventh embodiment (Embodiment E37) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^B$ is SO$_2$R$^3$, R$^3$ is —(CH$_2$)$_k$AryB1, and all other variables are as defined in Embodiment E1.

A thirty-eighth embodiment (Embodiment E38) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^B$ is SO$_2$R$^3$, R$^3$ is —(CH$_2$)$_k$HetB1, and all other variables are as defined in Embodiment E1.

A thirty-ninth embodiment (Embodiment E39) is a compound or a pharmaceutically acceptable salt thereof, having the Formula IA:

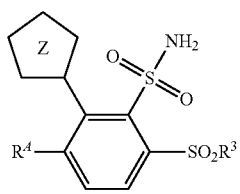

(IA)

wherein:
R$^A$ is AryA1; HetA1; C$_4$-C$_6$cycloalkyl; or C$_4$-C$_6$cycloalkenyl wherein said C$_4$-C$_6$cycloalkyl and C$_4$-C$_6$cycloalkenyl are optionally substituted with —NH$_2$ or NHC(O)(CH$_2$)$_{1-3}$NH$_2$;

R$^3$ is —(CH$_2$)$_k$HetB1; C$_1$-C$_6$alkyl optionally substituted with 1 or 2 substituents independently selected from —NR$^a$R$^b$, —OH, and cyclopropyl; C$_4$-C$_6$cycloalkyl optionally substituted with —NH$_2$; —OH; and -AryB1;

AryA1 is an aromatic ring system selected from:
1) a 5-6 membered monocyclic ring with 0, 1, or 2 heteroatom ring atoms independently selected from N and S, optionally substituted with 1 or 2 substituents independently selected from:
   a) —F,
   b) —C$_1$-C$_6$ alkyl,
   c) —CN,
   d) —CH$_2$OH,
   e) —C(O)NR$^a$R$^b$,
   f) —C(O)NH(CH$_2$)$_{2-4}$NH$_2$,
   g) —C(O)OR$^a$,
   h) —(CH$_2$)NHR$^a$,
   i) —NHC(=NH)NH$_2$;
   j) —NHC(O)CH$_3$;
   k) —NR$^a$SO$_2$—C$_1$-C$_6$alkyl,
   l) —NHSO$_2$cyclopropyl,
   m) —OR$^a$,
   n) —SO$_2$NR$^a$R$^b$,
   o) —SO$_2$NH-cyclopropyl,
   p) -AryA2, and
   q) -HetA2, 2) a 8- to 10-membered bicyclic ring with 1, 2, 3 or 4 heteroatom ring atoms selected from N, O and S, wherein an S atom optionally has one or two oxo substituents and wherein the ring is optionally substituted with 1 or 2 substituents independently selected from —F, —C$_1$-C$_6$ alkyl, —CH$_2$CF$_3$, —CF$_2$CH$_2$NH$_2$, —CF$_3$, —C(=NH)NH$_2$, —CN, —C(O)CF$_3$, —C(O)NR$^a$R$^b$, —C(O)NHCH$_2$C(O)OR$^a$, —C(O)OR$^a$, —(CH$_2$)$_{0-2}$NR$^a$R$^b$, —NHC(O)CH$_3$, —NHC(O)NH$_2$, —NHC(O)OR$^a$, —NHCH$_2$SO$_3$H, —NHSO$_2$CH$_3$, —OR$^a$, oxo, —CH$_2$-phenyl-OCH$_3$, and -HetA2;

AryB1 is an aromatic ring system selected from:
1) a 5-6 membered monocyclic aromatic ring with 0, 1, 2, or 3 N ring atoms, optionally substituted with 1 substituent selected from C$_1$-C$_6$ alkyl, —CF$_3$, and —OCH$_3$; or
2) a 9-membered bicyclic ring with 2 N ring atoms;

HetB1 is a saturated ring system selected from:
1) a carbon-linked 4-6-membered saturated monocyclic ring with 1 or 2 heteroatom ring atoms independently selected from N, O and S, wherein the S is substituted with an oxo group, and wherein the ring is optionally substituted with 1 or 2 substituents independently selected from
   a) —F,
   b) —C$_1$-C$_6$ alkyl,
   c) —C$_1$-C$_6$ hydroxyalkyl,
   d) —CN,
   e) —C(O)CH$_3$,
   f) —(CH$_2$)$_n$C(O)NR$^a$R$^b$,
   g) —C(O)NH-cyclopropyl,
   h) —C(O)OR$^a$,
   i) —(C$_1$-C$_4$alkyl)$_n$-NR$^a$R$^b$,
   j) —SO$_2$—C$_1$-C$_6$ alkyl, and
   k) oxo; and
2) a carbon-linked 6-10-membered bicyclic ring with 1 to 2 heteroatom ring atoms selected from N and S, optionally substituted with 1 or 2 substituents, independently selected from: —F, —C1-C6 alkyl, —CN, —CH2OH, —C(O)NRaRb, —C(O)NH(CH2)2-4NH2, —C(O)ORa, —(CH2)nNHRa, —NHC(=NH)NH2; —NHC(O)CH3; —NRaSO2-C1-C6alkyl, —NHSO2-cyclopropyl, —ORa, —SO2NRaRb, —SO2NH-cyclopropyl, -AryA2, and -HetA2; and R$^a$ and R$^b$ are independently H or C$_1$-C$_6$ alkyl
wherein all other variables are defined in Embodiment E1.

A fortieth embodiment (Embodiment E40) is a compound, or a pharmaceutically acceptable salt thereof, having the Formula IB:

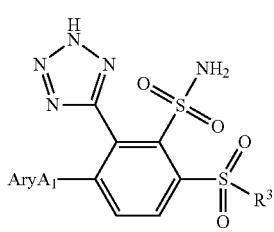

(IB)

wherein:
AryA1 is an aromatic ring system selected from:
1) a 5-6 membered monocyclic ring with 0 or 1 N ring atoms substituted with 1 or 2 substituents independently selected from F, —C$_1$-C$_6$ alkyl, —CONH—C$_{2-4}$ alkyl-NH$_2$, or —NHR$^a$; or 2) a 9-membered bicyclic ring with 2 or 3 heteroatom ring atoms selected from N and S, wherein the ring is optionally substituted with 1 or 2 substituents independently selected from —F, —C$_1$-C$_6$ alkyl, —C(O)OC$_1$-C$_6$alkyl, and —(CH$_2$)$_x$NR$^a$R$^b$; and R$^3$ is: C$_1$-C$_6$alkyl optionally substituted with 1, 2 or 3 substituents independently selected from F, —NR$^a$R$^b$, —N$^+$R$^a$R$^b$CH$_3$, —OH, and cyclopropyl; C$_4$-C$_6$cycloalkyl optionally substituted with 1 or 2 substituents independently selected from F, —NR$^a$R$^b$, and —OH; -AryB1; or HetB1; R$^a$ and R$^b$ are H or —CH$_3$; x is 0, 1 or 2, and all other variables are defined in Embodiment E1.

A forty-first embodiment of the invention (Embodiment E41) is: (1) a compound having a structure of any of the compounds numbered 1-379 in the Examples herein, (2) the free acid or free base form (when a basic amine group is present) of any compound numbered 1-379 herein that is depicted as a salt, (3) the zwitterionic form of any of compounds 1-379 which contains a basic amine group, wherein the tetrazole bears a negative charge and the amine group bears a positive charge, or (4) a pharmaceutically acceptable salt of the compounds described in (1), (2), and/or (3).

A forty-second embodiment of the invention (Embodiment E42) is a compound having the structure:

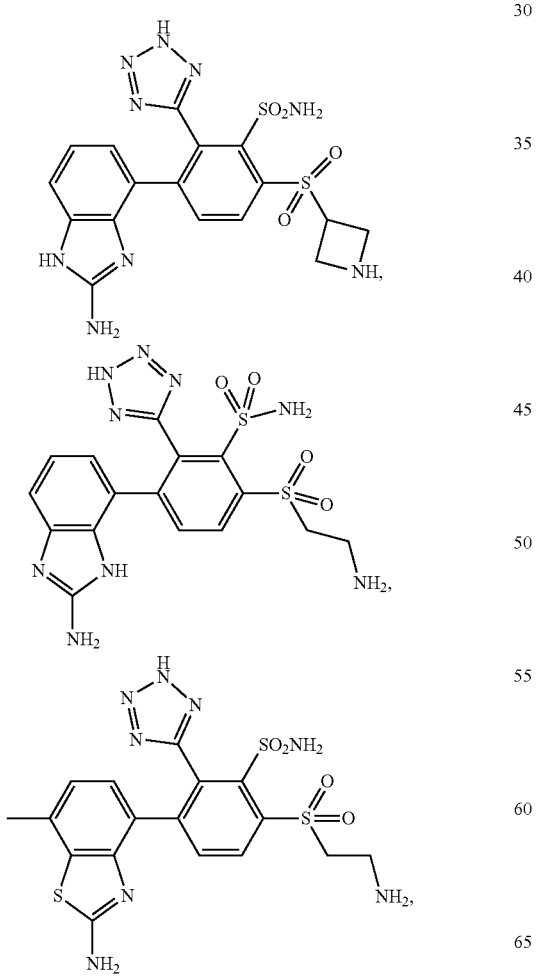

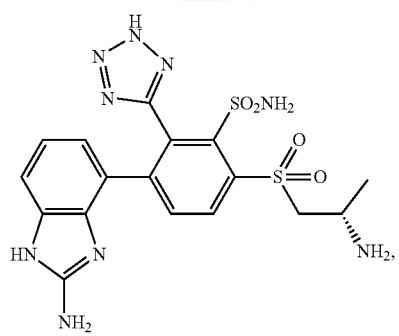

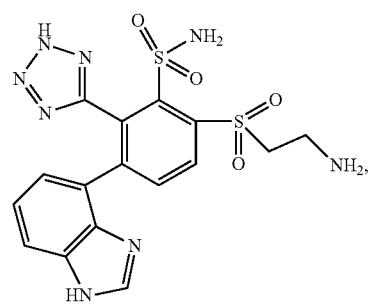

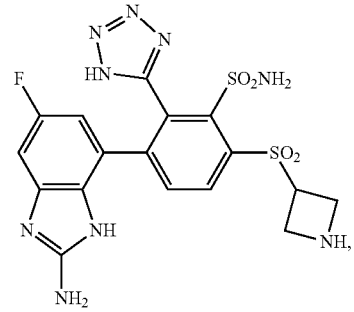

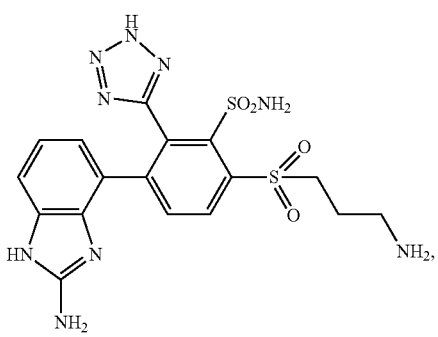

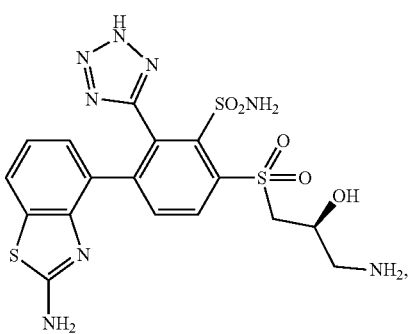

-continued
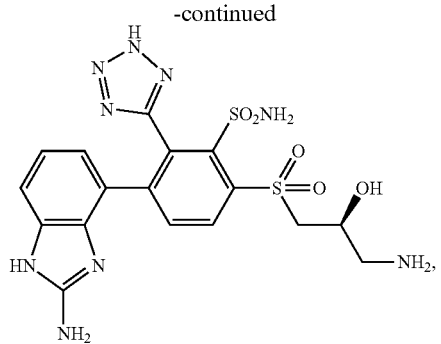
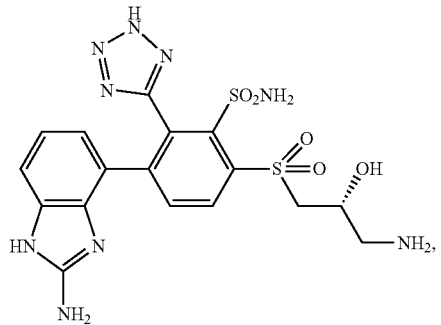
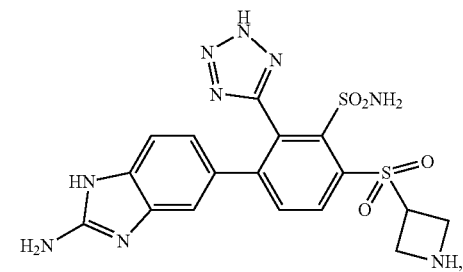
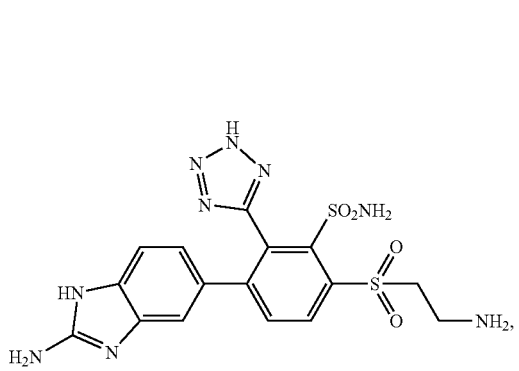
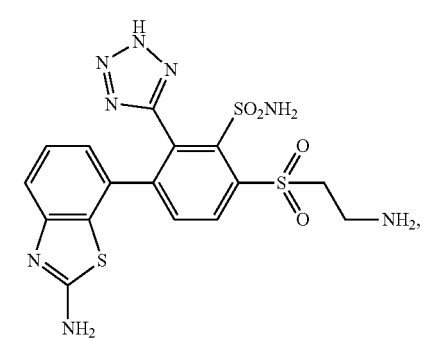
-continued
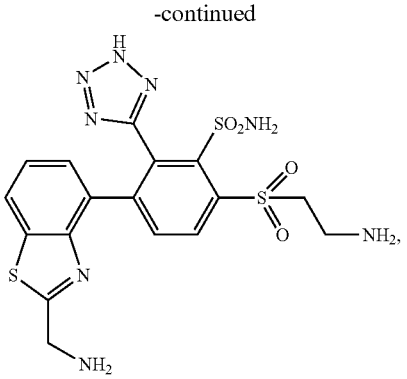
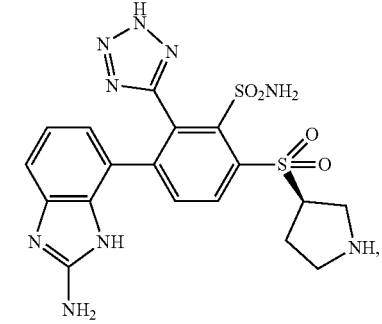
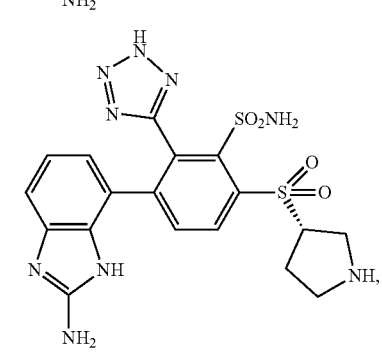
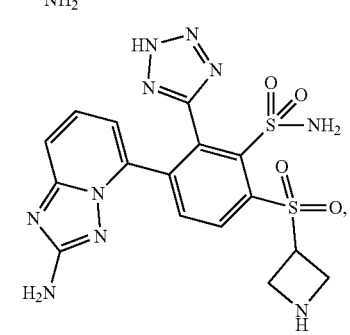
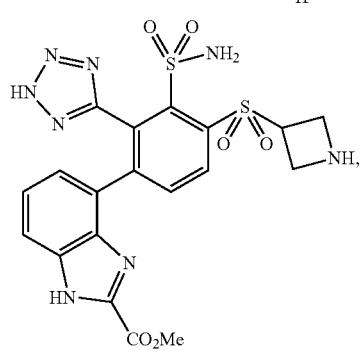

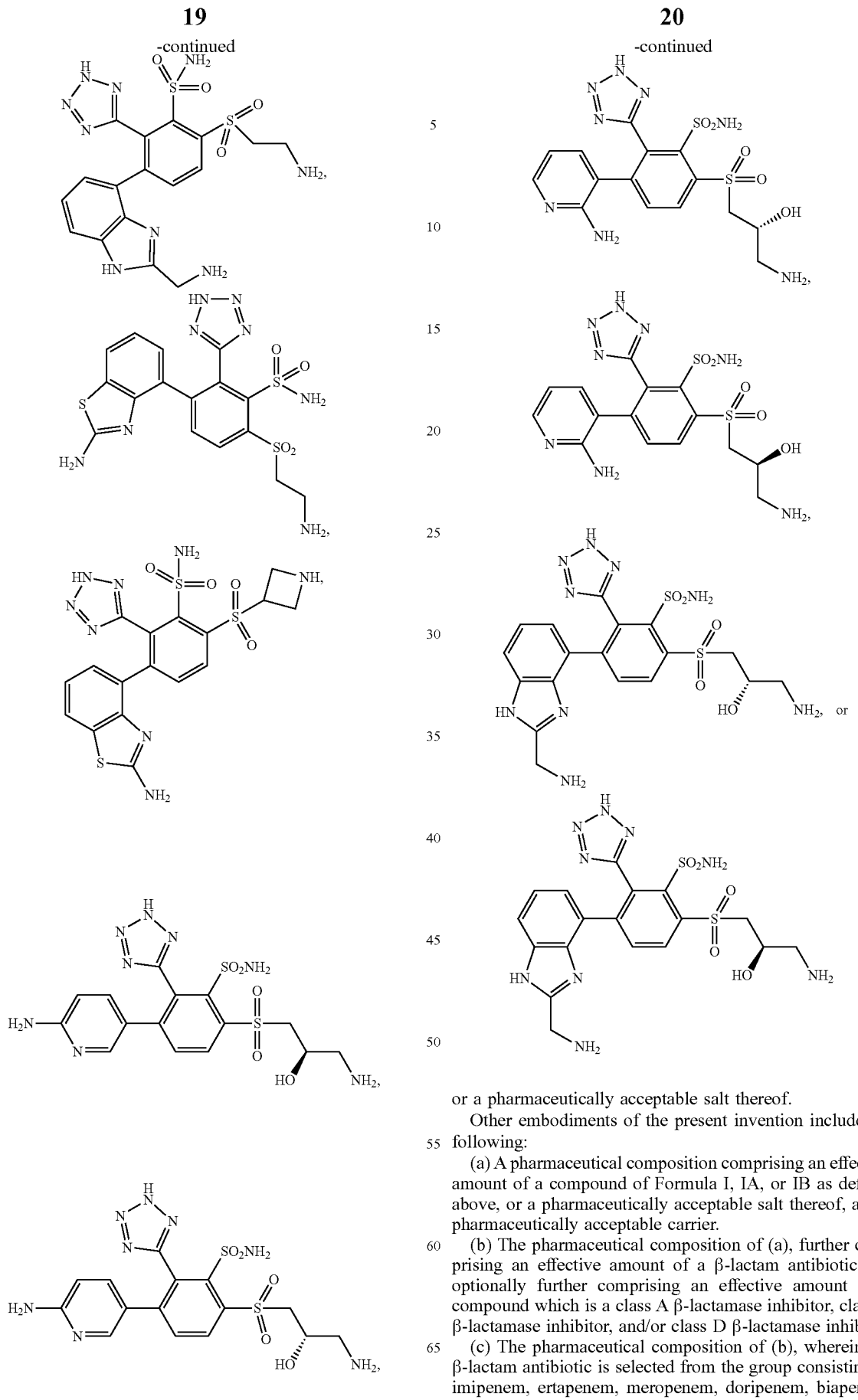

or a pharmaceutically acceptable salt thereof.

Other embodiments of the present invention include the following:

(a) A pharmaceutical composition comprising an effective amount of a compound of Formula I, IA, or IB as defined above, or a pharmaceutically acceptable salt thereof, and a pharmaceutically acceptable carrier.

(b) The pharmaceutical composition of (a), further comprising an effective amount of a β-lactam antibiotic and optionally further comprising an effective amount of a compound which is a class A β-lactamase inhibitor, class C β-lactamase inhibitor, and/or class D β-lactamase inhibitor.

(c) The pharmaceutical composition of (b), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, ceftolozane, and ceftazidime, and the class A, C and D β-lactamase inhibitor is selected from the group consisting of relebactam, avibactam, tazobactam, sulbactam, clavulanic acid, or CB-618.

(d) The pharmaceutical composition of (b), wherein the β-lactam antibiotic is imipenem.

(e) The pharmaceutical composition of (b), wherein the β-lactam antibiotic is ceftazidime.

(f) The pharmaceutical composition of (b), wherein the β-lactam antibiotic is ceftolozane.

(g) The pharmaceutical composition of (b), wherein the β-lactam antibiotic is piperacillin.

(h) The pharmaceutical composition of (a), further comprising effective amounts of a β-lactam antibiotic, a renal dehydropeptidase (DHP) inhibitor, and optionally, a class A, C and D β-lactamase inhibitor.

(i) The pharmaceutical composition of (h), wherein the β-lactam antibiotic is imipenem, the DHP inhibitor is cilastatin or a pharmaceutically acceptable salt thereof, and the class A, C and D β-lactamase inhibitor is relebactam.

(j) A combination of effective amounts of a compound of Formula I as defined above, or a pharmaceutically acceptable salt thereof, a β-lactam antibiotic, and optionally, a class A, C and D β-lactamase inhibitor.

(k) The combination of (j), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, ceftolozane, and ceftazidime.

(l) The combination of (j), wherein the β-lactam antibiotic is imipenem, optionally in combination with cilastatin, and the class A, C, D β-lactamase inhibitor is relebactam.

(m) The combination of (j), wherein the β-lactam antibiotic is ceftazidime and the class A, C, D β-lactamase inhibitor is avibactam.

(n) The combination of (j), wherein the β-lactam antibiotic is ceftolozane and the class A, C, D β-lactamase inhibitor is avibactam or relebactam.

(o) The combination of (j), wherein the β-lactam antibiotic is piperacillin.

(p) A combination of effective amounts of a compound of Formula I, IA, or IB as defined above, or a pharmaceutically acceptable salt thereof, a β-lactam antibiotic, a DHP inhibitor, and optionally a class A, C and D β-lactamase inhibitor.

(q) The combination of (p), wherein the β-lactam antibiotic is imipenem, the DHP inhibitor is cilastatin or a pharmaceutically acceptable salt thereof, and the class A, C and D β-lactamase inhibitor is relebactam.

(r) A method for treating a bacterial infection which comprises administering to a subject in need of such treatment a therapeutically effective amount of a compound of Formula I, IA, or IB as defined above, or a pharmaceutically acceptable salt thereof, optionally in combination with an effective amount of a β-lactam antibiotic.

(s) A method for treating a bacterial infection which comprises administering to a subject in need of such treatment a therapeutically effective amount of a compound of Formula I, IA, or IB as defined above, or a pharmaceutically acceptable salt thereof, in combination with effective amounts of a β-lactam antibiotic and a DHP inhibitor.

(t) A method for treating a bacterial infection which comprises administering to a subject in need of such treatment a therapeutically effective amount of the composition of (a), (b), (c), (d), (e), (f), (g), (h) or (i).

(u) A method for treating a bacterial infection which comprises administering to a subject in need of such treatment a therapeutically effective amount of the combination of (j), (k), (l), (m), (n), (o), (p), or (q).

(v) A method of treating a bacterial infection as set forth in (r), (s), (t), or (u) wherein the bacterial infection is due to *Pseudomonas* spp., *Klebsiella* spp., *Enterobacter* spp., *Escherichi* spp. a, *Morganella* spp., *Citrobacter* spp., *Serratia*, spp. or *Acinetobacter* spp.

The present invention also includes a compound of Formula I, IA, or IB, or a pharmaceutically acceptable salt thereof, (i) for use in, (ii) for use as a medicament for, or (iii) for use in the preparation (or manufacture) of a medicament for, inhibiting beta-lactamase activity or treating bacterial infection. In these uses, the compounds of the present invention can optionally be employed in combination with one or more β-lactam antibiotics, and may further be employed in combination with a class A, C, and/or D serine β-lactamase inhibitor and/or one or more DHP inhibitors.

Additional embodiments of the invention include the pharmaceutical compositions, combinations and methods set forth in (a)-(v) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments. In addition, the compound may optionally be used in the form of a prodrug that releases the active parent compound after dosing by intravenous or oral administration.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (v) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I, IA, or IB or its salt and a pharmaceutically acceptable carrier and optionally one or more excipients, it is understood that the term "substantially pure" is in reference to a compound of Formula I, IA, or IB or its salt per se; i.e., the purity of the active ingredient in the composition.

Definitions and Abbreviations

The term "β-lactamase inhibitor" refers to a compound which is capable of inhibiting enzyme activity from β-lactamases. As used herein, inhibiting β-lactamase activity means inhibiting the activity of a class A, B, C, and/or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I. Page, Ed.; Chapman and Hall, London, (1992) 198-228.

The term "metallo-β-lactamase inhibitor" refers to a compound which is capable of inhibiting metallo-β-lactamase activity. As used herein, inhibiting metallo-β-lactamase activity means inhibiting the activity of a class B metallo-β-lactamase. For antimicrobial applications inhibition at a 50% inhibitory concentration is preferably achieved at or below about 100 μg/mL, or at or below about 50 μg/mL, or at or below about 25 μg/mL.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include a metallo-β-lactamases of *Escherichia coli* (such as New Delhi Metallo-b-lactamase, NDM), *Serratia marcescens*(such as IMP), *Klebsiella* spp. (such as Verona integron-encoded metallo-β-lactamase, VIM)) and *Pseudomonas* spp (such as Verona integron-encoded metallo-β-lactamase, VIM)). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

Another embodiment of the present invention is a compound of Formula I, IA, or IB, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I, IA or IB, or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula I, IA and IB. Unless a specific stereochemistry is indicated, the present invention is meant to comprehend all such isomeric forms of these compounds. Centers of asymmetry that are present in the compounds of Formula I, IA and IB can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers, diastereomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, IA and IB or it can be done on a final racemic product. Absolute stereochemistry may be determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Aminoalkyl" means saturated carbon chains which may be linear or branched or combinations thereof which are substituted with one amino group which may be terminal (—$NH_2$) or internal (—NH—).

"Hydroxyalkyl" means saturated carbon chains which may be linear or branched or combinations thereof which are substituted with one hydroxyl (—OH) group.

"Diaminoalkyl" means saturated carbon chains which may be linear or branched or combinations thereof which are substituted with two amino (—$NH_2$) groups.

"Dihydroxyalkyl" means saturated carbon chains which may be linear or branched or combinations thereof which are substituted with two hydroxyl (—OH) groups.

"Hydroxyaminoalkyl" means saturated carbon chains which may be linear or branched or combinations thereof which are substituted with one hydroxyl (—OH) group and one amino (—$NH_2$) group.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Aromatic ring system" means monocyclic, bicyclic or tricyclic aromatic ring or ring system containing 5-14 ring atoms, wherein at least one of the rings is aromatic. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quaternary amine. In certain embodiments, a N ring atom can be in the form of an N-oxide.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, 1,2,3,4-tetrahydronaphthyl and the like. In one embodiment of the present invention, cycloalkyl is selected from: cyclopropane, cyclobutane, cyclopentane and cyclohexane.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" or "heterocycloalkyl" means a saturated or partly unsaturated non-aromatic monocyclic, bicyclic (including spirocyclic) or bridged carbocyclic ring or ring system comprising 3 to about 11 ring atoms, containing at least one ring heteroatom selected from N, S and O and the remainder of the ring atoms are carbon atoms. The nitrogen or sulfur atom of the heterocycloalkyl can be optionally oxidized to the corresponding N-oxide, S-oxide or S-dioxide. A heterocycloalkyl group can be joined via a ring carbon, or ring nitrogen atom, unless specified otherwise. The cycloheteroalkyl ring may be substituted on the ring carbons and/or the ring nitrogen(s). In one embodiment, a heterocycloalkyl group is monocyclic and has from about 3 to about 7 ring atoms (a "3 to 7-membered monocyclic heterocycloalkyl" group). In another embodiment, a heterocycloalkyl group is monocyclic has from about 4 to about 7 ring atoms (a "4 to 7-membered monocyclic heterocycloalkyl" group). In other embodiments, the heterocycloalkyl group is bicyclic and has 7-10 ring atoms, 8-10 ring atoms, or 9 or 10 ring atoms (a "9 or 10-membered bicyclic heterocycloalkyl" group). In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Examples of cycloheteroalkyl include tetrahydrofuran, piperazine, piperidine, morpholine, oxetane, tetrahydropyran, indolinyl, isoindolinyl, azabicyclooctane, hexahydrofuro[3,2-b]furan, and 2,3,3a,5,6,6a-hexahydrofuro[3,2-b]furan. Where the ring or ring system contains one or more N atoms, the N can be in the form of quarternary amine.

As used herein, a "carbon-linked heterocycloalkyl" refers to a heterocycloalkyl that is linked to the rest of the compound through a sulfur-carbon bond to an S, SO, or $SO_2$ linker, which is connected to the 6-membered core ring containing $X_1$ and $X_2$. For example, the following compounds of the invention contain a carbon-linked heterocycloalkyl:

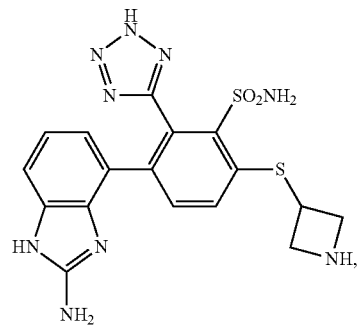

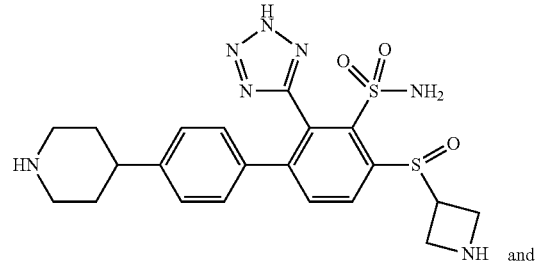

and

-continued

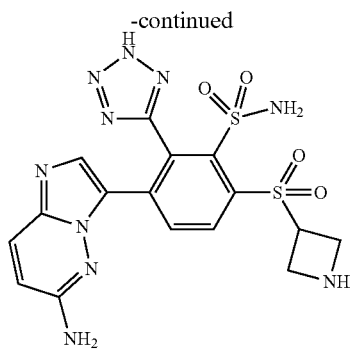

A carbon-linked heterocycloalkyl may be a 4-6 membered monocyclic ring, which may contain 1 or 2 heteroatom ring atoms independently selected from N, O and S or a 6- to 10-membered bicyclic ring with 1, 2, 3, or 4 heteroatom ring atoms selected from N, O and S. A bicyclic carbon-linked heterocycloalkyl may be bridged, fused or spirocyclic. A carbon-linked heterocycloalkyl may optionally be substituted with one to three substituents as defined herein.

"Heteroaryl" means monocyclic, bicyclic or tricyclic ring or ring system containing 5-14 carbon atoms and containing at least one ring heteroatom selected from N, S (including SO and $SO_2$) and O, wherein at least one of the heteroatom containing rings is aromatic. In the case of a heteroaryl ring system where one or more of the rings are saturated and contain one or more N atoms, the N can be in the form of quarternary amine. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. Examples of bicyclic heteroaryl rings include:

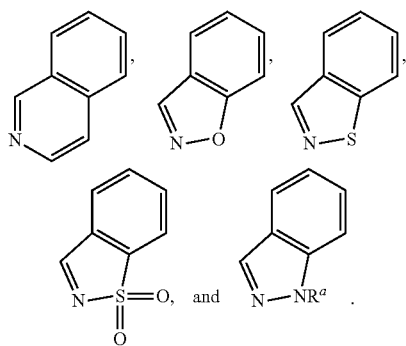

"Halogen" includes fluorine, chlorine, bromine and iodine.

"Oxo" means an oxygen atom connected to another atom by a double bond and is can be represented "=O".

Where any amine is present in the compound, the N atom may be optionally in the form of a quaternary amine having one or more appropriate additional substitutions, as further described herein.

When any ring atom is specified as being optionally substituted with, or in a specified form, for example, S substituted with oxo groups, or N in the form of a N-oxide, this does not preclude the substitution of any ring atom with the other listed optional substituents when not substituted with oxo groups or in the form of a N-oxide.

When any variable (e.g., n, $R^a$, $R^b$, etc.) occurs more than one time in any constituent or in Formula I, IA, or IB, its definition on each occurrence is independent of its definition at every other occurrence. Also, combinations of substituents and/or variables are permissible only if such combinations result in stable compounds.

A wavy line , as used herein, indicates a point of attachment to the rest of the compound. Lines drawn into a ring system, for example:

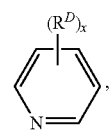

indicate that the bond may be attached to any of the substitutable ring atoms.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^4$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds of Formula I, IA, or IB, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I, IA, or IB. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I, IA, or IB, can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic ring and ring system variables or substituents described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formulas I, IA and IB.

The term "compound" refers to the compound and, in certain embodiments, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. Those skilled in the art will recognize those instances in which the compounds of the invention may form salts. The term "pharmaceutically acceptable salt" refers to a salt (including an inner salt such as a zwitterion) which possesses effectiveness similar to the parent compound and which is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

The compounds of Formula I, IA, and IB may exist as rapidly interconverting tautomers with different points of attachment of hydrogen accompanied by one or more double bond shifts. The individual tautomers as well as mixtures thereof are encompassed by the present invention. The ratio between the tautomeric forms will vary depending on the conditions. As is well known to one of ordinary skill in the art, such compounds may be drawn and named in different ways. For example, the following structures depicted below show different ways that an illustrative compound of the invention may be drawn:

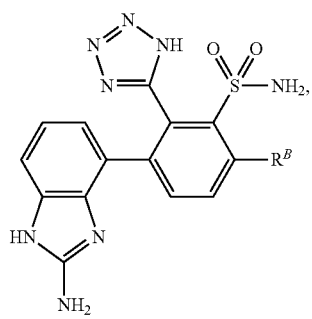

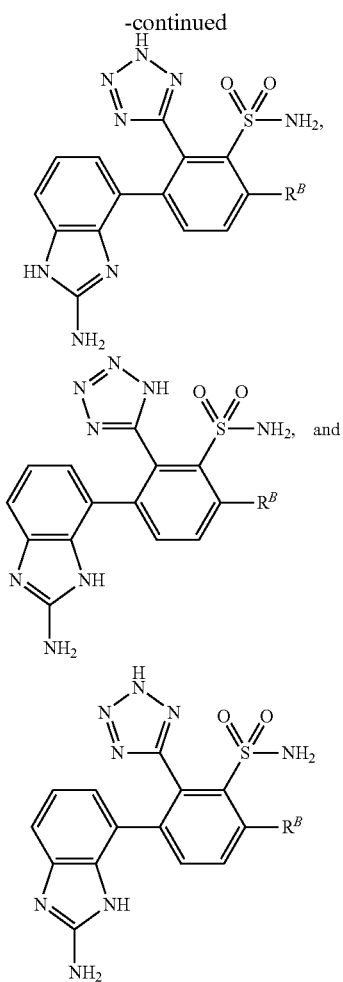

It is understood that all possible tautomeric forms of the compounds of Formula I, IA, and IB are contemplated as being within the scope of the instant invention, as well as mixtures thereof. It is further understood that while only one said tautomeric form of each example compound and embodiment of the invention may be depicted in the specification and appended claims, such depiction includes reference to all tautomeric forms of said compounds, which are included within the scope of the invention.

As set forth above, the present invention includes pharmaceutical compositions comprising a compound of Formula I, IA, or IB of the present invention, optionally one or more other active components (e.g., a β-lactam antibiotic), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, IA, or IB, or a pharmaceutically acceptable salt thereof, in combination with a β-lactam antibiotic and optionally a DHP inhibitor. The term "subject" (or, alternatively, "patient") as used herein refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In select embodiment, the subject is a human. In select embodiments, the subject has been the object of treatment, observation or experiment. The term "administration" and variants thereof (e.g., "administering" a compound) in reference to a compound of Formula I, IA, or IB mean providing the compound, or a pharmaceutically acceptable salt thereof, to the individual in need of treatment. When a compound or a salt thereof is provided in combination with one or more other active agents (e.g., a carbapenem antibiotic or a DHP inhibitor or both), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount," when used with a β-lactamase inhibitor (including a DHP inhibitor), means the amount of active compound sufficient to inhibit β-lactamase and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance) in combination with a β-lactam antibiotic. In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound. An "effective amount" of a β-lactam antibiotic is an amount sufficient to alleviate the symptoms of the disease or condition being treated (e.g., the healing of conditions associated with bacterial infection, and/or bacterial drug resistance).

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, 21$^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 μg/mL, and in additional embodiment at least about 10 μg/mL, and at least about 25 μg/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula I. Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula I, IA or IB to an experimental cell culture in vitro to prevent the growth of β-lactam resistant bacteria. The method can alternatively involve administration of a compound of Formula I, IA, or IB to an animal, including a human, to prevent the growth of β-lactam resistant bacteria in vivo. In these cases, the compound of Formula I, IA or IB is typically co-administered with a β-lactam antibiotic.

Compounds of the invention can be employed for the treatment, prophylaxis or inhibition of bacterial growth or infections due to bacteria that are resistant to β-lactam antibiotics in combination with a β-lactam antibiotic. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 μg/mL, and bacterial strains which are slightly resistant to imipenem are those against which the MIC of imipenem is >4 μg/mL.

Compounds of the invention can be used in combination with antibiotic agents for the treatment of infections caused by Class B-β-lactamase producing strains, in addition to those infections which are subsumed within the antibacterial spectrum of the antibiotic agent. Examples of class B-metallo-β-lactamase producing bacteria are *Pseudomonas aeruginosa*, *Pseudomonas putida*, *Enterobacter cloacae*, *Klebsiella pneumoniae*, *Klebsiella oxytoca*, *Escherichia coli*, *Serratia marcescens*, *Enterobacter aerogenes*, *Enterobacter asburiae*, *Citrobacter freundii*, *Proteus mirabilis*, *Morganella morganii*, *Providencia rettgeri*, and *Acinetobacter baumannii*.

It is generally advantageous to use a compound of Formula I, IA, or IB in admixture or conjunction with a carbapenem, penicillin, cephalosporin, or other β-lactam antibiotic, or a prodrug thereof. It is advantageous to use a compound of Formula I, IA, or IB in combination with one or more β-lactam antibiotics because of the class B β-lactamase inhibitory properties of the compounds. It is also advantageous to use a compound of Formula I, IA, or IB in combination with one or more Class A, C, and D β-lactamase inhibitors to further limit β-lactam susceptability. As already noted, the compound of Formula I, IA, or IB and the β-lactam antibiotic can be administered separately (at the same time or as different times) or in the form of a single composition containing both active ingredients.

Carbapenems, penicillins, cephalosporins and other β-lactam antibiotics suitable for use in the present invention include both those known to show instability to or to be otherwise susceptible to class B-β-lactamases.

When the compounds of Formula I, IA, or IB are combined with a carbapenem antibiotic, a dehydropeptidase (DHP) inhibitor can also be combined. Many carbapenems are susceptible to attack by a renal enzyme known as DHP. This attack or degradation may reduce the efficacy of the carbapenem antibacterial agent. Inhibitors of DHP and their use with carbapenems are disclosed in, e.g., U.S. Pat. Nos. 4,539,208; 4,616,038; 4,880,793; and 5,071,843. A preferred DHP inhibitor is 7-(L-2-amino-2-carboxyethylthio)-2-(2,2-dimethylcyclopropanecarboxamide)-2-heptenoic acid or a pharmaceutically acceptable salt thereof.

Carbapenems suitable for co-administration with compounds of the present invention include imipenem, ertapenem, meropenem, biapenem, (4R,5S,6S)-3-[3S,5S)-5-(3-carboxyphenyl-carbamoyl)pyrrolidin-3-ylthio]-6-(1R)-1-hydroxyethyl]-4-methyl-7-oxo-1-azabicyclo[3.2.0]hept-2-ene-2-carboxylic acid, (1S,5R,6S)-2-(4-(2-(((carbamoylmethyl)-1,4-diazoniabicyclo[2.2.2]oct-1-yl)-ethyl(1,8-naphthosultam)methyl)-6-[1(R)-hydroxyethyl]-1-methylcarbapen-2-em-3-carboxylate chloride, BMS181139 ([4R-[4α,5β,6β(R*)]]-4-[2-[(aminoiminomethyl)amino] ethyl]-3-[(2-cyanoethyl)thio]-6-(1-hydroxyethyl)-7-oxo-1-azabicyclo[3.2.0]hept-2-ene-2-carboxylic acid), BO2727 ([4R-3 [3S*,5 S*(R*)], 4α,5β,6β(R*)]]-6-(1-hydroxyethyl)-3-[[5-[1-hydroxy-3-(methylamino)propyl]-3-pyrrolidinyl] thio]-4-methyl-7-oxo-1-azabicyclo[3.2.0]hept-2-ene-2-carboxylic acid monohydrochloride), E1010 ((1R,5S,6S)-6-[1 (R)-hydroxymethyl]-2-[2(S)-[1(R)-hydroxy-1-[pyrrolidin-3 (R)-yl]methyl]pyrrolidin-4(S)-ylsulfanyl]-1-methyl-1-carba-2-penem-3-carboxylic acid hydrochloride) and S4661 ((1R,5S,6S)-2-[(3 S,5S)-5-(sulfamoylaminomethyl) pyrrolidin-3-yl]thio-6-[(1R)-1-hydroxyethyl]-1-methylcarbapen-2-em-3-carboxylic acid), (1S,5R,6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3 carboxylate chloride.

Penicillins suitable for co-administration with compounds of the present invention include benzylpenicillin, phenoxymethylpenicillin, carbenicillin, azidocillin, propicillin, ampicillin, amoxicillin, epicillin, ticarcillin, cyclacillin, pirbenicillin, azlocillin, mezlocillin, sulbenicillin, piperacillin, and other known penicillins. The penicillins may be used in the form of pro-drugs thereof; for example as in vivo hydrolysable esters, for example the acetoxymethyl, pivaloyloxymethyl, α-ethoxycarbonyloxy-ethyl and phthalidyl esters of ampicillin, benzylpenicillin and amoxicillin; as aldehyde or ketone adducts of penicillins containing a 6-α-aminoacetamido side chain (for example hetacillin, metampicillin and analogous derivatives of amoxicillin); and as esters of carbenicillin and ticarcillin, for example the phenyl and indanyl α-esters.

Cephalosporins suitable for co-administration with compound of the present invention include cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftolozane, ceftazidime, cefuroxime, cefmetazole, cefotaxime, ceftriaxone, cefipime, and other known cephalosporins, all of which may be used in the form of pro-drugs thereof.

β-Lactam antibiotics other than penicillins and cephalosporins that may be co-administered with compounds of the present invention include aztreonam, latamoxef (MOXALACTAM), and other known β-lactam antibiotics such as carbapenems like imipenem, ertapenem, meropenem or (4R,5S,6S)-3-[(3 S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, all of which may be used in the form of pro-drugs thereof.

In one embodiment, the antibiotic co-administered with a compound of the present invention is selected from the group consisting of imipenem, ertapenem, meropenem and (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid.

In another embodiment, the antibiotic co-administered with a compound of the present invention is selected from the group of penicillins consisting of ampicillin, amoxicillin, carbenicillin, piperacillin, azlocillin, mezlocillin, and ticarcillin. Such penicillins can optionally be used in the form of their pharmaceutically acceptable salts, for example their sodium salts. Ampicillin or amoxicillin can alternatively be employed in the form of fine particles of the zwitterionic form (generally as ampicillin trihydrate or amoxicillin trihydrate) for use in an injectable or infusable suspension. In an aspect of this embodiment, the penicillin co-administered with a compound of the present invention is amoxicillin, optionally in the form of its sodium salt or the trihydrate.

In another embodiment, the antibiotic co-administered with a compound of the present invention is selected from the group of cephalosporins consisting of cefotaxime, ceftriaxone, cefipime, and ceftazidime, which are optionally used in the form of their pharmaceutically acceptable salts, for example their sodium salts.

In certain embodiments of the invention, the compounds of the invention in combination with serine β-lactamase inhibitors (which can inhibit class A, C, D beta lactamases) in addition to β-lactam antibiotics. Serine β-lactamase inhibitors include but are not limited to avibactam, vaborbactam, relebactam, tazobactam, and clavulanic acid.

When co-administered with a β-lactam antibiotic, and optionally a β-lactamase inhibitor, the combination of the compound of the invention and the antibiotic can provide a synergistic effect. The terms "synergistic effect" and "synergy" indicate that the effect produced when two or more drugs are co-administered is greater than would be predicted based on the effect produced when the compounds are administered individually. While not wishing to be bound by theory, it is believed that the compounds of the present invention are β-lactamase inhibitors that act to prevent degradation of β-lactam antibiotics, thereby enhancing their efficacy and producing a synergistic effect.

Abbreviations employed herein include the following: Ac=acetyl=$CH_3C(=O)$; AcOH=acetic acid; ACN=MeCN=acetonitrile; aq=aqueous; BH3 DMS=borane dimethyl sulfide; BINAP=(2,2'-bis(diphenylphosphino)-1,1'-binaphthyl); BLI=β-lactamase inhibitor; Bn=benzyl; BOC (or Boc)=tert-butyloxycarbonyl; Boc anhydride=$Boc_2O$=di-tert-butyl dicarbonate; BrettPhos precatalyst generation 3=[(2-Di-cyclohexylphosphino-3,6-dimethoxy-2',4',6'-triisopropyl-1,1'-biphenyl)-2-(2'-amino-1,1'-biphenyl)]palladium(II) methanesulfonate; BPBD=N,N'-{bis(pyridin-2-yl)benzylidene}butane-1,4-diamine; CBZ (or Cbz)=carbobenzoxy (alternatively, benzyloxycarbonyl); $CH_3CN$=acetonitrile; CELITE=diatomaceous earth; conc.=concentrated; DBU=1,8-diazabicyclo[5.4.0]undec-7-ene; DCM=dichloromethane; DEAD=diethyl azodicarboxylate; DIAD=diisopropyl azodicarboxylate; DIBAL-H=diisobutylaluminum hydride; DIEA=N,N-Diisopropylethylamine; DIPEA=diisopropylethylamine (or Hunig's base); DMA=dimethylacetamide; DMAP=4-dimethylaminopyridine or N,N-dimethylaminopyridine; DME=1,2-dimethoxyethane; DMF=N,N-dimethylformamide; DMSO=dimethyl sulfoxide; DPPA=diphenylphosphoryl azide; EA=AcOEt=EtOAc=ethyl acetate; EDC=1-ethyl-3-(3-dimethylaminopropyl) carbodiimide; Et=ethyl; EtOH=ethanol; HATU=(1-[Bis(dimethylamino)methylene]-1H-1,2,3-triazolo[4,5-b]pyridinium 3-oxid hexafluorophosphate); hex=hexane; HOAt=1-Hydroxy-7-azabenzotriazole; HPLC=high-performance liquid chromatography; h or hr or hrs=hours; i-Pr=isopropyl alcohol; KOAc=potassium acetate; LCMS=LC-MS=liquid chromatography/mass spectrometry; LDA=lithium di-isopropyl amide; mCPBA=meta-chloroperoxybenzoic acid; Me=methyl; MeCN=acetonitrile; MeOH=methanol; MIC=minimum inhibitory concentration; min or mins=minutes; MPLC=medium pressure liquid chromatography; Ms=methanesulfonyl; MsCl=methane sulfonyl chloride; n-BuLi=n-butyllithium; NCS=N-Chlorosuccinimide; NIS=N-Iodosuccinimide; NMP=N-Methyl-2-pyrrolidone; NMR=nuclear magnetic resonance; PCy3 Pd G2=2nd Generation $PCy_3$ precatalyst=Chloro[(tricyclohexylphosphine)-2-(2'-aminobiphenyl)]palladium(II); Pd(dppf)$Cl_2$= [1,1'-Bis(diphenylphosphino)ferrocene]dichloropalladium (II); Pd/C=palladium on carbon; PE=Pet. ether=petroleum ether; Ph=phenyl; PMB=p-Methoxybenzyl; $PPh_3$ precatalyst generation 2=$2^{nd}$ PPh3 precatalyst=Chloro(triphenylphosphine) [2-(2'-amino-1,1'-biphenyl)]palladium(II); prep-HPLC=preparative HPLC; RBF=round bottom flask; RPLC=reverse phase liquid chromatography; RT=room temp.=room temperature; SFC=supercritical fluid chromatography; SM=starting material; TBAF=tetrabutylammonium fluoride; tBuXPhos precatalyst generation 3=[(2-Di-tert-butylphosphino-2',4',6'-triisopropyl-1,1'-biphenyl)-2-(2'-amino-1,1'-biphenyl)] palladium (II) methanesulfonate; TEA=triethylamine; TFA=trifluoroacetic acid; THF=tetrahydrofuran; TLC=thin layer chromatography; TMS=trimethylsilane; $TMSN_3$=azidotrimethylsilane; XPhos-Pd-2G or XPHOS Pd G2 precatalyst or Xphos precatalyst generation 2=Chloro(2-dicyclohexylphosphino-2',4',6'-triisopropyl-1,1'-biphenyl) [2-(2'-amino-1,1'-biphenyl)]palladium(II), X-Phos aminobiphenyl palladium chloride precatalyst.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

One general method for the preparation of compounds of this invention is outlined in Scheme I. According to the Scheme, intermediates 1a and 1b (prepared as described in Scheme VI and in the examples below) can be reacted selectively at the bromo position with alkyl, aryl or heteroaryl thiols in the presence of a base, for example cesium Scheme I:

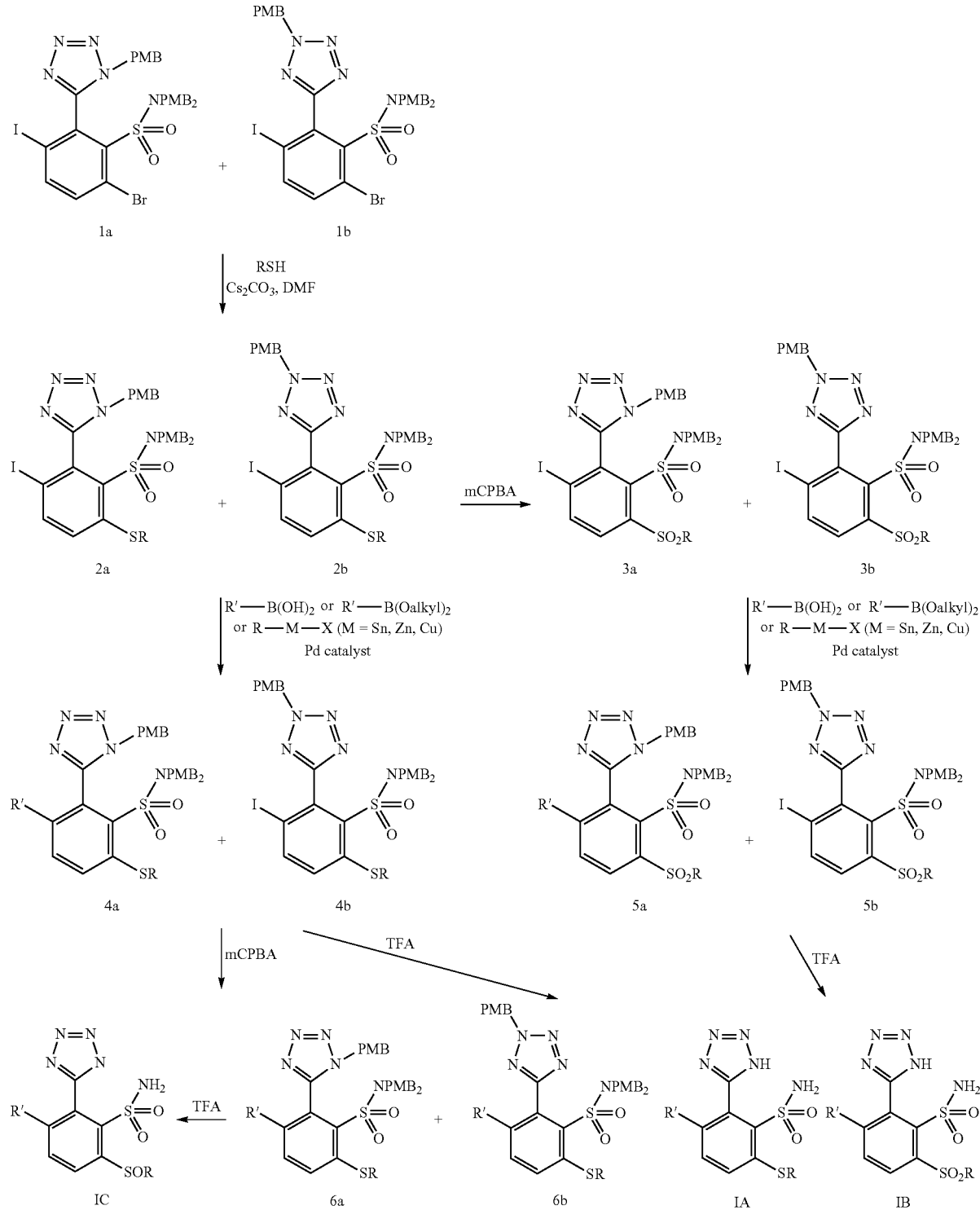

carbonate, to afford sulfides 2a and 2b. Oxidation of the sulfides using at least 2 equivalents of meta-chloroperoxybenzoic acid (m-CPBA) or by other oxidation conditions provides the sulfones 3a and 3b. Metal mediated coupling, for example using palladium catalysts, with alkyl, aryl, heteroaryl or vinyl boronic acids, boronic esters, organostannanes, organocopper or organo zinc reagents affords intermediates 5a and 5b. Final PMB protective group removal under acidic conditions such as by using TFA in the optional presence of a carbocation scavenger, such as anisole or triethylsilane, provides target compounds IB. When the organoboronate, organotin, organozinc, or organocopper reagent contains an acid labile protecting group (like tert-butoxycarbonyl) concurrent removal of this protecting group occurs in the final acidic removal of the PMB groups. This can be done in one step, or in stepwise fashion by treatment with TFA at room temperature to remove a group such as tert-butoxycarbonyl, then heating with TFA and anisole or thioanisole to remove the PMB group. To access sulfide compounds IA, intermediates 2a and 2b may be subjected to metal mediated coupling, for example using palladium catalysts, with alkyl, aryl, heteroaryl or vinyl boronic acids, boronic esters, organostannanes, organocopper or organo zinc reagents to give intermediates 4a and 4b. Final PMB protective group removal under acidic conditions such as by using TFA in the optional presence of a carbocation scavenger, such as anisole or triethylsilane, provides target compounds IA. Again, when the organoboronate, organotin, organozinc, or organocopper reagent contains an acid labile protecting group (like tert-butoxycarbonyl) concurrent removal of this protecting group occurs in the final acidic removal of the PMB groups. This can be done in one step, or in stepwise fashion by treatment with TFA at room temperature to remove a group such as tert-butoxycarbonyl, then heating with TFA and anisole or thioanisole to remove the PMB group. To access sulfoxide compounds IC, sulfides 4a and 4b may be treated with 1 equivalent of an oxidizing agent such as meta-chloroperoxybenzoic acid to give sulfoxides 6a and 6b. As previously described, final PMB protective group removal under acidic conditions such as by using TFA in the optional presence of a carbocation scavenger, such as anisole or triethylsilane, provides target compounds IC. The PMB protected tetrazole positional isomers 1a and 1b may be separated by chromatography and each individual isomer may be used in place of the isomer mixture with similar results.

Scheme II:

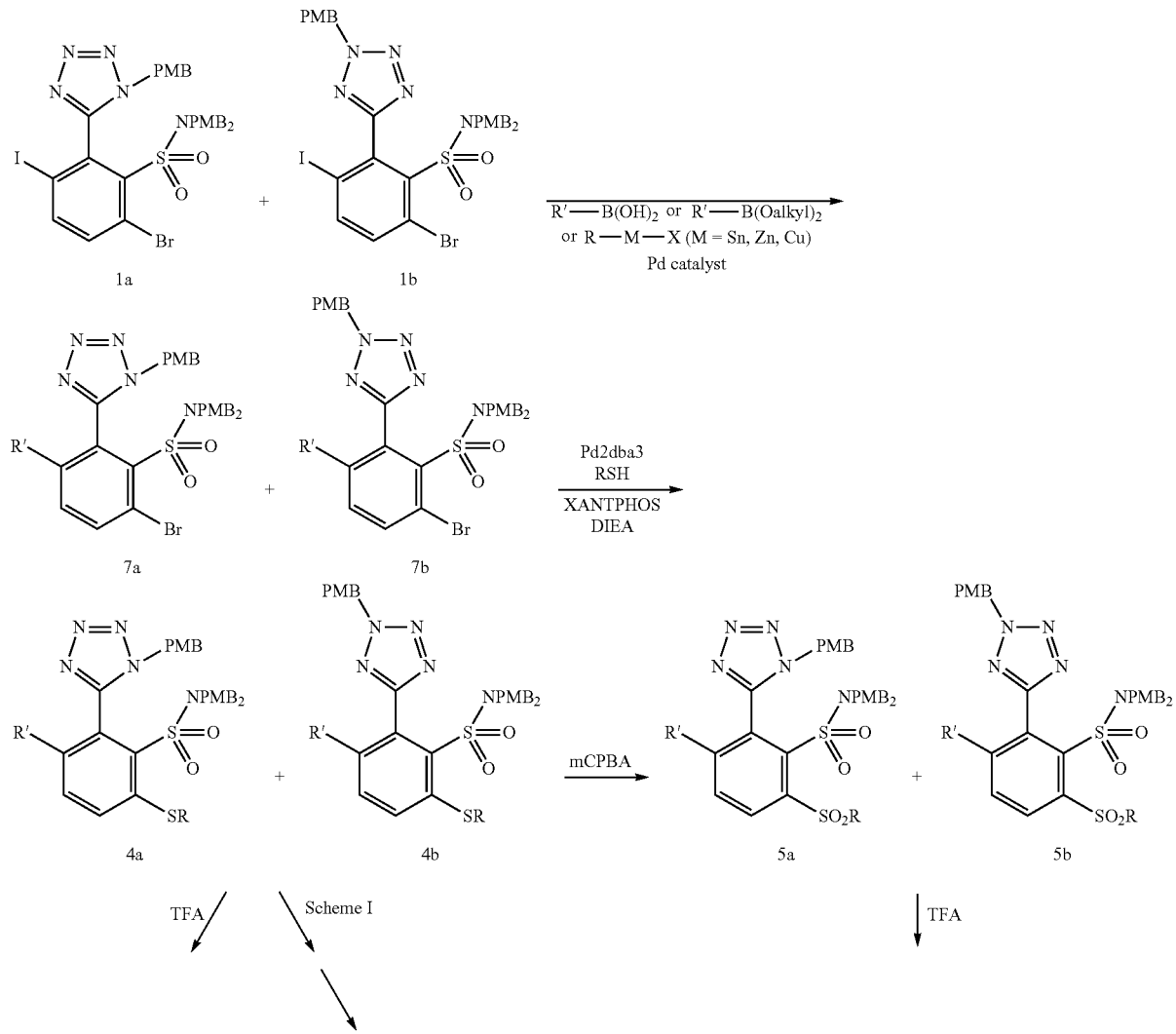

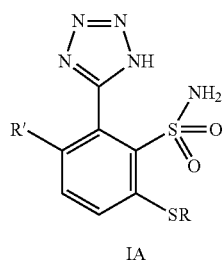

IA

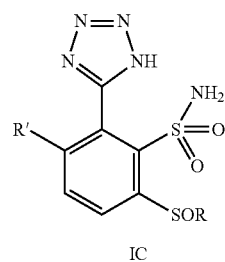

IC

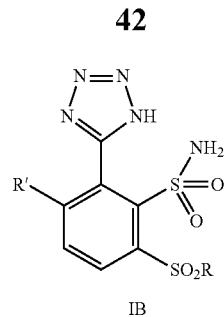

IB

An alternative method for making compounds IA, IB, and IC is depicted in Scheme II. According to the Scheme, intermediates 1a and 1b are selectively coupled at the iodo position with alkyl, aryl, heteroaryl or vinyl boronic acids, boronic esters, organostannanes, organocopper or organo zinc reagents using, for example, Palladium catalysis, to give intermediates 7a and 7b. These may then be reacted with alkyl, aryl or heteroaryl thiols, for example under palladium catalysis conditions, to give sulfides 4a and 4b. The sulfides may be oxidized, for example by using meta-chloroperoxybenzoic acid, to give sulfones 5a and 5b. As described in Scheme I, sulfides 4a and 4b may be carried on to make compounds IA and IC, and sulfones 5a and 5b may be progressed to compounds IB.

Scheme III:

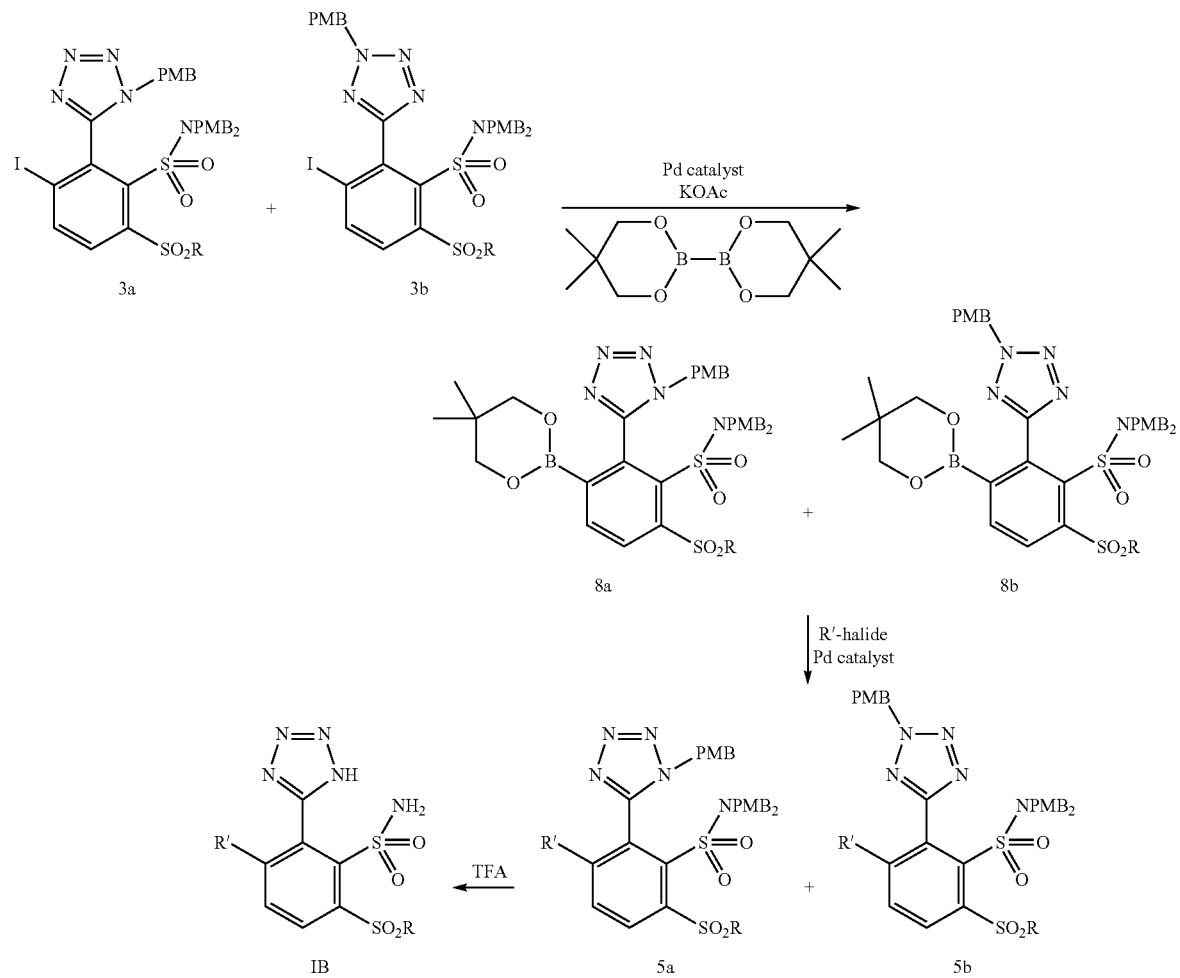

According to Scheme III, analogs IB may also be prepared from boronic acid or boronic ester precursors. Intermediates 3a and 3b may be converted to the corresponding boronic acids and boronic esters in a number of ways, for example, by coupling with 5,5,5',5'-tetramethyl-2,2'-bi(1,3,2-dioxaborinane) or other similar reagents using palladium catalysis. This affords the boronic esters 8a and 8b or their corresponding boronic acids (not shown). The boronic esters or boronic acids may be coupled with halide or triflate reagents to provide intermediates 5a and 5b, which can be deprotected as previously described in Scheme I to afford analogs IB.

Scheme IV:

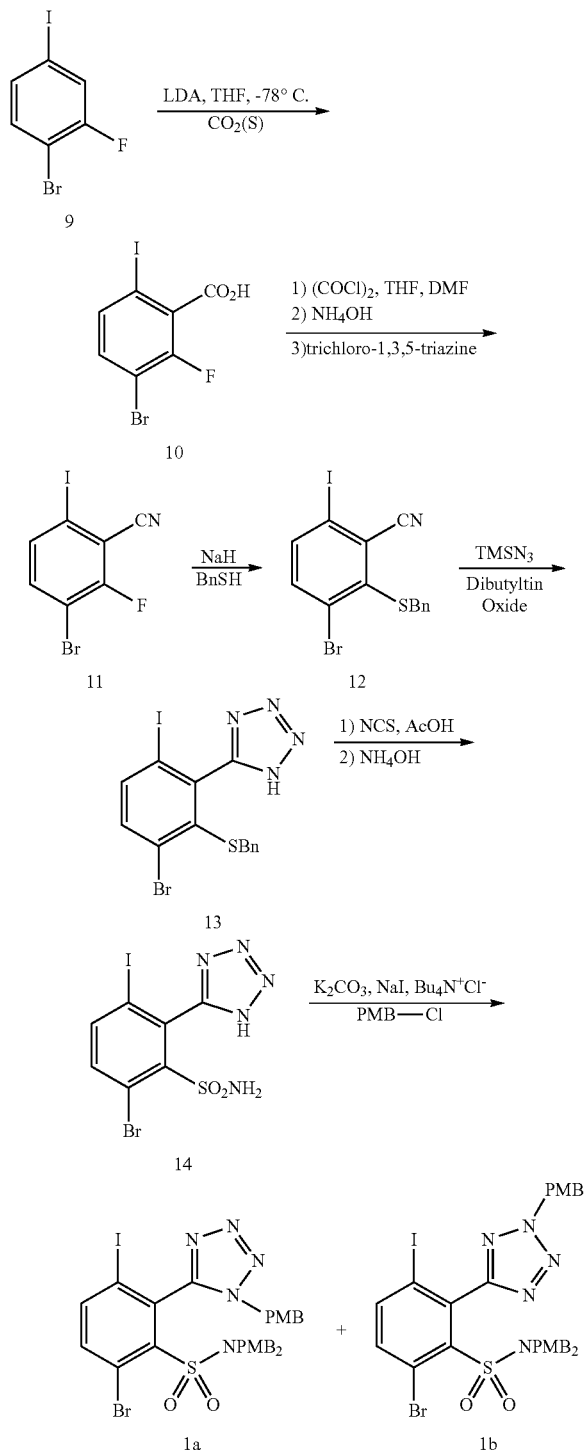

Intermediates 1a and 1b can be prepared according to Scheme VI. According to the Scheme, commercially available aryl fluoride 9 can be converted to the carboxylic acid 10 by treatment with LDA, followed by dry ice. The carboxylic acid functionality can be transformed to the corresponding nitrile 11 in numerous ways known in the art. One approach involves conversion to the acid chloride, for example using oxalyl chloride, followed by treatment with ammonium hydroxide to afford the carboxamide, and finally, dehydration, for example using trichloro-1,3,5-triazine, to give the nitrile 11. Nucleophilic aromatic substitution of the fluoride using benzyl mercaptan and a base such as sodium hydride provides the sulfide 12. The nitrile present in 12 can be converted to the tetrazole 13 using one of several methods, for example by treatment with trimethylsilyl azide and dibutyltin oxide. Conversion of the benzyl sulfide to the sulfonyl chloride can be accomplished in several ways, for example, by treatment with N-chloro succinimide in acetic acid. Treatment with ammonium hydroxide then affords the sulfonamide 14. Concommittant protection of the tetrazole and sulfonamide to afford positional isomer mixture 1a and 1b can be achieved by treatment with excess of paramethoxybenzyl chloride in the presence of a base, such as potassium carbonate, and NaI and tetrabutyl ammonium chloride as catalysts. Typically 1a and 1b are used as a mixture of regioisomers, but the isomers can optionally be separated and used individually in the same way. In the examples below, it should be understood that the mixture of regioisomers or the individual regioisomers may be used interchangeably (occasionally only one isomer is shown for the sake of simplicity).

REFERENCE EXAMPLE 1

6-bromo-3-iodo-2-(1-(4-methoxybenzyl)-1H-tetrazol-5-yl)benzenesulfonamide and 6-bromo-3-iodo-2-(2-(4-methoxybenzyl)-2H-tetrazol-5-yl)benzenesulfonamide

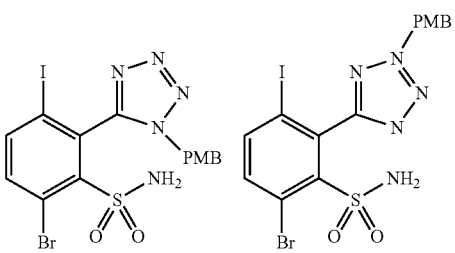

Step A: 3-bromo-2-fluoro-6-iodobenzoic Acid

Into a 2000-mL 3-necked RBF purged and maintained with an inert atmosphere of nitrogen was placed a solution of (i-Pr)$_2$NH (40.4 g, 400.00 mmol, 1.20 equiv) in THF (400 mL). This was followed by the addition of n-butyl lithium (146 mL, 1.10 equiv) dropwise with stirring at −20° C. over 30 minutes. A solution of 1-bromo-2-fluoro-4-iodobenzene (100 g, 332.34 mmol, 1.00 equiv) in THF (600 mL) was added dropwise with stirring at −78° C. The resulting solution was stirred for 90 minutes at −78° C. The reaction mixture was then poured into 1.5 L of dry ice, then concentrated under vacuum. The residue was diluted with 2000 mL of aq. sodium hydroxide (4 M), then washed with 2×800 mL of ether. The aq. solution was adjusted to pH 2 with HCl (2 M), then extracted with 3×800 mL of ethyl acetate. The organic layers were combined, washed with 3×500 mL of water, dried and concentrated under vacuum to afford the title compound.

Step B: 3-bromo-2-fluoro-6-iodobenzoyl Chloride

Into a 3000-mL RBF was placed 3-bromo-2-fluoro-6-iodobenzoic acid (235 g, 681.35 mmol, 1.00 equiv) and thionyl chloride (1175 mL). The resulting solution was stirred for 2 hours at 80° C. in an oil bath. The resulting mixture was cooled and concentrated under vacuum to afford the title compound.

Step C: 3-bromo-2-fluoro-6-iodobenzamide

Into a 10000-mL 4-necked RBF was placed a solution of $NH_4OH$ (840 g) in THF (2000 mL). A solution of 3-bromo-2-fluoro-6-iodobenzoyl chloride (223 g, 614 mmol, 1.00 equiv) in THF (2460 mL) was added dropwise with stirring at 0° C. The resulting solution was stirred for 60 minutes at room temperature. The resulting mixture was concentrated under vacuum. The solids were collected by filtration to afford the title compound.

Step D: 3-bromo-2-fluoro-6-iodobenzonitrile

Into a 10000-mL 4-necked RBF was placed a solution of 3-bromo-2-fluoro-6-iodobenzamide (223 g, 648 mmol, 1.00 equiv) in N,N-dimethylformamide (4460 mL), trichloro-1,3,5-triazine (840 g, 4.56 mol, 7.00 equiv). The resulting solution was stirred overnight at room temperature. The reaction mixture was poured into 10 L of aq. sodium bicarbonate. The solids were collected by filtration to afford the title compound.

Step E: 2-(benzylsulfanyl)-3-bromo-6-iodobenzonitrile

Into a 5000-mL 4-necked RBF purged and maintained with an inert atmosphere of nitrogen was placed a solution of sodium hydride (14.8 g, 617 mmol, 1.20 equiv) in 1,4-dioxane (1000 mL). A solution of phenylmethanethiol (38.1 g, 306.76 mmol, 1.00 equiv) in 1,4-dioxane (100 mL) was added dropwise with stirring at 0° C. over 20 min. To this was added a solution of 3-bromo-2-fluoro-6-iodobenzonitrile (100 g, 306.84 mmol, 1.00 equiv) in 1,4-dioxane (400 mL) dropwise with stirring at 0° C. The resulting solution was stirred for 60 minutes at room temperature and for an additional 60 minutes at 60° C. The reaction was then quenched by the addition of 750 mL of HCl (1 M). The resulting solution was diluted with 3 L of water, then extracted with 3×1 L of ethyl acetate. The organic layers were combined, dried and concentrated under vacuum. The residue was applied onto a silica gel column and eluted with ethyl acetate/petroleum ether (1:4) to afford the title compound.

Step F: 5-[2-(benzylsulfanyl)-3-bromo-6-iodophenyl]-1H-1,2,3,4-tetrazole

Into a 3000-mL 4-necked RBF was placed a solution of 2-(benzylsulfanyl)-3-bromo-6-iodobenzonitrile (54.0 g, 126 mmol, 1.00 equiv) in toluene (750 mL), $TMSN_3$ (43.4 g, 3.00 equiv) and dibutyltin oxide (6.3 g, 0.20 equiv). The resulting solution was stirred for 48 hr at 105° C. in an oil bath. The reaction mixture was cooled to RT. The resulting solution was diluted with 3 L of aq. sodium hydroxide, then extracted with ethyl acetate. The aqueous layer was adjusted to pH 3 with HCl (2 M), then extracted with 2×1 L of ethyl acetate. The organic layers were combined, washed with 2×1 L of water, dried over anhydrous sodium sulfate and concentrated under vacuum to provide the title compound.

Step G: 5-[2-(benzylsulfanyl)-3-bromo-6-iodophenyl]-1-[(4-methoxyphenyl)methyl]-1H-1,2,3,4-tetrazole and 5-[2-(benzylsulfanyl)-3-bromo-6-iodophenyl]-2-[(4-methoxyphenyl)methyl]-2H-1,2,3,4-tetrazole Into a 3000-mL 3-necked RBF purged and maintained with an inert atmosphere of nitrogen was placed a solution of 5-[2-(benzylsulfanyl)-3-bromo-6-iodophenyl]-1H-1,2,3,4-tetrazole (84.4 g, 178 mmol, 1.00 equiv) in chloroform (700 mL), a solution of potassium carbonate (49.0 g, 355 mmol, 2.00 equiv) in water (520 mL), and tetrabutylammonium chloride (10.2 g, 0.20 equiv). This was followed by the addition of para-methoxybenzyl chloride (42.2 g, 1.50 equiv) dropwise with stirring at 15° C. The resulting solution was stirred for 180 minutes at 50° C. in an oil bath. The reaction mixture was cooled to RT. The resulting solution was diluted with 200 mL of water, then extracted with 2×200 mL of DCM. The organic layers were combined, dried over sodium sulfate and concentrated under vacuum. The residue was applied onto a silica gel column and eluted with ethyl acetate/petroleum ether (1:2). This resulted in the title compound as a mixture of two isomers.

Step H: 6-bromo-3-iodo-2-(1-(4-methoxybenzyl)-1H-tetrazol-5-yl)benzene-1-sulfonyl chloride and 6-bromo-3-iodo-2-(2-(4-methoxybenzyl)-2H-tetrazol-5-yl)benzene-1-sulfonyl Chloride Into a 2000-mL 4-necked RBF purged and maintained with an inert atmosphere of nitrogen was placed mixture of 5-[2-(benzylsulfanyl)-3-bromo-6-iodophenyl]-1-[(4-methoxyphenyl)methyl]-1H-1,2,3,4-tetrazole and 5-[2-(benzylsulfanyl)-3-bromo-6-iodophenyl]-2-[(4-methoxyphenyl)methyl]-2H-1,2,3,4-tetrazole (50.0 g, 84.3 mmol, 1.00 equiv, 60%), dichloromethane (750 mL), AcOH (12.7 g, 211 mmol, 2.50 equivalents), and water (3.8 g, 2.5 equiv). This was followed by the addition of $SO_2Cl_2$ (28.3 g, 2.50 equivalents) dropwise with stirring at 0° C. The resulting solution was stirred for 60 minutes at room temperature. The resulting mixture was concentrated under vacuum to afford the title compound isomer mixture.

Step I: 6-bromo-3-iodo-2-(1-(4-methoxybenzyl)-1H-tetrazol-5-yl)benzenesulfonamide and 6-bromo-3-iodo-2-(2-(4-methoxybenzyl)-2H-tetrazol-5-yl)benzenesulfonamide Into a 2000-mL 4-necked RBF purged and maintained with an inert atmosphere of nitrogen was placed a solution of 6-bromo-3-iodo-2-(1-(4-methoxybenzyl)-1H-tetrazol-5-yl)benzene-1-sulfonyl chloride and 6-bromo-3-iodo-2-(2-(4-methoxybenzyl)-2H-tetrazol-5-yl)benzene-1-sulfonyl chloride (isomer mixture, 50.0 g, 52.7 mmol, 1.00 equiv, 60%) in tetrahydrofuran (300 mL) and a solution of $NH_4OH$ (200 mL) in tetrahydrofuran (200 mL). The resulting solution was stirred for 60 minutes at room temperature. The resulting solution was extracted with 3×150 mL of ethyl acetate. The organic layers were combined, dried over anhydrous sodium sulfate and concentrated under vacuum. The crude product was purified with Flash-Prep-HPLC under the following conditions: Column, C18 silica gel; mobile phase, H₂O: MeCN=25 increasing to H₂O: MeCN=55 within 30 min; Detector, UV 210 nm, to afford the title compound. H-NMR (DMSO-d6, 300 MHz, ppm): δ 3.727-3.748 (3H, d), 5.001-5.068 (0.78H, m), 5.428-5.477 (0.75H, m), 5.941 (0.5H, m), 6.823-6.958 (2H, m), 7.148-7.363 (2H, m), 7.732-7.864 (1.6H, m), 7.993-8.117 (3H, m).

REFERENCE EXAMPLE 2

6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide

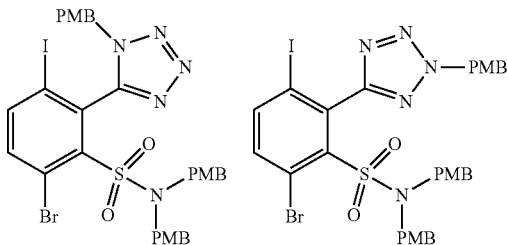

Step A: 3-bromo-2-fluoro-6-iodobenzoic Acid

Into a 5000-mL 4-necked RBF purged and maintained with an inert atmosphere of nitrogen, was placed bis(propan-2-yl)amine (121.2 g, 1.20 mol, 1.20 equiv), tetrahydrofuran (1000 mL). This was followed by the addition of butyllithium (440 mL, 1.10 equiv, 2.5 N) dropwise with stirring at −78° C. in 20 min. 60 min later, a solution of 1-bromo-2-fluoro-4-iodobenzene (300 g, 997 mmol, 1.00 equiv) in tetrahydrofuran (2000 mL) was added dropwise with stirring at −78° C. in 30 minutes. The resulting solution was stirred for 2 hours at −78° C. in a liquid nitrogen bath. The reaction was then quenched by pouring into 5000 g of dry ice. After stirring for 2 hours, the resulting mixture was concentrated under vacuum. The residue was dissolved in 3000 mL of 4N sodium hydroxide. The resulting solution was extracted with 2×1000 mL of ether and the aqueous layers combined. The pH of the solution was adjusted to 2-3 with hydrogen chloride (1 mmol/L). The resulting solution was extracted with 4×1000 mL of ethyl acetate and the organic layers combined and dried over anhydrous sodium sulfate and concentrated under vacuum. The crude product was purified by re-crystallization from hexane.

Step B: 3-bromo-2-fluoro-6-iodobenzoyl Chloride

Into a 5000-mL 3-necked RBF purged and maintained with an inert atmosphere of nitrogen, was placed 3-bromo-2-fluoro-6-iodobenzoic acid (273 g, 791.52 mmol, 1.00 equiv), tetrahydrofuran (2730 mL), N,N-dimethylformamide (27.3 mL). This was followed by the addition of (COCl)₂ (110.9 g, 1.10 equiv) dropwise with stirring at 20° C. for 20 minutes. The resulting solution was stirred for 1 hour at room temperature. The resulting mixture was concentrated under vacuum.

Step C: 3-bromo-2-fluoro-6-iodobenzamide

Into a 5000-mL 4-necked RBF purged and maintained with an inert atmosphere of nitrogen, was placed NH₄OH (1200 g). This was followed by the addition of a solution of 3-bromo-2-fluoro-6-iodobenzoyl chloride (280 g, 771 mmol, 1.00 equiv) in tetrahydrofuran (2800 mL) dropwise with stirring at 0° C. over 30 minutes. The resulting solution was stirred for 1 hour at room temperature. The resulting mixture was concentrated under vacuum. The solids were collected by filtration, washed with H₂O to afford the title compound.

Step D: 3-bromo-2-fluoro-6-iodobenzonitrile

Into a 10000-mL 4-necked RBF purged and maintained with an inert atmosphere of nitrogen, was placed 3-bromo-2-fluoro-6-iodobenzamide (270 g, 785.07 mmol, 1.00 equiv), N,N-dimethylformamide (5400 mL). This was followed by the addition of trichloro-1,3,5-triazine (1014 g, 5.50 mol, 7.00 equiv), in portions at 0° C. The resulting solution was stirred for 2 hours at room temperature. The reaction was then quenched by the addition of 15000 mL of sodium bicarbonate aq. The solids were collected by filtration to afford the title compound.

Step E: 2-(benzylsulfanyl)-3-bromo-6-iodobenzonitrile

Into a 5000-mL 4-necked RBF purged and maintained with an inert atmosphere of nitrogen, was placed sodium hydride (34 g, 852 mmol, 1.20 equiv, 60%), 1,4-dioxane (700 mL). This was followed by the addition of a solution of phenylmethanethiol (88.7 g, 714.15 mmol, 1.00 equiv) in 1,4-dioxane (950 mL) dropwise with stirring at 10° C. in 15 minutes. 30 minutes later, a solution of 3-bromo-2-fluoro-6-iodobenzonitrile (230 g, 705.73 mmol, 1.00 equiv) in 1,4-dioxane (1800 mL) was added dropwise with stirring at 10° C. The resulting solution was stirred for 2 hours at RT. The reaction was then quenched by pouring into 5000 mL of water/ice. The resulting solution was extracted with 5×1000 mL of ethyl acetate and the organic layers were combined. The resulting mixture was washed with 2×1000 mL of water and 2×1000 mL of sodium bicarbonate and 2×1000 mL of sodium chloride. The mixture was dried over anhydrous sodium sulfate and concentrated under vacuum. The crude product was purified by re-crystallization from ether to afford the title compound.

Step F: 5-[2-(benzylsulfanyl)-3-bromo-6-iodophenyl]-1H-1,2,3,4-tetrazole

Into a 2000-mL 4-necked RBF, was placed 2-(benzylsulfanyl)-3-bromo-6-iodobenzonitrile (66 g, 153.45 mmol, 1.00 equiv), toluene (660 mL), azidotrimethylsilane (44.2 g, 383.65 mmol, 2.50 equiv), and dibutylstannanone (7.7 g, 30.93 mmol, 0.20 equiv). The resulting solution was stirred for 48 hours at 105° C. in an oil bath. The reaction mixture was cooled to RT. The resulting mixture was concentrated under vacuum. The residue was purified by silica gel column with tetrahydrofuran:PE (100:1) to afford the title compound.

Step G: 6-bromo-3-iodo-2-(1H-1,2,3,4-tetrazol-5-yl)benzene-1-sulfonyl Chloride

Into a 2000-mL 3-necked RBF purged and maintained with an inert atmosphere of nitrogen, was placed 5-[2-(benzylsulfanyl)-3-bromo-6-iodophenyl]-1H-1,2,3,4-tetrazole (115.6 g, 244.33 mmol, 1.00 equiv), acetic acid (1156 mL), and water (115.6 mL), NCS (81.74 g, 612.15 mmol, 2.50 equiv). The resulting solution was stirred overnight at RT in an ice/salt bath. The resulting mixture was concentrated under vacuum to afford the title compound.

Step H: 6-bromo-3-iodo-2-(1H-1,2,3,4-tetrazol-5-yl) benzene-1-sulfonamide

Into a 3000-mL 4-necked RBF purged and maintained with an inert atmosphere of nitrogen, was placed NH₄OH (1180 mL), tetrahydrofuran (290 mL). This was followed by the addition of a solution of 6-bromo-3-iodo-2-(1H-1,2,3,4-tetrazol-5-yl)benzene-1-sulfonyl chloride (118 g, 262.54 mmol, 1.00 equiv) in tetrahydrofuran (300 mL) dropwise with stirring at 0° C. The resulting solution was stirred for 2 hours at 0-25° C. in an ice/salt bath (slowly warming to RT). The resulting mixture was concentrated under vacuum. The resulting solution was diluted with 500 mL of ether. After stirring for 30 minutes, the solids were collected by filtration to afford the title compound.

Step I: 6-bromo-3-iodo-N,N-bis[(4-methoxyphenyl) methyl]-2-[1-[(4-methoxyphenyl)methyl]-1H-1,2,3, 4-tetrazol-5-yl]benzene-1-sulfonamide and 6-bromo-3-iodo-N,N-bis[(4-methoxyphenyl) methyl]-2-[2-[(4-methoxyphenyl)methyl]-2H-1,2,3, 4-tetrazol-5-yl]benzene-1-sulfonamide Into a 3000-mL 4-necked RBF purged and maintained with an inert atmosphere of nitrogen, was placed 6-bromo-3-iodo-2-(1H-1,2,3,4-tetrazol-5-yl)benzene-1-sulfonamide (105 g, 244.17 mmol, 1.00 equiv), chloroform (1050 mL), potassium carbonate (168.9 g, 1.22 mol, 5.00 equiv), water (525 mL), NaI (11 g, 0.30 equiv), tetrabutyl(chloro)amine (20.4 g, 73.40 mmol, 0.30 equiv), and 1-(chloromethyl)-4-methoxybenzene (230 g, 1.47 mol, 6.00 equiv). The resulting solution was stirred overnight at 50° C. in an oil bath. The reaction mixture was cooled to RT. The resulting solution was extracted with 2×1000 mL of dichloromethane and the organic layers combined and dried over anhydrous sodium sulfate and concentrated under vacuum to afford the title compounds. LC-MS: (ES, m/z): 790 [M+H]⁺; H-NMR: (300 MHz, CDCl₃, ppm): δ 7.956-7.928 (m, 0.5H), 7.852-7.824 (m, 1H), 7.656-7.612 (m, 1.5H), 7.323-7.282 (m, 1.5H), 7.195-7.224 (m, 2H), 6.944-6.908 (m, 6H), 6.822-6.760 (m, 9H), 5.791 (m, 1H), 5.570-5.521 (m, 1H), 5.149-5.100 (m, 1H), 4.769-4.718 (m, 2H), 4.232-4.221 (m, 2H), 3.900-3.848 (m, 2H), 3.789-3.742 (m, 14H).

In the experimental procedures below, the compound of REFERENCE EXAMPLE 2 can be used as the mixture of para-methoxylbenzyl tetrazole regioisomers. Alternatively, the two regioisomers may be separated and each can be used as described below in the same fashion. In some REFERENCE EXAMPLES and EXAMPLES below, both regioisomers are explicitly used; however, in other cases, only one regioisomer is shown. It should be understood that in these cases the mixture of regioisomers was, typically, used.

REFERENCE EXAMPLE 3 tert-butyl 4-mercaptopiperidine-1-carboxylate

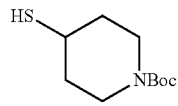

The title compound is commercially available (CAS No. 134464-79-2) from Synnovator, Inc. Alternatively, it may be prepared as follows: Into a 100 mL RBF di-tert-butyl 4,4'-disulfanediyldipiperidine-1-carboxylate (5.0 g, 11.57 mmol) was dissolved in AcOH (50 mL), and zinc (3.7 g, 57.85 mmol). After the resulting mixture was stirred at 60° C. for 16 hours, it was concentrated under vacuum. The residue was purified by silica gel column chromatography, eluted with ethyl acetate/petroleum ether (1/5) to give tert-butyl 4-mercaptopiperidine-1-carboxylate as a solid. ¹H NMR (300 MHz, DMSO): δ 3.82-3.78 (m, 2H), 2.95-2.71 (m, 3H), 2.63 (d, J=6.9 Hz, 1H), 1.90-1.87 (m, 2H), 1.39 (s, 9H), 1.37-1.32 (m, 2H).

REFERENCE EXAMPLE 4 tert-butyl 3-mercaptoazetidine-1-carboxylate

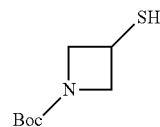

The title compound is commercially available (CAS No. 941585-25-7) from, for example, Synnovator, Inc. Alternatively, it may be prepared as follows:

Step A: tert-butyl 3-(acetylthio)azetidine-1-carboxylate

A solution of tert-butyl 3-iodoazetidine-1-carboxylate (10 g, 35.3 mmol) and potassium ethanethioate (16.14 g, 141 mmol) in DMF (60 ml) was stirred at 70° C. for 16 hours. The resulting mixture was quenched with water (80 mL), diluted with water (200 mL) and extracted with ethyl acetate (3×50 mL). The combined organic layers were washed with water (3×10 mL) and brine (3×10 mL), dried over anhydrous sodium sulfate and filtered. The filtrate was concentrated under vacuum and the residue was purified by silica-gel chromatography, eluted with ethyl acetate/petroleum ether (1/10). The combined organic fractions were concentrated under reduced pressure to give tert-butyl 3-(acetylthio) azetidine-1-carboxylate as an oil, which was used for the next reaction directly. ¹H NMR (400 MHz, CDCl₃): δ 4.40-4.35 (m, 2H), 4.19-4.15 (m, 1H), 3.84-3.80 (m, 2H), 2.35 (s, 3H), 1.45 (s, 9H).

Step B: tert-butyl 3-mercaptoazetidine-1-carboxylate

A solution of tert-butyl 3-(acetylthio)azetidine-1-carboxylate (8 g, 34.6 mmol) and NaOH (1.383 g, 34.6 mmol) in methanol (50 ml) and water (5 ml) was stirred at room temperature for 1 hour. The pH of the action solution was adjusted to 5 with hydrochloric acid (10%), diluted with water (80 mL) and extracted with ethyl acetate (3×60 mL). The combined organic layers were washed with water (3×10 mL) and brine (2×10 mL), dried over anhydrous sodium sulfate and filtered. The filtrate was concentrated under vacuum to give crude product. The residue was purified by silica gel chromatography, eluted with ethyl acetate/petroleum ether (10/90). The combined organic fractions were concentrated under reduced pressure to give tert-butyl 3-mercaptoazetidine-1-carboxylate as a solid. ¹H NMR (400

MHz, DMSO-d6): δ 4.22-4.20 (m, 2H), 3.69-3.64 (m, 3H), 3.43-3.41 (m, 1H), 1.37 (s, 9H).

REFERENCE EXAMPLE 5 tert-butyl 4-(2-(N,N-bis(4-methoxybenzyl)sulfamoyl)-4-iodo-3-(2-(4-methoxybenzyl)-2H-tetrazol-5-yl)phenylsulfonyl)piperidine-1-carboxylate

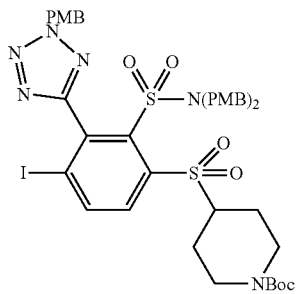

Step A: tert-butyl 4-(2-(N,N-bis(4-methoxybenzyl)sulfamoyl)-4-iodo-3-(2-(4-methoxybenzyl)-2H-tetrazol-5-yl)phenylthio)piperidine-1-carboxylate Sodium hydride (0.15 g, 3.80 mmol) was added to a stirred mixture of 6-bromo-3-iodo-N,N-bis(4-methoxybenzyl)-2-(2-(4-methoxybenzyl)-2H-tetrazol-5-yl)benzenesulfonamide (1.2 g, 1.5 mmol) and tert-butyl 4-mercaptopiperidine-1-carboxylate (0.726 g, 3.34 mmol) in DMF (20 mL) at 0° C. The mixture was stirred at RT for 2 hr, then it was quenched with saturated NH₄Cl aqueous, and diluted with ethyl acetate (20 mL). The mixture was separated, and the aqueous layer was extracted with ethyl acetate (3×40 mL). The combined extracts were washed with brine, dried over anhydrous MgSO₄, filtered and concentrated under reduced pressure. The residue was purified by silica gel column chromatography, eluted with ethyl acetate/petroleum ether (2:1) to give the title compound. LCMS [M+H]⁺: 927; ¹H NMR (300 MHz, CDCl₃): δ 7.94 (d, J=8.7 Hz, 1H), 7.30 (d, J=8.7 Hz, 1H), 7.22 (d, J=8.7 Hz, 2H), 6.94-6.90 (m, 4H), 6.81-6.72 (m, 6H), 5.50 (d, J=14.4 Hz, 1H), 5.13 (d, J=14.4 Hz, 1H), 4.73 (d, J=15.6 Hz, 2H), 4.09-4.00 (m, 1H), 3.89 (d, J=15.6 Hz, 2H), 3.90-3.81 (m, 1H), 3.78 (s, 9H), 3.50-3.39 (m, 1H), 3.11-2.89 (m, 2H), 2.12-2.01 (m, 1H), 1.85-1.56 (m, 3H).

Step B: tert-butyl 4-(2-(N,N-bis(4-methoxybenzyl)sulfamoyl)-4-iodo-3-(2-(4-methoxybenzyl)-2H-tetrazol-5-yl)phenylsulfonyl)piperidine-1-carboxylate Into a 100 mL RBF containing tert-butyl 4-((2-(N,N-bis(4-methoxybenzyl)sulfamoyl)-4-iodo-3-(2-(4-methoxybenzyl)-2H-tetrazol-5-yl)phenyl)thio)piperidine-1-carboxylate (1.0 g, 1.079 mmol) dissolved in DCM (10 ml), was added 3-chlorobenzoperoxoic acid (0.745 g, 4.32 mmol). The reaction mixture was stirred at RT overnight, and then partitioned between ethyl acetate (20 mL) and 10% aq. sodium thiosulfate (30 mL). The organic phase was separated, washed with sat. aq. sodium bicarbonate (50 mL), dried over anhydrous Na₂SO₄ and concentrated under reduced pressure. The residue was purified by silica gel column chromatography, and eluted with ethyl acetate/petroleum ether (1:1) to give the title compound. LCMS [M+H]⁺: 959.

REFERENCE EXAMPLE 6 tert-Butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate and tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate

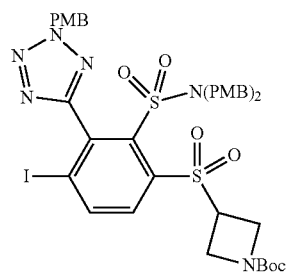

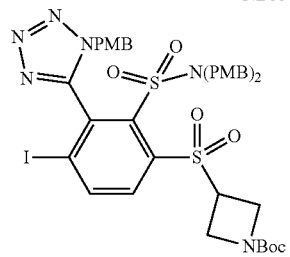

Step A: tert-butyl 3-((2-(N,N-bis(4-methoxybenzyl)sulfamoyl)-4-iodo-3-(2-(4-methoxybenzyl)-2H-tetrazol-5-yl)phenyl)thio)azetidine-1-carboxylate and tert-butyl 3-((2-(N,N-bis(4-methoxybenzyl)sulfamoyl)-4-iodo-3-(1-(4-methoxybenzyl)-1H-tetrazol-5-yl)phenyl)thio)azetidine-1-carboxylate Sodium hydride (1.32 g, 32.9 mmol)) was added to a stirred, cooled 0° C. mixture of 6-bromo-3-iodo-N,N-bis(4-methoxybenzyl)-2-(2-(4-methoxybenzyl)-2H-tetrazol-5-yl)benzenesulfonamide and 6-bromo-3-iodo-N,N-bis(4-methoxybenzyl)-2-(1-(4-methoxybenzyl)-1H-tetrazol-5-yl)benzenesulfonamide (10 g, 12.65 mmol) and tert-butyl 3-mercaptoazetidine-1-carboxylate (5.27 g, 27.8 mmol)) in DMF (42 mL) and the mixture was stirred at room temperature for 2 hours. The mixture was quenched with NH₄Cl solution, and diluted with EtOAc. The mixture was separated, and the aqueous layer was extracted with EtOAc. The combined extracts were washed with brine, dried over MgSO₄, filtered and the solvent was evaporated under reduced pressure. The crude product was purified with silica gel column chromatography using 0-100% EtOAc/hexanes as eluent to afford the title product. LC/MS [M+1]⁺: 900.03.

Step B: tert-Butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate and tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate To tert-butyl 3-((2-(N,N-bis(4-methoxybenzyl)sulfamoyl)-4-iodo-3-(2-(4-methoxybenzyl)-2H-tetrazol-5-yl)

phenyl)thio)azetidine-1-carboxylate and tert-butyl 3-((2-(N,N-bis(4-methoxybenzyl)sulfamoyl)-4-iodo-3-(1-(4-methoxybenzyl)-1H-tetrazol-5-yl)phenyl)thio)azetidine-1-carboxylate (10 g, 11.13 mmol) in DCM (56 mL) was added m-CPBA (11.2 g, 50.1 mmol). The reaction mixture was stirred at RT overnight, and then partitioned between EtOAc and 10% aq. sodium thiosulfate. The organic phase was separated, washed with sat. aq. sodium bicarbonate, dried (MgSO$_4$) and the volatiles were removed under reduced pressure. The residue was purified by silica gel column chromatography using 0 to 100% EtOAc in hexanes as eluent to afford the title compound. LC/MS [M+1]$^+$: 931.99.

REFERENCE EXAMPLE 7

(3-(N,N-Bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic Acid and (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic Acid

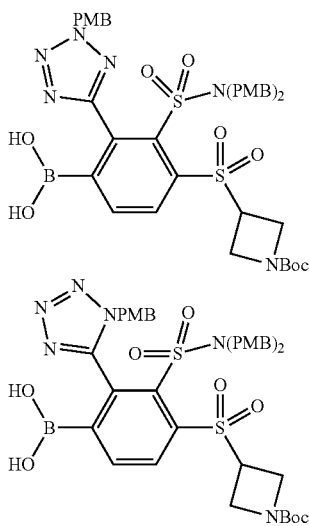

A mixture of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate and tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate (2.0 g, 2.15 mmol), 5,5,5',5'-tetramethyl-2,2'-bi(1,3,2-dioxaborinane) (1.46 mg, 6.45 mmol), PPh$_3$ precatalyst generation 2 (184 mg, 0.322 mmol) and KOAc (633 mg, 6.45 mmol) in dioxane (8.6 mL) was degassed with N$_2$. The resulting mixture was heated at 80° C. for 6 hours. LCMS indicated complete coversion to boronic acid with a minor amount of des-I side product. After cooling to RT, the mixture was filtered through CELITE, and rinsed with EtOAc. The filtrate was concentrated and the residue was purified by C18 reverse phase column chromatography (reverse phase ISCO 50 g HP C18 column) eluting with 0-100% MeCN/water (no acid additive) to afford the title compound. LC/MS [M+1]$^+$: 850.01.

REFERENCE EXAMPLE 8

(3-(N,N-bis(4-methoxybenzyl)sulfamoyl)-4-((1-(tert-butoxycarbonyl)azetidin-3-yl)thio)-2-(1-(4-methoxybenzyl)-1H-tetrazol-5-yl)phenyl)boronic Acid and (3-(N,N-bis(4-methoxybenzyl)sulfamoyl)-4-((1-(tert-butoxycarbonyl)azetidin-3-yl)thio)-2-(2-(4-methoxybenzyl)-2H-tetrazol-5-yl)phenyl)boronic Acid

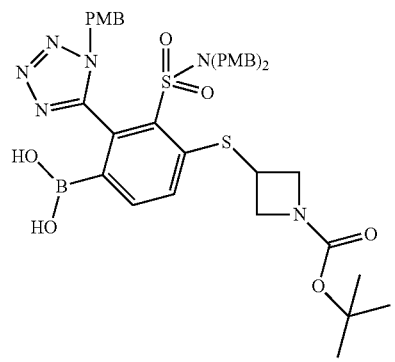

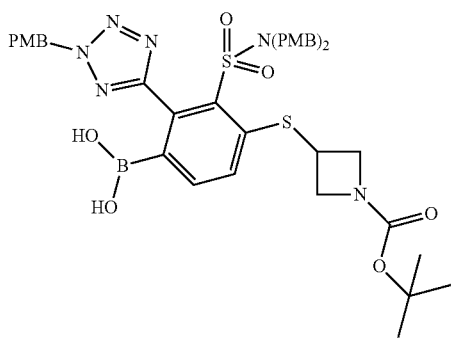

tert-Butyl 3-((2-(N,N-bis(4-methoxybenzyl)sulfamoyl)-4-iodo-3-(1-(4-methoxybenzyl)-1H-tetrazol-5-yl)phenyl)thio)azetidine-1-carboxylate, tert-butyl 3-((2-(N,N-bis(4-methoxybenzyl)sulfamoyl)-4-iodo-3-(2-(4-methoxybenzyl)-2H-tetrazol-5-yl)phenyl)thio)azetidine-1-carboxylate (980 mg, 1.090 mmol), Ph$_3$PPdG2 (94 mg, 0.164 mmol), 5,5,5',5'-tetramethyl-2,2'-bi(1,3,2-dioxaborinane) (739 mg, 3.27 mmol), and potassium acetate (321 mg, 3.27 mmol) were placed in a reaction vial. Dioxane (5452 µl) was added. The reaction mixture was degassed for 20 minutes before it was heated at 80° C. for 48 hours. LC-MS showed the reaction did not go to completion. Another 50 mgs of catalyst was added, and the reaction was heated at 80° C. for 12 hours. The product was purified with reverse phase ESCO C18 column (86 g), eluted with 0-100% CH$_3$CN/water. The correct fractions were combined, concentrated and lypholized to give the title compound. LC/MS [M+H]$^+$: 817.7.

REFERENCE EXAMPLE 9 tert-butyl N-(2-sulfanylethyl)carbamate

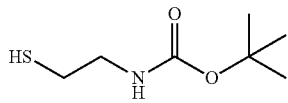

Into a 2000-mL 4-necked RBF purged and maintained with an inert atmosphere of nitrogen, was placed 2-aminoethane-1-thiol (50 g, 648.10 mmol, 1.00 equiv), DCM (1000 mL), di-tert-butyl dicarbonate (116 g, 531.51 mmol, 1.20 equiv), and TEA (134 g, 1.32 mol, 3.00 equiv). The resulting solution was stirred overnight at room temperature. The reaction was then quenched by the addition of 100 mL of water. The resulting mixture was washed with 2×500 mL of 0.5N hydrogen chloride and 2×500 mL of brine. The mixture was dried over anhydrous sodium sulfate and concentrated under vacuum. The residue was applied onto a silica gel column with ethyl acetate/petroleum ether (1:8) to give the title compound.

REFERENCE EXAMPLE 10 tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate

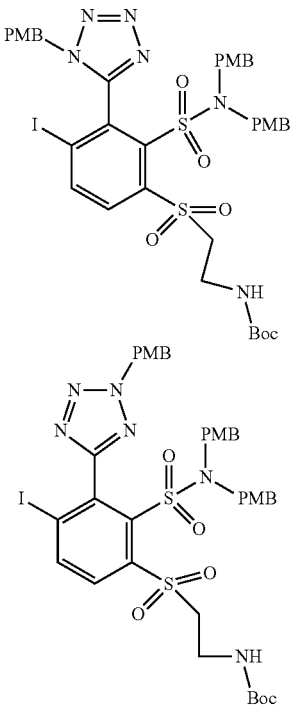

Step A: 2-fluoro-4-iodoaniline

Into a 20000-mL 4-necked RBF purged and maintained with an inert atmosphere of nitrogen, was placed 2-fluoroaniline (1256 g, 11.30 mol, 1.00 equiv), and $CCl_4$ (12560 mL). This was followed by the addition of NIS (3992.8 g, 17.75 mol, 2.00 equiv) in portions. The resulting solution was stirred overnight at room temperature. The reaction was then quenched by the addition of 5000 mL of water. The resulting mixture was washed with 3×2000 mL of $H_2O$. The resulting mixture was washed with 3×2000 mL of brine. The mixture was dried over anhydrous sodium sulfate and concentrated under vacuum. The residue was applied onto a silica gel column with ethyl acetate/petroleum ether (1:2) to afford the title compound.

Step B: 1-bromo-2-fluoro-4-iodobenzene

Into a 20000-mL 4-necked RBF purged and maintained with an inert atmosphere of nitrogen, was placed 2-fluoro-4-iodoaniline (1000 g, 4.22 mol, 1.00 equiv), water (1000 mL), and HBr (5000 mL). A solution of $NaNO_3$ (582 g, 2.00 equiv) in water (1900 mL) was then added dropwise with stirring at 0° C. CuBr (901 g) was added at 0° C. The resulting solution was stirred for 4 hours at 0° C. in an ice/salt bath. The resulting solution was extracted with 4×2000 mL of ethyl acetate and the organic layers combined. The resulting mixture was washed with 3×2000 mL of water and 3×2000 mL of brine. The mixture was dried over anhydrous sodium sulfate and concentrated under vacuum. The residue was applied onto a silica gel column with ethyl acetate/petroleum ether (1:7) to afford the title compound.

Step C: 3-bromo-2-fluoro-6-iodobenzoic Acid

Into a 20000-mL 4-necked RBF purged and maintained with an inert atmosphere of nitrogen, was placed LDA (2000 mL, 1.10 equiv), and tetrahydrofuran (5000 mL). A solution of 1-bromo-2-fluoro-4-iodobenzene (1090 g, 3.62 mol, 1.00 equiv) in tetrahydrofuran (5000 mL) was added dropwise with stirring. The resulting solution was stirred for 2 hours at −78° C. in a liquid nitrogen bath. The reaction was then quenched by the addition of 20000 g of dry ice. The resulting mixture was concentrated under vacuum. The resulting solution was diluted with 10000 mL of 4N sodium hydroxide, extracted with 3×3000 mL of ether and the aqueous layers combined. The pH of the solution was adjusted to 2-3 with hydrogen chloride (1 mol/L). The resulting solution was extracted with 5×3000 mL of ethyl acetate and the organic layers combined. The resulting mixture was washed with 2×3000 mL of brine. The mixture was dried over anhydrous sodium sulfate and concentrated under vacuum. The crude product was re-crystallized from Hexane:EA in the ratio of 100:1 to afford the title compound.

Step D: 3-bromo-2-fluoro-6-iodobenzoyl Chloride

Into a 10000-mL 4-necked RBF purged and maintained with an inert atmosphere of nitrogen, was placed 3-bromo-2-fluoro-6-iodobenzoic acid (600 g, 1.74 mol, 1.00 equiv), tetrahydrofuran (3000 mL), and N,N-dimethylformamide (60 mL). This was followed by the addition of $(COCl)_2$ (243.6 g, 1.10 equiv) dropwise with stirring at room temperature. The resulting solution was stirred for 1 hour at room temperature. The resulting mixture was concentrated under vacuum to afford the title compound.

Step E: 3-bromo-2-fluoro-6-iodobenzamide

Into a 20000-mL 4-necked RBF purged and maintained with an inert atmosphere of nitrogen, was placed tetrahydrofuran (3000 mL), and NH₄OH (3100 mL). This was followed by the addition of a solution of 3-bromo-2-fluoro-6-iodobenzoyl chloride (620 g, 1.71 mol, 1.00 equiv) in tetrahydrofuran (2000 mL) dropwise with stirring at 0° C. The resulting solution was stirred for 1 hour at room temperature in an ice/salt bath. The resulting mixture was concentrated under vacuum. The solids were collected by filtration, and washed with water to give the title compound.

Step F: 3-bromo-2-fluoro-6-iodobenzonitrile

Into a 20000-mL 4-necked RBF purged and maintained with an inert atmosphere of nitrogen, was placed 3-bromo-2-fluoro-6-iodobenzamide (1000 g, 2.91 mol, 1.00 equiv), and N,N-dimethylformamide (8000 mL). Trichloro-1,3,5-triazine (1070 g, 5.80 mol, 2.00 equiv) was added dropwise with stirring at 50° C. The resulting solution was stirred for 30 minutes at 60° C. The reaction was then quenched by the addition of 40000 mL of Ice sodium bicarbonate. The solids were collected by filtration to provide the title compound.

Step G: 2-(benzylsulfanyl)-3-bromo-6-iodobenzonitrile

Into a 10000-mL 4-necked RBF purged and maintained with an inert atmosphere of nitrogen, was placed 1,4-dioxane (2000 mL), and sodium hydride (62 g, 1.20 equiv). Phenylmethanethiol (162 g, 1.30 mol, 1.01 equiv) was then added dropwise with stirring. To this was added a solution of 3-bromo-2-fluoro-6-iodobenzonitrile (420 g, 1.29 mol, 1.00 equiv) in 1,4-dioxane (4300 mL) dropwise with stirring at 10° C. for 1 hour. The resulting solution was stirred for 1 hour at 20° C. in a water/ice bath. The reaction was then quenched by the addition of 6000 mL of water/ice. The resulting solution was extracted with 5×1500 mL of ethyl acetate and the organic layers were combined. The resulting mixture was washed with 3×1000 mL of sodium bicarbonate aq and 3×1000 mL of brine. The mixture was dried over anhydrous sodium sulfate and concentrated under vacuum. The crude product was purified by re-crystallization from ether to afford the title compound.

Step H: 5-[2-(benzylsulfanyl)-3-bromo-6-iodophenyl]-1H-1,2,3,4-tetrazole

Into a 3000-mL 4-necked RBF purged and maintained with an inert atmosphere of nitrogen, was placed 2-(benzylsulfanyl)-3-bromo-6-iodobenzonitrile (150 g, 348.76 mmol, 1.00 equiv), toluene (1500 mL), azidotrimethylsilane (100.5 g, 872.33 mmol, 2.50 equiv), and dibutylstannanone (17.4 g, 69.90 mmol, 0.20 equiv). The resulting solution was stirred for 48 hours at 107° C. in an oil bath. The reaction mixture was cooled to 40° C. The resulting mixture was concentrated under vacuum. The crude product was re-crystallized from ether:EA in the ratio of 1:1 to provide the title compound.

Step I: 6-bromo-3-iodo-2-(1H-1,2,3,4-tetrazol-5-yl)benzene-1-sulfonyl Chloride

Into a 2000-mL 4-necked RBF purged and maintained with an inert atmosphere of nitrogen, was placed 5-[2-(benzylsulfanyl)-3-bromo-6-iodophenyl]-1H-1,2,3,4-tetrazole (100 g, 211.36 mmol, 1.00 equiv), acetic acid (1000 mL), and water (100 mL). NCS (70.7 g, 529.47 mmol, 2.50 equiv) was then added in portions. The resulting solution was stirred for 2 hours at room temperature in a water/ice bath. The resulting mixture was concentrated under vacuum. The resulting solution was diluted with 2000 mL of EA. The resulting mixture was washed with 2×1000 mL of water and 2×1000 mL of Brine. The mixture was dried over anhydrous sodium sulfate and concentrated under vacuum to afford the title compound.

Step J: 6-bromo-3-iodo-2-(1H-1,2,3,4-tetrazol-5-yl)benzene-1-sulfonamide

Into a 2000-mL 4-necked RBF purged and maintained with an inert atmosphere of nitrogen, was placed NH₄OH (850 mL), and tetrahydrofuran (100 mL). A solution of 6-bromo-3-iodo-2-(1H-1,2,3,4-tetrazol-5-yl)benzene-1-sulfonyl chloride (85 g, 189.12 mmol, 1.00 equiv) in tetrahydrofuran (325 mL) was then added dropwise with stirring at 0° C. The resulting solution was stirred overnight at room temperature. The resulting mixture was concentrated under vacuum. The resulting solution was diluted with 500 mL of H₂O. The resulting solution was extracted with 3×500 mL of ethyl acetate and the aqueous layers combined. The pH of the solution was adjusted to 1-2 with hydrogen chloride (6 mol/L). The solids were collected by filtration to give a part of product. The filtrate was extracted with 2×500 mL of ethyl acetate and the organic layers combined and dried over anhydrous sodium sulfate and concentrated under vacuum to give the title compound.

Step K: 6-bromo-3-iodo-N,N-bis[(4-methoxyphenyl)methyl]-2-[1-[(4-methoxyphenyl)methyl]-1H-1,2,3,4-tetrazol-5-yl]benzene-1-sulfonamide and 6-bromo-3-iodo-N,N-bis[(4-methoxyphenyl)methyl]-2-[2-[(4-methoxyphenyl)methyl]-2H-1,2,3,4-tetrazol-5-yl]benzene-1-sulfonamide Into a 10000-mL 4-necked RBF purged and maintained with an inert atmosphere of nitrogen, was placed 6-bromo-3-iodo-2-(1H-1,2,3,4-tetrazol-5-yl)benzene-1-sulfonamide (400 g, 930.19 mmol, 1.00 equiv), chloroform (4000 mL), water (2000 mL), potassium carbonate (643.3 g, 4.65 mol, 5.00 equiv), NaI (42 g, 0.30 equiv), tetrabutylazanium chloride (77.84 g, 280.08 mmol, 0.30 equiv), and PMBCl (873.3 g, 6.00 equiv). The resulting solution was stirred overnight at 50° C. in an oil bath. The reaction mixture was cooled to room temperature. The resulting solution was extracted with 1500 mL of DCM and the organic layers combined and dried over anhydrous sodium sulfate and concentrated under vacuum. The residue was applied onto a silica gel column with ethyl acetate/petroleum ether (1:1) to afford the title compound.

Step L: tert-butyl N-[2-[(2-[bis[(4-methoxyphenyl)methyl]sulfamoyl]-4-iodo-3-[1-[(4-methoxyphenyl)methyl]-1H-1,2,3,4-tetrazol-5-yl]phenyl)sulfanyl]ethyl]carbamate Into a 5000-mL 4-necked RBF purged and maintained with an inert atmosphere of nitrogen, was placed 6-bromo-3-iodo-N,N-bis[(4-methoxyphenyl)methyl]-2-[1-[(4-methoxyphenyl)methyl]-1H-1,2,3,4-tetrazol-5-yl]benzene-1-sulfonamide (175 g, 221.39 mmol, 1.00 equiv), N,N-dimethylformamide (2100 mL), tert-butyl N-(2-sulfanylethyl)carbamate (43 g, 242.58 mmol, 1.10 equiv), and Cs₂CO₃ (215 g, 3.00 equiv). The resulting solution was stirred overnight at room temperature. The resulting solution was diluted with 3000 mL of ether. The resulting mixture was washed with 2×1500 mL of brine. The mixture was dried over anhydrous sodium sulfate and concentrated under vacuum to afford the title compound.

Step M: tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate Into a 3000-mL 4-necked RBF purged and maintained with an inert atmosphere of nitrogen, was placed tert-butyl N-[2-[(2-[bis[(4-methoxyphenyl)methyl]sulfamoyl]-4-iodo-3-[1-[(4-methoxyphenyl)methyl]-1H-1,2,3,4-tetrazol-5-yl]phenyl)sulfanyl]ethyl]carbamate (103 g, 116.15 mmol, 1.00 equiv), DCM (1545 mL), and m-CPBA (125.3 g, 726.08 mmol, 5.00 equiv). The resulting solution was stirred overnight at room temperature. The resulting solution was diluted with 5000 mL of ether. The resulting mixture was washed with 2×2000 mL of 0.5N sodium hydroxide and 2×1500 mL of brine. The mixture was dried over anhydrous sodium sulfate and concentrated under vacuum. The residue was applied onto a silica gel column with ethyl acetate/petroleum ether (1:2) to give the title compound.

REFERENCE EXAMPLE 11 tert-butyl (2-((2-(N,N-bis(4-methoxybenzyl)sulfamoyl)-4-(5,5-dimethyl-1,3,2-dioxaborinan-2-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate

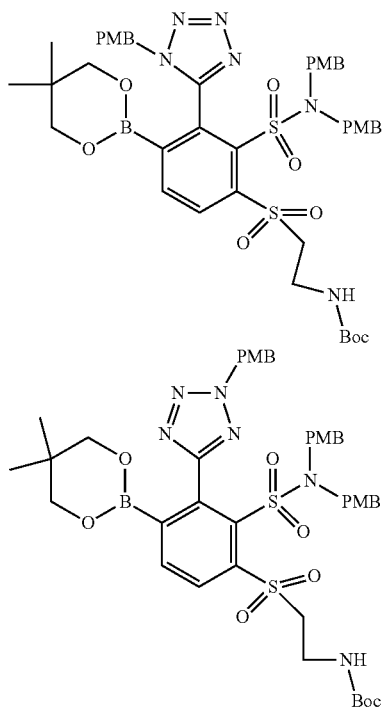

Into a 100-mL 3-necked RBF purged and maintained with an inert atmosphere of nitrogen, was placed tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (10 g, 10.88 mmol, 1.00 equiv), dioxane (30 mL), 2-(5,5-dimethyl-1,3,2-dioxaborinan-2-yl)-5,5-dimethyl-1,3,2-dioxaborinane (12.4 g, 54.90 mmol, 5.00 equiv), CH$_3$COOK (5.4 g, 55.02 mmol, 5.00 equiv), and 9-chloro-9-(triphenyl-$^5$-phosphanyl)-8-aza-9-palladatricyclo[8.4.0.0^2,7]tetradeca-1(14),2,4,6,10,12-hexaene (320 mg, 0.56 mmol, 0.05 equiv). The resulting solution was stirred overnight at 80° C. in an oil bath. The reaction mixture was cooled to room temperature. The resulting solution was diluted with 50 mL of EA. The solids were filtered out. The filtrate was concentrated under vacuum to afford the title compounds. LC-MS: (ES, m/z): 837 [M+H]$^+$ H-NMR (300 MHz, CDCl$_3$, ppm): δ 7.121 (m, 1H), 6.930-6.902 (m, 2H), 6.756-6.694 (m, 4H), 4.349 (m, 1H), 3.952-3.900 (m, 2H), 3.767-3.706 (m, 5H), 3.652-3.602 (m, 14H), 3.293-3.283 (m, 2H), 1.401 (s, 9H), 1.269-1.259 (m, 4H).

REFERENCE EXAMPLE 12 tert-butyl 4-(4-(4,4,5,5-tetramethyl-1,3,2-dioxaborolan-2-yl)phenyl)piperidine-1-carboxylate

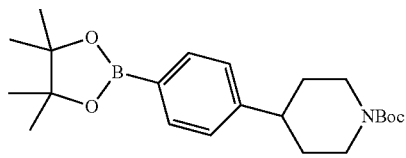 [SMILES: CC(C)(C)OC(=O)N1CCC(c2ccc(B3OC(C)(C)C(C)(C)O3)cc2)CC1]

Step A: tert-butyl 4-(4-bromophenyl)-4-hydroxypiperidine-1-carboxylate

A solution of 1,4-dibromobenzene (35.5 g, 150 mmol) in THF (250 mL) at −78° C. was treated with n-BuLi (2.5 M, 60 mL, 150 mmol) and stirred for 1 hour, followed by N-Boc-4-piperidone (10.0 g, 50 mmol) in THF (20 mL). After 1 hour the cooling bath was removed and the reaction mixture was stirred for 16 hours at 20° C. The mixture was diluted with saturated aqueous NH$_4$Cl, extracted with ethyl acetate, and the combined organic layers were washed with 0.1N HCl, brine, dried over anhydrous Na$_2$SO$_4$ and concentrated to get the crude product, which was purified by silica gel (PE:EA=10:1) to obtain the title compound. $^1$H NMR (300 MHz, CDCl3) δ: 7.48 (d, J1=6.9 Hz, J2=1.8 Hz, 2H), 7.34 (d, J1=6.9 Hz, J2=1.8 Hz, 2H), 4.02 (brs, 2H), 3.21 (brt, J=12.3 Hz, 2H), 1.91 (m, 2H), 1.61-1.71 (m, 3H), 1.47 (s, 9H).

Step B: 4-(4-bromophenyl)-1,2,3,6-tetrahydropyridine

A mixture of tert-butyl 4-(4-bromophenyl)-4-hydroxypiperidine-1-carboxylate (2.0 g, 14 mmol) in acetic acid (1 mL) and concentrated HCl (10 mL) was heated at 100° C. for 16 hours. The reaction mixture was cooled and washed with EA. The aqueous layer was basified by saturated NaHCO$_3$ solution and the solid K$_2$CO$_3$ to pH 8. Then the mixture was extracted with EA, dried and concentrated to obtain the title compound. $^1$H NMR (300 MHz, CDCl3) δ: 7.44 (d, J=8.7 Hz, 2H), 7.24 (d, J=9.0 Hz, 2H), 6.12 (s, 1H), 4.70 (brs, 1H), 3.51 (d, J=3.0 Hz, 2H), 3.10 (t, J=5.7 Hz, 2H), 2.42 (t, J=1.5 Hz, 2H).

Step C: tert-butyl 4-(4-bromophenyl)-5,6-dihydropyridine-1(2H)-carboxylate

To an ice-cooled mixture of 4-(4-bromophenyl)-1,2,3,6-tetrahydropyridine (1.3 g, 5.46 mmol) in 1,4-dioxane (4 mL) and 1N NaOH (6 mL) was added a solution of Boc$_2$O (1.2 g, 5.46 mmol) in 1,4-dioxane (4 mL) and the mixture was stirred for 2 hours at room temperature and concentrated to remove the dioxane, then extracted with EA. The combined organic layers were washed with 0.1 N HCl, water and brine, dried over anhydrous Na$_2$SO$_4$, and concentrated to obtain the title compound. $^1$H NMR (300 MHz, CDCl3) δ: 7.43 (d, J=8.7 Hz, 2H), 7.23 (d, J=8.4 Hz, 2H), 6.04 (brs, 1H), 4.06-4.10 (m, 2H), 3.62 (m, 2H), 2.49 (m, 2H), 1.48 (s, 9H).

Step D: tert-butyl 4-(4-(4,4,5,5-tetramethyl-1,3,2-dioxaborolan-2-yl)phenyl)-5,6-dihydropyridine-1(2H)-carboxylate To a solution of tert-butyl 4-(4-bromophenyl)-5,6-dihydropyridine-1(2H)-carboxylate (1.4 g, 4.1 mmol) in DMSO (30 mL) was added bis(pinacolato)-diboron (1.6 g, 6.2 mmol), Pd(PPh$_3$)$_2$Cl$_2$ (0.35 g) and KOAc (1.2 g, 12.3 mmol). The reaction mixture was heated at 100° C. for 16 hours under N$_2$. The reaction mixture was cooled and filtered, diluted with water (400 mL), and extracted with DCM (200 mL×3). The combined organic phases were washed with water and brine, then dried and concentrated. The crude product was purified by silica gel to obtain the title compound. $^1$H NMR (300 MHz, CDCl3) δ: 7.78 (d, J=8.4 Hz, 2H), 7.37 (d, J=8.4 Hz, 2H), 6.10 (s, 1H), 4.08 (s, 2H), 3.63 (m, 2H), 2.54 (m, 2H), 1.50 (s, 9H), 1.36 (s, 12H).

Step E: tert-butyl 4-(4-(4,4,5,5-tetramethyl-1,3,2-dioxaborolan-2-yl)phenyl)piperidine-1-carboxylate To the solution of tert-butyl 4-(4-(4,4,5,5-tetramethyl-1,3,2-dioxaborolan-2-yl)phenyl)-5,6-dihydropyridine-1(2H)-carboxylate (6.0 g, 15.6 mmol) in methanol (150 mL) was added Pd/C (10%, 0.6 g). The reaction mixture was stirred at room temperature under hydrogen gas for 16 hours. The Pd/C was filtered off and the filtrate was concentrated to obtain the title compound. $^1$H NMR (300 MHz, CDCl$_3$) δ: 7.75 (d, J=7.2 Hz, 2H), 7.21 (d, J=6.9 Hz, 2H), 4.25 (s, 2H), 2.61-2.82 (m, 3H), 1.60-1.83 (m, 4H), 1.47 (s, 9H), 1.33 (s, 12H).

REFERENCE EXAMPLE 13

2-amino-4-oxo-3,4-dihydroquinazolin-8-ylboronic Acid

Step A: 8-bromo-1H-benzo[d][1,3]oxazine-2,4-dione

Pyridine (2.20 g, 27.8 mmol) was added dropwise to a stirred solution of 2-amino-3-bromobenzoic acid (2.0 g, 9.3 mmol) and bis(trichloromethyl) carbonate (3.30 g, 11.1 mmol) in acetonitrile (30 ml)/CH$_2$Cl$_2$ (10.0 ml) at room temperature. The reaction mixture was stirred for 2 hours at 55° C. The reaction mixture was quenched with water (30 mL), then extracted with DCM (2×30 mL). The combined organic layers were washed with brine (30 mL), dried over anhydrous sodium sulfate and filtered. The filtrate was concentrated under vacuum to give crude title compound. The residue was used directly in the next step.

Step B: 2-amino-8-bromoquinazolin-4(3H)-One

Cyanamide (0.35 g, 8.3 mmol) was added to a stirred mixture of 8-bromo-1H-benzo[d][1,3]oxazine-2,4-dione (1.0 g, 4.13 mmol) and potassium hydroxide (0.70 g, 12.4 mmol) in DMF (20 ml) at room temperature. The reaction mixture was stirred for 3 hours at 100° C. to obtain the desired product. Upon completion of the reaction, the mixture was cooled to room temperature, HCl (1N, 13 ml) was added and the reaction concentrated. The residue was purified by silica gel chromatography, and eluted with methanol/dichloromethane (1/20). The combined organic fractions were concentrated under reduced pressure to give the title compound: LCMS [M+1]$^+$: 240/242. $^1$H NMR (400 MHz, DMSO, δ$_6$) δ 7.96 (dd, J=8.0 Hz, 2H), 7.85 (brs, 1H), 7.60 (brs, 2H), 7.14 (dd, J=7.6 Hz, 1H).

Step C: (2-amino-4-oxo-3,4-dihydroquinazolin-8-yl)boronic Acid

Potassium acetate (0.37 g, 3.8 mmol) was added to a stirred mixture of 5,5,5',5'-tetramethyl-2,2'-bi(1,3,2-dioxaborinane) (0.34 g, 1.5 mmol), 2-amino-8-bromoquinazolin-4(3H)-one (0.30 g, 1.3 mmol) and chloro(triphenylphosphine)[2-(2'-amino-1,1'-biphenyl)]palladium(II) (143 mg, 0.3 mmol) in dioxane (15.0 ml) at room temperature under Ar condition. The reaction mixture was stirred for 3 hours at 80° C., and concentrated. The product was purified by flash-MPLC with the following conditions: Column, C 18, 120 g; mobile phase: water (0.05% TFA) and acetonitrile; Detector, UV 220 and 254 nm. The collected fractions were combined and concentrated under vacuum to give the title compound: LCMS [M+1]$^+$: 206

REFERENCE EXAMPLE 14

2-amino-7-(trifluoromethyl)benzo[d]thiazol-4-ylboronic Acid

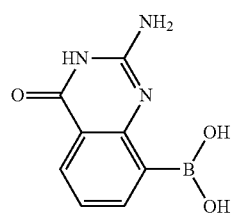 [SMILES: Nc1nc2c(B(O)O)cccc2c(=O)[nH]1]

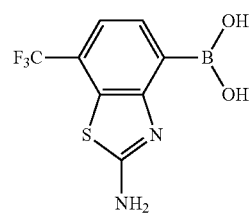

Step A: N-((2-bromo-5-(trifluoromethyl)phenyl) carbamothioyl)benzamide

To a solution of benzoyl isothiocyanate (3.85 g, 23.59 mmol) in acetone (50 mL) was added 2-bromo-5-(trifluoromethyl)aniline (5.66 g, 23.59 mmol) at 70° C. dropwise. Then the mixture was stirred at 70° C. for 0.5 hour. The reaction mixture was poured onto ice/water (100 mL). The resulting mixture was stirred for 10 minutes, and the mixture was filtered. The filtrate cake was washed by water (10 mL) and dried under vacuum to give the title compound: LCMS [M+H]$^+$: 403, 405 (1:1); $^1$H NMR (400 MHz, DMSO-d$_6$): δ 8.34 (s, 1H), 8.06-7.99 (m, 2H), 7.80-7.52 (m, 5H).

Step B: 1-(2-bromo-5-(trifluoromethyl)phenyl)thiourea

N-((2-bromo-5-(trifluoromethyl)phenyl)carbamothioyl) benzamide (5.0 g, 12.4 mmol) was added to 1 N aqueous sodium hydroxide (50 ml, 12.5 mmol) at room temperature. The reaction mixture was stirred at 80° C. for 1 hour. The reaction mixture was poured onto ice/hydrochloric acid (6 M, 30 mL) and stirred for 10 minutes. The pH was adjusted to 10 with conc. ammonium hydroxide solution, then the resulting precipitate was filtered and washed with water (10 mL) and dried. The crude solid was purified by column chromatography, eluting with a gradient (20%-50%) of ethyl acetate/petroleum ether, to give the title compound: LCMS [M+H]$^+$:299, 301 (1:1); $^1$H NMR (300 MHz, DMSO-d$_6$): δ 9.43 (s, 1H), 8.21-8.01 (brs, 1H), 8.08 (s, 1H), 7.89 (d, J=8.4 Hz, 1H), 7.78-7.55 (brs, 1H), 7.57 (d, J=8.4 Hz, 1H).

Step C: 4-bromo-7-(trifluoromethyl)benzo[d]thiazol-2-amine

Bromine (0.138 ml, 2.67 mmol) in acetic acid (1.000 ml) was added to a solution of 1-(2-bromo-5-(trifluoromethyl) phenyl)thiourea (200 mg, 0.669 mmol) in acetic acid (5 ml). The reaction mixture was stirred at 110° C. overnight under nitrogen. The reaction mixture was cooled, then aqueous sodium sulfite (10%, 30 mL) was added and the mixture was extracted with ethyl acetate (3×20 mL). The combined organic fractions were washed with brine (30 mL), dried (Na$_2$SO$_4$), filtered and the filtrate was concentrated under reduced pressure. The residue was purified by column chromatography, eluting with ethyl acetate/petroleum ether (0-40%) to give the title compound. LCMS [M+H]$^+$: 297, 299 (1:1); $^1$H NMR (400 MHz, DMSO-d$_6$): δ 8.22 (brs, 2H), 7.67 (d, J=8.4 Hz, 1H), 7.29 (d, J=8.4 Hz, 1H).

Step D: (2-amino-7-(trifluoromethyl)benzo[d]thiazol-4-yl)boronic Acid

4-Bromo-7-(trifluoromethyl)benzo[d]thiazol-2-amine (700 mg, 2.356 mmol), 4,4,4',4',5,5,5',5'-octamethyl-2,2'-bi (1,3,2-dioxaborolane) (2.99 g, 11.78 mmol), Pd(dppf)Cl$_2$ (519 mg, 0.707 mmol) and potassium acetate (694 mg, 7.07 mmol) were added to 1,4-dioxane (12 ml). The mixture was degassed 3 times with N$_2$, and stirred at 80° C. for 16 hours. The reaction mixture was filtered; the filtrate was collected and concentrated under vacuum. Then the residue was applied on Flash with C18 silica gel column (MeOH/water 0-10%) to give the title compound: LCMS [M+H]$^+$: 263; $^1$H NMR (400 MHz, DMSO-d$_6$): δ 7.74 (d, J=8.0 Hz, 1H), 7.43 (d, J=8.0 Hz, 1H).

REFERENCE EXAMPLE 15

2-amino-4-methylbenzo[d]thiazol-7-ylboronic Acid

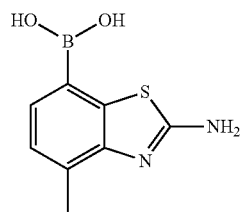

Step A: N-(4-bromo-2-methylphenylcarbamothioyl)benzamide 5-bromo-2-methylbenzenamine (10 g, 54 mmol) was added into a solution of benzoic cyanic thioanhydride (8.8 g, 54 mmol) in acetone (100 ml) at room temperature and stirred at 80° C. for 1 hour. The reaction solution was cooled and filtered. The filtrate was washed with EA and dried to give the title compound. LCMS [M+H]$^+$: 349, $^1$H NMR (DMSO-d6, 400 MHZ): δ 12.30 (s, 1H), 9.15 (s, 1H), 8.04 (d, J=2.0 Hz, 1H), 7.90 (d, J=5.2 Hz, 2H), 7.68-7.65 (m, 1H), 7.58-7.54 (m, 2H), 7.36 (dd, J=1.2 Hz, 1H), 7.36 (d, J=8.0 Hz, 1H), 2.34 (s, 3H).

Step B: N-(7-bromo-4-methylbenzo[d]thiazol-2-yl) benzamidene

Br$_2$ (4.20 ml, 82 mmol) in chloroform (50 ml) was added dropwise to a stirred solution of 1-(2-bromo-5-methylphenyl)thiourea (10 g, 29 mmol) in chloroform (200 ml) in an ice bath and then stirred at 80° C. for 4 hours. The reaction mixture was concentrated under vacuum and washed with EA (100 ml). The mixture was filtered and the filter cake was dried to give the title compound. LCMS [M+H]$^+$: 347, $^1$H NMR (DMSO-d6, 400 MHZ): δ8.10-8.02 (m, 2H), 7.67-7.55 (m, 3H), 7.42-7.34 (m, 1H), 7.18-12 (m, 1H), 2.69-2.63 (m, 3H).

Step C: 7-bromo-4-methylbenzo[d]thiazol-2-amine

A solution of N-(7-bromo-4-methylbenzo[d]thiazol-2-yl) benzamide (5.1 g, 14 mmol) and NaOH (5.6 g, 140 mmol) in water (100 ml) and MeOH (100 ml) was stirred at RT for 1 hour. The reaction mixture was diluted with water (80 mL) and extracted with DCM (3×80 mL). The combined organic layers were washed with water (1×30 mL) and brine (1×30 mL), dried over anhydrous sodium sulfate and filtered. The filtrate was concentrated under vacuum to give the title compound. LCMS [M+H]$^+$: 243, $^1$H NMR (DMSO-d6, 400 MHZ): δ 7.83 (s, 2H), 7.09 (d, J=8.0 Hz, 1H), 6.77 (d, J=8.0 Hz, 1H), 2.36 (s, 3H).

Step D: 2-amino-4-methylbenzo[d]thiazol-7-yl boronic Acid

A solution of 7-bromo-4-methylbenzo[d]thiazol-2-amine (2.9 g, 14 mmol), 5,5,5',5'-tetramethyl-2,2'-bi(1,3,2-dioxaborinane) (2.79 g, 12.3 mmol), 2nd PCy3 (0.972 g, 1.645 mmol) and potassium acetate (2.422 g, 24.7 mmol) in 1,4-Dioxane (40 ml) was stirred at 80° C. for 16 hours. The reaction mixture was concentrated under vacuum and the solid was dissolved with EA (3000 ml). The solution was washed with water (15% NaOH) and the aqueous phase was adjusted to pH 3 with 2 M hydrochloric acid. The mixture was extracted with EA (3×1000 ml) and the organic layers were dried over anhydrous sodium sulfate and filtered. The filtrate was concentrated under vacuum to give the title compound. LCMS [M+H]$^+$: 209, $^1$H NMR (DMSO-d6, 400 MHZ): δ 6.89 (d, J=7.2 Hz, 1H), 6.55 (d, J=7.2 Hz, 1H), 1.73 (s, 1H).

REFERENCE EXAMPLE 16

2-amino-7-methylbenzo[d]thiazol-4-ylboronic Acid

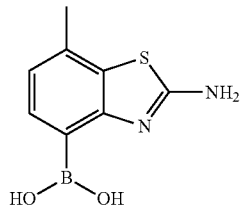

Step A: N-((2-bromo-5-methylphenyl)carbamothioyl)benzamide 2-bromo-5-methylbenzenamine (10 g, 54 mmol) was added into a solution of benzoic cyanic thioanhydride (8.8 g, 54 mmol) in acetone (100 ml) at room temperature and stirred at 80° C. for 1 hour. The reaction solution was cooled and filtered. The filtrate was washed with EA and dried to give the title compound as a solid. LCMS [M+1]$^+$349; $^1$H NMR (DMSO-d6, 400 MHZ): δ 12.54 (s, 1H), 9.16 (s, 1H), 8.06 (s, 1H), 7.90 (d, J=8.4 Hz, 2H), 7.73-7.65 (m, 1H), 7.60-7.54 (m, 3H), 7.20 (dd, J=8.0 Hz, 1H), 2.42 (s, 3H).

Step B: 1-(2-bromo-5-methylphenyl)thiourea

A solution of N-((2-bromo-5-methylphenyl)carbamothioyl)benzamide (5 g, 14 mmol) and NaOH (5.6 g, 140 mmol) in water (100 ml) and MeOH (100 ml) was stirred at 80° C. for 3 hours. The reaction mixture was diluted with water (80 mL) and extracted with DCM (3×80 mL). The combined organic layers were washed with water (3×10 mL) and brine (3×10 mL), dried over anhydrous sodium sulfate and filtered. The filtrate was concentrated under vacuum to give the title compound as a solid. LCMS [M+1]$^+$245; $^1$H NMR (DMSO-d6, 400 MHZ): δ 9.20 (s, 1H), 7.94 (d, J=7.2 Hz, 1H), 7.50 (d, J=8.0 Hz, 2H), 7.53 (s, 1H), 6.99 (dd, J=1.2 Hz, 1H), 2.26 (s, 3H).

Step C: 4-bromo-7-methylbenzo[d]thiazol-2-amine

Br$_2$ (4.20 ml, 82 mmol) in chloroform (50 mL) was added dropwise to a stirred solution of 1-(2-bromo-5-methylphenyl)thiourea (3.1 g, 13 mmol) in chloroform (200 mL) in an ice bath and then stirred at 80° C. for 4 hours. The reaction mixture was concentrated under vacuum and washed with EA (3×30 ml). The mixture was filtered and the filter cake was dried to give the title compound as a solid. LCMS [M+1]$^+$243; $^1$H NMR (DMSO-d6, 300 MHZ): δ 7.81 (s, 2H), 7.34 (d, J=10.8 Hz, 1H), 6.77 (d, J=10.8 Hz, 1H), 2.30 (s, 3H).

Step D: (2-amino-7-methylbenzo[d]thiazol-4-yl)boronic Acid

A solution of 4-bromo-7-methylbenzo[d]thiazol-2-amine (2.0 g, 8.3 mmol), 5,5,5',5'-tetramethyl-2,2'-bi(1,3,2-dioxaborinane) (2.79 g, 12.3 mmol), 2nd PCy$_3$ (0.972 g, 1.645 mmol) and potassium acetate (2.422 g, 24.7 mmol) in 1,4-Dioxane (40 ml) was stirred at 80° C. for 16 hours. The reaction mixture was concentrated under vacuum and the solid was dissolved with EA (300 ml). The solution was washed with water (15% NaOH) and the aqueous phase was adjust to pH 3 with 2 M HCl, and then extracted with EA (3×100 ml). The organic layers were dried over anhydrous sodium sulfate and filtered. The filtrate was concentrated under vacuum to give the title compound as a solid. LCMS [M+1]$^+$209; $^1$H NMR (DMSO-d6, 300 MHZ): δ 7.84 (s, 2H), 7.33 (d, J=8.0 Hz, 1H), 6.78 (d, J=8.0 Hz, 1H), 2.31 (s, 3H).

REFERENCE EXAMPLE 17

2-aminobenzo[d]oxazol-7-ylboronic Acid

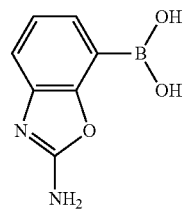 [SMILES: Nc1nc2cccc(B(O)O)c2o1]

Step A: 7-bromobenzo[d]oxazol-2-amine

A mixture of 2-amino-6-bromophenol (5 g, 26.6 mmol) and cyanogen bromide (1.67 ml, 31.9 mmol) in DCM (25 ml) and MeOH (50 ml) was stirred at RT for 4 hours. The resulting mixture was quenched with aqueous sodium hydrogen carbonate (200 mL), then diluted with water (200 mL). The precipitated solid was collected and dried under vacuum to give the title compound as a solid. LCMS [M+H]$^+$: 213; $^1$H NMR (DMSO-d6, 400 MHZ): δ 7.69 (s, 2H), 7.19-7.10 (m, 2H), 7.07-7.03 (m, 1H).

Step B: 2-aminobenzo[d]oxazol-7-ylboronic Acid

A mixture of 7-bromobenzo[d]oxazol-2-amine (1.00 g, 4.69 mmol), 2nd generation PCy3 precatalyst (0.554 g, 0.939 mmol), bis(pinacolato)diboron (2.38 g, 9.39 mmol) and potassium acetate (0.921 g, 9.39 mmol) in 1,4-Dioxane (4 mL) was stirred at 80° C. for 4 hours under nitrogen. The reaction mixture was concentrated under reduced pressure and then the residue was purified by Prep-HPLC with the following conditions: Column, Sunfire C$^{18}$, 19×150 mm; mobile phase: water (0.05% TFA) and acetonitrile (Gradient time: 7 min. B %: 10%-20%); Detector, UV 220 and 254 nm. The collected fractions were combined and concentrated under reduced pressure to give the title compound as a solid. LCMS [M+1]$^+$179; $^1$H NMR (DMSO-d6, 400 MHZ): 8.32-8.29 (brs, 2H), 7.38-7.33 (m, 1H), 7.28-7.27 (m, 1H), 7.18-7.12 (m, 1H).

REFERENCE EXAMPLE 18

2-aminobenzo[d]oxazol-4-ylboronic Acid

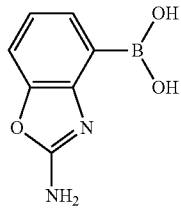 [SMILES: Nc1nc2c(B(O)O)cccc2o1]

Step A: 4-bromobenzo[d]oxazol-2-amine

A mixture of 2-amino-3-bromophenol (5 g, 26.6 mmol) and cyanic bromide (1.673 ml, 31.9 mmol) in DCM (25 ml) and MeOH (50 ml) was stirred at room temperature for 4 hr. The resulting mixture was quenched with aqueous sodium hydrogen carbonate (500 mL), diluted with water (20 mL) and extracted with DCM (3×20 mL). The combined organic layers were washed with water (3×10 mL) and brine (3×10 mL), dried over anhydrous sodium sulfate and filtered. The filtrate was concentrated under reduced pressure to give the title compound as a solid. LCMS [M+1]$^+$213; $^1$H NMR (DMSO-d6, 400 MHZ): 7.70 (s, 2H), 7.35 (s, J=7.6 Hz, 1H), 7.30 (s, J=8.4 Hz, 1H), 6.93-6.89 (m, 1H).

Step B: 2-aminobenzo[d]oxazol-4-ylboronic Acid

A solution of 4-bromobenzo[d]oxazol-2-amine (1.00 g, 4.69 mmol), Pd(dppf)Cl$_2$·CH$_2$Cl$_2$ (0.686 g, 0.939 mmol), bis(nneopentylglycolato)diboron (1.060 g, 4.69 mmol) and potassium acetate (0.921 g, 9.39 mmol) in 1,4-Dioxane (30 ml) was stirred at 80° C. for 24 hours under nitrogen. The reaction mixture was concentrated under reduced pressure and the residue was purified by Prep-HPLC with the following conditions: Column, Sunfire C 18, 19×150 mm; mobile phase: water (0.05% TFA) and acetonitrile (Gradient time: 7 min. B %: 10%-20%); Detector, UV 220 and 254 nm. The collected fractions were combined and concentrated under reduced pressure to give the title compound as a solid. LCMS [M+1]$^+$: 179.

REFERENCE EXAMPLE 19

6-(4,4,5,5-tetramethyl-1,3,2-dioxaborolan-2-yl)-1H-benzo[d]imidazol-2-amine

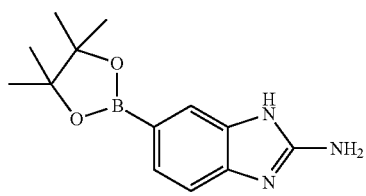 [SMILES: CC1(C)OB(c2ccc3nc(N)[nH]c3c2)OC1(C)C]

Step A: 2-nitro-4-(4,4,5,5-tetramethyl-1,3,2-dioxaborolan-2-yl)aniline

Into a 500-mL RBF purged and maintained with an inert atmosphere of argon, was placed a solution of 4,4,4',4',5,5, 5',5'-octamethyl-2,2'-bi(1,3,2-dioxaborolane) (25.70 g, 101.00 mmol), 4-bromo-2-nitroaniline (20.00 g, 92.00 mmol) and potassium acetate (27.10 g, 276.00 mmol) in DMF (250 mL). This was followed by the addition of PdOAc$_2$ (0.62 g, 2.76 mmol) at room temperature. The resulting mixture was stirred at 85° C. for 20 hours under argon. The reaction mixture was cooled to 20° C., quenched with water (200 mL) and filtered. The filtrate was concentrated under vacuum. The residue was purified by silica gel column chromatography, eluted with EA in PE (50%) to afford the crude product. The crude product was recrystallized from PE/EA (200 mL/10 mL), the solid was collected by filtration and dried over in vacuum to afford the title compound as a solid: LCMS [M+H]$^+$: 265; $^1$H NMR (400 MHz, DMSO-d$_6$): δ 8.26 (s, 1H), 7.70 (s, 2H), 7.55 (d, J=8.4 Hz, 1H), 6.97 (d, J=8.4 Hz, 1H), 1.27 (s, 12H).

Step B: 4-(4,4,5,5-tetramethyl-1,3,2-dioxaborolan-2-yl)benzene-1,2-diamine

Into a 250-mL RBF, was placed a solution of 2-nitro-4-(4,4,5,5-tetramethyl-1,3,2-dioxaborolan-2-yl)aniline (7.40 g, 25.20 mmol) in MeOH (50 mL) and DCM (50 mL). This was followed by the addition of Pd/C (134 g, 126 mmol, wet 10%) at room temperature. The reaction mixture was degassed with nitrogen 3 times and stirred under hydrogen for 16 hours at room temperature. The mixture was filtered. The filter cake was washed with DCM (3×10 mL). The combined organic layers were concentrated under reduced pressure and purified by silica gel column chromatography, eluted with EA in PE (30%) to afford the title compound as a solid: LCMS [M+H]$^+$: 235; $^1$H NMR (400 MHz, CD$_3$Cl): δ 7.23 (d, J=7.6 Hz, 1H), 7.17 (s, 1H), 6.70 (d, J=8.0 Hz, 1H), 3.19 (br, 4H), 1.32 (s, 12H).

Step C: 6-(4,4,5,5-tetramethyl-1,3,2-dioxaborolan-2-yl)-1H-benzo[d]imidazol-2-amine Into a 50-mL RBF purged and maintained with an inert atmosphere of argon, was placed a solution of 4-(4,4,5,5-tetramethyl-1,3,2-dioxaborolan-2-yl)benzene-1,2-diamine (2.00 g, 7.69 mmol) in MeOH (10 mL). This was followed by the addition of cyanogen bromide (0.83 g, 7.69 mmol) at 0° C. The resulting mixture was stirred at 0° C. for 2 hours under argon. The reaction was quenched with aqueous saturated sodium bicarbonate (30 mL) and extracted with EA (3×30 mL). The combined organic layers were washed with brine (70 mL), dried over anhydrous sodium sulfate and filtered. The filtrate was evaporated under reduced pressure and the residue was recrystallized from DCM (100 mL). The solid was collected by filtration and dried under reduced pressure to afford the title compound as a solid: LCMS [M+H]$^+$: 260; $^1$H NMR (400 MHz, DMSO-d$_6$): δ 10.70 (br, 1H), 7.40 (s, 1H), 7.23 (d, J=8.0 Hz, 1H), 7.06 (d, J=7.6 Hz, 1H), 6.24 (s, 2H), 1.23 (s, 12H).

REFERENCE EXAMPLE 20

7-amino-1,8-naphthyridin-4-ylboronic Acid

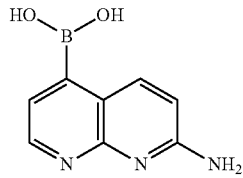

Step A: N-(6-aminopyridin-2-yl)acetamide

In a 100 mL three-necked RBF, acetic anhydride (2.1 ml, 27.5 mmol) in 20 mL THF was added dropwise to a stirred mixture of pyridine-2,6-diamine (3.00 g, 27.5 mmol) and triethylamine (2.78 g, 27.5 mmol) in THF (40 ml) at 0° C. After the reaction mixture was stirred at room temperature overnight, it was diluted with water (10 mL) and extracted with ethyl acetate (3×20 mL). The combined organic layers were washed with brine (2×10 mL), dried over anhydrous sodium sulfate and filtered. The filtrate was concentrated under vacuum. The residue was purified by silica gel column chromatography, eluted with ethyl acetate/petroleum ether (10/1) to give the title compound as a solid. LCMS [M+1]$^+$: 152; $^1$H NMR (300 MHz, CD$_3$OD): δ 7.38-7.32 (m, 1H), 718 (d, J=7.8 Hz, 1H), 6.24 (d, J=8.1 Hz, 1H), 2.08 (s, 3H).

Step B: N-(6-(((2,2-dimethyl-4,6-dioxo-1,3-dioxan-5-ylidene)methyl)amino)pyridin-2-yl)acetamide In a 25 mL RBF, 5-(methoxymethylene)-2,2-dimethyl-1,3-dioxane-4,6-dione (6.06 g, 32.5 mmol) was added to a stirred mixture of N-(6-aminopyridin-2-yl)acetamide (4.10 g, 27.1 mmol) in EtOH (5 ml) at room temperature. After the reaction mixture was stirred at 80° C. for 3 hours, it was cooled to RT and then concentrated under vacuum to give the title compound as a solid. LCMS [M+1]$^+$: 306; $^1$H NMR (300 MHz, CDCl$_3$): δ 11.18 (s, 1H), 9.27 (d, J=4.2 Hz, 1H), 8.06 (d, J=8.4 Hz, 1H), 7.90 (s, 1H), 7.77-7.72 (m, 1H), 6.73 (d, J=7.8 Hz, 1H), 2.26 (s, 3H), 1.76 (s, 6H).

Step C: N-(5-hydroxy-1,8-naphthyridin-2-yl)acetamide

In a 250 mL three-necked RBF, N-(6-(((2,2-dimethyl-4,6-dioxo-1,3-dioxan-5-ylidene)methyl)amino)pyridin-2-yl)acetamide (6.00 g, 19.65 mmol) was added slowly to a bottle of oxydibenzene (60 ml, 19.65 mmol) at 250° C. The reaction mixture was stirred at 250° C. for 15 min. After the resulting mixture was cooled to RT, ethoxyethane (100 mL) was added and some solid precipitated out. The solids were collected to give the title compound. LCMS [M+1]$^+$: 204; $^1$H NMR (300 MHz, DMSO-d6): δ 11.60 (s, 1H), 10.69 (s, 1H), 8.37 (d, J=7.5 Hz, 1H), 8.05 (d, J=8.7 Hz, 1H), 7.80 (d, J=7.8 Hz, 1H), 6.02 (d, J=7.5 Hz, 1H), 2.16 (s, 3H).

Step D: N-(5-bromo-1,8-naphthyridin-2-yl)acetamide

In a 25 mL RBF, phosphoryl tribromide (5.08 g, 17.7 mmol) was added to a stirred mixture of N-(5-hydroxy-1,8-naphthyridin-2-yl)acetamide (1.80 g, 8.86 mmol) in 1,4-dioxane (150 ml) at room temperature. The reaction mixture was stirred at 70° C. for 2 hours. The reaction was quenched with ice/water (20 mL), pH was adjusted to 8 with sodium carbonate and then extracted with ethyl acetate (3×20 mL). The combined organic layers were dried over sodium sulfate. The solid was filtered out. The filtrate was concentrated under vacuum to afford the title compound as a solid. LCMS [M+1]$^+$: 266, 268; $^1$H NMR (300 MHz, DMSO-d6): δ 11.26 (d, J=4.8 Hz, 1H), 8.81 (s, 1H), 8.57-8.49 (m, 2H), 7.88 (d, J=4.8 Hz, 1H), 2.27 (s, 3H).

Step E: 5-bromo-1,8-naphthyridin-2-amine

In a 25 mL RBF, N-(5-bromo-1,8-naphthyridin-2-yl)acetamide (0.30 g, 1.127 mmol) was added to a stirred mixture of 10% sulfuric acid (2 ml, 1.127 mmol) at 80° C. After the resulting mixture was stirred at 80° C. for 15 minutes, sodium carbonate was added to pH 8 and then extracted with ethyl acetate (3×20 mL). The organic layers were combined, dried over anhydrous sodium sulfate, and filtered. The filtrate was concentrated under vacuum to afford the title compound. LCMS [M+1]$^+$: 224, 226; $^1$H NMR (300 MHz, DMSO-d6): δ 8.50 (d, J=4.2 Hz, 1H), 8.08 (d, J=6.6 Hz, 1H), 7.48 (d, J=3.6 Hz, 1H), 7.11 (s, 2H), 6.93 (d, J=3.9 Hz, 1H).

Step F: 7-amino-1,8-naphthyridin-4-ylboronic Acid

In a 50 mL three-necked RBF, potassium acetate (26.30 mg, 0.268 mmol) was added to a stirred mixture of dichlorobis(tricyclohexylphosphine)palladium (9.88 mg, 0.013 mmol), 5-bromo-1,8-naphthyridin-2-amine (30.0 mg, 0.134 mmol), 4,4,4',4',5,5,5',5'-octamethyl-2,2'-bi(1,3,2-dioxaborolane) (0.10 g, 0.402 mmol) in dioxane (2 mL) at room temperature. The reaction mixture was stirred at 80° C. for 2 hr under nitrogen. The solid was filtered out. The filtrate was concentrated and the residue was purified by Prep-HPLC with the following conditions: Column, Xbridge C18, 19×150 mm; mobile phase: water (0.05% TFA) and acetonitrile (hold 34% acetonitrile for 8 min, hold 100% for 2 min, down to 34% in 2 min); Detector, UV 220 and 254 nm. The collected fractions were combined and concentrated under vacuum to give the title compound as a solid. LCMS [M+1]$^+$: 190; $^1$H NMR (300 MHz, CDCl$_3$): δ 8.88 (s 1H), 8.74 (d, J=6.6 Hz, 1H), 7.88 (t, J=6.6 Hz, 1H), 7.48 (d, J=3.6 Hz, 1H), 7.24-7.21 (m, 1H), 6.88-6.81 (m, 1H), 5.51 (brs, 2H).

REFERENCE EXAMPLE 21

(2-aminoquinolin-8-yl)boronic Acid

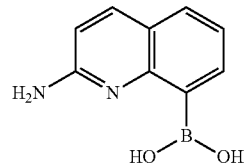

A solution of 8-bromoquinolin-2-amine (500 mg, 2.241 mmol), Pd(dppf)Cl$_2$ (328 mg, 0.448 mmol), bis(pinacolato)diboron (1138 mg, 4.48 mmol) and potassium acetate (440 mg, 4.48 mmol) in 1,4-dioxane (20 ml) was stirred at 80° C. for 2 hours under nitrogen. The reaction mixture was filtered and the filtrate was concentrated under vacuum to give crude product. The crude product was purified by column C18 eluting with CAN/0.05% TFA (15/85). The collected fractions were combined and concentrated under vacuum to give the title compound as a solid. LCMS [M+H]$^+$: 189; $^1$H NMR (300 MHz, CD$_3$OD): δ 8.32 (d, J=9.6 Hz, 1H), 8.20-8.10 (m, 1H), 7.94 (d, J=8.0 Hz, 1H), 7.64 (t, J=7.6 Hz, 1H), 7.13 (d, J=8.0 Hz, 1H),

REFERENCE EXAMPLE 22

8-(4,4,5,5-tetramethyl-1,3,2-dioxaborolan-2-yl)isoquinolin-3-amine

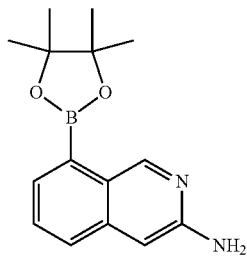 [SMILES: CC1(C)OB(c2cccc3cc(N)ncc23)OC1(C)C]

Step A: methyl 2,2-diethoxyacetimidate

Into a 100-mL RBF was placed a solution of 2,2-diethoxyacetonitrile (5.00 g, 38.83 mmol) and sodium methylate (30% in methanol, 1 mL) in methanol (30 mL) at room temperature. The resulting mixture was degassed with nitrogen 3 times and stirred at RT for 42 hours. The reaction was quenched with solid $CO_2$ and evaporated under vacuum. The residue was diluted with water (100 mL) and extracted with DCM (3×100 mL). The combined organics were washed with brine (200 mL), dried over anhydrous sodium sulfate and filtered. The solvent was evaporated under vacuum to yield the title compound: $^1$H NMR (400 MHz, $CD_3Cl$): δ 7.89 (s, 1H), 4.80 (s, 1H), 3.81 (s, 3H), 3.60-3.52 (m, 4H), 1.29-1.22 (m, 6H).

Step B: N-(2-bromobenzyl)-2,2-diethoxyacetimidamide

To a stirred solution of (2-bromophenyl)methanamine (3.44 g, 18.6 mmol) in methanol (40 mL) was added the solution of methyl 2,2-diethoxyacetimidate (3.6 g, 22.4 mmol) under argon atmosphere at room temperature, and the reaction was stirred for 3 hours. The mixture was evaporated under vacuum. The residue was diluted with DCM (300 mL) and washed with brine (3×200 mL), dried over anhydrous sodium sulfate and filtered. The solvent was evaporated under vacuum to yield the title compound: $^1$H NMR (400 MHz, $CD_3Cl$): 7.56-7.53 (m, 1H), 7.31-7.30 (m, 1H), 7.27-7.26 (m, 1H), 7.15-7.11 (m, 1H), 4.93 (s, 2H), 4.53 (s, 2H), 3.67-3.52 (m, 4H), 1.25-1.18 (m, 6H).

Step C: 8-bromoisoquinolin-3-amine

To the N-(2-bromobenzyl)-2,2-diethoxyacetimidamide (4.0 g, 12.7 mmol) was added conc. $H_2SO_4$ (58 g, 0.57 mmol) under argon atmosphere at 0° C. for 30 minutes and the reaction was stirred for 3 hours at 80° C. The mixture was poured into ice water and treated with 12 N NaOH at 0° C. until pH 12. The mixture was filtered and the filter cake was washed with water, and then dried. The crude product was purified by silica gel column chromatography, eluting with ethyl acetate/petroleum ether (1/2). This resulted in the title compound: LCMS [M+H]$^+$: 223, 225 (1:1); $^1$H NMR (400 MHz, $CD_3Cl$): δ 9.17 (s, 1H), 7.51-7.49 (m, 2H), 7.34-7.22 (m, 1H), 6.73 (s, 1H).

Step D: 8-(4,4,5,5-tetramethyl-1,3,2-dioxaborolan-2-yl)isoquinolin-3-amine

Into a 50-mL RBF was placed a mixture of 8-bromoisoquinolin-3-amine (950 mg, 4.26 mmol), 4,4,4',4',5,5,5',5'-octamethyl-2,2'-bi(1,3,2-dioxaborolane) (3.24 g, 12.78 mmol), Pd(dppf)Cl$_2$ (312 mg, 0.426 mmol), potassium acetate (1254 mg, 12.78 mmol) in 1,4-dioxane (38 ml) at room temperature. The resulting mixture was degassed with nitrogen 3 times and stirred at 80° C. for 5 hours. The mixture was filtered and the solvent was evaporated under reduced pressure. The residue was purified by column chromatography on silica gel Isolute Flash Si; 50 g prepacked, eluting with EA/PE (0-30%) to give the title compound. LCMS [M+H]$^+$: 271; $^1$H NMR (300 MHz, $CD_3Cl$): δ 9.73 (s, 1H), 7.88-7.86 (m, 1H), 7.66-7.64 (d, J=8.0 Hz, 1H), 7.56-7.53 (m, 1H), 6.83 (s, 1H), 4.09-5.01 (brs, 2H), 1.42-1.40 (m, 12H).

REFERENCE EXAMPLE 23

5-(4,4,5,5-Tetramethyl-1,3,2-dioxaborolan-2-yl)-1,7-naphthyridin-8-amine

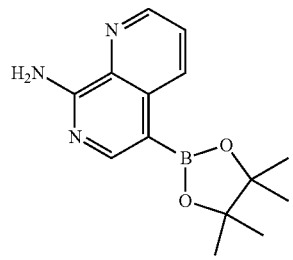 [SMILES: CC1(C)OB(c2cnc(N)c3ncccc23)OC1(C)C]

In a sealed tube, a mixture of chloro[di(1-adamantyl)-N-butylphosphine)2-(2-aminobiphenyl)]palladium(II) (0.060 g, 0.09 mmol), 4,4,4',4',5,5,5',5'-octamethyl-2,2'-bi(1,3,2-dioxaborolane) (0.453 g, 1.79 mmol), 5-bromo-1,7-naphthyridin-8-amine (0.200 g, 0.89 mmol) and potassium acetate (0.263 g, 2.68 mmol) in DMA (4 mL) was deoxygenated by bubbling a stream of nitrogen through 10 minutes. The tube was capped and the reaction mixture was heated to 85° C. overnight. After cooling, the mixture was filtered through CELITE and the filtrate partitioned between EtOAc and water. The organic phase was separated, washed with brine, dried (MgSO$_4$) and the volatiles removed under reduced pressure. The residue was purified by a 40 g C-18 column eluting with a mixture of acetonitrile and water, giving the title compound. LC/MS [M+H]+: 272.31.

REFERENCE EXAMPLE 24

3-Fluoro-6-(4,4,5,5-tetramethyl-1,3,2-dioxaborolan-2-yl)benzene-1,2-diamine and (2,3-diamino-4-fluorophenyl)boronic Acid

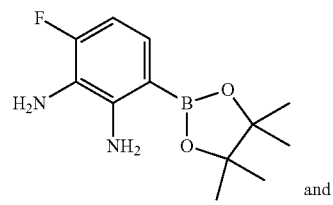

and

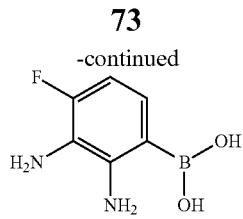

Step A: 3-chloro-6-fluoro-2-nitroaniline

To a solution of 3-chloro-2-nitroaniline (1 g, 5.79 mmol) in acetonitrile (20 mL), was added accufluor (1-fluoro-4-hydroxy-1,4-diazabicyclo[2.2.2]octane-1,4-diium tetrafluoroborate; 3.73 g, 11.59 mmol). The mixture was heated to 85° C. overnight under $N_2$. After cooling, the solvent was removed under reduced pressure and the resulting residue was purified by silica gel column chromatography using a gradient of EtOAc in hexanes as eluent to give the desired product. [LC/MS [M+H]+: 191.28]

Step B: 3-chloro-6-fluorobenzene-1,2-diamine

To a solution of 3-chloro-6-fluoro-2-nitroaniline (350 mg, 1.84 mmol) in EtOAc (20 mL) was added Pd/C (35 mg). The reaction mixture was shaked in a Parr bottle under 40 psi $H_2$ overnight. The reaction was stopped and the mixture was filtered through a CELITE pad. The filtrate was collected and the volatiles removed under reduced pressure. The resulting residue was purified by silica gel column chromatography using a gradient of EtOAc in hexanes as eluent to give the desired product. [LC/MS [M+H]+: 161.23]

Step C: 3-Fluoro-6-(4,4,5,5-tetramethyl-1,3,2-dioxaborolan-2-yl)benzene-1,2-diamine and (2,3-diamino-4-fluorophenyl)boronic Acid In a sealed tube, a mixture of chloro[(tricyclohexylphosphine)2-(2'-aminobiphenyl)] palladium(II) (0.032 g, 0.06 mmol), 4,4,4',4',5,5,5',5'-octamethyl-2,2'-bi(1,3,2-dioxaborolane) (0.139 g, 0.55 mmol), 3-chloro-6-fluorobenzene-1,2-diamine (0.044 g, 0.27 mmol) and potassium acetate (0.081 g, 0.82 mmol) in DMA (4 mL) was deoxygenated by bubbling a stream of nitrogen through for 10 minutes. The tube was capped and the reaction mixture was heated to 85° C. overnight. After cooling, the mixture was filtered through CELITE and the filtrate partitioned between EtOAc and water. The organic phase was separated, washed with brine, dried ($MgSO_4$) and the volatiles removed under reduced pressure. The residue was purified by silica gel column chromatography using a gradient of EtOAc in hexanes as eluent to give the desired mixture of the ester [LC/MS [M+H]+: 253.30] and boronic acid LC/MS [M+H]+: 171.30.

REFERENCE EXAMPLE 25

2-aminobenzo[d]thiazol-7-ylboronic Acid

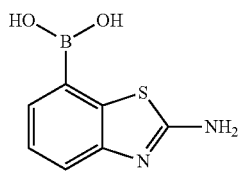 [SMILES: Nc1nc2cccc(B(O)O)c2s1]

A mixture of 4-bromobenzo[d]thiazol-2-amine (commercially available or prepared as described above, 2000 mg, 8.73 mmol) and bispinacolatodiboron (6651 mg, 26.2 mmol), potassium acetate (2570 mg, 26.2 mmol) and PCy3 Pd G2 (516 mg, 0.873 mmol) in dry dioxane (80 ml) was degassed, and heated at 80° C. for 48 hr. The mixture was concentrated, and the residue was dissolved in hydrochloric acid (2N, 100 mL). The aqueous was washed with ethyl acetate (60 mL), and concentrated. The residue was dissolved in methanol (50 ml). The solid was filtered off and the filtrate was concentrated to give a solid which was directly used. LCMS (M+1): 195.12.

REFERENCE EXAMPLES 26-29 below were prepared in an analagous fashion as described for REFERENCE EXAMPLE 25, starting from the aryl bromides starting materials (SM) indicated.

| REF EX NO | SM | Structure | Name | Calc'd Mass [M + H]+ | LC/MS m/e [M + H]+ |
|---|---|---|---|---|---|
| 26 | ![SM26] | ![Struct26] | (2-amino-3-cyanophenyl)boronic acid | 162.95 | 162.99 |
| 27 | ![SM27] | ![Struct27] | (2,3-diaminopyridin-4-yl)boronic acid | 154.07 | 154.1 |

| REF EX NO | SM | Structure | Name | Calc'd Mass [M + H]+ | LC/MS m/e [M + H]+ |
|---|---|---|---|---|---|
| 28 | (Br-benzimidazole) | (boronic acid benzimidazole) | (1H-benzo[d]imidazol-4-yl)boronic acid | 163.06 | 163.08 |
| 29 | (Boc-guanidino bromophenyl) | (Boc-guanidino phenyl boronic acid) | (2-(2-(tert-butoxycarbonyl)guanidino)phenyl)boronic acid | 281 | 281.29 |

REFERENCE EXAMPLE 30

Methyl 2-amino-3-(4,4,5,5-tetramethyl-1,3,2-dioxaborolan-2-yl)benzoate

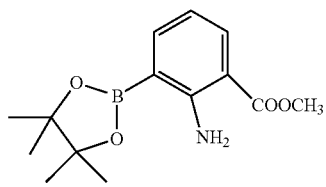 [SMILES: COC(=O)c1cccc(B2OC(C)(C)C(C)(C)O2)c1N]

A mixture of methyl 2-amino-3-bromobenzoate (4.26 g, 18.5 mmol), 4,4,4',4',5,5,5',5'-octamethyl-2,2'-bi(1,3,2-dioxaborolane) (14.1 g, 55.6 mmol), PCy3PdG2 (1.093 g, 1.852 mmol) and potassium acetate (5.45 g, 55.6 mmol) in dioxane (100 mL) was degassed and heated at 80° C. for 17 hours. The mixture was filtered through a CELITE pad, and the filtrate was partitioned between HCl (100 ml 2N) and EtOAc (100 ml). The organic was separated, and the aqueous was extracted with EtOAc (2×80). The combined organic layers were washed with brine, dried (MgSO4), and concentrated. The residue was purified by ISCO (120 g, EtOH-EtOAc (1:3) in hexane: 0-30% then 30%, then 70%). LCMS: 277.98.

REFERENCE EXAMPLE 31

2-Nitro-3-(4,4,5,5-tetramethyl-1,32-dioxaborolan-2-yl)aniline

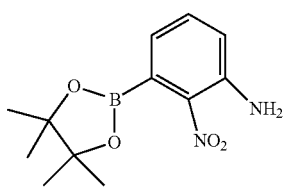 [SMILES: CC1(C)OB(c2cccc(N)c2[N+](=O)[O-])OC1(C)C]

2-Nitro-3-(4,4,5,5-tetramethyl-1,3,2-dioxaborolan-2-yl)aniline was made in the same way as that for REFERENCE EXAMPLE 30 starting from 3-bromo-2-nitroaniline. LCMS [M+1]: 265.14

REFERENCE EXAMPLE 32

(4,5-diaminopyridin-3-yl)boronic Acid

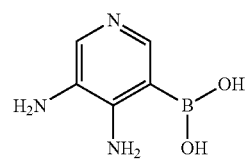

To a 25 mL RBF was added 5-bromopyridine-3,4-diamine (0.47 g, 2.5 mmol), 4,4,4',4',5,5,5',5'-octamethyl-2,2'-bi(1,3,2-dioxaborolane) (1.905 g, 7.50 mmol), chloro[(tricyclohexylphosphine)-2-(2'-aminobiphenyl)]Pd(II) (0.295 g, 0.5 mmol) and potassium acetate (0.245 g, 2.5 mmol) in dioxane (25 ml) and the reaction mixture was degassed and heated at 80° C. for 17 hours. The mixture was filtered and 50 ml 2N HCl was added to the filtrate, followed by addition of 50 mL of EtOAc. The aqueous layer was separated and concentrated in vacuo. The residue was dissolved in 10 ml of methanol. The inorganic salt was filtered off and the filtrate was concentrated. The crude solid was chromatographed over C18 column (80 g, Acetonitrile in H2O 0-100%) to give the desired product. LCMS: 154.13.

REFERENCE EXAMPLE 33

(2,3-diaminopyridin-4-yl)boronic Acid

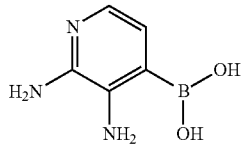 [SMILES: Nc1nccc(B(O)O)c1N]

To a 25 mL RBF was added 4-bromopyridine-2,3-diamine (0.564 g, 3.0 mmol), 4,4,4',4',5,5,5',5'-octamethyl-2,2'-bi(1,3,2-dioxaborolane) (2.285 g, 9.0 mmol), chloro[(tricyclohexylphosphine)-2-(2'-aminobiphenyl)]Pd(II) (0.354 g, 0.6 mmol) and potassium acetate (0.883 g, 9.0 mmol) in dioxane (25 ml). The reaction mixture was degassed and heated at 80° C. for 17 hours. The mixture was filtered 50 ml 2N HCl was added to the filtrate, followed by addition of 50 mL of EtOAc. The aqueous layer was separated and concentrated in vacuo. The residue was dissolved in 10 ml of methanol. The inorganic salt was filtered off and the filtrate was concentrated. The crude solid was chromatographed over C18 column (80 g, Acetonitrile in $H_2O$ 0-100%) to give the desired product (2,3-diaminopyridin-4-yl)boronic acid. LCMS: 154.12.

REFERENCE EXAMPLE 34

6-(4,4,5,5-tetramethyl-1,3,2-dioxaborolan-2-yl) benzo[d]oxazol-2-amine

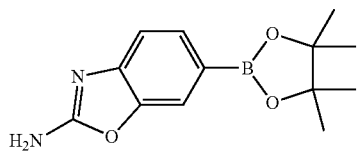 [SMILES: CC1(C)OB(c2ccc3nc(N)oc3c2)OC1(C)C]

In the reaction vessel 6-bromobenzo[d]oxazol-2-amine (500 mg, 2.347 mmol) and 4,4,4',4',5,5,5',5'-octamethyl-2,2'-bi(1,3,2-dioxaborolane) (1192 mg, 4.69 mmol) were combined, followed by 2nd Generation PCy3 precatalyst (277 mg, 0.469 mmol) and potassium acetate (691 mg, 7.04 mmol). Then dry 1,4-Dioxane (25 mL) was added to this flask. This mixture was degassed and then heated at 80° C. for 16 hours. The solid was removed by filtration, and the filtrate was concentrated under reduced pressure. The residue was dissolved in 20 ml ethyl acetate, and extracted with 2N HCl (2×150 ml). The aqueous was concentrated under reduced pressure. The crude material was applied onto silica gel column with ethyl acetate/petroleum ether (1:1) to get the product: LCMS [M+H]$^+$: 261; $^1$H NMR (400 MHz, CDCl$_3$): δ 7.70 (s, 1H), 7.66 (d, J=8.0 Hz, 1H), 7.33 (d, J=8.0 Hz, 1H), 5.89 (bs, 2H), 1.35-1.37 (m, 12H).

REFERENCE EXAMPLE 35

5-(4,4,5,5-tetramethyl-1,3,2-dioxaborolan-2-yl) benzo[d]oxazol-2-amine

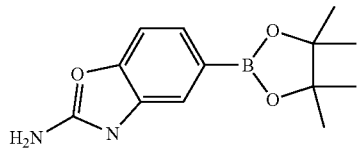

In the reaction vessel 5-bromobenzo[d]oxazol-2-amine (1 g, 4.69 mmol) and 4,4,4',4',5,5,5',5'-octamethyl-2,2'-bi(1,3,2-dioxaborolane) (1.788 g, 7.04 mmol) were combined, followed by 2nd Generation PCy3 precatalyst (551 mg, 0.939 mmol) and potassium acetate (1.382 g, 14.08 mmol). Then dry 1,4-Dioxane (25 mL) was added to this flask. This mixture was degassed and then heated at 80° C. for 16 hr. The solid was removed by filtration, and the filtrate was concentrated under reduced pressure. The residue was dissolved in 20 ml ethyl acetate, and extracted with 2N HCl (2×150 ml). The aqueous was concentrated under reduced pressure. The crude material was applied onto silica gel column with ethyl acetate/petroleum ether (1:1) to afford the title compound: LCMS [M+H]$^+$: 261; $^1$H NMR (400 MHz, CDCl$_3$): δ 7.78 (s, 1H), 7.55 (d, J=8.0 Hz, 1H), 7.28-7.26 (m, 1H), 5.98 (bs, 2H), 1.35-1.37 (m, 12H).

REFERENCE EXAMPLE 36

2-amino-1H-benzo[d]imidazol-4-ylboronic Acid

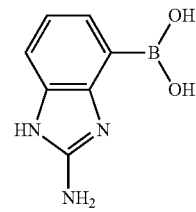

Step A: 4-bromo-1H-benzo[d]imidazol-2-amine

Cyanic bromide (74.3 g, 702 mmol) was added batchwise to a stirred solution of commercially available 3-bromobenzene-1,2-diamine (125 g, 668 mmol) in CH$_2$Cl$_2$ (500 ml), followed by addition of MeOH (1500 ml) at 0° C. The reaction solution was stirred for 5 hours at room temperature, and then concentrated to remove DCM. The residue was poured into 3500 ml of conc. aq. Na$_2$CO$_3$, filtered and washed with water (500 ml). The organic phase was dried over anhydrous Na$_2$SO$_4$, concentrated under reduced pressure to afford 110 g of 4-bromo-1H-benzo[d]imidazol-2-amine as a solid. LCMS [M+1]$^+$: 212/214; $^1$H NMR (400 MHz, DMSO d$_6$) δ 10.98 (brs, 1H), 7.09 (dd, J=8.4 Hz, 2H), 6.78-6.75 (m, 1H), 6.43 (brs, 2H).

Step B: (2-amino-1H-benzo[d]imidazol-7-yl)boronic Acid

Potassium acetate (83 g, 849 mmol) was added to a stirred mixture of 5,5,5',5'-tetramethyl-2,2'-bi(1,3,2-dioxaborinane)

(128 g, 566 mmol), 7-bromo-1H-benzo[d]imidazol-2-amine (60 g, 283 mmol) and chloro(triphenylphospine)[2-(2'-amino-1,1'-biphenyl)] palladium (II) (16.20 g, 28.3 mmol) in dioxane (1500 ml) at room temperature under Ar condition. The resulting mixture was stirred for 13 hours at 80° C., and then concentrated under reduced pressure. To the residue was added EA (3000 ml) and methanol (500 ml), then the reaction mixture was stirred for 30 minutes and filtered. The organic layer was extracted with 1N NaOH (4×250 ml), the aqueous layer was adjusted to pH=1 with 1N HCl. The aqueous layer was concentrated to 300 ml under vacuum and some solid precipitated out. The solid was collected and dried to give 60 g of (2-amino-1H-benzo[d]imidazol-7-yl) boronic acid. LCMS [M+1]$^+$: 178; $^1$H NMR (400 MHz, DMSO d$_6$) δ 12.61 (brs, 1H), 11.47 (brs, 1H), 8.24 (brs, 2H), 7.46 (dd, J=8.4 Hz, 2H), 7.22-7.18 (m, 1H).

REFERENCE EXAMPLE 37

2-amino-1-methyl-1H-benzo[d]imidazol-4-ylboronic Acid

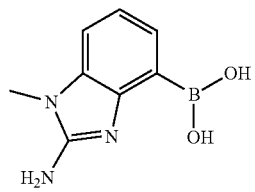

Step A: 3-bromo-N-methyl-2-nitrobenzenamine

A solution of 1-bromo-3-fluoro-2-nitrobenzene (10 g, 45.6 mmol) in NH$_2$CH$_3$ in THF (2 M, 100 ml) was stirred at 80° C. for 2 hours. The reaction mixture was concentrated under vacuum to give 3-bromo-N-methyl-2-nitrobenzenamine. LCMS [M+1]$^+$: 231, $^1$H NMR (CDCl$_3$, 400 MHZ): 7.21-7.16 (m, 1H), 6.97 (d, J=7.6 Hz, 1H), 6.76 (d, J=7.6 Hz, 1H), 2.94 (s, 3H).

Step B: 3-bromo-N1-methylbenzene-1,2-diamine

HCl (12 M) was added in drops into a stirred solution of 3-bromo-N-methyl-2-nitrobenzenamine (10.1 g, 44 mmol) and Zn dust (14 g, 0.2 mmol) in methanol (200 ml) at room temperature and stirred at room temperature for 2 hours. The reaction mixture was filtered and the filtrate was concentrated under vacuum to give 3-bromo-N1-methylbenzene-1,2-diamine. LCMS [M+1]$^+$: 201, $^1$H NMR (DMSO, 400 MHZ): 6.70 (d, J=8.0 Hz, 1H), 6.47 (t, J=8.0 Hz, 1H), 6.37 (d, J=8.0 Hz, 1H), 4.99 (s, 1H), 4.62 (s, 2H), 2.70 (s, 3H).

Step C: 4-bromo-1-methyl-1H-benzo[d]imidazol-2-amine

A solution of 3-bromo-N1-methylbenzene-1,2-diamine (3.2 g, 16 mmol) and BrCN (1.68 g, 16 mmol) in methanol (100 ml) was stirred at room temperature for 4 hours. The reaction mixture was poured into a saturated NaHCO$_3$ solution and filtered. The filter cake was dried to give the title compound. LCMS [M+1]$^+$: 226, $^1$H NMR (DMSO, 400 MHZ): 7.14-7.11 (m, 2H), 6.83-6.79 (m, 1H), 6.71 (s, 1H), 4.99 (s, 2H), 3.49 (s, 3H).

Step D: 2-amino-1-methyl-1H-benzo[d]imidazol-4-ylboronic Acid

A mixture of 4-bromo-1-methyl-1H-benzo[d]imidazol-2-amine (3.5 g, 15.5 mmol), bis(pinacolato)diboron (4.7 g, 18.6 mmol) and potassium acetate (4.5 g, 46.5 mmol) in 1,4-dioxane (100 ml) was stirred at 80° C. for 4 hours under nitrogen. The reaction mixture was concentrated under vacuum to give crude product. The product was purified by Prep-HPLC with the following conditions: Column, Sunfire C 18, 19×150 mm; mobile phase: water (0.05% TFA) and acetonitrile (Gradient time: 7 min. B %: 10%-20%); Detector, UV 220 and 254 nm. The collected fractions were combined and concentrated under vacuum to give 2-amino-1-methyl-1H-benzo[d]imidazol-4-ylboronic acid. LCMS [M+1]$^+$: 192.

REFERENCE EXAMPLE 38 tert-butyl 3-(3'-(N,N-bis(4-methoxybenzyl)sulfamoyl)-4'-bromo-2'-(2-(4-methoxybenzyl)-2H-tetrazol-5-yl)biphenyl-4-yl)azetidine-1-carboxylate

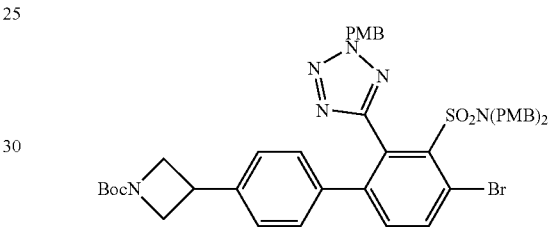

Step A: tert-butyl 3-(4-bromophenyl)azetidine-1-carboxylate

To a stirred solution of (4-bromophenyl)boronic acid (2.13 g, 10.60 mmol) in 2-propanol (20 mL) was added tert-butyl-3-iodoazetidine-1-carboxylate (2.00 g, 7.06 mmol) at room temperature. To the mixture was added (1S,2S)-2-aminocyclohexanol (0.08 g, 0.71 mmol), nickel (II) iodide (0.22 g, 0.71 mmol) and sodium bis(trimethylsilyl)amide (7.06 mL, 1.0 mol/L) under nitrogen. After the resulting mixture was stirred for 30 minutes at room temperature, it was irradiated with microwave radiation at 80° C. for 1 hours. The reaction was quenched with water (25 mL), extracted with EtOAc (3×150 mL). The combined organic layers were washed with brine (2×100 mL), dried over anhydrous Na$_2$SO$_4$ and concentrated under vacuum. The residue was purified by silica gel chromatography, eluted with EtOAc/PE (1/10) to afford the title compound: LCMS [M+H]$^+$: 312, 314 (1:1);

Step B: tert-butyl 3-(4-(4,4,5,5-tetramethyl-1,3,2-dioxaborolan-2-yl)phenyl)azetidine-1-carboxylate To a stirred mixture of 4,4,4',4',5,5,5',5'-octamethyl-2,2'-bi(1,3,2-dioxaborolane) (3.40 g, 13.45 mmol) and potassium acetate (3.30 g, 33.60 mmol) in DMF (35 mL) were added tert-butyl-3-(4-bromophenyl)azetidine-1-carboxylate (3.50 g, 11.20 mmol) and Pd(dppf)Cl$_2$ adduct CH$_2$Cl$_2$ (0.92 g, 1.12 mmol) at room temperature under nitrogen. The resulting mixture was degassed two times under nitrogen, and then stirred at 110° C. for 16 hours. The reaction was quenched with water (25 mL) and extracted with EtOAc (2×150 mL). The combined organic layers were washed with brine (2×100 mL), dried over anhydrous Na$_2$SO$_4$ and concentrated under vacuum. The residue was purified by silica gel chromatography, eluted with EtOAc/PE (1/10) to afford the title compound: LCMS [M+H]$^+$: 360;

Step C: tert-butyl 3-(3'-(N,N-bis(4-methoxybenzyl) sulfamoyl)-4'-bromo-2'-(2-(4-methoxybenzyl)-2H-tetrazol-5-yl)biphenyl-4-yl)azetidine-1-carboxylate A degassed solution of 6-bromo-3-iodo-N,N-bis-(4-methoxybenzyl)-2-(1-(4-methoxybenzyl)-1H-tetrazol-5-yl) benzenesulfonamide (1.60 g, 3.20 mmol), tert-butyl 3-(4-(4,4,5,5-tetramethyl-1,3,2-dioxaborolan-2-yl)phenyl) azetidine-1-carboxylate (1.30 g, 3.50 mmol), Na$_2$CO$_3$ (1.00 g, 9.50 mmol) and Pd(PPh$_3$)$_4$(0.37 g, 0.32 mmol) in 1,4-dioxane (50 mL) and water (5 mL) was stirred at 80° C. for 16 hours under nitrogen. The resulting mixture was cooled to room temperature and filtered. The filtrate was concentrated under vacuum. The residue was purified by silica gel chromatography, eluted with EtOAC/PE (1/2) to afford the title compound: LCMS [M+H]$^+$: 895, 897 (1:1); $^1$H NMR (400 MHz, CDCl$_3$): δ 8.08-8.00 (m, 1H), 7.43 (d, J=8.4 Hz, 2H), 7.07 (d, J=8.0 Hz, 1H), 7.02 (d, J=8.8 Hz, 3H), 6.88-6.80 (m, 9H), 6.79-6.71 (m, 2H), 5.19-5.15 (m, 1H), 4.92-4.88 (m, 1H), 4.82 (d, J=9.2 Hz, 1H), 4.34-4.30 (m, 2H), 4.14-4.10 (m, 1H), 3.99-3.91 (m, 2H), 3.89-3.80 (m, 2H), 3.78 (s, 9H), 3.70-3.60 (m, 1H), 1.49 (s, 9H).

REFERENCE EXAMPLE 39A and 39B tert-butyl (3'-(N,N-bis(4-methoxybenzyl)sulfamoyl)-4'-bromo-2'-(1-(4-methoxybenzyl)-1H-tetrazol-5-yl)-2,3,4,5-tetrahydro-[1,1'-biphenyl]-4-yl)carbamate and tert-butyl (3'-(N,N-bis(4-methoxybenzyl)sulfamoyl)-4'-bromo-2'-(2-(4-methoxybenzyl)-2H-tetrazol-5-yl)-2,3,4,5-tetrahydro-[1,1'-biphenyl]-4-yl) carbamate

39A

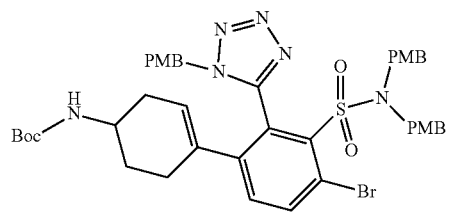

39B

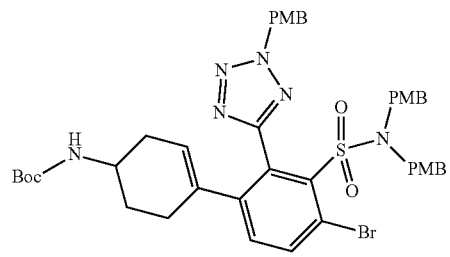

A mixture of 6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl) benzenesulfonamide (6.0 g, 7.59 mmol), tert-butyl (4-(4,4,5,5-tetramethyl-1,3,2-dioxaborolan-2-yl)cyclohex-3-en-1-yl)carbamate (2.94 g, 9.11 mmol), and sodium carbonate (1.609 g, 15.18 mmol), tetrakis(triphenylphosphine)palladium(0) (0.877 g, 0.759 mmol) was placed in a reaction vial. Dioxane (21 ml) and water (3 ml) were added. The reaction vessel was sealed, degassed and heated at 80° C. overnight. After the reaction cooled to RT, the reaction mixture was extracted with EtOAc, washed with water and brine, then dried (MgSO$_4$) and concentrated. The residue was purified by column chromatograph and eluted with EtOEt/hexane to give a mixture of regioisomeric products A and B. LC/MS A: 861.68 [M+H]$^+$ and B, LCMS: 861.59 [M+H]$^+$

REFERENCE EXAMPLE 40

3-(2-Aminobenzo[d]thiazol-4-yl)-6-bromo-N,N-bis (4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide

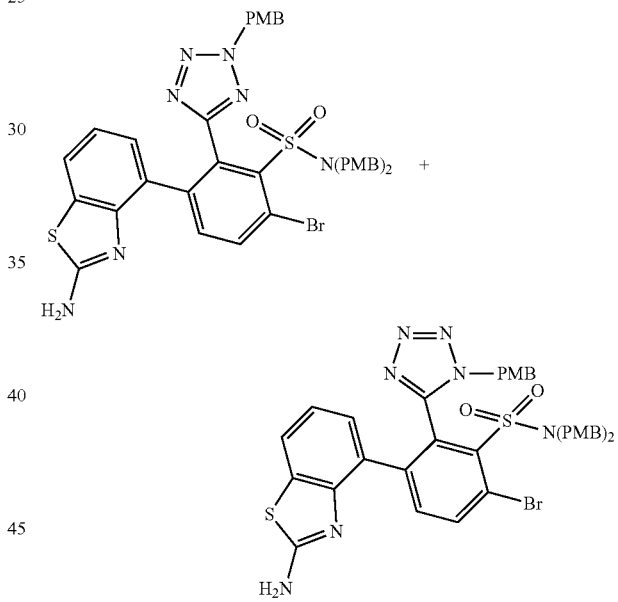

Step A: (2-Aminobenzo[d]thiazol-4-yl)boronic Acid

In a reaction vessel 4-bromobenzo[d]thiazol-2-amine (10 g, 43.6 mmol) and bispinacolatodiboron (33.3 g, 131 mmol) were combined, followed by addition of potassium acetate (12.85 g, 131 mmol) and PCy3 Pd G2 (2.58 g, 4.36 mmol). Then dry dioxane (400 ml) was added to this flask. This mixture was degassed and then heated at 80° C. for 72 hours. The solution was filtered, and the filtrate was concentrated under reduced pressure. The residue was dissolved in EtOAc (400 mL), and extracted with 2N HCl (2×150 ml). The aqueous layer was concentrated under reduced pressure. The crude material was dissolved in 3:1 CHCl$_3$:i-PrOH, dried over MgSO$_4$. The MgSO$_4$ was filtered off and the filtrate was concentrated. The material was used without further purification. LC/MS [M+H]$^+$: 195

Step B: 3-(2-Aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide Starting with a solution of 6-bromo-3-iodo-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)tetrazolidin-5-yl)benzenesulfonamide (7.3 g, 9.24 mmol) and (2-aminobenzo[d]thiazol-4-yl)boronic acid (1.971 g, 10.16 mmol), the title compounds were prepared in an analogous fashion as described for tert-butyl 3-(3'-(N,N-bis(4-methoxybenzyl)sulfamoyl)-4'-bromo-2'-(2-(4-methoxybenzyl)-2H-tetrazol-5-yl)biphenyl-4-yl)azetidine-1-carboxylate (REFERENCE EXAMPLE 38). LC/MS [M+H]+: 812, 814.

REFERENCE EXAMPLE 41 tert-Butyl 4-(3'-(N,N-bis(4-methoxybenzyl)sulfamoyl)-4'-((1-(tert-butoxycarbonyl)azetidin-3-yl)thio)-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-((1-(tert-butoxycarbonyl)azetidin-3-yl)thio)-2'-(1-(4-methoxybenzyl)-1H-tetrazol-5-yl)-[1,1'-biphenyl]-4-yl)piperidine-1-carboxylate

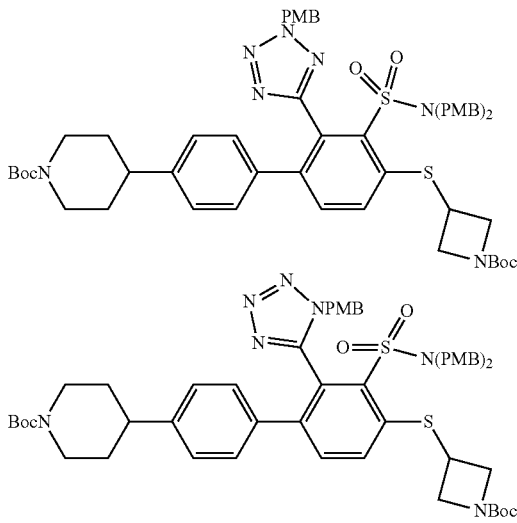

Step A: tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)piperidine-1-carboxylate A thick-wall flask was charged with tert-butyl 4-(4-(4,4,5,5-tetramethyl-1,3,2-dioxaborolan-2-yl)phenyl)piperidine-1-carboxylate (4.04 g, 10.44 mmol), 6-bromo-3-iodo-N,N-bis(4-methoxybenzyl)-2-(2-(4-methoxybenzyl)-2H-tetrazol-5-yl)benzenesulfonamide and 6-bromo-3-iodo-N,N-bis(4-methoxybenzyl)-2-(1-(4-methoxybenzyl)-1H-tetrazol-5-yl)benzenesulfonamide (5.5 g, 6.96 mmol), sodium carbonate (2.21 g, 20.87 mmol) and tetrakis(triphenylphosphine)palladium(0) (0.40 g, 0.348 mmol). The vial was degassed, sealed, and filled with dioxane (20.87 mL) and water (6.96 mL). The resulting mixture was heated for 16 hours at 80° C. The reaction mixture was filtered over celite to remove palladium. The filtrate was diluted with EtOAc and washed with water. The organic layer was dried over anhydrous MgSO4, filtered, concentrated. The residue was purified by silica gel column chromatography using 0-100% EtOAc/hexanes as mobile phase to give the title compound. LC/MS [M+2]+: 925.75.

Step B: tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)piperidine-1-carboxylate A mixture of tert-butyl 3-mercaptoazetidine-1-carboxylate (123 mg, 0.65 mmol), sodium 2-methylpropan-2-olate (57 mg, 0.60 mmol) and tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)piperidine-1-carboxylate (500 mg, 0.54 mmol) in DME (5 mL) in a sealed (thick wall) tube was deoxygenated by bubbling nitrogen for 15 minutes. The BrettPhos precatalyst generation 3 (49 mg, 0.054 mmol) was added and the nitrogen continued for another 5 minutes. The tube was sealed and heated at 85° C. overnight. After cooling, the reaction mixture was filtered through a pad of CELITE and the solid was thoroughly washed with ethyl acetate. The filtrate was washed with 1N aq. HCl, and brine, then dried (MgSO4) and the volatiles was removed under reduced pressure. The residue was purified by silica gel column chromatography using 0 to 100% EtOAc/hexanes as eluent to give the title product. LC/MS [M+1]+: 1033.34.

REFERENCE EXAMPLE 42 tert-Butyl 3-((2-(N,N-bis(4-methoxybenzyl)sulfamoyl)-4-(imidazo[1,2-a]pyridin-3-yl)-3-(2-(4-methoxybenzyl)-2H-tetrazol-5-yl)phenyl)thio)azetidine-1-carboxylate and tert-butyl 3-((2-(N,N-bis(4-methoxybenzyl)sulfamoyl)-4-(imidazo[1,2-a]pyridin-3-yl)-3-(1-(4-methoxybenzyl)-1H-tetrazol-5-yl)phenyl)thio)azetidine-1-carboxylate

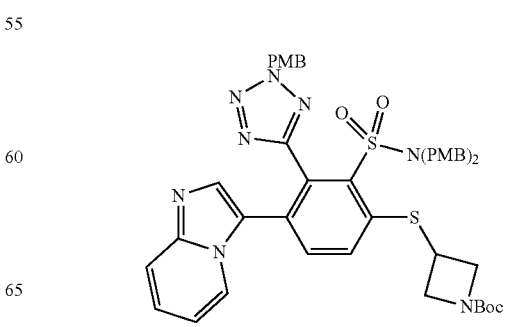

-continued

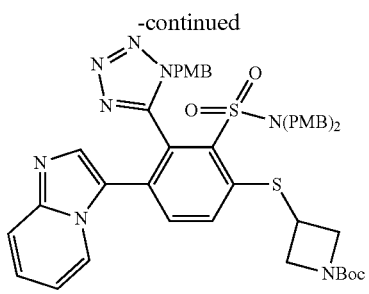

The title compound was prepared in a similar fashion to REFERENCE EXAMPLE 41, using commercially available 3-(4,4,5,5-tetramethyl-1,3,2-dioxaborolan-2-yl)imidazo[1,2-a]pyridine. LC/MS [M+1]+: 890.18

REFERENCE EXAMPLE 43

8-Bromoimidazo[1,2-a]pyridine

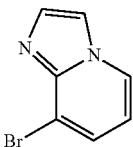

3-Bromopyridin-2-amine (274 mg, 1.584 mmol) and 2-chloroacetaldehyde (178 mg, 2.268 mmol) were dissolved in EtOH (2 mL). The mixture was heated at 80° C. for 1.5 hours. The reaction mixture was concentrated and the residue was purified by column chromatography (100% hexane to 65% EtOAc/Hexane, then 0-65% MeOH/EtOAc) to give the desired product. After concentration, the product was dissolved in 1/1 DCM/MeOH, and filtered to remove silica gel. The filtrates were concentrated to yield the pure product. LC/MS [M+H]+: 197.1, 199.1.

REFERENCE EXAMPLE 44

Ethyl 8-bromoimidazo[1,2-a]pyridine-2-carboxylate

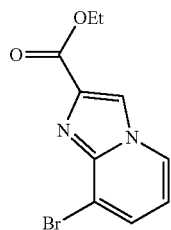 [SMILES: CCOC(=O)c1cn2cccc(Br)c2n1]

3-Bromopyridin-2-amine (500 mg, 2.89 mmol) and ethyl 3-bromo-2-oxopropanoate (820 mg, 4.20 mmol) were dissolved in EtOH (3 mL). The mixture was heated at 80° C. for 12 hours. The reaction was concentrated to a minimal volume of MeOH/EtOH, then ether was added. Solids that precipitated out were collected to give ethyl 8-bromoimidazo[1,2-a]pyridine-2-carboxylate. LC/MS [M+H]+: 269.6.

REFERENCE EXAMPLE 45

8-Bromoimidazo[1,2-a]pyridine-2-carboxamide

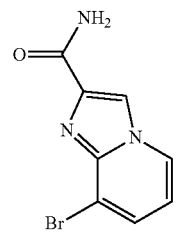 [SMILES: NC(=O)c1cn2cccc(Br)c2n1]

Ethyl 8-bromoimidazo[1,2-a]pyridine-2-carboxylate (100 mg, 0.372 mmol) was dissolved in 1 mL of 7N NH₃ in MeOH. The mixture was heated at 60° C. for 12 hours. The reaction mixture was concentrated to give the crude 8-bromoimidazo[1,2-a]pyridine-2-carboxamide, which was used without further purification. LC/MS [M+H]+: 240.1, 242.1.

REFERENCE EXAMPLE 46

5-Bromoimidazo[1,2-a]pyridine

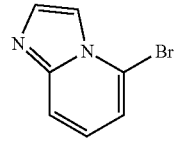

6-Bromopyridin-2-amine (274 mg, 1.584 mmol) and 2-chloroacetaldehyde (178 mg, 2.268 mmol) were dissolved in EtOH (2 mL). The mixture was heated at 60° C. for 12 hours. LC-MS showed the formation of the desired product, but there was still starting material remaining. Additional 170 mg of the 2-chloroacetaldehyde was added and the reaction was heated at 60° C. for 12 hours. LC-MS showed the reaction was completed. After cooling to room temperature, the reaction was concentrated. To the resulting residue was added ether, and the solids that precipitated out were collected to give 5-bromoimidazo[1,2-a]pyridine. LC/MS [M+H]+: 197.1, 199.1.

REFERENCE EXAMPLE 47

7-bromo-5-(trifluoromethyl)-1H-benzo[d]imidazol-2-amine

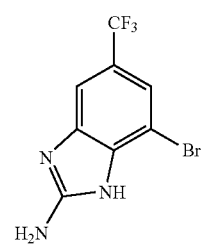

To a 25 mL microwave tube was added a solution of 3-bromo-5-(trifluoromethyl)benzene-1,2-diamine (0.510 g, 2.0 mmol) in 6 mL of methanol, followed by addition of cyanic bromide (0.254 g, 2.40 mmol) and 4 mL of water. The mixture was stirred for 16 hours. The reaction mixture was heated at 80° C. for 1 hour and no SM was left. The solvent was removed via rotary evaporator and the residue was purified via column chromatography (ISCO RediSep gold column, 40 g) using 0-10% MeOH/DCM as mobile phase to afford the product. LC-MS (M+H)$^+$: 280.10.

REFERENCE EXAMPLE 48

2-amino-7-bromo-1H-benzo[d]imidazole-5-carbonitrile

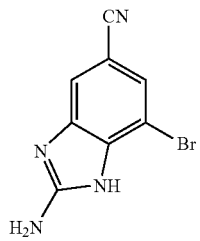

To a 25 mL microwave tube was added a solution of 3,4-diamino-5-bromobenzonitrile (212 mg, 1.0 mmol) in 6 mL of methanol, followed by addition of cyanic bromide (127 mg, 1.20 mmol) and 4 mL of water. The mixture was stirred for 16 hours. The reaction mixture was heated at 80° C. for 1 hr and no SM was left. The solvent was removed via rotavapor and the residue was purified via column chromatography (ISCO RediSep gold column, 40 g) using 0-10% MeOH/DCM as mobile phase to get the product. LC-MS (M+H)$^+$: 238.89.

REFERENCE EXAMPLE 49

7-bromo-5-fluoro-1H-benzo[d]imidazol-2-amine

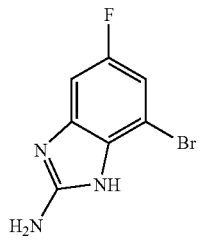

To a 25 mL microwave tube was added a solution of 3-bromo-5-fluorobenzene-1,2-diamine (0.410 g, 2.0 mmol) in 6 mL of methanol, followed by addition of cyanic bromide (0.254 g, 2.40 mmol) and 4 mL of water. The mixture was stirred for 16 hours. The reaction mixture was heated at 80° C. for 1 hour and no SM left. The solvent was removed via rotavapor and the residue was purified via column chromatography (ISCO RediSep gold column, 40 g) using 0-10% MeOH/DCM as mobile phase to afford the product. LC-MS [M+H]$^+$: 230.08.

REFERENCE EXAMPLE 50

(2-amino-6-fluoro-1H-benzo[d]imidazol-4-yl)boronic acid

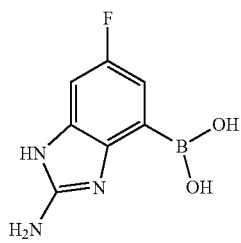 [SMILES: Nc1nc2c(B(O)O)cc(F)cc2[nH]1]

To a 200 mL RBF was charged a solution of 3-bromo-5-fluorobenzene-1,2-diamine (5 g, 24.39 mmol) in ethanol (100 ml), followed by addition of cyanic bromide (5.17 g, 48.8 mmol). The reaction mixture was heated at 80° C. overnight. The reaction mixture was cooled to RT, concentrated in vacuo, then it was purified by column chromatography (ISCO, 80 g, 0-20% MeOH in DCM) to give 4-bromo-6-fluoro-1H-benzo[d]imidazol-2-amine (4.2 g, 18.26 mmol). The intermediate was dissolved in 50 mL of anhydrous ethanol, followed by addition of 5,5,5',5'-tetramethyl-2,2'-bi(1,3,2-dioxaborinane) (7.86 g, 34.8 mmol), potassium acetate (3.41 g, 34.8 mmol), PCy3 Pd G2 (2.054 g, 3.48 mmol) and anhydrous ethanol (50 ml). This mixture was degassed for 20 minutes, and then was heated at 80° C. for 18 hours. The reaction mixture was acidified with 1.0 M HCl to ~pH=4, then was washed with EtOAc. The crude product was chromatographed over C18 column to give the desired product (2-amino-6-fluoro-1H-benzo[d]imidazol-4-yl)boronic acid. LC/MS (M+H)$^+$: 196.07.

REFERENCE EXAMPLE 51 tert-butyl 3-cyano-3-(5-(4,4,5,5-tetramethyl-1,3,2-dioxaborolan-2-yl)pyridin-2-yl)azetidine-1-carboxylate

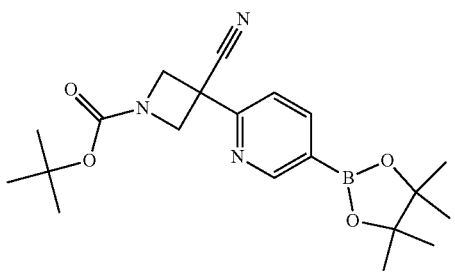 [SMILES: CC(C)(C)OC(=O)N1CC(C#N)(c2ccc(B3OC(C)(C)C(C)(C)O3)cn2)C1]

Step A: tert-butyl 3-(methanesulfonyloxy)azetidine-1-carboxylate

Into a 5000-mL 4-necked RBF purged and maintained with an inert atmosphere of nitrogen was placed a solution of tert-butyl 3-hydroxyazetidine-1-carboxylate (450 g, 2.60 mol, 1.00 equiv) in ethyl acetate (3000 mL) and TEA (315 g, 3.12 mol, 1.20 equiv). Methanesulfonyl chloride (367 g, 1.10 equiv) was added dropwise with stirring at 0° C. The resulting solution was stirred for 120 minutes at 0° C. The solid was filtered out. The filtrate was concentrated under vacuum to afford the title compound as a solid.

Step B: tert-butyl 3-cyanoazetidine-1-carboxylate

Into a 5000-mL RBF purged and maintained with an inert atmosphere of nitrogen was placed a solution of tert-butyl 3-(methanesulfonyloxy)azetidine-1-carboxylate (350 g, 1.39 mol, 1.00 equiv) in DMSO (2500 mL). NaCN (140 g, 2.86 mol, 2.00 equiv) was added in several batches. The resulting solution was stirred overnight at 140° C. The reaction mixture was cooled and then quenched by the addition of 3 L of aqueous $Fe_2SO_4$. The solid was filtered out. The filtrate was extracted with 3×2000 mL of ethyl acetate. The organic layers were combined, dried and concentrated under vacuum. The residue was applied onto a silica gel column and eluted with ethyl acetate/petroleum ether (1:3) to give the title compound as a solid.

Step C: tert-butyl 3-(5-bromopyridin-2-yl)-3-cyano-azetidine-1-carboxylate

Into a 500-mL 4-necked RBF purged and maintained with an inert atmosphere of nitrogen was placed a solution of LDA (1 M, 18 mL, 1.25 equiv) in tetrahydrofuran (100 mL). A solution of tert-butyl 3-cyanoazetidine-1-carboxylate (2.7 g, 14.8 mmol, 1.00 equiv) in tetrahydrofuran (100 mL) was added dropwise with stirring at −78° C. over 45 min. The reaction mixture was stirred for 45 minutes at −78° C., then a solution of 5-bromo-2-fluoropyridine (2.6 g, 14.77 mmol, 1.00 equiv) in tetrahydrofuran (100 mL) was added dropwise with stirring at −78° C. over 45 minutes. The resulting solution was stirred overnight at room temperature. The resulting solution was diluted with 200 mL of water, then extracted with 3×200 mL of ethyl acetate. The organic layers were combined, dried and concentrated under vacuum. The residue was applied onto a silica gel column with ethyl acetate/petroleum ether (20:1-5:1) to give the title compound as a solid.

Step D: tert-butyl 3-cyano-3-[5-(tetramethyl-1,3,2-dioxaborolan-2-yl)pyridin-2-yl]azetidine-1-carboxylate Into a 5000-mL 4-necked RBF purged and maintained with an inert atmosphere of nitrogen was placed a solution of tert-butyl 3-(5-bromopyridin-2-yl)-3-cyanoazetidine-1-carboxylate (80 g, 236.55 mmol, 1.00 equiv) in 1,4-dioxane (2000 mL), 4,4,4',4',5,5,5',5'-octamethyl-2,2'-bi(1,3,2-dioxaborolane) (90.8 g, 357.48 mmol, 1.50 equiv), Pd(dppf) Cl2 (3.5 g, 4.78 mmol, 0.02 equiv), and potassium acetate (70 g, 714.29 mmol, 3.00 equiv). The reaction mixture was stirred overnight at 80° C., then it was cooled to room temperature and diluted with 3000 mL of brine. The resulting solution was extracted with 3×1500 mL of ethyl acetate. The organic layers were combined, dried over anhydrous sodium sulfate and concentrated under vacuum. The residue was applied onto a silica gel column with ethyl acetate/petroleum ether (1;7) to give the title compound as a solid. LC-MS (ES, m/z): 386 [M+H]$^+$.

H-NMR (300 MHz, DMSO-d6): δ 1.323 (s, 12H), 1.413 (s, 9H), 4.34 (d, 2H, J=8.7 Hz), 4.44 (d, 2H, J=8.7 Hz), 7.70 (d, 1H), 8.13 (d, 1H), 8.83 (d, 1H).

REFERENCE EXAMPLE 52

5-(4,4,5,5-tetramethyl-1,3,2-dioxaborolan-2-yl)-3-(trifluoromethyl)-1H-indazole

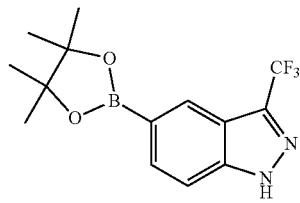 [SMILES: CC1(C)OB(c2ccc3[nH]nc(C(F)(F)F)c3c2)OC1(C)C]

Step A:
1-(5-bromo-2-fluorophenyl)-2,2,2-trifluoroethanone

Into a 10000-mL 4-necked RBF purged and maintained with an inert atmosphere of nitrogen, was placed a solution of diisopropylamine (280 g, 2.77 mol, 1.10 equiv) in tetrahydrofuran (4400 mL). This was followed by the addition of butyllithium (1106 mL, 1.10 equiv) dropwise with stirring at −40° C. in 15 minutes. The mixture was stirred for 40 minutes at −50° C. 1-bromo-4-fluorobenzene (440 g, 2.51 mol, 1.00 equiv) was added at <−80° C. for 10 minutes. The mixture was stirred for 1 hour at −78° C. To the mixture was added ethyl 2,2,2-trifluoroacetate (392.8 g, 2.77 mol, 1.10 equiv) at −80° C. in 45 minutes. The resulting solution was stirred for 1.5 hours at −80° C. The reaction was then quenched by the addition of 2000 ml of sat. NH$_4$Cl. The resulting solution was extracted with 2000 mL of ethyl acetate and the organic layers combined. The resulting mixture was washed with 2×2000 mL of sodium chloride (aq.). The mixture was dried over sodium sulfate and concentrated under vacuum. The crude product was purified by distillation under reduced pressure (10 mm Hg) and the fraction was collected at 70° C. to give the title compound as an oil.

Step B: 5-bromo-3-(trifluoromethyl)-1H-indazole

Into a 10-L 4-necked RBF, was placed a solution of 1-(5-bromo-2-fluorophenyl)-2,2,2-trifluoroethanone (300 g, 1.11 mol, 1.00 equiv) in butan-1-ol (5500 mL), and then NH$_2$NH$_2$.H$_2$O (80%) (934 g, 14.94 mol, 18.00 equiv, 80%) was added. The resulting solution was stirred for 5.5 hours at 110° C. in an oil bath. The reaction mixture was cooled to room temperature. The resulting solution was diluted with 3000 mL of H$_2$O. The resulting solution was extracted with 4×3000 mL of ethyl acetate and the organic layers combined. The resulting mixture was washed with 2×3000 mL of sodium chloride (aq.). The mixture was dried over anhydrous sodium sulfate and concentrated under vacuum. The residue was applied onto a silica gel column with dichloromethane to afford the title compound as a solid.

Step C: 5-(4,4,5,5-tetramethyl-1,3,2-dioxaborolan-2-yl)-3-(trifluoromethyl)-1H-indazole Into a 1000-mL 3-necked RBF purged and maintained with an inert atmosphere of nitrogen, was placed potassium acetate (66 g, 673.47 mmol, 3.00 equiv), a solution of 5-bromo-3-(trifluoromethyl)-1H-indazole (60 g, 226.42 mmol, 1.00 equiv) in 1,4-dioxane (600 mL), 4,4,5,5-tetramethyl-2-(4,4,5,5-tetramethyl-1,3,2-dioxaborolan-2-yl)-1,3,2-dioxaborolane (86 g, 338.58 mmol, 1.50 equiv). This was followed by the addition of Pd(dppf)Cl$_2$ (24.8 g, 33.93 mmol, 0.15 equiv) at 60° C. The resulting solution was stirred overnight at 90° C. The reaction mixture was cooled to room temperature. The resulting solution was diluted with 600 mL of H$_2$O. The resulting solution was extracted with 3×1200 mL of ethyl acetate and the organic layers combined. The resulting mixture was washed with 2×600 mL of brine. The mixture was dried over anhydrous sodium sulfate and concentrated under vacuum. The residue was applied onto a silica gel column with dichloromethane. Then the crude product was applied onto a silica gel column with PE~PE:EA (50:1) to give the title compound as a solid. LC-MS (ES, m/z): 313 [M+H]$^+$ H-NMR: (400 MHz, CDCl$_3$, ppm) δ1.383 (12H, s) 7.546 (1H, d, J=8.8 Hz) 7.906 (1H, d, J=8.4 Hz), 8.385 (1H, s) 10.598 (1H, s).

REFERENCE EXAMPLE 53

4-(4-(trifluoro-boranyl)thiazol-2-yl)morpholine, Potassium Salt

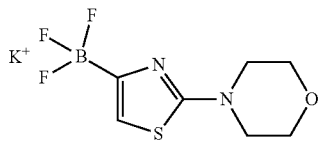

Step A: 4-(4-bromothiazol-2-yl)morpholine

Into a 2000-mL 4-necked RBF, was placed a solution of 2,4-dibromothiazole (150 g, 617.54 mmol, 1.00 equiv) in N,N-dimethylformamide (1000 mL), morpholine (60 g, 688.86 mmol, 1.00 equiv), and triethylamine (187 g, 1.85 mol, 3.00 equiv). The resulting solution was stirred for 1 hour at 80° C. in an oil bath. The mixture was cooled to RT. The resulting solution was diluted with 3000 mL of H$_2$O. The solids were collected by filtration. The filter cake was washed with 3×1000 mL of water. The solid was dried in an oven to give the title compound.

Step B: 4-[4-[trifluoro(potassio)-ˆ[5]-boranyl]thiophen-2-yl]morpholine

Into a 3000-mL 4-necked RBF, was placed a solution of 4-(4-bromo-1,3-thiazol-2-yl)morpholine (200 g, 802.80 mmol, 1.00 equiv) in tetrahydrofuran (2000 mL), and tris(propan-2-yl) borate (226 g, 1.20 mol, 1.50 equiv). This was followed by the addition of n-BuLi (2.5 M) (384 mL, 1.20 equiv) dropwise at −78° C. The mixture was stirred for 2 hours at this temperature. The resulting solution was warmed to RT and stirred for 2 hours. To this was added methanesulfonic acid (78.4 g, 815.73 mmol, 1.02 equiv) dropwise at 0° C. The mixture was stirred for 1 hour at RT. To the mixture was added H$_2$O (100 ml) dropwise at 0° C. and stirred for 0.5 hour. Then, KFH$_2$ (200 g, 3.33 mol, 4.14 equiv) was added and stirred overnight at room temperature. The resulting mixture was concentrated under vacuum. The crude product was purified by re-crystallization from acetone for several times to give the title compound as a solid. H-NMR: (DMSO, ppm): δ 6.39 (s, 1H), 3.68 (m, 4H), 3.34 (m, 4H).

REFERENCE EXAMPLE 54

5-(3-(4,4,5,5-tetramethyl-3,2-dioxaborolan-2-yl)phenyl)pyrrolidin-2-one

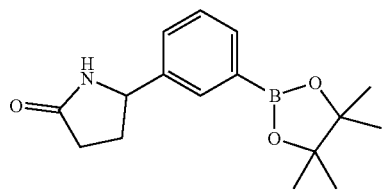 [SMILES: CC1(C)OB(c2cccc(C3CCC(=O)N3)c2)OC1(C)C]

Step A: methyl 4-(3-bromophenyl)-4-oxobutanoate

To a solution of 4-(3-bromophenyl)-4-oxobutanoic acid (735 g, 2.9 mol) in MeOH (7 L) was added SOCl$_2$ (511 g, 4.3 mol) at 0° C., then the mixture was stirred at RT overnight. After that time, most solvent was removed and the rest of the solvent was quenched by the addition of water. The aqueous layer was extracted with ethyl acetate, and the organic layer was washed with brine, dried over Na$_2$SO$_4$, then concentrated to afford the title compound.

Step B: 5-(3-bromophenyl)pyrrolidin-2-one

To a solution of methyl 4-(3-bromophenyl)-4-oxobutanoate (600 g, 2.2 mol) in isopropyl alcohol (18 L) was added NH$_4$OAc (1705 g, 22 mol), NaBH$_3$CN (697 g, 11.1 mol), 4 Å molecular sieves (746.7 g) at RT. Then the reaction mixture was stirred at 85° C. overnight. The mixture was filtered through a CELITE pad, and the filtrate was concentrated to give the crude product. The crude product was washed with methyl-t-butyl-ethyl, then filtered and concentrated to give the title compound.

Step C: 5-(3-(4,4,5,5-tetramethyl-1,3,2-dioxaborolan-2-yl)phenyl)pyrrolidin-2-one To a solution of 5-(3-bromophenyl)pyrrolidin-2-one (100 g, 0.4 mol) in 1,4-Dioxane (1.5 L) was added BPDB (155 g, 0.6 mol), KOAc (122 g, 1.2 mol), pd(dppf)$_2$Cl$_2$ (10 g) at room temperature. The reaction mixture was degassed under vacuum and purged with N$_2$ several times and then was warmed to 100° C. and stirred overnight. The solvent was removed, and the crude product was chromatographed on silica gel (eluted with petroleum ether/EtOAc from 10/1 to 1/2) to give the title compound. LC-MS: m/z=288 (M+1); $^1$HNMR (400 MHz, DMSO-d6) δ: 1.29 (s, 12H), 1.68-1.73 (m, 1H), 2.20-2.24 (m, 2H), 2.44-2.49 (m, 1H), 4.66-4.70 (m, 1H), 7.35-7.43 (m, 2H), 7.57-7.61 (m, 2H), 8.09 (s, 1H).

REFERENCE EXAMPLE 55

Potassium trifluoro(2-(pyrrolidin-1-yl)thiazol-4-yl)borate

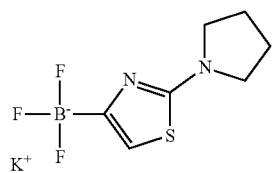 [SMILES: F[B-](F)(F)c1csc(N2CCCC2)n1 ; [K+]]

Step A: 4-bromo-2-(pyrrolidin-1-yl)-1,3-thiazole

Into a 2 L 4-necked RBF, was placed a solution of 2,4-dibromo-1,3-thiazole (250 g, 1.03 mol, 1.00 equiv) in N,N-dimethylformamide (700 mL), pyrrolidine (73 g, 1.03 mol, 1.00 equiv), triethylamine (311.7 g, 3.08 mol, 3.00 equiv). The resulting solution was stirred for 2 hours at 100° C. and then cooled to 30° C. The reaction mixture was then poured into 2 L of water/ice. The solid was collected by filtration. The filter cake was washed with 3×500 mL of water to give the title compound as a solid.

Step B: 2-(pyrrolidin-1-yl)-4-(trifluoro-^[4]-boranyl)-1,3-thiazole potassium Into a 5-L 4-necked RBF purged and maintained with an inert atmosphere of nitrogen, was placed a solution of 4-bromo-2-(pyrrolidin-1-yl)-1,3-thiazole (150 g, 643.42 mmol, 1.00 equiv) in tetrahydrofuran (2500 mL), B-(Oi-Pr)$_3$ (157.3 g, 1.30 equiv). To the reaction was added n-BuLi (349 mL, 1.30 equiv, 2.4 M) dropwise with stirring at −78° C. over 140 minutes. The reaction mixture was stirred for 2 hours at −78° C. and stirred for 2 hours at 30° C. To this solution was added CH$_3$SO$_3$H (61.8 g, 1.00 equiv) dropwise with stirring at 0° C. The resulting mixture was stirred for 1 hour at room temperature and then water (150 mL) was added dropwise with stirring at 0° C. in 10 minutes. The solution was stirred for 0.5 hour at 30° C. and then KHF$_2$ (211 g, 4.20 equiv) was added and stirred overnight at 30° C. The solid was collected by filtration. The crude product was dissolved in 500 mL of acetone. The resulting mixture was stirred at reflux for 30 min. The solid was filtered out. The filtrate was concentrated under vacuum. The resulting mixture was washed with 5×100 mL of ethanol. The solid was collected by filtration. The crude product was dissolved in 110 mL of MeOH/water (10:1). The mixture was stirred at reflux for 1 hr. The solid was collected by filtration. This resulted in the title compound as a solid. H-NMR: (300 MHz, DMSO, ppm): δ 6.407 (s, 1H), 3.480~3.536 (m, 4H), 1.966~2.031 (m, 4H).

REFERENCE EXAMPLE 56

2-((2-Nitro-3-(4,4,5,5-tetramethyl-1,3,2-dioxaborolan-2-yl)phenyl)amino)ethanol

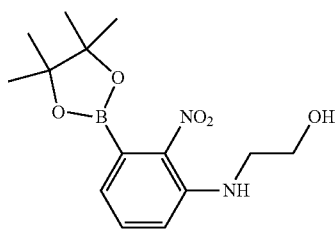 [SMILES: CC1(C)OB(c2cccc(NCCO)c2[N+](=O)[O-])OC1(C)C]

Step A: 2-((3-Bromo-2-nitrophenyl)amino)ethanol

To a stirred solution of 2-aminoethanol (2.08 g, 34.1 mmol) in DMA (50 mL) was added DIEA (12 mL, 68.21 mmol) and 1-bromo-3-fluoro-2-nitrobenzene (5.00 g, 22.73 mmol) at room temperature. The solution was warmed to 80° C. and stirred for 16 hours. The resulting solution was cooled to RT, diluted with water (500 mL). The resulting mixture was filtered. The filter cake was washing with water (2×50 mL). The filter cake was dried under vacuum to afford 2-((3-bromo-2-nitrophenyl)amino)ethanol, which was used in the next step without further purification: LCMS [M+1]$^+$: 261, 263.

Step B: 2-((2-Nitro-3-(4,4,5,5-tetramethyl-1,3,2-dioxaborolan-2-yl)phenyl)amino)ethanol To a stirred solution of 2-((3-bromo-2-nitrophenyl)amino)ethanol (2.00 g, 7.66 mmol) in 1,4 dioxane (40 mL) was added 4,4,4',4',5,5,5',5'-octamethyl-2,2'-bi(1,3,2-dioxaborolane) (9.73 g, 38.3 mmol), Pd(dppf)Cl$_2$ (1.12 g, 1.53 mmol) and KOAc (2.26 g, 23.0 mmol) at room temperature. The reaction mixture was degassed with nitrogen three times. The resulted mixture was stirred for 16 hours at 80° C. under nitrogen. The resulting mixture was diluted with water (100 mL) and extracted with EA (3×100 mL). The combined organic layers was washed with brine (3×200 mL), dried over anhydrous Na$_2$SO$_4$ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]$^+$: 309.

REFERENCE EXAMPLE 57

Tert-butyl (4-(3-(4,4,5,5-tetramethyl-1,3,2-dioxaborolan-2-yl)phenyl)-1H-imidazol-2-yl)carbamate

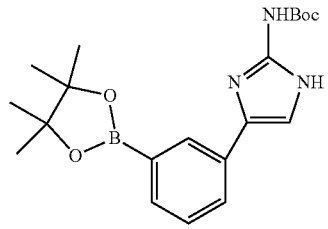 [SMILES: CC(C)(C)OC(=O)Nc1nc(-c2cccc(B3OC(C)(C)C(C)(C)O3)c2)c[nH]1]

Step A: Tert-butyl (4-(3-bromophenyl)-1H-imidazol-2-yl)carbamate

To a solution of 2-bromo-1-(3-bromophenyl)ethanone (3.00 g, 10.8 mmol) in DMF (30 mL) was added tert-butyl N-carbamimidoylcarbamate (3.50 g, 21.6 mmol). The reaction mixture was stirred at RT for 16 hours. The resulting mixture was quenched with water (60 mL), and then extracted with EA (3×30 mL). The combined organic layers was washed with brine (3×30 mL), dried over anhydrous Na$_2$SO$_4$ and filtered. The filtrate was concentrated under vacuum. The residue was purified by silica gel column chromatography, eluted with 15% EA in PE. The fractions containing desired product were combined and concentrated under vacuum to afford the title compound: LCMS [M+1]$^+$: 338, 340.

Step B: Tert-butyl (4-(3-(4,4,5,5-tetramethyl-1,3,2-dioxaborolan-2-yl)phenyl)-1H-imidazol-2-yl)carbamate To a solution of tert-butyl (4-(3-bromophenyl)-1H-imidazol-2-yl)carbamate (1.5 g, 4.44 mmol) in 1,4-dioxane (20 mL) was added 4,4,4',4',5,5,5',5'-octamethyl-2,2'-bi(1,3,2-dioxaborolane) (2.30 g, 8.87 mmol), Pd(dppf)Cl₂ adduct CH₂Cl₂ (0.60 g, 0.68 mmol) and KOAc (1.30 g, 13.31 mmol). The mixture was degassed with nitrogen three times. The reaction mixture was stirred for 16 hours at 80° C. under nitrogen. The resulting mixture was concentrated under vacuum to afford the title compound, which was used directly in next step: LCMS [M+1]⁺: 386.

REFERENCE EXAMPLE 58

Tert-butyl ((4-(5,5-dimethyl-1,3,2-dioxaborinan-2-yl)-1H-benzo[d]imidazol-2-yl) methyl)carbamate

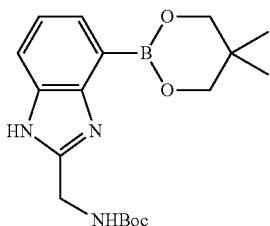 [SMILES: CC1(C)COB(c2cccc3[nH]c(CNC(=O)OC(C)(C)C)nc23)OC1]

Step A: Tert-butyl (2-((2-amino-3-bromophenyl)amino)-2-oxoethyl)carbamate

To a stirred solution of 3-bromobenzene-1,2-diamine (100 g, 0.54 mol) in THF (1 L) was added 2-((tert-butoxycarbonyl)amino)acetic acid (94 g, 0.54 mol), HATU (610 g, 1.60 mmol) and TEA (223 mL, 1.60 mmol) at room temperature. The reaction mixture was degassed with nitrogen three times and stirred overnight at RT. The resulting mixture was diluted with water (500 mL) and extracted with EA (3×200 mL). The combined organic layers was washed with water (3×500 mL) and brine (3×500 mL), dried over anhydrous Na₂SO₄ and filtered. The filtrate was concentrated under vacuum. The residue was purified by silica gel column chromatography, eluted with 60% EA in PE. The fractions containing desired product were combined and concentrated under vacuum to afford the title compound: LCMS [M+1]⁺: 344, 346.

Step B: Tert-butyl ((4-bromo-1H-benzo[d]imidazol-2-yl)methyl)carbamate

A solution of tert-butyl(2-((2-amino-3-bromophenyl)amino)-2-oxoethyl)carbamate (180 g, 523 mmol) in AcOH (250 mL) was stirred for 0.5 h at 60° C. The resulting mixture was concentrated under vacuum. The crude product was crystallized from EA/PE (50:1, 200 mL). The solid was collected by filtration and dried in vacuo to afford the title compound: LCMS [M+1]⁺: 326, 328.

Step C: Tert-butyl ((4-(5,5-dimethyl-1,3,2-dioxaborinan-2-yl)-1H-benzo[d]imidazol-2-yl) methyl)carbamate To a solution of tert-butyl((4-bromo-1H-benzo[d]imidazol-2-yl)methyl)carbamate (70.0 g, 215 mmol) in 1,4-dioxane (350 mL) were added 2nd PPh₃ precatalyst (11.3 g, 42.9 mmol), 5,5,5',5'-tetramethyl-2,2'-bi(1,3,2-dioxaborinane) (72.7 g, 322 mmol) and KOAc (63.2 g, 644 mmol) at room temperature. The reaction mixture was degassed with nitrogen three times and stirred at 80° C. for 16 hours. The resulting mixture was quenched with water (500 mL) and extracted with EA (3×400 mL). The combined organic layers was washed with water (3×800 mL) and brine (3×500 mL), dried over anhydrous Na₂SO₄ and filtered. The filtrate was concentrated under vacuum. The residue was purified by silica gel column chromatography, eluted with 60% EA in PE. The fractions containing desired product were combined and concentrated under vacuum to afford tert-butyl ((4-(5,5-dimethyl-1,3,2-dioxaborinan-2-yl)-1H-benzo[d]imidazol-2-yl)methyl)carbamate as a solid: LCMS [M+1]⁺: 360.

REFERENCE EXAMPLE 59

(R)-tert-butyl (1-mercaptopropan-2-yl)carbamate

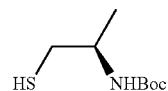

Step A: (R)-2-((tert-butoxycarbonyl)amino)propyl methanesulfonate

To a stirred solution of (R)-tert-butyl (1-hydroxypropan-2-yl)carbamate (5.00 g, 28.5 mmol) in DCM (30 mL) was added MsCl (6.54 g, 57.1 mmol) and TEA (8.65 g, 86 mmol) at 0° C. The reaction mixture was stirred at room temperature for 2 hours. The reaction mixture was diluted with EA (300 mL), washed with water (3×250 mL) and brine (3×250 mL), dried over anhydrous Na₂SO₄ and filtered. The filtrate was concentrated under vacuum to afford the title compound, which was used directly in the next step: LCMS [M+1]⁺254.

Step B: (R)—S-(2-((tert-butoxycarbonyl)amino)propyl) ethanethioate

To a stirred solution of (R)-2-((tert-butoxycarbonyl)amino)propyl methanesulfonate (7.00 g, 27.6 mmol) in DMF (60 mL) was added ethanethioic S-acid (4.21 g, 55.3 mmol) at room temperature. The reaction mixture was stirred at room temperature for 16 hours. The resulting mixture was diluted with water (150 mL) and extracted with EA (3×150 mL). The combined organic layers were washed with water (3×250 mL) and brine (3×300 mL), dried over anhydrous Na₂SO₄ and filtered. The filtrate was concentrated under vacuum. The residue was purified by silica gel column chromatography, eluted with 15% EA in PE. The fractions containing desired product were combined and concentrated under vacuum to afford the title compound: LCMS [M+1]⁺: 234.

Step C: (R)-tert-butyl (1-mercaptopropan-2-yl)carbamate

To a stirred solution of (R)—S-(2-((tert-butoxycarbonyl)amino)propyl) ethanethioate (4.70 g, 20.14 mmol) in MeOH (40 mL) and water (200 mL) was added NaOH (3.23 g, 80.56 mmol) at room temperature. The reaction mixture was stirred at room temperature for 3 hours. The reaction mixture was poured into ice-water (100 mL), adjusted with HCl (2N) to pH 7. The resulting mixture was extracted with EA (150 mL), washed with water (3×150 mL). The organic layer was dried over anhydrous Na$_2$SO$_4$ and filtered. The filtrate was concentrated under vacuum to afford the title compound, which was used directly in the next step: LCMS [M+1]$^+$: 192.

REFERENCE EXAMPLE 60

(2S,4S)-benzyl 2-(hydroxymethyl)-4-mercaptopyrrolidine-1-carboxylate

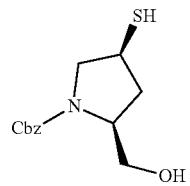 [SMILES: O=C(OCc1ccccc1)N1C[C@@H](S)C[C@H]1CO]

Step A: (2S,4R)-1-benzyl 2-methyl-4-((methyl sulfonyl)oxy)pyrrolidine-1,2-dicarboxylate To a stirred solution of (2S,4R)-1-benzyl 2-methyl-4-hydroxypyrrolidine-1,2-dicarboxylate (20 g, 71.6 mmol) in DCM (200 mL) was added MsCl (8.37 mL, 107 mmol) and TEA (29.9 mL, 215 mmol) at 0° C. The reaction mixture was stirred at RT for 2 hours. The reaction mixture was diluted with EA (300 mL), washed with water (3×250 mL) and brine (3×250 mL), dried over anhydrous Na$_2$SO$_4$ and filtered. The filtrate was concentrated under vacuum to afford the title compound, which was used directly in the next step: LCMS [M+1]$^+$: 358.

Step B: (2S,4S)-1-benzyl-2-methyl-4-(acetylthio) pyrrolidine-1,2-dicarboxylate

To a solution of (2S,4R)-1-benzyl-2-methyl-4-((methylsulfonyl)oxy) pyrrolidine-1,2-dicarboxylate (22.0 g, 61.6 mmol) in DMF (220 mL) was added potassium ethanethioate (14.1 g, 123 mmol) at RT. The reaction mixture was stirred at 40° C. for 16 hours. The resulting mixture was diluted with water (150 mL) and extracted with EA (3×300 ml). The combined organic layers were washed with water (3×300 mL) and brine (3×300 mL), dried over anhydrous Na$_2$SO$_4$ and filtered. Then filtrate was concentrated under vacuum. The residue was purified by silica gel column chromatography, eluted with 10% EA in PE. The fractions containing desired product were combined and concentrated under vacuum to afford the title compound: LCMS [M+1]$^+$: 338.

Step C: (2S,4S)-1-benzyl-2-methyl-4-mercaptopyrrolidine-1,2-dicarboxylate

To a solution of (2S,4S)-1-benzyl-2-methyl-4-(acetylthio) pyrrolidine-1,2-dicarboxylate (16 g, 47.40 mmol) in MeOH (160 mL) was added K$_2$CO$_3$ (19.7 g, 142 mmol) at room temperature. The reaction mixture was stirred at room temperature for 10 hours. The reaction mixture was poured into ice-water (100 mL), neutralized with conc. HCl to pH 7. The resulting mixture was extracted with EA (150 mL), washed with water (3×150 mL). The organic layer was dried over anhydrous Na$_2$SO$_4$ and filtered. The filtrate was concentrated under vacuum. The residue was purified by silica gel column chromatography, eluted with 20% EA in PE. The fractions containing desired product were combined and concentrated under vacuum to afford the title compound: LCMS [M+1]$^+$: 296.

Step D: (2S,4S)-benzyl 2-(hydroxymethyl)-4-mercaptopyrrolidine-1-carboxylate

To a stirred solution of (2S,4S)-1-benzyl-2-methyl-4-mercaptopyrrolidine-1,2-dicarboxylate (1.0 g, 3.39 mmol) in THF (10.0 mL) was added LiBH$_4$ (0.22 g, 10.16 mmol) slowly at 0° C. under nitrogen. The reaction mixture was stirred at RT for 2 hours under nitrogen. The resulting mixture was quenched with ice-water (100 mL) and extracted with EA (3×100 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]+268.

REFERENCE EXAMPLE 61

(R)-tert-butyl 2-(tert-butyldimethylsilyloxy)-3-mercaptopropylcarbamate

Step A: (R)-tert-butyl (2,3-dihydroxypropyl)carbamate

To a solution of (R)-3-aminopropane-1,2-diol (20 g, 220 mmol) in MeOH (200 mL) were added TEA (61 mL, 439 mmol) and di-tert-butyl dicarbonate (61 mL, 263 mmol) at RT. The reaction mixture was stirred at RT for 6 hours. The resulting mixture was concentrated under vacuum. The residue was purified by silica gel column chromatography, eluted with 10% MeOH in DCM. The fractions containing desired product were combined and concentrated under vacuum to afford the title compound: LCMS [M+1]$^+$: 192.

Step B: (R)-tert-butyl (2,3-bis((tert-butyldimethylsilyl)oxy)propyl)carbamate

To a solution of (R)-tert-butyl (2,3-dihydroxypropyl)carbamate (23 g, 120 mmol) in DCM (400 mL) were added 1H-imidazole (32.75 g, 480 mmol) and tert-butyl chlorodimethylsilane (40.0 g, 260 mmol) at 0° C. The mixture was stirred at RT for 16 hours. The resulting mixture was filtered. The filtrate was concentrated under vacuum. The residue was purified by silica gel column chromatography, eluted with 25% EA in PE. The fractions containing desired product were combined and concentrated under vacuum to afford the title compound: LCMS [M+1]$^+$: 420.

Step C: (R)-tert-butyl(2-((tert-butyldimethylsilyl)oxy)-3-hydroxypropyl)carbamate To a solution of (R)-tert-butyl-2,3-bis(tert-butyldimethylsilyloxy)propylcarbamate (20 g, 40 mmol) in DCM (20 mL)

was added AcOH (100 mL, 47.6 mmol) at RT. The reaction mixture was stirred at RT for 48 hours. The resulting mixture was filtered. The filtrate was concentrated under vacuum. The residue was purified by silica gel column chromatography, eluted with 25% EA in PE. The fractions containing desired product were combined and concentrated under vacuum to afford the title compound: LCMS [M+1]$^+$: 306.

Step D: (R)-3-((tert-butoxycarbonyl)amino)-2-((tert-butyldimethylsilyl)oxy)propyl methanesulfonate To a stirred solution of (R)-tert-butyl-2-(tert-butyldimethylsilyloxy)-3-hydroxypropylcarbamate (2.20 g, 7.20 mmol) in DCM (20 mL) was added TEA (2 mL, 14.46 mmol) and MsCl (0.8 mL, 10.8 mmol) at 0° C. The reaction mixture was stirred at RT for 2 hours. The resulting mixture was quenched with water (200 mL) and extracted with EA (3×200 mL). The combined organic layers was washed with water (2×100 mL) and brine (2×100 mL), dried over anhydrous MgSO$_4$ and filtered. The filtrate was concentrated under vacuum to afford the title compound, which was used directly in the next step: LCMS [M+1]$^+$384.

Step E: (R)—S-3-(tert-butoxycarbonylamino)-2-(tert-butyldimethylsilyloxy)propyl ethanethioate To a solution of (R)-3-(tert-butoxycarbonylamino)-2-(tert-butyldimethylsilyloxy) propyl methanesulfonate (2.60 g, 6.79 mmol) in DMF (50 mL) was added potassium ethanethioate (3.86 g, 27.18 mmol) at RT. The reaction mixture was stirred at 50° C. for 16 hours. The resulting mixture was quenched with water (100 mL) and extracted with EA (3×100 mL). The combined organic layers was washed with brine (2×100 mL), dried over anhydrous MgSO$_4$ and filtered. The filtrate was concentrated under vacuum. The residue was purified by silica gel column chromatography, eluted with 15% EA in PE. The fractions containing desired product were combined and concentrated under vacuum to afford the title compound: LCMS [M+1]$^+$: 364.

Step F: (R)-tert-butyl(2-((tert-butyldimethylsilyl)oxy)-3-mercaptopropyl)carbamate To a solution of (R)—S-3-(tert-butoxycarbonylamino)-2-(tert-butyldimethylsilyloxy) propyl ethanethioate (2.00 g, 5.49 mmol) in MeOH (20 mL) was added Na$_2$CO$_3$ (1.46 g, 13.77 mmol) and water (4 mL) at room temperature. The reaction mixture was stirred at RT for 1 hour. The resulting mixture was quenched with water (100 mL) and extracted with EA (3×100 mL). The combined organic layers were washed with brine (2×100 mL), dried over anhydrous Na$_2$SO$_4$ and filtered. The filtrate was concentrated under vacuum to afford (R)-tert-butyl(2-((tert-butyldimethylsilyl)oxy)-3-mercaptopropyl)carbamate as an oil, which was used in next step without further purification: LCMS [M+1]$^+$: 322.

REFERENCE EXAMPLE 62

(R)-tert-butyl (3-((tert-butyldimethylsilyl)oxy)-2-mercaptopropyl)carbamate

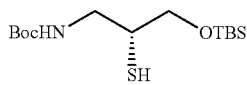

Step A: (S)-tert-butyl (3-((tert-butyldimethylsilyl)oxy)-2-hydroxypropyl)carbamate To a stirred solution of (S)-tert-butyl(2,3-dihydroxypropyl)carbamate (1.50 g, 7.84 mmol), and tert-butylchlorodimethylsilane (1.30 g, 8.63 mmol) in DCM (50 mL) was added 1H-imidazole (1.10 g, 15.69 mmol) at RT. The reaction mixture was stirred at room temperature for 3 h. The resulting mixture was filtered. The filtrate was concentrated under vacuum. The residue was purified by silica gel column chromatography, eluted with 33% EA in PE. The fractions containing desired product were combined and concentrated under vacuum to afford the title compound: LCMS [M+1]$^+$: 306.

Step B: (S)-2,2,3,3,11,11-hexamethyl-9-oxo-4,10-dioxa-8-aza-3-siladodecan-6-yl methanesulfonate To a solution of (R)-tert-butyl (3-((tert-butyldimethylsilyl)oxy)-2-hydroxypropyl) carbamate (2.00 g, 6.55 mmol) and triethylamine (2.80 mL, 19.64 mmol) in DCM (50 mL) was added MsCl (0.76 mL, 9.82 mmol) dropwise at −20° C. over 5 minutes. The reaction mixture was stirred at RT for 30 minutes. The resulting mixture was diluted with water (50 mL) and extracted with DCM (3×50 mL). The organic layers was washed with saturated aqueous NH$_4$Cl and dried over anhydrous Na$_2$SO$_4$ and filtered. The filtrate was concentrated under vacuum to afford the title compound, which was used directly in the next step: LCMS [M+1]$^+$: 384.

Step C: (R)—S-(2,2,3,3,11,11-hexamethyl-9-oxo-4,10-dioxa-8-aza-3-siladodecan-6-yl) ethanethioate To a solution of (S)-2,2,3,3,11,11-hexamethyl-9-oxo-4,10-dioxa-8-aza-3-siladodecan-6-yl methanesulfonate (2.30 g, 6.00 mmol) in DMF (30 mL) was added potassium thioacetate (2.70 g, 24.0 mmol) at RT. The reaction mixture was stirred at 80° C. for 16 hours. The resulting mixture was diluted with EA (150 mL), washed with water (3×50 mL) and brine (2×10 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 364.

Step D: (R)-tert-butyl(3-((tert-butyldimethylsilyl)oxy)-2-mercaptopropyl)carbamate To a solution of (R)—S-(2,2,3,3,11,11-hexamethyl-9-oxo-4,10-dioxa-8-aza-3-siladodecan-6-yl) ethanethioate (2.00 g, 5.50 mmol) in MeOH (5.0 mL) was added K$_2$CO$_3$ (1.8 g, 13.75 mmol) at 0° C. The reaction mixture was stirred for 0.5 hour at RT. The resulting mixture was neutralized with aqueous HCl (2 N) and extracted with EA (3×20 mL). The organic layer was dried over anhydrous Na$_2$SO$_4$ and filtered. The filtrate was concentrated under vacuum to afford the title compound, which was used directly in the next step: LCMS [M+1]$^+$: 322.

REFERENCE EXAMPLE 63

(S)-tert-butyl (2-((tert-butyldimethylsilyl)oxy)-3-mercaptopropyl)carbamate

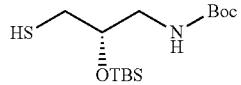

Step A: (S)-tert-butyl (2,3-dihydroxypropyl)carbamate

To a stirred solution of (S)-3-aminopropane-1,2-diol (30 g, 329 mmol) in MeOH (400 mL) were added TEA (67 mL, 329 mmol) and di-tert-butyl dicarbonate (93 g, 428 mmol) at RT. The reaction mixture was stirred at RT for 2 hours. The resulting mixture was concentrated under vacuum. The residue was purified by silica gel column chromatography, eluted with 10% MeOH in DCM. The fractions containing desired product were combined and concentrated under vacuum to afford the title compound: LCMS [M+1]$^+$: 192.

Step B: (S)-tert-butyl (2,3-bis((tert-butyldimethylsilyl)oxy)propyl)carbamate To a stirred solution of (S)-tert-butyl (2,3-dihydroxypropyl)carbamate (10 g, 52.3 mmol) in DCM (200 mL) was added tert-butylchlorodimethylsilane (17.34 g, 115 mmol) and 1H-imidazole (14.24 g, 209 mmol) at RT. The mixture was stirred at RT for 16 hours. The resulting mixture was filtered and filtrate was concentrated under vacuum. The residue was purified by silica gel column chromatography, eluted with 25% EA in PE. The fractions containing desired product were combined and concentrated under vacuum to afford the title compound: LCMS [M+1]$^+$: 420.

Step C: (S)-tert-butyl(2-((tert-butyldimethylsilyl)oxy)-3-hydroxypropyl)carbamate To a solution of (S)-tert-butyl(2,3-bis((tert-butyldimethylsilyl)oxy)propyl)carbamate (20 g, 47.6 mmol) in DCM (20 mL) was added AcOH (100 mL, 47.6 mmol) at RT. The reaction mixture was stirred at RT for 16 hours. The resulting solution was neutralized with the saturated aqueous NaHCO$_3$ to pH=7. The aqueous phase was extracted with EA (3×200 mL). The combined organic layers were concentrated under vacuum. The residue was purified by silica gel column chromatography, eluted with 25% EA in PE. The fractions containing desired product were combined and concentrated under vacuum to afford the title compound: LCMS [M+1]$^+$: 306.

Step D: (S)-3-((tert-butoxycarbonyl)amino)-2-((tert-butyldimethylsilyl)oxy)propyl methanesulfonate To a stirred solution of (S)-tert-butyl(2-((tert-butyldimethylsilyl)oxy)-3-hydroxypropyl)carbamate (2.00 g, 6.55 mmol) in DCM (20 mL) was added TEA (1.8 mL, 13.1 mmol) and MsCl (0.7 mL, 9.80 mmol) at 0° C. The reaction mixture was stirred at RT for 1 hour. The resulting mixture was quenched with water (100 mL) and extracted with EA (3×100 mL). The combined organic layers was washed with water (2×100 mL) and brine (2×100 mL), dried over anhydrous MgSO$_4$ and filtered. The filtrate was concentrated under vacuum to afford the title compound, which was used in next step without further purification: LCMS [M+1]$^+$: 384.

Step E: (S)—S-(3-((tert-butoxycarbonyl)amino)-2-((tert-butyldimethylsilyl)oxy)propyl) ethanethioate To a solution of (S)-3-((tert-butoxycarbonyl)amino)-2-((tert-butyldimethylsilyl)oxy)propyl methanesulfonate (2.3 g, 6.00 mmol) in DMF (30 mL) was added potassium ethanethioate (0.68 g, 6.0 mmol) at RT. The reaction mixture was stirred at 50° C. for 16 hours. The resulting mixture was diluted with water (50 mL) and extracted with EA (3×30 mL). The combined organic layers was washed with water (2×50 mL), brine (2×50 mL), dried over anhydrous MgSO$_4$ and filtered. The filtrate was concentrated under vacuum. The residue was purified by silica gel column chromatography, eluted with 15% EA in PE. The fractions containing desired product were combined and concentrated under vacuum to afford the title compound: LCMS [M+1]$^+$: 364.

Step F: (S)-tert-butyl (2-((tert-butyldimethylsilyl)oxy)-3-mercaptopropyl)carbamate To a solution of (S)—S-(3-((tert-butoxycarbonyl)amino)-2-((tert-butyldimethylsilyl)oxy)propyl) ethanethioate (1.90 g, 5.23 mmol) in MeOH (20 mL) and water (4 mL) was added Na$_2$CO$_3$ (1.40 g, 13.06 mmol) at RT. The reaction mixture was stirred at RT for 1 hour. The resulting mixture was diluted with water (50 mL) and extracted with EA (3×50 mL). The combined organic layers were washed with brine (3×50 mL), dried over anhydrous Na$_2$SO$_4$ and filtered. The filtrate was concentrated under vacuum to afford the title compound: LCMS [M+1]$^+$: 322

REFERENCE EXAMPLE 64

(S)-tert-butyl(1-mercaptopropan-2-yl)carbamate

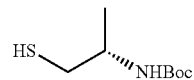

Step A: (S)-2-((tert-butoxycarbonyl)amino)propyl methanesulfonate

To a stirred solution of (S)-tert-butyl (1-hydroxypropan-2-yl)carbamate (1.00 g, 5.71 mmol) in DCM (10 mL) was added TEA (2.39 mL, 17.12 mmol) and MsCl (0.53 mL, 6.85 mmol) at 0° C. The reaction mixture was stirred at RT for 20 minutes under nitrogen. The resulting mixture was quenched with ice-water (50 mL) and extracted with EA (3×50 mL). The combined organic layers were washed with brine (1×100 mL), dried over anhydrous Na$_2$SO$_4$ and filtered. The filtrate was concentrated under vacuum to afford the title compound: LCMS [M+1-100]$^+$: 154.

Step B: (S)—S-(2-((tert-butoxycarbonyl)amino)propyl) ethanethioate

To a solution of (S)-2-((tert-butoxycarbonyl)amino)propyl methanesulfonate (1.40 g, 4.42 mmol) in DMF (10 mL) was added potassium ethanethioate (2.02 g, 17.69 mmol) at RT. The reaction mixture was stirred at 80° C. for 16 hours under nitrogen. The reaction was quenched with ice-water (150 mL) and extracted with EA (3×150 mL). The combined organic layers were washed with brine (2×200 mL), dried over anhydrous Na$_2$SO$_4$ and filtered. The filtrate was concentrated under vacuum. The residue was purified by silica gel column chromatography, eluted with 17% EA in PE. The fractions containing desired product were combined and concentrated under vacuum to afford the title compound: LCMS [2M+1]$^+$: 467.

Step C: (S)-tert-butyl(1-mercaptopropan-2-yl)carbamate

To a solution of (S)—S-(2-((tert-butoxycarbonyl)amino)propyl) ethanethioate (1.0 g, 3.64 mmol) in MeOH (10 mL) was added $K_2CO_3$ (1.18 g, 10.93 mmol) with stirring at 0° C.

The reaction mixture was stirred at RT for 3 hours under nitrogen. The pH of the resulting mixture was adjusted to ~7 at 0° C. and extracted with EA (3×50 mL). The combined organic layers were washed with brine (100 mL), dried over anhydrous $Na_2SO_4$ and filtered. The filtrate was concentrated under vacuum to afford the title compound, which was used directly in next step: LCMS $[2M+1]^+$: 383; $^1$H NMR (300 MHz, DMSO-$d_6$): δ 6.78 (brs, 1H), 3.51-3.46 (m, 1H), 2.54-2.48 (m, 1H), 2.24-2.18 (m, 1H), 1.38 (s, 9H), 1.06 (d, J=6.6 Hz, 3H).

REFERENCE EXAMPLE 65

(2S,4S)-1-tert-butyl 2-methyl 4-mercaptopyrrolidine-1,2-dicarboxylate

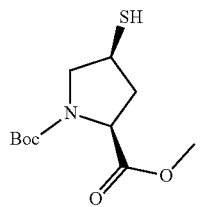 [SMILES: COC(=O)[C@@H]1C[C@H](S)CN1C(=O)OC(C)(C)C]

Step A: (2S,4R)-1-tert-butyl 2-methyl 4-((methylsulfonyl)oxy)pyrrolidine-1,2-dicarboxylate To a stirred solution of (2S,4R)-1-tert-butyl-2-methyl-4-hydroxypyrrolidine-1,2-dicarboxylate (7.9 g, 32 mmol) and TEA (14 mL, 96 mmol) in DCM (80 mL) was added methanesulfonyl chloride (5.5 g, 48 mmol) at 0° C. The mixture was stirred at RT for 2 hours. The resulting mixture was quenched with water (100 mL) and extracted with EA (3×200 mL). The combined organic layers were washed with water (3×200 mL) and brine (3×200 mL), dried over anhydrous $Na_2SO_4$ and filtered. The filtrate was concentrated under vacuum to afford the title compound, which was used in directly next step: LCMS $[M+1]^+$: 324.

Step B: (2S,4S)-1-tert-butyl-2-methyl 4-(acetylthio)pyrrolidine-1,2-dicarboxylate To a solution of (2S,4R)-1-tert-butyl-2-methyl-4-((methylsulfonyl)oxy) pyrrolidine-1,2-dicarboxylate (8.3 g, 26 mmol) in DMF (80 mL) was added potassium ethanethioate (5.9 g, 51 mmol) at RT. The mixture was stirred at 70° C. for 2 days. The resulting mixture was diluted with water (100 mL) and extracted with EA (3×200 mL). The combined organic layers was washed with water (3×200 mL) and brine (3×200 mL), dried over anhydrous $Na_2SO_4$ and filtered. The filtrate was concentrated under vacuum. The residue was purified by silica gel column chromatography, eluted with 10% EA in PE. The fractions containing desired product were combined and concentrated under vacuum to afford the title compound: LCMS $[M+1]^+$: 304.

Step C: (2S,4S)-1-tert-butyl 2-methyl 4-mercaptopyrrolidine-1,2-dicarboxylate To a solution of (2S,4S)-1-tert-butyl-2-methyl-4-(acetylthio)pyrrolidine-1,2-dicarboxylate (6.7 g, 22 mmol) in MeOH (70 mL) was added $K_2CO_3$ (9.1 g, 66 mmol) at room temperature. The reaction mixture was stirred at room temperature for 16 h. The resulting mixture was diluted with water (100 mL) and extracted with EA (3×200 mL). The combined organic layers were washed with water (3×200 mL) and brine (3×200 mL), dried over anhydrous $Na_2SO_4$ and filtered. The filtrate was concentrated under vacuum to afford the title compound, which was used in the next step without further purification: LCMS $[M+1]^+$: 262.

REFERENCE EXAMPLE 66

(R)-tert-butyl (1-hydroxy-3-mercaptopropan-2-yl)carbamate

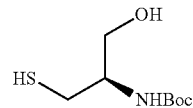

Step A: (S)-methyl 2-((tert-butoxycarbonyl)amino)-3-((methylsulfonyl)oxy)propanoate To a stirred solution of (S)-methyl-2-((tert-butoxycarbonyl)amino)-3-hydroxypropanoate (10 g, 45.60 mmol) in DCM (150 mL) was added TEA (19 mL, 137.00 mmol) and MsCl (10.45 g, 91.00 mmol) at 0° C. The reaction mixture was stirred at 20° C. for 1 hour. The resulting mixture was quenched with water (200 mL) and extracted with DCM (2×200 mL). The combined organic layers were washed with water (2×200 mL) and brine (2×200 mL), dried over anhydrous $Na_2SO_4$ and filtered. The filtrate was concentrated under vacuum to afford the title compound, which was used in the next step without further purification: LCMS $[M+23]^+$: 320; $^1$H NMR (400 MHz, $CDCl_3$): δ 5.30 (brs, 1H), 4.60-4.56 (m, 2H), 4.52-4.51 (m, 1H), 3.81 (s, 3H), 3.02 (s, 3H), 1.47 (s, 9H).

Step B: (R)-methyl-3-(acetylthio)-2-((tert-butoxycarbonyl)amino)propanoate

To a solution of (S)-methyl-2-((tert-butoxycarbonyl)amino)-3-((methylsulfonyl)-oxy)propanoate (13.00 g, 43.77 mmol) in DMF (150 mL) was added potassium ethanethioate (9.98 g, 87.54 mmol) at 20° C. The reaction mixture was stirred at 20° C. for 16 hours. The resulting mixture was diluted with water (500 mL) and extracted with EA (3×300 mL). The combined organic layers were washed with water (3×300 mL), brine (3×500 mL), dried over anhydrous $Na_2SO_4$ and filtered. The filtrate was concentrated under vacuum. The residue was purified by silica gel column chromatography, eluted with 5% EA in PE. The fractions containing desired product were combined and concentrated under vacuum to afford the title compound: LCMS $[M+23]^+$: 300; $^1$H NMR (400 MHz, $CDCl_3$): δ 5.23 (brs, 1H), 4.54-4.52 (m, 1H), 3.76 (s, 3H), 3.37-3.32 (m, 2H), 2.35 (s, 3H), 1.47 (s, 9H).

Step C: (R)-methyl-2-((tert-butoxycarbonyl)amino)-3-mercaptopropanoate

To a solution of (R)-methyl-3-(acetylthio)-2-((tert-butoxycarbonyl)-amino)propanoate (2.00 g, 7.21 mmol) in MeOH (50 mL) was added $K_2CO_3$ (2.99 g, 21.63 mmol) at 20° C. The reaction mixture was stirred at 20° C. for 16 hours. The resulting mixture was diluted with water (50 mL) and extracted with EA (2×200 mL). The combined organic layers were washed with water (2×200 mL), brine (2×200 mL), dried over anhydrous $Na_2SO_4$ and filtered. The filtrate was concentrated under vacuum to afford the title compound, which was used in next step without further purification: LCMS [2M+1]$^+$: 471; $^1$H NMR (300 MHz, CDCl$_3$): δ 5.40 (brs, 1H), 4.62-4.52 (m, 1H), 3.77 (s, 3H), 2.99-3.2.95 (m, 2H), 1.44 (s, 9H).

Step D: (R)-tert-butyl (1-hydroxy-3-mercaptopropan-2-yl)carbamate

To a stirred solution of (R)-methyl-2-((tert-butoxycarbonyl)amino)-3-mercaptopro-panoate (1.60 g, 5.10 mmol) in THF (50 mL) was added LiAlH$_4$ (0.77 g, 20.40 mmol) in several portions at 0° C. The reaction mixture was stirred at 20° C. for 1 hour. Then water (0.8 mL), 15% aqueous NaOH (2.4 mL) and water (0.8 mL) were added dropwise to the reaction mixture. The resulting mixture was filtered. The filtrate was concentrated under vacuum. The residue was purified by silica gel column chromatography, eluted with 30% EA in PE. The fractions containing desired product were combined and concentrated under vacuum to afford the title compound: LCMS [M+1]$^+$: 208.

REFERENCE EXAMPLE 67

(S)-tert-butyl (1-hydroxy-3-mercaptopropan-2-yl) carbamate

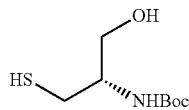

Step A: (R)-methyl-2-((tert-butoxycarbonyl)amino)-3-((methylsulfonyl)oxy)propanoate To a stirred solution of (R)-methyl-2-((tert-butoxycarbonyl)amino)-3-hydroxypropanoate (15.0 g, 68.40 mmol) in DCM (80 mL) was added MsCl (15.7 g, 137 mmol) and TEA (28.5 mL, 205 mmol) at 0° C. The reaction mixture was stirred at RT for 4 hours. The reaction mixture was concentrated under vacuum. The residue was dissolved in EA (100 mL). The resulting mixture was washed with brine (3×100 mL) and dried over anhydrous $Na_2SO_4$. The combined organic layer was concentrated under vacuum to afford the title compound, which was used directly in the next step: LCMS [M+23]$^+$: 320; $^1$HNMR (400 MHz, CDCl$_3$): δ 5.41 (brs, 1H), 4.62-4.60 (m, 2H), 4.55-4.52 (m, 1H), 3.83 (s, 3H), 3.04 (s, 3H), 1.48 (s, 9H).

Step B: (S)-methyl-3-(acetylthio)-2-((tert-butoxycarbonyl)amino)propanoate

To a solution of (R)-methyl-2-((tert-butoxycarbonyl) amino)-3-((methylsulfonyl) oxy)propanoate (13.0 g, 43.77 mmol) in DMF (80 mL) was added potassium ethanethioate (9.98 g, 87.54 mmol) at RT. The resulting mixture was stirred for 16 hours at room temperature. The resulting mixture was diluted with water (100 mL) and extracted with EA (3×100 mL). The combined organic layers were washed with water (2×150 mL) and brine (2×150 mL), dried over anhydrous $Na_2SO_4$ and filtered. The filtrate was concentrated under vacuum. The residue was purified by silica gel column chromatography, eluted with 10% EA in PE. The fractions containing desired product were combined and concentrated under vacuum to afford the title compound: LCMS [M+23]$^+$: 300; $^1$HNMR (400 MHz, DMSO-d$_6$): δ 5.24 (brs, 1H), 4.53-4.51 (m, 1H), 3.76 (s, 3H), 3.36-3.31 (m, 2H), 2.35 (s, 3H), 1.45 (s, 9H).

Step C: (S)-methyl-2-((tert-butoxycarbonyl)amino)-3-mercaptopropanoate

To a solution of (S)-methyl-3-(acetylthio)-2-((tert-butoxycarbonyl)amino)propanoate (1.50 g, 5.41 mmol) in MeOH (15 mL) was added $K_2CO_3$ (1.15 g, 10.8 mmol) at RT. The mixture was stirred at RT for 30 min. The reaction mixture was poured into ice water (50 mL) and neutralized with conc. HCl to pH 6-7. The solution was extracted with EA (3×50 mL). The organic layer was washed with water (3×50 mL) and brine (3×50 mL), dried over anhydrous $Na_2SO_4$ and filtered. The filtrate was concentrated under vacuum to afford the title compound, which was used in next step without further purification: LCMS [2M+1]$^+$: 471; $^1$H NMR (400 MHz, DMSO-d$_6$): δ 7.29 (brs, 1H), 4.15-4.13 (m, 1H), 3.32 (s, 3H), 2.84-2.79 (m, 1H), 2.73-2.68 (m, 1H), 2.66-2.57 (m, 1H), 1.39 (s, 9H).

Step D: (S)-tert-butyl-(1-hydroxy-3-mercaptopropan-2-yl)carbamate

To a stirred solution of (S)-methyl-2-((tert-butoxycarbonyl)amino)-3-mercaptopropanoate (1.50 g, 6.37 mmol) in THF (15 mL) was added LiAlH$_4$ (0.77 g, 20.40 mmol) in several portions at 0° C. The reaction mixture was stirred at 0° C. for 1 hour. The resulting mixture was quenched with water (0.8 mL), 15% aqueous NaOH (2.4 mL) and water (0.8 mL) were added dropwise into the resulting mixture, which was filtered. The filtrate was concentrated under vacuum. The residue was purified by silica gel column chromatography, eluted with 70% EA in PE. The fractions containing desired product were combined and concentrated under vacuum to afford the title compound: LCMS [M+1]$^+$: 208.

REFERENCE EXAMPLE 68

(S)-tert-butyl (3-((tert-butyldimethylsilyl)oxy)-2-mercaptopropyl)carbamate

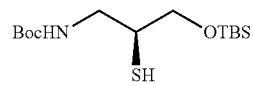

Step A: (R)-tert-butyl (3-((tert-butyldimethylsilyl)oxy)-2-hydroxypropyl)carbamate To a solution of (R)-tert-butyl (2,3-dihydroxypropyl)carbamate (5.0 g, 26.18 mmol), tert-butylchlorodimethylsilane (4.7 g, 31.41 mmol) in DCM (50 mL) was added 1H-imidazole (3.6 g, 52.35 mmol) at RT. The reaction mixture was stirred at RT for 3 hours. The resulting mixture was filtered. The filtrate was concentrated under vacuum. The residue was purified by silica gel column chromatography, eluted with 33% EA in PE. The fractions containing desired product were combined and concentrated under vacuum to afford the title product as an oil: LCMS [M+1]$^+$: 306.

Step B: (R)-2,2,3,3,11,11-hexamethyl-9-oxo-4,10-dioxa-8-aza-3-siladodecan-6-yl methanesulfonate To a solution of (R)-tert-butyl(3-((tert-butyldimethylsilyl)oxy)-2-hydroxypropyl) carbamate (5.0 g, 16.37 mmol) and TEA (7.0 mL, 49.10 mmol) in DCM (50 mL) was added MsCl (2 mL, 24.55 mmol) dropwise at −20° C. over 5 minutes. The reaction mixture was stirred at room temperature for 30 min. The resulting reaction mixture was diluted with water (50 mL) and extracted with DCM (3×50 mL). The organic layers was washed with saturated NH$_4$Cl and dried over anhydrous Na$_2$SO$_4$ and filtered. The filtrate was concentrated under vacuum to afford the title compound, which was used directly in the next step: LCMS [M+1]$^+$: 384.

Step C: (S)—S-(2,2,3,3,11,11-hexamethyl-9-oxo-4,10-dioxa-8-aza-3-siladodecan-6-yl) ethanethioate To a solution of (R)-2,2,3,3,11,11-hexamethyl-9-oxo-4,10-dioxa-8-aza-3-siladodecan-6-yl methanesulfonate (5.0 g, 13.04 mmol) in DMF (50 mL) was added potassium thioacetate (5.9 g, 52.10 mmol) at room temperature. The reaction mixture was stirred at 80° C. for 16 hours. The resulting mixture was diluted with EA (250 mL), washed with water (3×50 mL) and brine (2×10 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 364.

Step D: (S)-tert-butyl (3-((tert-butyldimethylsilyl)oxy)-2-mercaptopropyl)carbamate To a solution of (S)—S-(2,2,3,3,11,11-hexamethyl-9-oxo-4,10-dioxa-8-aza-3-siladodecan-6-yl)ethanethioate (3.0 g, 8.25 mmol) in MeOH (10 mL) was added K$_2$CO$_3$ (2.8 g, 20.62 mmol) at 0° C. The reaction mixture was stirred for 0.5 hour at RT. The resulting mixture was neutralized by aqueous HCl (2 N) and extracted with EA (3×20 mL). The organic layers was dried over anhydrous Na$_2$SO$_4$ and filtered. The filtrate was concentrated under vacuum to afford the title compound, which was used to make compounds of the invention without further purification: LCMS [M+1]$^+$: 322.

REFERENCE EXAMPLE 69

(R)-di-tert-butyl (3-mercaptopropane-1,2-diyl)dicarbamate

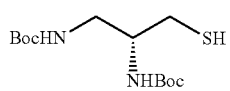

Step A: (R)-methyl 3-amino-2-(((benzyloxy)carbonyl)amino)propanoate hydroChloride To a solution of (R)-3-amino-2-(((benzyloxy)carbonyl)amino)propanoic acid (30.0 g, 126 mmol) in MeOH (30 mL) was added SOCl$_2$ (9.19 mL, 126 mmol) at 0° C. The mixture was stirred at 0° C. for 1.5 hours. The resulting mixture was concentrated under vacuum to afford the title compound, which was used directly in the next step: LCMS [M+1-36]$^+$: 253.

Step B: (R)-benzyl(1-amino-3-hydroxypropan-2-yl)carbamate

To a stirred solution of (R)-methyl-3-amino-2-(((benzyloxy)carbonyl)amino) propanoate hydrochloride (5.0 g, 17.32 mmol) in THF (5.0 mL) was added LiBH$_4$ (1.13 g, 52.0 mmol) slowly at 0° C. The mixture was stirred at 0° C. for 3 hours under nitrogen. The resulting mixture was quenched with saturated aqueous NH$_4$Cl (100 mL) and extracted with EA (3×100 mL). The combined organic layers were washed with water (3×100 mL) and brine (3×100 mL), dried over anhydrous Na$_2$SO$_4$ and filtered. The filtrate was concentrated under vacuum to afford the title compound, which was used directly in the next step: LCMS [M+1]$^+$: 225.

Step C: (R)-di-tert-butyl (3-hydroxypropane-1,2-diyl)dicarbamate

To a stirred solution of (R)-benzyl 1-amino-3-hydroxypropan-2-ylcarbamate (9.0 g, 47 mmol) and (Boc)$_2$O (26.0 g, 141 mmol) in MeOH (100 mL) was added Pd(OH)$_2$/C (20%, 1.0 g) at room temperature. The mixture was degassed with hydrogen three times. The mixture was stirred 2 hours at room temperature under hydrogen (1.5 atm). The resulting mixture was filtered. The filtrate was diluted with water (100 mL) and extracted with EA (3×100 mL). The combined organic layers was washed with water (2×30 mL) and brine (2×30 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 291.

Step D: (R)-2,3-bis((tert-butoxycarbonyl)amino)propyl methanesulfonate

To a stirred solution of (R)-di-tert-butyl 3-hydroxypropane-1,2-diyldicarbamate (4.30 g, 15 mmol) and TEA (4.10 mL, 30 mmol) in DCM (40 mL) was added MsCl (1.78 mL, 22.5 mmol) at 0° C. The reaction mixture was stirred at room temperature for 2 h. The resulting mixture was quenched with water (50 mL) and extracted with EA (3×100 mL). The combined organic layers was washed with water (2×30 mL) and brine (2×30 mL), dried over anhydrous Na$_2$SO$_4$ and filtered. The filtrate was concentrated under vacuum. The residue was purified by silica gel column chromatography, eluted with 4% MeOH in DCM. The fractions containing desired product were combined and concentrated under vacuum to afford the title compound: LCMS [M+1]$^+$: 369.

Step E: (R)—S-(2,3-bis((tert-butoxycarbonyl)amino)propyl) ethanethioate

To a solution of (R)-3-(benzyloxycarbonylamino)-2-(tert-butoxycarbonylamino) propyl methanesulfonate (4.0 g, 11 mmol) in DMF (40 mL) was added potassium ethanethioate (1.90 g, 16.5 mmol) at room temperature. The mixture was stirred at 50° C. for 16 h. The resulting mixture was quenched with water (50 mL) and extracted with EA (3×100 mL). The combined organic layers was washed with water (2×30 mL) and brine (2×30 mL), dried over anhydrous Na$_2$SO$_4$ and filtered. The filtrate was concentrated under vacuum. The residue was purified by silica gel column chromatography, eluted with 11% EA in PE. The fractions containing desired product were combined and concentrated to under vacuum afford the title compound: LCMS [M+1]$^+$: 349.

Step F: (R)-di-tert-butyl
(3-mercaptopropane-1,2-diyl)dicarbamate

To a solution of (R)—S-2,3-bis(tert-butoxycarbonylamino)propyl ethanethioate (2.8 g, 8 mmol) in MeOH (30 mL) was added K$_2$CO$_3$ (2.2 g, 16 mmol) at RT. The mixture was stirred at RT for 4 hours. The resulting mixture was quenched with water (100 mL) and extracted with EA (3×100 mL). The combined organic layers was washed with water (2×100 mL) and brine (2×100 mL), dried over anhydrous Na$_2$SO$_4$ and filtered. The filtrate was concentrated under vacuum to afford the title compound: LCMS [M+1]$^+$: 307.

REFERENCE EXAMPLE 70

(R)-benzyl tert-butyl
(3-mercaptopropane-2-diyl)dicarbamate

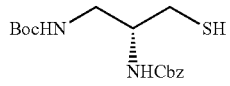

Step A: (R)-benzyl tert-butyl
(3-hydroxypropane-1,2-diyl)dicarbamate

To a solution of (R)-benzyl (1-amino-3-hydroxypropan-2-yl)carbamate (1.7 g, 7.58 mmol) and di-tert-butyl dicarbonate (2.0 g, 9.10 mmol) in DCM (20 mL) was added TEA (2.3 g, 22.74 mmol) at 0° C. The reaction mixture was stirred for 4 hours at RT. The resulting mixture was filtered. The filtrate was concentrated under vacuum. The residue was purified by silica gel column chromatography, eluted with 35% EA in PE. The fractions containing desired product was combined and concentrated under vacuum to afford the title compound, which was directly used for the next step: LCMS [M+1]$^+$: 325.

Step B: (R)-2-(((benzyloxy)carbonyl)amino)-3-((tert-butoxycarbonyl)amino)propyl methanesulfonate To a stirred solution of (R)-benzyl-tert-butyl (3-hydroxypropane-1,2-diyl)dicarbamate (2.2 g, 6.78 mmol) in DCM (20 mL) was added TEA (2.1 g, 20.35 mmol) and MsCl (1.2 g, 10.17 mmol) at 0° C. The reaction mixture was stirred for 1 hour at RT. The resulting mixture was diluted with water (30 mL) and extracted with EA (3×30 mL). The organic extract was dried over anhydrous Na$_2$SO$_4$ and filtered. The filtrate was concentrated under vacuum to afford the title compound, which was directly used for the next step: LCMS [M+1-100]$^+$: 303.

Step C: (R)—S-(2-(((benzyloxy)carbonyl)amino)-3-((tert-butoxycarbonyl)amino)propyl) ethanethioate To a solution of (R)-2-(((benzyloxy)carbonyl)amino)-3-((tert-butoxycarbonyl) amino)propyl methanesulfonate (2.4 g, 5.96 mmol) in DMF (25 mL) was added AcSK (1.0 g, 8.94 mmol) at RT. The mixture was stirred at 60° C. for 16 h. The resulting mixture was quenched with water (50 mL) and extracted with EA (3×20 mL). The combined organic layers was washed with brine (3×30 mL), dried over anhydrous Na$_2$SO$_4$ and filtered. The filtrate was concentrated under vacuum. The residue was purified by silica gel column chromatography, eluted with 60% EA in PE. The fractions containing desired product was combined and concentrated under vacuum to afford the title compound: LCMS [M+1-100]$^+$: 283.

Step D: (R)-benzyl tert-butyl
(3-mercaptopropane-1,2-diyl)dicarbamate

To a solution of (R)—S-(2-(((benzyloxy)carbonyl) amino)-3-((tert-butoxycarbonyl) amino)propyl)ethanethioate (2.0 g, 5.23 mmol) in MeOH (20 mL) was added K$_2$CO$_3$ (1.8 g, 13.07 mmol) room temperature. The reaction mixture was stirred at room temperature for 2 hours. The resulting mixture was quenched with water (20 mL) and extracted with EA (3×20 mL). The combined organic layers were washed with brine (3×20 mL), dried over anhydrous Na$_2$SO$_4$ and filtered. The filtrate was concentrated under vacuum to afford the title compound, which was directly used for the next step without further purification: LCMS [M+1]$^+$: 341.

REFERENCE EXAMPLE 71

(S)-di-tert-butyl
(3-mercaptopropane-1,2-diyl)dicarbamate

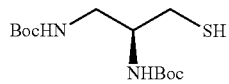

Step A: (S)-di-tert-butyl
(3-hydroxypropane-1,2-diyl)dicarbamate

TEA (3.0 mL, 23.65 mmol) was added to a solution of (S)-tert-butyl (1-amino-3-hydroxypropan-2-yl)carbamate (1.5 g, 7.88 mmol) and di-tert-butyl dicarbonate (2.1 g, 9.46 mmol) in DCM (20 mL) at 0° C. Then the mixture was stirred for 4 hours at RT. The resulting mixture was filtered. The filtrate was concentrated under vacuum. The residue was purified by silica gel column chromatography, eluted with 35% EA in PE. The fractions containing desired product were combined and concentrated under vacuum to afford the title compound: LCMS [M+1]$^+$: 291.

Step B:
(S)-2,3-bis((tert-butoxycarbonyl)amino)propyl methanesulfonate

To a stirred solution of (S)-di-tert-butyl (3-hydroxypropane-1,2-diyl)dicarbamate (2.0 g, 6.89 mmol) in DCM (20 mL) was added TEA (2.1 g, 20.66 mmol) and MsCl (1.2 g, 10.33 mmol) at 0° C. The mixture was stirred at room temperature for 1 hour. The resulting mixture was diluted with water (30 mL) and extracted with EA (3×30 mL). The combined organic layers were dried over anhydrous $Na_2SO_4$ and filtered. The filtrate was concentrated under vacuum to afford the title compound, which was directly used for the next step: LCMS $[M+1]^+$: 369.

Step C: (S)—S-(2,3-bis((tert-butoxycarbonyl) amino)propyl) ethanethioate

To a solution of (S)-2,3-bis((tert-butoxycarbonyl)amino) propyl methanesulfonate (2.2 g, 5.97 mmol) in DMF (25 mL) was added AcSK (1.0 g, 8.96 mmol) at room temperature. The mixture was stirred at 60° C. for 16 hours. The resulting mixture was quenched with water (20 mL) and extracted with EA (3×20 mL). The combined organic layers were washed with brine (3×30 mL), dried over anhydrous $Na_2SO_4$ and filtered. The filtrate was concentrated under vacuum. The residue was purified by silica gel column chromatography, eluted with 60% EA in PE. The fractions containing desired product was combined and concentrated under vacuum to afford the title compound: LCMS $[M+1]^+$: 349.

Step D: (S)-di-tert-butyl (3-mercaptopropane-1,2-diyl)dicarbamate

To a solution of (S)—S-(2,3-bis((tert-butoxycarbonyl) amino)propyl) ethanethioate (1.8 g, 5.17 mmol) in MeOH (20 mL) was added $K_2CO_3$ (1.8 g, 12.91 mmol) at room temperature. The reaction mixture was stirred at room temperature for 2 hours. The resulting mixture was quenched with water (20 mL) and extracted with EA (3×20 mL). The combined organic layers were washed with brine (3×20 mL), dried over anhydrous $Na_2SO_4$ and filtered. The filtrate was concentrated under vacuum to afford the title compound, which was directly used in the next step: LCMS $[M+1]^+$: 307.

REFERENCE EXAMPLE 72

(R)-tert-butyl (1-((2-(N,N-bis(4-methoxybenzyl) sulfamoyl)-4-iodo-3-(2-(4-methoxybenzyl)-2H-tetrazol-5-yl)phenyl)sulfonyl)propan-2-yl)carbamate

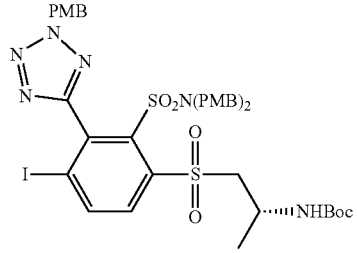

Step A: (R)-tert-butyl (1-((2-(N,N-bis(4-methoxybenzyl)sulfamoyl)-4-iodo-3-(2-(4-methoxy benzyl)-2H-tetrazol-5-yl)phenyl)thio)propan-2-yl)carbamate To a stirred solution of 6-bromo-3-iodo-N,N-bis(4-methoxybenzyl)-2-(2-(4-methoxybenzyl)-2H-tetrazol-5-yl) benzenesulfonamide (2.0 g, 2.53 mmol) in DMF (40 mL) was added (R)-tert-butyl (1-mercaptopropan-2-yl)carbamate (1.94 g, 10.12 mmol) and NaH (0.24 g, 10.12 mmol) at 0° C. under nitrogen. The reaction mixture was stirred at room temperature for 2 hours under nitrogen. The resulting mixture was quenched with water (100 mL) and extracted with EA (3×100 mL). The combined organic layers were washed with brine (3×150 mL), dried over anhydrous $Na_2SO_4$ and filtered. The filtrate was concentrated under vacuum to afford the title compound, which was used in the next step directly: LCMS $[M+1]^+$: 901.

Step B: (R)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate To a solution of (R)-tert-butyl (1-((2-(N,N-bis(4-methoxybenzyl)sulfamoyl)-4-iodo-3-(2-(4-methoxybenzyl)-2H-tetrazol-5-yl)phenyl)thio)propan-2-yl)carbamate (1.50 g, 1.67 mmol) in DCM (20 mL) was added m-CPBA (2.30 g, 13.32 mmol) at RT. The reaction mixture was stirred at RT for 16 hours. The resulting mixture was filtered. The filtrate was concentrated under vacuum. The residue was diluted with EA (150 mL) and washed with saturated aqueous $Na_2SO_3$ (3×100 mL) and saturated aqueous $NaHCO_3$ (3×150 mL). The organic layer was concentrated under vacuum. The residue was purified by silica gel column chromatography, eluted with 25% EA in PE. The fractions containing desired product were combined and concentrated under vacuum to afford the title compound: LCMS $[M+1]^+$: 933.

REFERENCE EXAMPLE 73

(2S,4S)-1-tert-butyl 2-methyl 4-((2-(N,N-bis(4-methoxybenzyl)sulfamoyl)-4-iodo-3-(2-(4-methoxybenzyl)-2H-tetrazol-5-yl)phenyl)sulfonyl)pyrrolidine-1,2-dicarboxylate

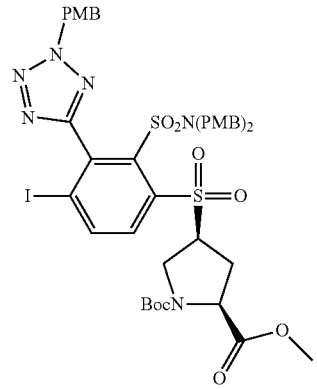

Step A: (2S,4S)-1-tert-butyl 2-methyl 4-((2-(N,N-bis(4-methoxybenzyl)sulfamoyl)-4-iodo-3-(2-(4-methoxybenzyl)-2H-tetrazol-5-ylphenyl)thio)pyrrolidine-1,2-dicarboxylate To a solution of 6-bromo-3-iodo-N,N-bis(4-methoxybenzyl)-2-(2-(4-methoxybenzyl)-2H-tetrazol-5-yl)benzenesulfonamide (3.0 g, 3.80 mmol) in DMF (40 mL) was added (2S,4S)-1-tert-butyl-2-methyl-4-mercaptopyrrolidine-1,2-dicarboxylate (1.5 g, 5.70 mmol) and Cs$_2$CO$_3$ (3.7 g, 11.40 mmol) at RT. The mixture was stirred at RT for 16 hours under nitrogen. The resulting mixture was diluted with water (100 mL) and extracted with EA (3×200 mL). The combined organic layers were washed with water (3×200 mL) and brine (3×200 mL), dried over anhydrous Na$_2$SO$_4$ and filtered. The filtrate was concentrated under vacuum to afford the title compound, which was used in the next step directly: LCMS [M+1]$^+$: 971.

Step B: (2S,4S)-1-tert-butyl 2-methyl-4-((2-(N,N-bis(4-methoxybenzyl)sulfamoyl)-4-iodo-3-(2-(4-methoxybenzyl)-2H-tetrazol-5-yl)phenyl)sulfonyl)pyrrolidine-12-dicarboxylate To a solution of (2S,4S)-1-tert-butyl-2-methyl-4-((2-(N,N-bis(4-methoxybenzyl) sulfamoyl)-4-iodo-3-(2-(4-methoxybenzyl)-2H-tetrazol-5-yl)phenyl)thio)pyrrolidine-1,2-dicarboxylate (3.3 g, 3.40 mmol) in DCM (40 mL) was added m-CPBA (3.5 g, 20.40 mmol). The mixture was stirred at RT for 16 hours. The resulting mixture was added into sat. aq. Na$_2$SO$_3$ (50 mL) and extracted with DCM (3×100 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 40% DCM in EA. The fractions containing desired product were combined and concentrated under vacuum to afford the title compound: LCMS [M+1]$^+$: 1003.

REFERENCE EXAMPLES 74-81 below were prepared using procedures similar to those described in REFERENCE EXAMPLES 72 and 73 using iodide and thiol starting materials prepared as described herein or commercially available

| EX. No. | Structure | Chemical Name | LC/MS [M + H] |
|---|---|---|---|
| 74 | 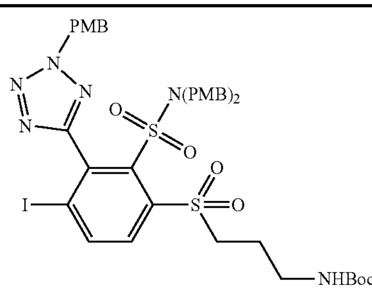 | tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propyl)carbamate | 933 |
| 75 | 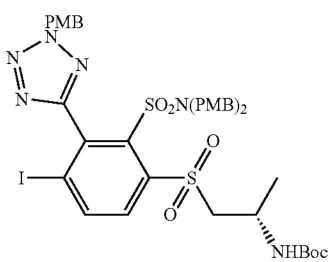 | (S)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate | 933 |
| 76 | 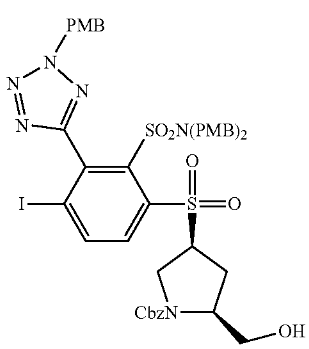 | (2S,4S)-benzyl 4-((2-(N,N-bis(4-methoxybenzyl)sulfamoyl)-4-iodo-3-(2-(4-methoxybenzyl)-2H-tetrazol-5-yl)phenyl)sulfonyl)-2-(hydroxymethyl)pyrrolidine-1-carboxylate | 1009 |
| 77 | 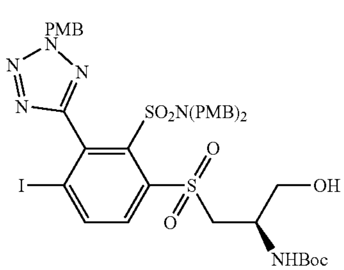 | (R)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)-3-hydroxypropan-2-yl)carbamate | 949 |

-continued

| EX. No. | Structure | Chemical Name | LC/MS [M + H] |
|---|---|---|---|
| 78 | 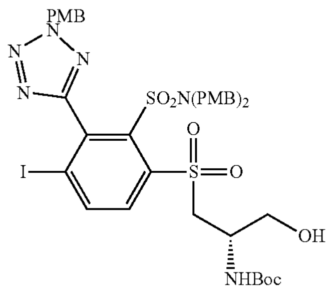 | (S)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)-3-hydroxypropan-2-yl)carbamate | 949 |
| 79 | 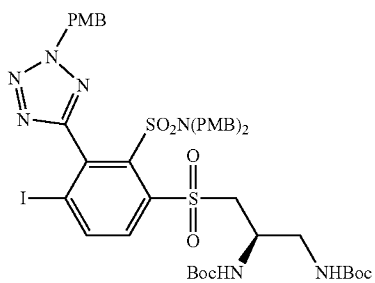 | (R)-di-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propane-1,2-diyl)dicarbamate | 1048 |
| 80 | 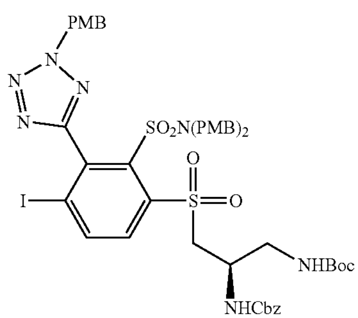 | (R)-benzyl tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propane-1,2-diyl)dicarbamate | 1082 |
| 81 | 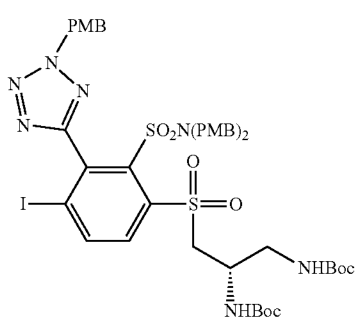 | ((S)-di-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propane-1,2-diyl)dicarbamate | 1048 |

REFERENCE EXAMPLE 82

(R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate

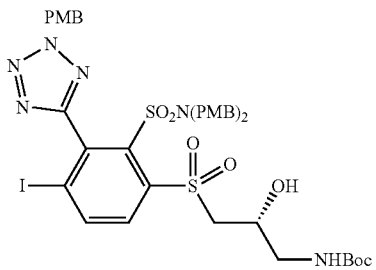

Step A: (R)-tert-butyl(3-((2-(N,N-bis(4-methoxybenzyl)sulfamoyl)-4-iodo-3-(2-(4-methoxy benzyl)-2H-tetrazol-5-yl)phenyl)thio)-2-((tert-butyldimethylsilyl)oxy)propyl) carbamate To a stirred solution of 6-bromo-3-iodo-N,N-bis(4-methoxybenzyl)-2-(2-(4-methoxybenzyl)-2H-tetrazol-5-yl)benzenesulfonamide (1.95 g, 2.47 mmol), (R)-tert-butyl-2-(tert-butyldimethylsilyloxy)-3-mercaptopropylcarbamate (1.59 g, 4.94 mmol) in DMF (15 mL) was added NaH (0.20 g, 8.21 mmol) at 0° C. under nitrogen. The reaction mixture was stirred at RT for 3 hours under nitrogen. The resulting mixture was quenched with water (100 mL) and extracted with EA (3×100 mL). The combined organic layers were washed with brine (3×100 mL), dried over anhydrous $Na_2SO_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1031.

Step B: (R)-tert-butyl(3-((2-(N,N-bis(4-methoxybenzyl)sulfamoyl)-4-iodo-3-(2-(4-methoxy benzyl)-2H-tetrazol-5-yl)phenyl)thio)-2-hydroxypropyl)carbamate To a solution of (R)-tert-butyl-3-(2-(N,N-bis(4-methoxybenzyl)sulfamoyl)-4-iodo-3-(2-(4-methoxybenzyl)-2H-tetrazol-5-yl)phenylthio)-2-(tert-butyldimethylsilyloxy)propylcarbamate (2.2 g, 2.14 mmol) in THF (40 mL) was added TBAF (6.4 mL, 6.40 mmol) at 0° C. The reaction mixture was stirred at RT for 1 hour. The resulting mixture was quenched with water (100 mL), extracted with EA (3×100 mL). The combined organic layers was washed with saturated aqueous $KHSO_4$ (5×100 mL), brine (1×100 mL), dried over anhydrous $MgSO_4$ and filtered. The filtrate was concentrated under vacuum. The residue was purified by silica gel column chromatography, eluting with 70% EA in PE. The fractions containing desired product were combined and concentrated under vacuum to afford the title compound: LCMS [M+1]$^+$: 917.

Step C: (R)-tert-butyl(3-((2-(N,N-bis(4-methoxybenzyl)sulfamoyl)-4-iodo-3-(2-(4-methoxy benzyl)-2H-tetrazol-5-yl)phenyl)sulfonyl)-2-hydroxypropyl)carbamate To a solution of (R)-tert-butyl(3-((2-(N,N-bis(4-methoxybenzyl)sulfamoyl)-4-iodo-3-(2-(4-methoxybenzyl)-2H-tetrazol-5-yl)phenyl)thio)-2-hydroxypropyl)carbamate (1.2 g, 1.31 mmol) in DCM (15 mL) was added m-CPBA (0.9 g, 5.23 mmol) at 0° C. The reaction mixture was stirred at RT for 16 hours. The resulting mixture was added into sat. aq. $Na_2SO_3$ (50 mL) and extracted with DCM (3×100 mL). The combined organic layers were washed with water (3×100 mL) and brine (3×100 mL), dried over anhydrous $Na_2SO_4$ and filtered. The filtrate was concentrated under vacuum. The residue was purified by silica gel column chromatography, eluting with 60% EA in PE. The fractions containing desired product were combined and concentrated under vacuum to afford the title compound: LCMS [M+1]$^+$: 949.

REFERENCE EXAMPLE 83

(R)-tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)-3-hydroxypropyl)carbamate

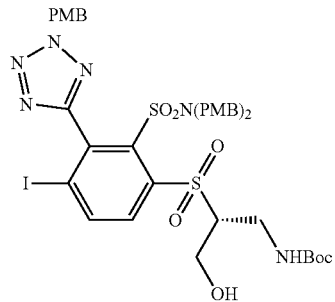

Step A: (R)-tert-butyl(2-((2-(N,N-bis(4-methoxybenzyl)sulfamoyl)-4-iodo-3-(2-(4-methoxybenzyl)-2H-tetrazol-5-yl)phenyl)thio)-3-((tert-butyldimethylsilyl)oxy)propyl)carbamate To a solution of (R)-tert-butyl (3-((tert-butyldimethylsilyl)oxy)-2-mercaptopropyl) carbamate (1.2 g, 3.80 mmol), 6-bromo-3-iodo-N,N-bis(4-methoxybenzyl)-2-(2-(4-methoxybenzyl)-2H-tetrazol-5-yl)benzenesulfonamide (1.5 g, 1.90 mmol) in DMF (13 mL) was added $Cs_2CO_3$ (2.5 g, 7.60 mmol) at room temperature. The reaction mixture was stirred at room temperature for 16 h under nitrogen. The resulting mixture was quenched with water (60 mL) and extracted with EA (3×50 mL). The organic layer was washed with brine (3×10 mL), dried over anhydrous $Na_2SO_4$ and filtered. The filtrate was concentrated under vacuum. The residue was purified by a silica gel column chromatography, eluted with 33% EA in PE. The fractions containing desired product were combined and concentrated under vacuum to afford the title compound: LCMS [M+1]$^+$: 1031.

Step B: (R)-tert-butyl(2-((2-(N,N-bis(4-methoxybenzyl)sulfamoyl)-4-iodo-3-(2-(4-methoxy benzyl)-2H-tetrazol-5-yl)phenyl)sulfonyl)-3-((tert-butyldimethylsilyl)oxy)propyl) carbamate To a solution of (R)-tert-butyl (2-((2-(N,N-bis(4-methoxybenzyl)sulfamoyl)-4-iodo-3-(2-(4-methoxybenzyl)-2H-tetrazol-5-yl)phenyl)thio)-3-((tert-butyldimethylsilyl) oxy)propyl)carbamate (1.0 g, 0.97 mmol) in DCM (15 mL) was added m-CPBA (0.66 g, 3.88 mmol) at RT. The reaction mixture was stirred at RT for 16 hours. The resulting mixture was added into saturated aqueous Na$_2$SO$_3$ (50 mL) and extracted with DCM (3×100 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1063.

Step C: (R)-tert-butyl(2-((2-(N,N-bis(4-methoxybenzyl)sulfamoyl)-4-iodo-3-(2-(4-methoxy benzyl)-2H-tetrazol-5-yl)phenyl)sulfonyl)-3-hydroxypropyl) carbamate To a solution of (R)-tert-butyl(2-((2-(N,N-bis(4-methoxybenzyl)sulfamoyl)-4-iodo-3-(2-(4-methoxybenzyl)-2H-tetrazol-5-yl)phenyl)sulfonyl)-3-((tert-butyldimethylsilyl)oxy)propyl)carbamate (1.0 g, 0.94 mmol) in THF (10 mL) was added TBAF (0.98 g, 3.76 mmol) at 0° C. The reaction mixture was stirred at room temperature for 0.5 hour. The resulting mixture was diluted with EA (100 mL), washed with saturated aqueous KHSO$_4$ (3×50 mL), dried over anhydrous Na$_2$SO$_4$ and filtered. The filtrate concentrated under vacuum to afford the title compound, which was used directly in the next step: LCMS [M+1]$^+$: 949.

REFERENCE EXAMPLE 84

(S)-tert-butyl (3-((2-(N,N-bis(4-methoxybenzyl) sulfamoyl)-4-iodo-3-(2-(4-methoxy benzyl)-2H-tetrazol-5-yl)phenyl)sulfonyl)-2-hydroxypropyl) carbamate

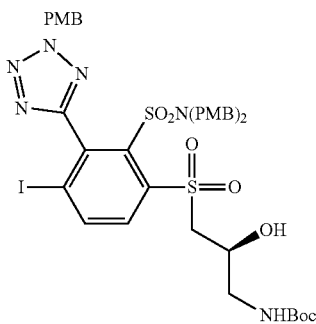

Step A: (S)-tert-butyl(3-((2-(N,N-bis(4-methoxybenzyl)sulfamoyl)-4-iodo-3-(2-(4-methoxy benzyl)-2H-tetrazol-5-yl)phenyl)thio)-2-((tert-butyldimethylsilyl)oxy)propyl) carbamate To a stirred solution of 6-bromo-3-iodo-N,N-bis(4-methoxybenzyl)-2-(2-(4-methoxybenzyl)-2H-tetrazol-5-yl) benzenesulfonamide (1.3 g, 1.65 mmol), (S)-tert-butyl(2-((tert-butyldimethylsilyl)oxy)-3-mercaptopropyl)carbamate (1.3 g, 4.11 mmol) in DMF (15 mL) was added NaH (0.15 g, 3.62 mmol) at 0° C. under nitrogen. The reaction mixture was stirred at room temperature for 3 hours. The resulting mixture was diluted with water (100 mL) and extracted with EA (3×100 mL). The combined organic layers were washed with brine (3×50 mL), dried over anhydrous Na$_2$SO$_4$ and filtered. The filtrate was concentrated under vacuum. The residue was purified by silica gel column chromatography, eluted with 15% EA in PE. The fractions containing desired product were combined and concentrated under vacuum to afford the title compound, which was used in next step without further purification: LCMS [M+1]$^+$: 1031.

Step B: (S)-tert-butyl(3-((2-(N,N-bis(4-methoxybenzyl)sulfamoyl)-4-iodo-3-(2-(4-methoxy benzyl)-2H-tetrazol-5-yl)phenyl)thio)-2-hydroxypropyl)carbamate To a solution of (S)-tert-butyl(3-((2-(N,N-bis(4-methoxybenzyl)sulfamoyl)-4-iodo-3-(2-(4-methoxybenzyl)-2H-tetrazol-5-yl)phenyl)thio)-2-((tert-butyldimethylsilyl) oxy) propyl)carbamate (2.5 g, 2.43 mmol) in THF (40 mL) was added TBAF (4.9 mL, 4.85 mmol) at 0° C. The reaction mixture was stirred at room temperature for 1 hour. The resulting mixture was quenched with water (50 mL) and extracted with EA (3×200 mL). The combined organic layers was washed with saturated aqueous KHSO$_4$ (2×200 mL) and brine (2×30 mL), dried over anhydrous Na$_2$SO$_4$ and filtered. The filtrate was concentrated under vacuum. The residue was purified by silica gel column chromatography, eluting with 15% EA in PE. The fractions containing desired product were combined and concentrated under vacuum to afford the title compound: LCMS [M+1]$^+$: 917.

Step C: (S)-tert-butyl(3-((2-(N,N-bis(4-methoxybenzyl)sulfamoyl)-4-iodo-3-(2-(4-methoxy benzyl)-2H-tetrazol-5-yl)phenyl)sulfonyl)-2-hydroxypropyl) carbamate To a solution of (S)-tert-butyl(3-((2-(N,N-bis(4-methoxybenzyl)sulfamoyl)-4-iodo-3-(2-(4-methoxybenzyl)-2H-tetrazol-5-yl)phenyl)thio)-2-hydroxypropyl) carbamate (1.3 g, 1.42 mmol) in DCM (15 mL) was added m-CPBA (0.98 g, 5.67 mmol) at 0° C. The reaction mixture was stirred at room temperature for 16 hours. The resulting mixture was added into saturated aqueous Na$_2$SO$_3$ (50 mL) and extracted with DCM (3×100 mL). The combined organic layers was washed with water (3×100 mL) and brine (3×100 mL), dried over anhydrous Na$_2$SO$_4$ and filtered. The filtrate was concentrated under vacuum. The residue was purified by silica gel column chromatography, eluting with 15% EA in PE. The fractions containing desired product were combined and concentrated under vacuum to afford the title compound: LCMS [M+1]$^+$: 949.

REFERENCE EXAMPLE 85

(S)-tert-butyl (2-((2-(N,N-bis(4-methoxybenzyl)sulfamoyl)-4-iodo-3-(2-(4-methoxy benzyl)-2H-tetrazol-5-yl)phenyl)sulfonyl)-3-hydroxypropyl)carbamate

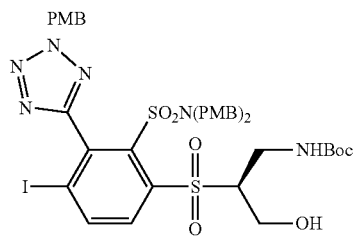

Step A: (S)-tert-butyl(2-((2-(N,N-bis(4-methoxybenzyl)sulfamoyl)-4-iodo-3-(2-(4-methoxybenzyl)-2H-tetrazol-5-yl)phenyl)thio)-3-((tert-butyldimethylsilyl)oxy)propyl)carbamate To a solution of (S)-tert-butyl (3-((tert-butyldimethylsilyl)oxy)-2-mercaptopropyl) carbamate (2.4 g, 7.59 mmol) and 6-bromo-3-iodo-N,N-bis(4-methoxybenzyl)-2-(2-(4-methoxybenzyl)-2H-tetrazol-5-yl)benzenesulfonamide (3.0 g, 3.80 mmol) in DMF (13 mL) was added $Cs_2CO_3$ (3.1 g, 9.49 mmol) at RT. The reaction mixture was stirred at RT for 16 hours under nitrogen. The resulting mixture was diluted with water (60 mL) and extracted with EA (3×50 mL). The organic layers were washed with brine (3×10 mL), dried over anhydrous $Na_2SO_4$ and filtered. The filtrate was concentrated under vacuum. The residue was purified by silica gel column chromatography, eluted with 33% EA in PE. The fractions containing desired product were combined and concentrated under vacuum to afford the title compound: LCMS [M+1]$^+$: 1031.

Step B: (S)-tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)-3-((tert-butyldimethylsilyl)oxy) propyl)carbamate To a solution of (S)-tert-butyl(2-((2-(N,N-bis(4-methoxybenzyl)sulfamoyl)-4-iodo-3-(2-(4-methoxybenzyl)-2H-tetrazol-5-yl)phenyl)thio)-3-((tert-butyldimethylsilyl) oxy) propyl)carbamate (1.0 g, 0.97 mmol) in DCM (15 mL) was added m-CPBA (0.66 g, 3.88 mmol) at 0° C. The reaction mixture was stirred at RT for 16 hours. The resulting mixture was added into saturated aqueous $Na_2SO_3$ (50 mL) and extracted with DCM (3×100 mL). The combined organic layers were washed with water (3×100 mL) and brine (3×100 mL), dried over anhydrous $Na_2SO_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1063.

Step C: (S)-tert-butyl(2-((2-(N,N-bis(4-methoxybenzyl)sulfamoyl)-4-iodo-3-(2-(4-methoxy benzyl)-2H-tetrazol-5-yl)phenyl)sulfonyl)-3-hydroxypropyl)carbamate To a solution of (S)-tert-butyl(2-((2-(N,N-bis(4-methoxybenzyl)sulfamoyl)-4-iodo-3-(2-(4-methoxybenzyl)-2H-tetrazol-5-yl)phenyl)sulfonyl)-3-((tert-butyldimethyl silyl)oxy)propyl)carbamate (1.0 g, 0.94 mmol) in THF (10 mL) was added TBAF (0.98 g, 3.76 mmol) at 0° C. The reaction mixture was stirred at RT for 0.5 hour. The resulting mixture was diluted with EA (100 mL), washed with saturated aqueous $KHSO_4$ (3×20 mL), dried over anhydrous $Na_2SO_4$ and filtered. The filtrate was concentrated under vacuum to afford the title compound, which was used directly in the next step: LCMS [M+1]$^+$: 949.

EXAMPLE 1

3-(2-amino-1H-benzo[d]imidazol-5-yl)-6-(azetidin-3-ylthio)-2-(2H-tetrazol-5-yl)benzenesulfonamide

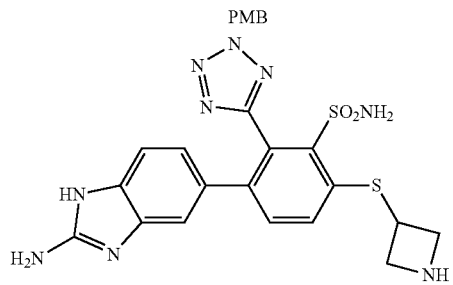 [SMILES: Nc1nc2cc(-c3ccc(SC4CNC4)c(S(N)(=O)=O)c3-c3nn[nH]n3)ccc2[nH]1]

Step A: 3-(2-amino-3H-benzo[d]imidazol-5-yl)-6-bromo-N,N-bis(4-methoxybenzyl)-2-(2-(4-methoxybenzyl)-2H-tetrazol-5-yl)benzenesulfonamide Into a 25-mL RBF purged and maintained with an inert atmosphere of argon, was placed a solution of 6-bromo-3-iodo-N,N-bis(4-methoxybenzyl)-2-(2-(4-methoxybenzyl)-2H-tetrazol-5-yl)benzenesulfonamide (0.63 g, 0.80 mmol), 6-(4,4,5,5-tetramethyl-1,3,2-dioxaborolan-2-yl)-1H-benzo[d]imidazol-2-amine (0.25 g, 0.96 mmol) and $Pd(PPh_3)_4$ (0.14 g, 0.12 mmol) in dioxane (7 mL). $Na_2CO_3$ (0.26 g, 2.41 mmol) in water (1.5 mL) was then added at room temperature. The resulting mixture was stirred at 80° C. for 18 hours under argon, cooled to 20° C., quenched with water (50 mL) and extracted with EtOAc (3×50 mL). The combined organics were washed with brine (2×50 mL), dried over anhydrous $Na_2SO_4$ and concentrated in vacuo. The residue was purified by silica gel column chromatography, eluted with EtOAc/PE (100/1) to afford the title compound as a solid: LCMS [M+H]$^+$: 795, 797.

Step B: tert-butyl 3-(4-(2-amino-1H-benzo[d]imidazol-5-yl)-2-(N,N-bis(4-methoxybenzyl)sulfamoyl)-3-(2-(4-methoxybenzyl)-2H-tetrazol-5-yl)phenylthio)azetidine-1-carboxylate A mixture of 3-(2-amino-1H-benzo[d]imidazol-5-yl)-6-bromo-N,N-bis(4-methoxybenzyl)-2-(2-(4-methoxybenzyl)-2H-tetrazol-5-yl)benzenesulfonamide (400 mg, 0.503 mmol), tert-butyl 3-mercaptoazetidine-1-carboxylate (381 mg, 2.011 mmol), $Pd_2(dba)_3$ (92 mg, 0.101 mmol), DIEA (0.263 ml, 1.508 mmol) and XantPhos (58.2 mg, 0.101 mmol) in 1,4-dioxane (5 ml) was stirred at 150° C. for 1 hour in a microwave. The reaction mixture was concentrated under vacuum. The residue was purified by silica gel chromatography, eluting with DCM/MeOH (10/1). The combined organic fractions were concentrated under reduced pressure to give the title compound as a solid. LCMS [M+H]+: 904.

Step C: 3-(2-amino-1H-benzo[d]imidazol-5-yl)-6-(azetidin-3-ylthio)-N-(4-methoxybenzyl)-2-(2-(4-methoxybenzyl)-2H-tetrazol-5-yl)benzenesulfonamide A solution of tert-butyl 3-((4-(2-amino-1H-benzo[d]imidazol-5-yl)-2-(N,N-bis(4-methoxybenzyl)sulfamoyl)-3-(2-(4-methoxybenzyl)-2H-tetrazol-5-yl)phenyl)thio)azetidine-1-carboxylate (120 mg, 0.133 mmol) and TFA (1 ml, 12.98 mmol) in DCM (10 ml) was stirred at room temperature for 1 hour. The reaction mixture was concentrated under vacuum to give the title compound as an oil. LCMS [M+H]+: 684.

Step D: 3-(2-amino-1H-benzo[d]imidazol-4-yl)-6-(azetidin-3-ylthio)-2-(2H-tetrazol-5-yl)benzenesulfonamide 3-(2-amino-1H-benzo[d]imidazol-5-yl)-6-(azetidin-3-ylthio)-N-(4-methoxybenzyl)-2-(2-(4-methoxybenzyl)-2H-tetrazol-5-yl)benzenesulfonamide (70 mg, 0.087 mmol) and TFA (8.36 ml, 109 mmol) in DCM (1 ml) were stirred at 80° C. for 2 hours. The reaction mixture was concentrated under vacuum to give crude product. The product was purified by Prep-HPLC with the following conditions: Column: X Bridge C18, 19×150 mm, 5 μM; Mobile Phase A: water/0.05% NH$_4$HCO$_3$, Mobile Phase B: ACN; Flow rate: 20 mL/min; Gradient: 35% B to 55% B in 8 min; 254 nm. The collected fractions were combined and concentrated under vacuum to give the title compound as a solid. LCMS [M+H]+: 444. $^1$H NMR (DMSO-d6, 300 MHZ δ 7.42 (d, J=8.0 Hz, 1H), 7.04 (d, J=8.0 Hz, 1H), 6.77 (d, J=8.0 Hz, 1H), 6.63 (s, 1H), 6.36 (d, J=8.0 Hz, 1H), 5.99 (brs, 1H), 4.30-4.11 (m, 1H), 4.04-3.99 (m, 1H), 3.71-3.63 (m, 1H), 3.49-3.46 (m, 2H). δ 8.50 (d, J=4.2 Hz, 1H), 8.08 (d, J=6.6 Hz, 1H), 7.48 (d, J=3.6 Hz, 1H), 7.11 (s, 2H), 6.93 (d, J=3.9 Hz, 1H).

EXAMPLE 2

3-(2-amino-1H-benzo[d]imidazol-4-yl)-6-(azetidin-3-ylthio)-2-(2H-tetrazol-5-yl)benzenesulfonamide

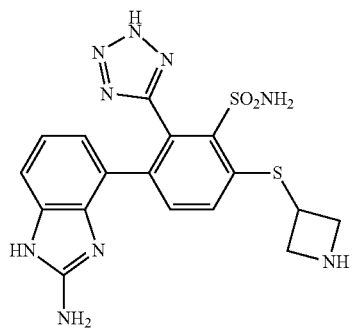 [SMILES: Nc1nc2c(-c3ccc(SC4CNC4)c(S(N)(=O)=O)c3-c3nn[nH]n3)cccc2[nH]1]

Step A: 2-nitro-3-(4,4,5,5-tetramethyl-1,3,2-dioxaborolan-2-yl)benzenamine

Into a 50-mL RBF purged and maintained with an inert atmosphere of argon, was placed a solution of 3-bromo-2-nitroaniline (20.00 g, 92 mmol) in 1,4-dioxane (300 mL). This was followed by the addition of [1,1'-bis(diphenylphosphino)ferrocene]dichloropalladium(II) (3.37 g, 4.61 mmol), potassium acetate (27.10 g, 276 mmol) and 4,4,4',4',5,5,5',5'-octamethyl-2,2'-bi(1,3,2-dioxaborolane) (35.10 g, 138 mmol) at room temperature. The resulting mixture was stirred at 85° C. for 16 hours under argon. The mixture was filtered out and the filtrate was concentrated under vacuum. The residue was purified by silica gel column chromatography, eluted with EA/PE (1/1) to afford the title compound as a solid: LCMS [M+H]+: 265; $^1$H NMR (400 MHz, CDCl$_3$): δ 7.35 (t, J=7.6 Hz, 1H), 6.79 (d, J=8.0 Hz, 1H), 6.74 (d, J=6.8 Hz, 1H), 1.42 (s, 12H).

Step B: 3-(4,4,5,5-tetramethyl-1,3,2-dioxaborolan-2-yl)benzene-1,2-diamine

Into a 250-mL RBF, was placed a solution of 2-nitro-3-(4,4,5,5-tetramethyl-1,3,2-dioxaborolan-2-yl)aniline (5.00 g, 18.93 mmol) in DCM (20 mL) and MeOH (20 mL). This was followed by the addition of Pd/C (20.15 g, 18.93 mmol) at room temperature. The reaction mixture was degassed with nitrogen 3 times, and then with hydrogen 3 times. The mixture was stirred under hydrogen for 16 hours at room temperature at 1.5 atm. The mixture was filtered and the filter cake was washed with DCM (3×10 mL). The combined organic layers were concentrated under reduced pressure and purified by silica gel column chromatography, eluting with EA/PE (2/3) to afford the title compound as a solid: LCMS [M+H]+: 235; $^1$H NMR (400 MHz, CDCl$_3$): δ 7.21 (d, J=7.6 Hz, 1H), 6.79 (d, J=7.6 Hz, 1H), 6.65 (t, J=7.6 Hz, 1H), 3.60 (br, 4H), 1.34 (s, 12H).

Step C: 2',3'-diamino-4-bromo-N,N-bis(4-methoxybenzyl)-2-(2-(4-methoxybenzyl)-2H-tetrazol-5-yl)-[1,1'-biphenyl]-3-sulfonamide Into a 50-mL RBF purged and maintained with an inert atmosphere of argon, was placed a solution of 6-bromo-3-iodo-N,N-bis(4-methoxybenzyl)-2-(2-(4-methoxybenzyl)-2H-tetrazol-5-yl)benzenesulfonamide (0.77 g, 0.97 mmol), 3-(4,4,5,5-tetramethyl-1,3,2-dioxaborolan-2-yl)benzene-1,2-diamine (0.50 g, 2.13 mmol) and Pd(Ph$_3$P)$_4$ (0.11 g, 0.10 mmol) in dioxane (10 mL). This was followed by the addition of sodium carbonate (0.31 g, 2.90 mmol) in water (1 mL) at room temperature. The resulting mixture was stirred at 80° C. for 18 hours under argon. The mixture was cooled to 20° C., quenched with water (50 mL) and extracted with EA (3×50 mL). The combined organic phase was washed with brine (3×50 mL), dried over anhydrous sodium sulfate and filtered. The filtrate was evaporated under reduced pressure and the residue was purified by silica gel column chromatography, eluted with EA/PE (3/2) to afford the title compound: LCMS [M+H]+: 770, 772 (1:1).

Step D: 3-(2-amino-1H-benzo[d]imidazol-7-yl)-6-bromo-N,N-bis(4-methoxybenzyl)-2-(2-(4-methoxybenzyl)-2H-tetrazol-5-yl)benzenesulfonamide Into a 25-mL RBF purged and maintained with an inert atmosphere of argon, was placed a solution of 2',3'-diamino-4-bromo-N,N-bis(4-methoxybenzyl)-2-(2-(4-methoxybenzyl)-2H-tetrazol-5-yl)-[1,1'-biphenyl]-3-sulfonamide (1.4 g, 1.82 mmol) in MeOH (5 ml) and DCM (5 mL). This was followed by the addition of cyanogen bromide (0.19 g, 1.82 mmol) at 0° C. The resulting mixture was stirred at 25° C. for 16 hours under an atmosphere of argon. The reaction was quenched with aq. sat. sodium bicarbonate (50 mL) and extracted with EA (3×50 mL). The combined organic layers were washed with brine (2×50 mL), dried over anhydrous sodium sulfate and filtered. The filtrate was evaporated under reduced pressure and the residue was recrystallized from DCM/EA/PE (10 mL/10 mL/50 mL). The solid was collected by filtration and dried in vacuum. The residue was purified by silica gel column chromatography, and eluted with EtOAc in petroleum ether (80%) to afford the title compound as a solid: LCMS [M+H]$^+$: 795, 797 (1:1); $^1$H NMR (300 MHz, CDCl$_3$): δ 8.10-8.00 (m, 1H), 7.78-7.71 (m, 1H), 6.99-6.56 (m, 14H), 6.44-6.38 (m, 1H), 5.10 (d, J=15.6 Hz, 1H), 4.90 (m, J=15.6 Hz, 1H), 4.79 (d, J=15.3 Hz, 2H), 3.89 (d, J=15.3 Hz, 2H), 3.74-3.71 (m, 9H).

Step E: tert-butyl 3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylthio)azetidine-1-carboxylate A solution of 3-(2-amino-1H-benzo[d]imidazol-4-yl)-6-bromo-N,N-bis(4-methoxybenzyl)-2-(2-(4-methoxybenzyl)-2H-tetrazol-5-yl)benzenesulfonamide (100 mg, 0.14 mmol), tert-butyl 3-mercaptoazetidine-1-carboxylate (100 mg, 0.57 mmol), Pd$_2$(dba)$_3$ (40 mg, 0.44 mmol), DIEA (0.1 ml, 0.57 mmol) and XantPhos (30 mg, 0.05 mmol) in 1,4-Dioxane (2 ml) was stirred at 150° C. for 1 hour in a microwave. The reaction mixture was concentrated under vacuum and the residue was purified by silica gel chromatography and eluted with DCM/MeOH (10/1). The combined organic fractions were concentrated under reduced pressure to give the title compound. LCMS [M+H]$^+$: 904.

Step F: 3-(2-amino-1H-benzo[d]imidazol-4-yl)-6-(azetidin-3-ylthio)-N-(4-methoxybenzyl)-2-(2-(4-methoxybenzyl)-2H-tetrazol-5-yl)benzenesulfonamide A solution of tert-butyl 3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylthio)azetidine-1-carboxylate (60 mg, 0.07 mmol) and TFA (1 ml, 12.98 mmol) in DCM (10 ml) was stirred at room temperature for 1 hour. The reaction mixture was concentrated under reduced pressure to give the title compounds. LCMS [M+H]$^+$: 684.

Step G: 3-(2-amino-1H-benzo[d]imidazol-4-yl)-6-(azetidin-3-ylthio)-2-(2H-tetrazol-5-yl)benzenesulfonamide A solution of 3-(2-amino-1H-benzo[d]imidazol-4-yl)-6-(azetidin-3-ylthio)-N-(4-methoxybenzyl)-2-(2-(4-methoxybenzyl)-2H-tetrazol-5-yl)benzenesulfonamide (40 mg, 0.059 mmol) and TFA (8.36 ml, 109 mmol) in DCM (1 ml) was stirred at 80° C. for 2 hours. The reaction mixture was concentrated under vacuum to give crude product. The product was purified by Prep-HPLC with the following conditions: Column: X Bridge C18, 19×150 mm, 5 μM; Mobile Phase A: water/0.05% NH$_4$HCO$_3$, Mobile Phase B: ACN; Flow rate: 20 mL/min; Gradient: 35% B to 55% B in 8 min; 254 nm. The collected fractions were combined and concentrated under vacuum to give the title compound as a solid. LCMS [M+H]$^+$: 444. $^1$H NMR (DMSO-d6, 400 MHZ): δ 7.87-7.69 (m, 3H), 7.13-7.11 (m, 1H), 6.86 (d, J=7.6 Hz, 1H), 6.48-6.46 (m, 1H), 6.08-6.06 (m, 3H), 4.45-4.42 (m, 2H), 4.21-4.14 (m, 1H), 3.80-3.75 (m, 2H).

EXAMPLE 3

3-(2-amino-3H-benzo[d]imidazol-4-yl)-6-(piperidin-4-ylthio)-2-(2H-tetrazol-5-yl)benzenesulfonamide

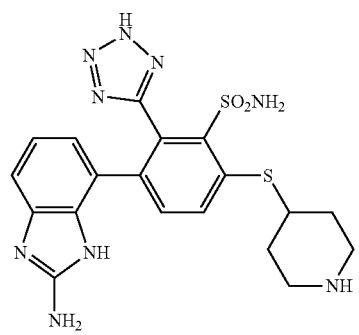 [SMILES: Nc1nc2cccc(-c3ccc(SC4CCNCC4)c(S(N)(=O)=O)c3-c3nn[nH]n3)c2[nH]1]

Step A: tert-butyl 4-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)phenyl)thio)piperidine-1-carboxylate To a solution of 3-(2-amino-1H-benzo[d]imidazol-7-yl)-6-bromo-N,N-bis(4-methoxybenzyl)-2-(2-(4-methoxybenzyl)-2H-tetrazol-5-yl)benzenesulfonamide (EXAMPLE 2, Step D, 200 mg, 0.251 mmol) in 1,4-dioxane (4 mL) was added tert-butyl 4-mercaptopiperidine-1-carboxylate (109 mg, 0.503 mmol), N,N-Diisopropylethylamine (97 mg, 0.754 mmol), Pd$_2$(dba)$_3$ (46.0 mg, 0.050 mmol) and Xantphos (29.1 mg, 0.050 mmol) at room temperature. The flask was degassed with nitrogen three times. Then the mixture was applied onto microwave reaction for 1 hour at 150° C. under an atmosphere of nitrogen. The solid was filtered out and the filtrate was concentrated under reduced pressure. The residue was then applied onto silica gel column to with methanol/dichloromethane (1:10) to give the title compound: LCMS [M+H]+: 932.

Step B: 3-(2-amino-3H-benzo[d]imidazol-4-yl)-N,N-bis(4-methoxybenzyl)-2-(2-(4-methoxybenzyl)-2H-tetrazol-5-yl)-6-(piperidin-4-ylthio)benzenesulfonamide To a solution of tert-butyl 4-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)phenyl)thio)piperidine-1-carboxylate (150 mg, 0.161 mmol) in Dichloromethane (1.5 ml) was added TFA (1.500 ml) at room temperature. After the resulting mixture was stirred for 1 hour at RT, it was concentrated under reduced pressure to give the crude product, which was used directly for the next step. LCMS [M+H]$^+$: 832 and 713.

Step C: 3-(2-amino-1H-benzo[d]imidazol-7-yl)-6-(piperidin-4-ylthio)-2-(2H-tetrazol-5-yl)benzenesulfonamide 3-(2-amino-3H-benzo[d]imidazol-4-yl)-N,N-bis(4-methoxybenzyl)-2-(2-(4-methoxybenzyl)-2H-tetrazol-5-yl)-

6-(piperidin-4-ylthio)benzenesulfonamide (50 mg, 0.070 mmol) was dissolved in TFA (5 ml) and stirred for 1 hour at room temperature. The resulting mixture was concentrated under reduced pressure to obtain the crude product. The crude product was then applied onto Prep-HPLC with the condition (Column: X Bridge RP C18, 19*150 mm, 5 μM; Mobile Phase A: water/10 mM NH$_4$HCO$_3$, Mobile Phase B: ACN; Flow rate: 20 mL/min; Gradient: 5-15% B in 8 min; UV: 254 nm) to give the title compound. LCMS [M+H]$^+$: 472; 1H NMR (300 MHz, DMSO-d$_6$): δ 7.62-7.44 (m, 4H), 6.86-6.84 (m, 1H), 6.49-6.44 (m, 1H), 6.09-6.04 (m, 3H), 3.89-3.87 (m, 2H), 3.06-2.89 (m, 3H), 2.16-2.12 (m, 2H), 1.81-1.70 (m, 2H).

EXAMPLE 4

4-(Azetidin-3-ylthio)-4'-(piperidin-4-yl)-2-(2H-tetrazol-5-yl)-[1,1'-biphenyl]-3-sulfonamide

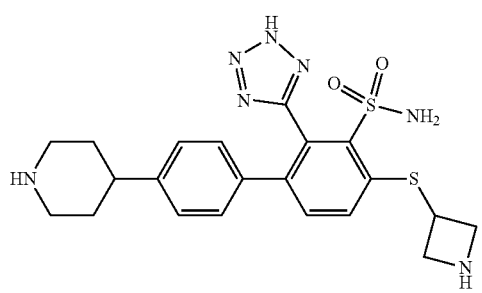 [SMILES: NS(=O)(=O)c1c(SC2CNC2)ccc(-c2ccc(C3CCNCC3)cc2)c1-c1nn[nH]n1]

To a solution of tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)piperidine-1-carboxylate (REFERENCE EXAMPLE 41, 30 mg, 0.029 mmol) in DCM (0.5 mL) was added anisole (32 μL, 0.29 mmol) and TFA (0.23 mL, 2.91 mmol) at RT. The resulting mixture was stirred at RT for 1 hour to remove both Boc and partial PMB protection. After removing the volatile under reduced pressure, the residue was dissolved in TFA (0.23 mL, 2.91 mmol) and anisole (32 μL, 0.291 mmol). The resulting mixture was heated at 80° C. for 1 hour to remove the final PMB protection. After removing the volatile under reduced pressure, the residue was purified by reverse phase HPLC (eluting with 3-30% MeCN/water with 0.1% TFA as additive) to afford the title compound. LC/MS [M+1]$^+$: 472.60.

EXAMPLE 5

4-(Azetidin-3-ylsulfinyl)-4'-(piperidin-4-yl)-2-(2H-tetrazol-5-yl)-[1,1'-biphenyl]-3-sulfonamide

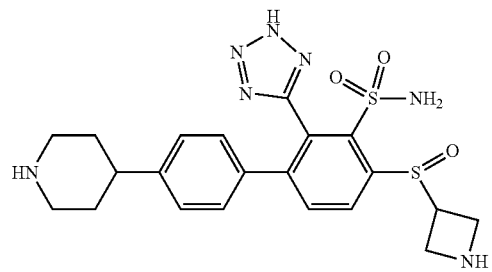 [SMILES: NS(=O)(=O)c1c(S(=O)C2CNC2)ccc(-c2ccc(C3CCNCC3)cc2)c1-c1nn[nH]n1]

Step A: tert-Butyl 4-(3'-(N,N-bis(4-methoxybenzyl)sulfamoyl)-4'-((1-(tert-butoxycarbonyl)azetidin-3-yl)sulfinyl)-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-((1-(tert-butoxycarbonyl)azetidin-3-yl)sulfinyl)-2'-(1-(4-methoxybenzyl)-1H-tetrazol-5-yl)-[1,1'-biphenyl]-4-yl)piperidine-1-carboxylate To tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)piperidine-1-carboxylate (REFERENCE EXAMPLE 41, 320 mg, 0.310 mmol) in DCM (5 mL) was added m-CPBA (83 mg, 0.372 mmol). The reaction mixture was stirred at RT overnight, and then partitioned between EtOAc and 10% aq. sodium thiosulfate. The organic phase was separated, washed with sat. aq. sodium bicarbonate, dried (MgSO$_4$) and the volatiles were removed under reduced pressure. The residue was purified by silica gel column chromatography using 0 to 100% EtOAc in hexanes as eluent to give the title product. LC/MS [M+1]$^+$: 1049.37.

Step B: 4-(Azetidin-3-ylsulfinyl)-4'-(piperidin-4-yl)-2-(2H-tetrazol-5-yl)-[1,1'-biphenyl]-3-sulfonamide The deprotection step was conducted in using a similar procedure to that of EXAMPLE 4 to afford the title compound. LC/MS [M+1]$^+$: 488.54.

EXAMPLE 6

4-(Azetidin-3-ylsulfonyl)-4'-piperidin-4-yl)-2-(2H-tetrazol-5-yl)-[1,1'-biphenyl]-3-sulfonamide

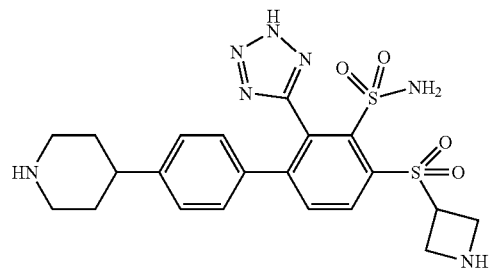 [SMILES: NS(=O)(=O)c1c(S(=O)(=O)C2CNC2)ccc(-c2ccc(C3CCNCC3)cc2)c1-c1nn[nH]n1]

Step A: tert-Butyl 4-(3'-(N,N-bis(4-methoxybenzyl)
sulfamoyl)-4'-((1-(tert-butoxycarbonyl)azetidin-3-yl)
sulfonyl)-2'-(2-(4-methoxybenzyl)-2H-tetrazol-5-yl)-
[1,1'-biphenyl]-4-yl)piperidine-1-carboxylate and
tert-butyl 4-(3'-(N,N-bis(4-methoxybenzyl)sulfa-
moyl)-4'-((1-(tert-butoxycarbonyl)azetidin-3-yl)sul-
fonyl)-2'-(1-(4-methoxybenzyl)-1H-tetrazol-5-yl)-[1,
1'-biphenyl]-4-yl)piperidine-1-carboxylate To tert-butyl 4-(3'-(N,N-bis(4-methoxybenzyl)sulfa-
moyl)-4'-bromo-2'-(2-(4-methoxybenzyl)-2H-tetrazol-5-
yl)-[1,1'-biphenyl]-4-yl)piperidine-1-carboxylate and tert-
butyl 4-(3'-(N,N-bis(4-methoxybenzyl)sulfamoyl)-4'-
bromo-2'-(1-(4-methoxybenzyl)-1H-tetrazol-5-yl)-[1,1'-
biphenyl]-4-yl)piperidine-1-carboxylate (REFERENCE
EXAMPLE 41, 80 mg, 0.077 mmol) in DCM (5 mL) was
added m-CPBA (44 mg, 0.194 mmol). The reaction mixture
was stirred at RT overnight, and then partitioned between
EtOAc and 10% aq. sodium thiosulfate. The organic phase
was separated, washed with sat. aq. sodium bicarbonate,
dried (MgSO$_4$) and the volatiles were removed under
reduced pressure. The residue was purified by silica gel
column chromatography using 0 to 100% EtOAc in hexanes
as eluent to give the title product. LC/MS [M+1]$^+$: 1065.37.

Step B: 4-(Azetidin-3-ylsulfonyl)-4'-(piperidin-4-
yl)-2-(2H-tetrazol-5-yl)-[1,1'-biphenyl]-3-sulfona-
mide The deprotection step was conducted using a similar
procedure to that of EXAMPLE 4 to afford the title com-
pound. LC/MS [M+1]$^+$: 504.68.

EXAMPLES 7-8 were prepared according to the general
procedures described above for EXAMPLES 4 and 5, start-
ing from REFERENCE EXAMPLE 42.

EXAMPLE 9

6-(Azetidin-3-ylsulfonyl)-3-(imidazo[1,2-a]pyridin-
3-yl)-2-(2H-tetrazol-5-yl)benzenesulfonamide

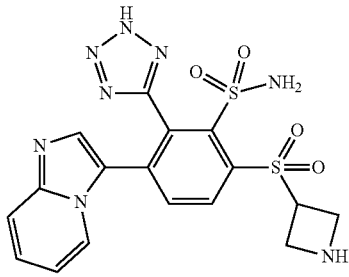 [SMILES: NS(=O)(=O)c1c(S(=O)(=O)C2CNC2)ccc(-c2cnc3ccccn23)c1-c1nn[nH]n1]

Step A: tert-Butyl 4-(3'-(N,N-bis(4-methoxybenzyl)
sulfamoyl)-4'-((1-(tert-butoxycarbonyl)azetidin-3-yl)
sulfinyl)-2'-(2-(4-methoxybenzyl)-2H-tetrazol-5-yl)-
[1,1'-biphenyl]-4-yl)piperidine-1-carboxylate and
tert-butyl 4-(3'-(N,N-bis(4-methoxybenzyl)sulfa-
moyl)-4'-((1-(tert-butoxycarbonyl)azetidin-3-yl)
sulfinyl)-2'-(1-(4-methoxybenzyl)-1H-tetrazol-5-yl)-
[1,1'-biphenyl]-4-yl)piperidine-1-carboxylate A microwave vial was charged with tert-butyl 3-((2-(N,
N-bis(4-methoxybenzyl)sulfamoyl)-4-iodo-3-(2-(4-
methoxybenzyl)-2H-tetrazol-5-yl)phenyl)sulfonyl)azeti-
dine-1-carboxylate and tert-butyl 3-((2-(N,N-bis(4-
methoxybenzyl)sulfamoyl)-4-iodo-3-(1-(4-
methoxybenzyl)-1H-tetrazol-5-yl)phenyl)sulfonyl)

| Ex. No. | Structure | Name | LC/MS m/e [M + H]$^+$ |
|---|---|---|---|
| 7 | 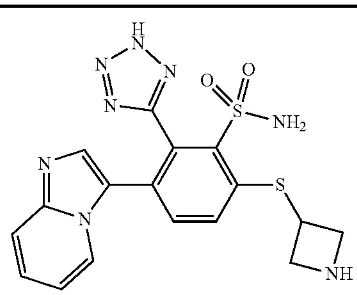 | 6-(azetidin-3-ylthio)-3-(imidazo[1,2-a]pyridin-3-yl)-2-(2H-tetrazol-5-yl)benzenesulfonamide | 429.33 |
| 8 | | 6-(azetidin-3-ylsulfinyl)-3-(imidazo[1,2-a]pyridin-3-yl)-2-(2H-tetrazol-5-yl)benzenesulfonamide | 445.48 | azetidine-1-carboxylate (REFERENCE EXAMPLE 6, 0.15 g, 0.161 mmol), 3-(4,4,5,5-tetramethyl-1,3,2-dioxaborolan-2-yl)imidazo[1,2-a]pyridine (0.047 g, 0.193 mmol), Na$_2$CO$_3$ (0.051 g, 0.483 mmol) and Pd (dppf)Cl$_2$ (0.020 g, 0.024 mmol). The vial was sealed, degassed, and filled with dioxane (1.3 mL) and water (0.322 mL). The resulting mixture was heated overnight at 80° C.

The reaction mixture was filtered over CELITE to remove palladium. The filtrate was diluted with EtOAc and washed with water. The organic layer was dried over anhydrous MgSO$_4$, filtered, concentrated and purified by silica gel column chromatography using 0-10% MeOH/DCM as mobile phase to afford the title compound. LC/MS [M+1]$^+$: 922.26.

Step B: 6-(Azetidin-3-ylsulfonyl)-3-(imidazo[1,2-a]pyridin-3-yl)-2-(2H-tetrazol-5-yl)benzenesulfonamide The deprotection step was conducted with TFA using a similar procedure to that of EXAMPLE 4 to afford the title compound. LC/MS [M+1]$^+$: 461.39.

EXAMPLE 10

3-(6-aminopyridin-3-yl)-6-(piperidin-4-ylsulfinyl)-2-(2H-tetrazol-5-yl)benzenesulfonamide

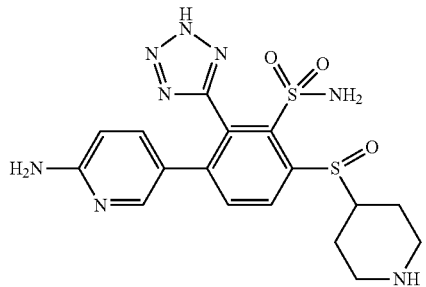

Step A: 3-(6-aminopyridin-3-yl)-6-bromo-N,N-bis(4-methoxybenzyl)-2-(2-(4-methoxybenzyl)-2H-tetrazol-5-yl)benzenesulfonamide Into a 100-mL RBF was placed a solution of 6-bromo-3-iodo-N,N-bis(4-methoxybenzyl)-2-(2-(4-methoxybenzyl)-2H-tetrazol-5-yl)benzenesulfonamide (2.00 g, 2.53 mmol), 5-(4,4,5,5-tetramethyl-1,3,2-dioxaborolan-2-yl)pyridin-2-amine (0.89 g, 4.05 mmol) and Pd(PPh$_3$)$_4$(0.29 g, 0.25 mmol) and sodium carbonate (0.81 g, 7.59 mmol) in dioxane (40 mL) and water (8 mL) at room temperature. The resulting mixture was degassed with nitrogen and stirred at 80° C. for 16 hr under nitrogen. The reaction was quenched with water (200 mL) and extracted with ethyl acetate (3×200 mL). The combined organics were washed with brine (3×200 mL), dried over anhydrous sodium sulfate, filtered and concentrated under vacuum. The residue was purified by a silica gel column chromatography, eluted with ethyl acetate/petroleum ether (4:1) to afford the title compound: LCMS [M+H]$^+$: 756, 758 (1:1).

Step B: tert-butyl 4-((4-(6-aminopyridin-3-yl)-2-(N,N-bis(4-methoxybenzyl)sulfamoyl)-3-(2-(4-methoxybenzyl)-2H-tetrazol-5-yl)phenyl)thio)piperidine-1-carboxylate Into a 8 mL sealed tube was placed 3-(6-aminopyridin-3-yl)-6-bromo-N,N-bis(4-methoxybenzyl)-2-(2-(4-methoxybenzyl)-2H-tetrazol-5-yl)benzenesulfonamide (500 mg, 0.661 mmol), tert-butyl 4-mercaptopiperidine-1-carboxylate (287 mg, 1.322 mmol), Pd$_2$dba$_3$ (60.5 mg, 0.066 mmol), XANTPHOS (76 mg, 0.132 mmol) and DIEA (0.346 ml, 1.982 mmol) in dioxane (7 ml). The reaction mixture was degassed with nitrogen 3 times and heated in a microwave at 150° C. for 30 minutes. After being cooled to RT, the resulting solution was diluted with EtOAc, washed with NaOH (2N) and brine. The organic layer was dried over anhydrous Na$_2$SO$_4$, filtered and concentrated under reduced pressure. The residue was purified by column chromatography (0-10% MeOH/DCM) to afford the title compound. LCMS [M+H]$^+$: 893;

Step C: tert-butyl 4-((4-(6-aminopyridin-3-yl)-2-(N,N-bis(4-methoxybenzyl)sulfamoyl)-3-(2-(4-methoxybenzyl)-2H-tetrazol-5-yl)phenyl)sulfinyl)piperidine-1-carboxylate tert-Butyl 4-((4-(6-aminopyridin-3-yl)-2-(N,N-bis(4-methoxybenzyl)sulfamoyl)-3-(2-(4-methoxybenzyl)-2H-tetrazol-5-yl)phenyl)thio)piperidine-1-carboxylate (200 mg, 0.224 mmol) was dissolved in dichloromethane (5 ml), mCPBA (77 mg, 0.448 mmol) was added and the reaction mixture was stirred for 1 hour at room temperature. The resulting mixture was diluted with DCM (15 mL), washed with sodium carbonate aq. (15 mL), and water (15 ml). The organic layer was dried over anhydrous sodium sulfate, filtered and concentrated under vacuum. The residue was purified by Prep-HPLC with: Column: X Bridge C18, 19*150 mm, 5 M; Mobile Phase A: water/0.05% TFA, Mobile Phase B: ACN; Flow rate: 20 mL/min; Gradient: 30% B to 70% B in 10 min; detected at 254 nm. The collected fractions were combined and concentrated under reduced pressure to give the title compound. LCMS [M+H]$^+$: 909

Step D: 3-(6-aminopyridin-3-yl)-6-(piperidin-4-ylsulfinyl)-2-(2H-tetrazol-5-yl)benzenesulfonamide Into a 10 mL RBF was placed tert-butyl 4-((4-(6-aminopyridin-3-yl)-2-(N,N-bis(4-methoxybenzyl)sulfamoyl)-3-(2-(4-methoxybenzyl)-2H-tetrazol-5-yl)phenyl)sulfinyl)piperidine-1-carboxylate (130 mg, 0.143 mmol) dissolved in DCM in anisole (1.0 mL), trifluoroacetic acid (2.0 mL) and the resulting reaction mixture was stirred at 80° C. for 3 hours. After the solvent was removed under reduced pressure, the residue was purified by Prep-HPLC with the following conditions: Column: X Bridge RP18, 19*150 mm, 5 μM; Mobile Phase A: water/0.05% NH$_4$HCO$_3$, Mobile Phase B: ACN; Flow rate: 20 mL/min; Gradient: 3% B to 12% B in 5 min; detected at 254 nm. The collected fractions were combined and concentrated under vacuum to give the title compound: LCMS [M+H]$^+$: 449; $^1$H NMR (300 MHz, DMSO/DCl): δ 8.31 (d, J=8.1 Hz, 1H), 8.11 (d, J=8.1 Hz, 1H), 7.79 (s, 1H), 7.46 (d, J=9.3 Hz, 1H), 6.97 (d, J=9.3 Hz, 1H), 3.53-3.29 (m, 3H), 3.10-2.99 (m, 2H), 2.43-1.97 (m, 3H), 1.43-1.37 (m, 1H).

EXAMPLE 11

3-(2-amino-1H-benzo[d]imidazol-5-yl)-6-(azetidin-3-ylsulfinyl)-2-(2H-tetrazol-5-yl)benzenesulfonamide

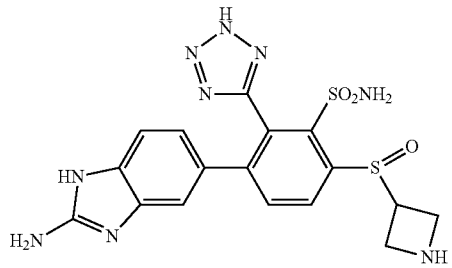 [SMILES: Nc1nc2cc(-c3ccc(S(=O)C4CNC4)c(S(N)(=O)=O)c3-c3nn[nH]n3)ccc2[nH]1]

The title compound was prepared as described for EXAMPLE 10, Steps B-D, starting from 3-(2-amino-1H-benzo[d]imidazol-5-yl)-6-bromo-N,N-bis(4-methoxybenzyl)-2-[2-(4-methoxybenzyl)-2H-tetrazol-5-yl]benzenesulfonamide (EXAMPLE 1, Step A) and tert-butyl 3-mercaptoazetidine-1-carboxylate, prepared as described herein. LCMS [M+H]$^+$: 504; $^1$H NMR (300 MHz, DMSO): δ 8.22 (d, J=8.4 Hz, 1H), 7.97 (d, J=8.4 Hz, 1H), 6.98 (d, J=6.9 Hz, 1H), 6.65-6.57 (m, 1H), 6.16 (d, J=7.2 Hz, 1H), 4.53-4.40 (m, 1H), 3.43 (d, J=12.9 Hz, 2H), 3.03-2.93 (m, 2H), 2.19-1.93 (m, 4H).

EXAMPLE 12

3-(2-amino-3H-benzo[d]imidazol-5-yl)-6-(piperidin-4-ylsulfinyl)-2-(2H-tetrazol-5-yl)benzenesulfonamide

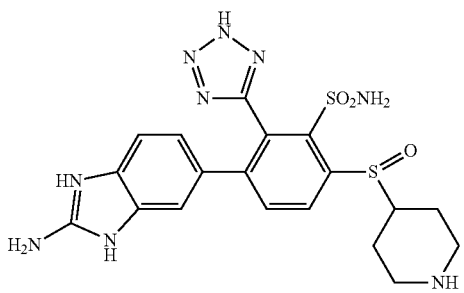 [SMILES: Nc1nc2ccc(-c3ccc(S(=O)C4CCNCC4)c(S(N)(=O)=O)c3-c3nn[nH]n3)cc2[nH]1]

The title compound was prepared as described EXAMPLE 10, Steps B-D, starting from 3-(2-amino-1H-benzo[d]imidazol-5-yl)-6-bromo-N,N-bis(4-methoxybenzyl)-2-[2-(4-methoxybenzyl)-2H-tetrazol-5-yl]benzenesulfonamide (EXAMPLE 1, Step A) and tert-butyl 4-mercaptopiperidine-1-carboxylate. LCMS [M+H]$^+$: 488.

EXAMPLE 13

3-(2-amino-1H-benzo[d]imidazol-4-yl)-6-(azetidin-3-ylsulfinyl)-2-(2H-tetrazol-5-yl)benzenesulfonamide

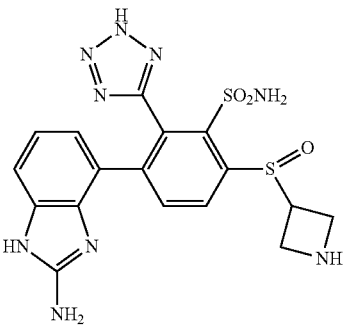 [SMILES: Nc1nc2c(-c3ccc(S(=O)C4CNC4)c(S(N)(=O)=O)c3-c3nn[nH]n3)cccc2[nH]1]

The title compound was prepared as described for EXAMPLE 10, Steps B-D, starting from 3-(2-amino-1H-benzo[d]imidazol-4-yl)-6-bromo-N,N-bis(4-methoxybenzyl)-2-(2-(4-methoxybenzyl)-2H-tetrazol-5-yl)benzenesulfonamide (EXAMPLE 2, Step D) and tert-butyl 3-mercaptoazetidine-1-carboxylate. LCMS [M+H]$^+$: 460; $^1$H NMR (DMSO-d6, 400 MHz): 8.40-8.10 (m, 3H), 6.92 (d, J=7.6 Hz, 1H), 6.51-6.40 (m, 1H), 6.39-6.25 (m, 1H), 6.10-6.03 (m, 1H), 4.52-4.42 (m, 1H), 4.37-4.30 (m, 1H), 4.28-4.15 (m, 2H), 3.86-3.80 (m, 1H).

EXAMPLE 14

3-(2-amino-3H-benzo[d]imidazol-4-yl)-6-(piperidin-4-ylsulfinyl)-2-(2H-tetrazol-5-yl)benzenesulfonamide

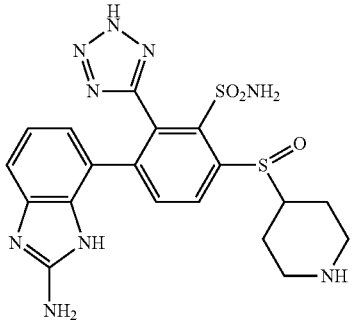 [SMILES: Nc1nc2cccc(-c3ccc(S(=O)C4CCNCC4)c(S(N)(=O)=O)c3-c3nn[nH]n3)c2[nH]1]

The title compound was prepared as described for EXAMPLE 10, Steps B-D, starting from 3-(2-amino-1H-benzo[d]imidazol-4-yl)-6-bromo-N,N-bis(4-methoxybenzyl)-2-(2-(4-methoxybenzyl)-2H-tetrazol-5-yl)benzenesulfonamide (EXAMPLE 2, Step D) and tert-butyl 4-mercaptopiperidine-1-carboxylate. LCMS [M+H]$^+$: 488.

EXAMPLE 15

3-(2-Amino-7-methyl-1H-benzo[d]imidazol-4-yl)-6-(azetidin-3-ylsulfonyl)-2-(2H-tetrazol-5-yl)benzenesulfonamide

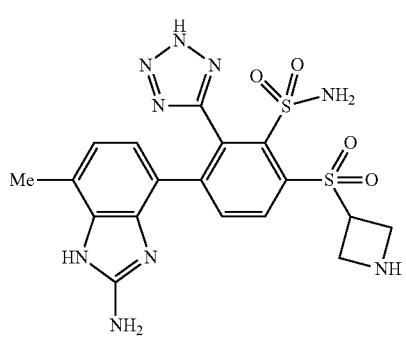 [SMILES: Cc1ccc(-c2ccc(S(=O)(=O)C3CNC3)c(S(N)(=O)=O)c2-c2nn[nH]n2)c2nc(N)[nH]c12]

Step A: tert-butyl 3-((4-(2-amino-7-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate and tert-butyl 3-((4-(2-amino-7-methyl-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate A microwave vial was charged with $Cs_2CO_3$ (115 mg, 0.353 mmol), 7-bromo-4-methyl-1H-benzo[d]imidazol-2-amine (commercially available from Ellanova Laboratories, 28.0 mg, 0.124 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid, (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid (100 mg, 0.118 mmol) and Xphos precatalyst generation 2 (9.27 mg, 0.012 mmol). The vial was sealed, degassed, and filled with dioxane (0.94 mL) and water (0.24 mL). The resulting mixture was heated overnight at 80° C. The reaction mixture was filtered over CELITE. The filtrate was diluted with EtOAc and washed with water. The organic layer was dried over anhydrous $MgSO_4$, filtered, concentrated and purified by silica gel column chromatography using 0-10% MeOH/DCM as mobile phase to afford the title compound LC/MS $[M+1]^+$: 951.17.

Step B: 3-(2-amino-7-methyl-1H-benzo[d]imidazol-4-yl)-6-(azetidin-3-ylsulfonyl)-2-(2H-tetrazol-5-yl)benzenesulfonamide The deprotection step was conducted with TFA using a similar procedure to that of EXAMPLE 4 to afford the title compound. LC/MS $[M+1]^+$: 490.5.

EXAMPLE 16

6-(Azetidin-3-ylsulfonyl)-3-(1H-pyrrolo[3,2-b]pyridin-6-yl)-2-(2H-tetrazol-5-yl)benzenesulfonamide

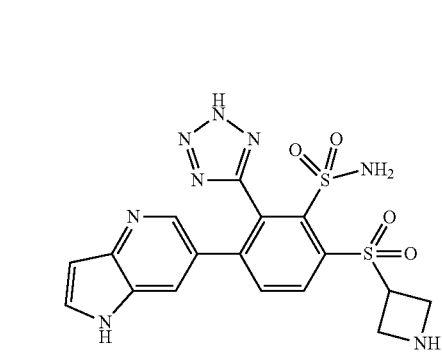 [SMILES: NS(=O)(=O)c1c(S(=O)(=O)C2CNC2)ccc(-c2cnc3cc[nH]c3c2)c1-c1nn[nH]n1]

Step A: tert-butyl 3-((2-(N,N-bis(4-methoxybenzyl)sulfamoyl)-3-(2-(4-methoxybenzyl)-2H-tetrazol-5-yl)-4-(1H-pyrrolo[3,2-b]pyridin-6-yl)phenyl)sulfonyl)azetidine-1-carboxylate and tert-butyl 3-((2-(N,N-bis(4-methoxybenzyl)sulfamoyl)-3-(1-(4-methoxybenzyl)-1H-tetrazol-5-yl)-4-(1H-pyrrolo[3,2-b]pyridin-6-yl)phenyl)sulfonyl)azetidine-1-carboxylate A microwave vial was charged with Xphos precatalyst generation 2 (7.42 mg, 9.43 µmol), $K_3PO_4$ (60.0 mg, 0.283 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid and (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid (80 mg, 0.094 mmol) and 6-bromo-1H-pyrrolo[3,2-b]pyridine (27.9 mg, 0.141 mmol). The vial was sealed, degassed, and filled with THF (0.75 mL) and water (0.2 mL). The resulting mixture was heated overnight at 70° C. The reaction mixture was filtered over CELITE. The filtrate was diluted with EtOAc and washed with water. The organic layer was dried over anhydrous $MgSO_4$, filtered, concentrated and purified by silica gel column chromatography using 0-10% MeOH/DCM as mobile phase to afford the title compound. LC/MS $[M+1]^+$: 922.20.

Step B: 6-(Azetidin-3-ylsulfonyl)-3-(1H-pyrrolo[3,2-b]pyridin-6-yl)-2-(2H-tetrazol-5-yl)benzenesulfonamide The deprotection step was conducted with TFA using a similar procedure to that of EXAMPLE 4 to afford the title compound. LC/MS $[M+1]^+$: 461.54.

EXAMPLE 17

3-(6-Aminoimidazo[1,2-b]pyridazin-3-yl)-6-(azetidin-3-ylsulfonyl)-2-(2H-tetrazol-5-yl)benzenesulfonamide

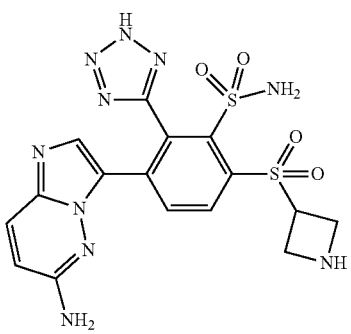 [SMILES: Nc1ccc2ncc(-c3ccc(S(=O)(=O)C4CNC4)c(S(N)(=O)=O)c3-c3nn[nH]n3)n2n1]

Step A: tert-butyl 3-((4-(6-aminoimidazo[1,2-b]pyridazin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate and tert-butyl 3-((4-(6-aminoimidazo[1,2-b]pyridazin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate A microwave vial was charged with Pd(dppf)Cl$_2$ (8.62 mg, 0.012 mmol), sodium carbonate (18.73 mg, 0.177 mmol), 3-bromoimidazo[1,2-b]pyridazin-6-amine (12.55 mg, 0.059 mmol) and (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid and (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid (50 mg, 0.059 mmol). The vial was sealed, degassed, and filled with dioxane (0.5 mL) and water (0.1 mL). The resulting mixture was heated overnight at 40° C. The reaction mixture was filtered over CELITE. The filtrate was diluted with EtOAc and washed with water. The organic layer was dried over anhydrous MgSO$_4$, filtered, concentrated and purified by silica gel column chromatography using 0-10% MeOH/DCM as mobile phase to afford the title compound. LC/MS [M+1]$^+$: 937.19.

Step B: 3-(6-Aminoimidazo[1,2-b]pyridazin-3-yl)-6-(azetidin-3-yl sulfonyl)-2-(2H-tetrazol-5-yl)benzenesulfonamide The deprotection step was conducted with TFA using a similar procedure to that of EXAMPLE 4 to afford the title compound. LC/MS [M+1]$^+$: 477.61.

EXAMPLE 18

3-(2-Amino-1-(2,2,2-trifluoroethyl)-1H-benzo[d]imidazol-4-yl)-6-((2-aminoethyl)sulfonyl)-2-(2H-tetrazol-5-yl)benzenesulfonamide

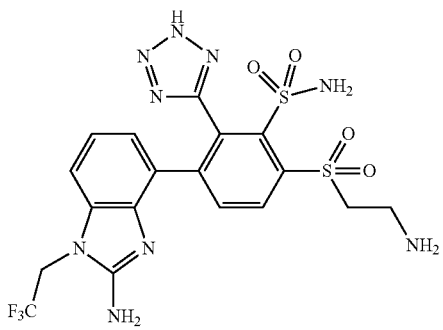 [SMILES: NCCS(=O)(=O)c1ccc(-c2cccc3c2nc(N)n3CC(F)(F)F)c(-c2nn[nH]n2)c1S(N)(=O)=O]

Step A: tert-butyl (2-((4-(2-amino-1-(2,2,2-trifluoroethyl)-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate and tert-butyl (2-((4-(2-amino-1-(2,2,2-trifluoroethyl)-1H-benzo[d]imidazol-4-)-2-(N,N-bis(4-methoxybenzyl)sulfamoyl)-3-(1-(4-methoxybenzyl)-1H-tetrazol-5-yl)phenyl)sulfonyl)ethyl)carbamate A microwave vial was charged with tert-butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate and tert-butyl (2-((2-(N,N-bis(4-methoxybenzyl)sulfamoyl)-4-(5,5-dimethyl-1,3,2-dioxaborinan-2-yl)-3-(1-(4-methoxybenzyl)-1H-tetrazol-5-yl)phenyl)sulfonyl)ethyl)carbamate (200 mg, 0.221 mmol), tBuXPhos precatalyst generation 3 (88 mg, 0.111 mmol), cesium carbonate (216 mg, 0.663 mmol), and 4-chloro-1-(2,2,2-trifluoroethyl)-1H-benzo[d]imidazol-2-amine (66.2 mg, 0.265 mmol). The vial was sealed, degassed, and filled with dioxane (0.88 mL) and water (0.22 mL). The resulting mixture was heated overnight at 40° C. The reaction mixture was filtered over CELITE. The filtrate was diluted with EtOAc and washed with water. The organic layer was dried over anhydrous MgSO$_4$, filtered, concentrated and purified by silica gel column chromatography using 0-10% MeOH/DCM as mobile phase to afford the title compound. LC/MS [M+1]$^+$: 1006.39.

Step B: 3-(2-Amino-1-(2,2,2-trifluoroethyl)-1H-benzo[d]imidazol-4-yl)-6-((2-aminoethyl)sulfonyl)-2-(2H-tetrazol-5-yl)benzenesulfonamide The deprotection step was conducted with TFA using a similar procedure to that of EXAMPLE 4 to afford the title compound. LC/MS [M+1]$^+$: 546.32.

EXAMPLE 19

3-(2-Amino-1-methyl-1H-benzo[d]imidazol-7-yl)-6-(azetidin-3-ylsulfonyl)-2-(2H-tetrazol-5-yl)benzenesulfonamide

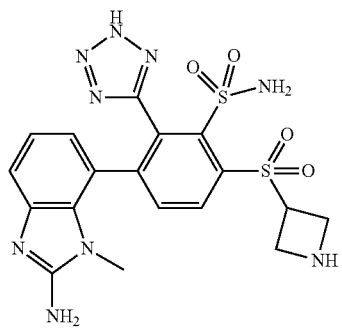 [SMILES: Cn1c(N)nc2cccc(-c3ccc(S(=O)(=O)C4CNC4)c(S(N)(=O)=O)c3-c3nn[nH]n3)c21]

Step A: tert-butyl 3-((4-(2-amino-1-methyl-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate and tert-butyl 3-((4-(2-amino-1-methyl-1H-benzo[d]imidazol-7-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate A microwave vial was charged with 2,2-dimethyl-1,3-propanediol (123 mg, 1.178 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid and (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid (200 mg, 0.236 mmol) in toluene (2 mL). The reaction mixture was heated at 80° C. for 1 hour. After removing the solvent, tBuXPhos precatalyst generation 3 (94 mg, 0.118 mmol), cesium carbonate (230 mg, 0.707 mmol), and 7-chloro-1-methyl-1H-benzo[d]imidazol-2-amine (51.4 mg, 0.283 mmol) were added. The vial was sealed, degassed, and filled with dioxane (1.26 mL) and water (0.32 mL). The resulting mixture was heated overnight at 40° C. The reaction mixture was filtered over CELITE. The filtrate was diluted with EtOAc and washed with water. The organic layer was dried over anhydrous MgSO$_4$, filtered, concentrated and purified by silica gel column chromatography using 0-10% MeOH/DCM as mobile phase to afford the title compound. LC/MS [M+1]$^+$: 950.58.

Step B: 3-(2-Amino-1-methyl-1H-benzo[d]imidazol-7-yl)-6-(azetidin-3-ylsulfonyl)-2-(2H-tetrazol-5-yl)benzenesulfonamide The deprotection step was conducted with TFA using a similar procedure to that of EXAMPLE 4 to afford the title compound. LC/MS [M+1]$^+$: 490.26.

EXAMPLE 20

3-(3-Amino-1H-indazol-6-yl)-6-azetidin-3-ylsulfonyl)-2-(2H-tetrazol-5-yl)benzenesulfonamide

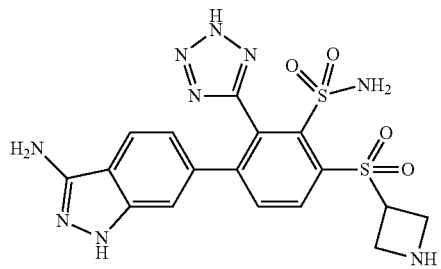 [SMILES: Nc1n[nH]c2cc(-c3ccc(S(=O)(=O)C4CNC4)c(S(N)(=O)=O)c3-c3nn[nH]n3)ccc12]

Step A: tert-butyl 3-((4-(3-amino-1H-indazol-6-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate and tert-butyl 3-((4-(3-amino-1H-indazol-6-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate A microwave vial was charged with 2,2-dimethyl-1,3-propanediol (73.6 mg, 0.707 mmol), Xphos precatalyst generation 2 (11.12 mg, 0.014 mmol), Cs$_2$CO$_3$ (138 mg, 0.424 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid, (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid (120 mg, 0.141 mmol) and 6-bromo-2H-indazol-3-amine (36.0 mg, 0.170 mmol). The vial was sealed, degassed, and filled with dioxane (1.2 mL) and water (0.24 mL). The resulting mixture was heated overnight at 40° C. The reaction mixture was filtered over CELITE. The filtrate was diluted with EtOAc and washed with water. The organic layer was dried over anhydrous MgSO$_4$, filtered, concentrated and purified by silica gel column chromatography using 0-10% MeOH/DCM as mobile phase to afford the title compound. LC/MS [M+1]$^+$: 936.48.

Step B: 3-(3-Amino-1H-indazol-6-yl)-6-(azetidin-3-ylsulfonyl)-2-(2H-tetrazol-5-yl)benzenesulfonamide The deprotection step was conducted with TFA using a similar procedure to that of EXAMPLE 4 to afford the title compound. LC/MS [M+1]$^+$: 476.56.

Examples 21-23 were prepared according to the general procedure described above for EXAMPLE 20, using the boronic acids or boronic esters (3-(N,N-Bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid and (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid (REFERENCE EXAMPLE 7) or tert-Butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate and tert-butyl (2-((2-(N,N-bis(4-methoxybenzyl)sulfamoyl)-4-(5,5-dimethyl-1,3,2-dioxaborinan-2-yl)-3-(1-(4-methoxybenzyl)-1H-tetrazol-5-yl)phenyl)sulfonyl)ethyl)carbamate (REFERENCE EXAMPLE 11), and commercially available aryl halides listed below.

| EX. NO. | Aryl halide | STRUCTURE/NAME | LC/MS: [M + 1]+ |
|---|---|---|---|
| 21 | 7-bromo-2H-indazol-3-amine | 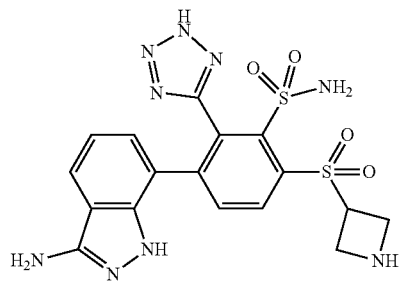 [SMILES: Nc1n[nH]c2c(-c3ccc(S(=O)(=O)C4CNC4)c(S(N)(=O)=O)c3-c3nn[nH]n3)cccc12]<br>3-(3-amino-1H-indazol-7-yl)-6-(azetidin-3-ylsulfonyl)-2-(2H-tetrazol-5-yl)benzenesulfonamide | 476.49 |
| 22 | 4-chloro-1-methyl-1H-benzo[d]imidazol-2-amine | 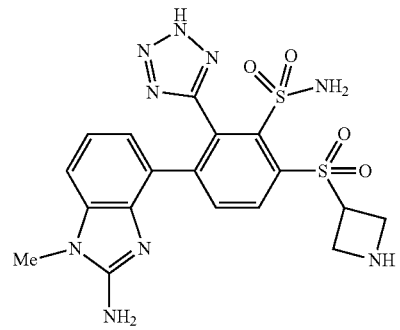 [SMILES: Cn1c(N)nc2c(-c3ccc(S(=O)(=O)C4CNC4)c(S(N)(=O)=O)c3-c3nn[nH]n3)cccc21]<br>3-(2-amino-1-methyl-1H-benzo[d]imidazol-4-yl)-6-(azetidin-3-ylsulfonyl)-2-(2H-tetrazol-5-yl)benzenesulfonamide | 490.35 |
| 23 | 4-bromo-7-methyl-1H-benzo[d]imidazol-2-amine | 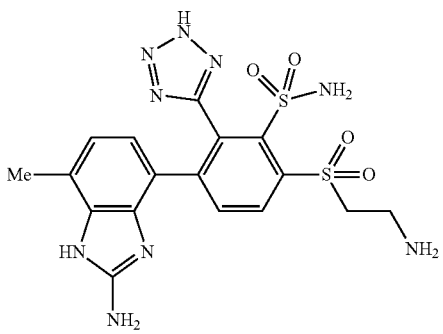 [SMILES: Cc1ccc(-c2ccc(S(=O)(=O)CCN)c(S(N)(=O)=O)c2-c2nn[nH]n2)c2nc(N)[nH]c12]<br>3-(2-amino-7-methyl-1H-benzo[d]imidazol-4-yl)-6-((2-aminoethyl)sulfonyl)-2-(2H-tetrazol-5-yl)benzenesulfonamide | 478.28 |

EXAMPLE 24

3-(6-aminopyridin-3-yl)-6-(piperidin-4-ylsulfonyl)-2-(2H-tetrazol-5-yl)benzenesulfonamide

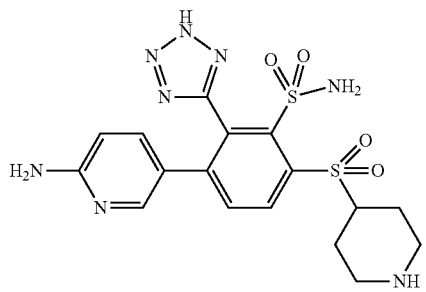 [SMILES: Nc1ccc(-c2ccc(S(=O)(=O)C3CCNCC3)c(S(N)(=O)=O)c2-c2nn[nH]n2)cn1]

Step A: tert-butyl 4-((4-(6-aminopyridin-3-yl)-2-(N,N-bis(4-methoxybenzyl)sulfamoyl)-3-(2-(4-methoxybenzyl)-2H-tetrazol-5-yl)phenyl)sulfonyl)piperidine-1-carboxylate Into a 100 mL RBF was placed tert-butyl 4-((2-(N,N-bis(4-methoxybenzyl)sulfamoyl)-4-iodo-3-(2-(4-methoxybenzyl)-2H-tetrazol-5-yl)phenyl)sulfonyl)piperidine-1-carboxylate (110 mg, 0.115 mmol), 5-(4,4,5,5-tetramethyl-1,3,2-dioxaborolan-2-yl)pyridin-2-amine (50.5 mg, 0.229 mmol), Na$_2$CO$_3$ (36.5 mg, 0.344 mmol) and Pd(Ph$_3$P)$_4$ (26.5 mg, 0.023 mmol) in dioxane/H$_2$O=4/1 (2.0 ml). The reaction mixture was degassed with nitrogen 3 times and stirred for 3 hours at 80° C. The solvent was removed under vacuum and the residue was purified by silica gel column chromatography, and eluted with ethyl acetate/petroleum ether (5:1) to give the title compound. LCMS [M+H]$^+$: 925

Step B: 3-(6-aminopyridin-3-yl)-6-(piperidin-4-ylsulfonyl)-2-(2H-tetrazol-5-yl)benzenesulfonamide Into a 10 mL RBF was placed a solution of tert-butyl 4-((4-(6-aminopyridin-3-yl)-2-(N,N-bis(4-methoxybenzyl)sulfamoyl)-3-(2-(4-methoxybenzyl)-2H-tetrazol-5-yl)phenyl)sulfonyl)piperidine-1-carboxylate (67 mg, 0.072 mmol) in DCM (2.0 ml) and trifluoroacetic acid (1.0 mL). The resulting solution reaction was stirred at room temperature for 1 hour and then concentrated under vacuum. The residue was dissolved in anisole (1.0 ml, 0.072 mmol), trifluoroacetic acid (2.0 mL), stirred at 80° C. for 3 hours and then concentrated under vacuum. The residue was purified by Prep-HPLC with the following conditions: Column: X Bridge RP18, 19*150 mm, 5 µM; Mobile Phase A: water/0.05% NH$_4$HCO$_3$, Mobile Phase B: ACN; Flow rate: 20 mL/min; Gradient: 5% B to 15% B in 5 min; detected at 254 nm. The collected fractions were combined and concentrated under vacuum to give the title compound: LCMS [M+H]$^+$: 465; $^1$H NMR (300 MHz, DMSO): δ 8.12 (d, J=8.7 Hz, 1H), 7.76 (d, J=8.4 Hz, 1H), 7.51 (br, 2H), 7.49 (s, 1H), 6.69-6.65 (m, 1H), 6.12 (d, J=8.7 Hz, 1H), 5.99 (br, 2H), 4.46-4.38 (m, 1H), 3.37-3.32 (m, 2H), 2.96-2.88 (m, 2H), 2.19-1.83 (m, 4H).

EXAMPLE 25

3-(6-aminopyridin-3-yl)-6-(azetidin-3-ylsulfonyl)-2-(2H-tetrazol-5-yl)benzenesulfonamide

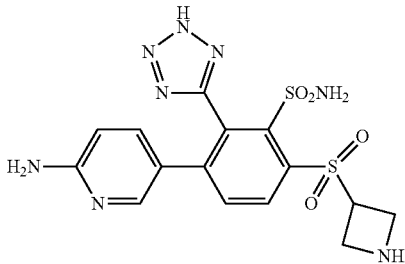 [SMILES: Nc1ccc(-c2ccc(S(=O)(=O)C3CNC3)c(S(N)(=O)=O)c2-c2nn[nH]n2)cn1]

Step A: tert-butyl 3-(4-(6-aminopyridin-3-yl)-2-(N,N-bis(4-methoxybenzyl)sulfamoyl)-3-(2-(4-methoxybenzyl)-2H-tetrazol-5-yl)phenylsulfonyl)azetidine-1-carboxylate A mixture of tert-butyl 3-(2-(bis(4-methoxybenzyl)aminooxysulfinyl)-4-iodo-3-(2-(4-methoxybenzyl)-2H-tetrazol-5-yl)phenylsulfonyl)azetidine-1-carboxylate (REFERENCE EXAMPLE 6, 150 mg, 0.161 mmol), 6-aminopyridin-3-ylboronic acid (44.0 mg, 0.322 mmol), Na$_2$CO$_3$ (51.2 mg, 0.483 mmol) and tetrakis(triphenylphosphine)palladium (0) (37.2 mg, 0.032 mmol) in Dioxane (10 ml) and water (1 ml) was stirred at 80° C. for 2 hours. After the resulting mixture was concentrated under vacuum, the residue was purified by silica gel chromatography, eluted with methanol/dichloromethane (1:10) to give the title compound. LCMS [M+H]$^+$: 897; hr NMR (DMSO-d6, 400 MHZ): δ 8.75 (d, J=8.4 Hz, 1H), 8.09 (d, J=8.4 Hz, 1H), 7.53 (s, 1H), 7.30-6.80 (m, 13H), 6.61 (d, J=8.4 Hz, 1H), 5.24-5.01 (m, 1H), 4.54-4.49 (m, 2H), 4.38-4.10 (m, 5H), 4.00-3.94 (m, 3H), 3.73-3.68 (m, 9H), 1.41 (s, 9H).

Step B: 3-(6-aminopyridin-3-yl)-6-(azetidin-3-ylsulfonyl)-N-(4-methoxybenzyl)-2-(2-(4-methoxybenzyl)-2H-tetrazol-5-yl)benzenesulfonamide A solution mixture of tert-butyl 3-(4-(6-aminopyridin-3-yl)-2-(N,N-bis(4-methoxybenzyl)sulfamoyl)-3-(2-(4-methoxybenzyl)-2H-tetrazol-5-yl)phenylsulfonyl)azetidine-1-carboxylate (87 mg, 0.1 mmol) and TFA (1 ml, 12.98 mmol) in DCM (5 ml) was stirred at room temperature for 1 hour. The reaction mixture was concentrated under vacuum to give the title compound. LCMS [M+1]: 677

Step C: 3-(6-aminopyridin-3-yl)-6-(azetidin-3-ylsulfonyl)-2-(2H-tetrazol-5-yl)benzenesulfonamide A solution of 3-(6-aminopyridin-3-yl)-6-(azetidin-3-ylsulfonyl)-N-(4-methoxybenzyl)-2-(2-(4-methoxybenzyl)-2H-tetrazol-5-yl)benzenesulfonamide (65 mg, 0.1 mmol) in TFA (10 ml, 130 mmol) was stirred at 80° C. for 2 hours. The reaction mixture was concentrated under vacuum and the residue was purified by Prep-HPLC with the following conditions: Column: X Bridge RP18, 19*150 mm, 5 µM; Mobile Phase A: water/0.05% NH$_4$HCO$_3$, Mobile Phase B: ACN; Flow rate: 20 mL/min; Gradient: 3% B to 15% B in 7 min; detected at 254 nm. The collected fractions were combined and concentrated under vacuum to give the title compound. LCMS [M+1]: 437; $^1$H NMR (DMSO-d6, 400

MHZ): δ 8.29 (d, J=8.4 Hz, 1H), 7.83 (d, J=8.4 Hz, 1H), 7.70 (brs, 1H), 7.55 (d, J=2.4 Hz, 1H), 6.73 (dd, J=8.4, 2.4 Hz, 1H), 6.16 (d, J=8.4 Hz, 1H), 6.05 (s, 2H), 5.23-5.21 (m, 1H), 4.26-4.20 (m, 4H).

The compounds below were prepared as described for EXAMPLE 25 starting from tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (REFERENCE EXAMPLE 6) and boronic acids or boronic esters prepared as described herein or available from commercial sources

| EX NO | Structure | Name | MW | LC/MS [M + H]+ |
|---|---|---|---|---|
| 26 | 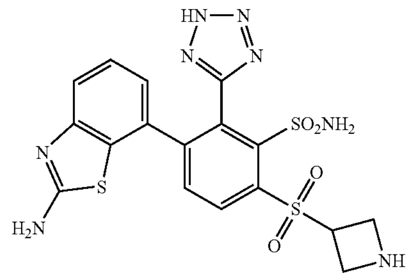 [SMILES: Nc1nc2cccc(-c3ccc(S(=O)(=O)C4CNC4)c(S(N)(=O)=O)c3-c3nn[nH]n3)c2s1] | 3-(2-aminobenzo[d]thiazol-7-yl)-6-(azetidin-3-ylsulfonyl)-2-(2H-tetrazol-5-yl)benzenesulfonamide | 492 | 493 |
| 27 | 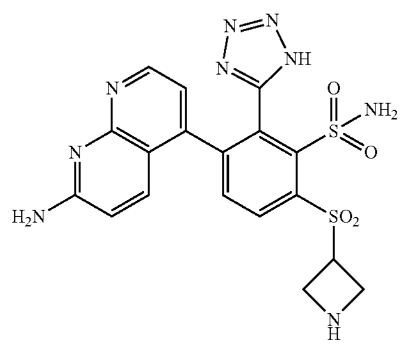 [SMILES: Nc1ccc2c(-c3ccc(S(=O)(=O)C4CNC4)c(S(N)(=O)=O)c3-c3nnn[nH]3)ccnc2n1] | 3-(7-amino-1,8-naphthyridin-4-yl)-6-(azetidin-3-ylsulfonyl)-2-(1H-tetrazol-5-yl)benzenesulfonamide | 487 | 488 |
| 28 | 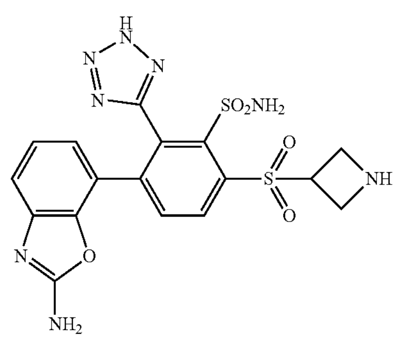 [SMILES: Nc1nc2cccc(-c3ccc(S(=O)(=O)C4CNC4)c(S(N)(=O)=O)c3-c3nn[nH]n3)c2o1] | 3-(2-aminobenzo[d]oxazol-7-yl)-6-(azetidin-3-ylsulfonyl)-2-(2H-tetrazol-5-yl)benzenesulfonamide | 476 | 477 |
| 29 | 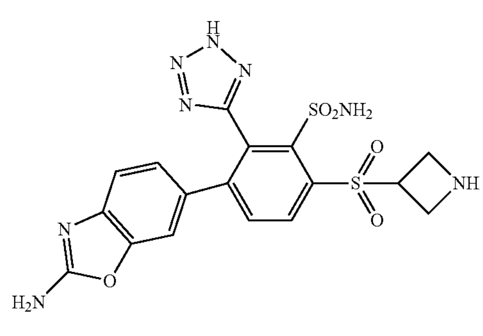 [SMILES: Nc1nc2ccc(-c3ccc(S(=O)(=O)C4CNC4)c(S(N)(=O)=O)c3-c3nn[nH]n3)cc2o1] | 3-(2-aminobenzo[d]oxazol-6-yl)-6-(azetidin-3-ylsulfonyl)-2-(2H-tetrazol-5-yl)benzenesulfonamide | 476 | 477 |

-continued

| EX NO | Structure | Name | MW | LC/MS [M + H]+ |
|---|---|---|---|---|
| 30 | 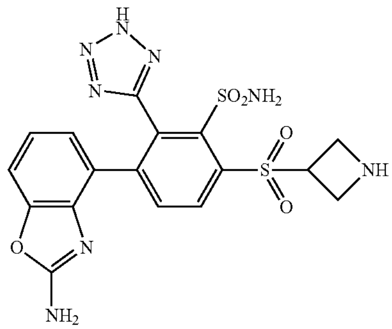 [SMILES: Nc1nc2c(-c3ccc(S(=O)(=O)C4CNC4)c(S(N)(=O)=O)c3-c3nn[nH]n3)cccc2o1] | 3-(2-aminobenzo[d]oxazol-4-yl)-6-(azetidin-3-ylsulfonyl)-2-(2H-tetrazol-5-yl)benzenesulfonamide | 476 | 477 |
| 31 | 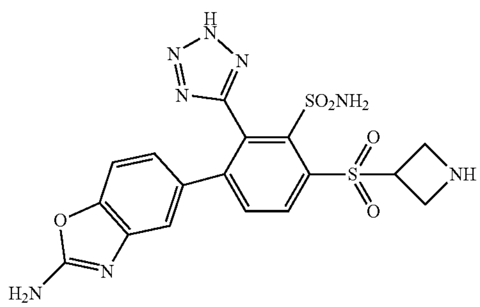 [SMILES: Nc1nc2cc(-c3ccc(S(=O)(=O)C4CNC4)c(S(N)(=O)=O)c3-c3nn[nH]n3)ccc2o1] | 3-(2-aminobenzo[d]oxazol-5-yl)-6-(azetidin-3-ylsulfonyl)-2-(2H-tetrazol-5-yl)benzenesulfonamide | 476 | 477 |
| 32 | 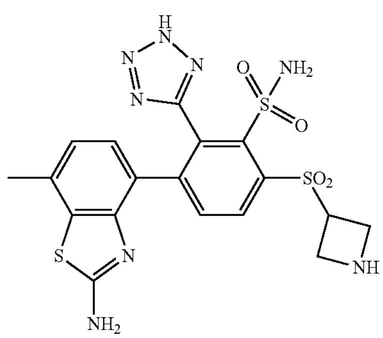 [SMILES: Cc1ccc(-c2ccc(S(=O)(=O)C3CNC3)c(S(N)(=O)=O)c2-c2nn[nH]n2)c2nc(N)sc12] | 3-(2-amino-7-methylbenzo[d]thiazol-4-yl)-6-(azetidin-3-ylsulfonyl)-2-(2H-tetrazol-5-yl)benzenesulfonamide | 506 | 507 |
| 33 | 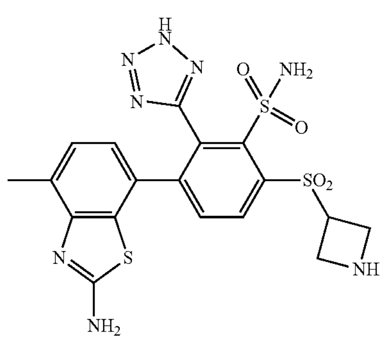 [SMILES: Cc1ccc(-c2ccc(S(=O)(=O)C3CNC3)c(S(N)(=O)=O)c2-c2nn[nH]n2)c2sc(N)nc12] | 3-(2-amino-4-methylbenzo[d]thiazol-7-yl)-6-(azetidin-3-ylsulfonyl)-2-(2H-tetrazol-5-yl)benzenesulfonamide | 506 | 507 |

-continued

| EX NO | Structure | Name | MW | LC/MS [M + H]+ |
|---|---|---|---|---|
| 34 | 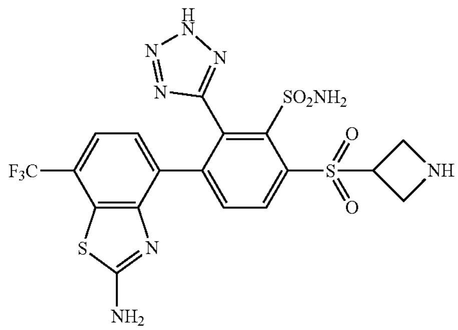 [SMILES: Nc1nc2c(-c3ccc(S(=O)(=O)C4CNC4)c(S(N)(=O)=O)c3-c3nn[nH]n3)ccc(C(F)(F)F)c2s1] | 3-(2-amino-7-(trifluoromethyl)benzo[d]thiazol-4-yl)-6-(azetidin-3-ylsulfonyl)-2-(2H-tetrazol-5-yl)benzenesulfonamide | 560 | 561 |
| 35 | 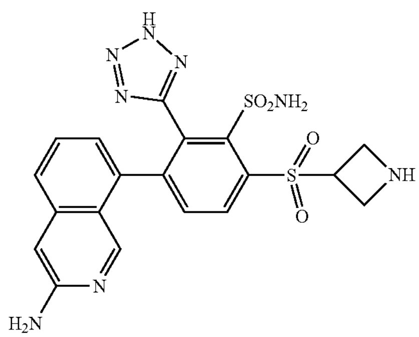 [SMILES: Nc1cc2cccc(-c3ccc(S(=O)(=O)C4CNC4)c(S(N)(=O)=O)c3-c3nn[nH]n3)c2cn1] | 3-(3-aminoisoquinolin-8-yl)-6-(azetidin-3-ylsulfonyl)-2-(2H-tetrazol-5-yl)benzenesulfonamide | 486 | 487 |
| 36 | 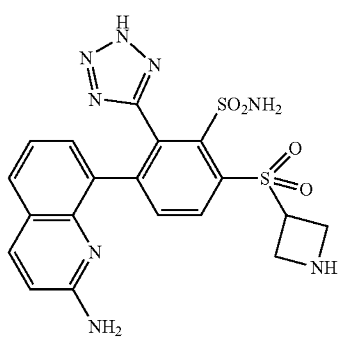 [SMILES: Nc1ccc2cccc(-c3ccc(S(=O)(=O)C4CNC4)c(S(N)(=O)=O)c3-c3nn[nH]n3)c2n1] | 3-(2-aminoquinolin-8-yl)-6-(azetidin-3-ylsulfonyl)-2-(2H-tetrazol-5-yl)benzenesulfonamide | 486 | 487 |
| 37 | 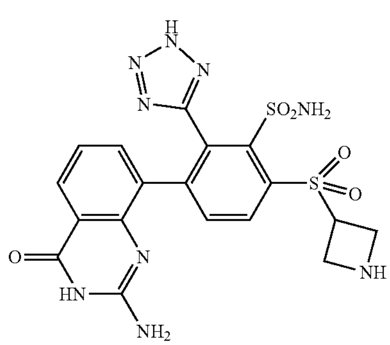 [SMILES: Nc1nc2c(-c3ccc(S(=O)(=O)C4CNC4)c(S(N)(=O)=O)c3-c3nn[nH]n3)cccc2c(=O)[nH]1] | 3-(2-amino-4-oxo-3,4-dihydroquinazolin-8-yl)-6-(azetidin-3-ylsulfonyl)-2-(2H-tetrazol-5-yl)benzenesulfonamide | 503 | 504 |

EXAMPLE 38

2-amino-4-(4-(azetidin-3-ylsulfonyl)-3-sulfamoyl-2-(2H-tetrazol-5-yl)phenyl)benzo[d]thiazole-7-carboxylic Acid

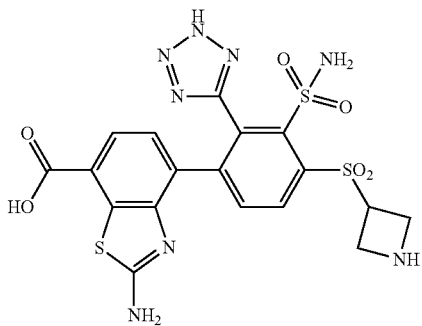 [SMILES: Nc1nc2c(-c3ccc(S(=O)(=O)C4CNC4)c(S(N)(=O)=O)c3-c3nn[nH]n3)ccc(C(=O)O)c2s1]

Step A: methyl 3-(3-benzoylthioureido)-4-bromobenzoate

Benzoyl isothiocyanate (3.12 g, 19.1 mmol) was added to a stirred mixture of methyl 3-amino-4-bromobenzoate (4.0 g, 17.4 mmol) in acetone (40 ml) and the mixture was stirred at 60° C. for 6 hours. After being cooled to RT, the reaction mixture was evaporated under vacuum. The residue was purified by column chromatography on silica gel Isolute Flash Si; 50 g prepacked, eluted with EA/PE (0-30%) to give the title compound: LCMS [M+H]$^+$: 393, 395 (1:1); $^1$H NMR (400 MHz, DMSO-d$_6$): δ 12.65 (s, 1H), 11.91 (s, 1H), 8.47 (d, J=2.0 Hz, 1H), 8.02-8.00 (m, 2H), 7.92-7.91 (m, 1H), 7.81-7.80 (m, 1H), 7.78-7.69 (m, 1H), 7.58-7.54 (m, 2H), 3.88 (s, 3H).

Step B: methyl 2-amino-4-bromobenzo[d]thiazole-7-carboxylate

Sodium bromide (0.16 g, 1.53 mmol) was added to a stirred, cooled 0° C. mixture of methyl 3-(3-benzoylthioureido)-4-bromobenzoate (3 g, 7.63 mmol) in H$_2$SO$_4$ (4.5 ml, 84 mmol) and the mixture was stirred at 80° C. for 6 hr. To the reaction mixture was added MeOH (30 ml) and the mixture was stirred at 80° C. for 16 hours. The reaction mixture was cooled, and the solvent was evaporated under reduced pressure. The residue was purified by column chromatography on silica gel Isolute Flash Si; 20 g prepacked, eluting with EA/PE (0-60%) to give the title compound: [M+H]$^+$: 287, 289 (1:1); $^1$H NMR (400 MHz, DMSO-d$_6$): δ 8.04 (brs, 2H), 7.60 (d, J=8.4 Hz, 1H), 7.53 (d, J=8.4 Hz, 1H), 3.91 (s, 3H).

Step C: 2-amino-7-(methoxycarbonyl)benzo[d]thiazol-4-ylboronic acid

To a solution of methyl 2-amino-4-bromobenzo[d]thiazole-7-carboxylate (2 g, 6.97 mmol) in dioxane (20 ml) was added Pd(dppf)Cl$_2$ (1.019 g, 1.393 mmol), 4,4,4',4',5,5,5',5'-octamethyl-2,2'-bi(1,3,2-dioxaborolane) (3.54 g, 13.93 mmol) and potassium acetate (2.051 g, 20.90 mmol). The mixture was degassed 3 times with N$_2$, and stirring at 80° C. for 16 hours. The mixture was filtered through the CELITE, and washing with ethyl acetate (100 mL). The filtration was extracted with 2N HCl (3×30 mL). The aqueous was concentrated under reduced pressure. The crude material was dissolved in 3:1 CHCl$_3$: i-PrOH, dried over MgSO$_4$. The MgSO$_4$ was filtered off and the filtrate was concentrated to give the title compound: LCMS [M+H]$^+$: 253; $^1$H NMR (400 MHz, DMSO-d$_6$): δ 10.35 (brs, 1H), 9.35 (brs, 1H), 7.89-7.86 (m, 1H), 7.82-7.80 (m, 1H), 3.95 (s, 3H).

Step D: methyl 2-amino-4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)benzo[d]thiazole-7-carboxylate (2-Amino-7-(methoxycarbonyl)benzo[d]thiazol-4-yl)boronic acid (0.542 g, 2.149 mmol), tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (1 g, 1.074 mmol), Pd(dppf)Cl$_2$ (0.236 g, 0.322 mmol), and Na$_2$CO$_3$ (0.455 g, 4.30 mmol) were added to a stirred mixture of dioxane (0.3 ml), and water (0.1 ml). The reaction mixture was degassed 3 times with N$_2$, and stirred at 80° C. for 16 hours. The reaction mixture was filtered and the solvent was evaporated under reduced pressure. The residue was purified by column chromatography on silica gel Isolute Flash Si; 50 g prepacked, eluting with EA/PE (0-70%) to give the title compound: LCMS [M+H]$^+$: 1011.

Step E: 2-amino-4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)benzo[d]thiazole-7-carboxylic acid To a solution of methyl 2-amino-4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)benzo[d]thiazole-7-carboxylate (250 mg, 0.28 mmol) in THF (2.5 ml) and MeOH (2.5 ml) was added 2 N NaOH (2.472 ml, 4.94 mmol). The resulting mixture was stirred at room temperature for 4 hours, and then adjusted to pH 3 with 2M HCl and filtered. The filtrate was washed with water (5 ml) and dried over anhydrous MgSO$_4$ to give the title compound. The product was used for the next step directly: LCMS [M+H]$^+$: 997.

Step F: 2-amino-4-(4-(azetidin-3-ylsulfonyl)-3-sulfamoyl-2-(2H-tetrazol-5-yl)phenyl)benzo[d]thiazole-7-carboxylic acid To a solution of 2-amino-4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)benzo[d]thiazole-7-carboxylic acid (120 mg, 0.120 mmol) in DCM (3 ml) was added TFA (0.093 ml, 1.203 mmol) with stirring at room temperature. The resulting solution was warmed to RT and stirred for 1 hour. The residue was concentrated to afford 2-amino-4-(4-(azetidin-3-ylsulfonyl)-2-(2-(4-methoxybenzyl)-2H-tetrazol-5-yl)-3-(N-(4-methoxybenzyl)sulfamoyl)phenyl)benzo[d]thiazole-7-carboxylic acid (80 mg, 0.082 mmol) as an oil. The solution of 2-amino-4-(4-(azetidin-3-ylsulfonyl)-2-(2-(4-methoxybenzyl)-2H-tetrazol-5-yl)-3-(N-(4-methoxybenzyl)sulfamoyl)phenyl)benzo[d]thiazole-7-carboxylic acid (80 mg, 0.103 mmol) in TFA (0.793 ml, 10.30 mmol) was stirring at RT. The resulting solution was warmed to 80° C. and stirred for 2 hours. The product was purified by Prep-HPLC with the following conditions: Column: XSelect CSH Prep C18 OBD Column, 5 μM, 19*150 mm; Mobile Phase A: water with 10 mmol NH₄HCO₃, Mobile Phase B: MeCN; Flow rate: 20 mL/min; Gradient: 5% B to 35% B in 8 min; 254/220 nm. The collected fractions were combined and concentrated under vacuum to afford the title compound: LCMS [M+H]⁺: 537; ¹H NMR (400 MHz, CD₃OD): δ 8.69 (d, J=8 Hz, 1H), 8.08 (d, J=8 Hz, 1H), 7.73 (d, J=8 Hz, 1H), 7.10 (d, J=8 Hz, 1H), 5.34-5.30 (m, 1H), 4.64-4.62 (m, 2H), 4.51-4.49 (m, 2H).

EXAMPLE 39

2-amino-4-(4-(azetidin-3-ylsulfonyl)-3-sulfamoyl-2-(2H-tetrazol-5-yl)phenyl)benzo[d]thiazole-7-carboxamide

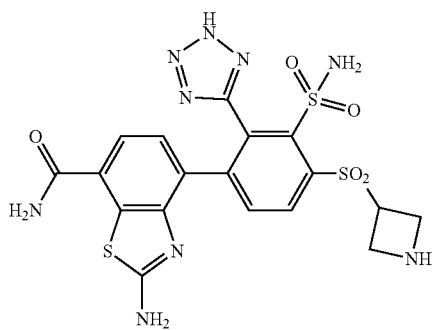 [SMILES: NC(=O)c1ccc(-c2ccc(S(=O)(=O)C3CNC3)c(S(N)(=O)=O)c2-c2nn[nH]n2)c2nc(N)sc12]

Step A: 2-amino-4-(3-(N,N-bis(4-methoxybenzyl) sulfamoyl)-4-((1-(tert-butoxycarbonyl)azetidin-3-yl) sulfonyl)-2-(2-(4-methoxybenzyl)-2H-tetrazol-5-yl) phenyl)benzo[d]thiazole-7-carboxylic acid To a solution of methyl 2-amino-4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)benzo[d]thiazole-7-carboxylate (Step D above, 250 mg, 0.247 mmol) in THF (2.5 ml) was added NaOH (2.47 ml, 4.94 mmol) with stirring at RT. The resulting mixture was warmed to RT and stirred for 4 hours. The pH of the solution was adjusted to 3 with hydrochloric acid (2M). The mixture was filtered, the filtrate was washed with water (5 ml) and dried to give 2-amino-4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)benzo[d]thiazole-7-carboxylic acid. The product was used for the next step directly: LCMS [M+H]⁺: 997.

Step B: tert-butyl 3-((4-(2-amino-7-carbamoylbenzo [d]thiazol-4-yl)-2-(N,N-bis(4-methoxybenzyl)sulfamoyl)-3-(2-(4-methoxybenzyl)-2H-tetrazol-5-yl) phenyl)sulfonyl)azetidine-1-carboxylate To a solution of 2-amino-4-(3-(N,N-bis(4-methoxybenzyl)sulfamoyl)-4-((1-(tert-butoxycarbonyl)azetidin-3-yl) sulfonyl)-2-(2-(4-methoxybenzyl)-2H-tetrazol-5-yl)phenyl) benzo[d]thiazole-7-carboxylic acid (220 mg, 0.221 mmol), HATU (126 mg, 0.331 mmol) and ammonium chloride (47.2 mg, 0.883 mmol) in DMF (4 ml) was added DIEA (0.058 ml, 0.331 mmol) with stirring at 0° C. The reaction mixture was degassed with nitrogen 3 times. The resulting solution was warmed to 0° C. and stirred for 4 hours. The reaction mixture was diluted with water (10 mL) and extracted with ethyl acetate (3×10 mL). The combined organic layers were washed with brine (20 mL), dried over anhydrous sodium sulfate and filtered. The filtrate was concentrated under vacuum to afford an oil. The residue was purified by silica gel column chromatography 12 g, eluting with EtOAc/ petroleum ether (1/1) to afford the title compound: LCMS [M+H]⁺: 996.

Step C: 2-amino-4-(4-(azetidin-3-ylsulfonyl)-3-sulfamoyl-2-(2H-tetrazol-5-yl)phenyl)benzo[d]thiazole-7-carboxamide To a solution of tert-butyl 3-((4-(2-amino-7-carbamoyl-benzo[d]thiazol-4-yl)-2-(N,N-bis(4-methoxybenzyl)sulfamoyl)-3-(2-(4-methoxybenzyl)-2H-tetrazol-5-yl)phenyl) sulfonyl)azetidine-1-carboxylate (140 mg, 0.141 mmol) in DCM (3 ml) was added TFA (1.083 ml, 14.05 mmol) with stirring at room temperature. The resulting solution was warmed to room temperature and stirred for 1 hr. The residue was concentrated to afford 2-amino-4-(4-(azetidin-3-ylsulfonyl)-2-(2-(4-methoxybenzyl)-2H-tetrazol-5-yl)-3-(N-(4-methoxybenzyl)sulfamoyl)phenyl)benzo[d]thiazole-7-carboxamide (0.103 mmol) as an oil. The solution of 2-amino-4-(4-(azetidin-3-ylsulfonyl)-2-(2-(4-methoxybenzyl)-2H-tetrazol-5-yl)-3-(N-(4-methoxybenzyl)sulfamoyl)phenyl) benzo[d]thiazole-7-carboxamide (100 mg, 0.129 mmol) in TFA (3 ml) was stirred at room temperature. The resulting solution was warmed to 80° C. and stirred for 2 hr. The product was purified by Prep-HPLC with the following conditions: Column: XBridge Prep C18 OBD Column 19x 150 mm 5 μM 13 nm; Mobile Phase A: water with 10 mmol NH₄HCO₃, Mobile Phase B: ACN; Flow rate: 15 mL/min; Gradient: 3% B to 23% B in 8 min; 254/220 nm. The collected fractions were combined and concentrated under vacuum to afford the title compound: LCMS [M+H]⁺: 536; ¹H NMR (300 MHz, CD₃OD): δ 8.69 (d, J=6 Hz, 1H), 8.08 (d, J=6 Hz, 1H), 7.81 (d, J=9 Hz, 1H), 7.17 (d, J=7.8 Hz, 1H), 5.34-5.26 (m, 1H), 4.64-4.59 (m, 2H), 4.51-4.43 (m, 2H).

EXAMPLE 40

3-(2-amino-1H-benzo[d]imidazol-5-yl)-6-(azetidin-3-ylsulfonyl)-2-(2H-tetrazol-5-yl)benzenesulfonamide

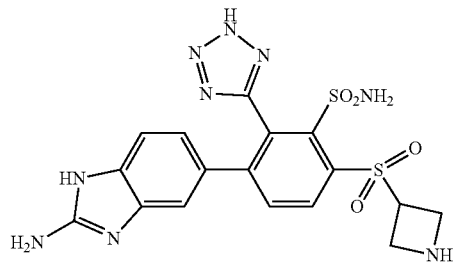 [SMILES: Nc1nc2cc(-c3ccc(S(=O)(=O)C4CNC4)c(S(N)(=O)=O)c3-c3nn[nH]n3)ccc2[nH]1]

Step A: tert-butyl 3-((4-(2-amino-1H-benzo[d]imi-dazol-5-yl)-2-(N,N-bis(4-methoxybenzyl)sulfa-moyl)-3-(2-(4-methoxybenzyl)-2H-tetrazol-5-yl)phenyl)sulfonyl)azetidine-1-carboxylate A solution of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (150 mg, 0.161 mmol), 5-(4,4,5,5-tetramethyl-1,3,2-dioxaborolan-2-yl)-1H-benzo[d]imidazol-2-amine (84 mg, 0.32 mmol), Na$_2$CO$_3$ (51.2 mg, 0.483 mmol) and tetrakis(triphenylphosphine)palladium (0) (37.2 mg, 0.032 mmol) in Dioxane (10 ml) and water (1 ml) was stirred at 80° C. for 2 hr. The reaction mixture was concentrated under vacuum and the residue was purified by silica gel chromatography, eluted with methanol/dichloromethane (1:10) to give the title compound. LCMS [M+H]$^+$: 936; $^1$H NMR (DMSO-d6, 400 MHZ): 8.74 (d, J=8.0 Hz, 1H), 8.64 (brs, 2H), 8.07 (d, J=8.0 Hz, 1H), 7.28-6.75 (m, 15H), 5.16-5.10 (m, 1H), 5.10-5.09 (m, 2H), 4.54-4.51 (m, 2H), 4.36-4.10 (m, 4H), 4.02-3.98 (m, 2H), 3.72 (s, 9H), 1.40 (s, 9H).

Step B: 3-(2-amino-1H-benzo[d]imidazol-5-yl)-6-(azetidin-3-ylsulfonyl)-N-(4-methoxybenzyl)-2-(2-(4-methoxybenzyl)-2H-tetrazol-5-yl)benzenesulfonamide A solution mixture of tert-butyl 3-((4-(2-amino-1H-benzo[d]imidazol-5-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (110 mg, 0.118 mmol) and TFA (1 ml, 12.98 mmol) in Dichloromethane (10 ml) was stirred at room temperature for 1 hr. The resulting mixture was concentrated under vacuum to give the title compound. LCMS [M+1]: 716

Step C: 3-(2-amino-1H-benzo[d]imidazol-5-yl)-6-(azetidin-3-ylsulfonyl)-2-(2H-tetrazol-5-yl)benzenesulfonamide A solution of 3-(2-amino-1H-benzo[d]imidazol-5-yl)-6-(azetidin-3-ylsulfonyl)-N-(4-methoxybenzyl)-2-(2-(4-methoxybenzyl)-2H-tetrazol-5-yl)benzenesulfonamide (80 mg, 0.112 mmol) in TFA (10 ml, 130 mmol) was stirred at 80° C. for 2 hr. The reaction mixture was concentrated under vacuum and the residue was purified by Prep-HPLC with the following conditions: Column: Phenomenex, 150*21.2 mm, 5 μM; Mobile Phase A: water/0.05% NH$_4$HCO$_3$, Mobile Phase B: ACN; Flow rate: 20 mL/min; Gradient: 30-65% B in 8 min; detected at 254 nm to give the title compound. LCMS [M+1]: 476; $^1$H NMR (DMSO-d6, 400 MHZ): 8.30 (d, J=8.4 Hz, 1H), 7.83 (d, J=8.4 Hz, 1H), 6.87 (d, J=8.4 Hz, 1H), 6.70 (s, 1H), 6.47 (d, J=8.0 Hz, 1H), 6.35 (brs, 1H), 5.27-5.19 (m, 1H), 4.20-4.16 (m, 2H), 4.08-4.03 (m, 2H).

EXAMPLE 41 was prepared according to the general procedures described for EXAMPLES 40 starting from REFERENCE EXAMPLE 5

| EX. No. | Structure | Name | LC/MS [M + 1]$^+$ |
|---|---|---|---|
| 41 | 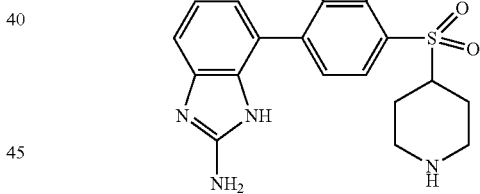 | 3-(2-amino-3H-benzo[d]imidazol-5-yl)-6-(piperidin-4-ylsulfonyl)-2-(2H-tetrazol-5-yl)benzenesulfonamide | 454 |

EXAMPLE 42

3-(2-amino-3H-benzo[d]imidazol-4-yl)-6-(piperidin-4-ylsulfonyl)-2-(2H-tetrazol-5-yl)benzenesulfonamide Step A: tert-butyl 4-((4-(2-amino-1H-benzo[d]imi-dazol-7-yl)-2-(N,N-bis(4-methoxybenzyl)sulfa-moyl)-3-(2-(4-methoxybenzyl)-2H-tetrazol-5-yl)phenyl)sulfonyl)piperidine-1-carboxylate Into a 100 mL RBF was placed a mixture of tert-butyl 4-((2-(N,N-bis(4-methoxybenzyl)sulfamoyl)-4-iodo-3-(2-(4-methoxybenzyl)-2H-tetrazol-5-yl)phenyl)sulfonyl)piperidine-1-carboxylate (150 mg, 0.156 mmol), (2-amino-1H-benzo[d]imidazol-7-yl)boronic acid (49.8 mg, 0.282 mmol), Na$_2$CO$_3$ (49.7 mg, 0.469 mmol) and Pd(Ph$_3$P)$_4$ (36.2 mg, 0.031 mmol) in dioxane/H$_2$O=4/1 (5.0 ml). The reaction mixture was degassed with nitrogen 3 times and stirred for 4 hours at 80° C. and then concentrated under vacuum. The residue was purified by silica gel column chromatography and eluted with methanol/DCM (1:15) to give the title compound. LCMS [M+H]$^+$: 964

Step B: 3-(2-amino-1H-benzo[d]imidazol-7-yl)-6-(piperidin-4-ylsulfonyl)-2-(2H-tetrazol-5-yl)benzenesulfonamide Into a 10 mL RBF was placed a solution of tert-butyl 4-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)piperidine-1-carboxylate (90 mg, 0.093 mmol) dissolved in DCM (2.0 ml). Trifluoroacetic acid (1.0 mL) was added. The reaction was stirred at room temperature for 1 hour. The solvent was removed under vacuum. The residue was dissolved in anisole (1.0 ml, 0.072 mmol) and trifluoroacetic acid (2.0 mL), then the reaction mixture was stirred at 80° C. for 3 hours. The solvent was removed under vacuum and the residue was purified by Prep-HPLC with the following conditions: Column: X Bridge RP18, 19*150 mm, 5 μM; Mobile Phase A: water/0.05% NH$_4$HCO$_3$, Mobile Phase B: ACN; Flow rate: 20 mL/min; Gradient: 5% B to 15% B in 5 min; 254 nm. The collected fractions were combined and concentrated under vacuum to give the title compound: LCMS [M+H]$^+$: 504; $^1$H NMR (300 MHz, DMSO): δ 8.22 (d, J=8.4 Hz, 1H), 7.97 (d, J=8.4 Hz, 1H), 6.98 (d, J=6.9 Hz, 1H), 6.65-6.57 (m, 1H), 6.16 (d, J=7.2 Hz, 1H), 4.53-4.40 (m, 1H), 3.43 (d, J=12.9 Hz, 2H), 3.03-2.93 (m, 2H), 2.19-1.93 (m, 4H).

EXAMPLE 43 was prepared according to the general procedures described for EXAMPLE 42, starting from tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (REFERENCE EXAMPLE 6)

| EX. No. | Structure | Name | LC/MS [M + H]$^+$ |
|---|---|---|---|
| 43 | 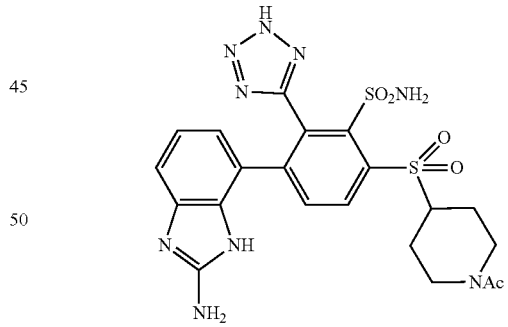 | 3-(2-amino-1H-benzo[d]imidazol-4-yl)-6-(azetidin-3-ylsulfonyl)-2-(2H-tetrazol-5-yl)benzenesulfonamide | 476 |

EXAMPLE 44

6-(1-acetylpiperidin-4-ylsulfonyl)-3-(2-amino-3H-benzo[d]imidazol-4-yl)-2-(2H-tetrazol-5-yl)benzenesulfonamide

Step A: (3-iodo-N-(4-methoxybenzyl)-2-(2-(4-methoxybenzyl)-2H-tetrazol-5-yl)-6-(piperidin-4-ylsulfonyl)benzenesulfonamide Into a 25-mL RBF was placed a solution of tert-butyl 4-((2-(N,N-bis(4-methoxybenzyl)sulfamoyl)-4-iodo-3-(2-(4-methoxybenzyl)-2H-tetrazol-5-yl)phenyl)sulfonyl)piperidine-1-carboxylate (700 mg, 0.730 mmol) in DCM (2 ml). This was followed by the addition of TFA (1.0 ml, 12.98 mmol) with stirring at 0° C. The resulting mixture was stirred at room temperature for 2 hours. The solvent was evaporated under reduced pressure, the residue was washed with aqueous sodium hydrogen carbonate (saturated, 20 mL) and extracted with DCM (3×20 ml). The combined organic layers were washed with brine (1×50 ml) and dried over anhydrous sodium sulfate and filtered. The filtrate was evaporated to afford the title compound: LCMS [M+H]$^+$: 739.1.

Step B: 6-(1-acetylpiperidin-4-ylsulfonyl)-3-iodo-N-(4-methoxybenzyl)-2-(2-(4-methoxybenzyl)-2H-tetrazol-5-yl)benzenesulfonamide Into a 25-mL RBF purged and maintained with an inert atmosphere of argon, was placed a solution of 3-iodo-N-(4-methoxybenzyl)-2-(2-(4-methoxybenzyl)-2H-tetrazol-5-yl)-6-(piperidin-4-ylsulfonyl)benzenesulfonamide (120 mg, 0.130 mmol) in DCM (1 ml). This was followed by the addition of TEA (65.8 mg, 0.650 mmol) and acetic anhydrate (26.5 mg, 0.260 mmol) with stirring at 0° C. The resulting mixture was stirred at room temperature for 1 hour under an atmosphere of argon. The solvent was evaporated under vacuum and the residue was purified by silica gel chromatography, eluting with EtOAc in petroleum ether (3:2) to afford the title compound: LCMS [M+H]$^+$: 781.1; $^1$H NMR (300 MHz, CD$_3$Cl): δ 8.32 (d, J=?, 1H), 7.99 (d, J=8.4 Hz, 1H), 7.33 (d, J=8.7 Hz, 2H), 7.08 (d, J=8.4 Hz, 2H), 6.84-6.73 (m, 4H), 6.54-6.52 (m, 1H), 4.78-4.69 (m, 1H), 4.39-4.31 (m, 1H), 4.05-3.91 (m, 3H), 3.77 (s, 6H), 3.73-3.69 (m, 1H), 3.11-3.01 (m, 1H), 2.53-2.45 (m, 1H), 2.04 (s, 3H).

Step C: 6-(1-acetylpiperidin-4-ylsulfonyl)-3-(2-amino-3H-benzo[d]imidazol-4-yl)-N-(4-methoxybenzyl)-2-(2-(4-methoxybenzyl)-2H-tetrazol-5-yl)benzenesulfonamide Into a 25-mL RBF purged and maintained with an inert atmosphere of argon, was placed a solution of 6-((1-acetylpiperidin-4-yl)sulfonyl)-3-iodo-N-(4-methoxybenzyl)-2-(2-(4-methoxybenzyl)-2H-tetrazol-5-yl)benzenesulfonamide (100 mg, 0.109 mmol), Pd(Ph$_3$P)$_4$ (12.58 mg, 10.89 μmol) and (2-amino-1H-benzo[d]imidazol-7-yl)boronic acid (19.27 mg, 0.109 mmol) in Dioxane (1 ml). This was followed by the addition of sodium carbonate (34.6 mg, 0.327 mmol) in water (0.2 ml) at room temperature. The resulting mixture was stirred at 80° C. for 18 hours under atmosphere of argon. The reaction was cooled to 20° C. and quenched with water (10 ml) and extracted with EA (3×10 ml). The combined organic layers were washed with brine (1×20 ml), dried over anhydrous sodium sulfate and filtered. The filtrate was evaporated under reduced pressure and the residue was purified by Prep-TLC, eluted with DCM/MeOH (10:1) to give the title compound: LCMS [M+H]$^+$: 786.2; $^1$H NMR (300 MHz, CD$_3$Cl): δ 8.36 (d, J=?, 1H), 7.85-7.78 (m, 1H), 7.65-7.63 (m, 1H), 7.15-6.85 (m, 4H), 6.78-6.51 (m, 6H), 4.71-4.61 (m, 1H), 4.38-4.29 (m, 1H), 4.09-3.94 (m, 2H), 3.89-3.84 (m, 1H), 3.76 (s, 6H), 3.75-3.70 (m, 1H), 3.15-3.01 (m, 1H), 2.53-2.45 (m, 1H), 2.04 (s, 3H).

Step D: 6-((1-acetylpiperidin-4-yl)sulfonyl)-3-(2-amino-1H-benzo[d]imidazol-7-yl)-2-(2H-tetrazol-5-yl)benzenesulfonamide Into a 25-mL RBF, was placed a solution of 6-((1-acetylpiperidin-4-yl)sulfonyl)-3-(2-amino-1H-benzo[d]imidazol-7-yl)-N-(4-methoxybenzyl)-2-(2-(4-methoxybenzyl)-2H-tetrazol-5-yl)benzenesulfonamide (40 mg, 0.051 mmol) in TFA. The mixture was stirred at 80° C. for 2 hours. The reaction was cooled to 20° C. and the solvent was evaporated. The residue was purified by Prep-HPLC with the following conditions: Column: Sunfire C18, 19*150 mm, 5 μM; Mobile Phase A: water/0.05% TFA, Mobile Phase B: ACN; Flow rate: 20 mL/min; Gradient: 5-30% B in 10 min; 254 nm. The collected fractions were combined and concentrated under reduced pressure to afford the title compound: LCMS [M+H]$^+$: 546.1; $^1$H NMR (300 MHz, DMSO): δ 8.27 (d, 1H), 7.98 (d, J=8.1 Hz, 1H), 7.48 (br, 2H), 7.19 (br, 2H), 7.10 (d, J=7.5 Hz, 1H), 6.79 (t, J=7.5 Hz, 1H), 6.36 (d, J=7.8 Hz, 1H), 4.55-4.51 (m, 1H), 4.47-4.38 (m, 1H), 4.01-3.96 (m, 1H), 3.17-3.08 (m, 1H), 2.73-2.64 (m, 1H), 2.04 (s, 3H), 1.97-1.84 (m, 1H), 1.80-1.73 (m, 1H), 1.65-1.58 (m, 1H).

EXAMPLES 45-46 were synthesized using the general procedure described for EXAMPLE 44, substituting methane sulfonyl chloride and ethyl chloroformate as the sulfonylating and acylating reagents.

| EX. NO. | Structure | Name | LC/MS [M + H]$^+$ |
|---|---|---|---|
| 45 | (structure) | 3-(2-amino-3H-benzo[d]imidazol-4-yl)-6-(1-(methylsulfonyl)piperidin-4-ylsulfonyl)-2-(2H-tetrazol-5-yl)benzenesulfonamide | 582 |

| EX. NO. | Structure | Name | LC/MS [M + H]+ |
|---|---|---|---|
| 46 | 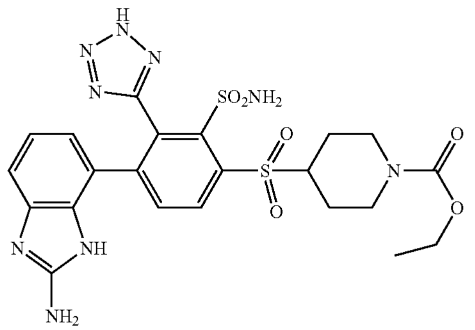 [SMILES: CCOC(=O)N1CCC(S(=O)(=O)c2ccc(-c3cccc4nc(N)[nH]c34)c(-c3nn[nH]n3)c2S(N)(=O)=O)CC1] | ethyl 4-(4-(2-amino-3H-benzo[d]imidazol-4-yl)-2-sulfamoyl-3-(2H-tetrazol-5-yl)phenylsulfonyl)piperidine-1-carboxylate | 576 |

EXAMPLE 47

3-(2-amino-3H-benzo[d]imidazol-4-yl)-6-(1-(2-hydroxyethyl)piperidin-4-ylsulfonyl)-2-(2H-tetrazol-5-yl)benzenesulfonamide

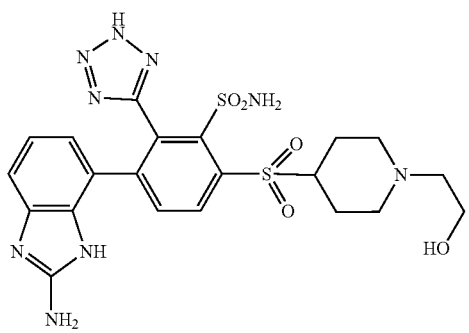 [SMILES: Nc1nc2cccc(-c3ccc(S(=O)(=O)C4CCN(CCO)CC4)c(S(N)(=O)=O)c3-c3nn[nH]n3)c2[nH]1]

Step A: 3-iodo-N-(4-methoxybenzyl)-2-(2-(4-methoxybenzyl)-2H-tetrazol-5-yl)-6-(piperidin-4-ylsulfonyl)benzenesulfonamide tert-butyl 4-((2-(N,N-bis(4-methoxybenzyl)sulfamoyl)-4-iodo-3-(2-(4-methoxybenzyl)-2H-tetrazol-5-yl)phenyl)sulfonyl)piperidine-1-carboxylate (400 mg, 0.417 mmol) was dissolved in DCM (3.0 ml), then TFA (1.5 mL) was added. The mixture was stirred for 1.5 hours at room temperature. The solvent was removed under vacuum. The residue was diluted with DCM (6.0 ml) and the pH of the resulting solution was adjusted to 7 with saturated aqueous sodium carbonate. The resulting mixture was extracted with DCM (3×10 mL). The combined organic layers were washed with brine (3×5 mL), dried over anhydrous sodium sulfate and filtered. The filtrate was concentrated under vacuum to give the title compound. LCMS [M+H]+: 739.

Step B: 6-((1-(2-hydroxyethyl)piperidin-4-yl)sulfonyl)-3-iodo-N-(4-methoxybenzyl)-2-(2-(4-methoxybenzyl)-2H-tetrazol-5-yl)benzenesulfonamide Into a 25 mL flask was placed 3-iodo-N-(4-methoxybenzyl)-2-(2-(4-methoxybenzyl)-2H-tetrazol-5-yl)-6-(piperidin-4-ylsulfonyl)benzenesulfonamide (150 mg, 0.203 mmol), 2-bromoethanol (50.8 mg, 0.406 mmol) and $K_2CO_3$ (84 mg, 0.609 mmol) in DMF (2.0 ml). The mixture was stirred for 18 hours at room temperature. The reaction mixture was quenched with water (5 mL), diluted with water (15 mL) and extracted with ethyl acetate (3×15 mL). The combined organic layers were washed with water (2×10 mL) and then brine (2×10 mL), dried over anhydrous sodium sulfate and filtered. The filtrate was concentrated under vacuum. The residue was purified by silica gel column chromatography, eluted with methanol/dichloromethane (1/15). The combined organic fractions were concentrated under reduced pressure to give the title compound. LCMS [M+H]+: 783;

Step C: 3-(2-amino-1H-benzo[d]imidazol-7-yl)-6-((1-(2-hydroxyethyl)piperidin-4-yl)sulfonyl)-N-(4-methoxybenzyl)-2-(2-(4-methoxybenzyl)-2H-tetrazol-5-yl)benzenesulfonamide Into a 10 mL flask was placed a mixture of 6-((1-(2-hydroxyethyl)piperidin-4-yl)sulfonyl)-3-iodo-N-(4-methoxybenzyl)-2-(2-(4-methoxybenzyl)-2H-tetrazol-5-yl)benzenesulfonamide (110 mg, 0.141 mmol), (2-amino-1H-benzo[d]imidazol-7-yl)boronic acid (62.2 mg, 0.351 mmol), $Pd(Ph_3P)_4$ (24.36 mg, 0.021 mmol) and $Na_2CO_3$ (44.7 mg, 0.422 mmol) in Dioxane/$H_2O$=4/1 (4.0 ml). The reaction mixture was degassed with nitrogen 3 times and stirred overnight at 80° C. The reaction mixture was diluted with water (3 mL) and extracted with DCM (3×15 mL). The combined organic layers were washed with brine (3×4 mL), dried over anhydrous sodium sulfate and filtered. The filtrate was concentrated under vacuum. The residue was purified by silica gel column chromatography, eluting with methanol/dichloromethane (1/10). The combined organic fractions were concentrated under reduced pressure to give the title compound. LCMS [M+H]+: 788.

Step D: 3-(2-amino-1H-benzo[d]imidazol-7-yl)-6-((1-(2-hydroxyethyl)piperidin-4-yl)sulfonyl)-2-(2H-tetrazol-5-yl)benzenesulfonamide Into a 10 mL flask was placed 3-(2-amino-1H-benzo[d]imidazol-7-yl)-6-((1-(2-hydroxyethyl)piperidin-4-yl)sulfonyl)-N-(4-methoxybenzyl)-2-(2-(4-methoxybenzyl)-2H-tetrazol-5-yl)benzenesulfonamide (60 mg, 0.076 mmol) and TFA (3.0 mL, 38.9 mmol). The reaction mixture was stirred at 80° C. for 2 hours. The solvent was removed under vacuum. The product was purified by Prep-HPLC with the following conditions: Column: Sunfire, 19×250 mm, 5 μM; Mobile Phase A: water/0.05% NH$_4$HCO$_3$, Mobile Phase B: ACN; Flow rate: 20 mL/min; Gradient: 30-64% B in 8 min; 254 nm. The collected fractions were combined and concentrated under vacuum to give the title compound. LCMS [M+H]$^+$: 548; $^1$H NMR (300 MHz, DMSO-D$_2$O): δ 8.25 (d, J=8.4 Hz, 1H), 7.95 (d, J=8.1 Hz, 1H), 7.06 (d, J=7.5 Hz, 1H), 6.74-6.67 (m, 1H), 6.28 (d, J=7.2 Hz, 1H), 4.41-4.28 (m, 1H), 3.78-3.63 (m, 2H), 3.40-3.37 (m, 2 H), 2.93-2.82 (m, 2H), 2.71-2.50 (m, 2H), 2.15-1.96 (m, 4H).

EXAMPLE 48

3-(2-amino-3H-benzo[d]imidazol-4-yl)-6-(1-(2-aminoethyl)piperidin-4-ylsulfonyl)-2-(2H-tetrazol-5-yl)benzenesulfonamide

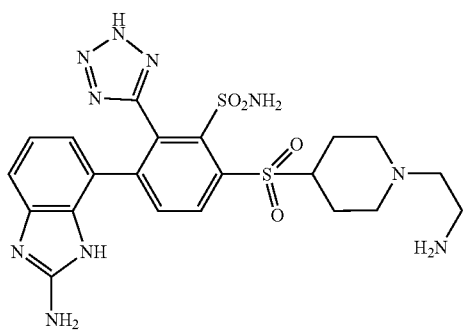 [SMILES: NCCN1CCC(S(=O)(=O)c2ccc(-c3cccc4nc(N)[nH]c34)c(-c3nn[nH]n3)c2S(N)(=O)=O)CC1]

Step A: tert-butyl 2-(4-(4-iodo-3-(2-(4-methoxybenzyl)-2H-tetrazol-5-yl)-2-(N-(4-methoxybenzyl)sulfamoyl)phenylsulfonyl)piperidin-1-yl)ethylcarbamate Into a 25 mL flask was placed 3-iodo-N-(4-methoxybenzyl)-2-(2-(4-methoxybenzyl)-2H-tetrazol-5-yl)-6-(piperidin-4-ylsulfonyl)benzenesulfonamide (160 mg, 0.217 mmol), tert-butyl (2-bromoethyl)carbamate (243 mg, 1.083 mmol) and triethylamine (110 mg, 1.083 mmol) in DMF (2.0 ml). The reaction mixture was stirred at room temperature for 24 hours and then quenched with water (10 mL) and extracted with ethyl acetate (3×15 mL). The combined organic layers were washed with water (2×10 mL) and brine (2×10 mL), dried over anhydrous sodium sulfate and filtered. The filtrate was concentrated under vacuum. The residue was purified by silica gel column chromatography, eluted with methanol/dichloromethane (1/10). The combined organic fractions were concentrated under reduced pressure to give the title compound. LCMS [M+H]$^+$: 882;

Step B: tert-butyl (2-(4-((4-(2-amino-1H-benzo[d]imidazol-7-yl)-3-(2-(4-methoxybenzyl)-2H-tetrazol-5-yl)-2-(N-(4-methoxybenzyl)sulfamoyl)phenyl)sulfonyl)piperidin-1-yl)ethyl)carbamate Into a 10 mL flask was placed tert-butyl (2-(4-((4-iodo-3-(2-(4-methoxybenzyl)-2H-tetrazol-5-yl)-2-(N-(4-methoxybenzyl)sulfamoyl)phenyl)sulfonyl)piperidin-1-yl)ethyl)carbamate (145 mg, 0.164 mmol), (2-amino-1H-benzo[d]imidazol-7-yl)boronic acid (72.8 mg, 0.411 mmol), Pd(Ph$_3$P)$_4$ (28.5 mg, 0.025 mmol) and Na$_2$CO$_3$ (52.3 mg, 0.493 mmol) in Dioxane/H$_2$O=4/1 (3.0 ml). The reaction mixture was degassed with nitrogen 3 times and stirred overnight at 80° C. The reaction mixture was diluted with water (3 mL) and extracted with DCM (3×15 mL). The combined organic layers were washed with brine (3×4 mL), dried over anhydrous sodium sulfate and filtered. The filtrate was concentrated under vacuum. The residue was purified by silica gel column chromatography and eluted with methanol/dichloromethane (1/10). The combined organic fractions were concentrated under reduced pressure to give the title compound as a solid. LCMS [M+H]$^+$: 887.

Step C: 3-(2-amino-1H-benzo[d]imidazol-7-yl)-6-((1-(2-aminoethyl)piperidin-4-yl)sulfonyl)-2-(2H-tetrazol-5-yl)benzenesulfonamide Into a 10 mL flask was placed tert-butyl (2-(4-((4-(2-amino-1H-benzo[d]imidazol-7-yl)-3-(2-(4-methoxybenzyl)-2H-tetrazol-5-yl)-2-(N-(4-methoxybenzyl)sulfamoyl)phenyl)sulfonyl)piperidin-1-yl)ethyl)carbamate (130 mg, 0.147 mmol) in DCM (2.0 mL). TFA (1.0 mL) was added at 0° C. The mixture was stirred for 2 hours at room temperature. The solvent was removed under vacuum. The residue was dissolved in TFA (3.0 mL) and was stirred for 2 hr at 80° C. The solvent was removed under vacuum. The product was purified by Prep-HPLC with the following conditions: Column: X Bridge C18, 19×150 mm, 5 μM; Mobile Phase A: water/0.05% NH$_4$HCO$_3$, Mobile Phase B: ACN; Flow rate: 20 mL/min; Gradient: 20-40% B in 8 min; 254 nm. The collected fractions were combined and concentrated under vacuum to give the title compound as a solid. LCMS [M+H]$^+$: 547; $^1$H NMR (300 MHz, CD$_3$OD): δ 8.45 (d, J=8.4 Hz, 1H), 7.94 (d, J=8.1 Hz, 1H), 7.22 (d, J=7.2 Hz, 1H), 7.09-7.06 (m, 1H), 6.80 (d, J=6.9 Hz, 1H), 4.35-4.21 (m, 1H), 3.13-2.99 (m, 4H), 2.68-2.57 (m, 2 H), 2.23-1.96 (m, 6H).

EXAMPLE 49

4-(4-(2-amino-3H-benzo[d]imidazol-4-yl)-2-sulfamoyl-3-(2H-tetrazol-5-yl)phenylsulfonyl)piperidine-1-carboxamide

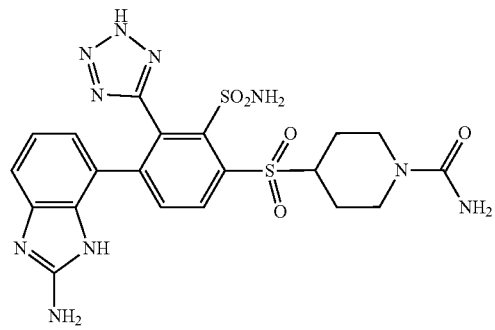 [SMILES: NC(=O)N1CCC(S(=O)(=O)c2ccc(-c3cccc4nc(N)[nH]c34)c(-c3nn[nH]n3)c2S(N)(=O)=O)CC1]

Step A: 4-((4-iodo-3-(2-(4-methoxybenzyl)-2H-tetrazol-5-yl)-2-(N-(4-methoxybenzyl)sulfamoyl)phenyl)sulfonyl)piperidine-1-carboxamide Into a 25 mL flask was placed 3-iodo-N-(4-methoxybenzyl)-2-(2-(4-methoxybenzyl)-2H-tetrazol-5-yl)-6-(piperidin-4-ylsulfonyl)benzenesulfonamide (200 mg, 0.271 mmol), TEA (0.189 ml, 1.354 mmol) and DCM (2.0 ml). Then isocyanatotrimethylsilane (312 mg, 2.71 mmol) was added and the mixture was stirred for 2 hours at room temperature. The solvent was removed under vacuum. The residue was purified by silica gel column chromatography, eluting with methanol/dichloromethane (1/15). The combined organic fractions were concentrated under reduced pressure to give the title compound as a solid. LCMS [M+H]$^+$: 782

Step B: 4-((4-(2-amino-1H-benzo[d]imidazol-7-yl)-3-(2-(4-methoxybenzyl)-2H-tetrazol-5-yl)-2-(N-(4-methoxybenzyl)sulfamoyl)phenyl)sulfonyl)piperidine-1-carboxamide Into a 10 mL flask was placed 4-((4-iodo-3-(2-(4-methoxybenzyl)-2H-tetrazol-5-yl)-2-(N-(4-methoxybenzyl)sulfamoyl)phenyl)sulfonyl)piperidine-1-carboxamide (120 mg, 0.154 mmol), (2-amino-1H-benzo[d]imidazol-7-yl)boronic acid (67.9 mg, 0.384 mmol), Pd(Ph$_3$P)$_4$ (26.6 mg, 0.023 mmol) and Na$_2$CO$_3$ (48.8 mg, 0.461 mmol) in dioxane/H$_2$O (4:1) (3.0 ml). The reaction mixture was degassed with nitrogen 3 times and stirred overnight at 80° C. The reaction mixture was diluted with water (3 mL) and extracted with DCM (3×15 mL). The combined organic layers were washed with brine (3×4 mL), dried over anhydrous sodium sulfate and filtered. The filtrate was concentrated under vacuum. The residue was purified by silica gel column chromatography, eluting with methanol/DCM (1/10). The combined organic fractions were concentrated under reduced pressure to give the title compound. LCMS [M+H]$^+$: 787.

Step C: 4-((4-(2-amino-1H-benzo[d]imidazol-7-yl)-2-sulfamoyl-3-(2H-tetrazol-5-yl)phenyl)sulfonyl)piperidine-1-carboxamide Into a 10 mL RBF was placed 4-((4-(2-amino-1H-benzo[d]imidazol-7-yl)-3-(2-(4-methoxybenzyl)-2H-tetrazol-5-yl)-2-(N-(4-methoxybenzyl)sulfamoyl)phenyl)sulfonyl)piperidine-1-carboxamide (60 mg, 0.076 mmol) and TFA (2.0 mL, 26.0 mmol). The reaction mixture was stirred at 80° C. for 2 hours. The solvent was removed under vacuum. The residue was purified by Prep-HPLC with the following conditions: Column: Sunfire, 19×250 mm, 5 µM; Mobile Phase A: water/0.05% TFA, Mobile Phase B: ACN; Flow rate: 20 mL/min; Gradient: 53-63% B in 8 min; 254 nm. The collected fractions were combined and concentrated under vacuum to give the title compound. LCMS [M+H]$^+$: 547; $^1$H NMR (300 MHz, DMSO-D$_2$O): δ 8.28 (d, J=8.4 Hz, 1H), 7.91 (d, J=8.1 Hz, 1H), 7.14 (d, J=7.8 Hz, 1H), 6.92-6.77 (m, 1H), 6.41 (d, J=7.8 Hz, 1H), 4.46-4.36 (m, 1H), 4.13-4.05 (m, 2H), 2.88-2.71 (m, 2 H), 1.99-1.80 (m, 2H), 1.75-1.56 (m, 2H).

EXAMPLE 50

2-(3-(4-(2-amino-1H-benzo[d]imidazol-4-yl)-2-sulfamoyl-3-(2H-tetrazol-5-yl)phenylsulfonyl)azetidin-1-yl)acetamide

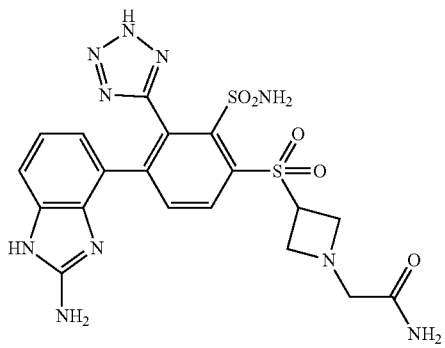 [SMILES: NC(=O)CN1CC(S(=O)(=O)c2ccc(-c3cccc4[nH]c(N)nc34)c(-c3nn[nH]n3)c2S(N)(=O)=O)C1]

Step A: 6-(azetidin-3-ylsulfonyl)-3-iodo-N-(4-methoxybenzyl)-2-(2-(4-methoxybenzyl)-2H-tetrazol-5-yl)benzenesulfonamide 6-(Azetidin-3-ylsulfonyl)-3-iodo-N-(4-methoxybenzyl)-2-(2-(4-methoxybenzyl)-2H-tetrazol-5-yl)benzenesulfonamide was prepared in a similar fashion to that of Step A in Example 47 starting from tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate.

Step B: 2-(3-((4-iodo-3-(2-(4-methoxybenzyl)-2H-tetrazol-5-yl)-2-(N-(4-methoxybenzyl)sulfamoyl) phenyl) sulfonyl)azetidin-1-yl)acetamide A solution of 6-(azetidin-3-ylsulfonyl)-3-iodo-N-(4-methoxybenzyl)-2-(2-(4-methoxybenzyl)-2H-tetrazol-5-yl) benzenesulfonamide (250 mg, 0.352 mmol), 2-chloroacetamide (329 mg, 3.52 mmol), KI (292 mg, 1.759 mmol) and TEA (0.490 ml, 3.52 mmol) in DMF (7 ml) was stirred at 25° C. for 48 hours. The reaction mixture was quenched with water (20 mL), diluted with water (40 mL) and extracted with ethyl acetate (3×30 mL). The combined organic layers were washed with water (2×10 mL) and brine (2×10 mL), dried over anhydrous sodium sulfate and filtered. The filtrate was concentrated under vacuum to give crude product. The residue was purified by silica gel chromatography, eluted with methanol/DCM (1:10). The combined organic fractions were concentrated under reduced pressure to give the title compound. LCMS [M+H]$^+$: 768; $^1$H NMR (CDCl$_3$, 400 MHZ): 8.36 (d, J=8.4 Hz, 1H), 8.10 (d, J=8.4 Hz, 1H), 7.35-7.32 (m, 2H), 7.20-7.05 (m, 2H), 6.85-6.76 (m, 4H), 5.03-5.00 (m, 1H), 3.98-3.65 (m, 8H), 3.00 (s, 2H).

Step C: 2-(3-(4-(2-amino-1H-benzo[d]imidazol-4-yl)-3-(2-(4-methoxybenzyl)-2H-tetrazol-5-yl)-2-(N-(4-methoxybenzyl)sulfamoyl)phenylsulfonyl)azetidin-1-yl)acetamide A solution of 2-(3-((4-iodo-3-(2-(4-methoxybenzyl)-2H-tetrazol-5-yl)-2-(N-(4-methoxybenzyl)sulfamoyl)phenyl)sulfonyl)azetidin-1-yl)acetamide (140 mg, 0.182 mmol), (2-amino-1H-benzo[d]imidazol-4-yl)boronic acid (64.6 mg, 0.365 mmol), Na₂CO₃ (38.7 mg, 0.365 mmol) and Pd(Ph₃P)₄ (42.2 mg, 0.036 mmol) in 1,4-dioxane (1 ml) and water (0.25 ml) was stirred at 80° C. for 2 hours. The reaction mixture was concentrated under vacuum to give crude product. The residue was purified by silica gel Isolute Flash Si; 20 g prepacked column chromatography, eluting with methanol/dichloromethane (20/80). The combined organic fractions were concentrated under reduced pressure to give the title compound. LCMS [M+H]⁺: 773

Step D: 2-(3-(4-(2-amino-1H-benzo[d]imidazol-4-yl)-2-sulfamoyl-3-(2H-tetrazol-5-yl)phenylsulfonyl)azetidin-1-yl)acetamide A solution of 2-(3-((4-(2-amino-1H-benzo[d]imidazol-4-yl)-3-(2-(4-methoxybenzyl)-2H-tetrazol-5-yl)-2-(N-(4-methoxybenzyl)sulfamoyl)phenyl)sulfonyl)azetidin-1-yl)acetamide (140 mg, 0.181 mmol) in TFA (13.96 µl, 0.181 mmol) was stirred at 80° C. for 2 hours. The reaction mixture was concentrated under vacuum to give crude product. The product was purified by Prep-HPLC with the following conditions: Column: X Bridge C18, 19*150 mm, 5 µM; Mobile Phase A: water/0.05% NH₄HCO₃, Mobile Phase B: ACN; Flow rate: 20 mL/min; Gradient: 10-50% B in 10 min; 254 nm. The collected fractions were combined and concentrated under vacuum to give the title compound. LCMS [M+H]⁺: 533; ¹H NMR (DMSO-d6, 400 MHZ): 8.36 (d, J=8.4 Hz, 1H), 7.98 (d, J=8.4 Hz, 1H), 7.50 (brs, 2H), 7.20-7.00 (m, 4H), 6.78 (brs, 2H), 6.80-6.75 (m, 1H), 6.22 (d, J=7.6 Hz, 1H), 5.04-5.00 (m, 1H), 3.75-3.60 (m, 4H), 3.10 (s, 2H).

Using the same general procedure as EXAMPLES 44-50, the following compounds were synthesized, starting from 6-(azetidin-3-ylsulfonyl)-3-iodo-N-(4-methoxybenzyl)-2-(2-(4-methoxybenzyl)-2H-tetraol-5-yl)benzenesulfonamide

| Ex. No. | Structure | Name | Calc'd Mass [M + H]⁺ | LC/MS m/e [M + H]⁺ |
|---|---|---|---|---|
| 51 | 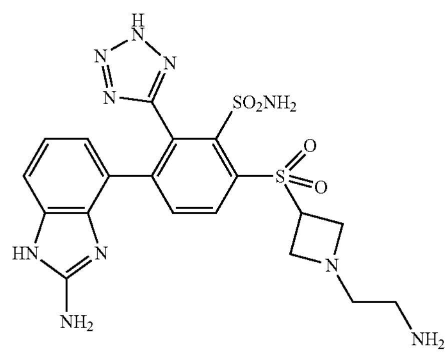 [SMILES: NCCN1CC(S(=O)(=O)c2ccc(-c3cccc4[nH]c(N)nc34)c(-c3nn[nH]n3)c2S(N)(=O)=O)C1] | 3-(2-amino-1H-benzo[d]imidazol-4-yl)-6-(1-(2-aminoethyl)azetidin-3-ylsulfonyl)-2-(2H-tetrazol-5-yl)benzenesulfonamide | 518 | 519 |
| 52 | 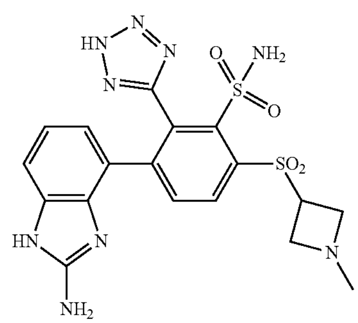 [SMILES: CN1CC(S(=O)(=O)c2ccc(-c3cccc4[nH]c(N)nc34)c(-c3nn[nH]n3)c2S(N)(=O)=O)C1] | 3-(2-amino-1H-benzo[d]imidazol-4-yl)-6-(1-methylazetidin-3-ylsulfonyl)-2-(2H-tetrazol-5-yl)benzenesulfonamide | 489 | 490 |
| 53 | 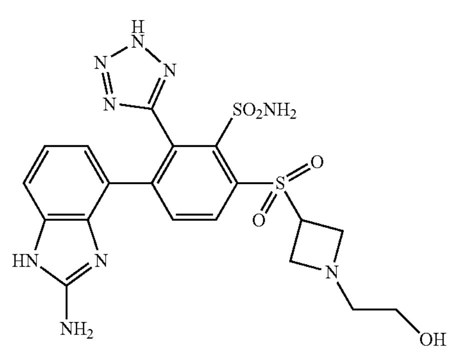 [SMILES: Nc1nc2c(-c3ccc(S(=O)(=O)C4CN(CCO)C4)c(S(N)(=O)=O)c3-c3nn[nH]n3)cccc2[nH]1] | 3-(2-amino-1H-benzo[d]imidazol-4-yl)-6-(1-(2-hydroxyethyl)azetidin-3-ylsulfonyl)-2-(2H-tetrazol-5-yl)benzenesulfonamide | 519 | 520 |

-continued

| Ex. No. | Structure | Name | Calc'd Mass [M + H]⁺ | LC/MS m/e [M + H]⁺ |
|---|---|---|---|---|
| 54 | 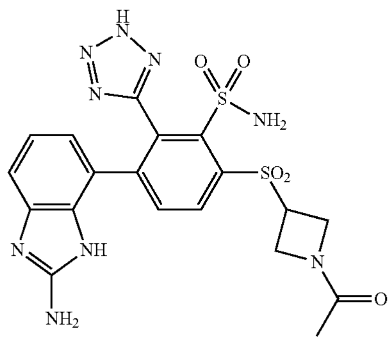 [SMILES: CC(=O)N1CC(S(=O)(=O)c2ccc(-c3cccc4nc(N)[nH]c34)c(-c3nn[nH]n3)c2S(N)(=O)=O)C1] | 6-(1-acetylazetidin-3-ylsulfonyl)-3-(2-amino-3H-benzo[d]imidazol-4-yl)-2-(2H-tetrazol-5-yl)benzenesulfonamide | 517 | 518 |
| 55 | 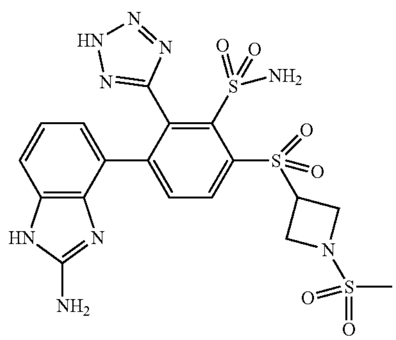 [SMILES: CS(=O)(=O)N1CC(S(=O)(=O)c2ccc(-c3cccc4[nH]c(N)nc34)c(-c3nn[nH]n3)c2S(N)(=O)=O)C1] | 3-(2-amino-1H-benzo[d]imidazol-4-yl)-6-(1-(methylsulfonyl)azetidin-3-ylsulfonyl)-2-(2H-tetrazol-5-yl)benzenesulfonamide | 553 | 554 |
| 56 | 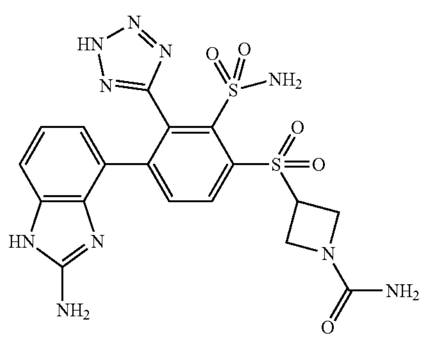 [SMILES: NC(=O)N1CC(S(=O)(=O)c2ccc(-c3cccc4[nH]c(N)nc34)c(-c3nn[nH]n3)c2S(N)(=O)=O)C1] | 3-(4-(2-amino-1H-benzo[d]imidazol-4-yl)-2-sulfamoyl-3-(2H-tetrazol-5-yl)phenylsulfonyl)azetidine-1-carboxamide | 518 | 519 |
| 57 | 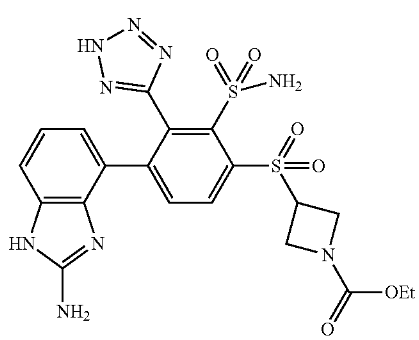 [SMILES: CCOC(=O)N1CC(S(=O)(=O)c2ccc(-c3cccc4[nH]c(N)nc34)c(-c3nn[nH]n3)c2S(N)(=O)=O)C1] | ethyl 3-(4-(2-amino-1H-benzo[d]imidazol-4-yl)-2-sulfamoyl-3-(2H-tetrazol-5-yl)phenylsulfonyl)azetidine-1-carboxylate | 547 | 548 |

EXAMPLE 58

6-(Azetidin-3-yl sulfonyl)-3-(imidazo[1,2-a]pyridin-8-yl)-2-(1H-tetrazol-5-yl)benzenesulfonamide

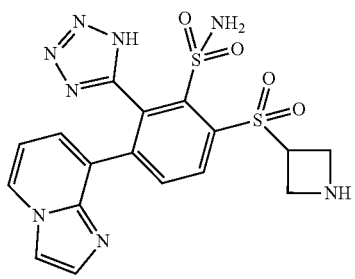 [SMILES: NS(=O)(=O)c1c(S(=O)(=O)C2CNC2)ccc(-c2cccn3ccnc23)c1-c1nnn[nH]1]

Step A: tert-Butyl 3-((2-(N,N-bis(4-methoxybenzyl)sulfamoyl)-4-(imidazo[1,2-a]pyridin-8-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-8-yl)-3-(2-(4-methoxybenzyl)-2H-tetrazol-5-yl)phenyl)sulfonyl)azetidine-1-carboxylate In a reaction vessel 8-bromoimidazo[1,2-a]pyridine (40 mg, 0.203 mmol) and 4,4,4',4',5,5,5',5'-octamethyl-2,2'-bi(1,3,2-dioxaborolane) (155 mg, 0.609 mmol) were combined, followed by addition of potassium acetate (59.8 mg, 0.609 mmol) and PCy3Pd G2 (11.99 mg, 0.020 mmol). Then dioxane (1015 µl) was added. This mixture was degassed and then heated at 80° C. for 16 hours. After the reaction was cooled to RT, tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (189 mg, 0.203 mmol), PdCl2(dppf)-CH2Cl2Adduct (16.6 mg, 0.020 mmol) and potassium carbonate (168 mg, 1.22 mmol) dissolved in 0.3 mL of water were added. The reaction mixture was degassed and then heated at 60° C. for 16 hours. LC-MS showed the formation of the desired product along with deboronation product. The reaction was cooled and filtered, and the filtrates were concentrated and purified by column chromatography (100% hexane to 100% EtOAc/Hexane) to give tert-butyl 3-((2-(N,N-bis(4-methoxybenzyl)sulfamoyl)-4-(imidazo[1,2-a]pyridin-8-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-8-yl)-3-(2-(4-methoxybenzyl)-2H-tetrazol-5-yl)phenyl)sulfonyl)azetidine-1-carboxylate. LC/MS [M+H]$^+$: 921.8.

Step B: 6-(Azetidin-3-ylsulfonyl)-3-(imidazo[1,2-a]pyridin-8-yl)-2-(1H-tetrazol-5-yl)benzenesulfonamide tert-Butyl 3-((2-(N,N-bis(4-methoxybenzyl)sulfamoyl)-4-(imidazo[1,2-a]pyridin-8-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-8-yl)-3-(2-(4-methoxybenzyl)-2H-tetrazol-5-yl)phenyl)sulfonyl)azetidine-1-carboxylate (36 mg, 0.039 mmol) was stirred at room temperature in TFA/DCM (1/1, 2 mL) for 1 hour. LC-MS showed the Boc and one PMB group were removed. The reaction was concentrated, co-evaporated with toluene 3×. The resulting compound was dissolved in TFA (2 mL) and heated at 60° C. for 2 hours. The reaction was concentrated and purified with reverse phase HPLC (0-20% CH3CN/water with 0.05% TFA). The correct fractions were combined, concentrated and lyophilized to give 6-(azetidin-3-ylsulfonyl)-3-(imidazo[1,2-a]pyridin-8-yl)-2-(1H-tetrazol-5-yl)benzenesulfonamide. LC/MS [M+H]$^+$: 461.4

EXAMPLES 59-60 were prepared in an analogous fashion as described for EXAMPLE 58, starting from tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate and using boronic acids or boronic esters that are commercially available, known, or prepared as described herein.

| Ex. No. | Structure | Name | Fragment SM | LC/MS m/e [M + H]$^+$ |
|---|---|---|---|---|
| 59 | 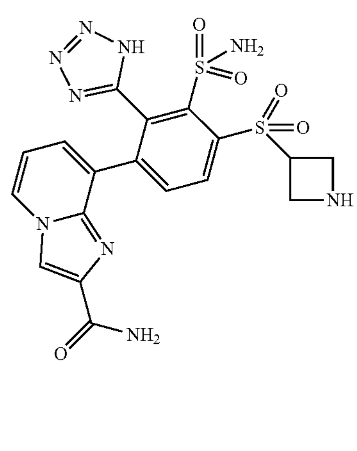 [SMILES: NC(=O)c1cn2cccc(-c3ccc(S(=O)(=O)C4CNC4)c(S(N)(=O)=O)c3-c3nnn[nH]3)c2n1] | 8-(4-(azetidin-3-ylsulfonyl)-3-sulfamoyl-2-(1H-tetrazol-5-yl)phenyl)imidazo[1,2-a]pyridine-2-carboxamide | Intermediate 1, 4 | 504.5 |

| Ex. No. | Structure | Name | Fragment SM | LC/MS m/e [M + H]+ |
|---|---|---|---|---|
| 60 | 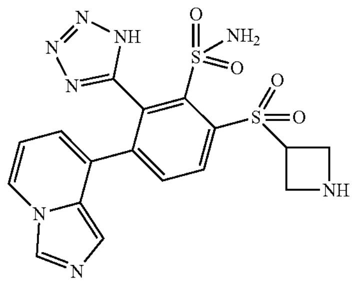 [SMILES: NS(=O)(=O)c1c(S(=O)(=O)C2CNC2)ccc(-c2cccn3cncc23)c1-c1nnn[nH]1] | 6-(azetidin-3-ylsulfonyl)-3-(imidazo[1,5-a]pyridin-8-yl)-2-(1H-tetrazol-5-yl)benzenesulfonamide | Intermediate 1, commercial Bromide | 461.4 |

EXAMPLE 61

8-(4-(Azetidin-3-ylsulfonyl)-3-sulfamoyl-2-(1H-tetrazol-5-yl)phenyl)imidazo[1,2-a]pyridine-2-carboxylic Acid

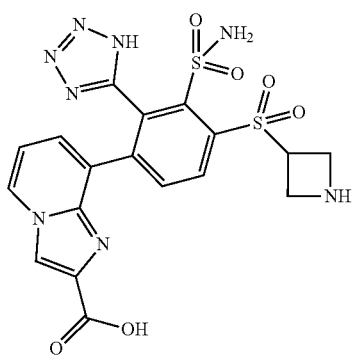 [SMILES: NS(=O)(=O)c1c(S(=O)(=O)C2CNC2)ccc(-c2cccn3cc(C(=O)O)nc23)c1-c1nnn[nH]1]

Step A: Ethyl 8-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)imidazo[1,2-a]pyridine-2-carboxylate and ethyl 8-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)imidazo[1,2-a]pyridine-2-carboxylate Ethyl 8-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)imidazo[1,2-a]pyridine-2-carboxylate and ethyl 8-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)imidazo[1,2-a]pyridine-2-carboxylate was prepared in a similar fashion to that of tert-Butyl 3-((2-(N,N-bis(4-methoxybenzyl)sulfamoyl)-4-(imidazo[1,2-a]pyridin-8-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-8-yl)-3-(2-(4-methoxybenzyl)-2H-tetrazol-5-yl)phenyl)sulfonyl)azetidine-1-carboxylate (StepA) from tert-butyl 3-((2-(N,N-bis(4-methoxybenzyl)sulfamoyl)-4-iodo-3-(1-(4-methoxybenzyl)-1H-tetrazol-5-yl)phenyl)sulfonyl) azetidine-1-carboxylate and tert-butyl 3-((2-(N,N-bis(4-methoxybenzyl)sulfamoyl)-4-iodo-3-(2-(4-methoxybenzyl)-2H-tetrazol-5-yl)phenyl)sulfonyl) azetidine-1-carboxylateyl and 8-bromoimidazo[1,2-a]pyridine-2-carboxylate. LC/MS [M+H]+: 993.7.

Step B: 8-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)imidazo[1,2-a]pyridine-2-carboxylic Acid and 8-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)imidazo[1,2-a]pyridine-2-carboxylic Acid Ethyl 8-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)imidazo[1,2-a]pyridine-2-carboxylate and ethyl 8-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)imidazo[1,2-a]pyridine-2-carboxylate (81 mg, 0.082 mmol) were dissolved in THF (1 mL) and water (0.5 mL). LiOH (31 mg, 1.294 mmol) was added. The mixture was stirred at room temperature for 12 hours. LC-MS showed the formation of the desired product. The reaction mixture was diluted with EtOAc and acidified to pH 4 by adding 1M HCl aqueous solution. The EtOAc layer was separated, washed with brine, filtered through a pad of anhydrous Na$_2$SO$_4$, and concentrated to give crude 8-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)imidazo[1,2-a]pyridine-2-carboxylic acid and 8-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)imidazo[1,2-a]pyridine-2-carboxylic acid, which was used directly in the next step. LC/MS [M+H]+: 965.4.

Step C: 8-(4-(Azetidin-3-ylsulfonyl)-3-sulfamoyl-2-(1H-tetrazol-5-yl)phenyl)imidazo[1,2-a]pyridine-2-carboxylic Acid 8-(4-(Azetidin-3-ylsulfonyl)-3-sulfamoyl-2-(1H-tetrazol-5-yl)phenyl)imidazo[1,2-a]pyridine-2-carboxylic acid was prepared in a similar fashion to the synthesis of 6-(azetidin-3-ylsulfonyl)-3-(imidazo[1,2-a]pyridin-8-yl)-2-(1H-tetrazol-5-yl)benzenesulfonamide (Step B). LC-MS [M+H]+: 505.4.

EXAMPLE 62

4-(4-(Azetidin-3-ylsulfonyl)-3-sulfamoyl-2-(1H-tetrazol-5-yl)phenyl)benzo[d]thiazole-2-carboximidamide

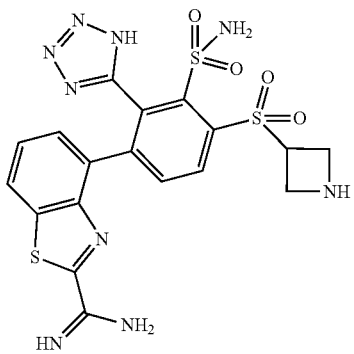 [SMILES: N=C(N)c1nc2c(-c3ccc(S(=O)(=O)C4CNC4)c(S(N)(=O)=O)c3-c3nnn[nH]3)cccc2s1]

Step A: tert-Butyl 3-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate The title compounds were prepared in a similar fashion to the synthesis of tert-butyl 3-((2-(N,N-bis(4-methoxybenzyl)sulfamoyl)-4-(imidazo[1,2-a]pyridin-8-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-8-yl)-3-(2-(4-methoxybenzyl)-2H-tetrazol-5-yl)phenyl)sulfonyl)azetidine-1-carboxylate (EXAMPLE 58, Step A) from tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (REFERENCE EXAMPLE 6) and (2-aminobenzo[d]thiazol-4-yl)boronic acid. LC/MS [M+H]$^+$: 953.6.

Step B: tert-Butyl 3-((2-(N,N-bis(4-methoxybenzyl)sulfamoyl)-4-(2-bromobenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl)sulfonyl)azetidine-1-carboxylate tert-butyl 3-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (621 mg, 0.652 mmol) were added portionwise to a solution of copper(II) bromide (175 mg, 0.782 mmol) and tert-butyl nitrite (107 mg, 1.042 mmol) in acetonitrile (2.4 mL) at room temperature under N$_2$. The mixture was stirred for 30 minutes. The reaction mixture was purified by column chromatography (100% hexane to 50% EtOAc/Hexane) to give tert-butyl 3-((2-(N,N-bis(4-methoxybenzyl)sulfamoyl)-4-(2-bromobenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl)sulfonyl)azetidine-1-carboxylate. LC/MS [M+H]$^+$: 1016.1, 1018.5.

Step C: tert-Butyl 3-((2-(N,N-bis(4-methoxybenzyl)sulfamoyl)-4-(2-cyanobenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)azetidine-1-carboxylate Copper(I) Cyanide (59.5 mg, 0.664 mmol) was added to tert-butyl 3-((2-(N,N-bis(4-methoxybenzyl)sulfamoyl)-4-(2-bromobenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl)sulfonyl)azetidine-1-carboxylate (563 mg, 0.554 mmol) in pyridine (2 mL). The mixture was heated at 120° C. for 1 hour and then cooled to room temperature. The mixture was purified by column chromatography (100% hexane to 50% EtOAc/Hexane) to give a mixture of desired product tert-butyl 3-((2-(N,N-bis(4-methoxybenzyl)sulfamoyl)-4-(2-cyanobenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)azetidine-1-carboxylate along with an impurity. LC-MS [M+H]$^+$: 963.6.

Step D: tert-Butyl 3-((2-(N,N-bis(4-methoxybenzyl)sulfamoyl)-4-(2-carbamimidoylbenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-carbamimidoylbenzo[d]thiazol-4-yl)-3-(2-(4-methoxybenzyl)-2H-tetrazol-5-yl)phenyl)sulfonyl)azetidine-1-carboxylate To a suspension of tert-butyl 3-((2-(N,N-bis(4-methoxybenzyl)sulfamoyl)-4-(2-cyanobenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)azetidine-1-carboxylate (122 mg, 0.127 mmol) in MeOH (0.5 mL) was added sodium methoxide (2.74 mg, 0.013 mmol). The mixture was stirred at room temperature for 1 hour. Ammonium chloride (13.55 mg, 0.253 mmol) was added and the mixture was stirred at room temperature for 24 hours. The reaction mixture was concentrated to give the crude title compound, which was used directly in the next step. LC-MS [M+H]$^+$: 980.7.

Step E: 4-(4-(Azetidin-3-ylsulfonyl)-3-sulfamoyl-2-(1H-tetrazol-5-yl)phenyl)benzo[d]thiazole-2-carboximidamide 4-(4-(Azetidin-3-ylsulfonyl)-3-sulfamoyl-2-(1H-tetrazol-5-yl)phenyl)benzo[d]thiazole-2-carboximidamide was prepared from tert-butyl 3-((2-(N,N-bis(4-methoxybenzyl)sulfamoyl)-4-(2-carbamimidoylbenzo[d]thiazol-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-carbamimidoylbenzo[d]thiazol-4-yl)-3-(2-(4-methoxybenzyl)-2H-tetrazol-5-yl)phenyl)sulfonyl)azetidine-1-carboxylate in a similar fashion to the preparation of 6-(azetidin-3-ylsulfonyl)-3-(imidazo[1,2-a]pyridin-8-yl)-2-(1H-tetrazol-5-yl)benzenesulfonamide (Step B). LC-MS [M+H]⁺: 520.3.

EXAMPLE 63

6-(Azetidin-3-ylthio)-3-(imidazo[1,2-a]pyridin-5-yl)-2-(1H-tetrazol-5-yl)benzenesulfonamide

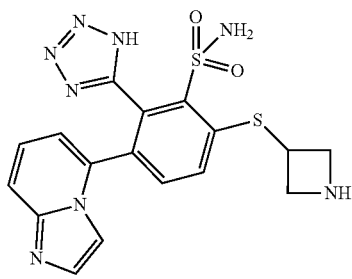 [SMILES: NS(=O)(=O)c1c(SC2CNC2)ccc(-c2cccc3nccn23)c1-c1nnn[nH]1]

Step A: tert-Butyl 3-((2-(N,N-bis(4-methoxybenzyl)sulfamoyl)-4-(imidazo[1,2-a]pyridin-5-yl)-3-(1-(4-methoxybenzyl)-1H-tetrazol-5-yl)phenyl)thio)azetidine-1-carboxylate and tert-butyl 3-((2-(N,N-bis(4-methoxybenzyl)sulfamoyl)-4-(imidazol[1,2-a]pyridin-5-yl)-3-(2-(4-methoxybenzyl)-2H-tetrazol-5-yl)phenyl)thio)azetidine-1-carboxylate (3-(N,N-bis(4-methoxybenzyl)sulfamoyl)-4-((1-(tert-butoxycarbonyl)azetidin-3-yl)thio)-2-(1-(4-methoxybenzyl)-1H-tetrazol-5-yl)phenyl)boronic acid and (3-(N,N-bis(4-methoxybenzyl)sulfamoyl)-4-((1-(tert-butoxycarbonyl)azetidin-3-yl)thio)-2-(2-(4-methoxybenzyl)-2H-tetrazol-5-yl)phenyl)boronic acid (120 mg, 0.147 mmol), 5-bromoimidazo[1,2-a]pyridine (37.6 mg, 0.191 mmol), Palladium Tetrakis (17.0 mg, 0.015 mmol), sodium carbonate (31.1 mg, 0.294 mmol) were placed in a reaction vessel, and dioxane (1102 µl) and water (367 µl) were added. The reaction was sealed, degassed for 25 minutes, and then heated at 60° C. for 12 hours. The reaction was purified by column chromatography (0-10% MeOH/EtOAc) to give the title compound. LC-MS [M+H]⁺: 889.8.

Step B: 6-(Azetidin-3-ylthio)-3-(imidazo[1,2-a]pyridin-5-yl)-2-(1H-tetrazol-5-yl)benzenesulfonamide 6-(Azetidin-3-ylthio)-3-(imidazo[1,2-a]pyridin-5-yl)-2-(1H-tetrazol-5-yl)benzenesulfonamide was prepared from tert-butyl 3-((2-(N,N-bis(4-methoxybenzyl)sulfamoyl)-4-(imidazo[1,2-a]pyridin-5-yl)-3-(1-(4-methoxybenzyl)-1H-tetrazol-5-yl)phenyl)thio)azetidine-1-carboxylate and tert-butyl 3-((2-(N,N-bis(4-methoxybenzyl)sulfamoyl)-4-(imidazo[1,2-a]pyridin-5-yl)-3-(2-(4-methoxybenzyl)-2H-tetrazol-5-yl)phenyl)thio)azetidine-1-carboxylate in a similar fashion to the preparation of 6-(azetidin-3-ylsulfonyl)-3-(imidazo[1,2-a]pyridin-8-yl)-2-(1H-tetrazol-5-yl)benzenesulfonamide (Step B). LC-MS [M+H]⁺: 429.4.

EXAMPLE 64

6-((2-Aminoethyl)sulfonyl)-3-(imidazo[1,2-a]pyridin-8-yl)-2-(1H-tetrazol-5-yl)benzenesulfonamide

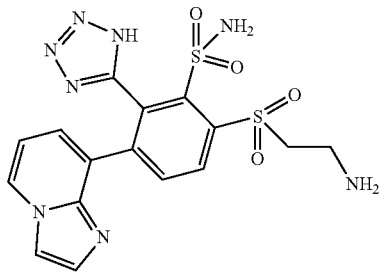 [SMILES: NCCS(=O)(=O)c1ccc(-c2cccn3ccnc23)c(-c2nnn[nH]2)c1S(N)(=O)=O]

Step A: tert-Butyl (2-((4-(2-aminopyridin-3-yl)-2-(N,N-bis(4-methoxybenzyl)sulfamoyl)-3-(1-(4-methoxybenzyl)-1H-tetrazol-5-yl)phenyl)sulfonyl)ethyl)carbamate and tert-butyl (2-((4-(2-aminopyridin-3-yl)-2-(N,N-bis(4-methoxybenzyl)sulfamoyl)-3-(2-(4-methoxybenzyl)-2H-tetrazol-5-yl)phenyl)sulfonyl)ethyl)carbamate tert-Butyl (2-((2-(N,N-bis(4-methoxybenzyl)sulfamoyl)-4-(5,5-dimethyl-1,3,2-dioxaborinan-2-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate (1200 mg, 1.326 mmol), Palladium Xphos precatalyst 2ⁿᵈ Generation (209 mg, 0.265 mmol), 3-bromopyridin-2-amine (275 mg, 1.591 mmol), sodium carbonate (281 mg, 2.65 mmol) were placed in a vial, then dioxane (9946 µl) and water (3315 µl) were added. The reaction was sealed and degassed for 20 minutes and then heated at 60° C. for 12 hours. The reaction mixture was purified by column chromatography (0-80% EtOAc/Hexane) to give the title compounds. LC-MS [M+H]⁺: 885.6.

Step B: tert-Butyl (2-((2-(N,N-bis(4-methoxybenzyl)sulfamoyl)-4-(imidazo[1,2-a]pyridin-8-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(imidazol[1,2-a]pyridin-8-yl)-3-(2-(4-methoxybenzyl)-2H-tetrazol-5-yl)phenyl)sulfonyl)ethyl)carbamate tert-Butyl (2-((4-(2-aminopyridin-3-yl)-2-(N,N-bis(4-methoxybenzyl)sulfamoyl)-3-(1-(4-methoxybenzyl)-1H-tetrazol-5-yl)phenyl)sulfonyl)ethyl)carbamate and tert-butyl (2-((4-(2-aminopyridin-3-yl)-2-(N,N-bis(4-methoxybenzyl)sulfamoyl)-3-(2-(4-methoxybenzyl)-2H-tetrazol-5-yl)phenyl)sulfonyl)ethyl)carbamate (171 mg, 0.193 mmol) and 2-chloroacetaldehyde (37.9 mg, 0.483 mmol) were heated in EtOH (500 ul) and THF (200 ul) at 75° C. for 12 hours. The reaction mixture was purified by column chromatography (0-15% MeOH/EtOAc) to give the title compounds. LC-MS [M+H]⁺: 909.6

Step C: 6-((2-Aminoethyl)sulfonyl)-3-(imidazo[1,2-a]pyridin-8-yl)-2-(1H-tetrazol-5-yl)benzenesulfonamide The title compound was prepared in a similar fashion to the synthesis of 6-(azetidin-3-ylsulfonyl)-3-(imidazo[1,2-a]pyridin-8-yl)-2-(1H-tetrazol-5-yl)benzenesulfonamide (Step B) from tert-butyl (2-((2-(N,N-bis(4-methoxybenzyl)sulfamoyl)-4-(imidazo[1,2-a]pyridin-8-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(imidazo[1,2-a]pyridin-8-yl)-3-(2-(4-methoxybenzyl)-2H-tetrazol-5-yl)phenyl)sulfonyl)ethyl)carbamate. LC-MS [M+H]+: 449.3.

EXAMPLE 65

3-(2-Aminoimidazo[1,2-a]pyridin-8-yl)-6-(azetidin-3-ylsulfonyl)-2-(H-tetraazol-5-yl)benzenesulfonamide

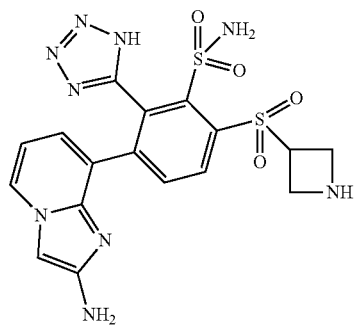 [SMILES: Nc1cn2cccc(-c3ccc(S(=O)(=O)C4CNC4)c(S(N)(=O)=O)c3-c3nnn[nH]3)c2n1]

Step A: tert-Butyl 3-((4-(2-aminopyridin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2-aminopyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid and (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid (1250 mg, 1.473 mmol) and 2,2-dimethylpropane-1,3-diol (767 mg, 7.36 mmol) were placed in a vial, then dioxane (11 mL) was added. The reaction mixture was degassed and heated at 80° C. for 1 hour. The reaction mixture was cooled to room temperature, to which, 2nd Generation Xphos Precatalyst (232 mg, 0.295 mmol), sodium carbonate (312 mg, 2.95 mmol), and 3-bromopyridin-2-amine (306 mg, 1.767 mmol) and water (3682 µl) were added. The reaction was sealed and degassed for 20 minutes and then heated at 40° C. for 12 hours. The reaction mixture was purified by column chromatography (0-80% EtOAc/Hexane) to give the title compounds. LC-MS [M+H]+: 897.6.

Step B: tert-Butyl 3-((2-(N,N-bis(4-methoxybenzyl)sulfamoyl)-3-(1-(4-methoxybenzyl)-1H-tetrazol-5-yl)-4-(2-((4-methylphenyl)sulfonamido)pyridin-3-yl)phenyl)sulfonyl)azetidine-1-carboxylate and tert-butyl 3-((2-(N,N-bis(4-methoxybenzyl)sulfamoyl)-3-(2-(4-methoxybenzyl)-2H-tetrazol-5-yl)-4-(2-((4-methylphenyl)sulfonamido)pyridin-3-yl)phenyl)sulfonyl)azetidine-1-carboxylate To a solution of tert-butyl 3-((4-(2-aminopyridin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2-aminopyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (467 mg, 0.521 mmol) in pyridine (1407 µl), was added 4-methylbenzene-1-sulfonyl chloride (149 mg, 0.781 mmol). The reaction mixture was sealed and heated at 80° C. for 12 hours. The reaction was concentrated and the residue was purified by column chromatography (0-100% EtOAc/Hexane) to give the title compounds. LC-MS [M+H]+: 1051.6.

Step C: tert-Butyl (Z)-3-((4-(1-(2-amino-2-oxoethyl)-2-(tosylimino)-1,2-dihydropyridin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl (Z)-3-((4-(1-(2-amino-2-oxoethyl)-2-(tosylimino)-1,2-dihydropyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate tert-butyl 3-((2-(N,N-bis(4-methoxybenzyl)sulfamoyl)-3-(1-(4-methoxybenzyl)-1H-tetrazol-5-yl)-4-(2-(4-methylphenylsulfonamido)pyridin-3-yl)phenyl)sulfonyl)azetidine-1-carboxylate and tert-butyl 3-((2-(N,N-bis(4-methoxybenzyl)sulfamoyl)-3-(2-(4-methoxybenzyl)-2H-tetrazol-5-yl)-4-(2-((4-methylphenyl)sulfonamido)pyridin-3-yl)phenyl)sulfonyl)azetidine-1-carboxylate (218 mg, 0.207 mmol), 2-iodoacetamide (78 mg, 0.421 mmol) and DIEA (73.5 µl, 0.421 mmol) were stirred in DMF (1000 uL) at 60° C. for 12 hours. The reaction was purified by column chromatography (0-15% MeOH/EtOAc) to give the title compounds. LC-MS [M+H]+: 1108.8.

Step D: N-(8-(3-(N,N-bis(4-methoxybenzyl)sulfamoyl)-2-(1-(4-methoxybenzyl)-1H-tetrazol-5-yl)-4-((1-(2,2,2-trifluoroacetyl)azetidin-3-yl)sulfonyl)phenyl)imidazo[1,2-a]pyridin-2-yl)-2,2,2-trifluoroacetamide and N-(8-(3-(N,N-bis(4-methoxybenzyl)sulfamoyl)-2-(2-(4-methoxybenzyl)-2H-tetrazol-5-yl)-4-((1-(2,2,2-trifluoroacetyl)azetidin-3-yl)sulfonyl)phenyl)imidazo[1,2-a]pyridin-2-yl)-2,2,2-trifluoroacetamide (Z)-tert-Butyl 3-((4-(1-(2-amino-2-oxoethyl)-2-(tosylimino)-1,2-dihydropyridin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl (Z)-3-((4-(1-(2-amino-2-oxoethyl)-2-(tosylimino)-1,2-dihydropyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (185 mg, 0.167 mmol) were placed in a vial. DCM (835 uL) was added followed by trifluoroacetic anhydride (584 µl, 4.14 mmol). The reaction was sealed and stirred at RT for 1 hour then at 30° C. for 1.5 hours. LC-MS showed that the reaction was completed, that the Boc group was lost during the reaction and the azetidine was acylated with trifluoroactyl group. The reaction mixture was concentrated and the residue was purified by column chromatography (100% hexane to 50% EtOAc/Hexane) to give the title compounds. LC-MS [M+H]+: 1028.5.

Step E: 3-(2-Aminoimidazo[1,2-a]pyridin-8-yl)-6-(azetidin-3-ylsulfonyl)-2-(1H-tetrazol-5-yl)benzene-sulfonamide N-(8-(3-(N,N-bis(4-methoxybenzyl)sulfamoyl)-2-(1-(4-methoxybenzyl)-1H-tetrazol-5-yl)-4-((1-(2,2,2-trifluoro-acetyl)azetidin-3-yl)sulfonyl)phenyl)imidazo[1,2-a]pyridin-2-yl)-2,2,2-trifluoroacetamide and N-(8-(3-(N,N-bis(4-methoxybenzyl)sulfamoyl)-2-(2-(4-methoxybenzyl)-2H-tetrazol-5-yl)-4-((1-(2,2,2-trifluoroacetyl)azetidin-3-yl)sulfonyl)phenyl)imidazo[1,2-a]pyridin-2-yl)-2,2,2-trifluoroacetamide (134 mg, 0.130 mmol) was dissolved in MeOH (1300 uL). Potassium carbonate (180 mg, 1.304 mmol) and water (130 ul) were added. The reaction mixture was heated at 80° C. for 5 hours. The resulting crude 3-(2-aminoimidazo[1,2-a]pyridin-8-yl)-6-(azetidin-3-ylsulfonyl)-N,N-bis(4-methoxybenzyl)-2-(1-(4-methoxybenzyl)-1H-tetrazol-5-yl)benzenesulfonamide and 3-(2-aminoimidazo[1,2-a]pyridin-8-yl)-6-(azetidin-3-ylsulfonyl)-N,N-bis(4-methoxybenzyl)-2-(2-(4-methoxybenzyl)-2H-tetrazol-5-yl)benzenesulfonamide (109 mg, 0.130 mmol) was heated in TFA (2 mL) at 60° C. for 2 hours. The reaction mixture was concentrated and purified with reverse phase HPLC (3-40% CH$_3$CN/water with 0.05% TFA) to afford the title compound. LC-MS [M+H]+: 476.4.

EXAMPLE 66

6-(Azetidin-3-ylsulfonyl)-3-(imidazo[1,2-a]pyridin-5-yl)-2-(1H-tetrazol-5-yl)benzenesulfonamide

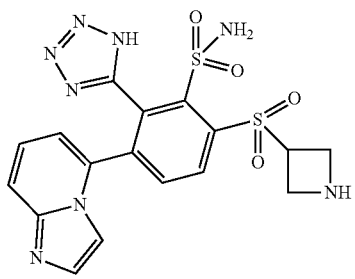 [SMILES: NS(=O)(=O)c1c(S(=O)(=O)C2CNC2)ccc(-c2cccc3nccn23)c1-c1nnn[nH]1]

Step A: tert-Butyl 3-((4-(6-aminopyridin-2-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(6-aminopyridin-2-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate tert-Butyl 3-((4-(6-aminopyridin-2-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(6-aminopyridin-2-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate were prepared in a similar fashion to that of tert-butyl 3-((4-(2-aminopyridin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2-aminopyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (Step A). LC-MS [M+H]+: 897.7.

Step B: tert-Butyl 3-((2-(N,N-bis(4-methoxybenzyl)sulfamoyl)-4-(imidazo[1,2-a]pyridin-5-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-5-yl)-3-(2-(4-methoxybenzyl)-2H-tetrazol-5-yl)phenyl)sulfonyl)azetidine-1-carboxylate tert-butyl 3-((4-(6-aminopyridin-2-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(6-aminopyridin-2-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (140 mg, 0.156 mmol) and 2-chloroacetaldehyde (32 mg, 0.408 mmol) was heated in ethanol (411 µl) and THF (200 ul) at 80° C. for 3 hours. The reaction mixture was purified by column chromatography (0-15% MeOH/EtOAc) to give tert-butyl 3-((2-(N,N-bis(4-methoxybenzyl)sulfamoyl)-4-(imidazo[1,2-a]pyridin-5-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-5-yl)-3-(2-(4-methoxybenzyl)-2H-tetrazol-5-yl)phenyl)sulfonyl)azetidine-1-carboxylatethe title compounds. LC-MS [M+H]+: 921.6.

Step C: 6-(Azetidin-3-ylsulfonyl)-3-(imidazo[1,2-a]pyridin-5-yl)-2-(1H-tetrazol-5-yl)benzenesulfonamide The title compound was prepared in a similar fashion as the synthesis of 6-(azetidin-3-ylsulfonyl)-3-(imidazo[1,2-a]pyridin-8-yl)-2-(1H-tetrazol-5-yl)benzenesulfonamide (Step B) from tert-butyl 3-((2-(N,N-bis(4-methoxybenzyl)sulfamoyl)-4-(imidazo[1,2-a]pyridin-5-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(imidazo[1,2-a]pyridin-5-yl)-3-(2-(4-methoxybenzyl)-2H-tetrazol-5-yl)phenyl)sulfonyl)azetidine-1-carboxylate. LC-MS [M+H]+: 461.2.

EXAMPLE 67

6-Amino-5-(4-(azetidin-3-ylsulfonyl)-3-sulfamoyl-2-(1H-tetrazol-5-yl)phenyl)picolinamide

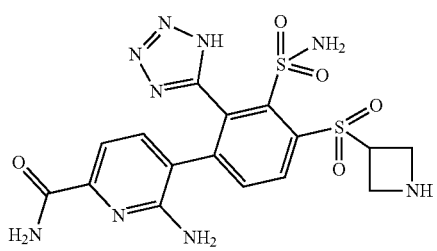 [SMILES: NC(=O)c1ccc(-c2ccc(S(=O)(=O)C3CNC3)c(S(N)(=O)=O)c2-c2nnn[nH]2)c(N)n1]

Step A: Methyl 6-amino-5-(3-(N,N-bis(4-methoxy-benzyl)sulfamoyl)-4-((1-(tert-butoxycarbonyl)azetidin-3-yl)sulfonyl)-2-(1-(4-methoxybenzyl)-1H-tetrazol-5-yl)phenyl)picolinate and methyl 6-amino-5-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)picolinate The title compounds were prepared in a similar fashion to the synthesis of tert-butyl 3-((4-(2-aminopyridin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2-aminopyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (Step A). LC-MS [M+H]$^+$: 955.6.

Step B: tert-Butyl 3-((4-(2-amino-6-carbamoylpyridin-3-yl)-2-(N,N-bis(4-methoxybenzyl)sulfamoyl)-3-(1-(4-methoxybenzyl)-1H-tetrazol-5-yl)phenyl) sulfonyl)azetidine-1-carboxylate and tert-butyl 3-((4-(2-amino-6-carbamoylpyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate Methyl 6-amino-5-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)picolinate and methyl 6-amino-5-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)picolinate (116 mg, 0.121 mmol) were treated with 7 M ammonia MeOH (2 mL) and heated at 80° C. for 3 hours. The reaction was cooled and concentrated to afford the title compounds, which were used directly in the next step. LC-MS [M+H]$^+$: 940.4.

Step C: 6-Amino-5-(4-(azetidin-3-ylsulfonyl)-3-sulfamoyl-2-(1H-tetrazol-5-yl)phenyl)picolinamide 6-Amino-5-(4-(azetidin-3-ylsulfonyl)-3-sulfamoyl-2-(1H-tetrazol-5-yl)phenyl)picolinamide was prepared in a similar fashion to the synthesis of 6-(azetidin-3-ylsulfonyl)-3-(imidazo[1,2-a]pyridin-8-yl)-2-(1H-tetrazol-5-yl)benzenesulfonamide (Step B) from tert-butyl 3-((4-(2-amino-6-carbamoylpyridin-3-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2-amino-6-carbamoylpyridin-3-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate. LC-MS [M+H]$^+$: 480.4.

EXAMPLE 68

4-(4-(azetidin-3-ylsulfonyl)-3-sulfamoyl-2-(1H-tetrazol-5-yl)phenyl)benzo[d]thiazole-2-carboxylic Acid

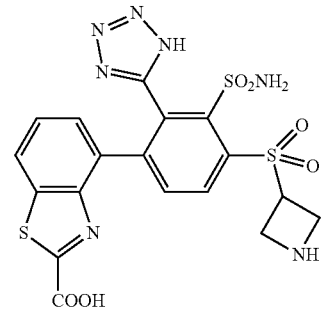 [SMILES: NS(=O)(=O)c1c(S(=O)(=O)C2CNC2)ccc(-c2cccc3sc(C(=O)O)nc23)c1-c1nnn[nH]1]

Step A: tert-butyl 3-((4-(2-aminobenzo[d]thiazol-4-yl)-2-(N,N-bis(4-methoxybenzyl)-sulfamoyl)-3-(2-(4-methoxybenzyl)-2H-tetrazol-5-yl)phenyl)sulfonyl)azetidine-1-carboxylate To a mixture of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (1.00 g, 1.07 mmol) in water (6 mL) and dioxane (18 mL) was added (2-aminobenzo[d]thiazol-4-yl)boronic acid (0.42 g, 2.15 mmol), Pd(dppf)Cl$_2$ (79 mg, 0.11 mmol) and Na$_2$CO$_3$ (0.46 g, 4.30 mmol) under nitrogen. The mixture was stirred at 80° C. for 16 hours. The reaction was cooled to 20° C. and quenched with water (50 mL) and extracted with EA (3×50 mL). The combined organic layers were washed with brine (4×25 mL), dried over anhydrous sodium sulfate and filtered. The residue was purified by a silica gel chromatography, eluting with ethyl acetate/petroleum ether (1:50 to 1:1) to afford the title compound: LCMS [M+H]$^+$: 953; $^1$H NMR (400 MHz, DMSO-d$_6$) δ 8.72 (d, J=8.8 Hz, 1H), 8.23 (d, J=8.4 Hz, 1H), 7.69-7.63 (m, 3H), 7.00-6.96 (m, 4H), 6.87-6.85 (m, 5H), 6.75-6.70 (m, 3H), 6.69 (brs, 2H), 5.11-5.10 (m, 1H), 4.88-4.86 (m, 2H), 4.51-4.47 (m, 2H), 4.33-4.31 (m, 2H), 4.20-4.17 (m, 1H), 4.06-3.97 (m, 3H), 3.72 (s, 9H), 1.42 (s, 9H).

Step B: tert-butyl 3-((2-(N,N-bis(4-methoxybenzyl) sulfamoyl)-4-(2-bromobenzo[d]thiazol-4-yl)-3-(2-(4-methoxybenzyl)-2H-tetrazol-5-yl)phenyl)sulfonyl) azetidine-1-carboxylate Into a 10 mL RBF purged and maintained with an inert atmosphere of argon, was placed a solution of tert-butyl 3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (0.70 g, 0.734 mmol) in acetonitrile (5 mL) under argon atmosphere, followed by the addition of tert-butyl nitrite (0.12 g, 1.18 mmol) and copper(II) bromide (0.20 g, 0.88 mmol) at room temperature. The resulting mixture was stirred at under argon atmosphere at 20° C. for 2 hours. The reaction was quenched with water (20 mL) and extracted with EA (3×20 mL). The combined organic layers were washed with brine (1×20 mL), dried over anhydrous sodium sulfate and filtered. The filtrate was evaporated under reduced pressure and the residue was purified by a silica gel column, eluted with EA/PE (1:50 to 1/1) to give the title compound: LCMS [M+H]$^+$: 1016, 1018 (1:1); $^1$H NMR (300 MHz, DMSO-d$_6$) δ 8.72 (d, J=8.4 Hz, 1H), 8.16 (d, J=8.4 Hz, 1H), 8.04 (d, J=7.8 Hz, 1H), 7.28-7.26 (m, 2H), 6.96-6.93 (m, 4H), 6.84-6.81 (m, 4H), 6.64-6.40 (m, 4H), 5.16-5.12 (m, 1H), 5.03-4.83 (m, 2H), 4.44-4.38 (m, 2H), 4.27-4.23 (m, 2H), 4.20-3.92 (m, 4H), 3.69 (s, 9H), 1.38 (s, 9H).

Step C: tert-butyl 3-((2-(N,N-bis(4-methoxybenzyl) sulfamoyl)-4-(2-cyanobenzo[d]thiazol-4-yl)-3-(2-(4-methoxybenzyl)-2H-tetrazol-5-yl)phenyl)sulfonyl) azetidine-1-carboxylate Into a 10-mL RBF purged and maintained with an inert atmosphere of argon, was placed a solution of tert-butyl 3-((2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl)sulfonyl)azetidine-1-carboxylate (0.10 g, 0.10 mmol) in DMSO (2 mL) under argon atmosphere, followed by the addition of cyanocopper (18 mg, 0.20 mmol) at room temperature. The resulting mixture was stirred at 100° C. for 8 hours under argon atmosphere. The reaction was quenched with FeSO$_4$ (aq., 20 mL) and extracted with EA (3×20 mL). The combined organic layers were washed with brine (1×20 mL), dried over anhydrous sodium sulfate and filtered. The filtrate was evaporated under reduced pressure and the residue was purified by silica gel chromatography, eluting with EA/PE (2/3) to give the title compound: LCMS [M+H]$^+$: 963; $^1$H NMR (300 MHz, DMSO-d$_6$) δ 8.78 (d, J=8.4 Hz, 1H), 8.31 (d, J=8.4 Hz, 1H), 8.21 (d, J=8.7 Hz, 1H), 7.54-7.53 (m, 2H), 7.00-6.94 (m, 5H), 6.88-6.86 (m, 4H), 6.67-6.40 (m, 3H), 5.22-5.18 (m, 1H), 4.51-4.45 (m, 2H), 4.33-4.21 (m, 4H), 4.11-3.96 (m, 4H), 3.73 (s, 9H), 1.42 (s, 9H).

Step D: 4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl) benzo[d]thiazole-2-carboxylic Acid Into a 10-mL RBF purged and maintained with an inert atmosphere of argon, was placed a solution of tert-butyl-3-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)azetidine-1-carboxylate (0.10 g, 0.10 mmol) in MeOH (2 mL) and THF (0.3 mL), followed by the addition of sodium methanolate (10.38 µl, 10.38 µmol) at room temperature. The resulting mixture was stirred at 20° C. for 5 minutes. The pH of the mixture was adjusted to ~6 with HCl (0.1 M), then it was stirred at 20° C. for 30 minutes. NaOH (2 M, 1 mL) was added into the mixture and it was stirred for 1 hour. The pH of the mixture was adjusted to ~6 with HCl (0.1 M). The mixture was extracted with EA (3×10 mL). The combined organic layers were washed with brine (1×20 mL), dried over anhydrous sodium sulfate and filtered. The filtrate was evaporated under reduced pressure to give the crude title compound: LCMS [M+H]$^+$: 982; $^1$H NMR (400 MHz, DMSO-d$_6$) δ 8.77 (d, J=8.4 Hz, 1H), 8.23 (d, J=8.4 Hz, 1H), 8.02 (d, J=8.4 Hz, 1H), 7.31-7.25 (m, 2H), 7.00-6.95 (m, 5H), 6.88-6.72 (m, 7H), 5.21-5.16 (m, 2H), 5.02-4.95 (m, 1H), 4.49-4.45 (m, 2H), 4.32-4.12 (m, 4H), 3.96-3.88 (m, 2H), 3.73 (s, 9H), 1.42 (s, 9H).

Step E: 4-(4-(azetidin-3-ylsulfonyl)-3-sulfamoyl-2-(1H-tetrazol-5-yl)phenyl)benzo[d]thiazole-2-carboxylic Acid A mixture of 4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)benzo[d]thiazole-2-carboxylic acid (70 mg, 0.07 mmol) in TFA (2 mL) was stirred at 25° C. for 30 minutes. The reaction mixture was concentrated under reduced pressure. The residue was dissolved in TFA (0.5 mL) and stirred at 60° C. for 1 hour. The reaction mixture was concentrated under reduced pressure. The residue was purified by Prep-HPLC. Column, Xbridge C18, 19×150 mm; mobile phase: Acetonitrile in water (0.05% NH$_4$HCO$_3$), 5%-20% in 8 min; Detector, UV 254 nm. The collected fractions were combined and concentrated under reduced pressure to give the title compound: LCMS [M+H]$^+$: 522; $^1$H NMR (400 MHz, DMSO-d$_6$) δ 8.39 (d, J=8.4 Hz, 1H), 7.99 (d, J=8.4 Hz, 1H), 7.92 (d, J=7.8 Hz, 1H), 7.16 (t, J=7.5 Hz, 1H), 6.70 (d, J=7.2 Hz, 1H), 5.32-5.24 (m, 1H), 4.39-4.33 (m, 2H), 4.27-4.22 (m, 2H).

EXAMPLE 69

3-(2-amino-1H-benzo[d]imidazol-5-yl)-6-(2-aminoethylsulfonyl)-2-(2H-tetrazol-5-yl)benzenesulfonamide

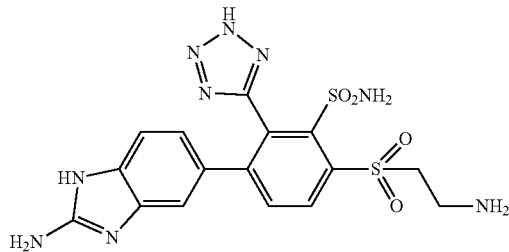 [SMILES: NCCS(=O)(=O)c1ccc(-c2ccc3[nH]c(N)nc3c2)c(-c2nn[nH]n2)c1S(N)(=O)=O]

Step A: tert-butyl 2-(4-(2-amino-1H-benzo[d]imidazol-5-yl)-2-(N,N-bis(4-methoxybenzyl)sulfamoyl)-3-(2-(4-methoxybenzyl)-2H-tetrazol-5-yl)phenylsulfonyl)ethylcarbamate To a solution of tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl) carbamate (300 mg, 0.327 mmol) in 1,4-dioxane (3 mL)/water (0.6 mL) (5:1) was added 6-(4,4,5,5-tetramethyl-1,3,2-dioxaborolan-2-yl)-1H-benzo[d]imidazol-2-amine (85 mg, 0.327 mmol), tetrakis(triphenylphosphine)palladium(0) (377 mg, 0.327 mmol) and potassium acetate (32.0 mg, 0.327 mmol) at room temperature. The flask was degassed with nitrogen three times. Then the mixture was stirred for 6 hours at 80° C. under an atmosphere of nitrogen. The solid was filtered out and the filtrate was concentrated under vacuum. The residue was then applied onto silica gel column with dichloromethane/methanol (20:1) to give the title compound (mixture of two tetrazole regioisomers): LCMS [M+H]$^+$: 924.

Step B: 3-(2-amino-1H-benzo[d]imidazol-5-yl)-6-(2-aminoethyl sulfonyl)-N,N-bis(4-methoxybenzyl)-2-(2-(4-methoxybenzyl)-2H-tetrazol-5-yl)benzenesulfonamide To a solution of tert-butyl (2-((4-(2-amino-1H-benzo[d] imidazol-5-yl)-2-(N,N-bis(4-methoxybenzyl)sulfamoyl)-3-

(2-(4-methoxybenzyl)-2H-tetrazol-5-yl)phenyl)sulfonyl) ethyl)carbamate (180 mg, 0.195 mmol) in DCM (1.5 mL) was added trifluoroacid (1.5 mL) at room temperature. The reaction system was then kept for 1 hour at room temperature. The resulting mixture was concentrated under reduced pressure to afford the crude product as a mixture with 3-(2-amino-1H-benzo[d]imidazol-5-yl)-6-((2-aminoethyl)sulfonyl)-N,N-bis(4-methoxybenzyl)-2-(2-(4-methoxybenzyl)-2H-tetrazol-5-yl)benzenesulfonamide and 3-(2-amino-1H-benzo[d]imidazol-5-yl)-6-((2-aminoethyl)sulfonyl)-N-(4-methoxybenzyl)-2-(2-(4-methoxybenzyl)-2H-tetrazol-5-yl)benzenesulfonamide. The crude product was then used directly for the next step: LCMS [M+H]$^+$: 824

Step C: 3-(2-amino-1H-benzo[d]imidazol-5-yl)-6-(2-aminoethyl sulfonyl)-2-(2H-tetrazol-5-yl)benzenesulfonamide 3-(2-amino-1H-benzo[d]imidazol-5-yl)-6-((2-aminoethyl)sulfonyl)-N,N-bis(4-methoxybenzyl)-2-(2-(4-methoxybenzyl)-2H-tetrazol-5-yl)benzenesulfonamide (50 mg, 0.061 mmol) and 3-(2-amino-1H-benzo[d]imidazol-5-yl)-6-((2-aminoethyl)sulfonyl)-N-(4-methoxybenzyl)-2-(2-(4-methoxybenzyl)-2H-tetrazol-5-yl)benzenesulfonamide (50 mg, 0.071 mmol) were dissolved in trifluoroacid (5 mL) at room temperature. The reaction was kept for 1 hour at 80° C. The resulting mixture was concentrated under reduced pressure to get the crude product. The crude product was then applied onto Prep-HPLC with the condition (Column: Sunfire C18, 19*150 mm, 5 μM; Mobile Phase A: water/ 0.05% TFA, Mobile Phase B: ACN; Flow rate: 20 mL/min; Gradient: 5-30% B in 10 min; 254 nm) to get the final product. LCMS [M+H]$^+$: 464; $^1$H NMR (300 MHz, DMSO-d$_6$): δ 8.43 (d, J=3.6 Hz, 1H), 8.20 (bs, 2H), 7.83 (d, J=8.4 Hz, 1H), 6.88 (d, J=8.1 Hz, 1H), 6.70 (d, J=1.2 Hz, 1H), 6.48-6.45 (m, 1H), 6.36 (bs, 1H), 4.12-4.07 (m, 2H), 3.16-3.10 (m, 2H).

EXAMPLES 70-80 below were prepared using the same general procedure as EXAMPLE 69, starting from tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl) carbamate and tert-butyl (2-((2-(N,N-bis(4-methoxybenzyl) sulfamoyl)-4-iodo-3-(2-(4-methoxybenzyl)-2H-tetrazol-5-yl)phenyl)sulfonyl)ethyl)carbamate and the corresponding boronic acids or boronic esters which were prepared as described herein or which w ere available from commercial sources.

| EX No. | Structure | Name | LC/MS [M + H]$^+$ |
|---|---|---|---|
| 70 | 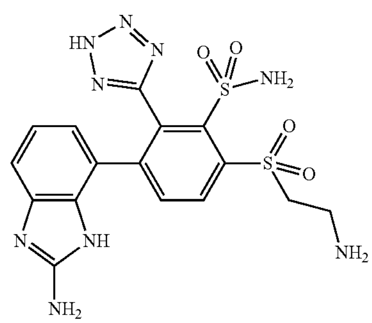 [SMILES: NCCS(=O)(=O)c1ccc(-c2cccc3nc(N)[nH]c23)c(-c2nn[nH]n2)c1S(N)(=O)=O] | 3-(2-amino-3H-benzo[d]imidazol-4-yl)-6-(2-aminoethylsulfonyl)-2-(2H-tetrazol-5-yl)benzenesulfonamide | 464 |
| 71 | 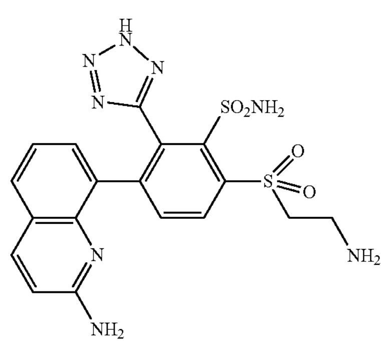 [SMILES: NCCS(=O)(=O)c1ccc(-c2cccc3ccc(N)nc23)c(-c2nn[nH]n2)c1S(N)(=O)=O] | 6-(2-aminoethylsulfonyl)-3-(2-aminoquinolin-8-yl)-2-(2H-tetrazol-5-yl)benzenesulfonamide | 475 |
| 72 | 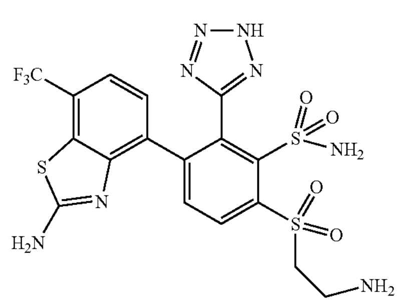 [SMILES: NCCS(=O)(=O)c1ccc(-c2ccc(C(F)(F)F)c3sc(N)nc23)c(-c2nn[nH]n2)c1S(N)(=O)=O] | 3-(2-amino-7-(trifluoromethyl)benzo[d]thiazol-4-yl)-6-(2-aminoethylsulfonyl)-2-(2H-tetrazol-5-yl)benzenesulfonamide | 549 |

-continued

| EX No. | Structure | Name | LC/MS [M + H]+ |
|---|---|---|---|
| 73 | 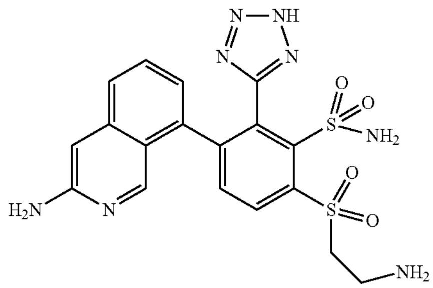 [SMILES: NCCS(=O)(=O)c1ccc(-c2cccc3cc(N)ncc23)c(-c2nn[nH]n2)c1S(N)(=O)=O] | 6-(2-aminoethylsulfonyl)-3-(3-aminoisoquinolin-8-yl)-2-(2H-tetrazol-5-yl)benzenesulfonamide | 475 |
| 74 | 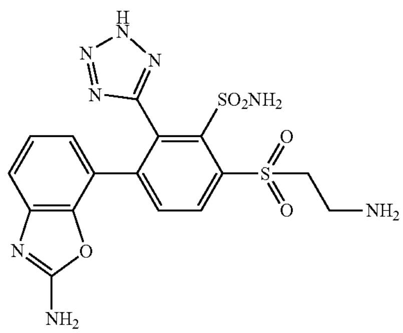 | 3-(2-aminobenzo[d]oxazol-7-yl)-6-(2-aminoethylsulfonyl)-2-(2H-tetrazol-5-yl)benzenesulfonamide | 465 |
| 75 | 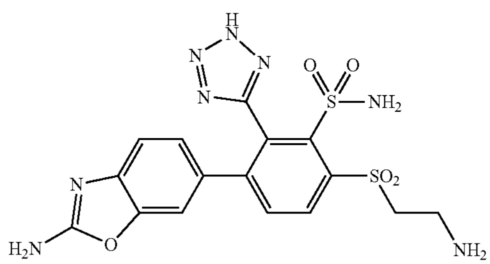 [SMILES: NCCS(=O)(=O)c1ccc(-c2ccc3nc(N)oc3c2)c(-c2nn[nH]n2)c1S(N)(=O)=O] | 3-(2-aminobenzo[d]oxazol-6-yl)-6-(2-aminoethylsulfonyl)-2-(2H-tetrazol-5-yl)benzenesulfonamide | 465 |
| 76 | 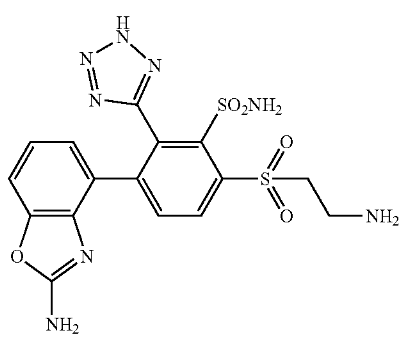 [SMILES: NCCS(=O)(=O)c1ccc(-c2cccc3oc(N)nc23)c(-c2nn[nH]n2)c1S(N)(=O)=O] | 3-(2-aminobenzo[d]oxazol-4-yl)-6-(2-aminoethylsulfonyl)-2-(2H-tetrazol-5-yl)benzenesulfonamide | 465 |
| 77 | 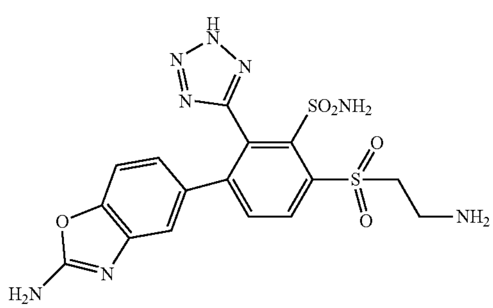 [SMILES: NCCS(=O)(=O)c1ccc(-c2ccc3oc(N)nc3c2)c(-c2nn[nH]n2)c1S(N)(=O)=O] | 3-(2-aminobenzo[d]oxazol-5-yl)-6-(2-aminoethylsulfonyl)-2-(2H-tetrazol-5-yl)benzenesulfonamide | 465 |

| EX No. | Structure | Name | LC/MS [M + H]+ |
|---|---|---|---|
| 78 | 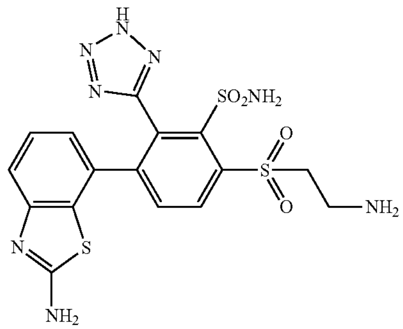 [SMILES: NCCS(=O)(=O)c1ccc(-c2cccc3nc(N)sc23)c(-c2nn[nH]n2)c1S(N)(=O)=O] | 3-(2-aminobenzo[d]thiazol-7-yl)-6-(2-aminoethylsulfonyl)-2-(2H-tetrazol-5-yl)benzenesulfonamide | 481 |
| 79 | 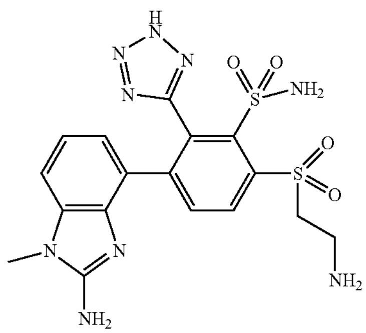 [SMILES: Cn1c(N)nc2c(-c3ccc(S(=O)(=O)CCN)c(S(N)(=O)=O)c3-c3nn[nH]n3)cccc21] | 3-(2-amino-1-methyl-1H-benzo[d]imidazol-4-yl)-6-(2-aminoethylsulfonyl)-2-(2H-tetrazol-5-yl)benzenesulfonamide | 478 |
| 80 | 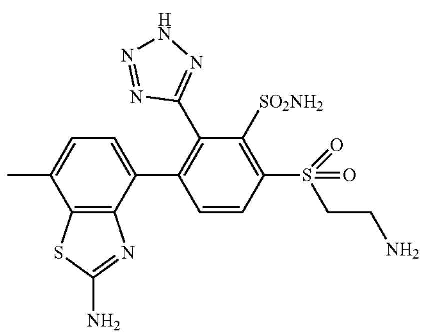 [SMILES: Cc1ccc(-c2ccc(S(=O)(=O)CCN)c(S(N)(=O)=O)c2-c2nn[nH]n2)c2nc(N)sc12] | 3-(2-amino-7-methylbenzo[d]thiazol-4-yl)-6-(2-aminoethylsulfonyl)-2-(2H-tetrazol-5-yl)benzenesulfonamide | 495 |

EXAMPLE 81

6-((2-aminoethyl)sulfonyl)-3-(2-aminothiazolo[5,4-c]pyridin-7-yl)-2-(2H-tetrazol-5-yl)benzenesulfonamide hydrochloride

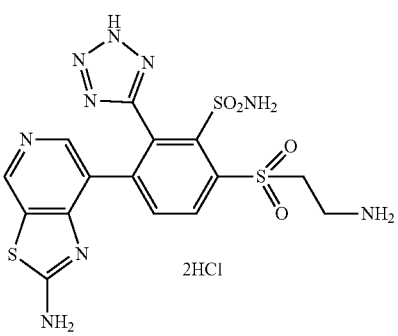 [SMILES: NCCS(=O)(=O)c1ccc(-c2cncc3sc(N)nc23)c(-c2nn[nH]n2)c1S(N)(=O)=O]

Step A:
N-(3,5-dibromopyridin-4-ylcarbamothioyl)benzamide

Into a mixture of 3,5-dibromopyridin-4-amine (10.00 g, 39.70 mmol) in acetone (100 mL) was added benzoyl isothiocyanate (12.96 g, 79.00 mmol). The resulting mixture was stirred at 60° C. and for 3 hours. The reaction mixture was cooled to room temperature, quenched by Na$_2$CO$_3$ (200 mL) and extracted with ethyl acetate (3×200 mL). The combined organic layer was washed with brine (4×50 mL), dried over anhydrous sodium sulfate and concentrated under reduced pressure, the residue was purified by a silica gel column, eluted with ethyl acetate/petroleum ether (1:50-1:5) to afford the title compound: LCMS [M+1]+ 414, 416, 418 (1:2:1); $^1$H NMR (300 MHz, DMSO-d$_6$) δ 12.19 (s, 1H), 12.04 (s, 1H), 8.02 (s, 2H), 7.75-7.57 (m, 5H).

Step B: N-(7-bromothiazolo[5,4-c]pyridin-2-yl)benzamide

In the 25 mL RBF was placed a solution of N-((3-bromo-5-fluoropyridin-4-yl)carbamothioyl)benzamide (3.00 g, 7.27 mmol) in DMF (10 mL), followed by the addition of Cs$_2$CO$_3$ (4.74 g, 14.54 mmol). After the mixture was stirred at 80° C. for 3 hours in an oil bath, it was poured into water (300 mL), then the solid was collected by filtration and dried in oven to give the title compound as a solid: LCMS [M+1]$^+$334, 336 (1:1); $^1$H NMR (400 MHz, DMSO-d$_6$) δ 13.57 (s, 1H), 9.22 (s, 1H), 8.71 (s, 1H), 8.19 (d, J=8.8 Hz, 2H), 7.73-7.69 (m, 1H), 7.62-7.58 (m, 2H).

Step C: 2-benzamidothiazolo[5,4-c]pyridin-7-yboronic acid

Into a 25 mL round flask was placed a solution of N-(7-bromothiazolo[5,4-c]pyridin-2-yl)benzamide (1.00 g, 2.99 mmol) in dioxane (10 mL), followed by the addition of Pd(dppf)Cl$_2$ (0.22 g, 0.30 mmol), 5,5,5',5'-tetramethyl-2,2'-bi(1,3,2-dioxaborinane) (1.35 g, 5.98 mmol) and potassium acetate (0.88 g, 8.98 mmol). The resulting mixture was degassed with nitrogen 3 times and stirred at 80° C. for 16 hours in an oil bath. The resulting mixture was then diluted with water (50 mL) and extracted with ethyl acetate (2×100 mL). The combined organic layer were washed with brine (2×100 mL), dried over anhydrous sodium sulfate and filtered. The filtrate was concentrated under vacuum. The crude product was purified by com-flash with the following conditions: water (0.05% NH$_4$CO$_3$) and acetonitrile (hold 45% acetonitrile for 30 min,); Detector, UV 220 and 254 nm. The collected fractions were combined and concentrated under vacuum to give 2-benzamidothiazolo[5,4-c]pyridin-7-yl)boronic acid as a solid: LCMS [M+1]$^+$300; $^1$H NMR (300 MHz, DMSO-d$_6$) δ 13.22 (brs, 1H), 9.22 (s, 1H), 8.72 (s, 1H), 7.68-7.53 (m, 5H).

Step D: tert-butyl (2-((4-(2-benzamidobenzo[d]thiazol-4-yl)-2-(N,N-bis(4-methoxybenzyl)sulfamoyl)-3-(2-(4-methoxybenzyl)-2H-tetrazol-5)phenyl)sulfonyl)ethyl)-carbamate In an 8 mL vial was placed a solution of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (0.10 g, 0.11 mmol) in dioxane (3 mL) and water (0.6 mL), followed by the addition of (2-benzamidobenzo[d]thiazol-4-yl)boronic acid (0.11 g, 0.38 mmol), Pd(Ph$_3$P)$_4$ (25 mg, 0.02 mmol) and Na$_2$CO$_3$ (35 mg, 0.33 mmol). The mixture was degassed with nitrogen 3 times and stirred at 80° C. for 16 hours in an oil bath. The resulting mixture was diluted with water (30 mL) and extracted with ethyl acetate (2×20 mL). The combined organic layer was washed with water (2×40 mL), brine (2×40 mL), dried over anhydrous sodium sulfate and filtered. The filtrate was concentrated under vacuum. The residue was purified by Prep-TLC with methanol/DCM (1/60) to give the title compound as a solid: LCMS [M+1]$^+$1046; $^1$H NMR (300 MHz, DMSO-d$_6$) δ 9.13 (s, 1H), 9.76 (d, J=8.4 Hz, 1H), 8.32 (d, J=8.4 Hz, 1H), 8.07 (s, 1H), 8.04 (s, 1H), 7.67-7.55 (m, 5H), 7.01-6.84 (m, 9H), 6.87-6.83 (m, 4H), 5.12-5.02 (m, 2H), 4.49-4.42 (m, 2H), 4.09-3.91 (m, 4H), 3.71 (s, 7H), 3.68 (s, 2H), 3.48-3.46 (m, 2H), 1.35 (s, 9H).

Step E: 6-((2-aminoethyl)sulfonyl)-3-(2-aminothiazolo[5,4-c]pyridin-7-yl)-2-(2H-tetrazol-5-yl)benzenesulfonamide hydroChloride In a 25 mL round flask was placed tert-butyl (2-((4-(2-benzamidothiazolo[5,4-c]pyridin-7-yl)-2-(N,N-bis(4-methoxybenzyl)sulfamoyl)-3-(2-(4-methoxybenzyl)-2H-tetrazol-5-yl)phenyl)sulfonyl)ethyl)carbamate (75 mg, 0.07 mmol), followed by the addition of HCl (10 mL, 37%). The mixture was stirred at 80° C. for 6 hours in an oil bath. The solvent was concentrated under reduced pressure. The product was purified by Prep-HPLC with the following conditions: Column, Xbridge C$^{18}$, 19×150 mm; mobile phase: water (0.05% TFA) and acetonitrile (5%~20%) for 8 min, hold 100% for 2 min, down to 5% in 2 min); Detector, UV 220 and 254 nm. The collected fractions were combined and concentrated under vacuum. To the product was added two drops HCl (aq.), then the reaction mixture was freeze dried to give the title compound as a solid: LCMS [M+1]$^+$482; $^1$H NMR (400 MHz, DMSO-d$_6$) δ 9.11 (brs, 2H), 9.03 (s, 1H), 8.60 (d, J=8.4 Hz, 1H), 8.20-8.15 (m, 4H), 7.44 (brs, 2H), 4.18 (t, J=7.2 Hz, 2H), 3.28-3.26 (m, 2H).

EXAMPLE 82

N-(4-(4-(2-aminoethylsulfonyl)-3-sulfamoyl-2-(2H-tetrazol-5-yl)phenyl)benzo[d]thiazol-2-yl)acetamide

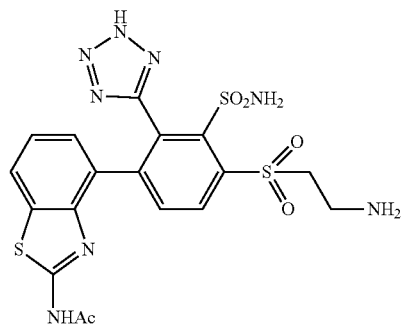 [SMILES: CC(=O)Nc1nc2c(-c3ccc(S(=O)(=O)CCN)c(S(N)(=O)=O)c3-c3nn[nH]n3)cccc2s1]

Step A: tert-butyl (2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate To a solution of tert-butyl (2-((2-(N, N-bis(4-methoxybenzyl)sulfamoyl)-4-iodo-3-(2-(4-methoxybenzyl)-2H-tetrazol-5-yl)phenyl)sulfonyl)ethyl)carbamate (1.5 g, 1.63 mmol) in dioxane (12 ml) was added Pd(dppf)Cl$_2$ (0.096 g, 0.163 mmol), Na$_2$CO$_3$ (0.692 g, 6.53 mmol) and (2-aminobenzo[d]thiazol-4-yl)boronic acid (0.633 g, 3.27 mmol) with stirring at room temperature. The reaction mixture was degassed with nitrogen 3 times. The resulting mixture was warmed to 80° C. and stirred overnight. The solution was concentrated under vacuum. The residue was purified by silica gel column chromatography 40 g, eluting with Acetonitrile/water+0.1% TFA (1/3) to afford the title compound: LCMS [M+H]$^+$: 941.

Step B: tert-butyl (2-((4-(2-acetamidobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate To a solution of tert-butyl (2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate (180 mg, 0.191 mmol) in THF (3 ml) was added acetic anhydride (39.1 mg, 0.383 mmol) and triethylamine (58.1 mg, 0.574 mmol) with stirring at room temperature. The resulting solution was warmed to 50° C. and stirred overnight. The reaction solution was cooled to room temperature, diluted with water (5 mL) and extracted with ethyl acetate (3×5 mL). The combined organic layers were washed with brine (5 mL), dried over anhydrous sodium sulfate and filtered. The filtrate was concentrated under vacuum to afford an oil. The residue was purified by silica gel column chromatography 20 g, eluting with EtOAc/petroleum ether (2:1) to afford the title compound: LCMS [M+H]+: 983.

Step C: N-(4-(4-((2-aminoethyl)sulfonyl)-2-(2-(4-methoxybenzyl)-2H-tetrazol-5-yl)-3-(N-(4-methoxybenzyl)sulfamoyl)phenyl)benzo[d]thiazol-2-yl)acetamide To a solution of tert-butyl (2-((4-(2-acetamidobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate (120 mg, 0.122 mmol) in DCM (3 ml) was added TFA (0.094 ml, 1.221 mmol) with stirring at room temperature. The resulting solution was warmed to room temperature and stirred for 1 hour. The residue was concentrated, and dissolved again in TFA (2 mL). The resulting mixture was dissolved at 80° C. for 2 hours. After evaporation, the crude product was purified by reverse phase prep-HPLC to afford the title compound: LCMS [M+H]+: 523; 1H NMR (300 MHz, DMSO): δ 8.25 (d, J=8.4 Hz, 1H), 7.86-7.79 (m, 2H), 7.08-7.05 (m, 1H), 6.81 (d, J=8.4 Hz, 1H), 4.16-4.11 (m, 2H), 3.27-3.24 (m, 2H), 2.13 (s, 3H).

EXAMPLES 83-84 below were prepared in an analogous fashion as EXAMPLE 82 starting from tert-butyl (2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate and using alternative acylating or sulfonylating reagents such as methane sulfonyl chloride and ethyl chloroformate.

EXAMPLE 85

6-(2-aminoethylsulfonyl)-2-(2H-tetrazol-5-yl)-3-(2-ureidobenzo[d]thiazol-4-yl)benzenesulfonamide

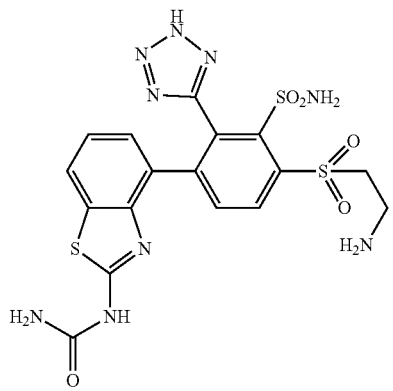 [SMILES: NCCS(=O)(=O)c1ccc(-c2cccc3sc(NC(N)=O)nc23)c(-c2nn[nH]n2)c1S(N)(=O)=O]

Step A: tert-butyl (2-((2-(N,N-bis(4-methoxybenzyl)sulfamoyl)-3-(2-(4-methoxybenzyl)-2H-tetrazol-5-yl)-4-(2-ureidobenzo[d]thiazol-4-yl)phenyl)sulfonyl)ethyl)carbamate To a solution of tert-butyl (2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate (300 mg, 0.319 mmol) in pyridine (3 ml) was added trichloromethyl carbonochloridate (189 mg, 0.956 mmol) and DMAP (156 mg, 1.275 mmol) with stirring at room temperature. The resulting solution was warmed to room temperature and stirred for 48 hours and then ammonia (5 ml) was added. The resulting solution was cooled to room

| EX NO | Structure | Name | MW | LC/MS [M + H]+ |
|---|---|---|---|---|
| 83 | 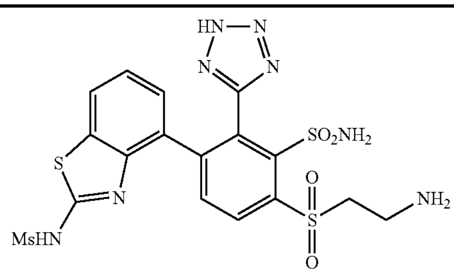 | 6-(2-aminoethylsulfonyl)-3-(2-(methylsulfonamido)benzo[d]thiazol-4-yl)-2-(2H-tetrazol-5-yl)benzenesulfonamide | 558 | 559 |
| 84 | | ethyl 4-(4-(2-aminoethylsulfonyl)-3-sulfamoyl-2-(2H-tetrazol-5-yl)phenyl)benzo[d]thiazol-2-ylcarbamate | 552 | 553 | temperature, diluted with water (10 mL), and extracted with ethyl acetate (3×10 mL). The combined organic layers were washed with brine (20 mL), dried over anhydrous sodium sulfate, filtered and concentrated under vacuum. The residue was purified by silica gel column chromatography, eluted with EtOAc/Petroleum ether (1/1) to afford the title compound as a solid: LCMS [M+H]$^+$: 985.

Step B: 6-((2-aminoethyl)sulfonyl)-2-(2H-tetrazol-5-yl)-3-(2-ureidobenzo[d]thiazol-4-yl)benzenesulfonamide To a solution of tert-butyl (2-((2-(N,N-bis(4-methoxybenzyl)sulfamoyl)-3-(2-(4-methoxybenzyl)-2H-tetrazol-5-yl)-4-(2-ureidobenzo[d]thiazol-4-yl)phenyl)sulfonyl)ethyl)carbamate (120 mg, 0.122 mmol) in DCM (3 ml) was added TFA (0.094 mL, 1.219 mmol) with stirring at room temperature. The resulting solution was warmed to room temperature and stirred for 1 hour. The residue was concentrated to afford 6-((2-aminoethyl)sulfonyl)-N-(4-methoxybenzyl)-2-(2-(4-methoxybenzyl)-2H-tetrazol-5-yl)-3-(2-ureidobenzo[d]thiazol-4-yl)benzenesulfonamide as an oil. The solution of 6-((2-aminoethyl)sulfonyl)-N-(4-methoxybenzyl)-2-(2-(4-methoxybenzyl)-2H-tetrazol-5-yl)-3-(2-ureidobenzo[d]thiazol-4-yl)benzenesulfonamide (50 mg, 0.065 mmol) in TFA (0.504 mL, 6.55 mmol) was stirred at room temperature. The resulting solution was stirred at 80° C. for 2 hours and then cooled to room temperature. After being concentrated under vacuum, the residue was purified by Prep-HPLC with the following conditions: Column: XBridge C18 OBD Prep Column, 100 Å, 5 µm, 19 mm×250 mm; Mobile Phase A: water with 0.05% NH$_4$HCO$_3$, Mobile Phase B: MeCN; Flow rate: 15 mL/min; Gradient: 17% B to 45% B in 8 min; 254/220 nm. The collected fractions were combined and concentrated under vacuum to afford the title compound: LCMS [M+H]$^+$: 524; $^1$H NMR (300 MHz, DMSO): δ 8.26 (d, J=8.4 Hz, 1H), 7.99-7.91 (m, 1H), 7.72-7.68 (m, 1H), 6.97-9.92 (m, 1H), 6.70 (d, J=7.2 Hz, 1H), 4.15 (t, J=6.9 Hz, 2H), 3.27-3.24 (m, 2H).

EXAMPLE 86

4-(4-(2-aminoethyl sulfonyl)-3-sulfamoyl-2-(2H-tetrazol-5-yl)phenyl)benzo[d]thiazole-2-carboximidamide

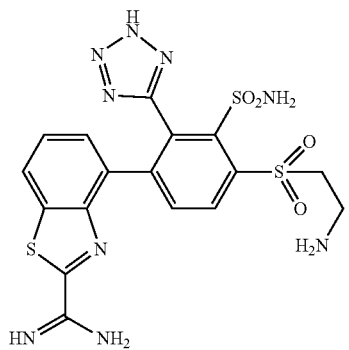 [SMILES: N=C(N)c1nc2c(-c3ccc(S(=O)(=O)CCN)c(S(N)(=O)=O)c3-c3nn[nH]n3)cccc2s1]

Step A: tert-butyl (2-((2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl)sulfonyl)ethyl)carbamate Into a 10 mL RBF purged and maintained with an inert atmosphere of argon, was placed a solution of tert-butyl nitrite (0.11 g, 1.02 mmol) and copper(II) bromide (0.17 g, 0.77 mmol) in acetonitrile (3 mL), followed by the addition a solution of tert-butyl (2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl) carbamate (described above, 0.60 g, 0.64 mmol) in acetonitrile (3 ml) at 0° C. The resulting mixture was stirred under argon atmosphere at 20° C. for 16 hours. The reaction was quenched with water (30 mL) and extracted with EA (3×30 mL). The combined organic layers were washed with brine 3×20 mL), dried over anhydrous sodium sulfate and filtered. The filtrate was evaporated under reduced pressure and the residue was purified by Prep-TLC, eluted with EA/PE (2/3) to give the title compound: LCMS [M+1]$^+$ 1004, 1006 (1:1); $^1$H NMR (400 MHz, CDCl$_3$) δ 8.75 (d, J=8.4 Hz, 1H), 8.00 (d, J=8.4 Hz, 1H), 7.71 (d, J=8.0 Hz, 1H), 7.21-7.19 (m, 1H), 7.07-7.03 (m, 5H), 6.82-6.77 (m, 4H), 6.63-6.01 (m, 4H), 5.32 (brs, 1H), 4.94-4.92 (m, 2H), 4.67-4.63 (m, 2H), 4.19-4.12 (m, 4H), 3.87-3.79 (m, 2H), 3.77 (s, 9H), 1.45 (s, 9H).

Step B: tert-butyl (2-((2-(N,N-bis(4-methoxybenzyl) sulfamoyl)-4-(2-cyanobenzo[d]thiazol-4-yl)-3-(2-(4-methoxy-benzyl)-2H-tetrazol-5-yl)phenyl)sulfonyl) ethyl)carbamate Into a 10 mL RBF purged and maintained with an inert atmosphere of argon, was placed a solution of tert-butyl (2-((2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl)sulfonyl)ethyl)carbamate (0.60 g, 0.60 mmol) in DMSO (4 mL), followed by the addition of cyanocopper (0.11 g, 1.19 mmol). The resulting mixture was stirred at 100° C. for 4 hours. The reaction was quenched with FeSO$_4$ (aq., 100 mL) and extracted with EA (3×100 mL). The combined organic layers were washed with brine (4×50 mL), dried over anhydrous sodium sulfate and filtered. The filtrate was evaporated under reduced pressure and the residue was purified by silica gel chromatography, eluting with EA/PE (2/3) to give the title compound: LCMS [M+1]$^+$951; $^1$H NMR (400 MHz, CDCl$_3$) δ 8.76 (d, J=8.4 Hz, 1H), 7.92 (d, J=8.4 Hz, 1H), 7.86 (d, J=9.2 Hz, 1H), 7.41-7.35 (m, 1H), 7.17-7.15 (m, 1H), 7.05-7.02 (m, 4H), 6.81-6.75 (m, 4H), 6.55-6.53 (m, 4H), 5.27 (brs, 1H), 5.01-4.85 (m, 2H), 4.63-4.59 (m, 2H), 4.15-4.08 (m, 4H), 3.87-3.83 (m, 2H), 3.76 (s, 9H), 1.40 (s, 9H).

Step C: tert-butyl (2-((2-(N,N-bis(4-methoxybenzyl) sulfamoyl)-4-(2-carbamimidoylbenzo[d]thiazol-4-yl)-3-(2-(4-methoxybenzyl)-2H-tetrazol-5yl)phenyl) sulfonyl)ethyl) carbamate Into a 25 mL RBF purged and maintained with an inert atmosphere of argon, was placed a solution of tert-butyl (2-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)ethyl)carbamate (60 mg, 0.05 mmol) in MeOH (3 mL) and THF (0.5 mL), followed by the addition of sodium methanolate (5.05 µL, 0.05 mmol). The resulting mixture was stirred at 20° C. for 0.5 hour. Then NH$_4$Cl (27 mg, 0.505 mmol) was added. The resulting mixture was stirred at 20° C. for 48 hours. The reaction was quenched with water (50 mL) and extracted with EA (3×100 mL). The combined organic layers were washed with brine (1×200 mL), dried over anhydrous sodium sulfate and filtered. The filtrate was evaporated under reduced pressure and the residue was purified by preparative TLC, eluted with EA/PE (5/1) to give the title compound: LCMS [M+1]$^+$968; $^1$H NMR (300 MHz, CDCl$_3$) δ 8.85 (d, J=8.4 Hz, 1H), 7.93-7.89 (m, 2H), 7.37-7.32 (m, 1H), 7.04-7.01 (m, 5H), 6.88-6.79 (m, 8H), 6.45-6.26 (m, 3H), 6.31 (brs, 1H), 5.07-4.95 (m, 2H), 4.74-4.67 (m, 2H), 4.14-4.08 (m, 4H), 3.88 (s, 9H), 3.80-3.76 (m, 2H), 1.44 (s, 9H).

Step D: 4-(4-((2-aminoethyl)sulfonyl)-3-sulfamoyl-2-(2H-tetrazol-5-yl)phenyl)benzo[d]thiazole-2-carboximidamide In the 25 mL RBF, was placed a solution of tert-butyl (2-((2-(N,N-bis(4-methoxybenzyl)sulfamoyl)-4-(2-carbamimidoylbenzo[d]thiazol-4-yl)-3-(2-(4-methoxybenzyl)-2H-tetrazol-5-yl)phenyl)sulfonyl)ethyl)carbamate (40 mg, 0.041 mmol) in TFA (2 mL). The mixture was stirred at room temperature for 1 hour. The solvent was concentrated under reduced pressure. The crude product was resolved in TFA (2 mL). The mixture was stirred at 80° C. for 1 hour. The solvent was concentrated under reduced pressure to give the crude product. The product was purified by Prep-HPLC with the following conditions: Column, Xbridge C$^{18}$, 19*150 mm; mobile phase: water (0.05% HCOOH) and acetonitrile (5-30% acetonitrile for 10 min, hold 100% for 2 min, down to 5% in 2 min); Detector, UV 220 and 254 nm. The collected fractions were combined and concentrated under vacuum. Then two drops HCl (aq.) were added and lyophilized to give the title compound: LCMS [M+1]$^+$508; $^1$H NMR (400 MHz, CDCl$_3$) δ 8.77-8.70 (m, 4H), 8.59 (d, J=8.4 Hz, 1H), 8.34 (d, J=8.0 Hz, 1H), 8.20-8.17 (m, 4H), 7.63-7.52 (m, 3H), 7.35-7.27 (m, 1H), 4.21-4.16 (m, 2H), 3.35-3.32 (m, 2H).

EXAMPLE 87

6-(2-aminoethylsulfonyl)-3-(2-(aminomethyl)benzo[d]thiazol-4-yl)-2-(2H-tetrazol-5-yl)benzenesulfonamide

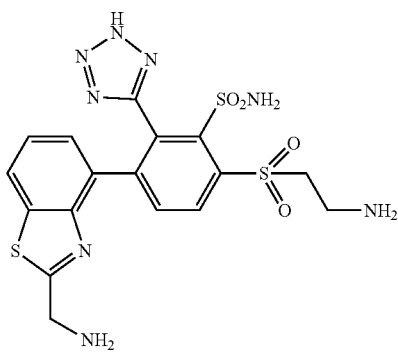 [SMILES: NCCS(=O)(=O)c1ccc(-c2cccc3sc(CN)nc23)c(-c2nn[nH]n2)c1S(N)(=O)=O]

Step A: tert-butyl (2-((4-(2-(aminomethyl)benzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate Into a 10-mL RBF purged and maintained with an inert atmosphere of argon, was placed a solution of tert-butyl (2-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)ethyl)carbamate (prepared as described above, 0.14 g, 0.15 mmol) in EtOAc (3 mL), followed by the addition of Pd(OH)$_2$ (31 mg, 0.04 mmol) at room temperature. The resulting mixture was stirred at 25° C. under hydrogen atmosphere for 16 hours. The mixture was filtered and the filtrate was evaporated. The residue was purified by silica gel chromatography, eluting with EtOAc in petroleum ether (3:2) to afford the title compound: LCMS [M+H]$^+$: 955; $^1$H NMR (400 MHz, CD$_3$Cl): δ 8.71 (d, J=8.4 Hz, 1H), 8.00 (d, J=8.0 Hz, 1H), 7.81 (d, J=8.0 Hz, 1H), 7.16-7.14 (m, 1H), 7.05-7.03 (m, 5H), 6.80-6.78 (m, 4H), 6.58-6.45 (m, 4H), 5.30 (brs, 1H), 4.88-4.85 (m, 2H), 4.67-4.63 (m, 2H), 4.15-4.06 (m, 4H), 3.86-381 (m, 4H), 3.76 (s, 9H), 1.43 (s, 9H).

Step B: 6-(2-aminoethylsulfonyl)-3-(2-(aminomethyl)benzo[d]thiazol-4-yl)-N-(4-methoxybenzyl)-2-(2-(4-methoxybenzyl)-2H-tetrazol-5-yl)benzenesulfonamide Into a 25-mL RBF, was placed a solution of tert-butyl (2-((4-(2-(aminomethyl)benzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate (80 mg, 0.08 mmol) in DCM (2 mL), followed by the addition of TFA (0.5 mL, 6.49 mmol) at 0° C. The resulting mixture was stirred at 20° C. for 1 hour and then the solvent was evaporated to give the crude product which was used directly in the next step: LCMS [M+H]$^+$: 735.

Step C: 6-(2-aminoethylsulfonyl)-3-(2-(aminomethyl)benzo[d]thiazol-4-yl)-2-(2H-tetrazol-5-yl)benzenesulfonamide Into a 25-mL RBF, was placed a solution of 6-((2-aminoethyl)sulfonyl)-3-(2-(aminomethyl)benzo[d]thiazol-4-yl)-N-(4-methoxybenzyl)-2-(2-(4-methoxybenzyl)-2H-tetrazol-5-yl)benzenesulfonamide (60 mg, 0.07 mmol) in TFA (2 mL, 26.0 mmol). The resulting mixture was stirred at 80° C. for 1 hour. The solvent was evaporated and the residue was purified by Prep-HPLC with the following conditions: Column: XSelect CSH Prep C18 OBD Column, 5 μM, 19*150 mm; Mobile Phase A: water with 10 mmol NH$_4$HCO$_3$, Mobile Phase B: MeCN; Flow rate: 20 mL/min; Gradient: 5% B to 40% B in 8 min; 254/220 nm. The collected fractions were combined and concentrated under reducing pressure to afford the title compound: LCMS [M+H]$^+$: 495; $^1$H NMR (400 MHz, CD$_3$OD) δ 8.50 (d, J=8.0 Hz, 1H), 7.96 (d, J=8.0 Hz, 1H), 7.88 (d, J=8.4 Hz, 1H), 7.27 (t, J=8.0 Hz, 1H), 7.10 (d, J=6.8 Hz, 1H), 4.31 (s, 2H), 4.10 (t, J=6.8 Hz, 2H), 3.38 (t, J=6.8 Hz, 2H).

EXAMPLE 88

4-(4-(2-aminoethylsulfonyl)-3-sulfamoyl-2-(2H-tetrazol-5-yl)phenyl)benzo[d]thiazole-2-carboxylic acid

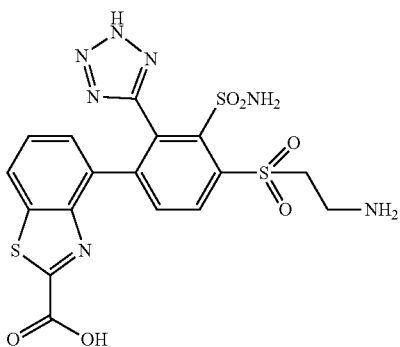 [SMILES: NCCS(=O)(=O)c1ccc(-c2cccc3sc(C(=O)O)nc23)c(-c2nn[nH]n2)c1S(N)(=O)=O]

Step A: methyl 4-(3-(N,N-bis(4-methoxybenzyl)sulfamoyl)-4-((2-((tert-butoxycarbonyl)amino)ethyl)sulfonyl-2-(2-(4-methoxybenzyl)-2H-tetrazol-5-yl)phenyl)benzo[d]thiazole-2-carboxylate Into a 10-mL RBF purged and maintained with an inert atmosphere of argon, was placed a solution of tert-butyl (2-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)ethyl)carbamate (prepared as described above, 0.01 g, 0.11 mmol) in MeOH (2 mL) and THF (0.3 mL). This was followed by the addition of sodium methanolate (10.51 µL, 10.51 µmol) at room temperature. The resulting mixture was stirred under argon atmosphere at 20° C. for 5 minutes. The pH of the mixture was adjusted to 6 with HCl (0.1 M, 0.5 mL), then it was stirred at 20° C. for 30 minutes. The mixture was extracted with EtOAc (3×10 mL). The combined organic layers were washed with brine (1×20 mL), dried over anhydrous sodium sulfate and filtered. The filtrate was evaporated under reduced pressure to afford the title compound: LCMS [M+H]$^+$: 984; $^1$H NMR (400 MHz, CDCl$_3$): δ 8.73 (d, J=8.4 Hz, 1H), 8.01 (d, J=8.4 Hz, 1H), 7.87 (d, J=7.6 Hz, 1H), 7.33-7.31 (m, 1H), 7.16-7.11 (m, 1H), 7.04-7.02 (m, 4H), 6.80-6.76 (m, 4H), 6.62-6.53 (m, 4H), 5.33 (brs, 1H), 4.92-4.85 (m, 2H), 4.69-4.64 (m, 2H), 4.15-4.11 (m, 2H), 4.00 (s, 3H), 3.85-375 (m, 4H), 3.75 (s, 9H), 1.44 (s, 9H).

Step B: methyl 4-(4-(2-aminoethylsulfonyl)-2-(2-(4-methoxybenzyl)-2H-tetrazol-5-yl)-3-(N-(4-methoxybenzyl)sulfamoyl)phenyl)benzo[d]thiazole-2-carboxylate Into a 25-mL RBF, was placed a solution of methyl 4-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)benzo[d]thiazole-2-carboxylate (0.10 g, 0.08 mmol) in DCM (2 mL). This was followed by the addition of TFA (0.5 mL, 6.49 mmol) at 0° C. The resulting mixture was stirred at 20° C. for 1 hour. The solvent was evaporated to give crude product, which was used directly in the next step: LCMS [M+H]$^+$: 764.

Step C: (methyl 4-(4-((2-aminoethyl)sulfonyl)-3-sulfamoyl-2-(2H-tetrazol-5-yl)phenyl)benzo[d]thiazole-2-carboxylate Into a 25-mL RBF, was placed a solution of methyl 4-(4-((2-aminoethyl)sulfonyl)-2-(2-(4-methoxybenzyl)-2H-tetrazol-5-yl)-3-(N-(4-methoxybenzyl)sulfamoyl)phenyl)benzo[d]thiazole-2-carboxylate (70 mg, 0.08 mmol) in TFA (3 mL). The resulting mixture was stirred at 80° C. for 1 hour. The solvent was evaporated to give the crude product which was used directly to the next step: LCMS [M+H]$^+$: 524.

Step D: 4-(4-((2-aminoethyl)sulfonyl)-3-sulfamoyl-2-(2H-tetrazol-5-yl)phenyl)benzo[d]thiazole-2-carboxylic Acid Into a 25-mL RBF, was placed a solution of methyl 4-(4-((2-aminoethyl)sulfonyl)-3-sulfamoyl-2-(2H-tetrazol-5-yl)phenyl)benzo[d]thiazole-2-carboxylate (50 mg, 0.07 mmol) in MeOH (2 mL), followed by the addition of sodium hydroxide (0.22 ml, 0.22 mmol) at 0° C. The resulting mixture was stirred at 20° C. for 1 hour. The solvent was evaporated and the residue was purified by Prep-HPLC with the following conditions: Column: XBridge C18 OBD Prep Column, 100 Å, 5 µm, 19 mm×250 mm; Mobile Phase A: water with 10 mmol NH$_4$HCO$_3$, Mobile Phase B: MeCN; Flow rate: 15 mL/min; Gradient: 17% B to 35% B in 8 min; 254/220 nm. The collected fractions were combined and concentrated under reducing pressure to give the title compound: LCMS [M+H]$^+$: 510; $^1$H NMR (300 MHz, DMSO-d$_6$): δ 8.42 (d, J=8.4 Hz, 1H), 8.02 (d, J=8.1 Hz, 1H), 7.93 (d, J=8.1 Hz, 1H), 7.17 (t, J=7.8 Hz, 1H), 6.69 (d, J=7.5 Hz, 1H), 4.26-4.18 (m, 2H), 3.29 (t, J=7.5 Hz, 2H).

EXAMPLE 89

4-(4-(2-aminoethyl sulfonyl)-3-sulfamoyl-2-(2H-tetrazol-5-yl)phenyl)benzo[d]thiazole-2-carboxamide

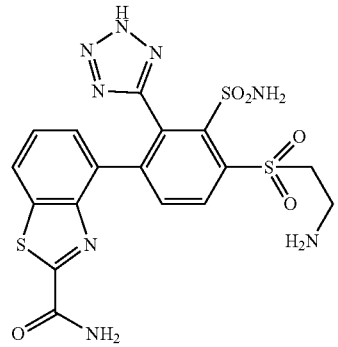 [SMILES: NCCS(=O)(=O)c1ccc(-c2cccc3sc(C(N)=O)nc23)c(-c2nn[nH]n2)c1S(N)(=O)=O]

Step A: tert-butyl (2-((2-(N,N-bis(4-methoxybenzyl)sulfamoyl)-4-(2-carbamoylbenzo[d]thiazol-4-yl)-3-(2-(4-methoxybenzyl)-2H-tetrazol-5-yl)phenyl)sulfonyl)ethyl)carbamate To a mixture of tert-butyl (2-((2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl)sulfonyl)ethyl)

carbamate (from synthesis of 4-(4-(2-aminoethyl sulfonyl)-3-sulfamoyl-2-(2H-tetrazol-5-yl)phenyl)benzo[d]thiazole-2-carboximidamide, Step B, 70 mg, 0.07 mmol) in methanol (2 mL) and H$_2$O (2 mL) was added sodium hydroxide (6 mg, 0.14 mmol) at 0° C. The resulting mixture was stirred at 25° C. for 2 hours and then was concentrated under reduced pressure. The residue was purified by a silica gel chromatography, eluting with ethyl acetate/petroleum ether (1:50-1:3) to afford the title compound: LCMS [M+H]$^+$: 969; $^1$H NMR (300 MHz, DMSO-d$_6$) δ 8.75 (d, J=8.4 Hz, 1H), 8.29 (d, J=8.4 Hz, 1H), 8.17 (d, J=8.1 Hz, 1H), 8.08-8.06 (m, 1H), 7.91-7.88 (m, 1H), 7.38 (t, J=7.8 Hz, 1H), 7.15-7.11 (m, 1H), 7.00-6.96 (m, 5H), 6.87-6.84 (m, 4H), 6.64-6.62 (m, 3H), 4.95-4.91 (m, 2H), 4.62-4.58 (m, 2H), 4.05-3.89 (m, 4H), 3.70 (s, 9H), 3.51-3.49 (m, 2H), 1.35 (s, 9H).

Step B: 4-(4-(2-aminoethylsulfonyl)-3-sulfamoyl-2-(2H-tetrazol-5-yl)phenyl)benzo[d]thiazole-2-carboxamide A mixture of tert-butyl (2-((2-(N,N-bis(4-methoxybenzyl)sulfamoyl)-4-(2-carbamoylbenzo[d]thiazol-4-yl)-3-(2-(4-methoxybenzyl)-2H-tetrazol-5-yl)phenyl)sulfonyl)ethyl)carbamate (0.10 g, 0.10 mmol) in TFA (2 mL) was stirred at 25° C. and for 45 min. The reaction mixture was concentrated under reduced pressure. The crude product was added to TFA (2 mL) and stirred at 80° C. for 2 hours. The reaction mixture was concentrated under reduced pressure, 4-(4-((2-aminoethyl)sulfonyl)-3-sulfamoyl-2-(2H-tetrazol-5-yl)phenyl)benzo[d]thiazole-2-carboxamide and the residue was purified by Prep-HPLC. Column, Xbridge C 18, 19×150 mm; mobile phase: acetonitrile in water (0.05% NH$_4$HCO$_3$), 34%-95% in 8 min; Detector, UV 254 nm. RT: 6.82 min. The collected fractions were combined and concentrated under reduced pressure to give the title compound as a solid: LCMS [M+H]$^+$: 509; $^1$H NMR (400 MHz, DMSO-d$_6$) δ 8.37 (d, J=8.4 Hz, 1H), 8.09-8.03 (m, 3H), 7.96-7.87 (m, 5H), 7.33 (t, J=7.6 Hz, 1H), 6.87-6.85 (m, 1H), 4.18 (t, J=7.2 Hz, 1H), 3.36-3.34 (m, 2H).

EXAMPLE 90

6-(2-aminoethylsulfonyl)-3-(2-(methylamino)benzo[d]thiazol-4-yl)-2-(2H-tetrazol-5-yl)benzene sulfonamide

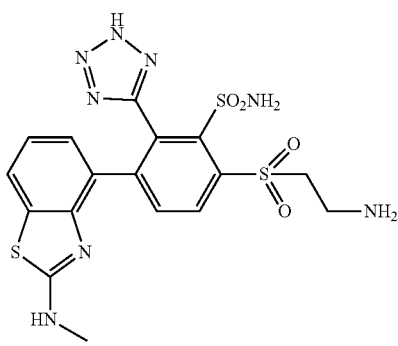 [SMILES: CNc1nc2c(-c3ccc(S(=O)(=O)CCN)c(S(N)(=O)=O)c3-c3nn[nH]n3)cccc2s1]

Step A: tert-butyl 2-(2-(N,N-bis(4-methoxybenzyl)sulfamoyl)-3-(2-(4-methoxybenzyl)-2H-tetrazol-5-yl)-4-(2-(methylamino)benzo[d]thiazol-4-yl)phenylsulfonyl)ethylcarbamate Into a 25-mL RBF purged and maintained with an inert atmosphere of argon, was placed tert-butyl (2-((2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl)sulfonyl)ethyl)carbamate (synthesis described above, 0.16 g, 0.16 mmol). This was followed by the addition of methylamine (3.18 mL, 6.37 mmol) in THF (4 mL) at room temperature. The resulting mixture was stirred under argon atmosphere at 60° C. for 4 hours. The reaction was cooled to 20° C. and the solvent was evaporated under reduced pressure, the residue was purified by silica gel chromatography, eluting with EtOAc in petroleum ether (1/1) to afford the title compound: LCMS [M+H]$^+$: 955.2; $^1$H NMR (400 MHz, CD$_3$Cl): δ 8.65 (d, J=8.8 Hz, 1H), 8.06 (d, J=8.8 Hz, 1H), 7.98 (d, J=8.0 Hz, 1H), 7.03-7.00 (m, 4H), 6.88-6.85 (m, 2H), 6.78-6.73 (m, 5H), 6.65-6.63 (m, 2H), 5.30 (brs, 1H), 5.05-4.96 (m, 2H), 4.67-4.64 (m, 2H), 4.14-4.10 (m, 3H), 3.79-377 (m, 1H), 3.76 (s, 9H), 3.02-2.98 (m, 5H), 1.44 (s, 9H).

Step B: 6-((2-aminoethyl)sulfonyl)-N-(4-methoxybenzyl)-2-(2-(4-methoxybenzyl)-2H-tetrazol-5-yl)-3-(2-(methylamino)benzo[d]thiazol-4-yl)benzenesulfonamide Into a 25-mL RBF, was placed a solution of tert-butyl (2-((2-(N,N-bis(4-methoxybenzyl)sulfamoyl)-3-(2-(4-methoxybenzyl)-2H-tetrazol-5-yl)-4-(2-(methylamino)benzo[d]thiazol-4-yl)phenyl)sulfonyl)ethyl)carbamate (0.14 g, 0.13 mmol) in DCM (2 ml). This was followed by the addition of TFA (0.5 ml, 6.49 mmol) at 0° C. The resulting mixture was stirred at 20° C. for 1 hour. The solvent was evaporated to afford the title compound, which was used directly into next step: LCMS [M+H]$^+$: 735.1.

Step C: 6-((2-aminoethyl)sulfonyl)-3-(2-(methylamino)benzo[d]thiazol-4-yl)-2-(2H-tetrazol-5-yl)benzenesulfonamide Into a 25-mL RBF, was placed a solution of 6-((2-aminoethyl)sulfonyl)-N-(4-methoxybenzyl)-2-(2-(4-methoxybenzyl)-2H-tetrazol-5-yl)-3-(2-(methylamino)benzo[d]thiazol-4-yl)benzenesulfonamide (0.10 g, 0.11 mmol) in TFA (3 ml, 38.9 mmol). The resulting mixture was stirred at 80° C. for 1 hour. The solvent was evaporated and the residue was purified by Prep-HPLC with the following conditions: Column: XBridge C18 OBD Prep Column, 100 Å, 5 μm, 19 mm×250 mm; Mobile Phase A: water with 10 mmol NH4HCO3, Mobile Phase B: MeCN; Flow rate: 15 mL/min; Gradient: 17% B to 35% B in 8 min; RT: 5.1 Min, 254/220 nm. The collected fractions were combined and concentrated under reducing pressure to give the title compound: LCMS [M+H]$^+$: 495.0; $^1$H NMR (400 MHz, DMSO): δ 8.27 (d, J=8.4 Hz, 1H), 8.02 (d, J=8.4 Hz, 1H), 7.98-7.96 (m, 1H), 7.71 (brs, 4H), 7.51 (d, J=7.6 Hz, 1H), 6.68 (t, J=8.0 Hz, 1H), 6.37 (d, J=7.6 Hz, 1H), 4.15 (t, J=7.6 Hz, 1H), 3.29 (t, J=7.6 Hz, 1H), 2.88 (d, J=4.4 Hz, 4H).

EXAMPLE 91

4-(4-((2-aminoethyl)sulfonyl)-3-sulfamoyl-2-(2H-tetrazol-5-yl)phenyl)-1H-benzo[d]imidazole-2-carboxylic Acid

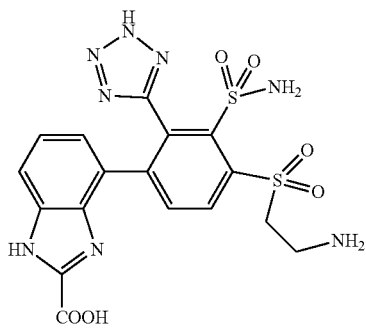 [SMILES: NCCS(=O)(=O)c1ccc(-c2cccc3[nH]c(C(=O)O)nc23)c(-c2nn[nH]n2)c1S(N)(=O)=O]

Step A: tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate Into a 50 mL RBF was placed 3-(4,4,5,5-tetramethyl-1,3,2-dioxaborolan-2-yl)benzene-1,2-diamine (153 mg, 0.653 mmol), tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (300 mg, 0.327 mmol), Pd(PPh$_3$)$_4$ (75 mg, 0.065 mmol) and sodium carbonate (104 mg, 0.980 mmol) in 1,4-dioxane (1.5 ml) and water (0.375 ml). The reaction mixture was degassed with nitrogen 3 times and stirred at 80° C. for 6 hours. Then the mixture was extracted with ethyl acetate (20 mL) and washed with water (20 mL). The organic layer was concentrated under vacuum. The residue was applied on a silica gel column with ethyl acetate/petrol ether(1/1) to give the title compound: LCMS [M+H]$^+$: 899; $^1$H NMR (300 MHz, d-DMSO): δ 8.65-8.63 (d, J=8.1 Hz, 1H), 8.13-8.10 (d, J=8.4 Hz, 1H), 7.23-7.06 (m, 1H), 7.06-6.89 (m, 6H), 6.89-6.71 (m, 6H), 6.55-6.39 (d, J=7.2 Hz, 1H), 6.31-6.12 (t, J=7.5 Hz, 1H), 5.96-5.80 (d, J=7.5 Hz, 1H), 5.02 (s, 2H), 4.80-4.39 (m, 4H), 4.10-3.92 (m, 2H), 3.71 (s, 9H), 3.53-3.38 (m, 2H), 1.35 (s, 9H).

Step B: tert-butyl (2-((2-(N,N-bis(4-methoxybenzyl)sulfamoyl)-3-(2-(4-methoxybenzyl)-2H-tetrazol-5-yl)-4-(2-(trichloromethyl)-1H-benzo[d]imidazol-4-yl)phenyl)sulfonyl)ethyl)carbamate Benzyl 2,2,2-trichloroacetimidate (47.7 mg, 0.189 mmol) was added to a solution of tert-butyl (2-((2'-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (170 mg, 0.189 mmol) in acetic acid (2 ml). After the mixture was stirred at RT for 1 hour, it was concentrated under reduced pressure to give the title compound: LCMS [M+H]$^+$: 1025, 1027, 1028 (8:10:5).

Step C: methyl 4-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-benzo[d]imidazole-2-carboxylate Into a 50 mL RBF was placed tert-butyl (2-((2-(N,N-bis(4-methoxybenzyl)sulfamoyl)-3-(2-(4-methoxybenzyl)-2H-tetrazol-5-yl)-4-(2-(trichloromethyl)-1H-benzo[d]imidazol-4-yl)phenyl)sulfonyl)ethyl)carbamate (170 mg, 0.166 mmol) and sodium carbonate (17.55 mg, 0.166 mmol) in methanol (2 ml). After the resulting mixture was stirred at 75° C., it was concentrated under vacuum. The residue was extracted with ethyl acetate (3×50 mL) and washed with hydrogen chloride (1 mol in water 2×100 mL). Then the organic layer was concentrated under vacuum. The residue was applied on a silica gel column with ethyl acetate/petrol ether (2/1) to give the title compound: LCMS [M+H]$^+$: 967.

Step D: methyl 4-(4-((2-aminoethyl)sulfonyl)-2-(2-(4-methoxybenzyl)-2H-tetrazol-5-yl)-3-(N-(4-methoxybenzyl)sulfamoyl)phenyl)-1H-benzo[d]imidazole-2-carboxylate Into a 50 mL RBF was placed methyl 4-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-benzo[d]imidazole-2-carboxylate (90 mg, 0.093 mmol) in DCM (1 ml) and trifluoroacetic acid (0.500 ml). The resulting mixture was stirred at RT for 1 hour. Then the mixture was concentrated under vacuum. The residue was used for next step directly: LCMS [M+H]$^+$: 747.

Step E: methyl 4-(4-((2-aminoethyl)sulfonyl)-3-sulfamoyl-2-(2H-tetrazol-5-yl)phenyl)-1H-benzo[d]imidazole-2-carboxylate Into a 25 mL RBF was placed methyl 4-(4-((2-aminoethyl)sulfonyl)-2-(2-(4-methoxybenzyl)-2H-tetrazol-5-yl)-3-(N-(4-methoxybenzyl)sulfamoyl)phenyl)-1H-benzo[d]imidazole-2-carboxylate (70 mg, 0.094 mmol) in trifluoroacetic acid (1.5 ml). The mixture was stirred at 80° C. and concentrated under vacuum. The residue was applied on flash with methanol/water (0-50% in 25 min) to give the title compound: LCMS [M+H]$^+$: 507.

Step F: 4-(4-((2-aminoethyl)sulfonyl)-3-sulfamoyl-2-(2H-tetrazol-5-yl)phenyl)-1H-benzo[d]imidazole-2-carboxylic acid Into a 25 mL RBF was placed methyl 4-(4-((2-aminoethyl)sulfonyl)-3-sulfamoyl-2-(2H-tetrazol-5-yl)phenyl)-1H-benzo[d]imidazole-2-carboxylate (80 mg, 0.158 mmol) in methanol (1 ml) and water (1.000 ml). NaOH (0.48 mL, 0.48 mmol, 1M aqueous solution) was added. After the resulting mixture was stirred at RT for 2 hours, it was adjusted to pH 4 with conc. HCl. The resulting mixture was applied on Prep-HPLC (condition: Column: Sunfire Prep C18 OBD Column 19*150 mm 5 μM 10 nm; Mobile Phase A: water with 0.05% TFA, Mobile Phase B: MeCN; Flow rate: 20 mL/min; Gradient: 5% B to 35% B in 8 min; 254/220 nm) to give the title compound: LCMS [M+H]$^+$: 493; $^1$H NMR (400 MHz, d-DMSO): δ 8.58-8.56 (d, J=8.4 Hz, 1H), 8.18-8.16 (d, J=8.4 Hz, 1H), 8.00 (brs, 3H), 7.52-7.50 (d, J=8.0 Hz, 1H), 7.34 (brs, 2H), 7.19-7.15 (t, J=8.0 Hz, 1H), 6.70-6.68 (d, J=6.8 Hz, 1H), 4.23-4.14 (t, J=7.6 Hz, 2H), 3.35-3.30 (t, J=7.2 Hz, 2H).

EXAMPLE 92

3-(2-amino-1H-benzo[d]imidazol-4-yl)-6-((S)-2-aminopropylsulfonyl)-2-(2H-tetrazol-5-yl)benzenesulfonamide

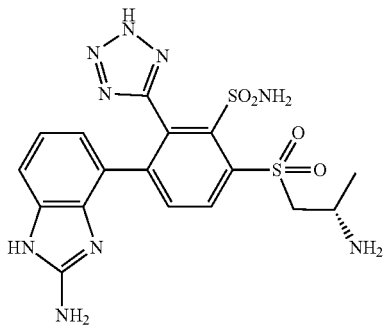 [SMILES: C[C@H](N)CS(=O)(=O)c1ccc(-c2cccc3[nH]c(N)nc23)c(-c2nn[nH]n2)c1S(N)(=O)=O]

Step A: (S)-2-((tert-butoxycarbonyl)amino)propyl methanesulfonate

Into a 50-mL RBF purged and maintained with an inert atmosphere of argon, was placed a solution of (S)-tert-butyl (1-hydroxypropan-2-yl)carbamate (1.00 g, 5.71 mmol) and TEA (2.39 mL, 17.12 mmol) in DCM (10 mL). This was followed by the addition of MsCl (0.53 mL, 6.85 mmol) at 0° C. The resulting mixture was stirred under argon atmosphere at room temperature for 20 minutes. The reaction was quenched with ice water (50 mL) and extracted with EtOAc (3×50 mL). The combined organic layers were washed with brine (4×25 mL), dried over anhydrous sodium sulfate and filtered. The filtrate was evaporated to afford the title compound, which was used directly in the next step: LCMS [M+H-100]$^+$: 154; $^1$H NMR (300 MHz, CD$_3$Cl) δ 4.59 (brs, 1H), 4.24-4.21 (m, 1H), 4.18-4.13 (m, 1H), 3.98-3.96 (m, 1H), 3.04 (s, 3H), 1.45 (s, 9H), 1.24 (d, J=6.9 Hz, 3H).

Step B: (S)—S-(2-((tert-butoxycarbonyl)amino)propyl) ethanethioate

Into a 50 mL RBF purged and maintained with an inert atmosphere of argon, was placed a solution of (S)-2-((tert-butoxycarbonyl)amino)propyl methanesulfonate (1.40 g, 4.42 mmol) in DMF (10 mL), followed by the addition of potassium ethanethioate (2.02 g, 17.69 mmol) at room temperature. The resulting mixture was stirred under argon atmosphere at 80° C. for 16 hours. The reaction was cooled to 20° C. and quenched with ice water (150 mL) and extracted with EtOAc (3×150 mL). The combined organic layers were washed with brine (2×200 mL), dried over anhydrous sodium sulfate and filtered. The filtrate was evaporated and the residue was purified by silica gel chromatography, eluting with EtOAc in Pet. ether (1/5) to afford the title compound: LCMS [2M+H]$^+$: 467; $^1$H NMR (300 MHz, CD$_3$Cl) δ 4.54 (brs, 1H), 3.87-3.85 (m, 1H), 3.05-3.02 (m, 2H), 2.36 (s, 3H), 1.44 (s, 9H), 1.22 (d, J=6.6 Hz, 3H).

Step C: (S)-tert-butyl(1-mercaptopropan-2-yl)carbamate

Into a 100-mL RBF purged and maintained with an inert atmosphere of argon, was placed a solution of (S)—S-(2-((tert-butoxycarbonyl)amino)propyl) ethanethioate (1.00 g, 3.64 mmol) in MeOH (10 mL), followed by the addition of potassium carbonate (0.48 mL, 10.93 mmol) at 0° C. The resulting mixture was stirred under argon atmosphere at room temperature for 3 hours. The pH of the mixture was adjusted to ~7 at 0° C. and extracted with EtOAc (3×50 mL). The combined organic layers were washed with brine (4×25 mL), dried over anhydrous sodium sulfate and filtered. The filtrate was evaporated to afford the crude title compound, which was used directly in the next step: LCMS [2M+H]$^+$: 383; $^1$H NMR (300 MHz, DMSO-d$_6$) δ 6.78 (brs, 1H), 3.51-3.46 (m, 1H), 2.54-2.48 (m, 1H), 2.24-2.18 (m, 1H), 1.38 (s, 9H), 1.06 (d, J=6.6 Hz, 3H).

Step D: (S)-tert-butyl (1-((2-(N,N-bis(4-methoxybenzyl)sulfamoyl)-4-iodo-3-(2-(4-methoxybenzyl)-2H-tetrazol-5-yl)phenyl)thio)propan-2-yl)carbamate Into a 100-mL RBF purged and maintained with an inert atmosphere of argon, was placed a solution of 6-bromo-3-iodo-N,N-bis(4-methoxybenzyl)-2-(2-(4-methoxybenzyl)-2H-tetrazol-5-yl)benzenesulfonamide (1.00 g, 1.27 mmol) and (S)-tert-butyl (1-mercaptopropan-2-yl)carbamate (0.97 g, 5.06 mmol) in DMF (10 mL), followed by the addition of sodium hydride (0.20 g, 5.06 mmol) at 0° C. The resulting mixture was stirred at 20° C. for 1 hour under atmosphere of argon. The reaction was quenched with water (100 mL) and extracted with EA (3×100 mL). The combined layers were washed with brine (2×200 mL), dried over anhydrous sodium sulfate and filtered. The filtrate was evaporated and the residue was purified by silica gel chromatography, eluting with EA/PE (1/1) to afford the title compound: LCMS [M+H]$^+$: 901;

$^1$H NMR (300 MHz, DMSO-d$_6$) δ 8.06-7.93 (m, 1H), 7.75-7.63 (m, 1H), 7.31-7.21 (m, 2H), 6.95-6.92 (m, 4H), 6.79-6.75 (m, 5H), 5.79-5.78 (m, 1H), 5.52-5.47 (m, 0.5H), 5.13-5.08 (m, 0.5H), 4.74-4.62 (m, 2H), 4.31-4.25 (m, 1H), 3.98-3.87 (m, 2H), 3.79 (s, 9H), 3.38-3.28 (m, 1H), 3.37-3.25 (m, 1H), 1.45 (s, 9H), 1.16 (d, J=6.3 Hz, 2H), 1.09 (d, J=6.3 Hz, 1H).

Step E: (S)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate Into a 50-mL RBF purged and maintained with an inert atmosphere of argon, was placed a solution of (S)-tert-butyl (1-((2-(N,N-bis(4-methoxybenzyl)sulfamoyl)-4-iodo-3-(2-(4-methoxybenzyl)-2H-tetrazol-5-yl)phenyl)thio)propan-2-yl)carbamate (0.80 g, 0.76 mmol) in DCM (8 mL), followed by the addition of m-CPBA (0.52 g, 3.02 mmol) at room temperature. The resulting mixture was stirred at 20° C. for 16 hours under atmosphere of argon. The reaction was quenched with NaHSO$_4$ (10%, 50 mL) and extracted with EA (3×50 mL). The combined layers were washed with NaHCO$_3$ (saturated, 3×40 mL), brine (3×40 mL), dried over anhydrous sodium sulfate and filtered. The filtrate was evaporated and the residue was purified by silica gel chromatography, eluting with EA/PE (2/1) to afford the title compound: LCMS [M+H]$^+$: 933; $^1$H NMR (300 MHz, DMSO-d$_6$) δ 8.32-8.21 (m, 2H), 6.97-6.94 (m, 3H), 6.89-6.87 (m, 2H), 6.80-6.73 (m, 7H), 5.78 (brs, 1H), 5.54-5.46 (m, 0.5H), 5.30-5.20 (m, 0.5H), 4.85-4.76 (m, 1H), 4.49-4.36 (m, 2H), 4.15-4.02 (m, 4H), 3.79-3.77 (m, 1H), 3.76 (s, 9H), 1.39 (s, 9H), 1.37-1.34 (m, 3H).

Step F: (S)-tert-butyl (1-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate Into a 25-mL RBF purged and maintained with an inert atmosphere of argon, was placed a solution of (S)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (0.20 g, 0.18 mmol), Pd(PPh$_3$)$_4$ (42 mg, 0.04 mmol) and (2-amino-1H-benzo[d]imidazol-4-yl)boronic acid (97 mg, 0.547 mmol) in dioxane (3 ml) followed by the addition of sodium carbonate (58 mg, 0.55 mmol) in water (0.5 mL) at room temperature. The resulting mixture was stirred at under argon atmosphere at 80° C. for 16 hours. The reaction was cooled to 20° C. and quenched with water (50 mL) and extracted with EA (3×50 mL). The combined organic layers were washed with brine (1×100 mL), dried over anhydrous sodium sulfate and filtered. The filtrate was evaporated under reduced pressure and the residue was purified by silica gel chromatography, eluting with MeOH/DCM (1/9) to give the title compound: LCMS [M+H]$^+$: 938;

Step G: ((S)-3-(2-amino-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide Into a 25-mL RBF, was placed a solution of (S)-tert-butyl (1-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate (0.10 g, 0.11 mmol) in DCM (3 mL) followed by the addition of TFA (0.5 mL, 6.49 mmol) at 0° C. The resulting mixture was stirred at 20° C. for 1 hour. The solvent was evaporated to give crude product. The crude product was used directly in the next step: LCMS [M+H]$^+$: 718.

Step H: (S)-3-(2-amino-1H-benzo[d]imidazol-4-yl)-6-((2-aminopropyl)sulfonyl)-2-(2H-tetrazol-5-yl)benzenesulfonamide Into a 25-mL RBF, was placed a solution of (S)-3-(2-amino-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide (70 mg, 0.07 mmol) in TFA (3 mL). The resulting mixture was stirred at 80° C. for 1 hour. The solvent was evaporated and the residue was purified by Prep-HPLC with the following conditions: Column: XSelect CSH Prep C18 OBD Column, 19×150 mm; Mobile Phase A: water with 10 mmol NH$_4$HCO$_3$, Mobile Phase B: MeCN; Flow rate: 20 mL/min; Gradient: 5% B to 35% B in 8 min; RT, 5.4 Min; 254/220 nm. The collected fractions were combined and concentrated under reducing pressure to give the title compound: LCMS [M+H]$^+$: 478; $^1$H NMR (300 MHz, DMSO-d$_6$) δ 8.29 (d, J=8.4 Hz, 1H), 8.04 (d, J=8.4 Hz, 1H), 6.93 (d, J=6.9 Hz, 1H), 6.52 (t, J=7.8 Hz, 1H), 6.27 (brs, 2H), 6.10 (d, J=7.5 Hz, 1H), 4.16-4.01 (m, 2H), 3.84-3.75 (m, 1H), 1.36 (d, J=6.6 Hz, 3H).

EXAMPLE 93

3-(2-aminobenzo[d]thiazol-4-yl)-6-((S)-2-aminopropylsulfonyl)-2-(2H-tetrazol-5-yl)benzenesulfonamide

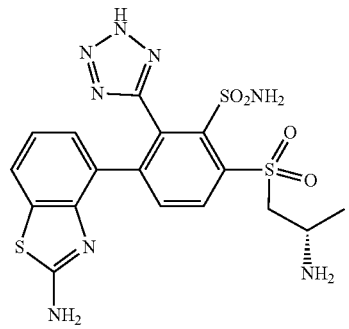 [SMILES: C[C@H](N)CS(=O)(=O)c1ccc(-c2cccc3sc(N)nc23)c(-c2nn[nH]n2)c1S(N)(=O)=O]

Step A: tert-butyl (S)-1-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)propan-2-ylcarbamate A mixture of (R)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (prepared as described above, Steps A-E, 250 mg, 0.268 mmol), (2-aminobenzo[d]thiazol-4-yl)boronic acid (78 mg, 0.402 mmol), 1,1'-Bis(diphenylphosphino)ferrocene-palladium(II) dichloride DCM complex (43.7 mg, 0.054 mmol) and sodium carbonate (85 mg, 0.804 mmol) in dioxane/H$_2$O=4/1 (1.0 mL) was prepared. The reaction mixture was degassed with nitrogen 3 times and stirred for 4 hours at 80° C. The reaction mixture was quenched with water (10 mL), and extracted with DCM (3×15 mL). The combined organic layers were washed with water (1×15 mL) and brine (1×15 mL), dried over anhydrous sodium sulfate and filtered. The filtrate was concentrated under vacuum. The residue was purified by silica gel column chromatography, then eluted with petroleum ether/ethyl acetate (1/1). The combined organic fractions were concentrated under reduced pressure to give the title compound: LCMS [M+H]$^+$: 955

Step B: (S)-3-(2-aminobenzo[d]thiazol-4-yl)-6-((2-aminopropyl)sulfonyl)-N-(4-methoxybenzyl)-2-(2-(4-methoxybenzyl)-2H-tetrazol-5-yl)benzenesulfonamide Into a 10 mL flask was placed (S)-tert-butyl (1-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate (200 mg, 0.209 mmol), and DCM (2.0 mL). Trifluoric acid (2 mL, 26.0 mmol) was added at 0° C. The reaction mixture was stirred at room temperature for 1 hour. The solvent was removed under vacuum to afford the title compound, which was used in next step without further purification: LCMS [M+H]$^+$: 735.

Step C: (S)-3-(2-aminobenzo[d]thiazol-4-yl)-6-((2-aminopropyl)sulfonyl)-2-(2H-tetrazol-5-yl)benzenesulfonamide Into a 25 mL flask was placed (S)-3-(2-aminobenzo[d]thiazol-4-yl)-6-((2-aminopropyl)sulfonyl)-N-(4-methoxybenzyl)-2-(2-(4-methoxybenzyl)-2H-tetrazol-5-yl)benzenesulfonamide (120 mg, 0.163 mmol), and trifluoroacetic acid (2 mL, 26.0 mmol). The reaction mixture was stirred at 80° C. for 2 hours. The solvent was removed under vacuum. The product was purified by Prep-HPLC with the following conditions: (Column: X Bridge C18, 19*150 mm, 5 µM; Mobile Phase A: water/0.05% NH$_4$HCO$_3$, Mobile Phase B: ACN; Flow rate: 20 mL/min; Gradient: 23-60% B in 8 min; 254 nm). The collected fractions were combined and concentrated under vacuum to give the title compound: LCMS [M+H]$^+$: 495; $^1$H NMR (300 MHz, DMSO-d6): δ 8.26 (d, J=8.4 Hz, 1H), 7.90 (d, J=8.4 Hz, 1H), 7.85-7.54 (m, 4H), 7.48 (t, J=3.3 Hz, 1H), 6.71 (t, J=7.8 Hz, 1H), 6.53-6.47 (m, 1H), 4.17-4.02 (m, 2H), 3.81 (dd, J$_a$=6.6 Hz, J$_b$=12.6 Hz, 1H), 1.38 (d, J=6.6 Hz, 3H);

EXAMPLE 94

6-(2-amino-2-methylpropylsulfonyl)-3-(2-aminobenzo[d]thiazol-4-yl)-2-(2H-tetrazol-5-yl)benzenesulfonamide

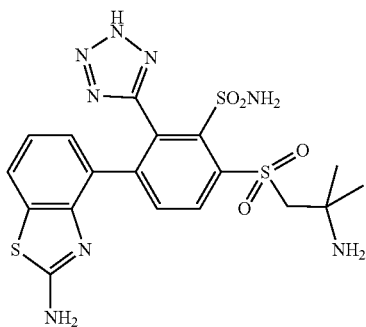 [SMILES: CC(C)(N)CS(=O)(=O)c1ccc(-c2cccc3sc(N)nc23)c(-c2nn[nH]n2)c1S(N)(=O)=O]

Step A: tert-butyl 1-hydroxy-2-methylpropan-2-ylcarbamate

In a 100 mL three-necked RBF, 4-methylmorpholine (6.50 ml, 24.60 mmol) was added drop wise to a stirred mixture of 2-((tert-butoxycarbonyl)amino)-2-methylpropanoic acid (5.00 g, 24.60 mmol) in tetrahydrofuran (10 ml) at −10° C. Then isobutyl carbonochloridate (7.80 ml, 24.60 mmol) was added dropwise to the mixture under nitrogen. The reaction mixture was stirred at −10° C. for 1 hour. The solids were filtered out. The filtrate was added dropwise to the sodium borohydride (1.86 g, 49.2 mmol) in water (20 mL). The reaction was stirred for 30 minutes. The reaction mixture was quenched with water/ice (20 mL), extracted with ethyl acetate (3×100 mL). The combined organic layers were washed with brine (3×50 mL), dried over anhydrous sodium sulfate and filtered. The filtrate was concentrated under vacuum. The residue was purified by silica gel column chromatography, eluting with ethyl acetate/petroleum ether (1/10) to give the title compound. LCMS [M+H]$^+$: 190. $^1$H NMR (400 MHz, DMSO-d$_6$): 4.69 (t, J=5.6 Hz, 1H), 3.29 (d, J=6.0 Hz, 2H), 1.37 (s, 9H), 1.16 (s, 6H).

Step B: S-(2-((tert-butoxycarbonyl) amino)-2-methylpropyl) ethanethioate

In the 50 mL three-necked RBF, diisopropyl diazene-1,2-dicarboxylate (5.13 g, 25.4 mmol) was added to a stirred mixture of tert-butyl (1-hydroxy-2-methylpropan-2-yl)carbamate (1.60 g, 8.45 mmol), and triphenylphosphine (6.65 g, 25.4 mmol) in tetrahydrofuran (10 ml) at −10° C. under nitrogen. The reaction mixture was stirred at −10° C. for 30 min. Ethanethioic S-acid (1.28 g, 16.91 mmol) was added dropwise to the mixture at that temperature. The reaction mixture was stirred at room temperature overnight. The mixture was concentrated under vacuum. The residue was purified by silica gel column chromatography, eluted with ethyl acetate/petroleum ether (1/5) to give the title compound. $^1$H NMR (300 MHz, CDCl$_3$): 4.97 (s, 1H), 3.46 (d, J=6.6 Hz, 2H), 2.25 (s, 3H), 1.39 (s, 9H), 1.28 (s, 6H)

Step C: di-tert-butyl (disulfanediylbis(2-methylpropane-2,1-diyl))dicarbamate

In a 50 ml RBF, NaOH (0.51 g, 12.94 mmol) was added to a stirred mixture of S-(2-((tert-butoxycarbonyl)amino)-2-methylpropyl) ethanethioate (1.6 g, 6.47 mmol) in 10 ml methanol/water (20/1) at room temperature. The reaction mixture was stirred at room temperature for 0.5 hour. The mixture was adjusted to pH 5 with 1N HCl and then extracted with ethyl acetate (3×50 mL). The organic layer was combined, then dried over sodium sulfate. The filtrate was concentrated under vacuum and the residue was purified by silica gel column chromatography, eluted with ethyl acetate/petroleum ether (1/10) to give the title compound. LCMS [M+H]$^+$: 409. $^1$H NMR (300 MHz, CDCl3): 2.85 (d, J=9.0 Hz 2H), 1.45 (s, 9H), 1.25 (s, 6H).

Step D: tert-butyl (1-mercapto-2-methylpropan-2-yl)carbamate

In a 50 mL RBF, zinc (0.88 g, 13.46 mmol) was added to a stirred mixture of di-tert-butyl ((disulfanediylbis(2-methylpropane-2,1-diyl))dicarbamate (1.10 g, 2.69 mmol) in zinc (0.88 g, 13.46 mmol) at room temperature. The reaction mixture was stirred at 50° C. overnight. The solids were filtered out and the filtrate was concentrated to give the title compound. LCMS [M+H−56]$^+$: 150. $^1$H NMR (300 MHz, CDCl3): 4.78 (brs, 1H), 2.85) d, J=8.4 Hz 2H),1.44 (s, 9H), 1.27 (s, 6H).

Step E: tert-butyl (1-((2-(N,N-bis(4-methoxybenzyl)sulfamoyl)-4-iodo-3-(2-(4-methoxybenzyl)-2H-tetrazol-5-yl)phenyl)thio)-2-methylpropan-2-yl)carbamate In the 50 mL three-necked RBF, cesium carbonate (2.47 g, 7.59 mmol) was added to a stirred mixture of tert-butyl (1-mercapto-2-methylpropan-2-yl)carbamate (0.78 g, 3.80 mmol), 6-bromo-3iodo-N,N-bis(4-methoxybenzyl)-2-(2-(4-methoxybenzyl)-2H-tetrazol-5-yl)benzenesulfonamide (1.50 g, 1.89 mmol) in N,N-dimethylformamide (5 ml) at room temperature. The reaction mixture was stirred at room temperature overnight under nitrogen and then diluted with water (20 mL extracted with ethyl acetate (3×50 mL). The combined organic layer was dried over sodium sulfate, filtered and concentrated. The residue was purified by silica gel column chromatography, eluted with ethyl acetate/petroleum ether (1/2) to give the title compound. LCMS [M+H]$^+$: 915. $^1$H NMR (300 MHz, CDCl$_3$): δ 7.97 (d, J=8.4 Hz, 1H), 7.88 (d, J=8.7 Hz, 1H), 7.48-7.42 (m, 1H), 7.32-7.26 (m, 1H), 6.94-6.90 (m, 4H), 6.82-6.75 (m, 6H), 5.75-5.12 (m, 1H), 4.73-4.68 (m, 2H), 4.21-4.13 (m, 2H), 3.94-3.89 (m, 1H), 3.76 (s, 9H), 3.73 (s, 2H), 1.43 (s, 9H), 1.26 (s, 6H)

Step F: tert-butyl (1-((2-(N,N-bis(4-methoxybenzyl) sulfamoyl)-4-iodo-3-(2-(4-methoxybenzyl)-2H-tetrazol-5-yl)phenyl)sulfonyl)-2-methylpropan-2-yl)carbamate In the 50 mL RBF, 3-chlorobenzoperoxoic acid (1.30 g, 7.54 mmol) was added to a stirred mixture of tert-butyl (1-((2-(N,N-bis(4-methoxybenzyl)sulfamoyl)-4-iodo-3-(2-(4-methoxybenzyl)-2H-tetrazol-5-yl)phenyl)thio)-2-methylpropan-2-yl)carbamate (1.15 g, 1.257 mmol) in dichloroemethane (5 ml) at room temperature. The reaction mixture was stirred at room temperature overnight. The reaction mixture was quenched with sodium bisulfate (10 mL), extracted with ethyl acetate (3×50 mL). The combined organic layers were washed with brine (1×10 mL), dried over anhydrous sodium sulfate, filtered and concentrated under vacuum. The residue was purified by silica gel column chromatography, eluted with ethyl acetate/petroleum ether (1/2) to give the title compound. LCMS [M+H]$^+$: 947. $^1$H NMR (300 MHz, CDCl$_3$): δ:8.50 (d, J=8.4 Hz, 1H), 8.25-8.21 (m, 1H), 7.43-7.26 (m, 1H), 7.32-7.26 (m, 1H), 6.914-6.88 (m, 2H), 6.79-6.69 (m, 8H), 5.45-5.22 (m, 1H), 4.62-4.10 (m, 2H), 4.10-4.00 (m, 2H), 3.94-3.89 (m, 1H), 3.74 (s, 9 H), 3.61 (s, 2H), 1.48 (s, 9H), 1.25 (s, 6H).

Step G: tert-butyl(1-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-2-methylpropan-2-yl)carbamate In a 50 three-necked RBF, tetrakis(triphenylphosphine)palladium(0) (0.18 g, 0.156 mmol) was added to a stirred mixture of sodium carbonate (0.25 g, 2.345 mmol), tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)-2-methylpropan-2-yl)carbamate (0.74 mg, 0.782 mmol), (2-aminobenzo[d]thiazol-4-yl)boronic acid (0.30 g, 1.563 mmol) in dioxane/water (4/1) (4 ml) at room temperature. The reaction mixture was stirred at 80° C. for 2 hours under nitrogen. The solids were filtered out and the filtrate was concentrated under reduced pressure. The residue was purified by silica gel column chromatography, eluted with ethyl acetate/petroleum ether (1/1) to give the title compound. LCMS [M+H]$^+$: 969. $^1$H NMR (300 MHz, CD$_3$OD): δ:8.71 (d, J=8.4 Hz, 1H), 8.64 (d, J=8.0 Hz, 1H), 8.15-7.94 (m, 1H), 7.21-7.00 (m, 3H), 6.99-7.26 (m, 1H), 7.32-7.26 (m, 1H), 6.99-6.80 (m, 2H), 6.79-6.69 (m, 8H), 5.53-4.80 (m, 1H), 4.62-4.10 (m, 2H), 4.10-4.00 (m, 2H), 3.94-3.89 (m, 1H), 3.74 (s, 9 H), 3.61 (s, 2H), 1.47 (s, 9H), 1.25 (s, 6H).

Step H: 6-((2-amino-2-methylpropyl)sulfonyl)-3-(2-aminobenzo[d]thiazol-4-yl)-N,N-bis(4-methoxybenzyl)-2-(2-(4-methoxybenzyl)-2H-tetrazol-5-yl)benzenesulfonamide 2,2,2-trifluoroacetate In the 50 mL RBF, 2,2,2-trifluoroacetic acid (2 ml, 0.43 mmol) was added to a stirred mixture of tert-butyl (1-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-2-methylpropan-2-yl)carbamate (0.42 g, 0.433 mmol) in DCM (1 ml) at room temperature. After the reaction mixture was stirred at room temperature for 1 hour, it was concentrated under vacuum to give the title compound. The residue was used for the next step directly without purification. LCMS [M+H]$^+$: 869.

Step I: 6-((2-amino-2-methylpropyl)sulfonyl)-3-(2-aminobenzo[d]thiazol-4-yl)-2-(2H-tetrazol-5-yl)benzenesulfonamide In the 50 mL RBF, 2,2,2-trifluoroacetic acid (2 ml, 0.173 mmol) was added to a stirred mixture of 6-((2-amino-2-methylpropyl)sulfonyl)-3-(2-aminobenzo[d]thiazol-4-yl)-N,N-bis(4-methoxybenzyl)-2-(2-(4-methoxybenzyl)-2H-tetrazol-5-yl)benzenesulfonamide 2,2,2-trifluoroacetate (0.17 g, 0.173 mmol). The reaction mixture was stirred at 80° C. for 2 hours and then concentrated under vacuum. The residue was purified by Prep-HPLC with the following conditions: Column, Xbridge C18, 19*150 mm; mobile phase: Phase A: water with 10 mmol NH$_4$HCO$_3$; Phase B: MeCN for 11 min, hold 80% to 85% in 11 min; Detector, UV 220 and 254 nm. The collected fractions were combined and concentrated under vacuum to give the title compound. LCMS [M+H]$^+$: 509; $^1$H NMR (300 MHz, DMSO-d6): 8.54 (d, J=8.1 Hz, 1H), 849 (d, J=4.5 Hz, 1H), 7.86 (d, J=8.1 Hz, 1H), 7.44 (d, J=6.9 Hz, 1H), 6.87 (d, J=4.8 Hz, 1H), 6.75 (s, 1H), 5.39-5.21 (m, 1H), 4.59-4.41 (M, 2H), 4.33-4.23 (m, 2H).

EXAMPLE 95

3-(2-aminobenzo[d]thiazol-4-yl)-6-((1-aminocyclopropyl)methylsulfonyl)-2-(2H-tetrazol-5-yl)benzenesulfonamide

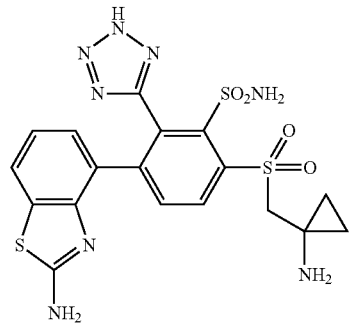 [SMILES: Nc1nc2c(-c3ccc(S(=O)(=O)CC4(N)CC4)c(S(N)(=O)=O)c3-c3nn[nH]n3)cccc2s1]

Step A: tert-butyl(1-(hydroxymethyl)cyclopropyl)carbamate

Into a 50 mL RBF purged and maintained with an inert atmosphere of argon, was placed a solution of 1-((tert-butoxycarbonyl)amino)cyclopropanecarboxylic acid (3.00 g, 14.91 mmol) in THF (10 mL), followed by the addition of borane-tetrahydrofuran complex (44.70 mL, 44.70 mmol) at 0° C. After the resulting mixture was stirred under argon atmosphere at 0° C. for 6 hours, the reaction was quenched with ice water (100 mL) and extracted with EtOAc (3×100 mL). The combined organic layers were washed with brine (4×50 mL), dried over anhydrous sodium sulfate and filtered. The filtrate was evaporated under reduced pressure. The residue was purified by silica gel chromatography, eluting with EtOAc in Pet. ether (1/1) to afford the title compound: $^1$H NMR (400 MHz, DMSO-d$_6$): δ 7.03 (brs, 1H), 4.55 (t, J=6.0 Hz, 1H), 3.75 (d, J=2.8 Hz, 2H), 1.34 (s, 9H), 0.63-0.59 (m, 2H), 0.53-0.51 (m, 2H).

Step B: ((1-((tert-butoxycarbonyl)amino)cyclopropyl)methyl methanesulfonate

Into a 100 mL RBF purged and maintained with an inert atmosphere of argon, was placed a solution of tert-butyl (1-(hydroxymethyl)cyclopropyl)carbamate (0.40 g, 1.71 mmol) and TEA (0.72 ml, 5.13 mmol) in DCM (4 mL), followed by the addition of MsCl (0.16 mL, 2.05 mmol) at 0° C. The resulting mixture was stirred under argon atmosphere at room temperature for 20 minutes. The reaction was quenched with ice water (20 mL) and extracted with EA (3×20 mL). The combined organic layers were washed with brine (3×20 mL), dried over anhydrous sodium sulfate and filtered. The filtrate was evaporated to afford crude product, which was used for the next step directly: $^1$H NMR (400 MHz, CD$_3$Cl): δ 5.08 (brs, 1H), 4.25 (s, 2H), 3.03 (s, 3H), 1.44 (s, 9H), 0.96-0.92 (m, 4H).

Step C: S-((1-((tert-butoxycarbonyl)amino)cyclopropyl)methyl) ethanethioate

Into a 100-mL RBF purged and maintained with an inert atmosphere of argon, was placed a solution of (1-((tert-butoxycarbonyl)amino)cyclopropyl)methyl methanesulfonate (0.50 g, 1.51 mmol) in DMF (5 mL), followed by the addition of potassium ethanethioate (0.69 g, 6.03 mmol) at room temperature. The resulting mixture was stirred under argon atmosphere at 80° C. for 16 hours. The reaction was cooled to 20° C. and quenched with ice water (50 mL) and extracted with EtOAc (3×50 mL). The combined organic layers were washed with brine (3×40 mL), dried over anhydrous sodium sulfate and filtered. The filtrate was evaporated and the residue was purified by silica gel chromatography, eluting with EtOAc in Pet. ether (1/1) to afford the title compound: LCMS [2M+H]$^+$: 491; $^1$H NMR (400 MHz, CD$_3$Cl): δ 4.98 (brs, 1H), 3.21 (s, 2H), 2.37 (s, 3H), 1.46 (s, 9H), 0.86-0.84 (m, 4H).

Step D: (tert-butyl (1-(mercaptomethyl)cyclopropyl)carbamate

Into a 25 mL RBF purged and maintained with an inert atmosphere of argon, was placed a solution of S-((1-((tert-butoxycarbonyl)amino)cyclopropyl)methyl) ethanethioate (0.32 g, 1.04 mmol) in MeOH (3 mL), followed by the addition of sodium hydroxide (83 mg, 2.09 mmol) at 0° C. The resulting mixture was stirred at room temperature for 20 minutes under argon atmosphere. The pH of the reaction was adjusted to ~7 at 0° C. and extracted with EtOAc (3×20 mL). The combined organic layers were washed with brine (2×25 mL), dried over anhydrous sodium sulfate and filtered. The filtrate was evaporated to afford crude title compound, which was used directly in the next step: LCMS [2M+H]$^+$: 407; $^1$H NMR (400 MHz, DMSO-d$_6$): δ 7.23 (brs, 1H), 2.67 (d, J=7.6 Hz, 2H), 2.51 (t, J=7.6 Hz, 1H), 1.38 (s, 9H), 0.68-0.66 (m, 4H).

Step E: tert-butyl (1-(((2-(N,N-bis(4-methoxybenzyl)sulfamoyl)-4-iodo-3-(2-(4-methoxybenzyl)-2H-tetrazol-5-yl)phenyl)thio)methyl)cyclopropyl)carbamate Into a 25-mL RBF purged and maintained with an inert atmosphere of argon, was placed a solution of 6-bromo-3-iodo-N,N-bis(4-methoxybenzyl)-2-(2-(4-methoxybenzyl)-2H-tetrazol-5-yl)benzenesulfonamide (0.35 g, 0.44 mmol) and tert-butyl (1-(mercaptomethyl)cyclopropyl)carbamate (0.18 g, 0.89 mmol) in DMF (4 mL), followed by the addition of sodium hydride (35 mg, 0.89 mmol) at 0° C. The resulting mixture was stirred at 20° C. for 1.5 hours under argon atmosphere. The reaction was quenched with water (20 mL) and extracted with EtOAc (3×30 mL). The combined layers were washed with brine (2×40 mL), dried over anhydrous sodium sulfate and filtered. The filtrate was evaporated and the residue was purified by silica gel chromatography, eluting with EtOAc in Pet. ether (2/3) to afford the title compound: LCMS [M+H]$^+$: 913; $^1$H NMR (300 MHz, CD$_3$Cl) δ 8.01 (d, J=5.1 Hz, 1H), 7.90 (d, J=8.7 Hz, 1H), 6.96-6.94 (m, 5H), 6.85-6.72 (m, 7H), 5.50-5.45 (m, 1H), 5.15 (brs, 1H), 5.13-5.09 (m, 1H), 4.69-4.64 (m, 2H), 4.01-3.95 (m, 2H), 3.79 (s, 2H), 3.78 (s, 9H), 1.41 (s, 9H), 0.87-0.85 (m, 2H), 0.76-0.74 (m, 2H).

Step F: tert-butyl (1-(((2-(N,N-bis(4-methoxybenzyl)sulfamoyl)-4-iodo-3-(2-(4-methoxybenzyl)-2H-tetrazol-5-yl)phenyl)-sulfonyl)methyl)cyclopropyl) carbamate Into a 25 mL RBF purged and maintained with an inert atmosphere of argon, was placed a solution of tert-butyl (1-(((2-(N,N-bis(4-methoxybenzyl)sulfamoyl)-4-iodo-3-(2-(4-methoxybenzyl)-2H-tetrazol-5-yl)phenyl)thio)methyl) cyclopropyl)carbamate (0.26 g, 0.29 mmol) in DCM (3 mL), followed by the addition of m-CPBA (0.20 g, 1.14 mmol) at room temperature. The resulting mixture was stirred at 20° C. for 16 hours under argon atmosphere. The reaction was quenched with Na$_2$SO$_3$ (10%, 20 mL) and extracted with EtOAc (3×30 mL). The combined layers were washed with NaHCO$_3$ (saturated, 2×40 mL), brine (2×40 mL), dried over anhydrous sodium sulfate and filtered. The filtrate was evaporated and the residue was purified by silica gel chromatography, eluting with EtOAc in petroleum ether (2/1) to afford the title compound: LCMS [M+H]$^+$: 945; $^1$H NMR (300 MHz, CD$_3$Cl): δ 8.24-8.21 (m 2H), 6.97-6.95 (m, 5H), 6.78-6.73 (m, 7H), 5.53-5.49 (m, 1H), 5.40 (brs, 1H), 5.23-5.18 (m, 1H), 4.54-4.49 (m, 2H), 3.97-3.87 (m, 2H), 3.80 (s, 2H), 3.78 (s, 9H), 1.41 (s, 9H), 1.19-0.95 (m, 4H).

Step G: tert-butyl (1-(((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)methyl)-cyclopropyl)carbamate Into a 25-mL RBF purged and maintained with an inert atmosphere of argon, was placed a solution of tert-butyl (1-(((2-(N,N-bis(4-methoxybenzyl)sulfamoyl)-4-iodo-3-(2-(4-methoxybenzyl)-2H-tetrazol-5-yl)phenyl)sulfonyl) methyl)cyclopropyl)carbamate (0.18 g, 0.19 mmol), 2nd generation Xphos precatalyst (0.02 g, 0.02 mmol) and (2-aminobenzo[d]thiazol-4-yl)boronic acid (55 mg, 0.29 mmol) in dioxane (2 mL), followed by the addition of sodium carbonate (60 mg, 0.57 mmol) in water (0.4 mL) at room temperature. The resulting mixture was stirred at 80° C. for 16 hours under argon atmosphere. The reaction was cooled to 20° C. and quenched with water (10 mL) and extracted with EtOAc (3×10 mL). The combined organic layers were washed with brine (1×20 mL), dried over anhydrous sodium sulfate and filtered. The filtrate was evaporated under reduced pressure and the residue was purified by silica gel chromatography, eluting with DCM/MeOH (10/1) to give the title compound: LCMS [M+H]$^+$:

967; ¹H NMR (400 MHz, CD₃Cl): δ 8.70 (d, J=7.6 Hz, 1H), 8.00 (d, J=8.4 Hz, 1H), 7.47 (d, J=7.6 Hz, 1H), 7.03-6.91 (m, 4H), 6.89-6.82 (m, 2H), 6.78-6.76 (m, 4H), 6.66-6.64 (m, 4H), 5.48-5.46 (m, 1H), 5.11 (brs, 1H), 4.86-4.84 (m, 2H), 4.75-4.71 (m, 2H), 4.29-4.21 (m, 2H), 3.76 (s, 9H), 3.74 (s, 2H), 1.42 (s, 9H), 1.07-0.96 (m, 4H).

Step H: (3-(2-aminobenzo[d]thiazol-4-yl)-6-(((1-aminocyclopropyl)methyl)sulfonyl)-N-(4-methoxybenzyl)-2-(2-(4-methoxybenzyl)-2H-tetrazol-5-yl)benzenesulfonamide Into a 50-mL RBF, was placed a solution of tert-butyl (1-(((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)methyl)cyclopropyl)carbamate (0.10 g, 0.10 mmol) in DCM (2 mL), followed by the addition of TFA (0.5 mL, 6.49 mmol) at 0° C. The resulting mixture was stirred at 20° C. for 1 hour. The solvent was evaporated to give the title compound, which was used directly in the next step: LCMS [M+H]⁺: 747.

Step I: 3-(2-aminobenzo[d]thiazol-4-yl)-6-(((1-aminocyclopropyl)methyl)sulfonyl)-2-(2H-tetrazol-5-yl)benzenesulfonamide Into a 25-mL RBF, was placed a solution of 3-(2-aminobenzo[d]thiazol-4-yl)-6-(((1-aminocyclopropyl)methyl)sulfonyl)-N-(4-methoxybenzyl)-2-(2-(4-methoxybenzyl)-2H-tetrazol-5-yl)benzenesulfonamide (0.10 g, 0.09 mmol) in TFA (2 mL). The resulting mixture was stirred at 80° C. for 1 hour. The solvent was evaporated and the residue was purified by Prep-HPLC with the following conditions: Column: X Bridge C18, 19*150 mm, 5 μM; Mobile Phase A: water/0.05% NH₄HCO₃, Mobile Phase B: ACN; Flow rate: 20 mL/min; Gradient: 40-60% B in 10 min; RT, 5.18 min; 254 nm. The collected fractions were combined and concentrated under reducing pressure to give the title compound: LCMS [M+H]⁺: 507; ¹H NMR (400 MHz, CD₃OD): δ 8.51 (d, J=8.4 Hz, 1H), 7.98 (d, J=8.4 Hz, 1H), 7.47 (d, J=7.6 Hz, 1H), 6.86 (t, J=7.6 Hz, 1H), 6.75 (d, J=8.0 Hz, 1H), 4.20 (s, 2H), 1.20-1.16 (m, 4H).

EXAMPLE 96

6-(2-amino-3-hydroxypropylsulfonyl)-3-(2-aminobenzo[d]thiazol-4-yl)-2-(2H-tetrazol-5-yl)benzenesulfonamide

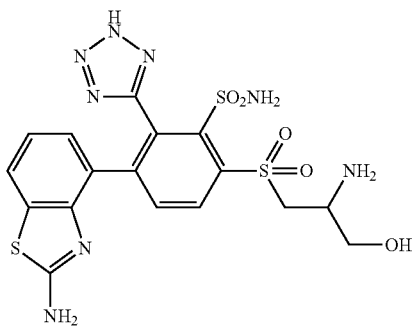 [SMILES: Nc1nc2c(-c3ccc(S(=O)(=O)CC(N)CO)c(S(N)(=O)=O)c3-c3nn[nH]n3)cccc2s1]

Step A: methyl 2-((tert-butoxycarbonyl)amino)-3-((methylsulfonyl)oxy)propanoate

MsCl (5.33 ml, 68.4 mmol) was added dropwise into a stirred solution of TEA (12.72 ml, 91 mmol) and methyl 2-((tert-butoxycarbonyl)amino)-3-hydroxypropanoate (10 g, 45.6 mmol) in DCM (60 ml) under ice bath and then the mixture was stirred at room temperature for 2 hours. The reaction mixture was quenched with water (30 mL), diluted with water (40 mL) and extracted with DCM (3×40 mL). The combined organic layers were washed with water (3×10 mL) and brine (3×10 mL), dried over anhydrous sodium sulfate and filtered. The filtrate was concentrated under vacuum to give the title compound.

Step B: methyl 3-(acetylthio)-2-((tert-butoxycarbonyl)amino)propanoate

A solution of methyl 2-((tert-butoxycarbonyl)amino)-3-((methylsulfonyl)oxy)propanoate (12 g, 40.4 mmol) and potassium thioacetate (4.61 g, 40.4 mmol) in DMF (70 ml) was stirred at room temperature for 3 hours. The reaction mixture was quenched with water (40 mL), diluted with water (80 mL) and extracted with ethyl acetate (3×50 mL). The combined organic layers were washed with water (3×10 mL) and brine (3×10 mL), dried over anhydrous sodium sulfate, filtered and concentrated under vacuum. The residue was purified by silica gel Isolute Flash Si; 50 g prepacked column chromatography, eluted with ethyl acetate/petroleum ether (1/10). The combined organic fractions were concentrated under reduced pressure to give the title compound. ¹H NMR (400 MHz, CD₃OD): 5.26 (bs, 1H), 4.53 (bs, 1H), 3.76 (s, 3H), 3.37-3.32 (m, 2H), 2.35 (s, 3H), 1.45 (s, 9H).

Step C: methyl 2-((tert-butoxycarbonyl)amino)-3-mercaptopropanoate

A solution of methyl 3-(acetylthio)-2-((tert-butoxycarbonyl)amino)propanoate (6 g, 21.63 mmol) and NaOH (3.46 g, 87 mmol) in methanol (50 ml) was stirred at room temperature for 2 hours. The reaction mixture was adjusted to pH 6 and extracted with DCM (150 mL), then the organic layer was dried over Na₂SO₄ and filtered. The filtrate was concentrated under vacuum to give the title compound. ¹H NMR (400 MHz, CD₃OD): 5.44 (bs, 1H), 4.63 (bs 1H), 3.79 (s, 3H), 3.02-2.96 (m, 3H), 1.46 (s, 9H).

Step D: tert-butyl (1-hydroxy-3-mercaptopropan-2-yl)carbamate

Lithium aluminum hydride (0.544 ml, 12.75 mmol) was added in portions to a stirred solution of methyl 2-((tert-butoxycarbonyl)amino)-3-mercaptopropanoate (1 g, 4.25 mmol) in THF (20 ml) at 0° C. and stirred at room temperature for 1 hour. The reaction mixture was quenched with water (0.25 ml), 15% NaOH (0.25 ml) and water (0.75 mL) in sequence. Then, the solution was adjusted to pH 6, extracted with DCM (3×50 mL), and dried over Na₂SO₄. The solution was filtered and the filtrate was concentrated under vacuum to give crude product. The residue was purified by silica gel Isolute Flash Si; 20 g prepacked column chromatography, eluted with ethyl acetate/petroleum ether (1/1). The combined organic fractions were concentrated under reduced pressure to give the title compound. $^1$H NMR (400 MHz, CD$_3$OD): 6.59 (d, J=7.6 Hz, 1H), 4.70 (bs 1H), 3.43-3.30 (m, 2H), 2.65-2.45 (m, 2H), 1.36, 1.38 (s, 9H).

Step E: tert-butyl (1-((2-(N,N-bis(4-methoxybenzyl) sulfamoyl)-4-iodo-3-(2-(4-methoxybenzyl)-2H-tetrazol-5-yl)phenyl)thio)-3-hydroxypropan-2-yl)carbamate A solution of tert-butyl (1-hydroxy-3-mercaptopropan-2-yl)carbamate (393 mg, 1.898 mmol), 6-bromo-3-iodo-N,N-bis(4-methoxybenzyl)-2-(2-(4-methoxybenzyl)-2H-tetrazol-5-yl)benzenesulfonamide (500 mg, 0.633 mmol) and Cs$_2$CO$_3$ (824 mg, 2.53 mmol) in DMF was stirred at room temperature for 16 hours. The reaction mixture was quenched with water (20 mL), diluted with water (60 mL) and extracted with ethyl acetate (3×50 mL). The combined organic layers were washed with water (3×10 mL) and brine (3×10 mL), dried over anhydrous sodium sulfate and filtered. The filtrate was concentrated under vacuum to give crude product. The residue was purified by silica gel Isolute Flash Si; 20 g prepacked column chromatography, eluted with DCM/petroleum ether (7/3), then ethyl acetate/DCM (7/3). The combined organic fractions were concentrated under reduced pressure to give the title compound.

Step F: tert-butyl (1-((2-(N,N-bis(4-methoxybenzyl) sulfamoyl)-4-iodo-3-(2-(4-methoxybenzyl)-2H-tetrazol-5-yl)phenyl)sulfonyl)-3-hydroxypropan-2-yl) carbamate A solution of tert-butyl (1-((2-(N,N-bis(4-methoxybenzyl)sulfamoyl)-4-iodo-3-(2-(4-methoxybenzyl)-2H-tetrazol-5-yl)phenyl)thio)-3-hydroxypropan-2-yl)carbamate (800 mg, 0.873 mmol) and m-CPBA (602 mg, 3.49 mmol) in DCM (50 ml) was stirred at room temperature for 16 hours. The reaction mixture was quenched with Na$_2$SO$_3$ and extracted with DCM (3×50 ml), dried by Na$_2$SO$_4$, filtered and concentrated under vacuum. The residue was purified by silica gel Isolute Flash Si; 20 g prepacked column chromatography, eluted with ethyl acetate/DCM (70/30). The combined organic fractions were concentrated under reduced pressure to give the title compound.

Step G: tert-butyl (1-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-3-hydroxypropan-2-yl)carbamate A solution of tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)-3-hydroxypropan-2-yl)carbamate (500 mg, 0.527 mmol), (2-aminobenzo[d]thiazol-4-yl)boronic acid (204 mg, 1.054 mmol), Pd(Ph$_3$P)$_4$ (122 mg, 0.105 mmol) and Na$_2$CO$_3$ (168 mg, 1.581 mmol) in 1,4-Dioxane (10 ml) and water (2 ml) was stirred at 80° C. for 3 hours under nitrogen. The reaction mixture was concentrated under vacuum to give crude product. The residue was purified by silica gel Isolute Flash Si; 20 g prepacked column chromatography, eluting with methanol/DCM (10/90). The combined organic fractions were concentrated under reduced pressure to give the title compound. LCMS (ESI) calc'd for LCMS (ESI) calc'd for C$_{46}$H$_{50}$N$_8$O$_{10}$S$_3$[M+H]$^+$: 971. found 971.

Step H: 6-((2-amino-3-hydroxypropyl)sulfonyl)-3-(2-aminobenzo[d]thiazol-4-yl)-2-(2H-tetrazol-5-yl) benzenesulfonamide A solution of tert-butyl (1-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-3-hydroxypropan-2-yl)carbamate (300 mg, 0.309 mmol) and TFA (2 ml, 26.0 mmol) in DCM (10 ml) was stirred at room temperature for 2 hours. The reaction mixture was concentrated under vacuum to give 6-((2-amino-3-hydroxypropyl)sulfonyl)-3-(2-aminobenzo[d]thiazol-4-yl)-N-(4-methoxybenzyl)-2-(2-(4-methoxybenzyl)-2H-tetrazol-5-yl) benzenesulfonamide as an oil. A solution of 6-((2-amino-3-hydroxypropyl)sulfonyl)-3-(2-aminobenzo[d]thiazol-4-yl)-N-(4-methoxybenzyl)-2-(2-(4-methoxybenzyl)-2H-tetrazol-5-yl)benzenesulfonamide (230 mg, 0.306 mmol) in TFA (10 ml, 130 mmol) was stirred at 80° C. for 2 hours. The reaction mixture was concentrated under vacuum to give crude product. The product was purified by Prep-HPLC with the following conditions: Column, Sunfire C$^{18}$, 19*150 mm; mobile phase: water (0.05% NH$_4$HCO$_3$) and acetonitrile (Gradient time: 7 min. B %: 40%-80%); Detector, UV 220 and 254 nm. The collected fractions were combined and concentrated under vacuum to give the title compound. LCMS [M+H]$^+$: 511; $^1$H NMR (300 MHz, CDCl$_3$): δ 8.25 (d, J=8.4 Hz, 1H), 7.88 (d, J=8.4 Hz, 1H), 7.49-7.47 (m, 3H), 6.71-6.67 (m, 1H), 6.48-6.46 (m, 1H), 5.25 (bs, 1H), 4.13-4.09 (m, 1H), 3.91-3.89 (m, 1H), 3.54-3.52 (m, 3H).

EXAMPLE 97

6-(3-amino-2-hydroxypropylsulfonyl)-3-(2-aminobenzo[d]thiazol-4-yl)-2-(2H-tetrazol-5-yl)benzenesulfonamide

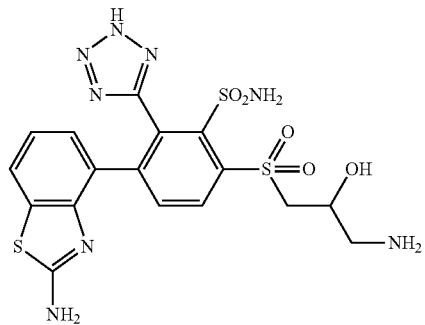 [SMILES: NCC(O)CS(=O)(=O)c1ccc(-c2cccc3sc(N)nc23)c(-c2nn[nH]n2)c1S(N)(=O)=O]

Step A: tert-butyl (2,3-dihydroxypropyl)carbamate

A solution of 3-aminopropane-1,2-diol (20 g, 220 mmol), TEA (61.2 ml, 439 mmol) and BOC$_2$O (61.2 ml, 263 mmol) in MeOH (200 ml) was stirred at room temperature for 6 hours. The reaction mixture was concentrated under vacuum to give crude product. The residue was purified by silica gel Isolute Flash Si; 20 g prepacked column chromatography, eluted with methanol/DCM (with 0.1% TFA)=1/10. The combined organic fractions were concentrated under reduced pressure to give the title compound. $^1$H NMR (CDCl$_3$, 400 MHZ): 3.76-3.73 (m, 1H), 3.60-3.57 (m, 2H), 3.28-3.25 (m, 2H), 1.45 (s, 9H).

Step B: tert-butyl (2,3-bis((tert-butyldimethylsilyl) oxy)propyl)carbamate

A solution of tert-butyl (2,3-dihydroxypropyl)carbamate (10 g, 52.3 mmol), tert-butylchlorodimethylsilane (17.34 g, 115 mmol) and 1H-imidazole (14.24 g, 209 mmol) in DCM (200 ml) was stirred at room temperature for 16 hours. The reaction mixture was filtered and filtrate was concentrated under vacuum to give crude product. The residue was purified by silica gel Isolute Flash Si; 20 g prepacked column chromatography, eluting with ethyl acetate/petroleum ether (1/3). The combined organic fractions were concentrated under reduced pressure to give the title compound. $^1$H NMR (CDCl$_3$, 400 MHZ): 3.72-3.69 (m, 1H), 3.49-3.43 (m, 2H), 3.21-3.13 (m, 2H), 1.39 (s, 9H), 0.86-0.81 (m, 18H), 0.04-0.00 (m, 12H).

Step C: tert-butyl (2-((tert-butyldimethylsilyl)oxy)-3-hydroxypropyl)carbamate

A solution of tert-butyl (2,3-bis((tert-butyldimethylsilyl)oxy)propyl)carbamate (10 g, 23.82 mmol) and acetic acid (50 ml, 23.82 mmol) in DCM (10 ml) and methanol (10 ml) was stirred at room temperature for 16 hours. The reaction mixture was concentrated under vacuum to give crude product. The residue was purified by silica gel Isolute Flash Si; 20 g prepacked column chromatography, eluting with ethyl acetate/petroleum ether (30/70). The combined organic fractions were concentrated under reduced pressure to give the title compound. $^1$H NMR (DMSO-d6, 400 MHZ): 4.55-4.52 (m, 1H), 3.65-3.62 (m, 1H), 3.27-3.25 (m, 2H), 3.03-2.82 (m, 2H), 1.37 (s, 9H), 0.86 (s, 9H), 0.03 (s, 6H).

Step D: 3-((tert-butoxycarbonyl)amino)-2-((tert-butyldimethylsilyl)oxy)propyl methanesulfonate MsCl (2.55 ml, 32.7 mmol) was added dropwise to s stirred solution of TEA (4.56 ml, 32.7 mmol) and tert-butyl (2-((tert-butyldimethylsilyl)oxy)-3-hydroxypropyl)carbamate (5 g, 16.37 mmol) in DCM (5 ml) at room temperature for 1 hour. The reaction mixture was quenched with water (20 mL), diluted with water (20 mL) and extracted with DCM (3×30 mL). The combined organic layers were washed with water (3×10 mL) and brine (2×10 mL), dried over anhydrous sodium sulfate and filtered. The filtrate was concentrated under vacuum to give the title compound. $^1$H NMR (CDCl$_3$, 400 MHZ): 4.75-4.72 (m, 1H), 4.15-4.10 (m, 2H), 3.26-3.23 (m, 2H), 3.03 (s, 3H), 1.44 (s, 9H), 0.90 (s, 9H), 0.11 (s, 6H).

Step E: S-(3-((tert-butoxycarbonyl)amino)-2-((tert-butyldimethylsilyl)oxy)propyl) ethanethioate A solution of 3-((tert-butoxycarbonyl)amino)-2-((tert-butyldimethylsilyl)oxy)propyl methanesulfonate (4 g, 10.43 mmol) and potassium ethanethioate (4.76 g, 41.7 mmol) in DMF (50 ml) was stirred at 60° C. for 16 hours. The reaction mixture was quenched with water (20 mL), diluted with water (20 mL) and extracted with ethyl acetate (3×30 mL). The combined organic layers were washed with water (2×10 mL) and brine (2×10 mL), dried over anhydrous sodium sulfate and filtered. The filtrate was concentrated under vacuum to give crude product. The residue was purified by silica gel Isolute Flash Si; 20 g prepacked column chromatography, eluting with ethyl acetate/petroleum ether (10/90). The combined organic fractions were concentrated under reduced pressure to give the title compound. LCMS [M+H]$^+$: 264.

Step F: tert-butyl (2-((tert-butyldimethylsilyl)oxy)-3-mercaptopropyl)carbamate

A solution of S-(3-((tert-butoxycarbonyl)amino)-2-((tert-butyldimethylsilyl)oxy)propyl) ethanethioate (2.3 g, 6.33 mmol) and Na$_2$CO$_3$ (1.341 g, 12.65 mmol) in methanol (30 ml) and water (4 ml) was stirred at room temperature for 2 hours. The reaction mixture was quenched with water (20 mL), diluted with water (20 mL) and extracted with ethyl acetate (3×50 mL). The combined organic layers were washed with water (3×10 mL) and brine (2×10 mL), dried over anhydrous sodium sulfate and filtered. The filtrate was concentrated under vacuum to give crude product. The residue was purified by silica gel Isolute Flash Si; 20 g prepacked column chromatography, eluting with ethyl acetate/petroleum ether (1/10). The combined organic fractions were concentrated under reduced pressure to give the title compound. $^1$H NMR (400 MHz, CDCl$_3$): 4.74 (bs, 1H), 3.86 (m, 1H), 3.32-3.28 (m, 2H), 2.67-2.62 (m, 1H), 2.54-2.51 (m, 1H), 1.44 (s, 9H), 0.90 (s, 9H).

Step G: tert-butyl (3-((2-(N,N-bis(4-methoxybenzyl)sulfamoyl)-4-iodo-3-(2-(4-methoxybenzyl)-2H-tetrazol-5-yl)phenyl)thio)-2-((tert-butyldimethylsilyl)oxy)propyl)carbamate A solution of 6-bromo-3-iodo-N,N-bis(4-methoxybenzyl)-2-(2-(4-methoxybenzyl)-2H-tetrazol-5-yl)benzenesulfonamide (1 g, 1.265 mmol), tert-butyl (2-((tert-butyldimethylsilyl)oxy)-3-mercaptopropyl)carbamate (0.814 g, 2.53 mmol) and Cs$_2$CO$_3$ (0.824 g, 2.53 mmol) in DMF (15 ml) was stirred at room temperature for 2 hours under nitrogen. The reaction mixture was quenched with water (40 mL), diluted with water (40 mL) and extracted with ethyl acetate (3×50 mL). The combined organic layers were washed with water (2×10 mL) and brine (3×10 mL), dried over anhydrous sodium sulfate and filtered. The filtrate was concentrated under vacuum to give crude product. The residue was purified by silica gel Isolute Flash Si; 20 g prepacked column chromatography, eluting with ethyl acetate/petroleum ether (1/1). The combined organic fractions were concentrated under reduced pressure to give the title compound. LCMS [M+H]$^+$: 436; $^1$H NMR (400 MHz, DMSO-d$_6$): δ 8.34 (d, J=8.0 Hz, 1H), 7.90 (d, J=8.4 Hz, 1H), 7.62-7.33 (m, 4H), 7.11-6.94 (m, 2H), 6.78 (t, J=8.0 Hz, 1H), 6.33 (d, J=7.6 Hz, 1H).

Step H: tert-butyl 3-(2-(N,N-bis(4-methoxybenzyl)sulfamoyl)-4-iodo-3-(2-(4-methoxybenzyl)-2H-tetrazol-5-yl)phenylthio)-2-hydroxypropylcarbamate A solution of tert-butyl (3-((2-(N,N-bis(4-methoxybenzyl)sulfamoyl)-4-iodo-3-(2-(4-methoxybenzyl)-2H-tetrazol-5-yl)phenyl)thio)-2-((tert-butyldimethylsilyl)oxy)propyl)carbamate (1.1 g, 1.067 mmol) and TBAF (4.27 ml, 4.27 mmol) in THF (6 ml) was stirred at room temperature for 1 hour. The reaction mixture was quenched with water (50 mL), diluted with water (20 mL) and extracted with ethyl acetate (3×40 mL). The combined organic layers were washed with water (3×10 mL) and brine (3×10 mL), dried over anhydrous sodium sulfate and filtered. The filtrate was concentrated under vacuum to give crude product. The residue was purified by silica gel Isolute Flash Si; 20 g prepacked column chromatography, eluting with ethyl acetate/petroleum ether (1/1). The combined organic fractions were concentrated under reduced pressure to give the title compound. $^1$H NMR (400 MHz, CDCl$_3$): δ 8.05 (d, J=8.4 Hz, 1H), 7.34-7.26 (m, 2H), 6.93-6.90 (m, 4H), 6.83-6.77 (m, 6H), 5.79 (s, 2H), 4.37-4.26 (m, 2H), 4.10-4.05 (m, 2H), 3.79 (s, 6H), 3.80-3.71 (m, 3H), 3.70-3.67 (m, 1H), 3.40-3.32 (m, 1H), 3.16-3.14 (m, 2H), 3.01-2.97 (m, 1H), 1.43 (s, 9H).

Step I: tert-butyl 3-(2-(N,N-bis(4-methoxybenzyl)sulfamoyl)-4-iodo-3-(2-(4-methoxybenzyl)-2H-tetrazol-5-yl)phenylsulfonyl)-2-hydroxypropylcarbamate A solution of tert-butyl (3-((2-(N,N-bis(4-methoxybenzyl)sulfamoyl)-4-iodo-3-(2-(4-methoxybenzyl)-2H-tetrazol-5-yl)phenyl)thio)-2-hydroxypropyl)carbamate (450 mg, 0.491 mmol) and m-CPBA (339 mg, 1.963 mmol) in DCM (5 ml) was stirred at room temperature for 16 hours. The reaction mixture was concentrated under vacuum to give crude product. The residue was purified by silica gel Isolute Flash Si; 20 g prepacked column chromatography, eluting with methanol/DCM (1/10). The combined organic fractions were concentrated under reduced pressure to give the title compound. LCMS [M+H]$^+$: 949.

Step J: tert-butyl 3-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)-2-hydroxypropylcarbamate A solution of tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate (370 mg, 0.390 mmol), (2-aminobenzo[d]thiazol-4-yl)boronic acid (151 mg, 0.780 mmol), Pd(PPh$_3$)4 (90 mg, 0.078 mmol) and Na$_2$CO$_3$ (83 mg, 0.780 mmol) in 1,4-dioxane (2 ml) and water (0.4 ml) was stirred at 80° C. for 16 hours under argon. The reaction mixture was concentrated under vacuum to give crude product. The residue was purified by silica gel Isolute Flash Si; 20 g prepacked column chromatography, eluting with methanol/DCM (1/10). The combined organic fractions were concentrated under reduced pressure to give the title compound. LCMS [M+H]$^+$: 971

Step K: 6-(3-amino-2-hydroxypropylsulfonyl)-3-(2-aminobenzo[d]thiazol-4-yl)-N-(4-methoxybenzyl)-2-(2-(4-methoxybenzyl)-2H-tetrazol-5-yl)benzenesulfonamide To a solution of tert-butyl (3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-2-hydroxypropyl)carbamate (250 mg, 0.257 mmol) in DCM (5 mL) was added TFA (1.983 ml, 25.7 mmol) at room temperature. The reaction was stirred for 1 hour at room temperature. The reaction was concentrated under vacuum to afford the title compound. LCMS [M+H]$^+$: 751.

Step L: 6-(3-amino-2-hydroxypropylsulfonyl)-3-(2-aminobenzo[d]thiazol-4-yl)-2-(2H-tetrazol-5-yl)benzenesulfonamide A solution of 6-((3-amino-2-hydroxypropyl)sulfonyl)-3-(2-aminobenzo[d]thiazol-4-yl)-2-(2-(4-methoxybenzyl)-2H-tetrazol-5-yl)benzenesulfonamide (120 mg, 0.190 mmol) in TFA (3 ml) was stirred for 1 hour at 80° C. The solution was concentrated under vacuum. The residue was purified by Prep-HPLC the following conditions: Column: XSelect CSH Prep C18 OBD Column, 19*150 mm; Mobile Phase A: water with 10 mmol NH$_4$HCO$_3$, Mobile Phase B: MeCN; Flow rate: 20 mL/min; Gradient: 5% B to 23% B in 8 min; 254/220 nm to afford the title compound. LCMS [M+H]$^+$: 511; $^1$H NMR (300 MHz, DMSO): δ 8.19 (d, J=6.3 Hz, 1H), 7.89 (d, J=6.3 Hz, 1H), 7.50-7.43 (m, 1H), 6.72-6.69 (m, 1H), 6.46-6.53 (m, 1H), 5.86 (bs), 4.25 (bs), 4.17-4.09 (m, 1H), 4.00-3.92 (m, 1H), 3.18-3.06 (m, 1H), 2.91-2.83 (m, 1H).

EXAMPLES 98-131

Parallel synthesis of 3-substituted 2-(1H-tetrazol-5-yl)-6-(azitidine sulfone)benzenesulfonamides

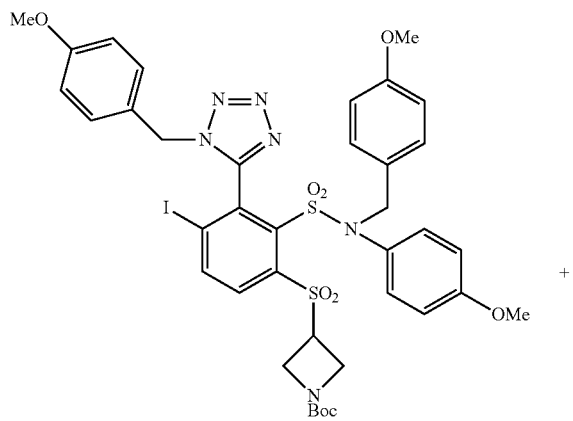

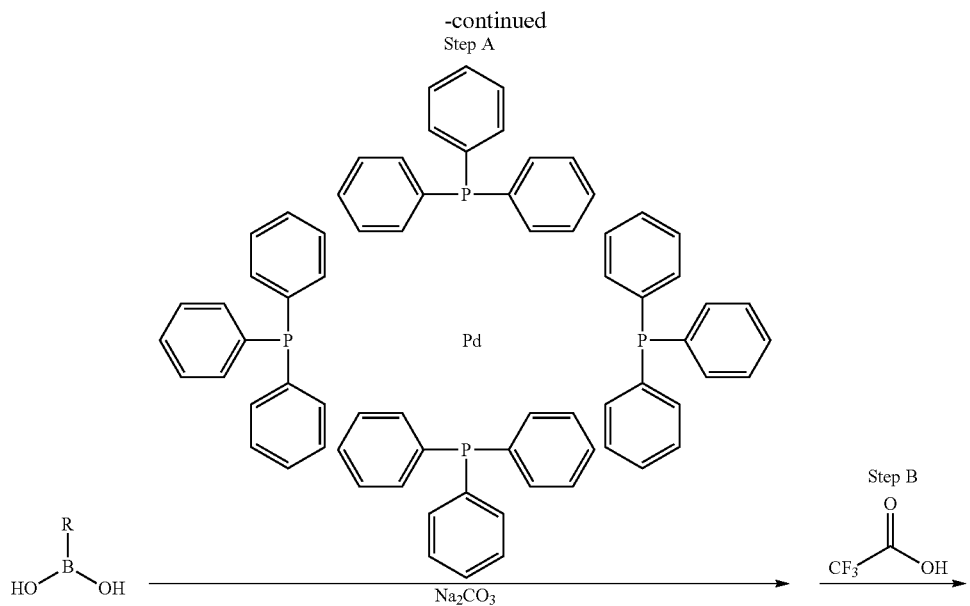

Step A: Palladium catalyzed C—C coupling of arylboronic esters and arylboronic acids with tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate In a glove box under a dry nitrogen atmosphere, arylboronic acids or esters or potassium trifluoroaryl borates (0.129 mmol) (commercially available, known, or prepared as described herein) and Pd(PPh3)4 (5 mg, 4.3 μmol) and 130 μL of 1N degassed aq. Na₂CO₃ solution were added into 2 dram vials. 1.0 mL of a solution of tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate prepared as described herein (40 mg, 0.043 mmol) in 1,4-Dioxane were added into each vial. The vials were capped and heated at 78° C. with stirring for 20 hours. After the vials were cooled to room temperature, the solvent was removed in a GeneVac. Into each residue was added 600 μL of H₂O and 2 mL of EtOAc. The organic layers were transferred into 2 dram vials. The organic solvent was removed in GeneVac to afford the crude intermediates which were deprotected without further purification in the subsequent step.

Step B: Removal of One p-Methoxybenzyl (PMB) Protecting & BOC Group by TFA Treatment The residues from Step A were each added TFA 0.7 mL alone with anilsole (0.3 mL). The vials were shaked at 25° C. for 3 hours. Solvent were removed under reduced pressure using Genevac. The crude materials were dissolved in 1 mL DMSO solution and purified with HPLC.

Step C: Removal of the Remaining p-Methoxybenzyl (PMB) Protecting Groups by TFA Treatment In 2 dram vials containing the intermediates from last step. 1 mL TFA was added and reactions agitated at 65° C. for 4 hours. The reactions were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 μm, 19×100 mm; solvent: gradient range 3-28% initial to 45-95% final MeCN (0.1% TFA) in water 0.1% TFA) 50 or 70 mL/min; 8 min run time] to afford Examples 98 to 131.

| Ex. No. | RB(OH)2 | Structure | Name | LC/MS m/e [M + H]+ |
|---|---|---|---|---|
| 98 | 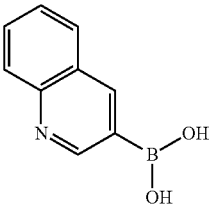 [SMILES: OB(O)c1cnc2ccccc2c1] | 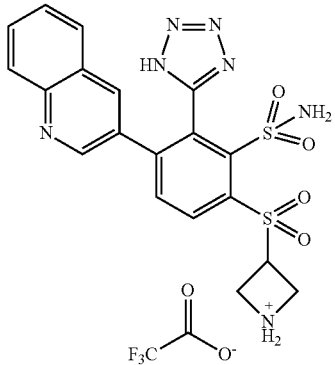 [SMILES: NS(=O)(=O)c1c(S(=O)(=O)C2CNC2)ccc(-c2cnc3ccccc3c2)c1-c1nnn[nH]1 ; O=C([O-])C(F)(F)F] | 3-((4-(quinolin-3-yl)-2-sulfamoyl-3-(1H-tetrazol-5-yl)phenyl)sulfonyl)azetidin-1-ium 2,2,2-trifluoroacetate | 472.08 |
| 99 | 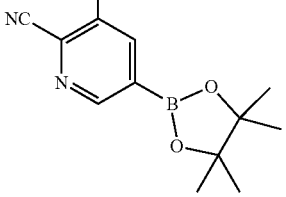 | 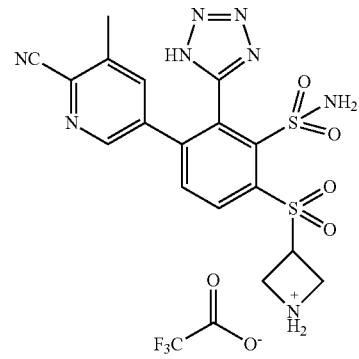 [SMILES: Cc1cc(-c2ccc(S(=O)(=O)C3CNC3)c(S(N)(=O)=O)c2-c2nnn[nH]2)cnc1C#N ; O=C([O-])C(F)(F)F] | 3-((4-(6-cyano-5-methylpyridin-3-yl)-2-sulfamoyl-3-(1H-tetrazol-5-yl)phenyl)sulfonyl)azetidin-1-ium 2,2,2-trifluoroacetate | 461.07 |
| 100 | 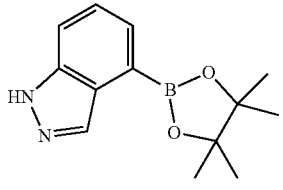 [SMILES: CC1(C)OB(c2cccc3[nH]ncc23)OC1(C)C] | 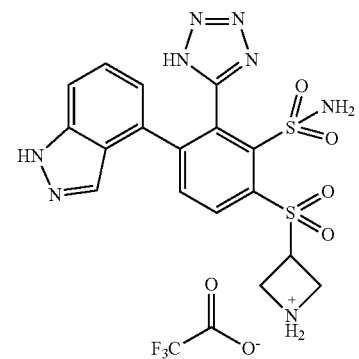 [SMILES: NS(=O)(=O)c1c(S(=O)(=O)C2CNC2)ccc(-c2cccc3[nH]ncc23)c1-c1nnn[nH]1 ; O=C([O-])C(F)(F)F] | 3-((4-(1H-indazol-4-yl)-2-sulfamoyl-3-(1H-tetrazol-5-yl)phenyl)sulfonyl)azetidin-1-ium 2,2,2-trifluoroacetate | 461.07 |
| 101 | 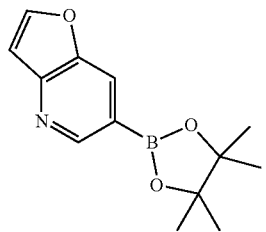 [SMILES: CC1(C)OB(c2cnc3ccoc3c2)OC1(C)C] | 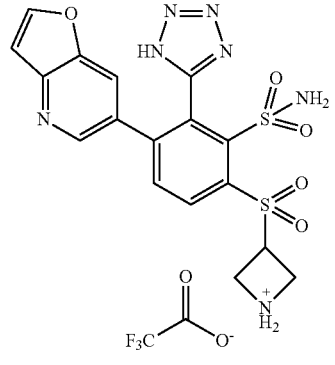 [SMILES: NS(=O)(=O)c1c(S(=O)(=O)C2CNC2)ccc(-c2cnc3ccoc3c2)c1-c1nnn[nH]1 ; O=C([O-])C(F)(F)F] | 3-((4-(furo[3,2-b]pyridin-6-yl)-2-sulfamoyl-3-(1H-tetrazol-5-yl)phenyl)sulfonyl)azetidin-1-ium 2,2,2-trifluoroacetate | 462.06 |

| Ex. No. | RB(OH)2 | Structure | Name | LC/MS m/e [M + H]+ |
|---|---|---|---|---|
| 102 | 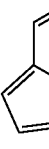 | 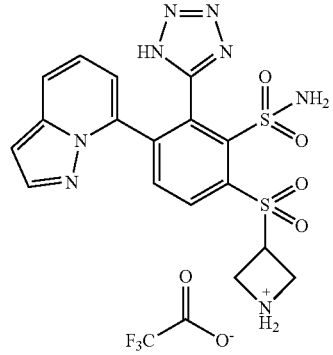 [SMILES: NS(=O)(=O)c1c(S(=O)(=O)C2CNC2)ccc(-c2cccc3ccnn23)c1-c1nnn[nH]1 ; O=C([O-])C(F)(F)F] | 3-((4-(pyrazolo[1,5-a]pyridin-7-yl)-2-sulfamoyl-3-(1H-tetrazol-5-yl)phenyl)sulfonyl)azetidin-1-ium 2,2,2-trifluoroacetate | 461.07 |
| 103 | 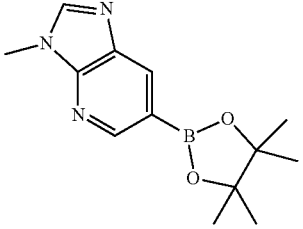 | 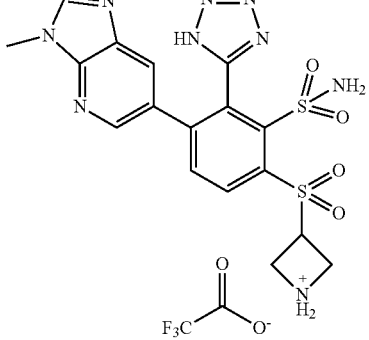 | 3-((4-(3-methyl-3H-imidazo[4,5-b]pyridin-6-yl)-2-sulfamoyl-3-(1H-tetrazol-5-yl)phenyl)sulfonyl)azetidin-1-ium 2,2,2-trifluoroacetate | 476.08 |
| 104 | 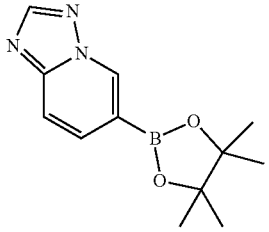 [SMILES: CC1(C)OB(c2ccc3ncnn3c2)OC1(C)C] | 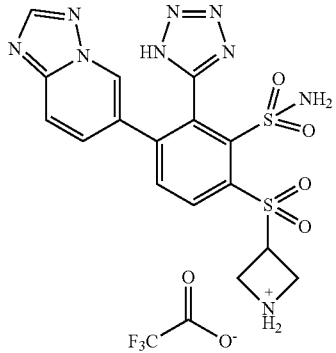 [SMILES: NS(=O)(=O)c1c(S(=O)(=O)C2CNC2)ccc(-c2ccc3ncnn3c2)c1-c1nnn[nH]1 ; O=C([O-])C(F)(F)F] | 3-((4-([1,2,4]triazolo[1,5-a]pyridin-6-yl)-2-sulfamoyl-3-(1H-tetrazol-5-yl)phenyl)sulfonyl)azetidin-1-ium 2,2,2-trifluoroacetate | 462.07 |
| 105 | 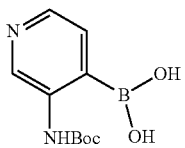 | 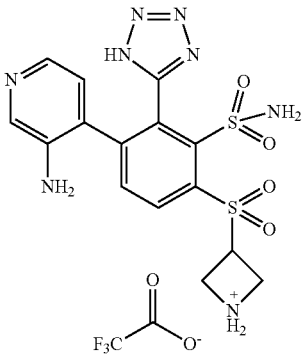 [SMILES: Nc1cnccc1-c1ccc(S(=O)(=O)C2CNC2)c(S(N)(=O)=O)c1-c1nnn[nH]1 ; O=C([O-])C(F)(F)F] | 3-((4-(3-aminopyridin-4-yl)-2-sulfamoyl-3-(1H-tetrazol-5-yl)phenyl)sulfonyl)azetidin-1-ium 2,2,2-trifluoroacetate | 436.08 |

| Ex. No. | RB(OH)2 | Structure | Name | LC/MS m/e [M + H]+ |
|---|---|---|---|---|
| 106 | | 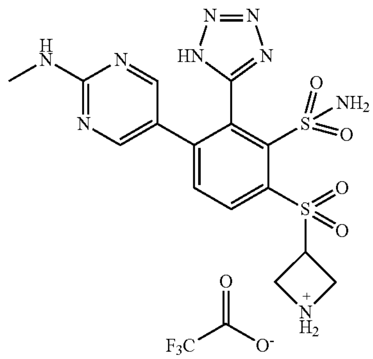 [SMILES: CNc1ncc(-c2ccc(S(=O)(=O)C3CNC3)c(S(N)(=O)=O)c2-c2nnn[nH]2)cn1 ; O=C([O-])C(F)(F)F] | 3-((4-(2-(methylamino)pyrimidin-5-yl)-2-sulfamoyl-3-(1H-tetrazol-5-yl)phenyl)sulfonyl)azetidin-1-ium 2,2,2-trifluoroacetate | 462.08 |
| 107 | | 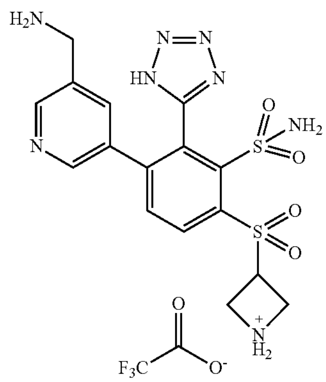 [SMILES: NCc1cncc(-c2ccc(S(=O)(=O)C3CNC3)c(S(N)(=O)=O)c2-c2nnn[nH]2)c1 ; O=C([O-])C(F)(F)F] | 3-((4-(5-(aminomethyl)pyridin-3-yl)-2-sulfamoyl-3-(1H-tetrazol-5-yl)phenyl)sulfonyl)azetidin-1-ium 2,2,2-trifluoroacetate | 450.09 |
| 108 | | 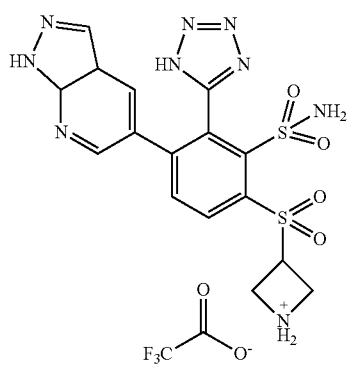 [SMILES: NS(=O)(=O)c1c(S(=O)(=O)C2CNC2)ccc(C2=CC3C=NNC3N=C2)c1-c1nnn[nH]1 ; O=C([O-])C(F)(F)F] | 3-((4-(3a,7a-dihydro-1H-pyrazolo[3,4-b]pyridin-5-yl)-2-sulfamoyl-3-(1H-tetrazol-5-yl)phenyl)sulfonyl)azetidin-1-ium 2,2,2-trifluoroacetate | 462.07 |
| 109 | | 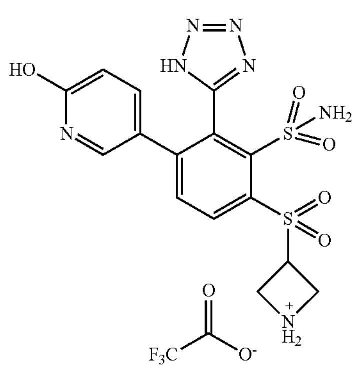 [SMILES: NS(=O)(=O)c1c(S(=O)(=O)C2CNC2)ccc(-c2ccc(O)nc2)c1-c1nnn[nH]1 ; O=C([O-])C(F)(F)F] | 3-((4-(6-hydroxypyridin-3-yl)-2-sulfamoyl-3-(1H-tetrazol-5-yl)phenyl)sulfonyl)azetidin-1-ium 2,2,2-trifluoroacetate | 437.05 |

| Ex. No. | RB(OH)2 | Structure | Name | LC/MS m/e [M + H]+ |
|---|---|---|---|---|
| 110 | 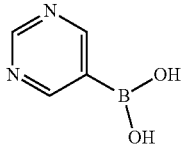 | 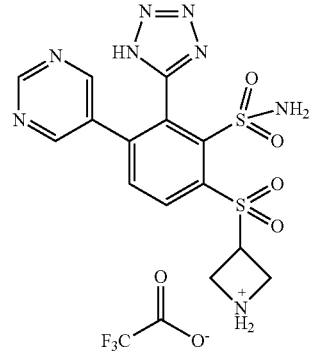 [SMILES: NS(=O)(=O)c1c(S(=O)(=O)C2CNC2)ccc(-c2cncnc2)c1-c1nnn[nH]1 ; O=C([O-])C(F)(F)F] | 3-((4-(pyrimidin-5-yl)-2-sulfamoyl-3-(1H-tetrazol-5-yl)phenyl)sulfonyl)azetidin-1-ium 2,2,2-trifluoroacetate | 423.06 |
| 111 | 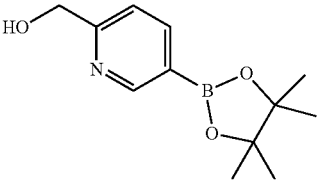 [SMILES: CC1(C)OB(c2ccc(CO)nc2)OC1(C)C] | 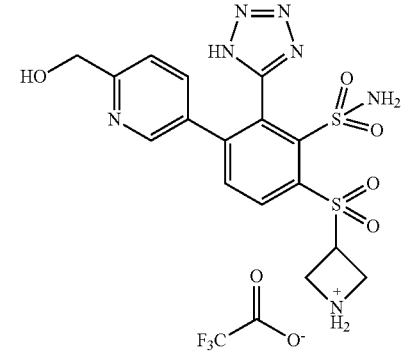 [SMILES: NS(=O)(=O)c1c(S(=O)(=O)C2CNC2)ccc(-c2ccc(CO)nc2)c1-c1nnn[nH]1 ; O=C([O-])C(F)(F)F] | 3-((4-(6-(hydroxymethyl)pyridin-3-yl)-2-sulfamoyl-3-(1H-tetrazol-5-yl)phenyl)sulfonyl)azetidin-1-ium 2,2,2-trifluoroacetate | 451.07 |
| 112 | 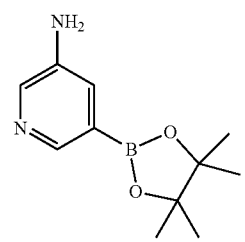 [SMILES: CC1(C)OB(c2cncc(N)c2)OC1(C)C] | 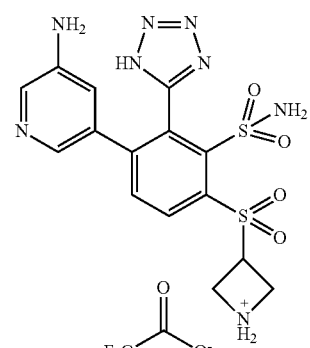 | 3-((4-(5-aminopyridin-3-yl)-2-sulfamoyl-3-(1H-tetrazol-5-yl)phenyl)sulfonyl)azetidin-1-ium 2,2,2-trifluoroacetate | 437.07 |
| 113 | 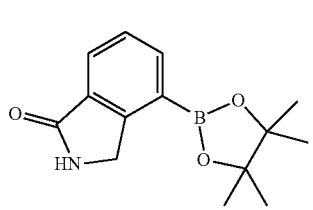 [SMILES: CC1(C)OB(c2cccc3c2CNC3=O)OC1(C)C] | 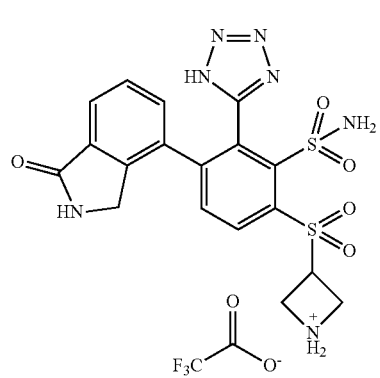 [SMILES: NS(=O)(=O)c1c(S(=O)(=O)C2CNC2)ccc(-c2cccc3c2CNC3=O)c1-c1nnn[nH]1 ; O=C([O-])C(F)(F)F] | 3-((4-(1-oxoisoindolin-4-yl)-2-sulfamoyl-3-(1H-tetrazol-5-yl)phenyl)sulfonyl)azetidin-1-ium 2,2,2-trifluoroacetate | 476.07 |

-continued

| Ex. No. | RB(OH)2 | Structure | Name | LC/MS m/e [M + H]+ |
|---|---|---|---|---|
| 114 | | 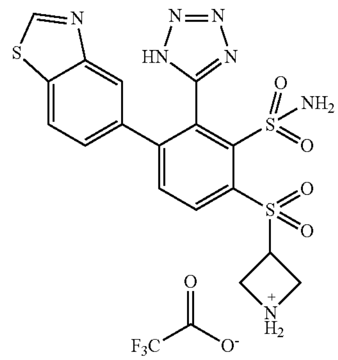 [SMILES: NS(=O)(=O)c1c(S(=O)(=O)C2CNC2)ccc(-c2ccc3scnc3c2)c1-c1nnn[nH]1 ; O=C([O-])C(F)(F)F] | 3-((4-(benzo[d]thiazol-5-yl)-2-sulfamoyl-3-(1H-tetrazol-5-yl)phenyl)sulfonyl)azetidin-1-ium 2,2,2-trifluoroacetate | 478.04 |
| 115 | | 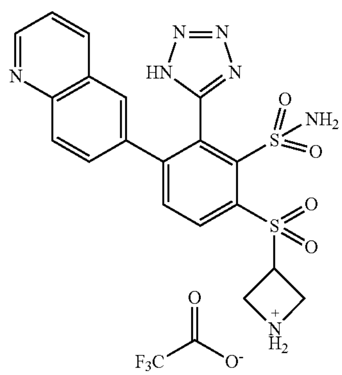 [SMILES: NS(=O)(=O)c1c(S(=O)(=O)C2CNC2)ccc(-c2ccc3ncccc3c2)c1-c1nnn[nH]1 ; O=C([O-])C(F)(F)F] | 3-((4-(quinolin-6-yl)-2-sulfamoyl-3-(1H-tetrazol-5-yl)phenyl)sulfonyl)azetidin-1-ium 2,2,2-trifluoroacetate | 472.08 |
| 116 | | 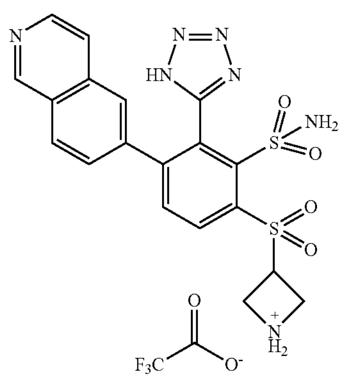 [SMILES: NS(=O)(=O)c1c(S(=O)(=O)C2CNC2)ccc(-c2ccc3cnccc3c2)c1-c1nnn[nH]1 ; O=C([O-])C(F)(F)F] | 3-((4-(isoquinolin-6-yl)-2-sulfamoyl-3-(1H-tetrazol-5-yl)phenyl)sulfonyl)azetidin-1-ium 2,2,2-trifluoroacetate | 472.08 |
| 117 | | 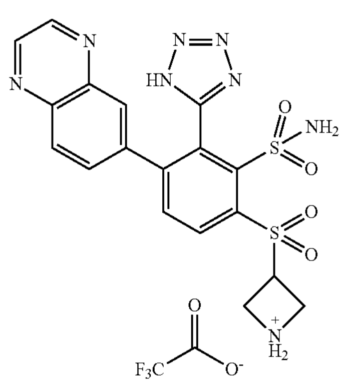 [SMILES: NS(=O)(=O)c1c(S(=O)(=O)C2CNC2)ccc(-c2ccc3nccnc3c2)c1-c1nnn[nH]1 ; O=C([O-])C(F)(F)F] | 3-((4-(quinoxalin-6-yl)-2-sulfamoyl-3-(1H-tetrazol-5-yl)phenyl)sulfonyl)azetidin-1-ium 2,2,2-trifluoroacetate | 473.07 |

-continued

| Ex. No. | RB(OH)2 | Structure | Name | LC/MS m/e [M + H]+ |
|---|---|---|---|---|
| 118 | 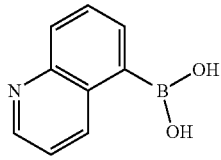 [SMILES: OB(O)c1cccc2ncccc12] | 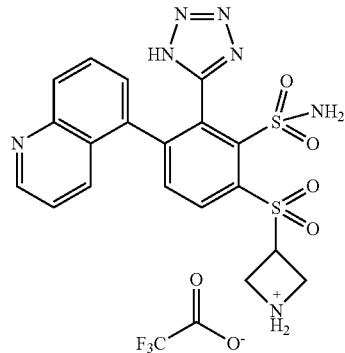 [SMILES: NS(=O)(=O)c1c(S(=O)(=O)C2CNC2)ccc(-c2cccc3ncccc23)c1-c1nnn[nH]1 ; O=C([O-])C(F)(F)F] | 3-((4-(quinolin-5-yl)-2-sulfamoyl-3-(1H-tetrazol-5-yl)phenyl)sulfonyl)azetidin-1-ium 2,2,2-trifluoroacetate | 472.08 |
| 119 | 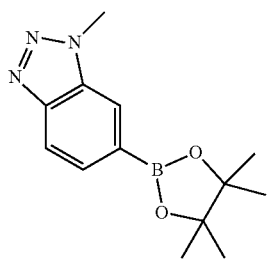 [SMILES: Cn1nnc2ccc(B3OC(C)(C)C(C)(C)O3)cc21] | 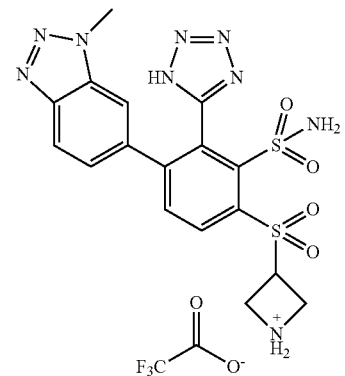 [SMILES: Cn1nnc2ccc(-c3ccc(S(=O)(=O)C4CNC4)c(S(N)(=O)=O)c3-c3nnn[nH]3)cc21 ; O=C([O-])C(F)(F)F] | 3-((4-(1-methyl-1H-benzo[d][1,2,3]triazol-6-yl)-2-sulfamoyl-3-(1H-tetrazol-5-yl)phenyl)sulfonyl)azetidin-1-ium 2,2,2-trifluoroacetate | 476.08 |
| 120 | 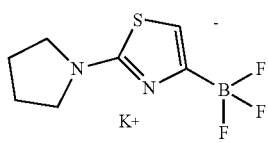 | 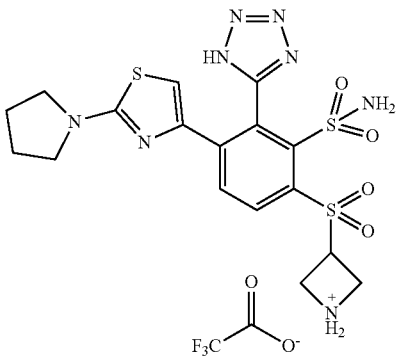 [SMILES: NS(=O)(=O)c1c(S(=O)(=O)C2CNC2)ccc(-c2csc(N3CCCC3)n2)c1-c1nnn[nH]1 ; O=C([O-])C(F)(F)F] | 3-((4-(2-(pyrrolidin-1-yl)thiazol-4-yl)-2-sulfamoyl-3-(1H-tetrazol-5-yl)phenyl)sulfonyl)azetidin-1-ium 2,2,2-trifluoroacetate | 497.08 |
| 121 | 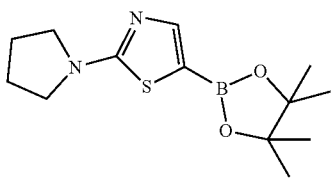 [SMILES: CC1(C)OB(c2cnc(N3CCCC3)s2)OC1(C)C] | 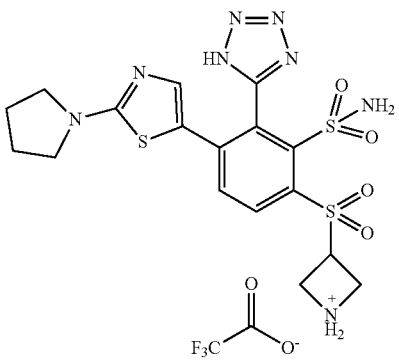 [SMILES: NS(=O)(=O)c1c(S(=O)(=O)C2CNC2)ccc(-c2cnc(N3CCCC3)s2)c1-c1nnn[nH]1 ; O=C([O-])C(F)(F)F] | 3-((4-(2-(pyrrolidin-1-yl)thiazol-5-yl)-2-sulfamoyl-3-(1H-tetrazol-5-yl)phenyl)sulfonyl)azetidin-1-ium 2,2,2-trifluoroacetate | 497.08 |

-continued

| Ex. No. | RB(OH)2 | Structure | Name | LC/MS m/e [M + H]+ |
|---|---|---|---|---|
| 122 | | 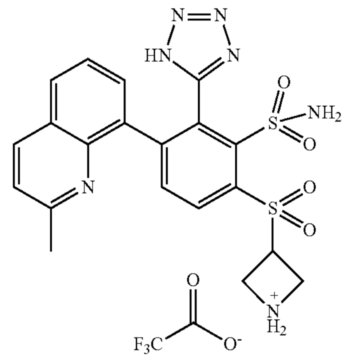 [SMILES: Cc1ccc2cccc(-c3ccc(S(=O)(=O)C4CNC4)c(S(N)(=O)=O)c3-c3nnn[nH]3)c2n1 ; O=C([O-])C(F)(F)F] | 3-((4-(2-methylquinolin-8-yl)-2-sulfamoyl-3-(1H-tetrazol-5-yl)phenyl)sulfonyl)azetidin-1-ium 2,2,2-trifluoroacetate | 486.09 |
| 123 | | 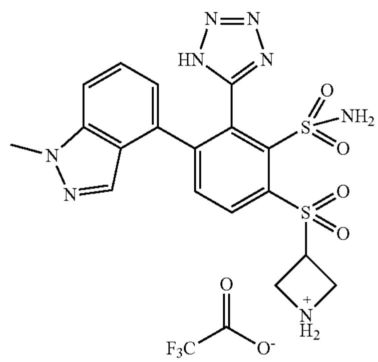 [SMILES: Cn1ncc2c(-c3ccc(S(=O)(=O)C4CNC4)c(S(N)(=O)=O)c3-c3nnn[nH]3)cccc21 ; O=C([O-])C(F)(F)F] | 3-((4-(1-methyl-1H-indazol-4-yl)-2-sulfamoyl-3-(1H-tetrazol-5-yl)phenyl)sulfonyl)azetidin-1-ium 2,2,2-trifluoroacetate | 475.09 |
| 124 | | 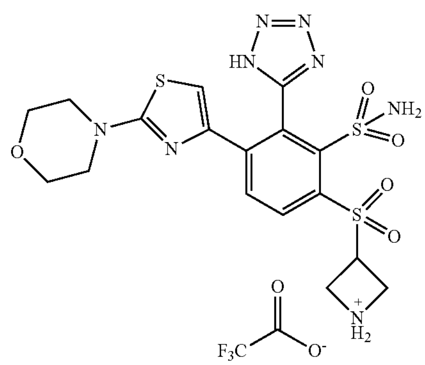 [SMILES: NS(=O)(=O)c1c(S(=O)(=O)C2CNC2)ccc(-c2csc(N3CCOCC3)n2)c1-c1nnn[nH]1 ; O=C([O-])C(F)(F)F] | 3-((4-(2-morpholinothiazol-4-yl)-2-sulfamoyl-3-(1H-tetrazol-5-yl)phenyl)sulfonyl)azetidin-1-ium 2,2,2-trifluoroacetate | 513.07 |
| 125 | | 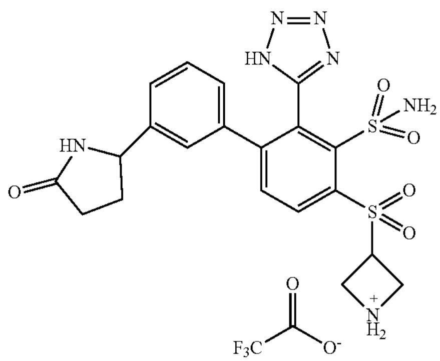 [SMILES: NS(=O)(=O)c1c(S(=O)(=O)C2CNC2)ccc(-c2cccc(C3CCC(=O)N3)c2)c1-c1nnn[nH]1 ; O=C([O-])C(F)(F)F] | 3-((3'-(5-oxopyrrolidin-2-yl)-3-sulfamoyl-2-(1H-tetrazol-5-yl)-[1,1'-biphenyl]-4-yl)sulfonyl)azetidin-1-ium 2,2,2-trifluoroacetate | 504.11 |

-continued

| Ex. No. | RB(OH)2 | Structure | Name | LC/MS m/e [M + H]+ |
|---|---|---|---|---|
| 126 | 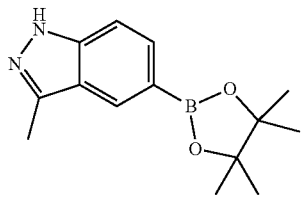 [SMILES: Cc1n[nH]c2ccc(B3OC(C)(C)C(C)(C)O3)cc12] | 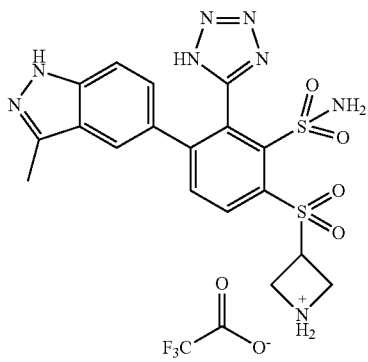 [SMILES: Cc1n[nH]c2ccc(-c3ccc(S(=O)(=O)C4CNC4)c(S(N)(=O)=O)c3-c3nnn[nH]3)cc12 ; O=C([O-])C(F)(F)F] | 3-((4-(3-methyl-1H-indazol-5-yl)-2-sulfamoyl-3-(1H-tetrazol-5-yl)phenyl)sulfonyl)azetidin-1-ium 2,2,2-trifluoroacetate | 475.09 |
| 127 | 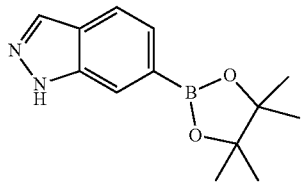 [SMILES: CC1(C)OB(c2ccc3cn[nH]c3c2)OC1(C)C] | 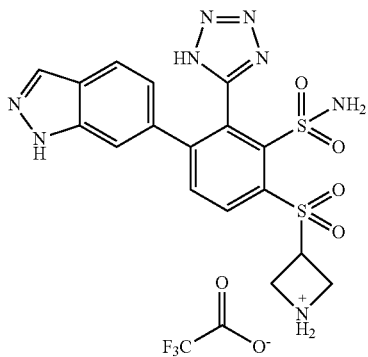 [SMILES: NS(=O)(=O)c1c(S(=O)(=O)C2CNC2)ccc(-c2ccc3cn[nH]c3c2)c1-c1nnn[nH]1 ; O=C([O-])C(F)(F)F] | 3-((4-(1H-indazol-6-yl)-2-sulfamoyl-3-(1H-tetrazol-5-yl)phenyl)sulfonyl)azetidin-1-ium 2,2,2-trifluoroacetate | 461.07 |
| 128 | 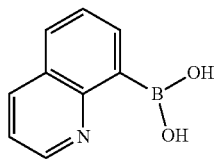 [SMILES: OB(O)c1cccc2cccnc12] | 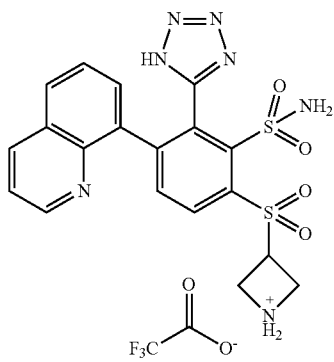 [SMILES: NS(=O)(=O)c1c(S(=O)(=O)C2CNC2)ccc(-c2cccc3cccnc23)c1-c1nnn[nH]1 ; O=C([O-])C(F)(F)F] | 3-((4-(quinolin-8-yl)-2-sulfamoyl-3-(1H-tetrazol-5-yl)phenyl)sulfonyl)azetidin-1-ium 2,2,2-trifluoroacetate | 472.08 |
| 129 | 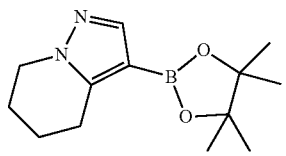 [SMILES: CC1(C)OB(c2cnn3c2CCCC3)OC1(C)C] | 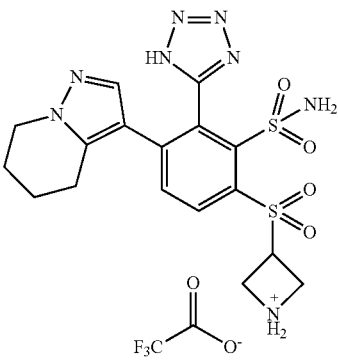 [SMILES: NS(=O)(=O)c1c(S(=O)(=O)C2CNC2)ccc(-c2cnn3c2CCCC3)c1-c1nnn[nH]1 ; O=C([O-])C(F)(F)F] | 3-((2-sulfamoyl-4-(4,5,6,7-tetrahydropyrazolo[1,5-a]pyridin-3-yl)-3-(1H-tetrazol-5-yl)phenyl)sulfonyl)azetidin-1-ium 2,2,2-trifluoroacetate | 465.11 |

-continued
| Ex. No. | RB(OH)2 | Structure | Name | LC/MS m/e [M + H]+ |
|---|---|---|---|---|
| 130 | | 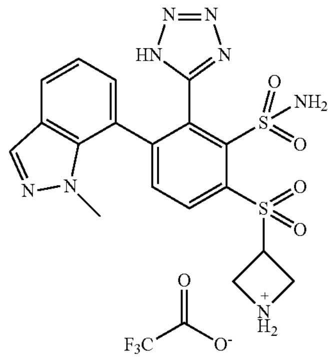 [SMILES: Cn1ncc2cccc(-c3ccc(S(=O)(=O)C4CNC4)c(S(N)(=O)=O)c3-c3nnn[nH]3)c21 ; O=C([O-])C(F)(F)F] | 3-((4-(1-methyl-1H-indazol-7-yl)-2-sulfamoyl-3-(1H-tetrazol-5-yl)phenyl)sulfonyl)azetidin-1-ium 2,2,2-trifluoroacetate | 475.09 |
| 131 | | 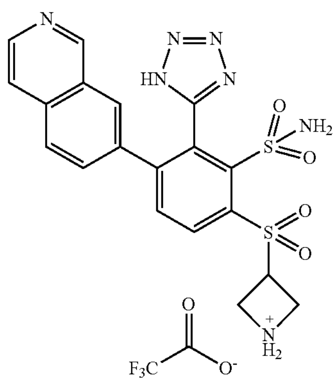 [SMILES: NS(=O)(=O)c1c(S(=O)(=O)C2CNC2)ccc(-c2ccc3ccncc3c2)c1-c1nnn[nH]1 ; O=C([O-])C(F)(F)F] | 3-((4-(isoquinolin-7-yl)-2-sulfamoyl-3-(1H-tetrazol-5-yl)phenyl)sulfonyl)azetidin-1-ium 2,2,2-trifluoroacetate | 472.08 |
EXAMPLES 132-174
Parallel Synthesis of 3-Substituted 2-(1H-tetrazol-5-yl)-6-(ethylamine sulfone)benzenesulfonamides
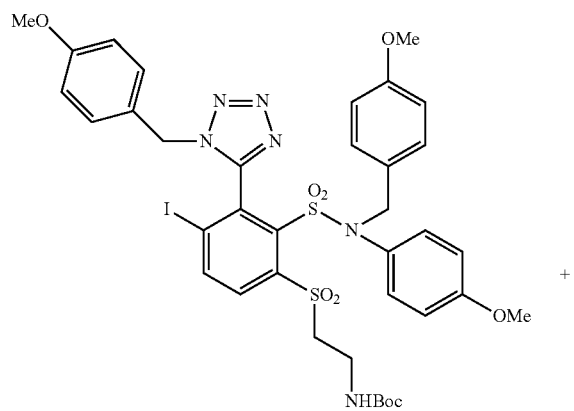

-continued
Step A

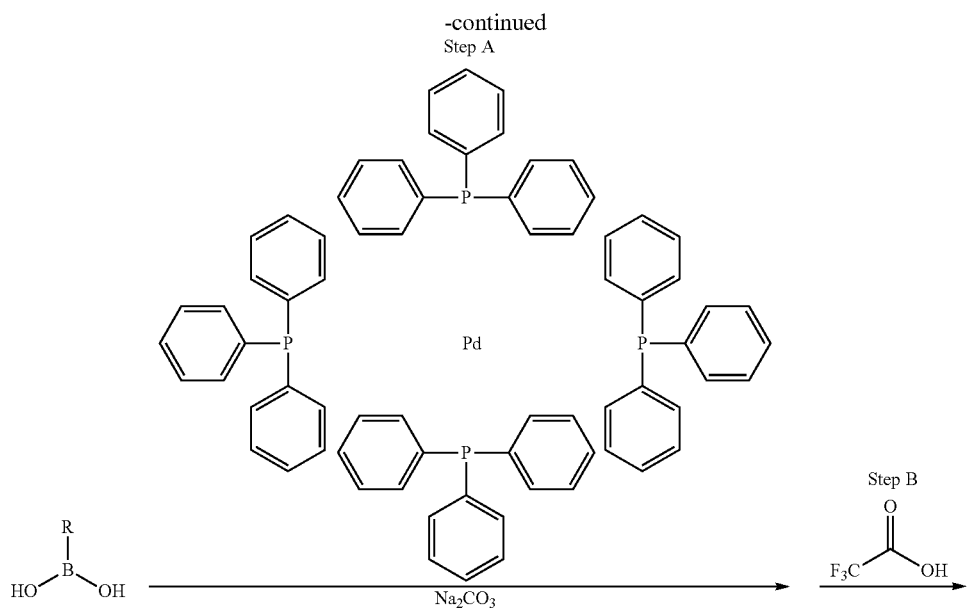

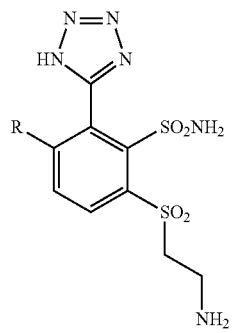

Step A: Palladium catalyzed C—C coupling of arylboronic ester and aryliodide In a glove box under a dry nitrogen atmosphere, arylboronic acids or esters (0.129 mmol) (commercially available, known from the literature) and Pd(PPh3)4 (5 mg, 4.3 μmol) and 130 μL of 1N degassed aq. Na2CO3 solution were added into 2 dram vials. 1.0 mL of a solution of tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl) carbamate (40 mg, 0.043 mmol) in 1,4-Dioxane were added into each vial. The vials were capped and heated at 78° C. with stirring for 20 hours. After the vials were cooled to room temperature, the solvent was removed in a GeneVac. Into each residue was added 600 μL of H2O and 2 mL of EtOAc. The organic layers were transferred into 2 dram vials. The organic solvent was removed in GeneVac to afford the crude intermediates which were deprotected without further purification in the subsequent step.

Step B: Removal of One p-methoxybenzyl (PMB) Protecting & BOC Group by TFA Treatment To the residues from Step A were each added TFA 0.7 mL with anisole (0.3 mL) The vials were shaked at 25° C. for 3 hours. Solvent was removed under reduced pressure using Genevac. The crude materials were dissolved in 1 mL DMSO solution and purified with HPLC.

Step C: Removal of the Remaining p-methoxybenzyl (PMB) Protecting Group by TFA Treatment In 2 dram vials containing the intermediates from last step, 1 mL TFA was added and the reactions were agitated at 65° C. for 4 hours, then concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 μm, 19×100 mm; solvent: gradient range 3-28% initial to 45-95% final MeCN (0.1% TFA) in water 0.1% TFA) 50 or 70 mL/min; 8 min run time] to afford EXAMPLES 132 to 174

| Ex. No. | RB(OH)2 | Structure | Name | LC/MS m/e [M + H]+ |
|---|---|---|---|---|
| 132 | | 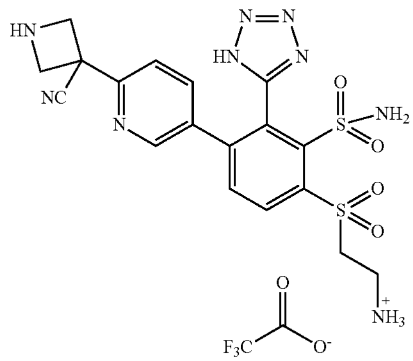 [SMILES: N#CC1(c2ccc(-c3ccc(S(=O)(=O)CCN)c(S(N)(=O)=O)c3-c3nnn[nH]3)cn2)CNC1 ; O=C([O-])C(F)(F)F] | 2-((4-(6-(3-cyanoazetidin-3-yl)pyridin-3-yl)-2-sulfamoyl-3-(1H-tetrazol-5-yl)phenyl)sulfonyl)ethanaminium 2,2,2-trifluoroacetate | 489.09 |
| 133 | | 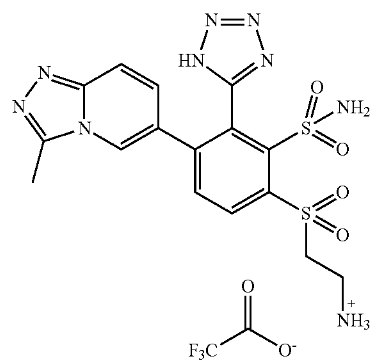 [SMILES: Cc1nnc2ccc(-c3ccc(S(=O)(=O)CCN)c(S(N)(=O)=O)c3-c3nnn[nH]3)cn12 ; O=C([O-])C(F)(F)F] | 2-((4-(3-methyl-[1,2,4]triazolo[4,3-a]pyridin-6-yl)-2-sulfamoyl-3-(1H-tetrazol-5-yl)phenyl)sulfonyl)ethanaminium 2,2,2-trifluoroacetate | 463.08 |
| 134 | | 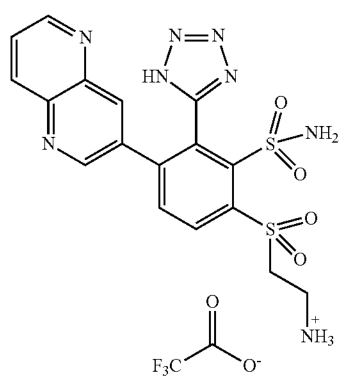 [SMILES: NCCS(=O)(=O)c1ccc(-c2cnc3cccnc3c2)c(-c2nnn[nH]2)c1S(N)(=O)=O ; O=C([O-])C(F)(F)F] | 2-((4-(1,5-naphthyridin-3-yl)-2-sulfamoyl-3-(1H-tetrazol-5-yl)phenyl)sulfonyl)ethanaminium 2,2,2-trifluoroacetate | 460.08 |
| 135 | | 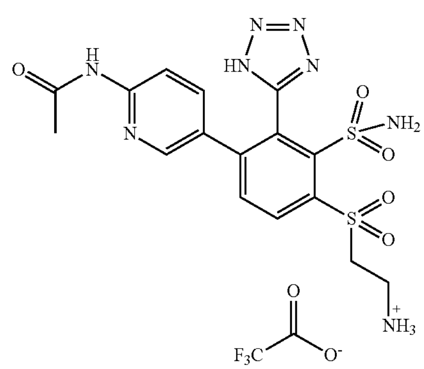 [SMILES: CC(=O)Nc1ccc(-c2ccc(S(=O)(=O)CCN)c(S(N)(=O)=O)c2-c2nnn[nH]2)cn1 ; O=C([O-])C(F)(F)F] | 2-((4-(6-acetamidopyridin-3-yl)-2-sulfamoyl-3-(1H-tetrazol-5-yl)phenyl)sulfonyl)ethanaminium 2,2,2-trifluoroacetate | 466.08 |

| Ex. No. | RB(OH)2 | Structure | Name | LC/MS m/e [M + H]+ |
|---|---|---|---|---|
| 136 | 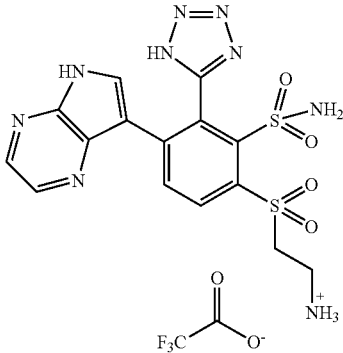 | 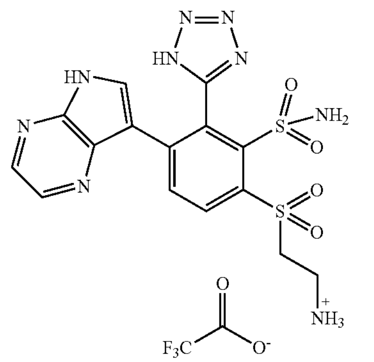 [SMILES: NCCS(=O)(=O)c1ccc(-c2c[nH]c3nccnc23)c(-c2nnn[nH]2)c1S(N)(=O)=O ; O=C([O-])C(F)(F)F] | 2-((4-(5H-pyrrolo[2,3-b]pyrazin-7-yl)-2-sulfamoyl-3-(1H-tetrazol-5-yl)phenyl)sulfonyl)ethanaminium 2,2,2-trifluoroacetate | 449.08 |
| 137 | 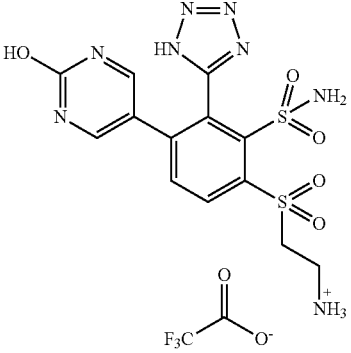 | 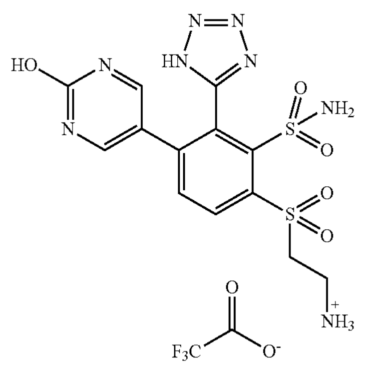 [SMILES: NCCS(=O)(=O)c1ccc(-c2cnc(O)nc2)c(-c2nnn[nH]2)c1S(N)(=O)=O ; O=C([O-])C(F)(F)F] | 2-((4-(2-hydroxypyrimidin-5-yl)-2-sulfamoyl-3-(1H-tetrazol-5-yl)phenyl)sulfonyl)ethanaminium 2,2,2-trifluoroacetate | 426.06 |
| 138 | 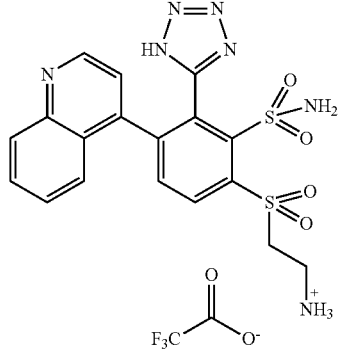 | 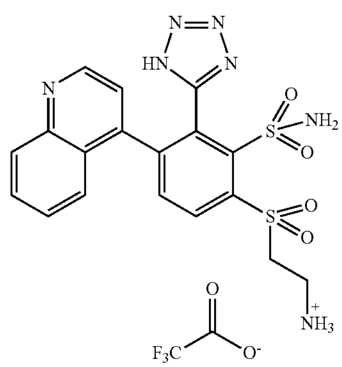 [SMILES: NCCS(=O)(=O)c1ccc(-c2ccnc3ccccc23)c(-c2nnn[nH]2)c1S(N)(=O)=O ; O=C([O-])C(F)(F)F] | 2-((4-(quinolin-4-yl)-2-sulfamoyl-3-(1H-tetrazol-5-yl)phenyl)sulfonyl)ethanaminium 2,2,2-trifluoroacetate | 459.07 |
| 139 | 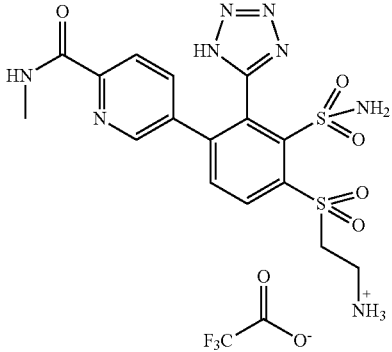 | 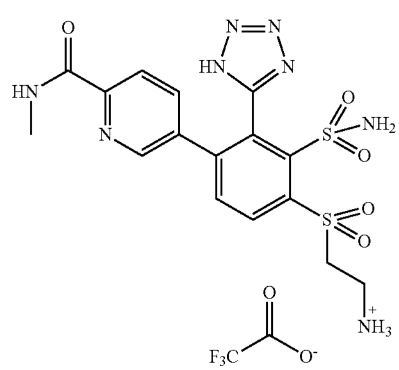 [SMILES: CNC(=O)c1ccc(-c2ccc(S(=O)(=O)CCN)c(S(N)(=O)=O)c2-c2nnn[nH]2)cn1 ; O=C([O-])C(F)(F)F] | 2-((4-(6-(methylcarbamoyl)pyridin-3-yl)-2-sulfamoyl-3-(1H-tetrazol-5-yl)phenyl)sulfonyl)ethanaminium 2,2,2-trifluoroacetate | 466.08 |

-continued

| Ex. No. | RB(OH)2 | Structure | Name | LC/MS m/e [M + H]+ |
|---|---|---|---|---|
| 140 | | 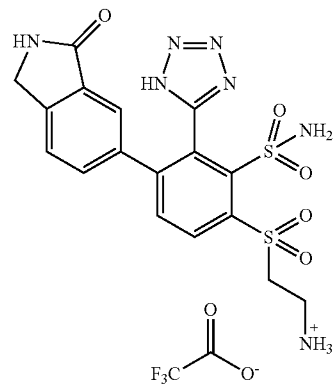 [SMILES: NCCS(=O)(=O)c1ccc(-c2ccc3c(c2)C(=O)NC3)c(-c2nnn[nH]2)c1S(N)(=O)=O ; O=C([O-])C(F)(F)F] | 2-((4-(3-oxoisoindolin-5-yl)-2-sulfamoyl-3-(1H-tetrazol-5-yl)phenyl)sulfonyl)ethanaminium 2,2,2-trifluoroacetate | 463.07 |
| 141 | | 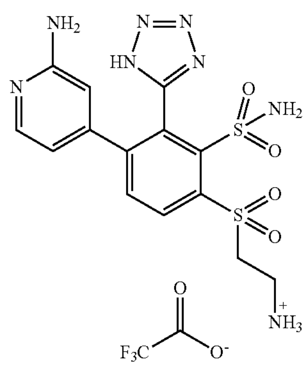 [SMILES: NCCS(=O)(=O)c1ccc(-c2ccnc(N)c2)c(-c2nnn[nH]2)c1S(N)(=O)=O ; O=C([O-])C(F)(F)F] | 2-((4-(2-aminopyridin-4-yl)-2-sulfamoyl-3-(1H-tetrazol-5-yl)phenyl)sulfonyl)ethanaminium 2,2,2-trifluoroacetate | 424.08 |
| 142 | | 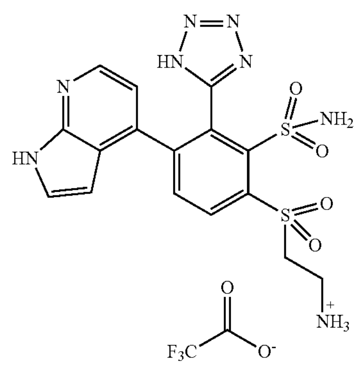 [SMILES: NCCS(=O)(=O)c1ccc(-c2ccnc3[nH]ccc23)c(-c2nnn[nH]2)c1S(N)(=O)=O ; O=C([O-])C(F)(F)F] | 2-((4-(1H-pyrrolo[2,3-b]pyridin-4-yl)-2-sulfamoyl-3-(1H-tetrazol-5-yl)phenyl)sulfonyl)ethanaminium 2,2,2-trifluoroacetate | 448.07 |
| 143 | | 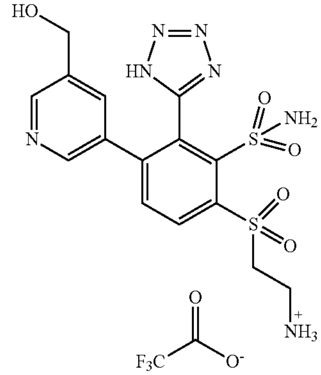 [SMILES: NCCS(=O)(=O)c1ccc(-c2cncc(CO)c2)c(-c2nnn[nH]2)c1S(N)(=O)=O ; O=C([O-])C(F)(F)F] | 2-((4-(5-(hydroxymethyl)pyridin-3-yl)-2-sulfamoyl-3-(1H-tetrazol-5-yl)phenyl)sulfonyl)ethanaminium 2,2,2-trifluoroacetate | 439.08 |

-continued

| Ex. No. | RB(OH)2 | Structure | Name | LC/MS m/e [M + H]+ |
|---|---|---|---|---|
| 144 | 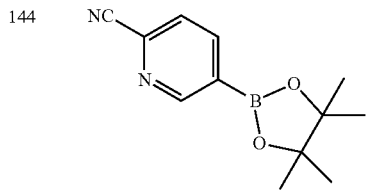 | 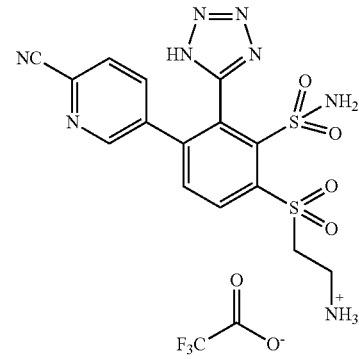 [SMILES: N#Cc1ccc(-c2ccc(S(=O)(=O)CCN)c(S(N)(=O)=O)c2-c2nnn[nH]2)cn1 ; O=C([O-])C(F)(F)F] | 2-((4-(6-cyanopyridin-3-yl)-2-sulfamoyl-3-(1H-tetrazol-5-yl)phenyl)sulfonyl)ethanaminium 2,2,2-trifluoroacetate | 434.07 |
| 145 | 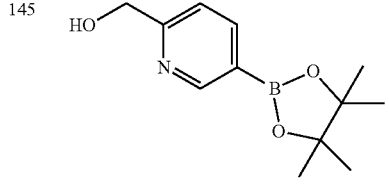 | 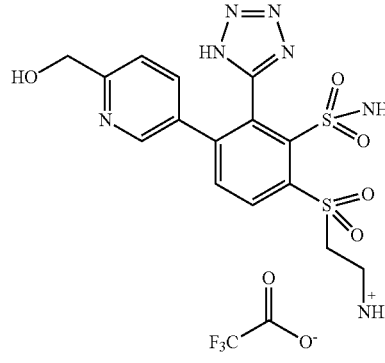 | 2-((4-(6-(hydroxymethyl)pyridin-3-yl)-2-sulfamoyl-3-(1H-tetrazol-5-yl)phenyl)sulfonyl)ethanaminium 2,2,2-trifluoroacetate | 439.07 |
| 146 | 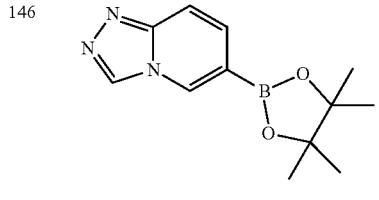 | 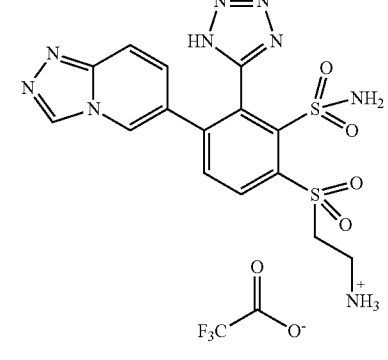 | 2-((4-([1,2,4]triazolo[4,3-a]pyridin-6-yl)-2-sulfamoyl-3-(1H-tetrazol-5-yl)phenyl)sulfonyl)ethanaminium 2,2,2-trifluoroacetate | 449.07 |
| 147 | 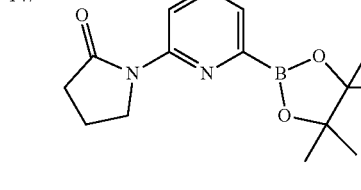 | 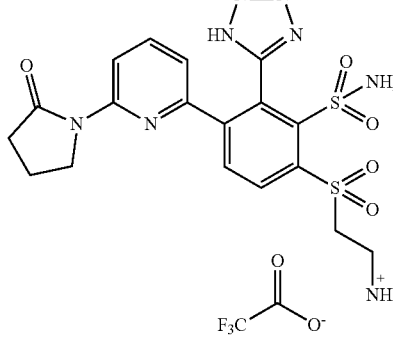 | 2-((4-(6-(2-oxopyrrolidin-1-yl)pyridin-2-yl)-2-sulfamoyl-3-(1H-tetrazol-5-yl)phenyl)sulfonyl)ethanaminium 2,2,2-trifluoroacetate | 492.09 |

| Ex. No. | RB(OH)2 | Structure | Name | LC/MS m/e [M + H]+ |
|---|---|---|---|---|
| 148 | 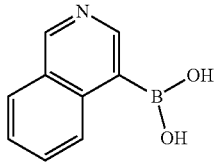 | 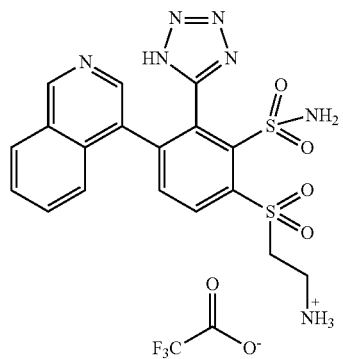 [SMILES: NCCS(=O)(=O)c1ccc(-c2cncc3ccccc23)c(-c2nnn[nH]2)c1S(N)(=O)=O ; O=C([O-])C(F)(F)F] | 2-((4-(isoquinolin-4-yl)-2-sulfamoyl-3-(1H-tetrazol-5-yl)phenyl)sulfonyl)ethanaminium 2,2,2-trifluoroacetate | 459.07 |
| 149 | 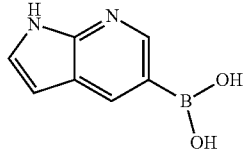 [SMILES: OB(O)c1cnc2[nH]ccc2c1] | 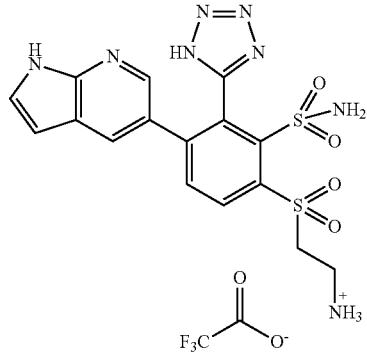 [SMILES: NCCS(=O)(=O)c1ccc(-c2cnc3[nH]ccc3c2)c(-c2nnn[nH]2)c1S(N)(=O)=O ; O=C([O-])C(F)(F)F] | 2-((4-(1H-pyrrolo[2,3-b]pyridin-5-yl)-2-sulfamoyl-3-(1H-tetrazol-5-yl)phenyl)sulfonyl)ethanaminium 2,2,2-trifluoroacetate | 448.07 |
| 150 | 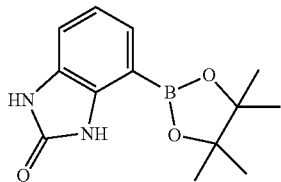 [SMILES: CC1(C)OB(c2cccc3[nH]c(=O)[nH]c23)OC1(C)C] | 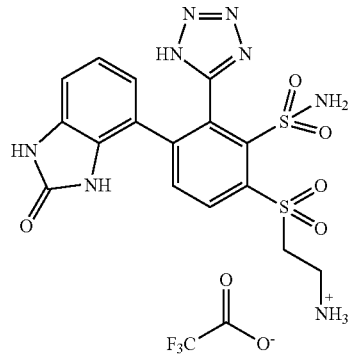 [SMILES: NCCS(=O)(=O)c1ccc(-c2cccc3[nH]c(=O)[nH]c23)c(-c2nnn[nH]2)c1S(N)(=O)=O ; O=C([O-])C(F)(F)F] | 2-((4-(2-oxo-2,3-dihydro-1H-benzo[d]imidazol-4-yl)-2-sulfamoyl-3-(1H-tetrazol-5-yl)phenyl)sulfonyl)ethanaminium 2,2,2-trifluoroacetate | 465.07 |
| 151 | 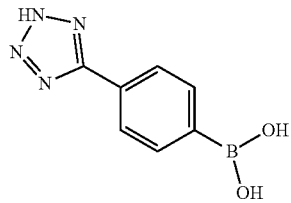 [SMILES: OB(O)c1ccc(-c2nn[nH]n2)cc1] | 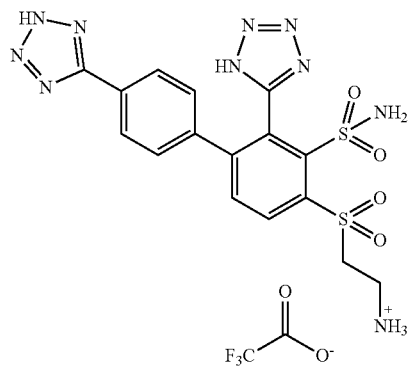 [SMILES: NCCS(=O)(=O)c1ccc(-c2ccc(-c3nn[nH]n3)cc2)c(-c2nnn[nH]2)c1S(N)(=O)=O ; O=C([O-])C(F)(F)F] | 2-((3-sulfamoyl-2-(1H-tetrazol-5-yl)-4'-(2H-tetrazol-5-yl)-[1,1'-biphenyl]-4-yl)sulfonyl)ethanaminium 2,2,2-trifluoroacetate | 477.08 |

-continued

| Ex. No. | RB(OH)2 | Structure | Name | LC/MS m/e [M + H]+ |
|---|---|---|---|---|
| 152 | | 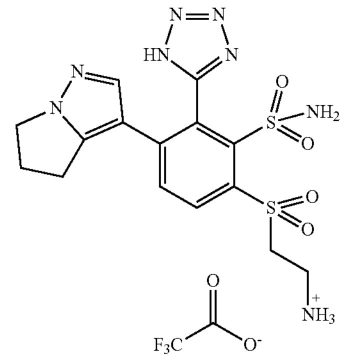 [SMILES: NCCS(=O)(=O)c1ccc(-c2cnn3c2CCC3)c(-c2nnn[nH]2)c1S(N)(=O)=O ; O=C([O-])C(F)(F)F] | 2-((4-(5,6-dihydro-4H-pyrrolo[1,2-b]pyrazol-3-yl)-2-sulfamoyl-3-(1H-tetrazol-5-yl)phenyl)sulfonyl)ethanaminium 2,2,2-trifluoroacetate | 439.09 |
| 153 | | 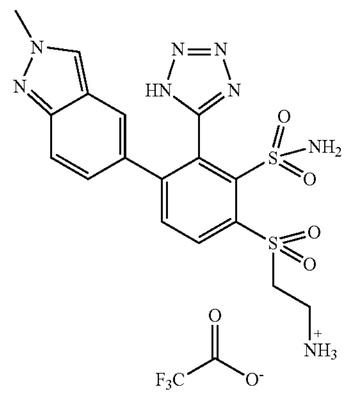 [SMILES: Cn1cc2cc(-c3ccc(S(=O)(=O)CCN)c(S(N)(=O)=O)c3-c3nnn[nH]3)ccc2n1 ; O=C([O-])C(F)(F)F] | 2-((4-(2-methyl-2H-indazol-5-yl)-2-sulfamoyl-3-(1H-tetrazol-5-yl)phenyl)sulfonyl)ethanaminium 2,2,2-trifluoroacetate | 463.09 |
| 154 | | 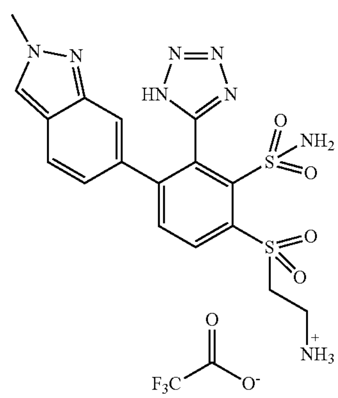 [SMILES: Cn1cc2ccc(-c3ccc(S(=O)(=O)CCN)c(S(N)(=O)=O)c3-c3nnn[nH]3)cc2n1 ; O=C([O-])C(F)(F)F] | 2-((4-(2-methyl-2H-indazol-6-yl)-2-sulfamoyl-3-(1H-tetrazol-5-yl)phenyl)sulfonyl)ethanaminium 2,2,2-trifluoroacetate | 463.09 |
| 155 | | 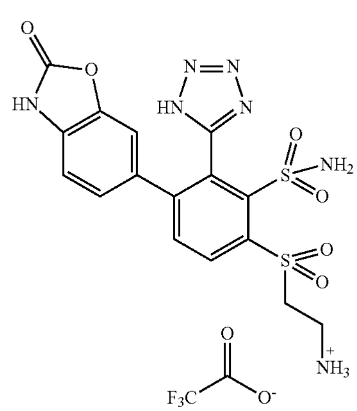 [SMILES: NCCS(=O)(=O)c1ccc(-c2ccc3[nH]c(=O)oc3c2)c(-c2nnn[nH]2)c1S(N)(=O)=O ; O=C([O-])C(F)(F)F] | 2-((4-(2-oxo-2,3-dihydrobenzo[d]oxazol-6-yl)-2-sulfamoyl-3-(1H-tetrazol-5-yl)phenyl)sulfonyl)ethanaminium 2,2,2-trifluoroacetate | 466.05 |

| Ex. No. | RB(OH)2 | Structure | Name | LC/MS m/e [M + H]+ |
|---|---|---|---|---|
| 156 | 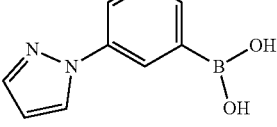 | 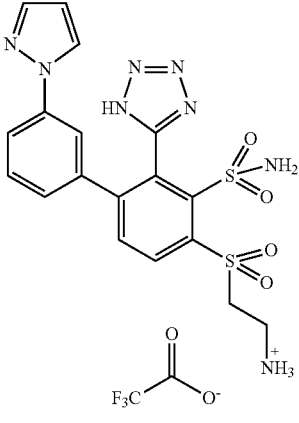 [SMILES: NCCS(=O)(=O)c1ccc(-c2cccc(-n3cccn3)c2)c(-c2nnn[nH]2)c1S(N)(=O)=O ; O=C([O-])C(F)(F)F] | 2-((3'-(1H-pyrazol-1-yl)-3-sulfamoyl-2-(1H-tetrazol-5-yl)-[1,1'-biphenyl]-4-yl)sulfonyl)ethanaminium 2,2,2-trifluoroacetate | 475.09 |
| 157 | 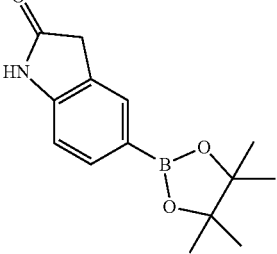 | 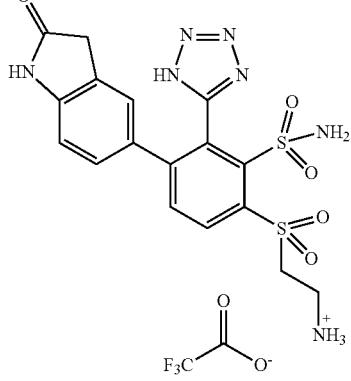 | 2-((4-(2-oxoindolin-5-yl)-2-sulfamoyl-3-(1H-tetrazol-5-yl)phenyl)sulfonyl)ethanaminium 2,2,2-trifluoroacetate | 464.07 |
| 158 | 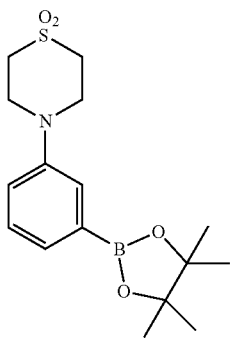 [SMILES: CC1(C)OB(c2cccc(N3CCS(=O)(=O)CC3)c2)OC1(C)C] | 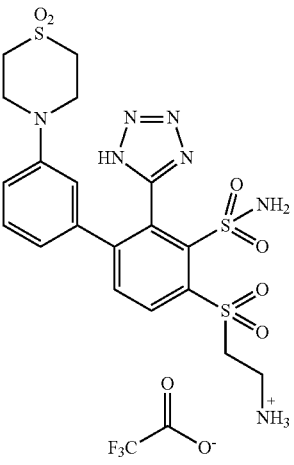 [SMILES: NCCS(=O)(=O)c1ccc(-c2cccc(N3CCS(=O)(=O)CC3)c2)c(-c2nnn[nH]2)c1S(N)(=O)=O ; O=C([O-])C(F)(F)F] | 2-((3'-(1,1-dioxidothiomorpholino)-3-sulfamoyl-2-(1H-tetrazol-5-yl)-[1,1'-biphenyl]-4-yl)sulfonyl)ethanaminium 2,2,2-trifluoroacetate | 542.09 |

-continued

| Ex. No. | RB(OH)2 | Structure | Name | LC/MS m/e [M + H]+ |
|---|---|---|---|---|
| 159 | 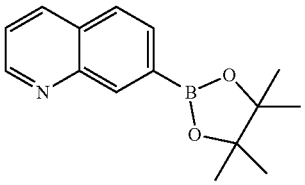 [SMILES: CC1(C)OB(c2ccc3cccnc3c2)OC1(C)C] | 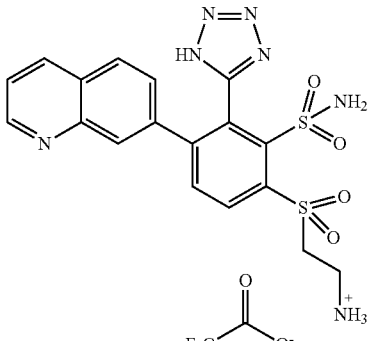 | 2-((4-(quinolin-7-yl)-2-sulfamoyl-3-(1H-tetrazol-5-yl)phenyl)sulfonyl)ethanaminium 2,2,2-trifluoroacetate | 460.08 |
| 160 | 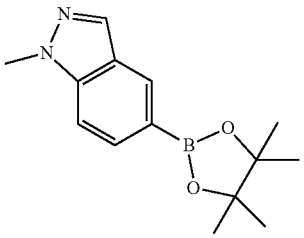 | 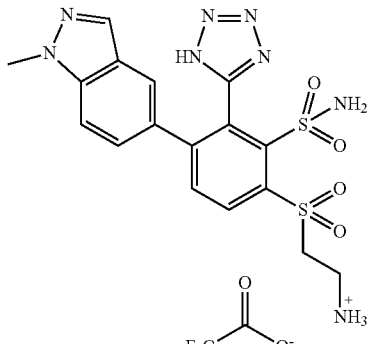 | 2-((4-(1-methyl-1H-indazol-5-yl)-2-sulfamoyl-3-(1H-tetrazol-5-yl)phenyl)sulfonyl)ethanaminium 2,2,2-trifluoroacetate | 463.09 |
| 161 | 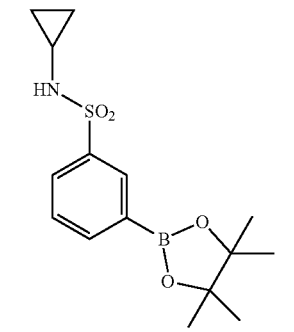 [SMILES: CC1(C)OB(c2cccc(S(=O)(=O)NC3CC3)c2)OC1(C)C] | 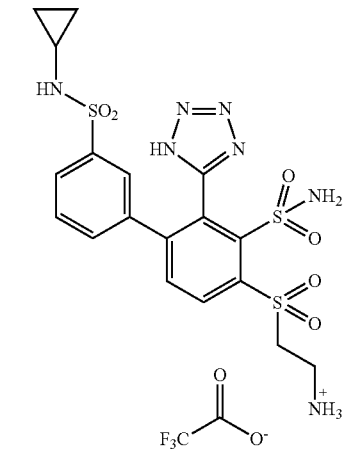 [SMILES: NCCS(=O)(=O)c1ccc(-c2cccc(S(=O)(=O)NC3CC3)c2)c(-c2nnn[nH]2)c1S(N)(=O)=O ; O=C([O-])C(F)(F)F] | 2-((3'-(N-cyclopropylsulfamoyl)-3-sulfamoyl-2-(1H-tetrazol-5-yl)-[1,1'-biphenyl]-4-yl)sulfonyl)ethanaminium 2,2,2-trifluoroacetate | 528.07 |
| 162 | 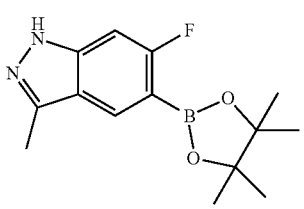 [SMILES: Cc1n[nH]c2cc(F)c(B3OC(C)(C)C(C)(C)O3)cc12] | 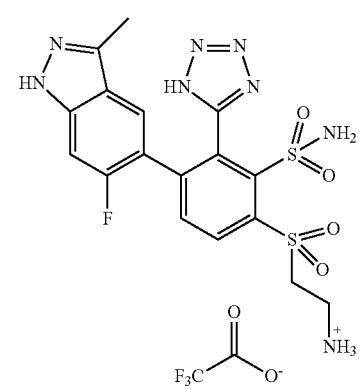 [SMILES: Cc1n[nH]c2cc(F)c(-c3ccc(S(=O)(=O)CCN)c(S(N)(=O)=O)c3-c3nnn[nH]3)cc12 ; O=C([O-])C(F)(F)F] | 2-((4-(6-fluoro-3-methyl-1H-indazol-5-yl)-2-sulfamoyl-3-(1H-tetrazol-5-yl)phenyl)sulfonyl)ethanaminium 2,2,2-trifluoroacetate | 481.08 |

| Ex. No. | RB(OH)2 | Structure | Name | LC/MS m/e [M + H]+ |
|---|---|---|---|---|
| 163 | | 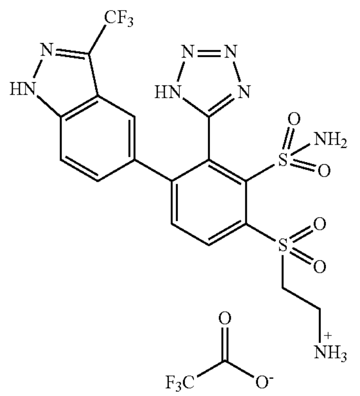 [SMILES: NCCS(=O)(=O)c1ccc(-c2ccc3[nH]nc(C(F)(F)F)c3c2)c(-c2nnn[nH]2)c1S(N)(=O)=O ; O=C([O-])C(F)(F)F] | 2-((2-sulfamoyl-3-(1H-tetrazol-5-yl)-4-(3-(trifluoromethyl)-1H-indazol-5-yl)phenyl)sulfonyl)ethanaminium 2,2,2-trifluoroacetate | 517.06 |
| 164 | | 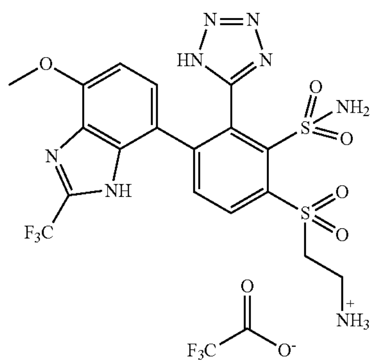 [SMILES: COc1ccc(-c2ccc(S(=O)(=O)CCN)c(S(N)(=O)=O)c2-c2nnn[nH]2)c2[nH]c(C(F)(F)F)nc12 ; O=C([O-])C(F)(F)F] | 2-((4-(4-methoxy-2-(trifluoromethyl)-1H-benzo[d]imidazol-7-yl)-2-sulfamoyl-3-(1H-tetrazol-5-yl)phenyl)sulfonyl)ethanaminium 2,2,2-trifluoroacetate | 547.07 |
| 165 | | 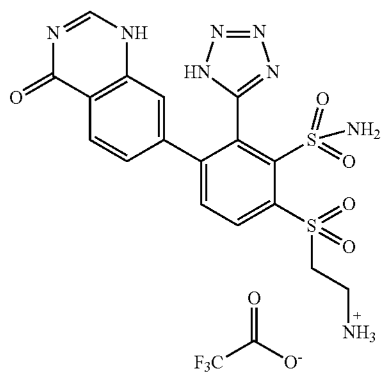 [SMILES: NCCS(=O)(=O)c1ccc(-c2ccc3c(=O)nc[nH]c3c2)c(-c2nnn[nH]2)c1S(N)(=O)=O ; O=C([O-])C(F)(F)F] | 2-((4-(4-oxo-1,4-dihydroquinazolin-7-yl)-2-sulfamoyl-3-(1H-tetrazol-5-yl)phenyl)sulfonyl)ethanaminium 2,2,2-trifluoroacetate | 477.07 |
| 166 | | 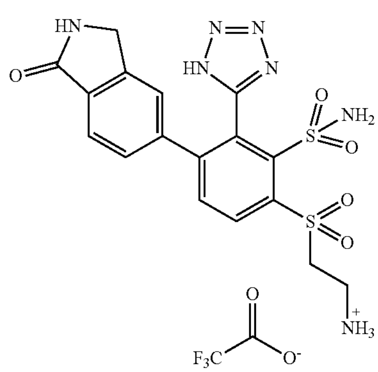 [SMILES: NCCS(=O)(=O)c1ccc(-c2ccc3c(c2)CNC3=O)c(-c2nnn[nH]2)c1S(N)(=O)=O ; O=C([O-])C(F)(F)F] | 2-((4-(1-oxoisoindolin-5-yl)-2-sulfamoyl-3-(1H-tetrazol-5-yl)phenyl)sulfonyl)ethanaminium 2,2,2-trifluoroacetate | 464.07 |

| Ex. No. | RB(OH)2 | Structure | Name | LC/MS m/e [M + H]+ |
|---|---|---|---|---|
| 167 | 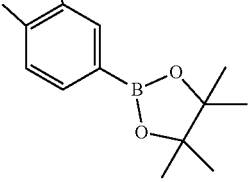 | 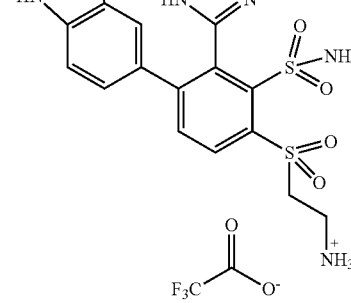 | 2-((4-(1H-indazol-5-yl)-2-sulfamoyl-3-(1H-tetrazol-5-yl)phenyl)sulfonyl)ethanaminium 2,2,2-trifluoroacetate | 449.07 |
| 168 | 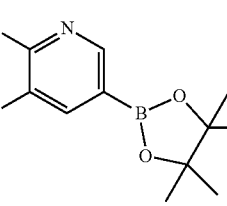 | 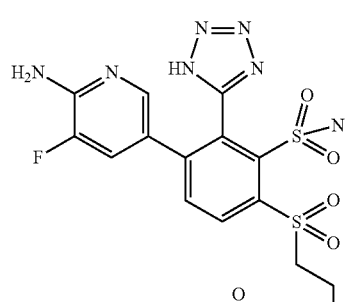 | 2-((4-(6-amino-5-fluoropyridin-3-yl)-2-sulfamoyl-3-(1H-tetrazol-5-yl)phenyl)sulfonyl)ethanaminium 2,2,2-trifluoroacetate | 443.06 |
| 169 | 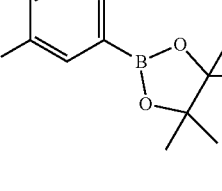 | 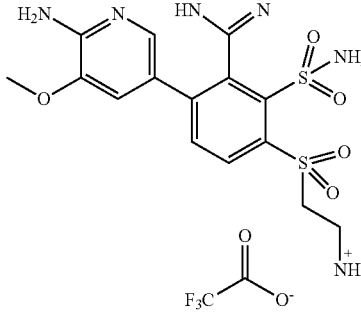 | 2-((4-(6-amino-5-methoxypyridin-3-yl)-2-sulfamoyl-3-(1H-tetrazol-5-yl)phenyl)sulfonyl)ethanaminium 2,2,2-trifluoroacetate | 455.08 |
| 170 | 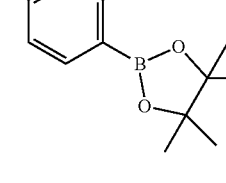 | 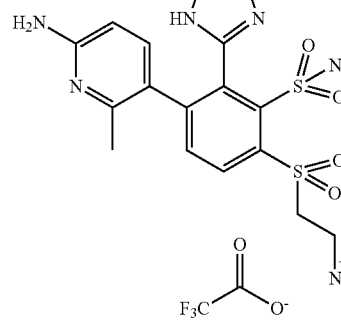 | 2-((4-(6-amino-2-methylpyridin-3-yl)-2-sulfamoyl-3-(1H-tetrazol-5-yl)phenyl)sulfonyl)ethanaminium 2,2,2-trifluoroacetate | 439.09 |

-continued

| Ex. No. | RB(OH)2 | Structure | Name | LC/MS m/e [M + H]+ |
|---|---|---|---|---|
| 171 | | 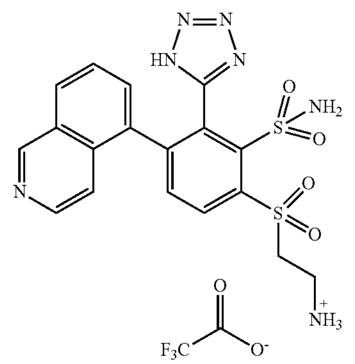 [SMILES: NCCS(=O)(=O)c1ccc(-c2cccc3cnccc23)c(-c2nnn[nH]2)c1S(N)(=O)=O ; O=C([O-])C(F)(F)F] | 2-((4-isoquinolin-5-yl)-2-sulfamoyl-3-(1H-tetrazol-5-yl)phenyl)sulfonyl)ethanaminium 2,2,2-trifluoroacetate | 460.08 |
| 172 | | 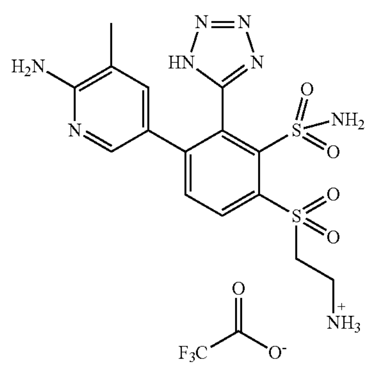 [SMILES: Cc1cc(-c2ccc(S(=O)(=O)CCN)c(S(N)(=O)=O)c2-c2nnn[nH]2)cnc1N ; O=C([O-])C(F)(F)F] | 2-((4-(6-amino-5-methylpyridin-3-yl)-2-sulfamoyl-3-(1H-tetrazol-5-yl)phenyl)sulfonyl)ethanaminium 2,2,2-trifluoroacetate | 439.09 |
| 173 | | 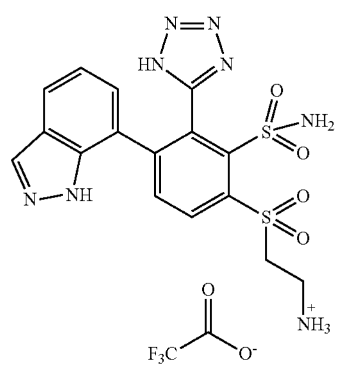 [SMILES: NCCS(=O)(=O)c1ccc(-c2cccc3cn[nH]c23)c(-c2nnn[nH]2)c1S(N)(=O)=O ; O=C([O-])C(F)(F)F] | 2-((4-(1H-indazol-7-yl)-2-sulfamoyl-3-(1H-tetrazol-5-yl)phenyl)sulfonyl)ethanaminium 2,2,2-trifluoroacetate | 448.08 |
| 174 | | 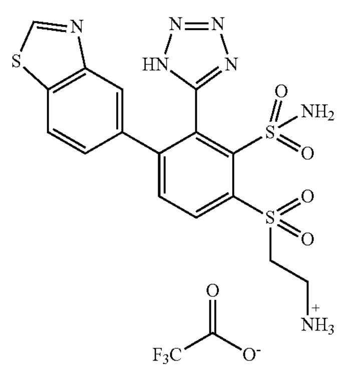 [SMILES: NCCS(=O)(=O)c1ccc(-c2ccc3scnc3c2)c(-c2nnn[nH]2)c1S(N)(=O)=O ; O=C([O-])C(F)(F)F] | 2-((4-(benzo[d]thiazol-5-yl)-2-sulfamoyl-3-(1H-tetrazol-5-yl)phenyl)sulfonyl)ethanaminium 2,2,2-trifluoroacetate | 466.04 |

EXAMPLES 175 and 176

3-(2-amino-3H-benzo[d]imidazol-4-yl)-6-((1r,3r)-3-aminocyclobutylsulfonyl)-2-(2H-tetrazol-5-yl)benzenesulfonamide and 3-(2-amino-3H-benzo[d]imidazol-4-yl)-6-((1s, 3s)-3-aminocyclobutylsulfonyl)-2-(2H-tetrazol-5-yl)benzenesulfonamide

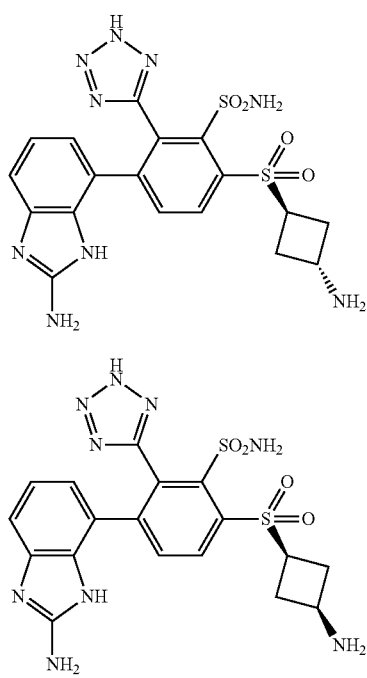

Step A: tert-butyl 3-hydroxycyclobutylcarbamate

To a solution of tert-butyl (3-oxocyclobutyl)carbamate (200 mg, 1.08 mmol) in ethanol (3 mL) was slowly added sodium borohydride (41 mg, 1.08 mmol) at 0° C. The reaction mixture was warmed to room temperature and stirred for 1 hour. It was quenched with water (5 mL). The solvent was removed under reduced pressure. The water layer was extracted with ethyl acetate (3×20 mL). The combined organic layer was washed with brine, dried over anhydrous magnesium sulfate, filtered and concentrated under vacuum. The residue was purified by silica gel column chromatography eluting with DCM/methanol (10:1) to afford the title compound: LCMS [M+hr−56]$^+$: 173; $^1$H NMR (300 MHz, CDCl$_3$): δ 4.71-4.40 (m, 1H), 4.13-4.00 (m, 1H), 3.83-3.67 (m, 1H), 2.81-2.72 (m, 1H), 2.32-2.21 (m, 2H), 2.08-1.74 (m, 2H), 1.44 (s, 9H).

Step B: 3-(tert-butoxycarbonylamino)cyclobutyl methanesulfonate

In a round-bottomed flask charged with tert-butyl (3-hydroxycyclobutyl)carbamate (150 mg, 0.801 mmol) and triethylamine (243 mg, 2.403 mmol) was added DCM (2 mL). Methanesulfonyl chloride (0.187 ml, 2.403 mmol) was added dropwise via syringe at −20° C. over 5 minutes. The reaction mixture was stirred at room temperature for 2 hours, then diluted with water (15 mL) and extracted with DCM (2×15 mL). The organic layer was washed with saturated NH$_4$Cl, dried over MgSO$_4$, filtered and concentrated in vacuo to afford the title compound: $^1$H NMR (300 MHz, CDCl$_3$): δ 5.22-5.19 (m, 0.5H), 4.76-4.68 (m, 2H), 5.32-4.16 (m, 0.5H), 3.90-3.73 (m, 1H), 3.01 (s, 4H), 3.29-2.88 (m, 2H), 2.67-2.64 (m, 1H), 2.49-2.34 (m, 1H), 2.23-2.09 (m, 1H), 1.44 (s, 9H).

Step C: S-3-(tert-butoxycarbonylamino)cyclobutyl ethanethioate

The mixture of 3-((tert-butoxycarbonyl)amino)cyclobutyl methanesulfonate (3.0 g, 11.31 mmol) and potassium thioacetate (5.17 g, 45.2 mmol) in N,N-dimethylformamide (8 mL) was heated at 70° C. overnight. The resulting mixture was diluted with ethyl acetate (15 mL), washed with water (30 mL) and brine (2×30 mL), dried over sodium sulfate and concentrated. The residue was purified by preparative thin layer chromatography eluting with a mixture of petroleum ether and ethyl acetate (1:1) to afford the title compound: LCMS [M+hr −15]$^+$: 231; $^1$H NMR (300 MHz, CDCl$_3$): δ 4.87-4.60 (bs, 1H), 4.36-4.21 (bs, 1H), 3.96-3.90 (m, 1H), 2.87-2.83 (m, 1H), 2.46-2.29 (m, 2H), 2.27 (d, J=1.2 Hz, 3H), 1.95-1.91 (m, 1H), 1.43 (s, 9H).

Step D: di-tert-butyl 3,3'-disulfanediylbis(cyclobutane-3,1-diyl)dicarbamate A solution of S-(3-((tert-butoxycarbonyl)amino)cyclobutyl) ethanethioate (2.5 g, 10.19 mmol) in MeOH (33 ml) was cooled to 0° C. Sodium hydroxide (4.08 mL, 40.8 mmol) was added slowly to the reaction system. The resulting mixture was then stirred for 2 hours at room temperature. The reaction was neutralized by HCl solution (2 N) and extracted with ethyl acetate (3×20 mL). The organic layers were concentrated under reduced pressure to afford the title compound: LCMS [M+H]$^+$: 405; $^1$H NMR (400 MHz, CDCl$_3$): δ4.81-4.67 (bs, 2H), 4.46-4.37 (m, 1H), 3.95-3.88 (m, 1H), 3.59-3.51 (bs, 1H), 3.17-3.02 (m, 1H), 2.97-2.86 (m, 2H), 2.45-2.36 (m, 2H), 2.36-2.23 (m, 2H), 1.91-1.76 (m, 2H), 1.56 (s, 18H).

Step E: tert-butyl (3-mercaptocyclobutyl)carbamate

To a solution of di-tert-butyl (disulfanediylbis(cyclobutane-3,1-diyl))dicarbamate (1 g, 2.472 mmol) in acetic acid (10 ml) was added zinc (0.808 g, 12.36 mmol) at room temperature. The mixture was stirred for 16 hours at 50° C. The solid was filtered out and the filtrate was concentrated under vacuum to afford the title compound: LCMS [M+hr−15]$^+$: 189.

Step F: tert-butyl 3-(2-(N,N-bis(4-methoxybenzyl)sulfamoyl)-4-iodo-3-(2-(4-methoxybenzyl)-2H-tetrazol-5-yl)phenylthio)cyclobutylcarbamate Sodium hydride (45.5 mg, 1.898 mmol) was added to a stirred, cooled to 0° C. mixture of 6-bromo-3-iodo-N,N-bis(4-methoxybenzyl)-2-(2-(4-methoxybenzyl)-2H-tetrazol-5-yl)benzenesulfonamide (500 mg, 0.633 mmol) and tert-butyl (3-mercaptocyclobutyl)carbamate (257 mg, 1.265 mmol) in DMF (25 mL) and the mixture was stirred at room temperature for 2 hours. The mixture was quenched with NH$_4$Cl solution, diluted with ethyl acetate. The mixture was separated and the aqueous layer was extracted with ethyl acetate. The combined extracts were washed with brine, dried over MgSO$_4$, filtered and the solvent was evaporated under reduced pressure. The residue was purified by silica gel column chromatography, eluting with ethyl acetate/petroleum ether (1/1). The combined organic fractions were concentrated under reduced pressure to afford the title compound: LCMS [M+H]$^+$: 913

Step G: tert-butyl 3-(2-(N,N-bis(4-methoxybenzyl) sulfamoyl)-4-iodo-3-(2-(4-methoxybenzyl)-2H-tetrazol-5-yl)phenylsulfonyl)cyclobutylcarbamate The tert-butyl (3-((2-(N,N-bis(4-methoxybenzyl)sulfamoyl)-4-iodo-3-(2-(4-methoxybenzyl)-2H-tetrazol-5-yl) phenyl)thio)cyclobutyl)carbamate (500 mg, 0.548 mmol) was dissolved in DCM (6 mL), and 3-chlorobenzoperoxoic acid (473 mg, 2.74 mmol) was added. The reaction mixture was stirred for 8 hours at room temperature, and then partitioned between ethyl acetate and 10% aq. sodium thiosulfate. The organic phase was separated, washed with saturated aqueous sodium bicarbonate, dried ($Na_2SO_4$) and the volatiles removed under reduced pressure. The residue was applied onto silica gel column with ethyl acetate/petroleum ether (1:1) to afford the title compound: LCMS [M+H]$^+$: 945

Step H: tert-butyl 3-(4-(2-amino-3H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)cyclobutylcarbamate To a solution of tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)cyclobutyl)carbamate (500 mg, 0.529 mmol) in 1,4-dioxane (5 mL)/water (1 mL) (5:1) was added 1,1'-bis(diphenylphosphino)ferrocene-palladium(ii) dichloride DCM complex (86 mg, 0.106 mmol), (2-amino-1H-benzo[d]imidazol-7-yl)boronic acid (187 mg, 1.058 mmol) and sodium carbonate (168 mg, 1.588 mmol) at room temperature. The flask was degassed with nitrogen three times. Then the mixture was stirred for 16 hours at 80° C. under an atmosphere of nitrogen. The solid was filtered out and the filtrate was concentrated under reduced pressure. The residue was then purified by silica gel column with DCM/methanol (90:10) to afford the title compound: LCMS [M+H]$^+$: 950

Step I: 3-(2-amino-1H-benzo[d]imidazol-7-yl)-6-((3-aminocyclobutyl)sulfonyl)-N-(4-methoxybenzyl)-2-(2-(4-methoxybenzyl)-2H-tetrazol-5-yl)benzenesulfonamide To a solution of tert-butyl (3-((4-(2-amino-1H-benzo[d] imidazol-7-yl)-2-(N,N-bis(4-methoxybenzyl)sulfamoyl)-3-(2-(4-methoxybenzyl)-2H-tetrazol-5-yl)phenyl)sulfonyl)cyclobutyl)carbamate (500 mg, 0.526 mmol) in DCM (6 mL) was added triflroroacid (3 mL) at room temperature. The reaction system was then kept for 1 hour at room temperature. The resulting mixture was concentrated under reduced pressure to afford the title compound: LCMS [M+H]$^+$: 730

Step J: 3-(2-amino-1H-benzo[d]imidazol-7-yl)-6-(((1r,3r)-3-aminocyclobutyl)sulfonyl)-2-(2H-tetrazol-5-yl)benzenesulfonamide and 3-(2-amino-1H-benzo[d]imidazol-7-yl)-6-(((1s, 3s)-3-aminocyclobutyl)sulfonyl)-2-(2H-tetrazol-5-yl) benzenesulfonamide 3-(2-amino-1H-benzo[d]imidazol-7-yl)-6-((3-aminocyclobutyl)sulfonyl)-N-(4-methoxybenzyl)-2-(2-(4-methoxybenzyl)-2H-tetrazol-5-yl)benzenesulfonamide (340 mg, 0.466 mmol) was dissolved in triflroroacid (4 mL) at room temperature. The reaction was kept at 80° C. for 1 hour. The resulting mixture was concentrated under reduced pressure to afford the crude product. The crude product was then applied onto Prep-HPLC with the condition (Column: X Bridge C18, 19*150 mm, 5 μM; Mobile Phase A: water/0.05% $NH_4HCO_3$, Mobile Phase B: ACN; Flow rate: 20 mL/min; Gradient: 27-40% B in 8 min; 254 nm; Retention time: 6.45 min, 7.60 min) to afford the final product 3-(2-amino-1H-benzo[d]imidazol-7-yl)-6-(((1r,3r)-3-aminocyclobutyl)sulfonyl)-2-(2H-tetrazol-5-yl)benzenesulfonamide: LCMS [M+H]$^+$: 490; $^1$H NMR (300 MHz, DMSO-d6): δ 8.30 (d, J=12.3 Hz, 1H), 8.01 (d, J=7.2 Hz, 1H), 7.94-7.33 (m, 2H), 6.98 (d, J=7.2 Hz, 1H), 6.62-6.52 (m, 2H), 6.17 (d, J=7.5 Hz, 1H), 4.81-4.69 (m, 1H), 3.78-3.67 (m, 1H), 2.2.59-2.51 (m, 4H) and 3-(2-amino-1H-benzo[d] imidazol-7-yl)-6-(((1s, 3s)-3-aminocyclobutyl)sulfonyl)-2-(2H-tetrazol-5-yl)benzenesulfonamide. LCMS (ESI) calc'd for $C_{18}H_{19}N_9O_4S_2$[M+H]$^+$: 490. found 490. $^1$H NMR (300 MHz, DMSO-d6): δ 8.29 (d, J=7.8 Hz, 1H), 8.03 (d, J=8.4 Hz, 1H), 7.85-7.33 (m, 2H), 6.97 (d, J=7.8 Hz, 1H), 6.54 (t, J=7.8 Hz, 1H), 6.33 (bs, 1.5H), 6.10 (d, J=7.5 Hz, 1H), 5.12-5.02 (m, 1H), 3.97-3.89 (m, 1H), 2.82-2.72 (m, 2H), 2.56-2.51 (m, 1H);

EXAMPLES 177-180 were prepared using the same general procedure as EXAMPLES 175 and 176 starting from 6-bromo-3-iodo-N,N-bis(4-methoxybenzyl)-2-(2-(4-methoxybenzyl)-2H-tetrazol-5-yl)benzenesulfonamide, the appropriate boronic acids, and tert-butyl (3-mercaptocyclobutyl)carbamate or the corresponding thiol, tert-butyl (4-mercaptocyclohexyl)carbamate, which was prepared in a similar fashion as tert-butyl (3-mercaptocyclobutyl)carbamate.

| EX NO | Structure | Name | LC/MS [M + H]$^+$ |
|---|---|---|---|
| 177 | 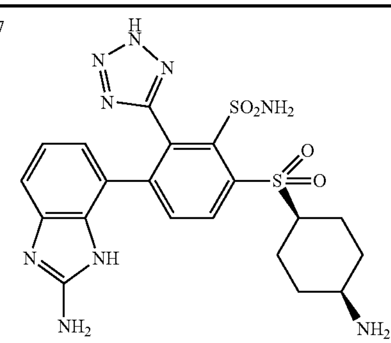 | 3-(2-amino-3H-benzo[d]imidazol-4-yl)-6-((1s,4s)-4-aminocyclohexylsulfonyl)-2-(2H-tetrazol-5-yl)benzenesulfonamide | 518 |

| EX NO | Structure | Name | LC/MS [M + H]+ |
|---|---|---|---|
| 178 | 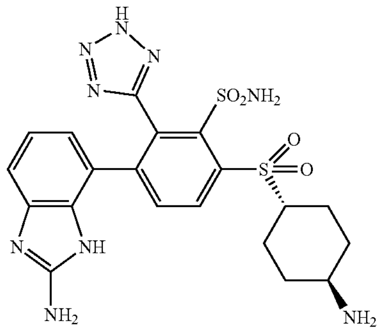 [SMILES: Nc1nc2cccc(-c3ccc(S(=O)(=O)[C@H]4CC[C@H](N)CC4)c(S(N)(=O)=O)c3-c3nn[nH]n3)c2[nH]1] | 3-(2-amino-3H-benzo[d]imidazol-4-yl)-6-((1r,4r)-4-aminocyclohexylsulfonyl)-2-(2H-tetrazol-5-yl)benzenesulfonamide | 518 |
| 179 | 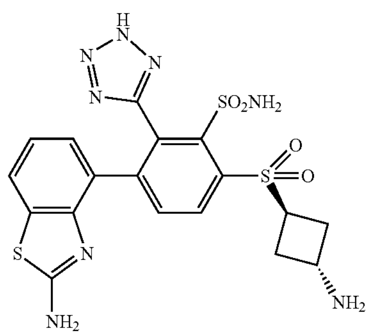 [SMILES: Nc1nc2c(-c3ccc(S(=O)(=O)[C@H]4C[C@H](N)C4)c(S(N)(=O)=O)c3-c3nn[nH]n3)cccc2s1] | 3-(2-aminobenzo[d]thiazol-4-yl)-6-((1r,3r-3-aminocyclobutylsulfonyl)-2-(2H-tetrazol-5-yl)benzenesulfonamide | 507 |
| 180 | 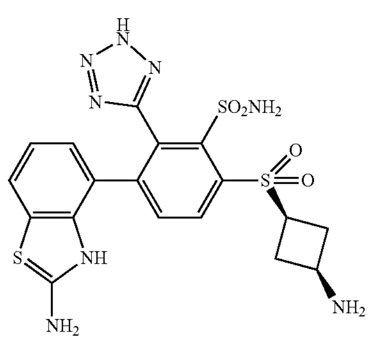 | 3-(2-aminobenzo[d]thiazol-4-yl)-6-((1s,3s)-3-aminocyclobutylsulfonyl)-2-(2H-tetrazol-5-yl)benzenesulfonamide | 507 |

EXAMPLE 181

3-(2-amino-3H-benzo[d]imidazol-4-yl)-6-((R)-pyrrolidin-3-ylsulfonyl)-2-(2H-tetrazol-5-yl)benzenesulfonamide

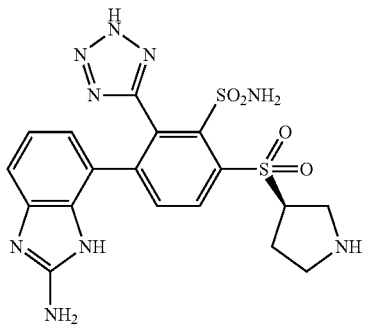 [SMILES: Nc1nc2cccc(-c3ccc(S(=O)(=O)[C@@H]4CCNC4)c(S(N)(=O)=O)c3-c3nn[nH]n3)c2[nH]1]

Step A: (S)-tert-butyl 3-(methylsulfonyloxy)pyrrolidine-1-carboxylate

Into a 100-mL RBF purged and maintained with an inert atmosphere of argon, were placed a solution of (S)-tert-butyl 3-hydroxypyrrolidine-1-carboxylate (3 g, 16.02 mmol) and TEA (6.70 ml, 48.1 mmol) in DCM (30 ml)) under argon atmosphere. This was followed by the addition of Ms-Cl (1.498 ml, 19.23 mmol) dropwised at 0° C. The resulting mixture was stirred under argon atmosphere at room temperature for 20 minutes. The reaction was quenched with ice water (100 ml) and extracted with EtOAc (3×100 ml). The combined organic layers were washed with brine (1×200 ml), dried over anhydrous sodium sulfate and filtered. The filtrate was evaporated to afford the title compound which was used directly in next step.

Step B: (R)-tert-butyl 3-(acetylthio)pyrrolidine-1-carboxylate

Into a 100-mL RBF purged and maintained with an inert atmosphere of argon, were placed a solution of (S)-tert-butyl 3-((methylsulfonyl)oxy)pyrrolidine-1-carboxylate (4.0 g, 11.3 mmol) in DMF (40 ml). This was followed by the addition of potassium ethanethioate (5.17 g, 45.2 mmol) at room temperature. The resulting mixture was stirred under argon atmosphere at 80° C. for 16 hours. The reaction was cooled to 20° C. and quenched with ice water (150 ml) and extracted with EtOAc (3×150 ml). The combined organic layers were washed with brine (2×200 ml), dried over anhydrous sodium sulfate and filtered. The filtrate was evaporated and the residue was purified by silica gel chromatography, eluting with EtOAc in Pet. ether (35%) to afford the title compound: LCMS [2M+H]$^+$: 491.1; $^1$H NMR (300 MHz, CD$_3$Cl): δ 3.99-3.95 (m, 1H), 3.79-3.73 (m, 1H), 3.45-3.40 (m, 2H), 3.28-3.18 (m, 1H), 2.34 (s, 3H), 2.32-2.27 (m, 1H), 1.90-1.86 (m, 1H), 1.47 (s, 9H).

Step C: (R)-tert-butyl 3-mercaptopyrrolidine-1-carboxylate

Into a 100-mL RBF purged and maintained with an inert atmosphere of argon, was placed a solution of (R)-tert-butyl 3-(acetylthio) pyrrolidine-1-carboxylate (1.8 g, 7.34 mmol) in MeOH (20 ml). This was followed by the addition of sodium hydroxide (0.587 g, 14.67 mmol) in water (1 ml) dropwise at 0° C. The resulting mixture was stirred under argon atmosphere at room temperature for 20 minutes. The pH of the reaction was adjusted to 7 at 0° C. and extracted with EtOAc (3×50 ml). The combined organic layers were washed with brine (1×100 ml), dried over anhydrous sodium sulfate and filtered. The filtrate was evaporated to afford the crude title compound, which was used directly into next step: LCMS [2M+H]$^+$: 407.1

Step D: (R)-tert-butyl 3-(2-(N,N-bis(4-methoxybenzyl)sulfamoyl)-4-iodo-3-(2-(4-methoxybenzyl)-2H-tetrazol-5-yl)phenylthio)pyrrolidine-1-carboxylate Into a 100-mL RBF purged and maintained with an inert atmosphere of argon, was placed a solution of 6-bromo-3-iodo-N,N-bis(4-methoxybenzyl)-2-(2-(4-methoxybenzyl)-2H-tetrazol-5-yl)benzenesulfonamide (1.5 g, 1.898 mmol) and (R)-tert-butyl 3-mercaptopyrrolidine-1-carboxylate (0.772 g, 3.80 mmol) in DMF (15 ml). This was followed by the addition of sodium hydrate (0.152 g, 3.80 mmol) at 0° C. The resulting mixture was stirred at 20° C. for 1 hour under argon atmosphere. The reaction was quenched with water (100 ml) and extracted with EtOAc (3×100 ml). The combined layers were washed with brine (saturated, 2×200 ml), dried over anhydrous sodium sulfate and filtered. The filtrate was evaporated and the residue was purified by silica gel chromatography, eluting with EtOAc in Pet. ether (1/1) to afford the title compound: LCMS [M+H]$^+$: 913.2; $^1$H NMR (300 MHz, CD$_3$OD): δ 8.08 (d, J=8.4 Hz, 1H), 7.53 (d, J=8.7 Hz, 1H), 7.16 (d, J=8.7 Hz, 1H), 6.88 (d, J=5.7 Hz, 4H), 6.77 (d, J=8.4 Hz, 6H), 5.51 (d, J=14.7 Hz, 1H), 5.20 (d, J=14.7 Hz, 1H), 4.68 (dd, J$_a$=5.4 Hz, J$_b$=15.3 Hz, 2H), 4.07 (bs, 1H), 3.81 (d, J=15.6 Hz, 1H), 3.77 (s, 9H), 3.49-3.46 (m, 1H), 3.15-3.11 (m, 1H), 2.96-2.93 (m, 1H), 2.17-2.16 (m, 1H), 1.78-1.70 (m, 1H), 1.39 (s, 9H).

Step E: (R)-tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)pyrrolidine-1-carboxylate Into a 50-mL RBF purged and maintained with an inert atmosphere of argon, was placed a solution of (R)-tert-butyl 3-((2-(N,N-bis(4-methoxybenzyl)sulfamoyl)-4-iodo-3-(2-(4-methoxybenzyl)-2H-tetrazol-5-yl)phenyl)thio)pyrrolidine-1-carboxylate (1.3 g, 1.424 mmol) in DCM (15 ml). This was followed by the addition of m-CPBA (0.983 g, 5.70 mmol) at room temperature. The resulting mixture was stirred at 20° C. for 16 hours under argon atmosphere. The reaction was quenched with NaHSO$_4$ (10%, 50 ml) and extracted with EtOAc (3×50 ml). The combined layers were washed with NaHCO$_3$ (saturated, 3×40 ml), brine (saturated, 3×40 ml), dried over anhydrous sodium sulfate and filtered. The filtrate was evaporated and the residue was purified by silica gel chromatography, eluting with EtOAc in Pet. ether (67%) to afford the title compound: LCMS [M+H]$^+$: 945.1.

Step F: (R)-tert-butyl 3-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)pyrrolidine-1-carboxylate Into a 25-mL RBF purged and maintained with an inert atmosphere of argon, was placed a solution of (R)-tert-butyl 3-((2-(N,N-bis(4-methoxybenzyl)sulfamoyl)-4-iodo-3-(2-

(4-methoxybenzyl)-2H-tetrazol-5-yl)phenyl)sulfonyl)pyrrolidine-1-carboxylate (200 mg, 0.212 mmol), Pd(dppf)Cl$_2$ (34.6 mg, 0.042 mmol) and (2-amino-1H-benzo[d]imidazol-7-yl)boronic acid (74.9 mg, 0.423 mmol) in dioxane (2 ml). This was followed by the addition of Na$_2$CO$_3$ (67.3 mg, 0.635 mmol) in water (0.4 ml) at room temperature. The resulting mixture was stirred at under argon atmosphere at 80° C. for 16 hours. The reaction was cooled to 20° C. and quenched with water (10 ml) and extracted with EtOAc (3×10 ml). The combined organic layers were washed with brine (1×20 ml), dried over anhydrous sodium sulfate and filtered. The filtrate was evaporated under reduced pressure and the residue was purified by silica gel chromatography, eluting with DCM/MeOH (10/1) to give the title compound: LCMS [M+H]$^+$: 950.2; $^1$H NMR (400 MHz, CD$_3$OD): 8.75 (d, J=7.6 Hz, 1H), 8.21 (d, J=8.0 Hz, 1H), 7.10-6.49 (m, 17H), 4.96-4.92 (m, 1H), 4.72-4.65 (m, 2H), 4.06-4.01 (m, 2H), 3.83-3.52 (m, 6H), 3.75 (s, 9H), 2.78-2.77 (m, 1H), 2.50-2.45 (m, 1H), 1.49 (s, 9H).

Step G: (R)-3-(2-amino-1H-benzo[d]imidazol-7-yl)-N-(4-methoxybenzyl)-2-(2-(4-methoxybenzyl)-2H-tetrazol-5-yl)-6-(pyrrolidin-3-ylsulfonyl)benzenesulfonamide Into a 25-mL RBF, was placed a solution of (R)-tert-butyl 3-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)pyrrolidine-1-carboxylate (170 mg, 0.179 mmol) in DCM (2 ml). This was followed by the addition of TFA (0.5 ml, 6.49 mmol) at 0° C. The resulting mixture was stirred at 20° C. for 1 hour. The solvent was evaporated and the residue was used directly into next step without further purification: LCMS [M+H]$^+$: 730.2.

Step H: (R)-3-(2-amino-1H-benzo[d]imidazol-7-yl)-6-(pyrrolidin-3-ylsulfonyl)-2-(2H-tetrazol-5-yl)benzenesulfonamide Into a 25-mL RBF, was placed a solution of (R)-3-(2-amino-1H-benzo[d]imidazol-7-yl)-N-(4-methoxybenzyl)-2-(2-(4-methoxybenzyl)-2H-tetrazol-5-yl)-6-(pyrrolidin-3-ylsulfonyl)benzenesulfonamide (110 mg, 0.128 mmol) in TFA (2 ml, 26.0 mmol). The resulting mixture was stirred at 80° C. for 1 hour. The solvent was evaporated and the residue was purified by Prep-HPLC with the following conditions: Column: X Bridge C18, 19*150 mm, 5 µM; Mobile Phase A: water/0.05% NH$_4$HCO$_3$, Mobile Phase B: ACN; Flow rate: 20 mL/min; Gradient: 40-60% B in 10 min, 254 nm. The collected fractions were combined and concentrated under reducing pressure to give the title compound: LCMS [M+H]$^+$: 490.0;

$^1$HNMR (400 MHz, CD$_3$OD): δ 8.52 (d, J=8.4 Hz, 1H), 7.98 (d, J=8.0 Hz, 1H), 7.12 (d, J=8.0 Hz, 1H), 6.90 (t, J=8.0 Hz, 1H), 6.60 (d, J=7.6 Hz, 1H), 5.15-5.11 (m, 1H), 3.71 (d, J=8.4 Hz, 1H), 3.50-3.41 (m, 2H), 3.26-3.20 (m, 1H), 2.58-2.51 (m, 1H), 2.40-2.32 (m, 1H).

EXAMPLES 182-190 were prepared using the same general procedure as EXAMPLE 181 starting from 6-bromo-3-iodo-N,N-bis(4-methoxybenzyl)-2-(2-(4-methoxybenzyl)-2H-tetrazol-5-yl)benzenesulfonamide, the appropriate boronic acids, and (R)-tert-butyl 3-mercaptopyrrolidine-1-carboxylate or its (S)-enantiomer which is made in the same fashion, starting from the enantiomeric alcohol.

| EX NO | Structure | Name | LC/MS [M + H]$^+$ |
|---|---|---|---|
| 182 | 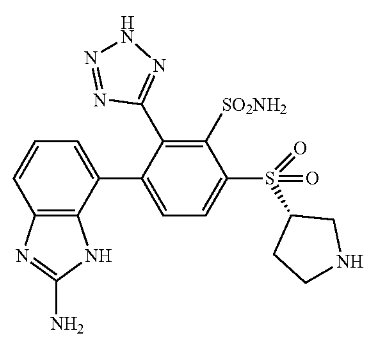 [SMILES: Nc1nc2cccc(-c3ccc(S(=O)(=O)[C@H]4CCNC4)c(S(N)(=O)=O)c3-c3nn[nH]n3)c2[nH]1] | 3-(2-amino-3H-benzo[d]imidazol-4-yl)-6-((S)-pyrrolidin-3-ylsulfonyl)-2-(2H-tetrazol-5-yl)benzenesulfonamide | 490 |
| 183 | 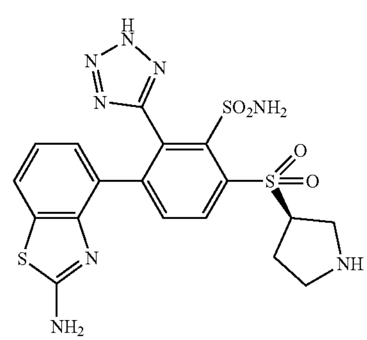 [SMILES: Nc1nc2c(-c3ccc(S(=O)(=O)[C@@H]4CCNC4)c(S(N)(=O)=O)c3-c3nn[nH]n3)cccc2s1] | 3-(2-aminobenzo[d]thiazol-4-yl)-6-((R)-pyrrolidin-3-ylsulfonyl)-2-(2H-tetrazol-5-yl)benzenesulfonamide | 507 |

-continued

| EX NO | Structure | Name | LC/MS [M + H]+ |
|---|---|---|---|
| 184 | 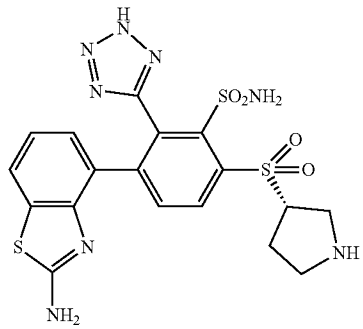 [SMILES: Nc1nc2c(-c3ccc(S(=O)(=O)[C@H]4CCNC4)c(S(N)(=O)=O)c3-c3nn[nH]n3)cccc2s1] | 3-(2-aminobenzo[d]thiazol-4-yl)-6-((S)-pyrrolidin-3-ylsulfonyl)-2-(2H-tetrazol-5-yl)benzenesulfonamide | 507 |
| 185 | 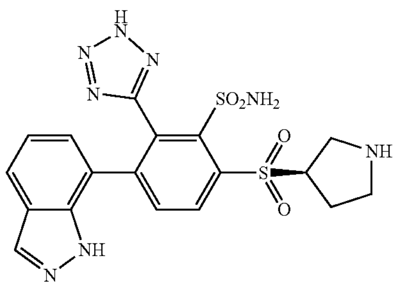 [SMILES: NS(=O)(=O)c1c(S(=O)(=O)[C@@H]2CCNC2)ccc(-c2cccc3cn[nH]c23)c1-c1nn[nH]n1] | 3-(1H-indazol-7-yl)-6-((R)-pyrrolidin-3-ylsulfonyl)-2-(2H-tetrazol-5-yl)benzenesulfonamide | 475 |
| 186 | 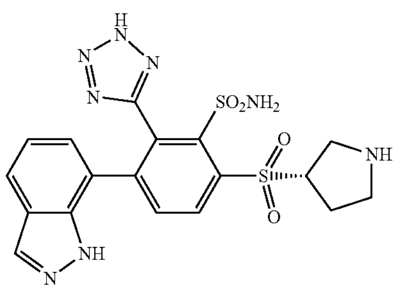 [SMILES: NS(=O)(=O)c1c(S(=O)(=O)[C@H]2CCNC2)ccc(-c2cccc3cn[nH]c23)c1-c1nn[nH]n1] | 3-(1H-indazol-7-yl)-6-((S)-pyrrolidin-3-ylsulfonyl)-2-(2H-tetrazol-5-yl)benzenesulfonamide | 475 |
| 187 | 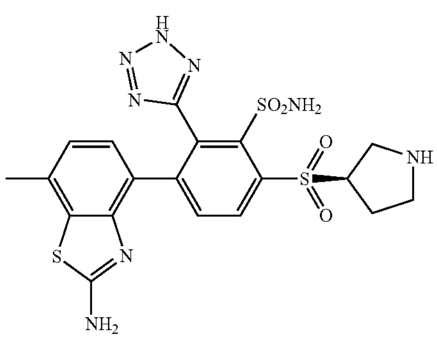 [SMILES: Cc1ccc(-c2ccc(S(=O)(=O)[C@@H]3CCNC3)c(S(N)(=O)=O)c2-c2nn[nH]n2)c2nc(N)sc12] | 3-(2-amino-7-methylbenzo[d]thiazol-4-yl)-6-((R)-pyrrolidin-3-ylsulfonyl)-2-(2H-tetrazol-5-yl)benzenesulfonamide | 521 |
| 188 | 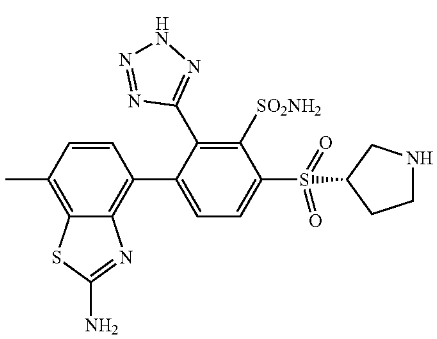 [SMILES: Cc1ccc(-c2ccc(S(=O)(=O)[C@H]3CCNC3)c(S(N)(=O)=O)c2-c2nn[nH]n2)c2nc(N)sc12] | 3-(2-amino-7-methylbenzo[d]thiazol-4-yl)-6-((S)-pyrrolidin-3-ylsulfonyl)-2-(2H-tetrazol-5-yl)benzenesulfonamide | 521 |

| EX NO | Structure | Name | LC/MS [M + H]+ |
|---|---|---|---|
| 189 | 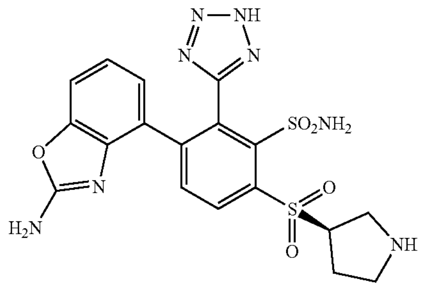 [SMILES: Nc1nc2c(-c3ccc(S(=O)(=O)[C@@H]4CCNC4)c(S(N)(=O)=O)c3-c3nn[nH]n3)cccc2o1] | 3-(2-aminobenzo[d]oxazol-4-yl)-6-((R)-pyrrolidin-3-ylsulfonyl)-2-(2H-tetrazol-5-yl)benzenesulfonamide | 491 |
| 190 | 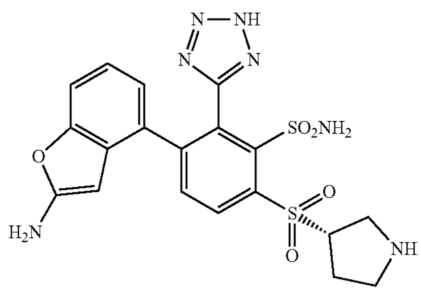 [SMILES: Nc1cc2c(-c3ccc(S(=O)(=O)[C@H]4CCNC4)c(S(N)(=O)=O)c3-c3nn[nH]n3)cccc2o1] | 3-(2-aminobenzo[d]oxazol-4-yl)-6-((S)-pyrrolidin-3-ylsulfonyl)-2-(2H-tetrazol-5-yl)benzenesulfonamide | 491 |

EXAMPLE 191

3-(1H-indazol-7-yl)-6-(methylsulfonyl)-2-(2H-tetrazol-5-yl)benzenesulfonamide

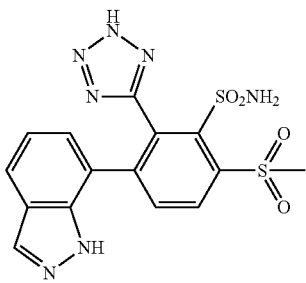 [SMILES: CS(=O)(=O)c1ccc(-c2cccc3cn[nH]c23)c(-c2nn[nH]n2)c1S(N)(=O)=O]

Step A: 3-iodo-N,N-bis(4-methoxybenzyl)-2-(2-(4-methoxybenzyl)-2H-tetrazol-5-yl)-6-(methylsulfonyl)benzenesulfonamide A solution of 3-iodo-N,N-bis(4-methoxybenzyl)-2-(2-(4-methoxybenzyl)-2H-tetrazol-5-yl)-6-(methylthio)-benzenesulfonamide (prepared as described in the previous example, 0.10 g, 0.13 mmol) and 3-chloroperoperoxybenzoic (91 mg, 0.53 mmol) in DCM (20 mL) was stirred at room temperature for 16 hours. The reaction mixture was quenched with water (20 mL), and extracted with DCM (3×30 mL). The combined organic layers were washed with water (1×20 mL) and brine (1×20 mL), dried over anhydrous sodium sulfate and filtered. The filtrate was concentrated under vacuum to give crude product. The residue was purified by silica gel chromatography, eluting with methanol/DCM (1/10). The combined organic fractions were concentrated under reduced pressure to give the title compound: LCMS [M+1]+ 790; $^1$H NMR (400 MHz, DMSO-d$_6$) δ 8.62 (d, J=8.8 Hz, 1H), 8.27 (d, J=8.4 Hz, 1H), 7.22 (d, J=8.8 Hz, 2H), 6.92-6.80 (m, 10H), 5.42-5.38 (m, 1H), 5.28-5.25 (m, 1H), 4.57-4.53 (m, 2H), 3.85-3.81 (m, 2H), 3.73 (s, 9H), 3.61 (s, 3H).

Step B: 3-(1H-indazol-7-yl)-N,N-bis(4-methoxybenzyl)-2-(2-(4-methoxybenzyl)-2H-tetrazol-5-yl)-6-(methylsulfonyl)benzenesulfonamide To a mixture of 3-iodo-N,N-bis(4-methoxybenzyl)-2-(2-(4-methoxybenzyl)-2H-tetrazol-5-yl)-6-(methyl-sulfonyl)benzenesulfonamide (0.20 g, 0.25 mmol) in H$_2$O (2.00 mL) and dioxane (10 mL), was added 7-(4,4,5,5-tetramethyl-1,3,2-dioxaborolan-2-yl)-1H-indazole (0.12 g, 0.51 mmol), Na$_2$CO$_3$ (81 mg, 0.76 mmol) and Pd(dppf)Cl$_2$CH$_2$Cl$_2$ (41 mg, 0.05 mmol) under nitrogen. The resulting mixture was stirred at 80° C. for 3 hours. The reaction mixture was concentrated under reduced pressure, the residue was purified by a silica gel column, eluted with ethyl acetate/petroleum ether (1:50-1:1) to afford the title compound:

LCMS [M+1]⁺780; ¹H NMR (400 MHz, DMSO-d₆) δ 13.04 (s, 1H), 8.80 (d, J=8.4 Hz, 1H), 8.34 (d, J=8.4 Hz, 1H), 8.15 (s, 1H), 7.05-6.99 (m, 5H), 6.87-6.85 (m, 5H), 6.78-6.76 (m, 1H), 6.66-6.64 (m, 2H), 6.49-6.46 (m, 1H), 4.92-4.75 (m, 2H), 4.60-4.56 (m, 2H), 4.06-3.97 (m, 2H), 3.81 (s, 3H), 3.77 (s, 9H).

Step C: 3-(1H-indazol-7-yl)-6-(methylsulfonyl)-2-(2H-tetrazol-5-yl)benzenesulfonamide A mixture of 3-(1H-indazol-7-yl)-N,N-bis(4-methoxybenzyl)-2-(2-(4-methoxybenzyl)-2H-tetrazol-5-yl)-6-(methylsulfonyl)benzenesulfonamide (0.19 g, 0.24 mmol) in TFA (10 mL) was stirred at 80° C. and for 1 hour. The reaction mixture was concentrated under reduced pressure, then the residue was purified by Prep-HPLC. Column, Xbridge C18, 19×150 mm; mobile phase: acetonitrile in water (0.05% NH₄HCO₃), 34%-95% in 8 min; Detector, UV 254 nm. RT: 6.82 min. The collected fractions were combined and concentrated under reduced pressure to give the title compound: LCMS [M+1]⁺420; ¹H NMR (400 MHz, DMSO-d₆) δ 12.97 (s, 1H), 8.36 (d, J=8.0 Hz, 1H), 8.07 (s, 1H), 7.94 (d, J=8.8 Hz, 1H), 7.61 (brs, 1H), 7.59 (d, J=7.6 Hz, 1H), 7.05 (brs, 2H), 6.83 (t, J=7.6 Hz, 1H), 6.53 (d, J=7.2 Hz, 1H), 3.62 (s, 3H).

EXAMPLES 192-193 were prepared using the same general procedure as EXAMPLE 191 starting from 3-iodo-N,N-bis(4-methoxybenzyl)-2-(2-(4-methoxybenzyl)-2H-tetrazol-5-yl)-6-(methylsulfonyl)benzenesulfonamide (Step A) and the appropriate boronic acids or boronic esters, prepared as described herein or commercially available.

| EX NO | Structure | Name | MW | LCMS [M + H]⁺ |
|---|---|---|---|---|
| 192 | 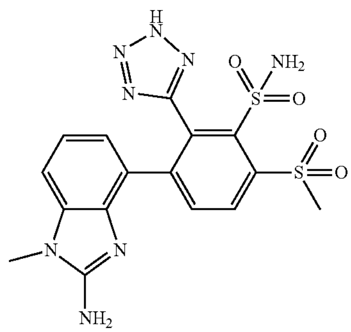 [SMILES: Cn1c(N)nc2c(-c3ccc(S(C)(=O)=O)c(S(N)(=O)=O)c3-c3nn[nH]n3)cccc21] | 3-(2-amino-1-methyl-1H-benzo[d]imidazol-4-yl)-6-(methylsulfonyl)-2-(2H-tetrazol-5-yl)benzenesulfonamide | 448 | 449 |
| 193 | 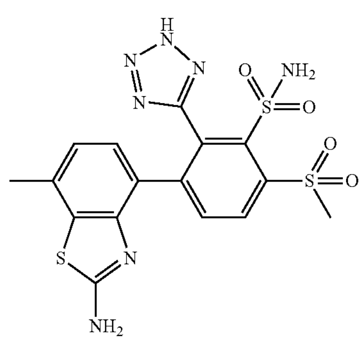 [SMILES: Cc1ccc(-c2ccc(S(C)(=O)=O)c(S(N)(=O)=O)c2-c2nn[nH]n2)c2nc(N)sc12] | 3-(2-amino-7-methylbenzo[d]thiazol-4-yl)-6-(methylsulfonyl)-2-(2H-tetrazol-5-yl)benzenesulfonamide | 465 | 466 |

EXAMPLE 194

3-(2-aminobenzo[d]thiazol-4-yl)-6-(3-aminopropyl-sulfonyl)-2-(2H-tetrazol-5-yl)benzenesulfonamide

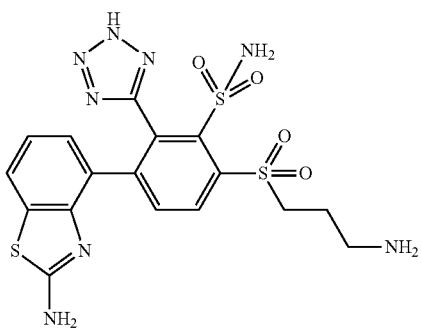 [SMILES: NCCCS(=O)(=O)c1ccc(-c2cccc3sc(N)nc23)c(-c2nn[nH]n2)c1S(N)(=O)=O]

Step A: 3-((tert-butoxycarbonyl)amino)propyl methanesulfonate

Into a 100 mL flask was placed tert-butyl (3-hydroxypropyl)carbamate (2.0 g, 11.41 mmol), Et$_3$N (1.591 ml, 11.41 mmol) and DCM (25 ml). MsCl (0.889 ml, 11.41 mmol) was added at 0° C. The reaction mixture was stirred at room temperature for 1 hour. The reaction mixture was quenched with water (20 mL), and extracted with ethyl acetate (3×40 mL). The combined organic layers were washed with water (2×25 mL) and brine (2×25 mL), dried over anhydrous sodium sulfate and filtered. The filtrate was concentrated under vacuum to afford the title compound, which was used in the next step directly.

Step B: S-(3-((tert-butoxycarbonyl)amino)propyl) ethanethioate

A mixture of 3-((tert-butoxycarbonyl)amino)propyl methanesulfonate (2.9 g, 11.45 mmol) and potassium ethanethioate (1.307 g, 11.45 mmol) in DMF (25 ml) was stirred at 80° C. for 18 hours. The reaction mixture was quenched with water (50 mL), and extracted with ethyl acetate (2×50 mL). The combined organic layers were washed with water (1×40 mL) and brine (2×20 mL), dried over anhydrous sodium sulfate and filtered. The filtrate was concentrated under vacuum. The residue was purified by silica gel column chromatography and eluted with ethyl acetate/petroleum ether (1/4). The combined organic fractions were concentrated under reduced pressure to give the title compound. LCMS [M+H-56]$^+$: 178; $^1$H NMR (300 MHz, CDCl$_3$): δ 4.76 (br, 1H), 3.16-3.15 (m, 2H), 2.91 (t, J=6.9 Hz, 2H), 2.33 (s, 3H), 1.77 (q, J=6.9 Hz, 2H), 1.45 (s, 9H).

Step C: tert-butyl 3-mercaptopropylcarbamate

S-(3-((tert-butoxycarbonyl)amino)propyl) ethanethioate (2.0 g, 8.57 mmol) was dissolved in MeOH (20 ml). A solution of NaOH (0.857 g, 21.43 mmol) in water was added at 0° C. The reaction mixture was stirred at room temperature for 1 hour. The pH of the solution was adjusted to 5 with 1M HCl. The reaction mixture was extracted with ethyl acetate (2×30 mL). The combined organic layers were washed with water (2×15 mL) and brine (2×15 mL), dried over anhydrous sodium sulfate and filtered. The filtrate was concentrated under vacuum to afford the title compound. LCMS [M+H-56]$^+$: 136; $^1$H NMR (300 MHz, DMSO): δ 6.82 (br, 1H), 3.03-2.97 (m, 2H), 2.51-2.41 (m, 2H), 2.31-2.26 (m, 1H), 1.68-1.58 (m, 2H), 1.37 (s, 9H).

Step D: tert-butyl (3-((2-(N,N-bis(4-methoxybenzyl)sulfamoyl)-4-iodo-3-(2-(4-methoxybenzyl)-2H-tetrazol-5-yl)phenyl)thio)propyl)carbamate A mixture of 6-bromo-3-iodo-N,N-bis(4-methoxybenzyl)-2-(2-(4-methoxybenzyl)-2H-tetrazol-5-yl)benzenesulfonamide (0.5 g, 0.633 mmol) and tert-butyl (3-mercaptopropyl)carbamate (0.266 g, 1.392 mmol) in DMF (8.0 ml) was prepared. NaH (0.152 g, 3.80 mmol) was added at 0° C. The mixture was stirred at room temperature for 2 hours. The mixture was quenched with water (25 mL), extracted with ethyl acetate (3×15 mL), washed with water (20 mL) brine (20 mL), dried over MgSO$_4$, filtered and the solvent was evaporated under reduced pressure. The residue was purified by silica gel column chromatography, eluting with ethyl acetate/petroleum ether (1/1). The combined organic fractions were concentrated under reduced pressure to give the title compound. LCMS [M+H]$^+$: 901.

Step E: tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propyl)carbamate tert-butyl (3-((2-(N,N-bis(4-methoxybenzyl)sulfamoyl)-4-iodo-3-(2-(4-methoxybenzyl)-2H-tetrazol-5-yl)phenyl)thio)propyl)carbamate (0.4 g, 0.444 mmol) was dissolved in DCM (10 ml), to which 3-chlorobenzoperoxoic acid (0.306 g, 1.776 mmol) was added. The reaction mixture was stirred at room temperature overnight, and then partitioned between EtOAc (20 mL) and 10% aq. sodium thiosulfate (30 mL). The organic phase was separated, washed with sat. aq. sodium bicarbonate (50 mL), dried (Na$_2$SO$_4$) and the volatiles removed under reduced pressure. The residue was purified by silica gel column chromatography, eluting with ethyl acetate/petroleum ether (1/1). The combined organic fractions were concentrated under reduced pressure to give the title compound. LCMS [M+H]$^+$: 933.

Step F: tert-butyl (3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate Into a 25 mL RBF was placed tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propyl)carbamate (170 mg, 0.182 mmol), (2-aminobenzo[d]thiazol-4-yl)boronic acid (53.0 mg, 0.273 mmol), Na$_2$CO$_3$ (57.9 mg, 0.547 mmol) and PdCl$_2$(dppf)-CH$_2$Cl$_2$ Adduct (22.32 mg, 0.027 mmol) in dioxane/H$_2$O=4/1 (5.0 ml). The reaction mixture was degassed with nitrogen 3 times and stirred for 4 hours at 80° C. The reaction mixture was quenched with water (10 mL) and extracted with DCM (3×15 mL). The combined organic layers were washed with water (2×10 mL) and brine (2×10 mL), dried over anhydrous sodium sulfate and filtered. The filtrate was concentrated under vacuum. The residue was purified by silica gel column chromatography, eluting with methanol/DCM (1/15). The combined organic fractions were concentrated under reduced pressure to give the title compound. LCMS [M+H]$^+$: 955.

Step G: 3-(2-aminobenzo[d]thiazol-4-yl)-6-((3-aminopropyl)sulfonyl)-2-(2H-tetrazol-5-yl)benzenesulfonamide Into a 10 mL flask was placed tert-butyl (3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate (100 mg, 0.105 mmol) and TFA (2.0 mL) was added at 0° C. The reaction mixture was stirred at room temperature for 2 hours. The solvent was removed under vacuum. The residue was dissolved in TFA (3.0 mL). The reaction mixture was stirred at 80° C. for 2 hours. The solvent was removed under vacuum. The product was purified by Prep-HPLC with the following conditions: Column: X Bridge RP18, 19*150 mm, 5 µM; Mobile Phase A: water/0.05% NH$_4$HCO$_3$, Mobile Phase B: ACN; Flow rate: 20 mL/min; Gradient: 5% B to 15% B in 5 min; 254 nm. The collected fractions were combined and concentrated under vacuum to afford the title compound. LCMS [M+H]$^+$: 495; $^1$H NMR (300 MHz, DMSO): δ 8.16 (d, J=6.9 Hz, 1H), 7.88 (d, J=8.4 Hz, 1H), 7.64 (br, 4H), 7.49-7.46 (m, 3H), 6.72-6.67 (m, 1H), 6.47 (d, J=7.8 Hz, 1H), 3.95-3.89 (m, 2H), 3.01-2.96 (m, 2H), 2.11-2.01 (m, 2H).

EXAMPLES 195 was prepared using the same general procedure as EXAMPLE 194 starting from tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propyl)carbamate (Step E), except (2-amino-1-methyl-1H-benzo[d]imidazol-4-yl)boronic acid was used in Step F.

EXAMPLE 196

2'-Amino-4-(azetidin-3-ylsulfonyl)-3'-cyano-2-(2H-tetrazol-5-yl)-[1,1'-biphenyl]-3-sulfonamide

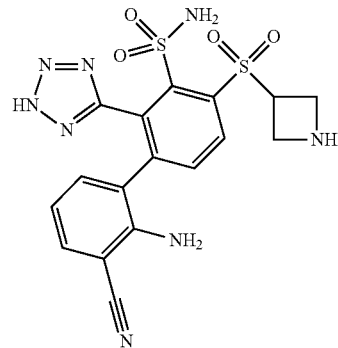 [SMILES: N#Cc1cccc(-c2ccc(S(=O)(=O)C3CNC3)c(S(N)(=O)=O)c2-c2nn[nH]n2)c1N]

Step A: tert-butyl 3-((2'-amino-3-(N,N-bis(4-methoxybenzyl)sulfamoyl)-3'-cyano-2-(2-(4-methoxybenzyl)-2H-tetrazol-5-yl)-[1,1'-biphenyl]-4-yl)sulfonyl)azetidine-1-carboxylate A suspension of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (2.00 g, 2.15 mmol), (2-amino-3-cyanophenyl)boronic acid (1.04 g, 6.45 mmol), tetrakis(triphenylphosphine)palladium(0) (0.248 g, 0.215 mmol) and sodium carbonate (0.683 g, 6.45 mmol) in dioxane (40 ml) and water (15 ml) was degassed and heated at 80° C. for 17 hours. The mixture was diluted with AcOEt, then washed with brine. The organic layer was dried (MgSO$_4$) and concentrated. The crude material was purified by ISCO (0-50% then 50% EtOAc in hexane). LCMS [M+1]: 921.47.

Step B: 2'-amino-4-(azetidin-3-ylsulfonyl)-3'-cyano-2-(2H-tetrazol-5-yl)-[1,1'-biphenyl]-3-sulfonamide The tert-butyl 3-((2'-amino-3-(N,N-bis(4-methoxybenzyl)sulfamoyl)-3'-cyano-2-(2-(4-methoxybenzyl)-2H-tetrazol-5-yl)-[1,1'-biphenyl]-4-yl)sulfonyl)azetidine-1-carboxylate (30 mg, 0.033 mmol) was dissolved in DCM (4 mL), stirred at RT for 2 hours with 2 ml TFA and two drops of anisole, and concentrated. The residue was heated at 80° C.

| EX NO | Structure | Name | LCMS [M + H]$^+$ |
|---|---|---|---|
| 195 | | 3-(2-amino-1-methyl-1H-benzo[d]imidazol-4-yl)-6-(3-aminopropylsulfonyl)-2-(2H-tetrazol-5-yl)benzenesulfonamide | 492 | in 2 ml TFA for 40 minutes. TFA was removed, and the crude material was purified by reverse phase HPLC (7-50% AcCN in water with 0.05% TFA). LCMS [M+1]: 461.26.

EXAMPLES 197-198 were prepared from the indicated starting materials (SMs) according to the general procedure described for EXAMPLE 196.

| EX No. | SMs | Structure | Name | LC/MS m/e [M + H]+ |
|---|---|---|---|---|
| 197 | | 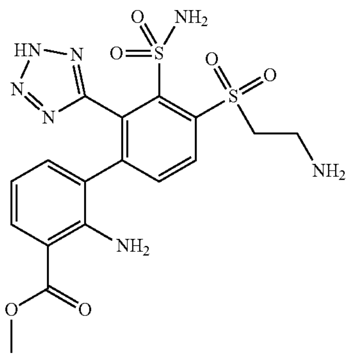 [SMILES: COC(=O)c1cccc(-c2ccc(S(=O)(=O)CCN)c(S(N)(=O)=O)c2-c2nn[nH]n2)c1N] | methyl 2-amino-4'-((2-aminoethyl)sulfonyl)-3'-sulfamoyl-2'-(2H-tetrazol-5-yl)-[1,1'-biphenyl]-3-carboxylate | 482.18. |
| 198 | | 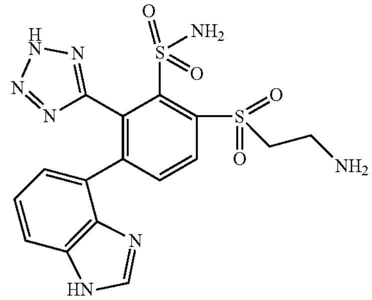 [SMILES: NCCS(=O)(=O)c1ccc(-c2cccc3[nH]cnc23)c(-c2nn[nH]n2)c1S(N)(=O)=O] | 6-((2-aminoethyl)sulfonyl)-3-(1H-benzo[d]imidazol-4-yl)-2-(2H-tetrazol-5-yl)benzenesulfonamide | 449.20 |

EXAMPLE 199

2-Amino-4'-((2-aminoethyl)sulfonyl)-3'-sulfamoyl-2'-(2H-tetrazol-5-yl)-[1,1'-biphenyl]-3-carboxylic Acid

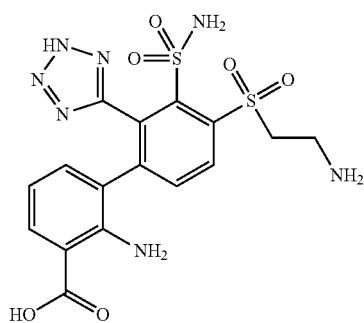 [SMILES: NCCS(=O)(=O)c1ccc(-c2cccc(C(=O)O)c2N)c(-c2nn[nH]n2)c1S(N)(=O)=O]

Methyl 2-amino-4'-((2-aminoethyl)sulfonyl)-3'-sulfamoyl-2'-(2H-tetrazol-5-yl)-[1,1'-biphenyl]-3-carboxylate (0.10 g, 0.21 mmol) was dissolved in MeOH (10 ml), and heated with sodium hydroxide (1 N, 2.077 mL, 2.077 mmol) at 60° C. for 0.5 hour. The mixture was cooled to RT, 2 N hydrochloric acid (3 mL) was added and the reaction mixture concentrated under vacuum. The residue was dissolved in methanol (5 ml). The solid was filtered off, and the filtrate was concentrated, and purified by reverse phase HPLC (10-50% AcCN in water with 0.05% TFA). LCMS [M+1]: 468.15.

EXAMPLE 200

3-(3H-[1,2,3]triazolo[4,5-b]pyridin-7-yl)-6-(azetidin-3-ylsulfonyl)-2-(2H-tetrazol-5-yl)benzenesulfonamide

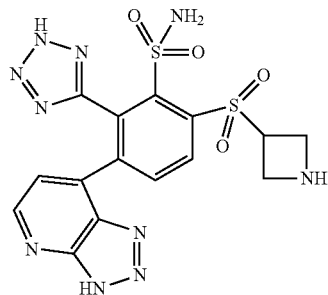 [SMILES: NS(=O)(=O)c1c(S(=O)(=O)C2CNC2)ccc(-c2ccnc3[nH]nnc23)c1-c1nn[nH]n1]

Step A: tert-butyl 3-((2-(N,N-bis(4-methoxybenzyl)sulfamoyl)-4-(2,3-diaminopyridin-4-yl)-3-(2-(4-methoxybenzyl)-2H-tetrazol-5-yl)phenyl)sulfonyl)azetidine-1-carboxylate A suspension of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (5.00 g, 5.37 mmol), (2,3-diaminopyridin-4-yl)boronic acid (2.465 g, 16.11 mmol), tetrakis(triphenylphosphine)palladium(0) (0.621 g, 0.537 mmol) and sodium carbonate (1.708 g, 16.11 mmol) in 1,4-dioxane (100 mL) and water (30 mL) was degassed and heated at 80° C. for 17 hours. The mixture was diluted with AcOEt, then washed with brine. The organic layer was dried (MgSO₄) and concentrated. The crude material was purified by ISCO (0-50% then 50% 3:1 EtOAc/EtOH in hexane. LCMS [M+1]: 912.57.

Step B: 3-(3H-[1,2,3]triazolo[4,5-b]pyridin-7-yl)-6-(azetidin-3-ylsulfonyl)-2-(2H-tetrazol-5-yl)benzenesulfonamide To a cold (ice bath) mixture of tert-butyl nitrite (0.016 ml, 0.132 mmol) and copper(II) bromide (0.027 g, 0.121 mmol) in 10 ml MeCN was added tert-butyl 3-((2-(N,N-bis(4-methoxybenzyl)sulfamoyl)-4-(2,3-diaminopyridin-4-yl)-3-(2-(4-methoxybenzyl)-2H-tetrazol-5-yl)phenyl)sulfonyl)azetidine-1-carboxylate (0.10 g, 0.11 mmol) in 5 mL acetonitrile. Reaction mixture was stirred cold for 1.5 hours then warmed to RT, and stirred overnight. Volatiles were removed under reduced pressure. To the resulting residue was added saturated KHSO₄ (1N, 10 mL), and the resulting mixture was extracted with ethyl acetate. The organic layer was washed with aqueous sodium hydrogen carbonate. The organic layer was dried over Na₂SO₄, filtered and evaporated. The residue was dissolved in DCM (30 mL), and stirred at RT for 4 hours with 3 mL TFA and a few drops of anisole and concentrated. The residue was heated at 80° C. in 2 ml TFA for 40 minutes. TFA was removed under reduced pressure. The crude material was purified by reverse phase HPLC (7-42% AcCN in water with 0.1% TFA). LCMS [M+1]: 463.27.

EXAMPLE 201

6-(Azetidin-3-ylsulfonyl)-3-(benzo[d]thiazol-4-yl)-2-(2H-tetrazol-5-yl)benzenesulfonamide

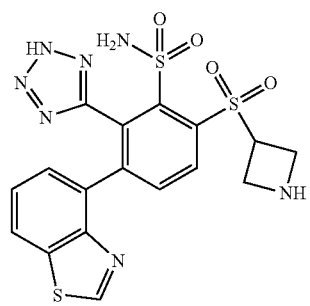 [SMILES: NS(=O)(=O)c1c(S(=O)(=O)C2CNC2)ccc(-c2cccc3scnc23)c1-c1nn[nH]n1]

Step A: tert-butyl 3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate A suspension of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (4 g, 4.30 mmol), (2-aminobenzo[d]thiazol-4-yl)boronic acid (1.667 g, 8.59 mmol), tetrakis(triphenylphosphine)palladium(0) (0.497 g, 0.430 mmol) in dioxane (60 ml) and water (20 ml) was degassed and heated at 80° C. for 17 hours. The mixture was diluted with AcOEt, washed with brine. The organic layer was dried (MgSO$_4$) and concentrated. The crude material was purified by ISCO (0-50% then 50% EtOAc in hexane. LCMS: 953.65.

Step B: tert-butyl 3-((2-(N,N-bis(4-methoxybenzyl) sulfamoyl)-4-(2-bromobenzo[d]thiazol-4-yl)-3-(2-(4-methoxybenzyl)-2H-tetrazol-5-yl)phenyl)sulfonyl) azetidine-1-carboxylate Copper(II) bromide (1.040 g, 4.66 mmol) was suspended in acetonitrile (80 mL), and cooled to 0° C., then tert-butyl nitrite (0.769 mL, 5.82 mmol) was added and stirred for 5 min. tert-butyl 3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (3.7 g, 3.88 mmol) in acetonitrile (30 ml) was then added. The mixture was stirred at 0° C. for 2 hours, warmed to room temperature and stirred for 16 hours. The resultant mixture was poured into/saturated aqueous KHSO$_4$. The aqueous was extracted with EtOAc. The organic layers were combined, washed with brine, dried (MgSO$_4$) and concentrated. The residue was purified by ISCO (120 g column, eluting with 0-25% EtOAc/hexane then 25% EtOAc. LCMS [M+1]: 1016.49, 1018.46.

Step C: tert-butyl 3-((2-(N,N-bis(4-methoxybenzyl) sulfamoyl)-3-(2-(4-methoxybenzyl)-2H-tetrazol-5-yl)-4-(2-((2-(trimethylsilyl)ethyl)thio)benzo[d]thiazol-4-yl)phenyl)sulfonyl)azetidine-1-carboxylate A mixture of tert-butyl 3-((2-(N,N-bis(4-methoxybenzyl) sulfamoyl)-4-(2-bromobenzo[d]thiazol-4-yl)-3-(2-(4-methoxybenzyl)-2H-tetrazol-5-yl)phenyl)sulfonyl)azetidine-1-carboxylate (1.8 g, 1.770 mmol), N-ethyl-N-isopropylpropan-2-amine (0.925 ml, 5.31 mmol)), Pd$_2$dba$_3$ (0.162 g, 0.177 mmol), (9,9-dimethyl-9H-xanthene-4,5-diyl)bis(diphenylphosphine) (0.205 g, 0.354 mmol), and N-ethyl-N-isopropylpropan-2-amine (0.925 ml, 5.31 mmol) in dioxane (15 ml) was degassed and heated in a microwave oven 135° C. for 30 minutes. The mixture was cooled to RT, diluted with EtOAc, washed with NaOH (2N) and brine. The organic layer was dried (MgSO$_4$), and concentrated. The crude material was directly used in the next step. LCMS [M+1]: 1070.58.

Step D: tert-butyl 3-((2-(N,N-bis(4-methoxybenzyl) sulfamoyl)-3-(2-(4-methoxybenzyl)-2H-tetrazol-5-yl)-4-(2-((2-(trimethylsilyl)ethyl)sulfonyl)benzo[d] thiazol-4-yl)phenyl)sulfonyl)azetidine-1-carboxylate To a solution of tert-butyl 3-((2-(N,N-bis(4-methoxybenzyl)sulfamoyl)-3-(2-(4-methoxybenzyl)-2H-tetrazol-5-yl)-4-(2-((2-(trimethylsilyl)ethyl)thio)benzo[d]thiazol-4-yl) phenyl)sulfonyl)azetidine-1-carboxylate (crude 2.8 g, 2.62 mmol) in DCM (50 ml) was added solid 3-chlorobenzoperoxoic acid (2.93 g, 13.08 mmol) in portion at 0° C. The mixture was stirred at 0° C. for 3 hours, diluted with ether (150 ml), washed with 1 N NaOH and brine. The organic layer was dried (MgSO$_4$), and concentrated. The crude material was purified by ISCO (80 g column, EtOAc in hexane 0-30% then 30% then 30-60% and 60%). LCMS [M+1]: 1102.45.

Step E: 6-(azetidin-3-ylsulfonyl)-3-(benzo[d]thiazol-4-yl)-2-(2H-tetrazol-5-yl)benzenesulfonamide A solution of tert-butyl 3-((2-(N,N-bis(4-methoxybenzyl) sulfamoyl)-3-(2-(4-methoxybenzyl)-2H-tetrazol-5-yl)-4-(2-((2-(trimethylsilyl)ethyl)sulfonyl)benzo[d]thiazol-4-yl)phenyl)sulfonyl)azetidine-1-carboxylate (0.25 g, 0.227 mmol) in THF (20 ml) was stirred with tetrabutylammonium fluoride (0.907 ml, 0.907 mmol) at RT under N$_2$ for 0.5 hour. The mixture was diluted with AcOEt, washed with KHSO$_4$ aqueous, dried over MgSO$_4$, and concentrated. LCMS [M+1]: 938.48. The residue was dissolved in DCM (30 ml), stirred at RT for 2 hours with 3 ml TFA and a few drops of anisole, and concentrated. The residue was heated at 80° C. in 5 ml TFA for 60 minutes. TFA was evaporated under reduced pressure, and the crude material was purified by reverse phase HPLC (7-42% AcCN in water with 0.1% TFA). LCMS [M+1]: 478.15.

EXAMPLE 202

3-(2-amino-1-(azetidin-3-yl)-1H-benzo[d]imidazol-4-yl)-6-((2-aminoethyl)sulfonyl)-2-(2H-tetrazol-5-yl)benzenesulfonamide

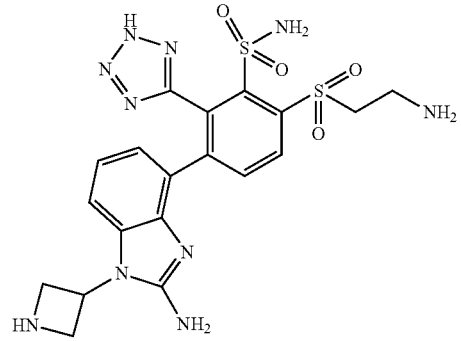 [SMILES: NCCS(=O)(=O)c1ccc(-c2cccc3c2nc(N)n3C2CNC2)c(-c2nn[nH]n2)c1S(N)(=O)=O]

Step A: tert-butyl (2-((3-(N,N-bis(4-methoxybenzyl) sulfamoyl)-3'-bromo-2-(2-(4-methoxybenzyl)-2H-tetrazol-5-yl)-2'-nitro-[1,1'-biphenyl]-4-yl)sulfonyl) ethyl)carbamate A suspension of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (4.3 g, 4.68 mmol), 2-nitro-3-(4,4,5,5-tetramethyl-1,3,2-dioxaborolan-2-yl)aniline (3.71 g, 14.04 mmol), tetrakis(triphenylphosphine)palladium(0) (0.541 g, 0.468 mmol) and sodium carbonate (1.488 g, 14.04 mmol) in dioxane (40 ml) and water (15 ml) was degassed and heated at 80° C. for 17 hours. The mixture was diluted with AcOEt, then washed with brine. The organic layer was dried (MgSO$_4$) and concentrated. The crude material was purified by ISCO (120 g column, 0-50% then 50% EtOAc in hexane. LCMS [M+1]: 929.43.

Step B: tert-butyl (2-((3-(N,N-bis(4-methoxybenzyl) sulfamoyl)-3'-bromo-2-(2-(4-methoxybenzyl)-2H-tetrazol-5-yl)-2'-nitro-[1,1'-biphenyl]-4-yl)sulfonyl) ethyl)carbamate Copper(II) bromide (0.894 g, 4.00 mmol) was suspended in acetonitrile (40 ml) and cooled to 0° C., and then tert-butyl nitrite (0.661 ml, 5.01 mmol) was added and stirred for 5 minutes. tert-Butyl 2-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)ethyl) carbamate (3.71 g, 4.00 mmol) in acetonitrile (30 ml) was then added. The mixture was stirred at 0° C. for 2 hours, warmed to RT, stirred for 16 hours, poured into saturated aqueous KHSO₄, and extracted with EtOAc. The combined organic layers were washed with brine, dried (MgSO₄) and concentrated. The crude material was purified by ISCO (120 g column, eluting with 0-50% EtOAc/hexane then 50%. LCMS [M+1]: 992.3, 994.3.

Step C: tert-butyl 3-((3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-2-nitro-[1,1'-biphenyl]-3-yl)amino)azetidine-1-carboxylate A mixture of tert-butyl (2-((3-(N,N-bis(4-methoxybenzyl)sulfamoyl)-3'-bromo-2-(2-(4-methoxybenzyl)-2H-tetrazol-5-yl)-2'-nitro-[1,1'-biphenyl]-4-yl)sulfonyl)ethyl)carbamate (1.8 g, 1.8 mmol), tert-butyl 3-aminoazetidine-1-carboxylate (0.62 g, 3.6 mmol), BINAP (0.169 g, 0.272 mmol), cesium carbonate (1.181 g, 3.63 mmol) and palladium(II) acetate (0.041 g, 0.181 mmol) in toluene (50 ml) was degassed, stirred at 80° C. for 16 hours. The mixture was cooled to RT, poured into water, and extracted with EtOAc. The organic layers were dried over MgSO₄, filtered, and concentrated in vacuo. The residue was purified by ISCO (80 g column, EtOAc in hexane (0-50% then 50%, 50%-90% and 90%) LCMS [M+1]: 1084.16.

Step D: tert-butyl 3-((2-amino-3'-(N,N-bis(4-methoxybenzyl)sulfamoyl)-4'-((2-((tert-butoxycarbonyl)amino)ethyl)sulfonyl)ethyl)sulfonyl-2'-(2-(4-methoxybenzyl)-2H-tetrazol-5-yl)-[1,1'-biphenyl]-3-yl)amino)azetidine-1-carboxylate A solution of tert-butyl 3-((3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-2-nitro-[1,1'-biphenyl]-3-yl)amino)azetidine-1-carboxylate (1.26 g, 1.16 mmol) in MeOH (30 mL) was hydrogenated at 50 psi H₂ and over palladium hydroxide on carbon (0.106 g, 0.151 mmol) at RT overnight. The catalyst was filtered off and the filtrate was concentrated. The crude material was separated by ISCO column (80 g silica gel, 0-50%, then 50% EtOAc in hexane). LCMS [M+1]: 1054.65.

Step E: tert-butyl 3-(2-amino-4-(3-(N,N-bis(4-methoxybenzyl)sulfamoyl)-4-((2-((tert-butoxycarbonyl)amino)eethyl)sulfonyl)-2-(2-(4-methoxybenzyl)-2H-tetrazol-5-yl)phenyl)-1H-benzo[d]imidazol-1-yl)azetidine-1-carboxylate A solution of cyanogen bromide (0.015 mL, 0.285 mmol) in ethanol (10 mL) was added to a flask containing tert-butyl 3-((2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-yl)amino)azetidine-1-carboxylate (0.15 g, 0.142 mmol). The flask was sealed and its contents were stirred for 2 hours at 50° C. The reaction mixture was concentrated under reduced pressure, diluted with DCM and washed twice with 1 M NaOH and once with brine. The combined organic fractions were dried over MgSO₄, filtered and concentrated under reduced pressure. The crude material was directly used in the next step.

Step F: 3-(2-amino-1-(azetidin-3-yl)-1H-benzo[d]imidazol-4-yl)-6-((2-aminoethyl)sulfonyl)-2-(2H-tetrazol-5-yl)benzenesulfonamide The crude tert-butyl 3-(2-amino-4-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-benzo[d]imidazol-1-yl)azetidine-1-carboxylate was dissolved in DCM (4 mL), and stirred at RT for 2 hours with 2 mL TFA and two drops anisole, and concentrated. The residue was heated at 80° C. in 2 mL TFA for 40 min. TFA was evaporated under reduced pressure, and the crude material was purified by reverse phase HPLC (10-50% AcCN in water with 0.05% TFA). LCMS [M+1]: 519.30.

EXAMPLES 203, 204 and 205

3-(4-aminocyclohexyl)-6-((azetidin-3-ylmethyl)sulfonyl)-2-(1H-tetrazol-5-yl)benzenesulfonamide;
3-((1r,4r)-4-aminocyclohexyl)-6-((azetidin-3-ylmethyl)sulfonyl)-2-(1H-tetrazol-5-yl)benzenesulfonamide and 3-((1s, 4s)-4-aminocyclohexyl)-6-((azetidin-3-ylmethyl)sulfonyl)-2-(1H-tetrazol-5-yl)benzenesulfonamide

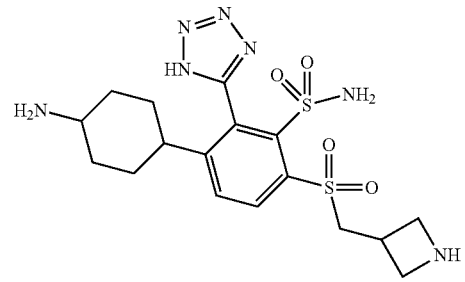

203

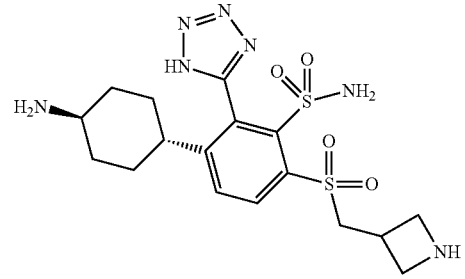

204

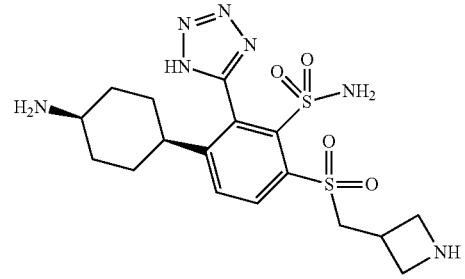

205

Step A: tert-butyl 3-(((3-(N,N-bis(4-methoxybenzyl)sulfamoyl)-4'-((tertbutoxycarbonyl)amino)-2-(1-(4-methoxybenzyl)-1H-tetrazol-5-yl)-2',3',4',5'-tetrahydro-[1,1'-biphenyl]-4-yl)thio)methyl)azetidine-1-carboxylate A mixture of the tert-butyl 3-(mercaptomethyl)azetidine-1-carboxylate (231 mg, 1.134 mmol), sodium 2-methylpropan-2-olate (109 mg, 1.134 mmol) and tert-butyl (3'-(N,N- bis(4-methoxybenzyl)sulfamoyl)-4'-bromo-2'-(1-(4-methoxybenzyl)-1H-tetrazol-5-yl)-2,3,4,5-tetrahydro-[1,1'-biphenyl]-4-yl)carbamate (650 mg, 0.756 mmol) in DME in a sealed tube was deoxygenated by bubbling nitrogen for 10 minutes. Then BRETTPHOS-PD-G3 (103 mg, 0.113 mmol) was added. The reaction tube was sealed and heated to 75° C. overnight. After cooling to RT, the reaction mixture was filtered through a pad of CELITE and the solid was thoroughly washed with ethyl acetate. The filtrate was washed with 1N aq. HCl, brine, dried (MgSO$_4$) and concentrated under reduced pressure. The residue was purified by silica gel column chromatography using EtOAc in hexanes as eluent to give the desired sulfide product.

Step B: tert-butyl 3-(((3-(N,N-bis(4-methoxybenzyl)sulfamoyl)-4'-((tert-butoxycarbonyl)amino)-2-(1-(4-methoxybenzyl)-1H-tetrazol-5-yl)-2',3',4',5'-tetrahydro-[1,1'-biphenyl]-4-yl)sulfonyl)methyl)azetidine-1-carboxylate mCPBA (158 mg, 0.704 mmol) was added to a stirred solution of starting material tert-butyl 3-(((2-(N,N-bis(4-methoxybenzyl)sulfamoyl)-4-(4-((tert-butoxycarbonyl)amino)cyclohexyl)-3-(1-(4-methoxybenzyl)-1H-tetrazol-5-yl)phenyl)thio)methyl)azetidine-1-carboxylate (630 mg, 0.640 mmol) in DCM (5 mL) at room temperature and the mixture was stirred at room temperature overnight. The reaction mixture was diluted with water (60 mL) and the mixture was extracted with DCM (2×60 mL). The organic phase was combined and dried (MgSO$_4$). The residue was purified by column chromatography on silica gel, eluting with EtOAc/isohexane to give the sulfone product.

Step C: tert-butyl 3-(((2-(N,N-bis(4-methoxybenzyl)sulfamoyl)-4-(4-((tert-butoxycarbonyl)amino)cyclohexyl)-3-(1-(4-methoxybenzyl)-1H-tetrazol-5-yl)phenyl)sulfonyl)methyl)azetidine-1-carboxylate Dihydroxypalladium (154 mg, 0.220 mmol) or PtO$_2$ was added to a solution of starting material tert-butyl 3-(((3-(N,N-bis(4-methoxybenzyl)sulfamoyl)-4'-((tert-butoxycarbonyl)amino)-2-(1-(4-methoxybenzyl)-1H-tetrazol-5-yl)-2',3',4',5'-tetrahydro-[1,1'-biphenyl]-4-yl)sulfonyl)methyl)azetidine-1-carboxylate (223 mg, 0.220 mmol) in methanol (1 ml) and EtOAc (2 ml) at RT. The solution was degassed by reduced pressure, then hydrogenated (using 45 Psi) at room temperature overnight. The reaction mixture was filtered through CELITE and washed with EtOAc, and concentrated to obtain the desired product.

Step D: 3-(4-aminocyclohexyl)-6-((azetidin-3-ylmethyl)sulfonyl)-N-(4-methoxybenzyl)-2-(1-(4-methoxybenzyl)-1H-tetrazol-5-yl)benzenesulfonamide tert-butyl 3-(((2-(N,N-bis(4-methoxybenzyl)sulfamoyl)-4-(4-((tert-butoxycarbonyl)amino)cyclohexyl)-3-(1-(4-methoxybenzyl)-1H-tetrazol-5-yl)phenyl)sulfonyl)methyl)azetidine-1-carboxylate (0.7 mmol) was dissolved in DCM (4 mL). Anisole (0.12 ml) and TFA (8 ml) were added at 0° C. and the mixture was stirred at 0° C. for 2 hours. The reaction mixture was concentrated to afford the crude Boc deprotected product. The crude material was placed on the vacuum for at least 3 hours and used as is.

Step E: 3-(4-aminocyclohexyl)-6-((azetidin-3-ylmethyl)sulfonyl)-2-(1H-tetrazol-5-yl)benzenesulfonamide 3-(4-aminocyclohexyl)-6-((azetidin-3-ylmethyl)sulfonyl)-N-(4-methoxybenzyl)-2-(1-(4-methoxybenzyl)-1H-tetrazol-5-yl)benzenesulfonamide obtained from step D (0.16 mmol) was dissolved in anisole (0.3 ml) and TFA (3 ml), heated to 80° C. for 2 hours. The reaction mixture was concentrated. The residue was purified by reverse phase HPLC to give the final product, 3-(4-aminocyclohexyl)-6-((azetidin-3-ylmethyl)sulfonyl)-2-(1H-tetrazol-5-yl)benzenesulfonamide. LC/MS [M+2]/2: 228.75 3-(4-aminocyclohexyl)-6-((azetidin-3-ylmethyl)sulfonyl)-2-(1H-tetrazol-5-yl)benzenesulfonamide was further separated by reverse phase HPLC to give two products, 3-((1r,4r)-4-aminocyclohexyl)-6-((azetidin-3-ylmethyl)sulfonyl)-2-(1H-tetrazol-5-yl) benzenesulfonamide and 3-((1s, 4s)-4-aminocyclohexyl)-6-((azetidin-3-ylmethyl)sulfonyl)-2-(1H-tetrazol-5-yl)benzenesulfonamide. LC/MS [M+2]/2: 228.75

EXAMPLES 206-213 were prepared according to the general procedure of EXAMPLES 203, 204 and 205 using tert-butyl (3'-(N,N-bis(4-methoxybenzyl)sulfamoyl)-4'-bromo-2'-(1-(4-methoxybenzyl)-1H-tetrazol-5-yl)-2,3,4,5-tetrahydro-[1,1'-biphenyl]-4-yl)carbamate and thiols that are commercially available, known, or prepared as described herein.

| Ex. No. | Structure | Name | Calc'd Mass [M + H]⁺ | LC/MS m/e [M + H]⁺ |
|---|---|---|---|---|
| 206 | 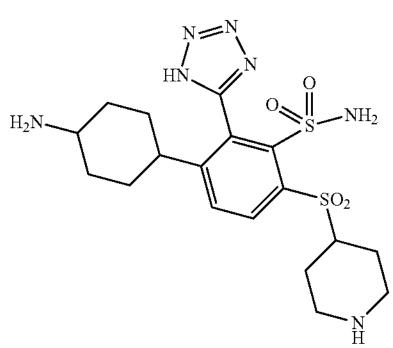 [SMILES: NC1CCC(c2ccc(S(=O)(=O)C3CCNCC3)c(S(N)(=O)=O)c2-c2nnn[nH]2)CC1] | 3-(4-aminocyclohexyl)-6-(piperidin-4-ylsulfonyl)-2-(1H-tetrazol-5-yl)benzenesulfonamide | 470.16 | 228.80 |

-continued

| Ex. No. | Structure | Name | Calc'd Mass [M + H]⁺ | LC/MS m/e [M + H]⁺ |
|---|---|---|---|---|
| 207 | 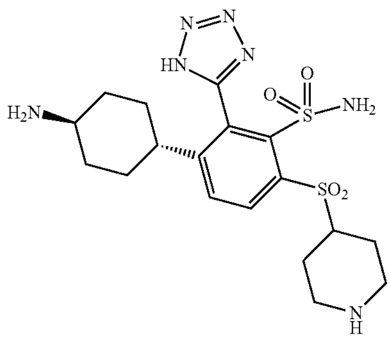 [SMILES: NS(=O)(=O)c1c(S(=O)(=O)C2CCNCC2)ccc([C@H]2CC[C@H](N)CC2)c1-c1nnn[nH]1] | 3-((1r,4r)-4-aminocyclohexyl)-6-(piperidin-4-ylsulfonyl)-2-(1H-tetrazol-5-yl)benzenesulfonamide | 470.16 | 228.75 |
| 208 | 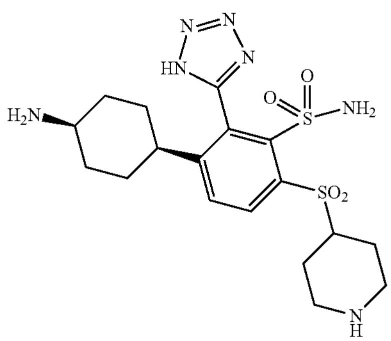 [SMILES: NS(=O)(=O)c1c(S(=O)(=O)C2CCNCC2)ccc([C@H]2CC[C@@H](N)CC2)c1-c1nnn[nH]1] | 3-((1s,4s)-4-aminocyclohexyl)-6-(piperidin-4-ylsulfonyl)-2-(1H-tetrazol-5-yl)benzenesulfonamide | 470.16 | 228.79 |
| 209 | 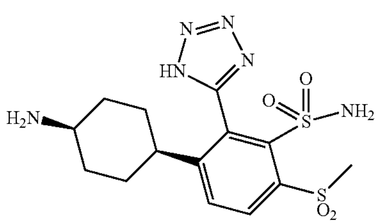 [SMILES: CS(=O)(=O)c1ccc([C@H]2CC[C@@H](N)CC2)c(-c2nnn[nH]2)c1S(N)(=O)=O] | 3-((1s,4s)-4-aminocyclohexyl)-6-(methylsulfonyl)-2-(1H-tetrazol-5-yl)benzenesulfonamide | 401.10 | 401.34 |
| 210 | 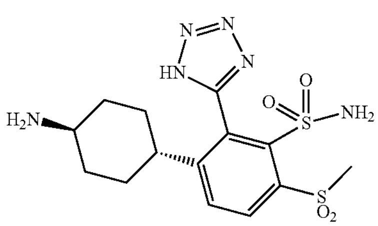 [SMILES: CS(=O)(=O)c1ccc([C@H]2CC[C@H](N)CC2)c(-c2nnn[nH]2)c1S(N)(=O)=O] | 3-((1r,4r)-4-aminocyclohexyl)-6-(methylsulfonyl)-2-(1H-tetrazol-5-yl)benzenesulfonamide | 401.10 | 401.39 |
| 211 | 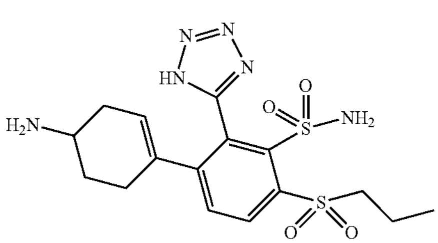 [SMILES: CCCS(=O)(=O)c1ccc(C2=CCC(N)CC2)c(-c2nnn[nH]2)c1S(N)(=O)=O] | 4'-amino-4-(propylsulfonyl)-2-(1H-tetrazol-5-yl)-2',3',4',5'-tetrahydro-[1,1'-biphenyl]-3-sulfonamide | 427.11 | 427.41 |

| Ex. No. | Structure | Name | Calc'd Mass [M + H]+ | LC/MS m/e [M + H]+ |
|---|---|---|---|---|
| 212 | 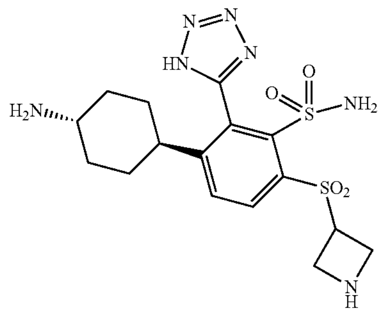 [SMILES: NS(=O)(=O)c1c(S(=O)(=O)C2CNC2)ccc([C@H]2CC[C@H](N)CC2)c1-c1nnn[nH]1] | 3-((1r,4r)-4-aminocyclohexyl)-6-(azetidin-3-ylsulfonyl)-2-(1H-tetrazol-5-yl)benzenesulfonamide | 442.13 | 221.82 |
| 213 | 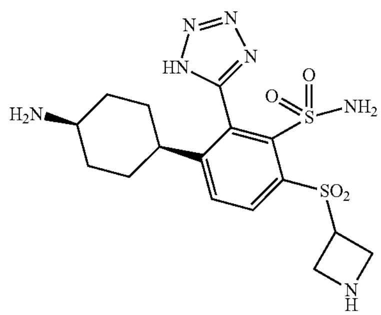 [SMILES: NS(=O)(=O)c1c(S(=O)(=O)C2CNC2)ccc([C@H]2CC[C@@H](N)CC2)c1-c1nnn[nH]1] | 3-((1s,4s)-4-aminocyclohexyl)-6-(azetidin-3-ylsulfonyl)-2-(1H-tetrazol-5-yl)benzenesulfonamide | 442.13 | 221.57 |

EXAMPLE 214

3-(2-amino-[1,2,4]triazolo[1,5-a]pyridin-5-yl)-6-(azetidin-3-ylsulfonyl)-2-(2H-tetrazol-5-yl)benzenesulfonamide

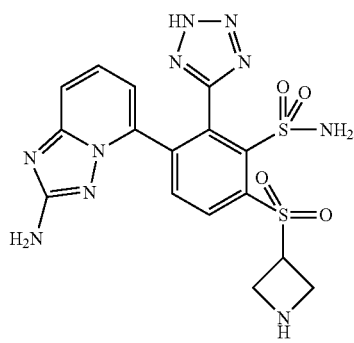 [SMILES: Nc1nc2cccc(-c3ccc(S(=O)(=O)C4CNC4)c(S(N)(=O)=O)c3-c3nn[nH]n3)n2n1]

Step A: tert-butyl 3-((4-(6-aminopyridin-2-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate A reaction flask was charged with 2,2-dimethylpropane-1,3-diol (0.614 g, 5.89 mmol), 2nd generation Xphos precatalyst (0.232 g, 0.295 mmol), cesium carbonate (0.768 g, 2.356 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid (1 g, 1.178 mmol) and 6-bromopyridin-2-amine (0.245 g, 1.414 mmol). The vial was sealed, degassed, and filled with dioxane (15 ml) and water (3 ml). The resulting mixture was heated overnight at 40° C. The reaction mixture was filtered over CELITE. The filtrate was diluted with EtOAc and washed with water. The organic layer was dried over anhydrous MgSO4, filtered, concentrated and purified by silica gel column chromatography to give the title product.

Step B: tert-butyl 3-((2-(N,N-bis(4-methoxybenzyl)sulfamoyl)-4-(6-(3-(ethoxycarbonyl)thioureido)pyridin-2-yl)-3-(2-(4-methoxybenzyl)-2H-tetrazol-5-yl)phenyl)sulfonyl)azetidine-1-carboxylate Ethoxycarbonyl isothiocyanate (0.088 ml, 0.747 mmol) was added to a stirred solution of starting material tert-butyl 3-((4-(6-aminopyridin-2-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (447 mg, 0.498 mmol) in DCM (11 ml) at 0° C. and the mixture was warmed to room temperature and stirred overnight. LCMS indicated an incomplete reaction. Another 0.5 eq. of O-ethyl carbonisothiocyanatidate was added at 0° C. The reaction mixture stirred at RT for 3 additional hours. The mixture was diluted with water (30 mL), then extracted with DCM (2×30 mL). The residue was purified by column chromatography on silica gel and eluted with EtOAc/isohexane to give the desired product.

Step C: tert-butyl 3-((4-(2-amino-[1,2,4]triazolo[1,5-a]pyridin-5-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate Hunig's base (0.313 ml, 1.79 mmol) was added to a suspension of hydroxylamine hydrochloride (156 mg, 2.24 mmol) in EtOH/MeOH (1:1) and the mixture was stirred at RT for 30 minutes. The resulting mixture was then added to a solution of starting material tert-butyl 3-((2-(N,N-bis(4-methoxybenzyl)sulfamoyl)-4-(6-(3-(ethoxycarbonyl)thioureido)pyridin-2-yl)-3-(2-(4-methoxybenzyl)-2H-tetrazol-5-yl)phenyl)sulfonyl)azetidine-1-carboxylate (461 mg, 0.448 mmol) in THF (1.5 mL). The mixture was slowly heated to reflux (80° C.) for 3 hours. The mixture was diluted with water (50 mL), and extracted with ethyl acetate (2×50 mL). The residue was purified by column chromatography on silica gel, eluting with EtOAc/isohexane to give the title product.

Step D: 3-(2-amino-[1,2,4]triazolo[1,5-a]pyridin-5-yl)-6-(azetidin-3-ylsulfonyl)-N-(4-methoxybenzyl)-2-(2-(4-methoxybenzyl)-2H-tetrazol-5-yl)benzenesulfonamide The Boc protective group and one para-methoxybenzyl protective group on the sulfonamide were removed according to the procedure described for EXAMPLES 203-205, Step D.

Step E: 3-(2-amino-[1,2,4]triazolo[1,5-a]pyridin-5-yl)-6-(azetidin-3-ylsulfonyl)-2-(2H-tetrazol-5-yl)benzenesulfonamide The last two para-methoxybenzyl protective groups were removed according to the procedure described for EXAMPLES 203-205, Step E. LCMS: 477.35 [M+H]+

EXAMPLE 215

3-(2-amino-[1,2,4]triazolo[1,5-a]pyridin-6-yl)-6-(azetidin-3-ylsulfonyl)-2-(2H-tetrazol-5-yl)benzenesulfonamide

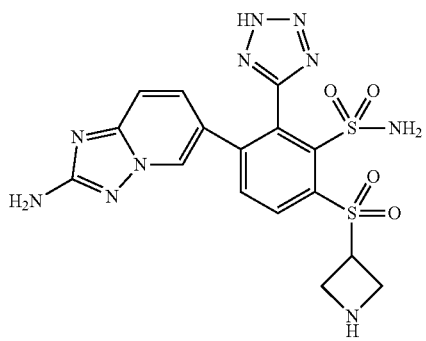 [SMILES: Nc1nc2ccc(-c3ccc(S(=O)(=O)C4CNC4)c(S(N)(=O)=O)c3-c3nn[nH]n3)cn2n1]

Step A: tert-butyl 3-((4-(2-amino-[1,2,4]triazolo[1,5-a]pyridin-6-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate A microwave vial was charged with cesium carbonate (235 mg, 0.721 mmol), 6-bromo-[1,2,4]triazolo[1,5-a]pyridin-2-amine (51.2 mg, 0.240 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid (204 mg, 0.240 mmol) and 2nd generation Xphos precatalyst (18.91 mg, 0.024 mmol). The vial was sealed, degassed, and filled with dioxane (1.8 ml) and water (0.6 ml). The resulting mixture was heated overnight at 60° C. The mixture was filtered, washed with ethyl acetate and concentrated. The residue was purified by column chromatography on silica gel 12 g, eluting with EtOAc/isohexane to give the product.

Step B: 3-(2-amino-[1,2,4]triazolo[1,5-a]pyridin-6-yl)-6-(azetidin-3-ylsulfonyl)-N-(4-methoxybenzyl)-2-(2-(4-methoxybenzyl)-2H-tetrazol-5-yl)benzenesulfonamide The Boc protective group and one para-methoxybenzyl protective group on the sulfonamide were removed according to the procedure described for EXAMPLES 367-369, Step D.

Step C: 3-(2-amino-[1,2,4]triazolo[1,5-a]pyridin-6-yl)-6-(azetidin-3-ylsulfonyl)-2-(2H-tetrazol-5-yl)benzenesulfonamide The last two para-methoxybenzyl protective groups were removed according to the procedure described for EXAMPLES 367-369, Step E. LCMS: 477.34 [M+H]+.

EXAMPLE 216

3-(2-amino-[,2,4]triazolo[1,5-a]pyridin-8-yl)-6-(azetidin-3-ylsulfonyl)-2-(2H-tetrazol-5-yl)benzenesulfonamide

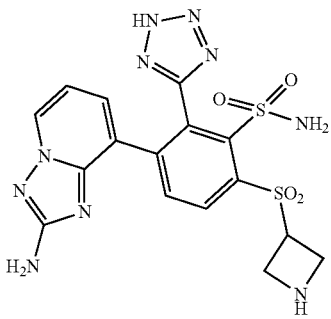 [SMILES: Nc1nc2c(-c3ccc(S(=O)(=O)C4CNC4)c(S(N)(=O)=O)c3-c3nn[nH]n3)cccn2n1]

Step A: (2-amino-[1,2,4]triazolo[1,5-a]pyridin-8-yl)boronic acid

Potassium acetate (691 mg, 7.04 mmol) and chloro[(tricyclohexylphosphine)-2-(2'-aminobiphenyl)]palladium(ii) (139 mg, 0.235 mmol), bis(pinacolato)diboron (1192 mg, 4.69 mmol) were added to a stirred solution of starting material 8-bromo-[1,2,4]triazolo[1,5-a]pyridin-2-amine (500 mg, 2.347 mmol) in dimethylsulfoxide at room temperature and the mixture was degassed and stirred at 90° C. overnight. The mixture was filtered through a pad of CELITE, diluted with water (30 mL) and the mixture was extracted with ethyl acetate (3×30 mL). The residue was purified by reverse phase column chromatography on silica gel 86 g C18, eluting with acetonitrile/water to give the title product as a solid after concentration.

Step B: tert-butyl 3-((4-(2-amino-[1,2,4]triazolo[1,5-a]pyridin-8-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (2-Amino-[1,2,4]triazolo[1,5-a]pyridin-8-yl)boronic acid (37.3 mg, 0.209 mmol) and sodium carbonate (42.7 mg, 0.403 mmol), PdCl$_2$(dppf)$_2$(23.58 mg, 0.032 mmol) were added to a stirred solution of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (150 mg, 0.161 mmol) in dioxane (5 ml) and water (1 ml) at room temperature and the mixture was degassed for 10 minutes, and then stirred at 80° C. overnight. The mixture was diluted with water (60 mL), extracted with ethyl acetate (2×60 mL). The residue was purified by column chromatography on silica gel, eluting with EtOAc/isohexane to give the product.

Step C: 3-(2-amino-[1,2,4]triazolo[1,5-a]pyridin-8-yl)-6-(azetidin-3-ylsulfonyl)-N-(4-methoxybenzyl)-2-(2-(4-methoxybenzyl)-2H-tetrazol-5-yl)benzenesulfonamide The Boc protective group and one para-methoxybenzyl protective group on the sulfonamide were removed according to the procedure described for EXAMPLES 203-205, Step D.

Step D: 3-(2-amino-[1,2,4]triazolo[1,5-a]pyridin-8-yl)-6-(azetidin-3-ylsulfonyl)-2-(2H-tetrazol-5-yl)benzenesulfonamide The last two para-methoxybenzyl protective groups were removed according to the procedure described for EXAMPLES 203-205, Step E. LCMS: 477.48 [M+H]

EXAMPLES 217-221 were made starting from tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate and boronic acids or boronic esters that are commercially available, known, or prepared as described herein by using the same general method described for EXAMPLE 216.

| Ex. No. | Structure | Name | Calc'd Mass [M + H]$^+$ | LC/MS m/e [M + H]$^+$ |
|---|---|---|---|---|
| 217 | 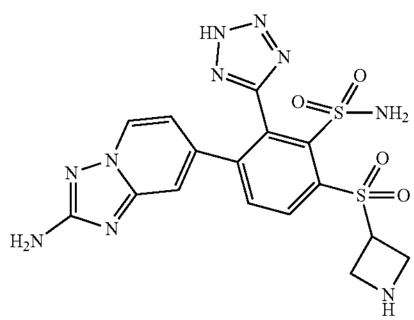 [SMILES: Nc1nc2cc(-c3ccc(S(=O)(=O)C4CNC4)c(S(N)(=O)=O)c3-c3nn[nH]n3)ccn2n1] | 3-(2-amino-[1,2,4]triazolo[1,5-a]pyridin-7-yl)-6-(azetidin-3-ylsulfonyl)-2-(2H-tetrazol-5-yl)benzenesulfonamide | 477 | 477.28 |
| 218 | 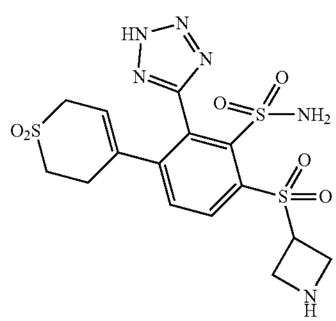 [SMILES: NS(=O)(=O)c1c(S(=O)(=O)C2CNC2)ccc(C2=CCS(=O)(=O)CC2)c1-c1nn[nH]n1] | 6-(azetidin-3-ylsulfonyl)-3-(1,1-dioxido-3,6-dihydro-2H-thiopyran-4-yl)-2-(2H-tetrazol-5-yl)benzenesulfonamide | 475 | 475.51 |
| 219 | 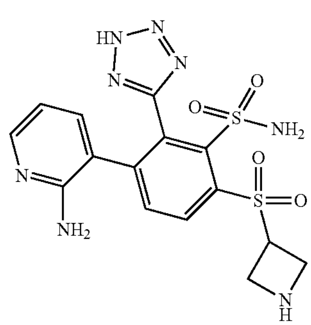 [SMILES: Nc1ncccc1-c1ccc(S(=O)(=O)C2CNC2)c(S(N)(=O)=O)c1-c1nn[nH]n1] | 3-(2-aminopyridin-3-yl)-6-(azetidin-3-ylsulfonyl)-2-(2H-tetrazol-5-yl)benzenesulfonamide | 437 | 437.30 |

| Ex. No. | Structure | Name | Calc'd Mass [M + H]+ | LC/MS m/e [M + H]+ |
|---|---|---|---|---|
| 220 | 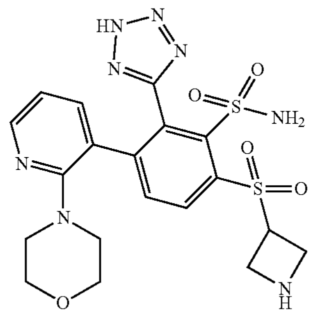 [SMILES: NS(=O)(=O)c1c(S(=O)(=O)C2CNC2)ccc(-c2cccnc2N2CCOCC2)c1-c1nn[nH]n1] | 6-(azetidin-3-ylsulfonyl)-3-(2-morpholinopyridin-3-yl)-2-(2H-tetrazol-5-yl)benzenesulfonamide | 507 | 507.42 |
| 221 | 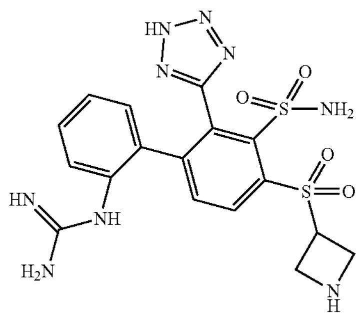 [SMILES: N=C(N)Nc1ccccc1-c1ccc(S(=O)(=O)C2CNC2)c(S(N)(=O)=O)c1-c1nn[nH]n1] | 4-(azetidin-3-ylsulfonyl)-2'-guanidino-2-(2H-tetrazol-5-yl)-[1,1'-biphenyl]-3-sulfonamide | 478 | 478.37 |

EXAMPLE 222

6-(azetidin-3-ylsulfonyl)-3-(tetrahydro-2H-pyran-4-yl)-2-(2H-tetrazol-5-yl)benzenesulfonamide

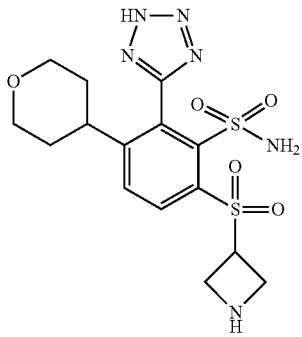 [SMILES: NS(=O)(=O)c1c(S(=O)(=O)C2CNC2)ccc(C2CCOCC2)c1-c1nn[nH]n1]

Step A: tert-butyl 3-((2-(N,N-bis(4-methoxybenzyl)sulfamoyl)-4-(3,6-dihydro-2H-pyran-4-yl)-3-(2-(4-methoxybenzyl)-2H-tetrazol-5-yl)phenyl)sulfonyl)azetidine-1-carboxylate (3,6-dihydro-2H-pyran-4-yl)boronic acid (27.5 mg, 0.215 mmol) and sodium carbonate (28.5 mg, 0.269 mmol), PdCl2(dppf)2 (15.72 mg, 0.021 mmol) were added to a stirred solution of starting material tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (100 mg, 0.107 mmol) in dioxane (2 ml) and water (0.5 ml) at room temperature nd the mixture was degassed for 10 minutes, and then stirred at 80° C. overnight. The mixture was diluted with water (30 mL), extracted with ethyl acetate (2×30 mL). The organic phase was combined and concentrated. The residue was purified by column chromatography on silica gel 12 g, eluting with EtOAc/isohexane to give as a solid product.

Step B: tert-butyl 3-((2-(N,N-bis(4-methoxybenzyl)sulfamoyl)-3-(2-(4-methoxybenzyl)-2H-tetrazol-5-yl)-4-(tetrahydro-2H-pyran-4-yl)phenyl)sulfonyl)azetidine-1-carboxylate Dihydroxypalladium (32.7 mg, 0.070 mmol) was added to a stirred solution of starting material tert-butyl 3-((2-(N,N-bis(4-methoxybenzyl)sulfamoyl)-4-(3,6-dihydro-2H-pyran-4-yl)-3-(2-(4-methoxybenzyl)-2H-tetrazol-5-yl)phenyl)sulfonyl)azetidine-1-carboxylate (62 mg, 0.070 mmol) in methanol (1 ml) and EtOAc (2 ml) at RT. The solution was degassed by reduced pressure and hydrogenated (using parr shaker,45 Psi) at room temperature overnight. The reaction mixture was filtered through CELITE and washed with EtOAc, concentrated and the residue was used directly in the next step.

Step C: 6-(azetidin-3-ylsulfonyl)-N-(4-methoxybenzyl)-2-(2-(4-methoxybenzyl)-2H-tetrazol-5-yl)-3-(tetrahydro-2H-pyran-4-yl)benzenesulfonamide The Boc protective group and one para-methoxybenzyl protective group on the sulfonamide were removed according to the procedure described for EXAMPLES 203-205, Step D.

Step D: 6-(azetidin-3-ylsulfonyl)-3-(tetrahydro-2H-pyran-4-yl)-2-(2H-tetrazol-5-yl)benzenesulfonamide The last two para-methoxybenzyl protective groups were removed according to the procedure described for EXAMPLES 203-205, Step E. LCMS: 429.33 [M+H]+.

EXAMPLE 223

3-(6-aminopyridin-2-yl)-6-(azetidin-3-ylsulfonyl)-2-(2H-tetrazol-5-yl)benzenesulfonamide

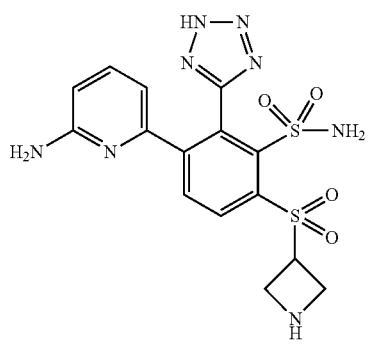 [SMILES: Nc1cccc(-c2ccc(S(=O)(=O)C3CNC3)c(S(N)(=O)=O)c2-c2nn[nH]n2)n1]

Step A: tert-butyl 3-((4-(6-aminopyridin-2-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate A reaction flask was charged with 2,2-dimethylpropane-1,3-diol (0.614 g, 5.89 mmol), 2nd generation Xphos precatalyst (0.232 g, 0.295 mmol), cesium carbonate (0.768 g, 2.356 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid (1 g, 1.178 mmol) and 6-bromopyridin-2-amine (0.245 g, 1.414 mmol). The vial was sealed, degassed, and filled with dioxane (15 ml) and water (3 ml). The resulting mixture was heated overnight at 40° C. The reaction mixture was filtered over CELITE. The filtrate was diluted with EtOAc and washed with water. The organic layer was dried over anhydrous MgSO$_4$, filtered, concentrated and purified by silica gel column chromatography using EtOAc/Hex as mobile phase to give the product.

Step B: 3-(6-aminopyridin-2-yl)-6-(azetidin-3-ylsulfonyl)-N-(4-methoxybenzyl)-2-(2-(4-methoxybenzyl)-2H-tetrazol-5-yl)benzenesulfonamide The Boc protective group and one para-methoxybenzyl protective group on the sulfonamide from Step A were removed according to the procedure described for EXAMPLES 203-205, Step D.

Step C: 3-(6-aminopyridin-2-yl)-6-(azetidin-3-ylsulfonyl)-2-(2H-tetrazol-5-yl)benzenesulfonamide The last two para-methoxybenzyl protective groups of 3-(6-aminopyridin-2-yl)-6-(azetidin-3-ylsulfonyl)-N-(4-methoxybenzyl)-2-(2-(4-methoxybenzyl)-2H-tetrazol-5-yl)benzenesulfonamide were removed according to the procedure described for EXAMPLES 203-205, Step E. LCMS: 437.24 [M+H]+

EXAMPLE 224

6-(azetidin-3-ylsulfonyl)-3-(2,3-diaminopyridin-4-yl)-2-(2H-tetrazol-5-yl)benzenesulfonamide

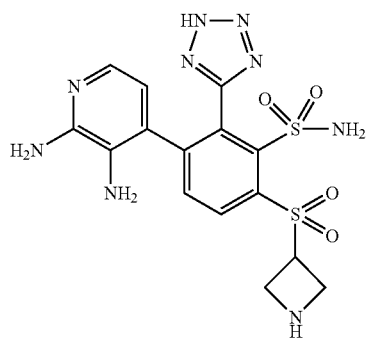 [SMILES: Nc1nccc(-c2ccc(S(=O)(=O)C3CNC3)c(S(N)(=O)=O)c2-c2nn[nH]n2)c1N]

The title compound was prepared using the same general methods as EXAMPLE 223. $^1$H NMR: 8.65 (1H, d, J=8.34 Hz), 8.15 (1H, d, J=8.56 Hz), 6.95 (1H, d, 8.07 Hz), 6.28 (1H, d, 8.13 Hz), 5.25 (1H, m), 4.6 (2H, m), 4.45 (2H, m).

EXAMPLE 225

3-(2-amino-[1,2,4]triazolo[1,5-a]pyridin-5-yl)-6-((2-aminoethyl)sulfonyl)-2-(2H-tetrazol-5-yl)benzenesulfonamide

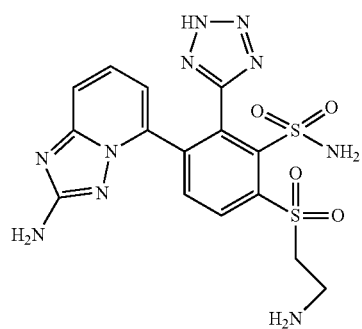 [SMILES: NCCS(=O)(=O)c1ccc(-c2cccc3nc(N)nn23)c(-c2nn[nH]n2)c1S(N)(=O)=O]

Step A: 5-(tributylstannyl)-[1,2,4]triazolo[1,5-a]pyridin-2-amine

Sodium carbonate (533 mg, 5.03 mmol) and 1,1,1,2,2,2-hexabutyldistannane (5.12 ml, 10.06 mmol), PPh$_3$PdG$_2$ (288 mg, 0.503 mmol) were added to a stirred solution of starting material 5-bromo-[1,2,4]triazolo[1,5-a]pyridin-2-amine (536 mg, 2.52 mmol) in DMF (6 ml) at room temperature. The mixture was degassed and stirred at 110° C. overnight. The mixture was concentrated, extracted with EtOAc, washed with water and brine. The organic phase was dried (MgSO$_4$), filtered and concentrated. The residue was purified by column chromatography on silica gel 40 g, eluting with EtOAc/isohexane to give the title product as a oil product.

Step B: tert-butyl (2-((4-(2-amino-[1,2,4]triazolo[1,5-a]pyridin-5-yl)-2-(N,N-bis(4-methoxybenzyl)sulfamoyl)-3-(2-(4-methoxybenzyl)-2H-tetrazol-5-yl)phenyl)sulfonyl)ethyl)carbamate Sodium carbonate (63.4 mg, 0.599 mmol) and 5-(tributylstannyl)-[1,2,4]triazolo[1,5-a]pyridin-2-amine (132 mg, 0.311 mmol), chloro(triphenylphosphine) [2-(2'-amino-1,1'-biphenyl)]palladium(ii) (41.1 mg, 0.072 mmol) were added to a stirred solution of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (220 mg, 0.239 mmol) in dimethylformamide (3 ml) at room temperature and the mixture was degassed for 10 minutes, and stirred at 80° C. for 3 hours. The reaction mixture was filtered and concentrated. The residue was purified by column chromatography on silica gel, eluting with EtOAc/isohexane to give the title product.

Step C: 3-(2-amino-[1,2,4]triazolo[1,5-a]pyridin-5-yl)-6-((2-aminoethyl)sulfonyl)-N-(4-methoxybenzyl)-2-(2-(4-methoxybenzyl)-2H-tetrazol-5-yl)benzenesulfonamide The Boc protective group and one para-methoxybenzyl protective group on the sulfonamide from Step A were removed according to the procedure described for EXAMPLES 203-205, Step D.

Step D: 3-(2-amino-[1,2,4]triazolo[1,5-a]pyridin-5-yl)-6-((2-aminoethyl)sulfonyl)-2-(2H-tetrazol-5-yl)benzenesulfonamide The last two para-methoxybenzyl protective groups of 3-(6-aminopyridin-2-yl)-6-(azetidin-3-ylsulfonyl)-N-(4-methoxybenzyl)-2-(2-(4-methoxybenzyl)-2H-tetrazol-5-yl)benzenesulfonamide were removed according to the procedure described for EXAMPLES 203-205, Step E. LCMS: 233.43; 465.39 [M+H]+.

EXAMPLES 226, 227, and 228

4'-(piperidin-4-yl)-4-(piperidin-4-ylthio)-2-(1H-tetrazol-5-yl)-[1,1'-biphenyl]-3-sulfonamide and 4'-(piperidin-4-yl)-4-(piperidin-4-ylsulfinyl)-2-(1H-tetrazol-5-yl)-[1,1'-biphenyl]-3-sulfonamide and 4'-(piperidin-4-yl)-4-(piperidin-4-ylsulfonyl)-2-(1H-tetrazol-5-yl)-[1,1'-biphenyl]-3-sulfonamide

226

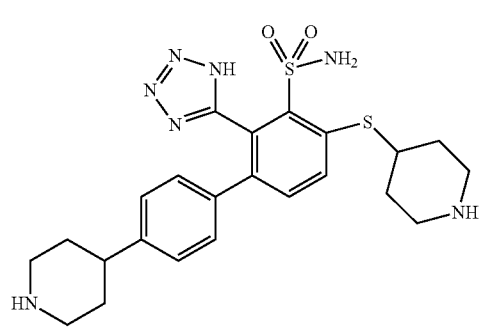

227

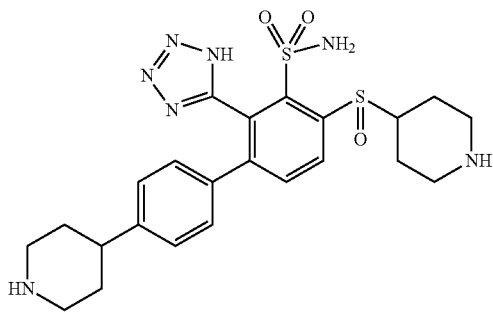

228

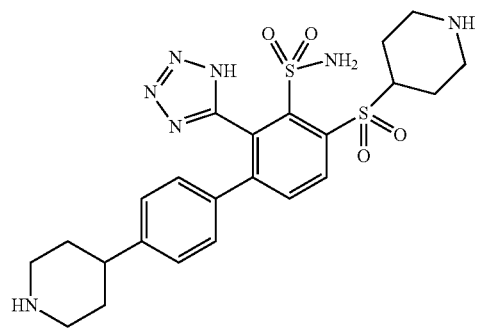

Step A: tert-butyl 4-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)piperidine-1-carboxylate and tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate A mixture of tert-butyl 4-(4-(4-,5,5,5-tetramethyl-1,3,2-dioxaborolan-2-yl)phenyl)piperidine-1-carboxylate (0.81 g, 2.1 mmol), the aryl iodides (1.10 g, 1.39 mmol) and sodium carbonate (0.44 g, 4.2 mmol) in dioxane (4.5 mL) and water (1.5 ml) was deoxygenated by bubbling a stream of nitrogen through the suspension for 10 minutes. Tetrakis(triphenylphosphine)palladium(O) (0.08 g, 0.07 mmol) was added and deoxygenation was continued for a further 5 minutes. The tube containing the reaction mixture was sealed and heated to 85° C. (oil bath temperature) overnight. After cooling, the reaction was partitioned between EtOAc and water. The organic phase was separated, dried (MgSO₄) and the volatiles removed under reduced pressure. The residue was purified by silica gel column chromatography using a 40 g column and a gradient of EtOAc in hexanes as eluent, giving the desired carbamates. LC/MS [M+H]+: 926.08 and 926.10.

Step B: tert-butyl 4-(3'-(N,N-bis(4-methoxybenzyl)sulfamoyl)-4'-((1-(tert-butoxycarbonyl)piperidin-4-yl)thio)-2'-(1-(4-methoxybenzyl)-1H-tetrazol-5-yl)-[1,1'-biphenyl]-4-yl)piperidine-1-carboxylate and tert-butyl 4-(3'-(N,N-bis(4-methoxybenzyl)sulfamoyl)-4'-((1-(tert-butoxycarbonyl)piperidin-4-yl)thio)-2'-(2-(4-methoxybenzyl)-2H-tetrazol-5-yl)[1,1'-biphenyl]-4-yl)piperidine-1-carboxylate A mixture of the products from the previous step (0.50 g, 0.54 mmol), tert-butyl 4-mercaptopiperidine-1-carboxylate (0.14 g, 0.55 mmol) and sodium tert-butoxide (0.057 g, 0.59 mmol) in DME (5 mL) was deoxygenated by bubbling a stream of nitrogen through the suspension for 15 minutes. Xphos Biphenyl precatalyst (CAS#1310584-14-5; 0.049 g, 0.054 mmol) was added and deoxygenation was continued for a further 5 minutes. The tube containing the reaction mixture was sealed and heated to 75° C. (oil bath temperature) overnight. After cooling, the mixture was filtered through a pad of CELITE and the solid was washed thoroughly with EtOAc. The filtrate was washed with 1N HCl, brine, dried (MgSO₄). and the volatiles removed under reduced pressure. The residue was purified by silica gel column chromatography using a 40 g column and a gradient of EtOAc in hexanes as eluent giving the desired sulfides. LC/MS [M+H]⁺: 1061.07 and 1061.11

Step C: 4'-(piperidin-4-yl)-4-(piperidin-4-ylthio)-2-(2H-tetrazol-5-yl)-[1,1'-biphenyl]-3-sulfonamide TFA (3 mL) was added to a mixture of the protected tetrazoles (0.050 g, 0.09 mmol) and anisole (10 drops from a pipette) and the mixture was stirred at room temperature for 1 hour. The volatiles were removed under reduced pressure and additional TFA (3 mL) was added to the residue. The mixture was heated to 85° C. (oil bath temperature) under an atmosphere of nitrogen for 2 hours. After cooling, the volatiles were removed under reduced pressure and the crude product was purified by reverse phase HPLC using a gradient of acetonitrile (containing 0.1% TFA) in water (containing 0.1% TFA) to give the trifluoroacetate salt of the desired product. LC/MS [M+H]⁺: 500.64.

Step D: tert-butyl 4-(3'-(N,N-bis(4-methoxybenzyl)sulfamoyl)-4'-((1-(tert-butoxycarbonyl)piperidin-4-yl)sulfonyl)-2'-(1-(4-methoxybenzyl)-1H-tetrazol-5-yl)-[1,1'-biphenyl]-4-yl)piperidine-1-carboxylate and tert-butyl 4-(3'-(N,N-bis(4-methoxybenzyl)sulfamoyl)-4'-((1-(tert-butoxycarbonyl)piperidin-4-yl)sulfonyl)-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-((1-(tert-butoxycarbonyl)piperidin-4-yl)sulfonyl)-2'-(2-(4-methoxybenzyl)-2H-tetrazol-5-yl)-[1,1'-biphenyl]-4-yl)piperidine-1-carboxylate and tert-butyl 4-(3'-(N,N-bis(4-methoxybenzyl)sulfamoyl)-4'-((1-(tert-butoxycarbonyl)piperidin-4-yl)sulfinyl)-2'-(2-(4-methoxybenzyl)-2H-tetrazol-5-yl)-[1,1'-biphenyl]-4-yl)piperidine-1-carboxylate MCPBA (0.107 g of 77% pure material, 0.48 mmol) was added to a stirred solution of the sulfides (0.34 g, 0.32 mmol) in DCM (5 mL) and the resulting reaction mixture was stirred at room temperature overnight. The reaction was partitioned between EtOAc and 10% aq. sodium thiosulfate. The organic phase was separated, washed with sat. aq. sodium bicarbonate, dried (MgSO₄) and the volatiles removed under reduced pressure. The residue was purified by silica gel column chromatography using a 40 g column and a gradient of EtOAc in hexanes as eluent to give the sulfones [LC/MS [M+H]⁺: 1093.19 followed by the sulfoxides. LC/MS [M+H]⁺: 1077.23.

Step E: 4'-(piperidin-4-yl)-4-(piperidin-4-ylsulfonyl)-2-(2H-tetrazol-5-yl)-[1'-biphenyl]-3-sulfonamide TFA (5 mL) was added to a mixture of the bis-carbamates (0.10 g, 0.09 mmol) and anisole (10 drops from a pipette) and the resulting reaction mixture heated to 80° C. (oil bath temperature) for 2 hours. After cooling, the volatiles were removed under reduced pressure and the residue purified by reverse phase HPLC using a gradient of acetonitrile (containing 0.1% TFA) in water (containing 0.1% TFA) as gradient to obtain the titled compound as its TFA salt. LC/MS [M+H]⁺: 532.70.

Step F: 4'-(piperidin-4-yl)-4-(piperidin-4-ylsulfinyl)-2-(2H-tetrazol-5-yl)-[1,1'-biphenyl]-3-sulfonamide Using the transformation described in Step E above, the sulfoxides obtained in step D were converted to the trifluoroacetate of the titled amine. LC/MS [M+H]⁺: 516.66.

EXAMPLES 229 and 230

6-(azetidin-3-ylsulfonyl)-3-(1-methyl-3-(2,2,2-trifluoroacetyl)-1H-indol-4-yl)-2-(1H-tetrazol-5-yl)benzenesulfonamide and 6-(azetidin-3-ylsulfonyl)-3-(2-(4-methoxybenzyl)-1-methyl-1H-indol-4-yl)-2-(1H-tetrazol-5-yl)benzenesulfonamide

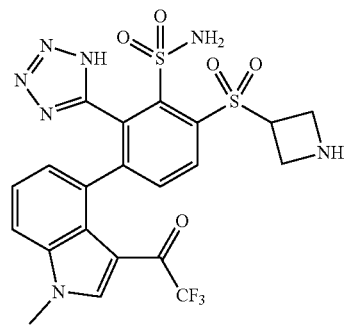

229

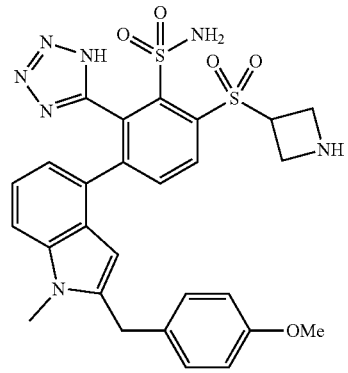

230

Step A: tert-butyl 3-((2-((11-azanyl)sulfonyl)-3-(1-(4-methoxybenzyl)-1H-tetrazol-5-yl)-4-(1-methyl-1H-indol-4-yl)phenyl)sulfonyl)azetidine-1-carboxylate compound with 1,2-bis(4-methoxyphenyl)ethane and tert-butyl 3-((2-(N,N-bis(4-methoxybenzyl)sulfamoyl)-3-(2-(4-methoxybenzyl)-2H-tetrazol-5-yl)-4-(1-methyl-1H-indol-4-yl)phenyl)sulfonyl)azetidine-1-carboxylate A stream of nitrogen was bubbled through a mixture of 1-methyl-4-(4,4,5,5-tetramethyl-1,3,2-dioxaborolan-2-yl)-1H-indole (0.041 g, 0.11 mmol), tert-Butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate and tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate (0.100 g, 0.107 mmol) and sodium carbonate (0.0342 g, 0.32 mmol) in dioxane (1.5 mL) and water (0.5 mL) for 15 minutes. PdCl$_2$(dppf)-methylene chloride adduct was added and the resulting reaction mixture was heated to 90° C. (oil bath temperature) under an atmosphere of nitrogen overnight. After cooling, the reaction was filtered through a pad of CELITE and the solid washed thoroughly with methanol. The filtrate was concentrated under reduced pressure and the residue partitioned between EtOAc and water. The organic phase was separated, dried (MgSO$_4$) and the volatiles removed under reduced pressure. The crude reaction product was purified by silica gel column chromatography using a 12 g column and a gradient of EtOAc in hexanes as eluent, giving the desired products.

Step B: 6-(azetidin-3-ylsulfonyl)-3-(1-methyl-3-(2,2,2-trifluoroacetyl)-1H-indol-4-yl)-2-(1H-tetrazol-5-yl)benzenesulfonamide and 6-(azetidin-3-ylsulfonyl)-3-(2-(4-methoxybenzyl)-1-methyl-1H-indol-4-yl)-2-(1H-tetrazol-5-yl)benzenesulfonamide TFA (1 mL) was added to a mixture of the protected intermediate from the previous step (0.015 g, 0.016 mmol) and anisole (3 drops from a pipette) in DCM (2 ml), cooled in an ice bath while a steam of nitrogen bubbled through the solution. After 1 hour, the volatiles were removed under reduced pressure and additional TFA (1 ml) was added to the residue and the mixture heated to 80° C. (oil bath temperature) for 2 hours. After cooling, the volatiles were removed under reduced pressure and the crude reaction product purified by reverse phase HPLC using a gradient of acetonitrile (containing 0.1% TFA) in water (containing 0.1% TFA) to give the 3-trifluoroacetyl substituted indole (as the TFA salt) [LC/MS [M+H]$^+$: 570.37] followed by 2-alkyl substituted indole (as the TFA salt) LC/MS [M+H]$^+$: 595.46.

EXAMPLE 231

6-(azetidin-3-ylsulfonyl)-3-(2-(4-methoxybenzyl)-1H-indol-4-yl)-2-(1H-tetrazol-5-yl)benzenesulfonamide

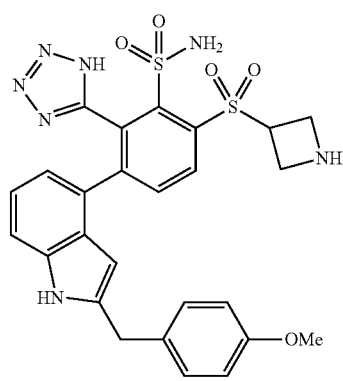 [SMILES: COc1ccc(Cc2cc3c(-c4ccc(S(=O)(=O)C5CNC5)c(S(N)(=O)=O)c4-c4nnn[nH]4)cccc3[nH]2)cc1]

Using (1H-indol-4-yl)boronic acid instead of 1-methyl-4-(4,4,5,5-tetramethyl-1,3,2-dioxaborolan-2-yl)-1H-indole in Step A of the previous example and following the same protocols, the TFA salt of the titled compound was obtained. LC/MS [M+H]$^+$: 580.66.

EXAMPLE 232

3-(2-aminobenzo[d]thiazol-4-yl)-6-(phenylsulfonyl)-2-(1H-tetrazol-5-yl)benzenesulfonamide

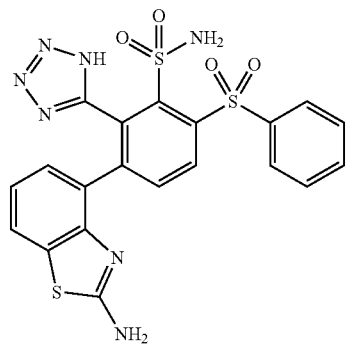

Step A: 3-iodo-N,N-bis(4-methoxybenzyl)-2-(1-(4-methoxybenzyl)-1H-tetrazol-5-yl)-6-(phenylthio)benzenesulfonamide and 3-iodo-N,N-bis(4-methoxybenzyl)-2-(2-(4-methoxybenzyl)-2H-tetrazol-5-yl)-6-(phenylthio)benzenesulfonamide Sodium hydride (0.056 g of a 60% dispersion in mineral oil, 1.27 mmol) was added, in one portion, to a stirred solution of thiophenol (0.139 g, 1.27 mmol) in anhydrous DMF (5 ml) at room temperature under an atmosphere of nitrogen. After stirring for 20 minutes, the aryl bromide (0.500 g, 0.63 mmol) was added and stirring was maintained for 4 hours. The reaction was quenched by the addition of sat. aq. ammonium chloride and the organics extracted into EtOAc. The organic phase was separated, washed with water (3×), dried (MgSO$_4$) and the volatiles removed under reduced pressure. The residue was purified by silica gel column chromatography using a 40 g column and a gradient of EtOAc in hexanes as eluent. LC/MS [M+H]$^+$: 820.40.

Step B: 3-iodo-N,N-bis(4-methoxybenzyl)-2-(1-(4-methoxybenzyl)-1H-tetrazol-5-yl)-6-(phenylsulfonyl)benzenesulfonamide and 3-iodo-N,N-bis(4-methoxybenzyl)-2-(2-(4-methoxybenzyl)-2H-tetrazol-5-yl)-6-(phenylsulfonyl)benzenesulfonamide MCPBA (0.353 g of 77% pure material, 1.57 mmol) was added, in one portion, to a stirred solution of the sulfides from the previous step (0.43 g, 0.52 mmol) in DCM (10 mL) and the resulting reaction mixture was stirred at room temperature overnight. The reaction mixture was partitioned between EtOAc and 10% aq. sodium thiosulfate. The organic phase was separated, washed with sat. aq. sodium bicarbonate, dried (MgSO$_4$) and the volatiles removed under reduced pressure. The residue was purified by silica gel column chromatography using a 40 g column and a gradient of EtOAc in hexanes as eluent, giving the desired sulfones. LC/MS [M+H]$^+$: 852.59

Step C: 3-(2-aminobenzo[d]thiazol-4-yl)-N,N-bis(4-methoxybenzyl)-2-(1-(4-methoxybenzyl)-1H-tetrazol-5-yl)-6-(phenylsulfonyl)benzenesulfonamide and 3-(2-aminobenzo[d]thiazol-4-yl)-N,N-bis(4-methoxybenzyl)-2-(2-(4-methoxybenzyl)-2H-tetrazol-5-yl)-6-(phenylsulfonyl)benzenesulfonamide A stream of nitrogen was bubbled through a mixture of the sulfones from the previous step (0.050 g, 0.06 mmol), (2-aminobenzo[d]thiazol-4-yl)boronic acid (0.017 g, 0.09 mmol) and sodium carbonate (0.019 g, 0.18 mmol) in dioxane (1 mL) and water (0.30 mL) for 15 minutes. The catalyst [PdCl$_2$(dppf)] (0.0064 g) was added and the resulting reaction mixture was heated to 90° C. (oil bath temperature) overnight. After cooling, the mixture was filtered through a pad of CELITE and the solid was washed thoroughly with methanol. The filtrate was concentrated under reduced pressure and the residue partitioned between EtOAc and water. The organic phase was separated, dried (MgSO$_4$) and the volatiles removed under reduced pressure. The crude reaction product was purified by silica gel column chromatography using a 12 g column and a gradient of EtOAc in hexanes as eluent to give the title compounds. LC/MS [M+H]$^+$: 874.88.

Step D: 3-(2-aminobenzo[d]thiazol-4-yl)-6-(phenylsulfonyl)-2-(1H-tetrazol-5-yl)benzenesulfonamide TFA was added to a mixture of the benzthiazoles from the previous step and the mixture was heated to 80° C. (oil bath temperature) for 2 hours. After cooling, the volatiles were removed under reduced pressure and the residue purified by reverse phase HPLC using a gradient of acetonitrile (containing 0.1% TFA) in water (containing 0.1% TFA) as eluent to give the desired product. LC/MS [M+H]$^+$: 514.46.

EXAMPLE 233

3-(2-aminobenzo[d]thiazol-4-yl)-6-(pyridin-2-ylsulfonyl)-2-(1H-tetrazol-5-yl)benzenesulfonamide

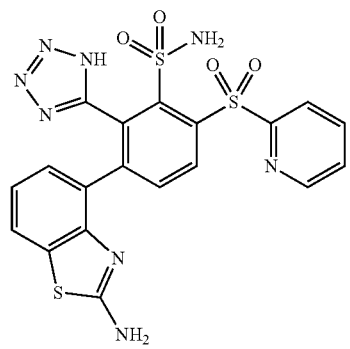 [SMILES: Nc1nc2c(-c3ccc(S(=O)(=O)c4ccccn4)c(S(N)(=O)=O)c3-c3nnn[nH]3)cccc2s1]

Step A: 3-iodo-N,N-bis(4-methoxybenzyl)-2-(1-(4-methoxybenzyl)-1H-tetrazol-5-yl)-6-(phenylthio)benzenesulfonamide and 3-iodo-N,N-bis(4-methoxybenzyl)-2-(2-(4-methoxybenzyl)-2H-tetrazol-5-yl)-6-(pyridin-2-ylthio)benzenesulfonamide Using 2-mercaptopyridine instead of thiophenol in Step A of the synthesis of 3-(2-aminobenzo[d]thiazol-4-yl)-6-(phenylsulfonyl)-2-(1H-tetrazol-5-yl)benzenesulfonamide (EXAMPLE 397), the title compounds were obtained. LC/MS [M+H]$^+$: 821.36.

Step B: 3-iodo-N,N-bis(4-methoxybenzyl)-2-(1-(4-methoxybenzyl)-1H-tetrazol-5-yl)-6-(pyridin-2-yl sulfonyl)benzenesulfonamide and 3-iodo-N,N-bis(4-methoxybenzyl)-2-(2-(4-methoxybenzyl)-2H-tetrazol-5-yl)-6-(pyridin-2-ylsulfonyl)benzenesulfonamide Sodium periodate (0.328 g, 1.54 mmol) in water (2 mL) was added to a solution of the sulfides from the previous step (0.210 g, 0.26 mmol) in DCM (2 mL) and the resulting reaction mixture was stirred at room temperature overnight. Ether was added and stirring continued for a further 0.5 hour. The organic phase was separated, dried (MgSO$_4$) and the volatiles removed under reduced pressure. The crude reaction product was purified by silica gel column chromatography using a 12 g column and a gradient of EtOAc in hexanes as eluent to give the desired sulfones. LC/MS [M+H]$^+$: 853.46

Step C: 3-(2-aminobenzo[d]thiazol-4-yl)-N,N-bis(4-(4-methoxybenzyl)-1H-tetrazol-5-yl)-6-(pyridin-2-ylsulfonyl)benzenesulfonamide and 3-(2-aminobenzo[d]thiazol-4-yl)-N,N-bis(4-methoxybenzyl)-2-(2-(4-methoxybenzyl)-2H-tetrazol-5-yl)-6-(pyridin-2-ylsulfonyl)benzenesulfonamide The title compounds were prepared from 3-iodo-N,N-bis(4-methoxybenzyl)-2-(1-(4-methoxybenzyl)-1H-tetrazol-5-yl)-6-(pyridin-2-ylsulfonyl)benzenesulfonamide and 3-iodo-N,N-bis(4-methoxybenzyl)-2-(2-(4-methoxybenzyl)-2H-tetrazol-5-yl)-6-(pyridin-2-ylsulfonyl)benzenesulfonamide according to the procedure used in EXAMPLE 232, Step C. LC/MS [M+H]$^+$: 875.51

Step D: 3-(2-aminobenzo[d]thiazol-4-yl)-6-(pyridin-2-ylsulfonyl)-2-(1H-tetrazol-5-yl)benzenesulfonamide The title compound was prepared from 3-(2-aminobenzo[d]thiazol-4-yl)-N,N-bis(4-methoxybenzyl)-2-(1-(4-methoxybenzyl)-1H-tetrazol-5-yl)-6-(pyridin-2-ylsulfonyl)benzenesulfonamide and 3-(2-aminobenzo[d]thiazol-4-yl)-N,N-bis(4-methoxybenzyl)-2-(2-(4-methoxybenzyl)-2H-tetrazol-5-yl)-6-(pyridin-2-ylsulfonyl)benzenesulfonamide using the same procedure as described for the synthesis of EXAMPLE 232, Step D. LC/MS [M+H]$^+$: 515.27

EXAMPLES 234, 235 and 236

4-(Methylthio)-4'-(piperidin-4-yl)-2-(1H-tetrazol-5-yl)-[1,1'-biphenyl]-3-sulfonamide and 4-(methylsulfinyl)-4'-(piperidin-4-yl)-2-(1H-tetrazol-5-yl)-[1,1'-biphenyl]-3-sulfonamide and 4-(methylsulfonyl)-4'-(piperidin-4-yl)-2-(1H-tetrazol-5-yl)-[1,1'-biphenyl]-3-sulfonamide

234

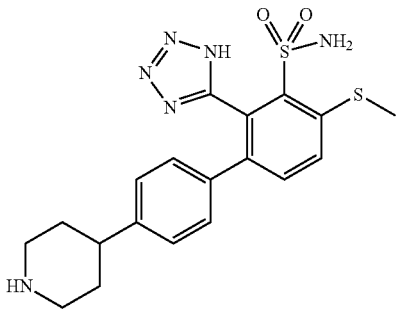

235

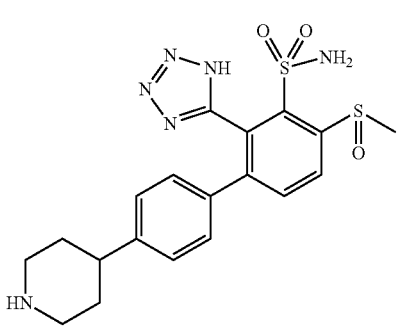

236

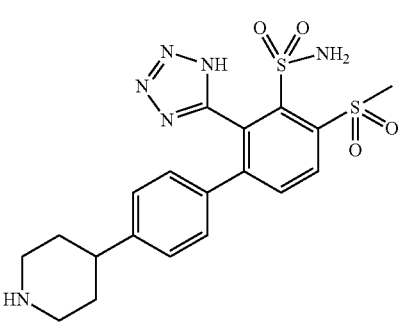

Step A: 3-Iodo-N,N-bis(4-methoxybenzyl)-2-(1-(4-methoxybenzyl)-1H-tetrazol-5-yl)-6-(methylthio) benzenesulfonamide and 3-iodo-N,N-bis(4-methoxybenzyl)-2-(2-(4-methoxybenzyl)-2H-tetrazol-5-yl)-6-(methylthio)benzenesulfonamide and N,N-bis(4-methoxybenzyl)-2-(1-(4-methoxybenzyl)-1H-tetrazol-5-yl)-3,6-bis(methylthio)benzenesulfonamide and N,N-bis(4-methoxybenzyl)-2-(2-(4-methoxybenzyl)-2H-tetrazol-5-yl)-3,6-bis(methylthio)benzenesulfonamide Sodium methanethiolate (0.400 g, 5.71 mmol) was added to a stirred solution of 6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl) benzenesulfonamide (2.10 g, 2.66 mmol) in anhydrous DMF (1 ml) under an atmosphere of nitrogen. The resulting reaction mixture was stirred at room temperature for 10 minutes, quenched with sat. aq. sodium bicarbonate and the organics extracted into EtOAc. The organic phase was separated, dried (MgSO$_4$) and the volatiles removed under reduced pressure. The residue was purified by silica gel column chromatography using a gradient of EtOAc in hexanes as eluent to give the monosulfides LC/MS [M+H]$^+$: 758.76 and 758.76, followed by the disulfides LC/MS [M+H]$^+$: 678.85

Step B: tert-Butyl 4-(3'-(N,N-bis(4-methoxybenzyl)sulfamoyl)-2'-(1-(4-methoxybenzyl)-1H-tetrazol-5-yl)-4'-(methylthio)-[1,1'-biphenyl]-4-yl)piperidine-1-carboxylate and tert-butyl 4-(3'-(N,N-bis(4-methoxybenzyl)sulfamoyl)-2'-(2-(4-methoxybenzyl)-2H-tetrazol-5-yl)-4'-(methylthio)-[1,1'-biphenyl]-4-yl)piperidine-1-carboxylate In a sealed tube, a mixture of tert-butyl 4-(4-(4,4,5,5-tetramethyl-1,3,2-dioxaborolan-2-yl)phenyl)piperidine-1-carboxylate (0.276 g, 0.71 mmol), the aryl iodides (0.360 g, 0.48 mmol) and sodium carbonate (0.151 g, 1.43 mmol) in 1,4-dioxane (4 mL) and water (1 mL) was degassed by bubbling a stream of nitrogen through for 10 minutes. Palladium tetrakis(triphenylphosphine) (0.028 g, 0.02 mmol) was added and bubbling was continued for a further 5 minutes. The tube was sealed and the resulting reaction mixture was heated to 85° C. (oil bath temperature) overnight. After cooling, the reaction mixture was partitioned between EtOAc and water. The organic phase was separated, dried (MgSO$_4$) and the volatiles removed under reduced pressure. The residue was purified by silica gel column chromatography using a 40 g column and a gradient of EtOAc in hexanes as eluent to give the desired products. LC/MS [M+H]$^+$: 892.27 and 892.25

Step C: 4-(Methylthio)-4'-(piperidin-4-yl)-2-(2H-tetrazol-5-yl)-[1,1'-biphenyl]-3-sulfonamide TFA (2 ml) was added to a mixture of the protected tetrazoles (0.076 g, 0.09 mmol) and anisole (a few drops from a pipette) in DCM (4 ml) and the mixture was stirred at room temperature for 1 hour. The volatiles were removed under reduced pressure and additional TFA (2 ml) was added to the residue. The mixture was heated to 80° C. for 4 hours. After cooling, the volatiles were removed under reduced pressure and the crude product was purified by reverse phase HPLC using a gradient of acetonitrile (containing 0.1% TFA) in water (containing 0.1% TFA) to give the trifluoroacetate salt of the desired product. LC/MS [M+H]$^+$: 431.55.

Step D: tert-Butyl 4-(3'-(N,N-bis(4-methoxybenzyl)sulfamoyl)-2'-(1-(4-methoxybenzyl)-1H-tetrazol-5-yl)-4'-(methylsulfonyl)-[1,1'-biphenyl]-4-yl)piperidine-1-carboxylate and tert-butyl 4-(3'-(N,N-bis(4-methoxybenzyl)sulfamoyl)-2'-(2-(4-methoxybenzyl)-2H-tetrazol-5-yl)-4'-(methylsulfonyl)-[1,1'-biphenyl]-4-yl)piperidine-1-carboxylate and tert-butyl 4-(3'-(N,N-bis(4-methoxybenzyl)sulfamoyl)-2'-(1-(4-methoxybenzyl)-1H-tetrazol-5-yl)-4'-(methylsulfinyl)-[1,1'-biphenyl]-4-yl)piperidine-1-carboxylate and tert-butyl 4-(3'-(N,N-bis(4-methoxybenzyl)sulfamoyl)-2'-(1-(4-methoxybenzyl)-1H-tetrazol-5-yl)-4'-(methylsulfinyl)-[1,1'-biphenyl]-4-yl)piperidine-1-carboxylate compound with tert-butyl 4-(3'-(N,N-bis(4-methoxybenzyl)sulfamoyl)-2'-(2-(4-methoxybenzyl)-2H-tetrazol-5-yl)-4'-(methylsulfinyl)-[1,1'-biphenyl]-4-yl)piperidine-1-carboxylate (1:1)

MCPBA (1.41 g of 77% pure material, 6.3 mmol) was added to a stirred solution of the sulfides (1.36 g, 1.80 mmol) in DCM (10 mL) and the resulting reaction mixture was stirred at room temperature for 3 hours. The reaction was partitioned between EtOAc and 10% aq. sodium thiosulfate. The organic phase was separated, washed with sat. aq. sodium bicarbonate, dried (MgSO$_4$) and the volatiles removed under reduced pressure. The residue was purified by silica gel column chromatography using a 40 g column and a gradient of EtOAc in hexanes as eluent to give the sulfone LC/MS [M+H]$^+$: 924.22 and 924.22 followed by the sulfoxides. LC/MS [M+H]$^+$: 908.22.

Step E: 4-(Methylsulfinyl)-4'-(piperidin-4-yl)-2-(2H-tetrazol-5-yl)-[1,1'-biphenyl]-3-sulfonamide Using the transformation described in Step C above, the sulfoxides obtained in step D were converted to the trifluoroacetate of the titled amine. LC/MS [M+H]$^+$: 447.49

Step F: 4-(Methylsulfonyl)-4'-(piperidin-4-yl)-2-(2H-tetrazol-5-yl)-[1,1'-biphenyl]-3-sulfonamide Using the transformation described in Step C above, the sulfones obtained in step D were converted to the trifluoroacetate of the titled amine. LC/MS [M+H]$^+$: 463.57

EXAMPLE 237

3-(6-Aminopyridin-3-yl)-6-(methylsulfonyl)-2-(2H-tetrazol-5-yl)benzenesulfonamide

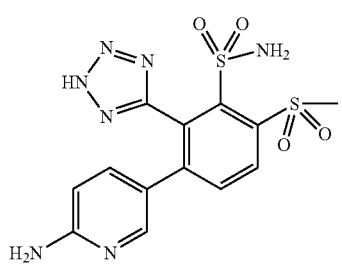 [SMILES: CS(=O)(=O)c1ccc(-c2ccc(N)nc2)c(-c2nn[nH]n2)c1S(N)(=O)=O]

Step A: 3-Iodo-N,N-bis(4-methoxybenzyl)-2-(1-(4-methoxybenzyl)-1H-tetrazol-5-yl)-6-(methylsulfonyl)benzenesulfonamide and 3-iodo-N,N-bis(4-methoxybenzyl)-2-(2-(4-methoxybenzyl)-2H-tetrazol-5-yl)-6-(methylsulfonyl)benzenesulfonamide MCPBA (1.41 g of 77% pure material, 6.28 mmol) was added, in one portion, to a stirred solution of the sulfides (1.36 g, 1.80 mmol) in DCM (10 mL) and the resulting reaction mixture was stirred at room temperature for 3 hours, then partitioned between EtOAc and 10% aq. sodium thiosulfate. The organic phase was separated, washed with sat. aq. sodium bicarbonate, dried (MgSO$_4$) and the volatiles removed under reduced pressure. The residue was purified by silica gel column chromatography using a 40 g column and a gradient of EtOAc in hexanes as eluent to give the desired sulfones. LC/MS [M+H]$^+$: 790.81 and 790.82.

Step B: 3-(6-Aminopyridin-3-yl)-N,N-bis(4-methoxybenzyl)-2-(1-(4-methoxybenzyl)-1H-tetrazol-5-yl)-6-(methylsulfonyl)benzenesulfonamide and 3-(6-aminopyridin-3-yl)-N,N-bis(4-methoxybenzyl)-2-(2-(4-methoxybenzyl)-2H-tetrazol-5-yl)-6-(methyl sulfonyl)benzenesulfonamide A mixture of (6-aminopyridin-3-yl)boronic acid hydrochloride (0.0497 g, 0.29 mmol), the sulfones (0.150 g, 0.19 mmol) and sodium carbonate (0.060 g, 0.57 mmol) in dioxane (4 ml) and water (1 ml) in a sealed tube was deoxygenated by bubbling a stream of nitrogen through for 10 minutes. Then [1,1'-Bis(diphenylphosphino)ferrocene]dichloropalladium(II) complex with DCM (0.016 g, 0.02 mmol) was added and bubbling was continued for a further 5 min. The tube was sealed and the reaction mixture was heated to 80° C. overnight. After cooling, the mixture was partitioned between EtOAc and water. The organic phase was separated, dried (MgSO$_4$) and the volatiles removed under reduced pressure. The crude product was purified by silica gel column chromatography to give the amino-pyridine. LC/MS [M+H]$^+$: 756.89

Step C: 3-(6-Aminopyridin-3-yl)-6-(methylsulfonyl)-2-(1H-tetrazol-5-yl)benzenesulfonamide TFA (2 mL) was added to a mixture of the protected tetrazoles (0.074 g, 0.1 mmol) and the resulting solution was heated to 80° C. for 1.5 hours. After cooling, the volatiles were removed under reduced pressure and the residue purified by reverse phase HPLC using a gradient of acetonitrile (containing 0.1% TFA) in water (containing 0.1% TFA) as eluent to give the trifluoroacetate salt of the desired aminopyridine. LC/MS [M+H]$^+$: 756.89

EXAMPLES 238-241 were prepared according to the general procedure described above for EXAMPLE 237 using boronic acids or boronic esters that are commercially available, known, or prepared as described herein and 3-iodo-N,N-bis(4-methoxybenzyl)-2-(1-(4-methoxybenzyl)-1H-tetrazol-5-yl)-6-(methylsulfonyl)benzenesulfonamide and 3-iodo-N,N-bis(4-methoxybenzyl)-2-(2-(4-methoxybenzyl)-2H-tetrazol-5-yl)-6-(methylsulfonyl)benzenesulfonamide.

| Ex. No. | Structure | Name | Calc'd Mass [M + H]+ | LC/MS m/e [M + H]+ |
|---|---|---|---|---|
| 238 | 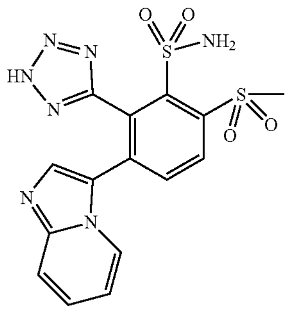 [SMILES: CS(=O)(=O)c1ccc(-c2cnc3ccccn23)c(-c2nn[nH]n2)c1S(N)(=O)=O] | 3-(Imidazo[1,2-a]pyridin-3-yl)-6-(methylsulfonyl)-2-(2H-tetrazol-5-yl)benzenesulfonamide | 420.05 | 420.48 |
| 239 | 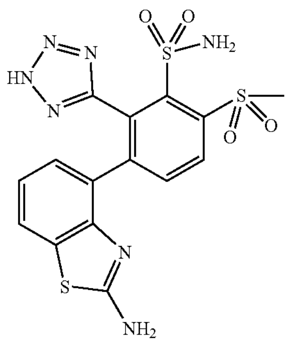 [SMILES: CS(=O)(=O)c1ccc(-c2cccc3sc(N)nc23)c(-c2nn[nH]n2)c1S(N)(=O)=O] | 3-(2-aminobenzo[d]thiazol-4-yl)-6-(methylsulfonyl)-2-(2H-tetrazol-5-yl)benzenesulfonamide | 452.02 | 452.32 |
| 240 | 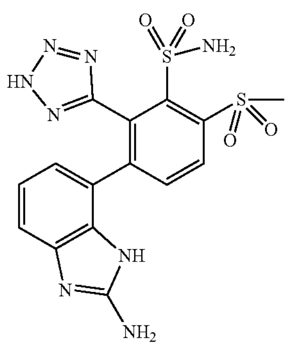 [SMILES: CS(=O)(=O)c1ccc(-c2cccc3nc(N)[nH]c23)c(-c2nn[nH]n2)c1S(N)(=O)=O] | 3-(2-Amino-1H-benzo[d]imidazol-7-yl)-6-(methylsulfonyl)-2-(2H-tetrazol-5-yl)benzenesulfonamide | 435.06 | 435.34 |
| 241 | 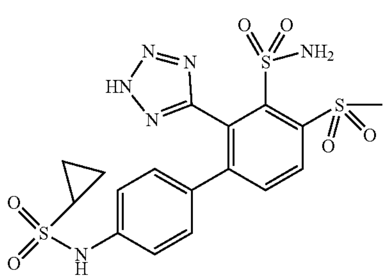 [SMILES: CS(=O)(=O)c1ccc(-c2ccc(NS(=O)(=O)C3CC3)cc2)c(-c2nn[nH]n2)c1S(N)(=O)=O] | 4'-(Cyclopropanesulfonamido)-4-(methylsulfonyl)-2-(2H-tetrazol-5-yl)-[1,1'-biphenyl]-3-sulfonamide | 499.04 | 499.39 |

EXAMPLE 242

4'-(Piperidin-4-yl)-4-(pyridin-4-ylthio)-2-(2H-tetrazol-5-yl)-[1,1'-biphenyl]-3-sulfonamide

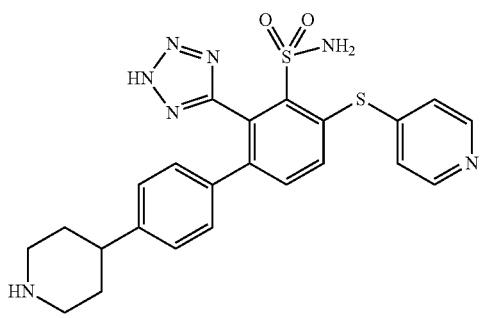 [SMILES: NS(=O)(=O)c1c(Sc2ccncc2)ccc(-c2ccc(C3CCNCC3)cc2)c1-c1nn[nH]n1]

The title compound was prepared according to the general procedure described above for EXAMPLE 234 (Steps A-C) utilizing 4-mercaptopyridine instead of methane thiolate. The trifluoroacetate salt of the desired amine was obtained following reverse phase HPLC, LC/MS [M+H]$^+$: 494.42

EXAMPLE 243

4-(Azetidin-3-ylthio)-4'-(cyclopropanesulfonamido)-2-(2H-tetrazol-5-yl)-[1,1'-biphenyl]-3-sulfonamide

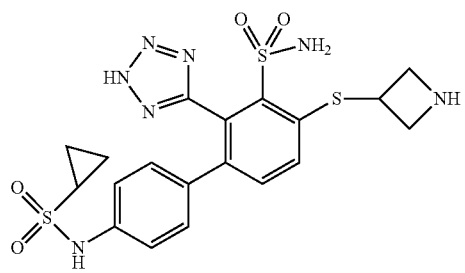 [SMILES: NS(=O)(=O)c1c(SC2CNC2)ccc(-c2ccc(NS(=O)(=O)C3CC3)cc2)c1-c1nn[nH]n1]

Step A: 4-Bromo-4'-(cyclopropanesulfonamido)-N,N-bis(4-methoxybenzyl)-2-(1-(4-methoxybenzyl)-1H-tetrazol-5-yl)-[1,1'-biphenyl]-3-sulfonamide and 4-bromo-4'-(cyclopropanesulfonamido)-N,N-bis(4-methoxybenzyl)-2-(2-(4-methoxybenzyl)-2H-tetrazol-5-yl)-[1,1'-biphenyl]-3-sulfonamide In a sealed tube, a mixture of (4-(cyclopropanesulfonamido)phenyl)boronic acid (0.457 g, 1.90 mmol) a mixture of 6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide (1.00 g, 1.27 mmol) and sodium carbonate (0.402 g, 3.80 mmol) in dioxane (4 mL) and water (1 mL) was deoxygenated by bubbling a stream of nitrogen through for 10 minutes. Palladium tetrakis(triphenylphosphine) was added and bubbling was continued for a further 5 minutes. The tube was sealed and the reaction mixture heated to 80° C. overnight. After cooling, the mixture was partitioned between EtOAc and water. The organic phase was separated, dried (MgSO$_4$) and the volatiles removed under reduced pressure. The residue was purified by silica gel column chromatography using a 40 g column and a gradient of EtOAc in hexanes as eluent to give the desired sulfonamides. LC/MS [M+H]$^+$: 861.73 and 861.74.

Step B: tert-Butyl 3-((3-(N,N-bis(4-methoxybenzyl)sulfamoyl)-4'-(cyclopropanesulfonamido)-2-(1-(4-methoxybenzyl)-1H-tetrazol-5-yl)-[1,1'-biphenyl]-4-yl)thio)azetidine-1-carboxylate and tert-butyl 3-((3-(N,N-bis(4-methoxybenzyl)sulfamoyl)-4'-(cyclopropanesulfonamido)-2-(2-(4-methoxybenzyl)-2H-tetrazol-5-yl)-[1,1'-biphenyl]-4-yl)thio)azetidine-1-carboxylate Sodium hydride (0.033 g of a 60% dispersion in mineral oil, 0.84 mmol) was added to tert-butyl 3-mercaptoazetidine-1-carboxylate (0.145 g, 0.77 mmol) in anhydrous DMF (3 ml) and the mixture stirred at room temperature under an atmosphere of nitrogen for 10 minutes, then the aryl bromides (0.30 g, 0.35 mmol) in anhydrous DMF (3 mL) were added. The resulting reaction mixture was stirred at room temperature for 2 hours, then at 50° C. for 10 minutes. After cooling, the reaction was quenched by the addition of sat. aq. ammonium chloride and the organics extracted into EtOAc. The organic phase was separated, washed with sat. aq. sodium bicarbonate, dried (MgSO$_4$) and the volatiles removed under reduced pressure. The residue was purified by silica gel column chromatography using a 40 g column and a gradient of EtOAc in hexanes as eluent. LC/MS [M+H]$^+$: 969.23.

Step C: 4-(Azetidin-3-ylthio)-4'-(cyclopropanesulfonamido)-2-(2H-tetrazol-5-yl)-[1,1'-biphenyl]-3-sulfonamide TFA (2 mL) was added to a mixture of tert-Butyl 3-((3-(N,N-bis(4-methoxybenzyl)sulfamoyl)-4'-(cyclopropanesulfonamido)-2-(1-(4-methoxybenzyl)-1H-tetrazol-5-yl)-[1,1'-biphenyl]-4-yl)thio)azetidine-1-carboxylate and tert-butyl 3-((3-(N,N-bis(4-methoxybenzyl)sulfamoyl)-4'-(cyclopropanesulfonamido)-2-(2-(4-methoxybenzyl)-2H-tetrazol-5-yl)-[1,1'-biphenyl]-4-yl)thio)azetidine-1-carboxylate (0.120 g, 0.124 mmol) and anisole (a few drops from a pipette) and the resulting reaction mixture was heated to 80° C. for 1.5 hours. After cooling, the volatiles were removed under reduced pressure and the residue purified by reverse phase HPLC using a gradient of acetonitrile (containing 0.1% TFA) in water (containing 0.1% TFA) as eluent, giving the trifluoroacetate salt of the desired amine. LC/MS [M+H]$^+$: 508.45.

EXAMPLE 244

4-(Azetidin-3-ylsulfonyl)-4'-(cyclopropanesulfonamido)-2-(2H-tetrazol-5-yl)-[1,1'-biphenyl]-3-sulfonamide

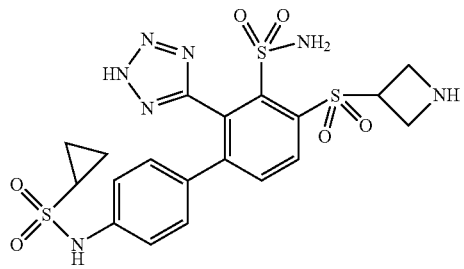 [SMILES: NS(=O)(=O)c1c(S(=O)(=O)C2CNC2)ccc(-c2ccc(NS(=O)(=O)C3CC3)cc2)c1-c1nn[nH]n1]

Using the processes described in Steps D and E of EXAMPLE 236, the title compound was prepared from tert-Butyl 3-((3-(N,N-bis(4-methoxybenzyl)sulfamoyl)-4'-(cyclopropanesulfonamido)-2-(1-(4-methoxybenzyl)-1H-tetrazol-5-yl)-[1,1'-biphenyl]-4-yl)thio)azetidine-1-carboxylate and tert-butyl 3-((3-(N,N-bis(4-methoxybenzyl)sulfamoyl)-4'-(cyclopropanesulfonamido)-2-(2-(4-methoxybenzyl)-2H-tetrazol-5-yl)-[1,1'-biphenyl]-4-yl)thio)azetidine-1-carboxylate (Step B in EXAMPLE 243). LC/MS [M+H]+: 540.46

EXAMPLES 245 and 246

3-((4'-(Cyclopropanesulfonamido)-3-sulfamoyl-2-(2H-tetrazol-5-yl)-[1,1'-biphenyl]-4-yl)sulfonyl)-N-cyclopropylazetidine-1-carboxamide and 3-((4'-(cyclopropanesulfonamido)-3-sulfamoyl-2-(2H-tetrazol-5-yl)-[1,1'-biphenyl]-4-yl)sulfonyl)azetidine-1-carboxamide

245

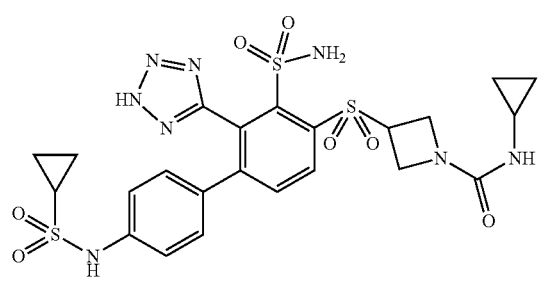

246

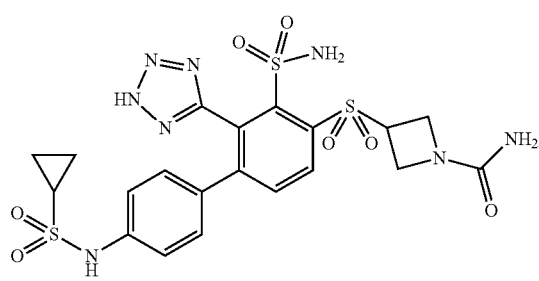

Triethylamine (0.031 mL, 0.023 g, 0.22 mmol) followed by cyclopropylisocyanate (0.011 g, 0.14 mmol) were added to the trifluoroacetate salt of 4-(azetidin-3-ylsulfonyl)-4'-(cyclopropanesulfonamido)-2-(2H-tetrazol-5-yl)-[1,1'-biphenyl]-3-sulfonamide (EXAMPLE 244; 0.070 g, 0.09 mmol) in anhydrous DCM (1 mL). The resulting reaction mixture was stirred at room temperature for 0.5 hour, followed by heating to 50° C. for 10 minutes. After cooling, the reaction mixture was filtered and the filtrate concentrated under reduced pressure. The resulting residue was dissolved in TFA (1 ml) and the solution was heated to 80° C. for 1 hour. After cooling, the volatiles were removed under reduced pressure and the crude reaction product was purified by reverse phase HPLC using a gradient of acetonitrile (containing 0.1% TFA) in water (containing 0.1% TFA) to obtain the desired cyclopropyl analogue. LC/MS [M+H]+: 623.54 and the unsubstituted derivative LC/MS [M+H]+: 583.51

EXAMPLE 247

4-(Azetidin-3-ylsulfonyl)-2-(2H-tetrazol-5-yl)-[1,1'-biphenyl]-3,3'-disulfonamide

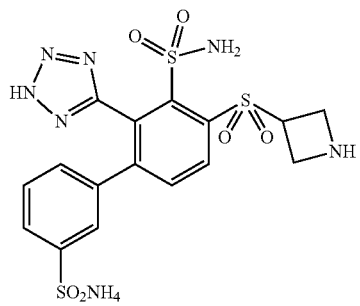

Step A: tert-butyl 3-((3-(N,N-bis(4-methoxybenzyl)sulfamoyl)-2-(1-(4-methoxybenzyl)-1H-tetrazol-5-yl)-3'-sulfamoyl-[1,1'-biphenyl]-4-yl)sulfonyl)azetidine-1-carboxylate and tert-butyl 3-((3-(N,N-bis(4-methoxybenzyl)sulfamoyl)-2-(2-(4-methoxybenzyl)-2H-tetrazol-5-yl)-3'-sulfamoyl-[1,1'-biphenyl]-4-yl)sulfonyl)azetidine-1-carboxylate A mixture of 3-(4,4,5,5-tetramethyl-1,3,2-dioxaborolan-2-yl)benzenesulfonamide (23 mg, 0.081 mmol), tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate (50 mg, 0.054 mmol) and sodium carbonate (17.1 mg, 0.161 mmol) in aqueous dioxane (4 mL) in a sealed tube was deoxygenated by bubbling a stream of nitrogen through it for 10 minutes, then [1,1'-Bis(diphenylphosphino)ferrocene]dichloropalladium(II), complex with DCM (4.4 mg, 0.0054 mmol) was added and bubbling was continued for a further 5 minutes. The tube was sealed and heated to 80° C. (oil bath temp, overnight). After cooling, the reaction was partitioned between EtOAc and water. The organic phase was separated, dried (MgSO4) and the volatiles removed under reduced pressure. The residue was used directly in the next step. LC/MS [M+H]+: 961.18

Step B: 4-(Azetidin-3-ylsulfonyl)-2-(2H-tetrazol-5-yl)-[1,1'-biphenyl]-3,3'-disulfonamide TFA (1 mL) was added to a mixture of the carbamates (0.050 g, 0.05 mmol) in DCM (2 mL) and anisole (5 drops from a pipette) while cooled in an ice bath while a stream of nitrogen was bubbling through the solution. When the addition was complete, the mixture was stirred for 1 hour. The volatiles were removed under reduced pressure and TFA (1 mL) was added to the residue and the mixture heated to 80° C. for 1.5 hours. After cooling the volatiles were removed under reduced pressure and the crude reaction product purified by reverse phase HPLC using a gradient of acetonitrile (containing 0.1% TFA) in water (containing 0.1% TFA) to give the trifluoroacetate salt of the desired product. LC/MS [M+H]+: 500.53.

EXAMPLE 248 was prepared according to the general procedure described for EXAMPLE 247, using 5-(4,4,5,5-Tetramethyl-1,3,2-dioxaborolan-2-yl)-1,7-naphthyridin-8-amine, prepared as described herein.

| Ex. No. | Structure | Name | Calc'd Mass [M + H]+ | LC/MS m/e [M + H]+ |
|---|---|---|---|---|
| 248 | 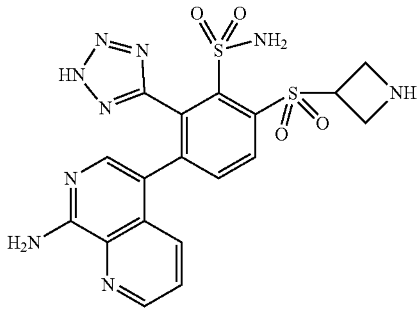 [SMILES: Nc1ncc(-c2ccc(S(=O)(=O)C3CNC3)c(S(N)(=O)=O)c2-c2nn[nH]n2)c2cccnc12] | 3-(8-Amino-1,7-naphthyridin-5-yl)-6-(azetidin-3-ylsulfonyl)-2-(2H-tetrazol-5-yl)benzenesulfonamide | 488.08 | 488.40 |

EXAMPLE 249

6-(Azetidin-3-ylsulfonyl)-3-(1,1-dioxido-3-oxo-2,3-dihydrobenzo[d]isothiazol-4-yl)-2-(2H-tetrazol-5-yl)benzenesulfonamide

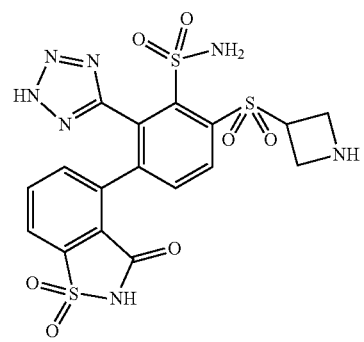 [SMILES: NS(=O)(=O)c1c(S(=O)(=O)C2CNC2)ccc(-c2cccc3c2C(=O)NS3(=O)=O)c1-c1nn[nH]n1]

A mixture of [1,1'-Bis(diphenylphosphino)ferrocene]dichloropalladium(II) complex with DCM (0.006 g), 4-bromobenzo[d]isothiazole-3(2H)-one 1,1-dioxide (0.028 g, 0.16 mmol) and sodium carbonate (0.022 g, 0.21 mmol) in dioxane (2 mL) and water (0.5 mL) was deoxygenated by bubbling through a stream of nitrogen for 10 minutes. The reaction mixture was heated to 85° C. overnight. After cooling, the reaction mixture was filtered through a pad of CELITE and the filtrate partitioned between EtOAc and water. The organic phase was separated, washed with sat. aq. sodium bicarbonate, dried (MgSO$_4$) and the volatiles removed under reduced pressure.

The crude reaction product was dissolved in DCM (1 mL) and anisole (5 drops) was added. After cooling in an ice bath, a stream of nitrogen was bubbled through the mixture. TFA (1 mL) was added and stirring continued for a further 1 hour. The volatiles were removed under reduced pressure and additional TFA (1 mL) was added before heating to 80° C. for 1 hour. After cooling, the mixture was concentrated under reduced pressure and the crude reaction product purified by reverse HPLC using a gradient of acetonitrile (containing 0.1% TFA) in water (containing 0.1% TFA), giving the trifluoroacetate salt of the desired amine. LC/MS [M+H]+: 526.99.

EXAMPLE 250

3-(2-Aminobenzo[d]thiazol-4-yl)-2-(2H-tetrazol-5-yl)-6-((3-(trifluoromethyl)phenyl)sulfonyl)benzenesulfonamide

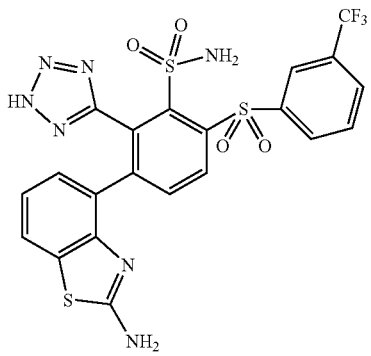 [SMILES: Nc1nc2c(-c3ccc(S(=O)(=O)c4cccc(C(F)(F)F)c4)c(S(N)(=O)=O)c3-c3nn[nH]n3)cccc2s1]

Step A: 3-Iodo-N,N-bis(4-methoxybenzyl)-2-(1-(4-methoxybenzyl)-1H-tetrazol-5-yl)-6-((3-(trifluoromethyl)phenyl)sulfonyl)benzenesulfonamide and 3-iodo-N,N-bis(4-methoxybenzyl)-2-(2-(4-methoxybenzyl)-2H-tetrazol-5-yl)-6-((3-(trifluoromethyl)phenyl)sulfonyl)benzenesulfonamide Using sodium 3-(trifluoromethyl)benzenethiolate instead of sodium methanethiolate in Step A of the preparation of EXAMPLE 234 and subsequent oxidation of the resulting sulfides as described in Step A of the synthesis of EXAMPLE 237, gave the desired sulfones. LC/MS [M+H]+: 920.51.

Step B: 3-(2-Aminobenzo[d]thiazol-4-yl)-N,N-bis
(4-methoxybenzyl)-2-(1-(4-methoxybenzyl)-1H-
tetrazol-5-yl)-6-((3-(trifluoromethyl)phenyl)sulfo-
nyl)benzenesulfonamide and 3-(2-aminobenzo[d]
thiazol-4-yl)-N,N-bis(4-methoxybenzyl)-2-(2-(4-
methoxybenzyl)-2H-tetrazol-5-yl)-6-((3-
(trifluoromethyl)phenyl)sulfonyl)
benzenesulfonamide Using (2-aminobenzo[d]thiazol-4-yl)boronic acid and the iodides in Step A (above) and the procedure set forth in Step B of EXAMPLE 237, the titled benzthiazoles were obtained. LC/MS [M+H]$^+$: 961.18

Step C: 3-(2-Aminobenzo[d]thiazol-4-yl)-2-(2H-
tetrazol-5-yl)-6-((3-(trifluoromethyl)phenyl)sulfo-
nyl)benzenesulfonamide The products obtained in Step B were treated with TFA at 80° C. and the crude reaction product purified by reverse phase HPLC using a gradient of acetonitrile (containing 0.1% TFA) in water (containing 0.1% TFA) to give the trifluoroacetate salt of the desired titled compound. LC/MS [M+H]$^+$: 582.32

EXAMPLE 251

3-(2-Amino-7-fluoro-1H-benzo[d]imidazol-4-yl)-6-
(azetidin-3-ylsulfonyl)-2-(2H-tetrazol-5-yl)benzene-
sulfonamide

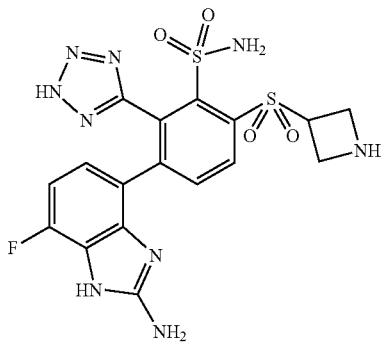 [SMILES: Nc1nc2c(-c3ccc(S(=O)(=O)C4CNC4)c(S(N)(=O)=O)c3-c3nn[nH]n3)ccc(F)c2[nH]1]

Step A: tert-Butyl 3-((2',3'-diamino-3-(N,N-bis(4-
methoxybenzyl)sulfamoyl)-4'-fluoro-2-(1-(4-
methoxybenzyl)-1H-tetrazol-5-yl)-[1,1'-biphenyl]-4-
yl)sulfonyl)azetidine-1-carboxylate and tert-butyl
3-((2',3'-diamino-3-(N,N-bis(4-methoxybenzyl)sul-
famoyl)-4'-fluoro-2-(2-(4-methoxybenzyl)-2H-tetra-
zol-5-yl)-[1,1'-biphenyl]-4-yl)sulfonyl)azetidine-1-
carboxylate To a 10 mL microwave vial was charged Na$_2$CO$_3$ (68.3 mg, 0.645 mmol), (2,3-diamino-4-fluorophenyl)boronic acid (60 mg, 0.353 mmol), (tert-butyl 3-((2-(N,N-bis(4-methoxybenzyl)sulfamoyl)-4-iodo-3-(1-(4-methoxyben-zyl)-1H-tetrazol-5-yl)phenyl)sulfonyl)azetidine-1-carboxy-late (200 mg, 0.215 mmol) and tetrakis(triphenylphosphine) palladium (25 mg, 0.021 mmol). The vial was sealed, degassed, and filled with dioxane and water (4:1). The resulting mixture was heated overnight at 80° C. The reaction mixture was filtered through CELITE. The filtrate was diluted with EtOAc and washed with water. The organic layer was dried over anhydrous MgSO$_4$, filtered, concentrated and purified by silica gel column chromatography (RediSep gold column, 24 g) using 0-100% EtOAc/Hexane as mobile phase to give desired product. LC/MS [M+H]$^+$: 929.70

Step B: tert-Butyl 3-((4-(2-amino-4-fluoro-1H-
benzo[d]imidazol-7-yl)-2-(N,N-bis(4-methoxyben-
zyl)sulfamoyl)-3-(1-(4-methoxybenzyl)-1H-tetrazol-
5-yl)phenyl)sulfonyl)azetidine-1-carboxylate and
tert-butyl 3-((4-(2-amino-4-fluoro-1H-benzo[d]imi-
dazol-7-yl)-2-(N,N-bis(4-methoxybenzyl)sulfa-
moyl)-3-(2-(4-methoxybenzyl)-2H-tetrazol-5-yl)
phenyl)sulfonyl)azetidine-1-carboxylate To tert-Butyl 3-((2',3'-diamino-3-(N,N-bis(4-methoxy-benzyl)sulfamoyl)-4'-fluoro-2-(1-(4-methoxybenzyl)-1H-tetrazol-5-yl)-[1,1'-biphenyl]-4-yl)sulfonyl)azetidine-1-car-boxylate and tert-butyl 3-((2',3'-diamino-3-(N,N-bis(4-methoxybenzyl)sulfamoyl)-4'-fluoro-2-(2-(4-methoxybenzyl)-2H-tetrazol-5-yl)-[1,1'-biphenyl]-4-yl) sulfonyl)azetidine-1-carboxylate (Step A; 0.05 g, 0.05 mmol) was added cyanogen bromide (0.007 g, 0.07 mmol) in a mixture of methanol (1 mL) and water (2 mL) and the reaction mixture was heated to 50° C. for 1 hour. After cooling, the volatiles were removed under reduced pressure to give the desired benzimidazoles. LC/MS [M+H]$^+$: 954.78 and 954.80.

Step C: 3-(2-Amino-7-fluoro-1H-benzo[d]imidazol-
4-yl)-6-(azetidin-3-ylsulfonyl)-2-(2H-tetrazol-5-yl)
benzenesulfonamide To the solution of crude tert-butyl 3-((4-(2-amino-4-fluoro-1H-benzo[d]imidazol-7-yl)-2-(N,N-bis(4-methoxy-benzyl)sulfamoyl)-3-(1-(4-methoxybenzyl)-1H-tetrazol-5-yl)phenyl)sulfonyl)azetidine-1-carboxylate and tert-butyl 3-((4-(2-amino-4-fluoro-1H-benzo[d]imidazol-7-yl)-2-(N,N-bis(4-methoxybenzyl)sulfamoyl)-3-(2-(4-methoxyben-zyl)-2H-tetrazol-5-yl)phenyl)sulfonyl)azetidine-1-carboxy-late (88 mg, 0.092 mmol) was added 1 mL DCM and 5 drops of anisole with N$_2$ bubbling in an ice bath. Then TFA (1 mL) was added and the mixture was stirred for 1 hour. The reaction mixture was concentrated and to the residue was added neat TFA. The resulting mixture was heated at 80° C. for 1.5 hours. After removing the volatiles the residue was purified by reverse phase HPLC using 3-50% 13 min ACN/H2O with 0.05% TFA. LC/MS [M+H]$^+$: 494.34.

EXAMPLE 252

Methyl 4-(4-(azetidin-3-yl sulfonyl)-3-sulfamoyl-2-(2H-tetrazol-5-yl)phenyl)-1H-benzo[d]imidazole-2-carboxylate

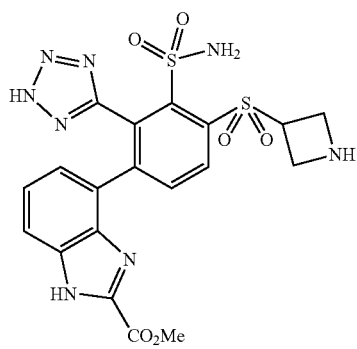 [SMILES: COC(=O)c1nc2c(-c3ccc(S(=O)(=O)C4CNC4)c(S(N)(=O)=O)c3-c3nn[nH]n3)cccc2[nH]1]

Step A: tert-butyl 3-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)azetidine-1-carboxylate and tert-butyl 3-((2'3'-diamino-3-(N,N-bis(4-methoxybenzyl)sulfamoyl)-2-(1-(4-methoxybenzyl)-1H-tetrazol-5-yl)-[1,1'-biphenyl]-4-yl)sulfonyl)azetidine-1-carboxylate Cesium carbonate (0.118 g, 1.13 mmol), 3-bromobenzene-1,2-diamine hydrochloride (0.076 g, 0.34 mmol), 2,2-dimethylpropane-1,3-diol (0.118 g, 1.131 mmol), (3-(N,N-bis(4-methoxybenzyl)-2H-tetrazol-5-yl)phenyl)boronic acid (0.100 g, 0.118 g) and $2^{nd}$ generation XPHOS precatalyst (0.0185 g, 0.024 mmol) in dioxane (2 ml) and water (0.5 ml) was deoxygenated in a sealed vial and heated to 85° C. overnight. After cooling, the reaction mixture was filtered through a pad of CELITE and the filtered partitioned between EtOAc and water. The organic phase was separated, dried (MgSO$_4$) and the volatiles removed under reduced pressure. The residue was purified by silica gel column chromatography (40 g column) using a gradient of EtOAc in hexanes as eluent to give the desired products. LC/MS [M+H]$^+$: 911.62 and 911.67.

Step B: tert-Butyl 3-((2-(N,N-bis(4-methoxybenzyl)sulfamoyl)-3-(2-(4-methoxybenzyl)-2H-tetrazol-5-yl)-4-(2-(trichloromethyl)-1H-benzo[d]imidazol-4-yl)phenyl)sulfonyl)azetidine-1-carboxylate and tert-butyl 3-((2-(N,N-bis(4-methoxybenzyl)sulfamoyl)-3-(1-(4-methoxybenzyl)-1H-tetrazol-5-yl)-4-(2-(trichloromethyl)-1H-benzo[d]imidazol-4-yl)phenyl)sulfonyl)azetidine-1-carboxylate Anisole (1 drop) was added to a mixture of the diamines (Step A; 0.020 g, 0.02 mmol) and benzyl 2,2,2-trichloroacetimidate (0.005 g, 0.02 mmol) followed by AcOH (1 ml). The resulting reaction mixture was stirred at RT for 3 hours, then the volatiles removed under reduced pressure to give the desired products. LC/MS [M+H]$^+$: 1039.48, 1041.43.

Step C: Methyl 4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)-1H-benzo[d]imidazole-2-carboxylate and methyl 4-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)-1H-benzo[d]imidazole-2-carboxylate A mixture of the trichloromethylbenzimidazoles (0.020 g, 0.02 mmol) and sodium carbonate (0.002 g, 0.02 mmol) in anhydrous MeOH (1 ml) was heated to 80° C. overnight. After cooling, the methanol was removed under reduced pressure and the residue partitioned between EtOAc and 10% aq. HCl. The organic phase was separated, dried (MgSO$_4$) and the volatiles removed under reduced pressure to give the desired methyl esters. LC/MS [M+H]$^+$: 979.69

Step D: Methyl 4-(4-(azetidin-3-ylsulfonyl)-3-sulfamoyl-2-(2H-tetrazol-5-yl)phenyl)-1H-benzo[d]imidazole-2-carboxylate To a solution of methyl 4-(3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)-1H-benzo[d]imidazole-2-carboxylate and methyl 4-(3-(N,N-bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)-1H-benzo[d]imidazole-2-carboxylate (20 mg, 0.020 mmol) was added 1 mL DCM and 5 drops of anisole with N$_2$ bubbling in ice bath. Then TFA 1 mL was added and the mixture was stirred for 1 hour. The mixture was concentrated and to the residue was added neat TFA. The mixture was then stirred at 80° C. for 1.5 hours. After removing the volatiles the residue was purified by reverse phase HPLC using 3-50% 13 min ACN/H$_2$O with 0.05% TFA. LC/MS [M+H]$^+$: 519.35.

EXAMPLE 253

4-(4-(Azetidin-3-ylsulfonyl)-3-sulfamoyl-2-(2H-tetrazol-5-yl)phenyl)-1H-benzo[d]imidazole-2-carboxylic Acid

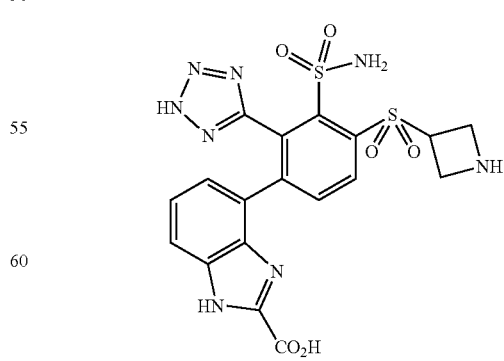

Trifluoroacetate salt: lithium hydroxide (0.011 g, 0.47 mmol) was added to methyl 4-(4-(azetidin-3-ylsulfonyl)-3- sulfamoyl-2-(2H-tetrazol-5-yl)phenyl)-1H-benzo[d]imidazole-2-carboxylate: TFA (0.005 g) in dioxane (2 mL) and water (0.25 mL) and the resulting reaction mixture was stirred at room temperature overnight. A few drops of aq. HCl were added and the volatiles were removed under reduced pressure. The residue was purified by reverse phase HPLC using a gradient of acetonitrile (containing 0.1% TFA) in water (containing 0.1% TFA) to give the desired trifluoroacetate salt of the titled compound. LC/MS [M+H]$^+$: 505.36.

Hydrochloride salt: Excess 1N aq. HCl was added to the trifluoroacetate salt (obtained above) and the resulting mixture concentrated under reduced pressure to give the desired hydrochloride salt of the titled compound. LC/MS [M+H]$^+$: 505.39.

EXAMPLE 254

4-(4-(Azetidin-3-ylsulfonyl)-3-sulfamoyl-2-(2H-tetrazol-5-yl)phenyl)-1H-benzo[d]imidazole-2-carboxamide

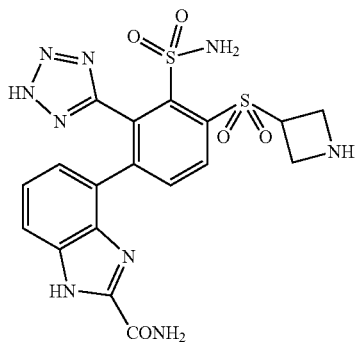 [SMILES: NC(=O)c1nc2c(-c3ccc(S(=O)(=O)C4CNC4)c(S(N)(=O)=O)c3-c3nn[nH]n3)cccc2[nH]1]

Step A: tert-Butyl 3-((2-(N,N-bis(4-methoxybenzyl)sulfamoyl)-4-(2-carbamoyl-1H-benzo[d]imidazol-4-yl)-3-(2-(4-methoxybenzyl)-2H-tetrazol-5-yl)phenyl)sulfonyl)azetidine-1-carboxylate and tert-butyl 3-((2-(N,N-bis(4-methoxybenzyl)sulfamoyl)-4-(2-carbamoyl-1H-benzo[d]imidazol-4-yl)-3-(1-(4-methoxybenzyl)-1H-tetrazol-5-yl)phenyl)sulfonyl)azetidine-1-carboxylate To tert-butyl 3-((2-(N,N-bis(4-methoxybenzyl)sulfamoyl)-3-(2-(4-methoxybenzyl)-2H-tetrazol-5-yl)-4-(2-(trichloromethyl)-1H-benzo[d]imidazol-4-yl)phenyl)sulfonyl)azetidine-1-carboxylate and tert-butyl 3-((2-(N,N-bis(4-methoxybenzyl)sulfamoyl)-3-(1-(4-methoxybenzyl)-1H-tetrazol-5-yl)-4-(2-(trichloromethyl)-1H-benzo[d]imidazol-4-yl)phenyl)sulfonyl)azetidine-1-carboxylate (0.025 g, 0.02 mmol) in acetonitrile (1 mL) and water (0.25 mL) was added 7 M ammonia in methanol (7 µl, 0.05 mmol) followed by potassium carbonate (0.010 g, 0.07 mmol). The resulting reaction mixture was stirred at room temperature overnight. The volatiles were removed under reduced pressure to give the desired carboxamides. LC/MS [M+H]$^+$: 964.69 and 964.54.

Step B: 4-(4-(Azetidin-3-ylsulfonyl)-3-sulfamoyl-2-(2H-tetrazol-5-yl)phenyl)-1H-benzo[d]imidazole-2-carboxamide Using the procedure and purification process outlined in Step D of Example 252, the carbamates obtained in Step A were transformed into the trifluoroacetate salts of the titled compound. LC/MS [M+H]$^+$: 504.37

By following the same general procedure as EXAMPLE 254, substituting the appropriate reactants and reagents, the following compounds were synthesized and characterized by LC/MS.

| Ex. No. | Structure | Name | LC/MS m/e [M + H]$^+$ |
|---|---|---|---|
| 255 | 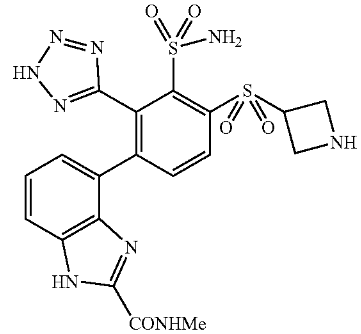 | 4-(4-(Azetidin-3-ylsulfonyl)-3-sulfamoyl-2-(2H-tetrazol-5-yl)phenyl)-N-methyl-1H-benzo[d]imidazole-2-carboxamide | 518.36 |

| Ex. No. | Structure | Name | LC/MS m/e [M + H]+ |
|---|---|---|---|
| 256 | 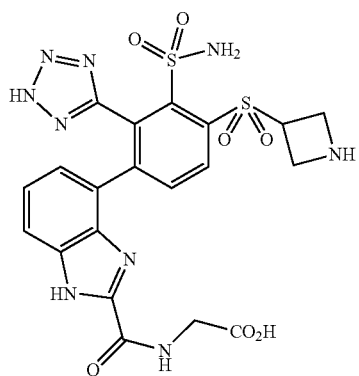 [SMILES: NS(=O)(=O)c1c(S(=O)(=O)C2CNC2)ccc(-c2cccc3[nH]c(C(=O)NCC(=O)O)nc23)c1-c1nn[nH]n1] | Methyl (4-(4-(azetidin-3-ylsulfonyl)-3-sulfamoyl-2-(2H-tetrazol-5-yl)phenyl)-1H-benzo[d]imidazole-2-carbonyl)glycinate | 576.31 |

EXAMPLE 257

(4-(4-(azetidin-3-yl sulfonyl)-3-sulfamoyl-2-(2H-tetrazol-5-yl)phenyl)-1H-benzo[d]imidazole-2-carbonyl)glycine

EXAMPLES 258 and 259

3-(2-Aminobenzo[d]thiazol-4-yl)-6-((2-morpholinoethyl)sulfonyl)-2-(2H-tetrazol-5-yl)benzenesulfonamide and 3-(2-aminobenzo[d]thiazol-4-yl)-6-((2-(3-oxomorpholino)ethyl)sulfonyl)-2-(2H-tetrazol-5-yl)benzenesulfonamide

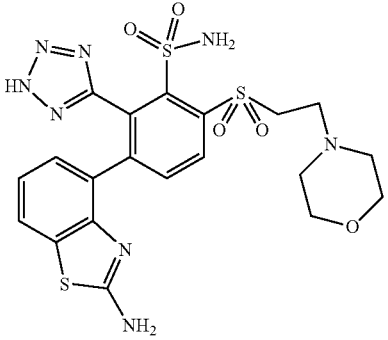

258

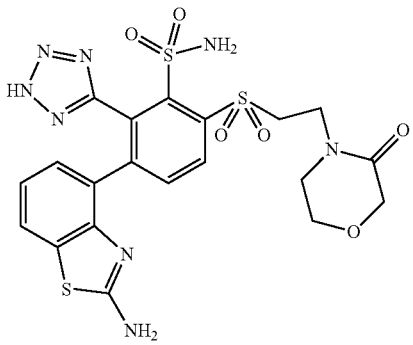

259

Using the product from EXAMPLE 256 and the procedures set out in EXAMPLE 253, the trifluoroacetate and hydrochloride salts of the titled compound were obtained. LC/MS [M+H]+: 562.37.

Step A: 3-Iodo-N,N-bis(4-methoxybenzyl)-2-(1-(4-methoxybenzyl)-1H-tetrazol-5-yl)-6-((2-morpholinoethyl)thio)benzenesulfonamide and 3-iodo-N,N-bis(4-methoxybenzyl)-2-(2-(4-methoxybenzyl)-2H-tetrazol-5-yl)-6-((2-morpholinoethyl)thio)benzenesulfonamide The title compounds were prepared from 6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide according to the protocol set forth in Step A of 4-(Methylthio)-4'-(piperidin-4-yl)-2-(1H-tetrazol-5-yl)-[1,1'-biphenyl]-3-sulfonamide (EXAMPLE 234), substituting sodium 2-morpholinoethane-1-thiolate for sodium methanethiolate. LC/MS [M+H]+: 857.53 and 857.56.

Step B: 3-Iodo-N,N-bis(4-methoxybenzyl)-2-(1-(4-methoxybenzyl)-1H-tetrazol-5-yl)-6-((2-morpholinoethyl)sulfonyl)benzenesulfonamide and 3-iodo-N,N-bis(4-methoxybenzyl)-2-(2-(4-methoxybenzyl)-2H-tetrazol-5-yl)-6-((2-morpholinoethyl)sulfonyl)benzenesulfonamide and 3-iodo-N,N-bis(4-methoxybenzyl)-2-(1-(4-methoxybenzyl)-1H-tetrazol-5-yl)-6-((2-(3-oxomorpholino)ethyl)sulfonyl)benzenesulfonamide and 3-iodo-N,N-bis(4-methoxybenzyl)-2-(2-(4-methoxybenzyl)-2H-tetrazol-5-yl)-6-((2-(3-oxomorpholino)ethyl)sulfonyl)benzenesulfonamide Sodium periodate (0.282 g, 1.32 mmol) in water (2 ml) was added to a mixture of the sulfides from the previous step (0.188 g, 0.219 mmol) and ruthenium trichloride (0.002 g) in DCM (2 mL) and the resulting reaction mixture was stirred at room temperature overnight. Ether was added and stirring was continued for a further 30 min. The organic phase was separated, dried (MgSO4) and the volatiles removed under reduced pressure. The residue was purified by silica gel column chromatography using a 12 g column and a gradient of EtOAc in hexanes as eluent, giving a mixture of morpholines and morpholinones. LC/MS [M+H]+: 889.4 and 903.3.

Step C: 3-(2-Aminobenzo[d]thiazol-4-yl)-N,N-bis(4-methoxybenzyl)-2-(1-(4-methoxybenzyl)-1H-tetrazol-5-yl)-6-((2-morpholinoethyl)sulfonyl)benzenesulfonamide and 3-(2-aminobenzo[d]thiazol-4-yl)-N,N-bis(4-methoxybenzyl)-2-(2-(4-methoxybenzyl)-2H-tetrazol-5-yl)-6-((2-morpholinoethyl)sulfonyl)benzenesulfonamide and 3-(2-aminobenzo[d]thiazol-4-yl)-N,N-bis(4-methoxybenzyl)-2-(1-(4-methoxybenzyl)-1H-tetrazol-5-yl)-6-((2-(3-oxomorpholino)ethyl)sulfonyl)benzenesulfonamide and 3-(2-aminobenzo[d]thiazol-4-yl)-N,N-bis(4-methoxybenzyl)-2-(2-(4-methoxybenzyl)-2H-tetrazol-5-yl)-6-((2-(3-oxomorpholino)ethyl)sulfonyl)benzenesulfonamide A mixture of (2-Aminobenzo[d]thiazol-4-yl)boronic acid (21.1 mg, 0.109 mmol) and 3-Iodo-N,N-bis(4-methoxybenzyl)-2-(1-(4-methoxybenzyl)-1H-tetrazol-5-yl)-6-((2-morpholinoethyl)sulfonyl)benzenesulfonamide and 3-iodo-N,N-bis(4-methoxybenzyl)-2-(2-(4-methoxybenzyl)-2H-tetrazol-5-yl)-6-((2-morpholinoethyl)sulfonyl)benzenesulfonamide and 3-iodo-N,N-bis(4-methoxybenzyl)-2-(1-(4-methoxybenzyl)-1H-tetrazol-5-yl)-6-((2-(3-oxomorpholino)ethyl)sulfonyl)benzenesulfonamide and 3-iodo-N,N-bis(4-methoxybenzyl)-2-(2-(4-methoxybenzyl)-2H-tetrazol-5-yl)-6-((2-(3-oxomorpholino)ethyl)sulfonyl) benzenesulfonamide (50 mg, 0.054 mmol), [1,1'-Bis(diphenylphosphino)ferrocene]dichloropalladium(II), complex with DCM (4.4 mg, 0.0054 mmol), Na2CO3 (17.3 mg, 0.163 mmol) and dioxane/water (4 mL/1 mL) was heated at 85° C. overnight. After cooling, the reaction mixture was filtered through ceilite and extracted with EtOAc. The organic layer was separated, dried, and concentrated. The residue was purified by ISCO (0-100% EtOAc/Hexane) to obtain two compounds. Each was carried to deprotection for NMR structure determination. LC/MS [M+H]+: 925.51 and LC/MS [M+H]+: 911.55

Step D: 3-(2-Aminobenzo[d]thiazol-4-yl)-6-((2-morpholinoethyl)sulfonyl)-2-(2H-tetrazol-5-yl)benzenesulfonamide The morpholines obtained in Step C (above) were treated with TFA at 80° C. and the crude reaction product purified by reverse phase HPLC using a gradient of acetonitrile (containing 0.1% TFA) in water (containing 0.1% TFA) to give the trifluoroacetate salt of the desired titled compound. LC/MS [M+H]+: 551.33

Step E: 3-(2-Aminobenzo[d]thiazol-4-yl)-6-((2-(3-oxomorpholino)ethyl)sulfonyl)-2-(2H-tetrazol-5-yl)benzenesulfonamide The morpholinones obtained in Step C (above) were treated with TFA at 80° C. and the crude reaction product purified by reverse phase HPLC using a gradient of acetonitrile (containing 0.1% TFA) in water (containing 0.1% TFA) to give the trifluoroacetate salt of the desired titled compound. LC/MS [M+H]+: 565.25

EXAMPLE 260

3-(2-amino-5-(trifluoromethyl)-1H-benzo[d]imidazol-7-yl)-6-(azetidin-3-ylsulfonyl)-2-(1H-tetrazol-5-yl)benzenesulfonamide

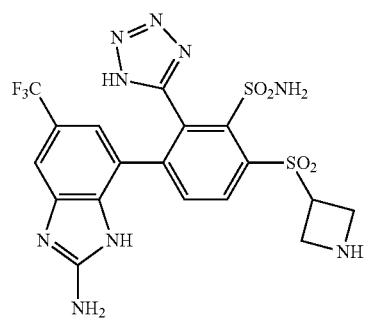 [SMILES: Nc1nc2cc(C(F)(F)F)cc(-c3ccc(S(=O)(=O)C4CNC4)c(S(N)(=O)=O)c3-c3nnn[nH]3)c2[nH]1]

Step A: tert-butyl 3-((4-(2-amino-5-(trifluoromethyl)-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate To a 10 mL RBF was added cesium carbonate (57.6 mg, 0.177 mmol), 7-bromo-5-(trifluoromethyl)-1H-benzo[d]

imidazol-2-amine (17.32 mg, 0.062 mmol), (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid (50 mg, 0.059 mmol) and Xphos Pd G2 (4.64 mg, 0.006 mmol). The flask was sealed, degassed, and filled with dioxane (0.8 ml) and water (0.200 ml). The resulting mixture was heated at 80° C. overnight. The reaction mixture was filtered through a CELITE pad to removed palladium. The filtrate was diluted with EtOAc and washed with water. The organic phase was dried over anhydrous $MgSO_4$, filtered, concentrated and purified by silica gel column chromatography (ISCO RediSep gold column, 40 g) using 0-10% MeOH/DCM as mobile phase to get the title compound. LC/MS (M+H)+: 1005.01.

Step B: tert-butyl 3-((4-(2-amino-5-(trifluoromethyl)-1H-benzo[d]imidazol-7-yl)-2-(N,N-bis(4-methoxybenzyl)sulfamoyl)-3-(2-(4-methoxybenzyl)-2H-tetrazol-5-yl)phenyl)-sulfonyl)azetidine-1-carboxylate A solution of tert-butyl 3-((4-(2-amino-5-(trifluoromethyl)-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)-azetidine-1-carboxylate (20 mg, 0.020 mmol) in DCM (0.2 ml) was concentrated in vacuum. The residue was dissolved in anisole (21.65 μl, 0.199 mmol) and TFA (153 μl, 1.992 mmol) at 0° C. The resulting mixture was stirred at RT for 1.0 hour. The reaction mixture was concentrated in vacuum, then dissolved in 0.5 mL of TFA and heated at 80° C. for 1 hour. After removing the volatile, the residue was purified by reverse phase HPLC (3-60% acetonitrile in $H_2O$) to give the desired product. LC/MS $[M+2H]^{2+}$: 272.85.

EXAMPLES 261-266 were prepared according to the general procedure described for EXAMPLE 260, starting from (3-(N,N-bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid or tert-butyl (2-((2-(N,N-bis(4-methoxybenzyl)sulfamoyl)-4-(5,5-dimethyl-1,3,2-dioxaborinan-2-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate and using aryl/heteroaryl halides that are commercially available, known, or prepared as described herein.

| Ex. No. | Structure | Name | Calc'd Mass $[M + H]^+$ | LC/MS m/e $[M + 2H]^{2+}$ |
|---|---|---|---|---|
| 261 | 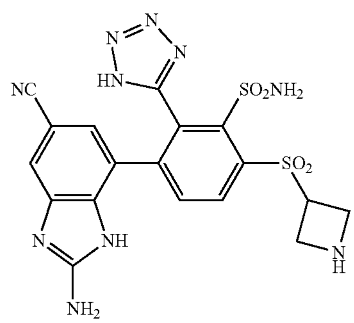 [SMILES: N#Cc1cc(-c2ccc(S(=O)(=O)C3CNC3)c(S(N)(=O)=O)c2-c2nnn[nH]2)c2[nH]c(N)nc2c1] | 3-(2-amino-5-cyano-1H-benzo[d]imidazol-7-yl)-6-(azetidin-3-ylsulfonyl)-2-(1H-tetrazol-5-yl)benzenesulfonamide | 501.1 | 251.08 |
| 262 | 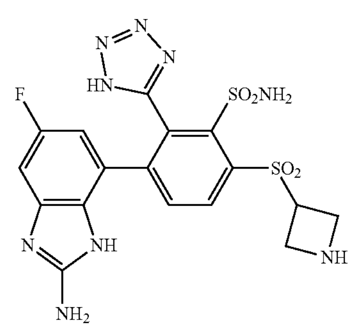 [SMILES: Nc1nc2cc(F)cc(-c3ccc(S(=O)(=O)C4CNC4)c(S(N)(=O)=O)c3-c3nnn[nH]3)c2[nH]1] | 3-(2-amino-5-fluoro-1H-benzo[d]imidazol-7-yl)-6-(azetidin-3-ylsulfonyl)-2-(1H-tetrazol-5-yl)benzenesulfonamide | 494.1 | 247.84 |
| 263 | 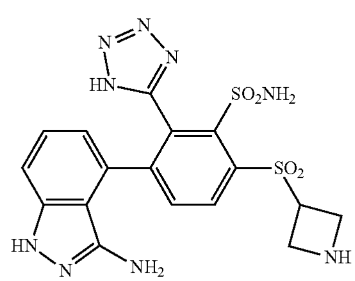 [SMILES: Nc1n[nH]c2cccc(-c3ccc(S(=O)(=O)C4CNC4)c(S(N)(=O)=O)c3-c3nnn[nH]3)c12] | 3-(3-amino-1H-indazol-4-yl)-6-(azetidin-3-ylsulfonyl)-2-(1H-tetrazol-5-yl)benzenesulfonamide | 476.1 | 238.71 |

| Ex. No. | Structure | Name | Calc'd Mass [M + H]⁺ | LC/MS m/e [M + 2H]²⁺ |
|---|---|---|---|---|
| 264 | 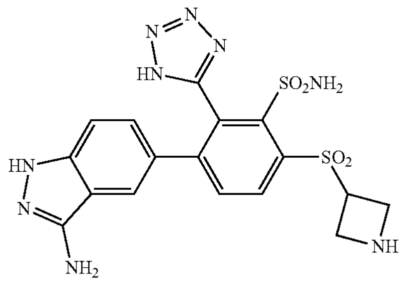 [SMILES: Nc1n[nH]c2ccc(-c3ccc(S(=O)(=O)C4CNC4)c(S(N)(=O)=O)c3-c3nnn[nH]3)cc12] | 3-(3-amino-1H-indazol-5-yl)-6-(azetidin-3-ylsulfonyl)-2-(1H-tetrazol-5-yl)benzenesulfonamide | 476.08 | 238.68 |
| 265 | 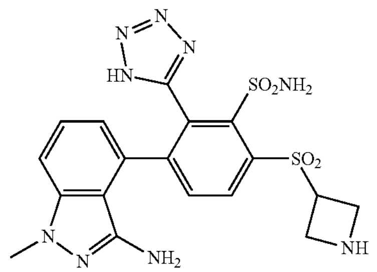 [SMILES: Cn1nc(N)c2c(-c3ccc(S(=O)(=O)C4CNC4)c(S(N)(=O)=O)c3-c3nnn[nH]3)cccc21] | 3-(3-amino-1-methyl-1H-indazol-4-yl)-6-(azetidin-3-ylsulfonyl)-2-(1H-tetrazol-5-yl)benzenesulfonamide | 490.10 | [M + H]⁺ 490.39 |
| 266 | 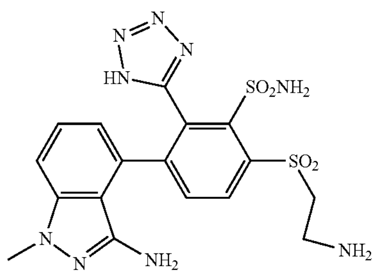 [SMILES: Cn1nc(N)c2c(-c3ccc(S(=O)(=O)CCN)c(S(N)(=O)=O)c3-c3nnn[nH]3)cccc21] | 3-(3-amino-1-methyl-1H-indazol-4-yl)-6-((2-aminoethyl)sulfonyl)-2-(1H-tetrazol-5-yl)benzenesulfonamide | 478.10 | [M + H]⁺ 478.30 |

EXAMPLE 267

3-(2-amino-1H-benzo[d]imidazol-4-yl)-6-((R)-2-aminopropyl sulfonyl)-2-(2H-tetrazol-5-yl)benzenesulfonamide

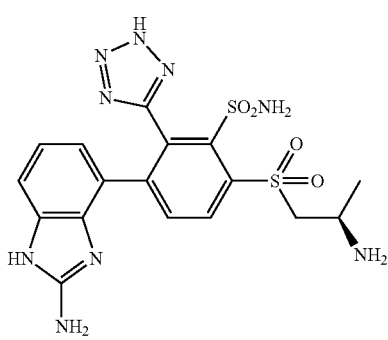 [SMILES: C[C@@H](N)CS(=O)(=O)c1ccc(-c2cccc3[nH]c(N)nc23)c(-c2nn[nH]n2)c1S(N)(=O)=O]

Step A: (R)-2-((tert-butoxycarbonyl)amino)propyl methanesulfonate

To a stirred solution of (R)-tert-butyl (1-hydroxypropan-2-yl)carbamate (5.00 g, 28.50 mmol) in DCM (30 mL) was added methanesulfonyl chloride (6.54 g, 57.10 mmol) and TEA (8.65 g, 86.00 mmol) at 0° C. The resulting mixture was stirred at RT for 1 hour. The reaction was quenched with ice water (50 mL) and extracted with EtOAc (3×50 mL). The combined organic layers were washed with brine (3×30 mL), dried over anhydrous sodium sulfate and filtered. The filtrate was evaporated to afford the title compound as a solid: LCMS [M+H-100]⁺: 154; ¹H NMR (400 MHz, CDCl₃) δ 4.66 (brs, 1H), 4.25-4.24 (m, 1H), 4.18-4.15 (m, 1H), 3.99-3.97 (m, 1H), 3.05 (s, 3H), 1.46 (s, 9H), 1.25 (d, J=6.8 Hz, 3H).

Step B: (R)—S-(2-((tert-butoxycarbonyl)amino)propyl) ethanethioate

To a solution of (R)-2-((tert-butoxycarbonyl)amino)propyl methanesulfonate (7.00 g, 27.60 mmol) in DMF (60 mL) was added potassium ethanethioate (6.30 g, 55.3 mmol). The mixture was stirred at RT overnight. The reaction mixture was diluted with water (60 mL) and extracted with EA (3×80 mL). The combined organic layer was washed with water (3×100 mL) and brine (3×80 mL), dried over anhydrous Na₂SO₄ and filtered. The filtrate was concentrated under vacuum. The residue was purified by silica gel chromatography, eluting with 15%-17% EA in PE to afford the title compound as an oil: LCMS [2M+H]⁺: 467; ¹H NMR (300

MHz, CDCl₃) δ 4.54 (brs, 1H), 3.85-3.83 (m, 1H), 3.04-2.96 (m, 2H), 2.33 (s, 3H), 1.42 (s, 9H), 1.15 (d, J=6.6 Hz, 3H).

Step C:
(R)-tert-butyl(1-mercaptopropan-2-yl)carbamate

To a solution of (R)—S-(2-((tert-butoxycarbonyl)amino)propyl) ethanethioate (4.70 g, 20.14 mmol) in MeOH (40 mL) was added potassium ethanethioate (8.34 g, 60.42 mmol) and stirred at RT for 30 min. The pH of the reaction was adjusted to ~7 at 0° C. and extracted with EtOAc (3×50 mL). The combined organic layers were washed with brine (2×100 mL), dried over anhydrous sodium sulfate and filtered. The filtrate was evaporated to afford the title compound as a solid: LCMS [2M+H]⁺: 383; ¹H NMR (300 MHz, CDCl₃) δ 4.75 (brs, 1H), 3.83-3.81 (m, 1H), 2.66-2.62 (m, 2H), 1.44 (s, 9H), 1.15 (d, J=6.6 Hz, 3H).

Step D: (R)-tert-butyl(1-((2-(N,N-bis(4-methoxybenzyl)sulfamoyl)-4-iodo-3-(2-(4-methoxybenzyl)-2H-tetrazol-5-yl)phenyl)thio)propan-2-yl)carbamate To a solution of 6-bromo-3-iodo-N,N-bis(4-methoxybenzyl)-2-(2-(4-methoxybenzyl)-2H-tetrazol-5-yl)benzenesulfonamide (2.00 g, 2.53 mmol) in DMF (40 mL) was added (R)-tert-butyl(1-mercaptopropan-2-yl)carbamate (1.94 g, 10.12 mmol) and sodium hydride (0.24 g, 10.12 mmol) under N₂. The mixture was stirred at RT for 2 hours. The reaction was quenched with water (100 mL) and extracted with EA (3×100 mL). The combined layers were washed with brine (2×200 mL), dried over anhydrous sodium sulfate and filtered. The filtrate was evaporated. The crude product was purified by silica gel chromatography, eluting with 30% EA in DCM to afford the title compound as a solid: LCMS [M+H]⁺: 901; ¹H NMR (400 MHz, DMSO-d₆) δ 8.18 (d, J=8.8 Hz, 1H), 7.2 (d, J=8.0 Hz, 1H), 7.30-7.24 (m, 4H), 6.89-6.84 (m, 8H), 5.95-5.93 (m, 2H), 4.30-4.26 (m, 1H), 4.17-4.15 (m, 2H), 4.03-3.98 (m, 1H), 3.91-3.87 (m, 1H), 3.73 (s, 9H), 3.70-3.65 (m, 4H), 1.34 (s, 9H), 1.19 (d, J=6.4 Hz, 3H).

Step E: (R)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate To a solution of (R)-tert-butyl(1-((2-(N,N-bis(4-methoxybenzyl)sulfamoyl)-4-iodo-3-(2-(4-methoxybenzyl)-2H-tetrazol-5-yl)phenyl)thio)propan-2-yl)carbamate (1.50 g, 1.67 mmol) in DCM (20 mL) was added 3-chlorobenzoperoxoic acid (2.30 g, 13.32 mmol). The mixture was stirred at RT for 16 hours. The reaction was quenched with NaHSO₄ (10%, 50 mL) and extracted with EA (3×50 mL). The combined layers were washed with NaHCO₃ (saturated, 3×40 mL), brine (3×40 mL), dried over anhydrous sodium sulfate and filtered. The filtrate was evaporated. The crude product was purified by silica gel chromatography, eluting with 25%-29% EA in PE to afford the title compound as a solid: LCMS [M+H]⁺: 933.

Step F: (R)-tert-butyl(1-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate To a stirred solution of (R)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (0.30 g, 0.32 mmol) in 1,4-dioxane (3 mL) and water (0.5 mL) were added (2-amino-1H-benzo[d]imidazol-4-yl)boronic acid (0.17 g, 0.97 mmol), Na₂CO₃ (0.10 g, 0.97 mmol) and Pd(PPh₃)₄(74 mg, 0.06 mmol) under nitrogen atmosphere at RT. The resulting mixture was stirred at 80° C. overnight. The reaction was cooled to 20° C. and quenched with water (50 mL) and extracted with EA (3×50 mL). The combined organic layers were washed with brine (2×100 mL), dried over anhydrous sodium sulfate and filtered. The filtrate was evaporated. The crude product was purified by silica gel chromatography, eluting with 2%-4% MeOH in DCM to afford the title compound as a solid: LCMS [M+H]⁺: 938.

Step G: (R)-3-(2-amino-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide A mixture of (R)-tert-butyl(1-((4-(2-amino-1H-benzo[d]imidazol-4-yl)-2-(N,N-bis(4-methoxybenzyl)-sulfamoyl)-3-(2-(4-methoxybenzyl)-2H-tetrazol-5-yl)phenyl)sulfonyl)propan-2-yl)carbamate (0.12 g, 0.13 mmol) and TFA (3 mL) was stirred at RT for 45 min. The reaction mixture was evaporated in a vacuum to afford the title compound as an oil: LCMS [M+H]⁺: 718.

Step H: (R)-3-(2-amino-1H-benzo[d]imidazol-4-yl)-6-((2-aminopropyl)sulfonyl)-2-(2H-tetrazol-5-yl)benzenesulfonamide A mixture of (R)-3-(2-amino-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide (80 mg, 0.11 mmol) and TFA (4 mL) was stirred at 80° C. for 1 hour. The reaction mixture was purified by Prep-HPLC with following condition: Column, Xbridge C18, 19×150 mm; mobile phase: acetonitrile in water (0.05% NH₄HCO₃), 3%-23% in 8 min; Detector, UV 254 nm. The collected fractions were combined and concentrated under reducing pressure to afford the title compound as a solid: LCMS [M+H]⁺: 478; ¹H NMR (300 MHz, DMSO-d₆) δ 8.28 (d, J=8.4 Hz, 1H), 8.04 (d, J=8.1 Hz, 1H), 6.94 (d, J=7.8 Hz, 1H), 6.52 (t, J=7.8 Hz, 1H), 6.27 (brs, 2H), 6.10 (d, J=8.4 Hz, 1H), 4.17-4.02 (m, 2H), 3.83-3.76 (m, 1H), 1.36 (d, J=6.6 Hz, 3H).

EXAMPLE 268

3-(2-aminobenzo[d]thiazol-4-yl)-6-((R)-2-aminopropylsulfonyl)-2-(2H-tetrazol-5-yl)benzenesulfonamide

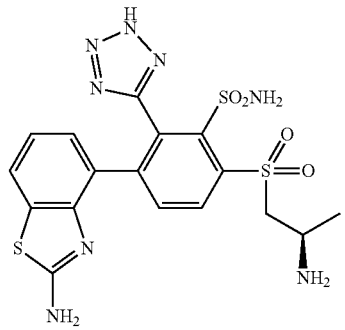 [SMILES: C[C@@H](N)CS(=O)(=O)c1ccc(-c2cccc3sc(N)nc23)c(-c2nn[nH]n2)c1S(N)(=O)=O]

Step A: (R)-tert-butyl (1-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate Into a 25 mL RBF was placed (R)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (200 mg, 0.214 mmol), (2-aminobenzo[d]thiazol-4-yl)boronic acid (83 mg, 0.429 mmol), Pd(dppf)Cl$_2$—CH$_2$Cl$_2$ (31 mg, 0.043 mmol) and Na$_2$CO$_3$ (68.2 mg, 0.643 mmol) in 1,4-dioxane (0.9 ml) and water (0.3 ml). The resulting mixture was evacuated and purged with nitrogen 3 times and stirred at 80° C. for 16 hours. Then the mixture was diluted with 50 mL of ethyl acetate and washed with water (3×50 mL). The organic layer was collected, dried over anhydrous Na$_2$SO$_4$, filtered and concentrated under vacuum. The residue was applied on a silica gel column eluting with EA/PE(1/1) to give the title compound as a solid: LCMS [M+H]$^+$ 955

Step B: 3-(2-aminobenzo[d]thiazol-4-yl)-6-((R)-2-aminopropylsulfonyl)-N-(4-methoxybenzyl)-2-(2-(4-methoxybenzyl)-2H-tetrazol-5-yl)benzenesulfonamide In a 25 mL RBF was placed (R)-tert-butyl (1-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate (120 mg, 0.126 mmol) in DCM (1.0 ml) and TFA (1.0 ml). After the resulting solution was stirred at RT for 1 hour under N$_2$, the solvent was removed under vacuum to give the title compound, which was used for the next step directly. LCMS [M+H]$^+$: 735.

Step C: (R)-3-(2-aminobenzo[d]thiazol-4-yl)-6-((2-aminopropyl)sulfonyl)-2-(2H-tetrazol-5-yl)benzenesulfonamide Into a 25 mL RBF was placed (R)-3-(2-aminobenzo[d]thiazol-4-yl)-6-((2-aminopropyl)sulfonyl)-N-(4-methoxybenzyl)-2-(2-(4-methoxybenzyl)-2H-tetrazol-5-yl)benzenesulfonamide (70 mg, crude) in TFA (2 ml). After the resulting solution was stirred at 80° C. for 1 hour, it was concentrated under vacuum. The pH of the residue was adjusted to about 9 with NH$_4$HCO$_3$. Then it was applied on Prep-HPLC (condition: Column: XBridge Prep C18 OBD Column, 19×150 mm, 5 µM; Mobile Phase A: water with 10 mmol of NH$_4$HCO$_3$, Mobile Phase B: MeCN; Flow rate: 20 mL/min; Gradient: 3% B to 30% B in 8 min; 254/220 nm) to give the title compound as a solid: LCMS [M+H]$^+$: 495; $^1$H NMR (300 MHz, d-DMSO): δ 8.27 (d, J=8.4 Hz, 1H), 7.91 (d, J=8.4 Hz, 1H), 7.48 (d, J=6.6 Hz, 1H), 6.70 (t, J=7.8 Hz, 1H), 6.49 (d, J=7.8 Hz, 1H), 4.21-3.93 (m, 2H), 3.90 (q, J=6.6 Hz, 1H), 1.38 (d, J=6.6 Hz, 3H).

EXAMPLE 269

3-(2-aminobenzo[d]thiazol-4-yl)-6-(2-aminopropylsulfonyl)-2-(2H-tetrazol-5-yl)benzenesulfonamide

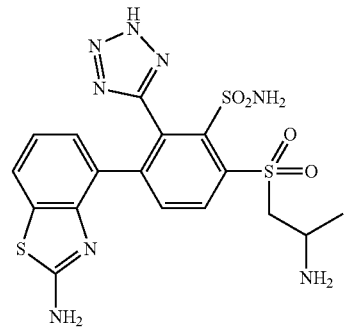 [SMILES: CC(N)CS(=O)(=O)c1ccc(-c2cccc3sc(N)nc23)c(-c2nn[nH]n2)c1S(N)(=O)=O]

Step A: tert-butyl 1-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)propan-2-ylcarbamate To a solution of tert-butyl 1-(2-(N,N-bis(4-methoxybenzyl)sulfamoyl)-4-iodo-3-(2-(4-methoxybenzyl)-2H-tetrazol-5-yl)phenylsulfonyl)propan-2-ylcarbamate (260 mg, 0.215 mmol) in dioxane (5 mL) and H$_2$O (1 mL), was added 2-aminobenzo[d]thiazol-4-ylboronic acid (97 mg, 0.5 mmol) and Na$_2$CO$_3$ (89 mg, 0.84 mmol). Under an atmosphere of N$_2$, Pd(dppf)Cl$_2$ (20 mg, 0.03 mmol) was added to the mixture. The resulting mixture was stirred at 80° C. for 12 hours. After cooling to room temperature, the reaction mixture was quenched with water (10 mL). The resulting mixture was extracted with ethyl acetate (3×10 mL). The combined organic layers were washed with brine (2×10 mL), dried over anhydrous sodium sulfate and filtered. The filtrate was concentrated under reduced pressure. The residue was purified by column chromatography over silica gel using gradient of 0-50% methanol in DCM as eluent to afford the title compound as an oil. LCMS [M+H]$^+$ 955.0; $^1$H NMR (CD$_3$OD, 300 MHZ) δ: 8.70 (d, J=2.1 Hz, 1H), 8.10 (t, J=8.4 Hz, 1H), 7.49 (d, J=7.8 Hz, 1H), 6.95 (d, J=8.4 Hz, 4H), 6.85-6.59 (m, 10H), 4.70 (d, J=15.9 Hz, 2H), 4.38-3.49 (m, 14 H), 1.98 (s, 2H), 1.52-1.11 (m, 12 H).

Step B: 3-(2-aminobenzo[d]thiazol-4-yl)-6-(2-aminopropylsulfonyl)-N-(4-methoxybenzyl)-2-(2-(4-methoxybenzyl)-2H-tetrazol-5-yl)benzenesulfonamide To a solution of tert-butyl 1-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)propan-2-ylcarbamate (170 mg, 0.178 mmol) in DCM (4 mL) was added TFA (2 mL). Then the mixture was stirred for 1 hour at RT. The reaction mixture was concentrated under vacuum to give the title compound as an oil, which was used for the next step directly. LCMS [M+H]$^+$ 735.0

Step C: 3-(2-aminobenzo[d]thiazol-4-yl)-6-(2-aminopropylsulfonyl)-2-(2H-tetrazol-5-yl)benzenesulfonamide A solution of 3-(2-aminobenzo[d]thiazol-4-yl)-6-(2-aminopropylsulfonyl)-N-(4-methoxybenzyl)-2-(2-(4- methoxybenzyl)-2H-tetrazol-5-yl)benzenesulfonamide (150 mg, 0.2 mmol) in TFA (4 mL) was stirred at 80° C. for 1 hour. The reaction mixture was concentrated under vacuum to give crude product. The product was purified by Prep-HPLC with the following conditions: Column: XSelect CSH Prep C18 OBD Column, 19*150 mm; Mobile Phase A: water with 10 mmol $NH_4HCO_3$, Mobile Phase B: MeCN; Flow rate: 20 mL/min; Gradient: 3% B to 34% B in 8 min; UV detection 254/220 nm. The collected fractions were combined and concentrated under vacuum to give the title compound as a solid. LCMS [M+H]$^+$ 495.0. $^1$H NMR (DMSO-d$_6$, 300 MHz) δ: 8.25 (d, J=2.1 Hz, 1H), 7.98-7.41 (m, 8H), 6.68 (t, J=7.8 Hz, 1H), 6.45 (d, J=7.5 Hz, 1H), 4.19-4.01 (m, 2H), 3.79 (q, J=6.0 Hz, 1H), 1.36 (d, J=6.6 Hz, 3H), 1.23 (s, 1H).

EXAMPLE 270

3-(2-amino-1H-benzo[d]imidazol-4-yl)-6-(3-aminopropylsulfonyl)-2-(2H-tetrazol-5-yl)benzenesulfonamide dihydrochloride

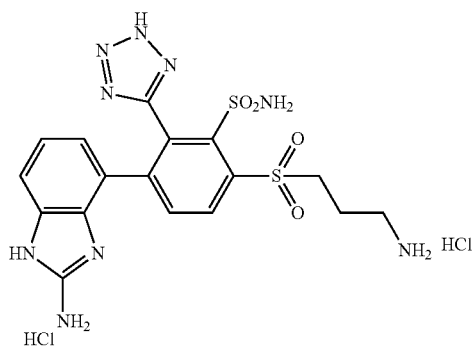 [SMILES: NCCCS(=O)(=O)c1ccc(-c2cccc3[nH]c(N)nc23)c(-c2nn[nH]n2)c1S(N)(=O)=O ; Cl ; Cl]

Step A: tert-butyl (3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate Into a 50 mL RBF was placed (2-amino-1H-benzo[d]imidazol-4-yl)boronic acid (3.79 mg, 0.021 mmol), tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propyl)carbamate (200 mg, 0.214 mmol), Pd(dppf)Cl$_2$ (127 mg, 0.214 mmol) and sodium carbonate (68.2 mg, 0.643 mmol) in 1,4-dioxane (1.5 ml) and water (0.500 ml). The reaction mixture was evacuated and backfilled with nitrogen 3 times and stirred at 80° C. for 4 hours. Then the mixture was extracted with ethyl acetate (4×25 mL) and the combined organic layers were washed with water (4×25 mL). The organic layer was collected and dried over sodium sulfate. Then it was concentrated under vacuum. The residue was applied on a silica gel column eluted with ethyl acetate/petroleum ether (3/1) to give the title compound as a solid: LCMS [M+H]$^+$: 938; $^1$H NMR (300 MHz, d-DMSO): δ 10.93 (s, 1H), 8.70-8.58 (d, J=8.4 Hz, 1H), 8.40-8.28 (d, J=7.2 Hz, 1H), 7.09-6.81 (m, 12H), 6.78-6.55 (m, 3H), 6.50-6.20 (m, 3H), 4.88-4.53 (m, 2H), 4.09-3.88 (m, 4H), 3.83-3.70 (m, 2H), 3.71 (s, 9H), 3.19-2.93 (m, 2H), 1.89-1.72 (m, 2H), 1.36 (s, 9H).

Step B: 3-(2-amino-1H-benzo[d]imidazol-4-yl)-6-(3-aminopropylsulfonyl)-N-(4-methoxybenzyl)-2-(2-(4-methoxybenzyl)-2H-tetrazol-5-yl)benzenesulfonamide Into a 25 mL RBF was placed tert-butyl (3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate (100 mg, 0.107 mmol) in DCM (1.0 ml) and trifluoroacetic acid (1.0 ml). After the resulting mixture was stirred at RT for 1 hour, the solvent was removed under vacuum to give the title compound, which was used for the next step directly. LCMS [M+H]$^+$: 718.

Step C: 3-(2-amino-1H-benzo[d]imidazol-4-yl)-6-((3-aminopropyl)sulfonyl)-2-(2H-tetrazol-5-yl)benzenesulfonamide dihydroChloride Into a 25 mL RBF was placed 3-(2-amino-1H-benzo[d]imidazol-4-yl)-6-((3-aminopropyl)sulfonyl)-N-(4-methoxybenzyl)-2-(2-(4-methoxybenzyl)-2H-tetrazol-5-yl)benzenesulfonamide in trifluoroacetic acid (2 ml). After the mixture was stirred at 80° C. for 1 hour, it was concentrated under vacuum. The pH of the residue was adjusted to 9 with ammonium bicarbonate and then applied on Prep-HPLC (condition: Column: XSelect CSH Prep C18 OBD Column, 19×150 mm; Mobile Phase A: water with 10 mmol $NH_4HCO_3$, Mobile Phase B: MeCN; Flow rate: 20 mL/min; Gradient: 5% B to 36% B in 8 min; 254/220 nm) to give the title compound as a solid.: LCMS [M+H]$^+$: 478; $^1$H NMR (300 MHz, d-DMSO): δ 12.5 (brs, 1H), 8.51-8.48 (d, J=8.1 Hz, 1H), 8.30-8.05 (brs, 3H), 8.10-8.07 (d, J=8.4 Hz, 1H), 8.00 (brs, 2H), 7.45 (s, 2H), 7.28-7.25 (d, J=8.1 Hz, 1H), 7.05-6.99 (t, J=8.1 Hz, 1H), 6.70-6.50 (m, 1H), 3.95-3.92 (t, J=7.2 Hz, 2H), 3.07-2.91 (m, 2H), 2.13-2.08 (t, J=6.3 Hz, 2H).

EXAMPLES 271 and 272

6-(2-aminoethylsulfonyl)-3-(5,6,7,8-tetrahydroquinolin-4-yl)-2-(2H-tetrazol-5-yl)benzenesulfonamide and 6-(2-aminoethylsulfonyl)-3-(1,2,3,4-tetrahydroquinolin-4-yl)-2-(2H-tetrazol-5-yl)benzenesulfonamide

271

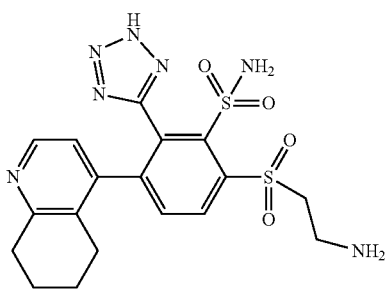

-continued

272

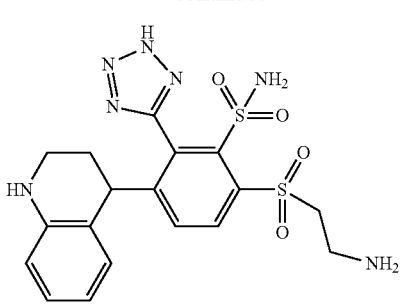

Step A: 4-(4,4,5,5-tetramethyl-1,3,2-dioxaborolan-2-yl)quinoline

To a stirred solution of 4-bromoquinoline (2.00 g, 9.61 mmol) in 1,4-dioxane (15 mL) were added 4,4,4',4',5,5,5',5'-octamethyl-2,2'-bi(1,3,2-dioxaborolane) (3.66 g, 14.42 mmol), acetylpotassium (2.37 g, 28.80 mmol) and Pd(dppf)Cl$_2$ (1.41 g, 1.92 mmol) under nitrogen at RT. After the resulting mixture was stirred at 100° C. for 2 hours, it was diluted with water (100 mL) and extracted with ethyl acetate (3×100 mL). The combined organic layers were washed with brine (3×100 mL), dried over anhydrous sodium sulfate and filtered. The filtrate was concentrated under vacuum. The residue was purified by silica gel chromatography, eluting with 10%-50% EA in PE to afford crude of 4-(4,4,5,5-tetramethyl-1,3,2-dioxaborolan-2-yl)quinoline as a solid (purity ~60%). LCMS [M+1]$^+$256; $^1$H NMR (300 MHz, DMSO-d$_6$) δ 8.97 (d, J=4.2 Hz, 1H), 8.59 (d, J=8.4 Hz, 1H), 8.07 (d, J=8.1 Hz, 1H), 7.88-7.83 (m, 2H), 7.71 (t, J=7.2 Hz, 1H), 1.40 (s, 12H).

Step B: tert-butyl-(2-((2-(N,N-bis(4-methoxybenzyl)sulfamoyl)-4-(isoquinolin-4-yl)-3-(2-(4-methoxybenzyl)-2H-tetrazol-5-yl)phenyl)sulfonyl)ethyl)carbamatas To a stirred solution of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (0.50 g, 0.54 mmol) in 1,4-dioxane (3 mL) were added 4-(4,4,5,5-tetramethyl-1,3,2-dioxaborolan-2-yl)quinoline (0.28 g, 1.09 mmol), Na$_2$CO$_3$ (0.23 g, 2.18 mmol) dissolved in water (1 mL) and Pd(dppf)Cl$_2$ (40 mg, 0.05 mmol) under nitrogen atmosphere at RT. The mixture was stirred at 80° C. for 3 hours. The resulting mixture was diluted with water (50 mL) and extracted with ethyl acetate (3×100 mL). The combined organic layers were washed with brine (3×50 mL), dried over anhydrous sodium sulfate and filtered. The filtrate was concentrated under vacuum. The residue was purified by silica gel chromatography, eluting with 1%-3% MeOH in DCM to afford the title compound as a solid: LCMS [M+1]$^+$920.

Step C: tert-butyl 2-(2-(N,N-bis(4-methoxybenzyl)sulfamoyl)-3-(2-(4-methoxybenzyl)-2H-tetrazol-5-yl)-4-(1,2,3,4-tetrahydroquinolin-4-yl)phenylsulfonyl)ethylcarbamate and tert-butyl 2-(2-(N,N-bis(4-methoxybenzyl)sulfamoyl)-3-(2-(4-methoxybenzyl)-2H-tetrazol-5-yl)-4-(5,6,7,8-tetrahydroquinolin-4-yl)phenylsulfonyl)ethylcarbamate To a solution of tert-butyl (2-((2-(N,N-bis(4-methoxybenzyl)sulfamoyl)-3-(2-(4-methoxybenzyl)-2H-tetrazol-5-yl)-4-(quinolin-4-yl)phenyl)sulfonyl)ethyl)carbamate (0.35 g, 0.38 mmol) in MeOH (15 mL) was added platinum(IV) oxide (86 mg, 0.38 mmol) and hydrogen chloride (37% aq, 14 mg, 0.38 mmol) and stirred at 15° C. at 15 atm of H$_2$ for 18 hours. The reaction mixture was filtered with CELITE and neutralized with NaOH solution (2 M) to pH~7, then evaporated. The residue was purified by silica gel chromatography, eluting with 1-3% MeOH in DCM to afford the title compounds as a mixture. This mixture was used for the next step directly. LCMS [M+1]$^+$924.

Step D: 6-(2-aminoethylsulfonyl)-N-(4-methoxybenzyl)-2-(2-(4-methoxybenzyl)-2H-tetrazol-5-yl)-3-(5,6,7,8-tetrahydroquinolin-4-yl)benzenesulfonamide and 6-(2-aminoethylsulfonyl)-N-(4-methoxybenzyl)-2-(2-(4-methoxybenzyl)-2H-tetra 1-5-yl)-3-(1,2,3,4-tetrahydroquinolin-4-yl)benzenesulfonamide The mixture of tert-butyl 2-(2-(N,N-bis(4-methoxybenzyl)sulfamoyl)-3-(2-(4-methoxybenzyl)-2H-tetrazol-5-yl)-4-(1,2,3,4-tetrahydroquinolin-4-yl)phenylsulfonyl)ethylcarbamate and tert-butyl 2-(2-(N,N-bis(4-methoxybenzyl)sulfamoyl)-3-(2-(4-methoxybenzyl)-2H-tetrazol-5-yl)-4-(5,6,7,8-tetrahydroquinolin-4-yl)phenylsulfonyl)ethylcarbamate (0.10 g, 0.11 mol) in TFA (2 mL) was stirred at room temperature for 1 hour. The reaction mixture was concentrated under reduced pressure to give the title compounds as a mixture that was used directly in the next step: LCMS [M+1]$^+$704.

Step E: 6-((2-aminoethyl)sulfonyl)-3-(5,6,7,8-tetrahydroquinolin-4-yl)-2-(2H-tetrazol-5-yl)benzenesulfonamide and 6-((2-aminoethyl)sulfonyl)-3-(1,2,3,4-tetrahydroquinolin-4-yl)-2-(2H-tetrazol-5-yl)benzenesulfonamide The mixture of 6-(2-aminoethylsulfonyl)-N-(4-methoxybenzyl)-2-(2-(4-methoxybenzyl)-2H-tetrazol-5-yl)-3-(5,6,7,8-tetrahydroquinolin-4-yl)benzenesulfonamide and 6-(2-aminoethylsulfonyl)-N-(4-methoxybenzyl)-2-(2-(4-methoxybenzyl)-2H-tetrazol-5-yl)-3-(1,2,3,4-tetrahydroquinolin-4-yl)benzenesulfonamide (90 mg, 0.11 mmol) and TFA (3 mL) was stirred at 80° C. for 1 hour. After being evaporated under reduced pressure, the residue was purified by Prep-HPLC(Column, Xbridge C18, 19×150 mm; mobile phase: acetonitrile in water (0.05% NH$_4$HCO$_3$), 2%-40% in 8 min; Detector, UV 254 nm.) to afford 6-((2-aminoethyl)sulfonyl)-3-(1,2,3,4-tetrahydroquinolin-4-yl)-2-(2H-tetrazol-5-yl)benzenesulfonamide as a solid: LCM: [M+1]$^+$464; hr NMR (300 MHz, DMSO-d$_6$) δ 8.12 (d, J=8.4 Hz, 1H), 7.45 (brs, 4H), 7.35 (d, J=8.4 Hz, 1H), 6.88 (t, J=6.9 Hz, 1H), 6.51 (d, J=8.1 Hz, 1H), 6.43 (d, J=7.2 Hz, 1H), 6.36 (t, J=7.2 Hz, 1H), 5.82 (brs, 1H), 4.32 (t, J=6.6 Hz, 1H), 4.09-4.03 (m, 2H), 3.20 (t, J=7.2 Hz, 1H), 3.01-2.98 (m, 2H), 1.80-1.74 (m, 1H), 1.64-1.59 (m, 1H) and 6-((2-aminoethyl)sulfonyl)-3-(5,6,7,8-tetrahydroquinolin-4-yl)-2-(2H-tetrazol-5-yl)benzenesulfonamide as a solid: LCM: [M+1]$^+$464; $^1$H NMR (300 MHz, DMSO-d$_6$) δ 8.27 (d, J=8.1 Hz, 1H), 8.10 (d, J=4.8 Hz, 1H), 7.98-7.95 (m, 1H), 6.59 (d, J=4.8 Hz, 1H), 4.15 (t, J=6.9 Hz, 2H), 3.28-3.26 (m, 2H), 2.75-2.73 (m, 2H), 2.27-2.25 (m, 2H), 1.69-1.53 (m, 4H).

EXAMPLE 273

3-(2-amino-1H-benzo[d]imidazol-4-yl)-6-((R)-2-amino-3-hydroxypropylsulfonyl)-2-(2H-tetrazol-5-yl)benzenesulfonamide

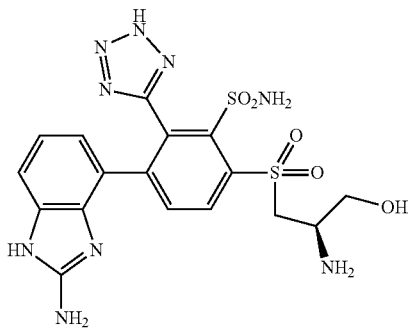 [SMILES: Nc1nc2c(-c3ccc(S(=O)(=O)C[C@H](N)CO)c(S(N)(=O)=O)c3-c3nn[nH]n3)cccc2[nH]1]

Step A: (S)-methyl 2-((tert-butoxycarbonyl)amino)-3-((methylsulfonyl)oxy)propanoate In the 250 mL round flask was placed (S)-methyl 2-((tert-butoxycarbonyl)amino)-3-hydroxypropanoate (10.0 g, 45.60 mmol) in DCM (150 mL), followed by the addition of triethylamine (13.85 g, 137.00 mmol) and methanesulfonyl chloride (10.45 g, 91.00 mmol) at 0° C. The mixture was stirred at 20° C. for 1 hour. The resulting mixture was diluted with water (20 mL) and extracted with DCM (2×200 mL). The combined organic layers were washed with water (2×200 mL), brine (2×200 mL), dried over anhydrous sodium sulfate and filtered. The filtrate was concentrated under vacuum to give the title compound: LCMS [M+Na]$^+$ 320; $^1$H NMR (400 MHz, CDCl$_3$) δ 5.30 (brs, 1H), 4.60-4.56 (m, 2H), 4.52-4.51 (m, 1H), 3.81 (s, 3H), 3.02 (s, 3H), 1.47 (s, 9H).

Step B: (R)-methyl-3-(acetylthio)-2-((tert-butoxycarbonyl)amino)propanoate

In the 250 mL round flask was placed (S)-methyl-2-((tert-butoxycarbonyl)amino)-3-((methylsulfonyl)-oxy)propanoate (13.00 g, 43.77 mmol) in DMF (150 mL), followed by the addition of potassium ethanethioate (9.98 g, 87.54 mmol). The mixture was stirred at 20° C. for 16 hours. The resulting mixture was diluted with water (500 mL) and extracted with ethyl acetate (3×300 mL). The combined organic layers were washed with water (3×300 mL), brine (3×500 mL), dried over anhydrous sodium sulfate and filtered. The filtrate was concentrated under vacuum. The residue was applied onto a silica gel column chromatography, eluting with ethyl acetate/petroleum ether (5/95) and concentrated under vacuum to afford the title compound as an oil: LCMS [M+Na]$^+$320; $^1$H NMR (400 MHz, CDCl$_3$) δ 5.23 (brs, 1H), 4.54-4.52 (m, 1H), 3.76 (s, 3H), 3.37-3.32 (m, 2H), 2.35 (s, 3H), 1.47 (s, 9H).

Step C: (R)-methyl-2-((tert-butoxycarbonyl)amino)-3-mercaptopropanoate

In the 100 mL round flask was placed (R)-methyl-3-(acetylthio)-2-((tert-butoxycarbonyl)-amino)propanoate (2.00 g, 7.21 mmol) in MeOH (50 mL), followed by the addition of K$_2$CO$_3$ (2.99 g, 21.63 mmol). The mixture was stirred at 20° C. for 16 hours. The resulting mixture was diluted with water (50 mL) and extracted with ethyl acetate (2×200 mL). The combined organic layers were washed with water (2×200 mL), brine (2×200 mL), dried over anhydrous sodium sulfate and filtered. The filtrate was concentrated under vacuum to give the title compound as an oil: LCMS [2M+1]$^+$ 471; $^1$H NMR (300 MHz, CDCl$_3$) δ 5.40 (brs, 1H), 4.54-4.52 (m, 1H), 3.76 (s, 3H), 3.37-3.32 (m, 2H), 2.35 (s, 3H), 1.44 (s, 9H).

Step D: (R)-tert-butyl(1-hydroxy-3-mercaptopropan-2-yl)carbamate

In the 100 mL round flask was placed (R)-methyl-2-((tert-butoxycarbonyl)amino)-3-mercaptopro-panoate (1.60 g, 5.10 mmol) in THF (50 mL), followed by the addition of LiAlH$_4$ (0.77 g, 20.40 mmol). The resulting mixture was stirred at 20° C. for 1 hour. Water (0.8 mL) was added dropwise, then 15% NaOH aq. (2.4 mL) and water (0.8 mL) were added dropwise and the mixture was filtered. The filtrate was concentrated under vacuum. The residue was applied onto a silica gel column chromatography, eluted with ethyl acetate/petroleum ether (1/2) and concentrated under vacuum to afford the title compound as an oil: LCM: [M+1]$^+$208.

Step E: (R)-tert-butyl(1-((2-(N,N-bis(4-methoxybenzyl)sulfamoyl)-4-iodo-3-(2-(4-methoxybenzyl)-2H-tetrazol-5-yl)phenyl)thio)-3-hydroxypropan-2-yl)carbamate In the 50 mL round flask was placed 6-bromo-3-iodo-N,N-bis(4-methoxybenzyl)-2-(2-(4-methoxy-benzyl)-2H-tetrazol-5-yl)benzenesulfonamide (1.00 g, 1.27 mmol) in DMF (10 mL), followed by the addition of (R)-tert-butyl(1-hydroxy-3-mercaptopropan-2-yl)carbamate (0.52 g, 2.53 mmol) and Cs$_2$CO$_3$ (1.24 g, 3.80 mmol). Under N$_2$ protection, the mixture was stirred at 20° C. for 16 hours. The resulting mixture was diluted with water (20 mL) and extracted with ethyl acetate (2×200 mL). The combined organic layers were washed with water (2×200 mL), brine (2×200 mL), dried over anhydrous sodium sulfate and filtered. The filtrate was concentrated under vacuum. The residue was applied onto a silica gel chromatography, eluting with ethyl acetate/petroleum ether (40/60) and concentrated under vacuum to afford the title compound as a solid: LCMS [M+1]$^+$917; $^1$H NMR (400 MHz, CDCl$_3$) δ 8.02-8.00 (m, 2H), 7.23-7.21 (m, 2H), 6.94-6.89 (m, 4H), 6.81-6.71 (m, 6H), 5.52-5.48 (m, 1H), 5.15-5.11 (m, 2H), 4.67-4.62 (m, 2H), 3.97-3.87 (m, 3H), 3.79 (s, 3H), 3.78 (s, 6H), 3.77-3.73 (m, 4H), 1.41 (s, 9H).

Step F: (R)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)-3-hydroxypropan-2-yl)carbamate In the 50 mL RBF was placed a solution of (R)-tert-butyl (1-((2-(N,N-bis(4-methoxy-benzyl)sulfamoyl)-4-iodo-3-(2-(4-methoxybenzyl)-2H-tetrazol-5-yl)phenyl)thio)-3-hydroxypropan-2-yl)carbamate (0.69 g, 0.75 mmol) in DCM (5 mL), followed by the addition of m-CPBA (0.52 g, 3.01 mmol). The mixture was stirred at 20° C. for 16 hours. The resulting mixture was diluted with NaHSO$_3$ (saturated, 100 mL) and extracted with ethyl acetate (3×100 mL). The combined organic layers were washed with NaHCO$_3$ (aq.)

(2×100 mL), brine (2×100 mL), dried over anhydrous sodium sulfate and filtered. The filtrate was concentrated under vacuum. The residue was applied onto a silica gel column, eluted with ethyl acetate/petroleum ether (30/70) to afford the title compound as a solid: LCMS [M+1]$^+$949; $^1$H NMR (300 MHz, CDCl$_3$) δ 8.25-8.20 (m, 2H), 7.26-7.16 (m, 2H), 6.97-6.94 (m, 4H), 6.79-6.72 (m, 6H), 5.55-5.46 (m, 1H), 5.30-5.18 (m, 2H), 4.48-4.38 (m, 2H), 4.19-3.95 (m, 5H), 3.88-3.83 (m, 2H), 3.82 (s, 3H), 3.81 (s, 6H), 1.39 (s, 9H).

Step G: (R)-tert-butyl(1-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)-3-hydroxy-propan-2-yl)carbamate In the 50 mL RBF was placed a solution of (R)-tert-butyl (1-((2-(N,N-bis(4-methoxy-benzyl)sulfamoyl)-4-iodo-3-(2-(4-methoxybenzyl)-2H-tetrazol-5-yl)phenyl)sulfonyl)-3-hydroxypropan-2-yl)carbamate (0.20 g, 0.21 mmol) in dioxane (3 mL) and water (0.75 mL). Followed by the addition Na$_2$CO$_3$ (67 mg, 0.63 mmol), Pd(dppf)Cl$_2$ (31 mg, 0.04 mmol) and (2-amino-1H-benzo[d]imidazol-4-yl)boronic acid (0.11 g, 0.63 mmol). The mixture was evacuated and backfilled with nitrogen 3 times and stirred at 80° C. for 6 hours in an oil bath. The resulting mixture was diluted with water (100 mL) and extracted with ethyl acetate (3×200 mL). The combined organic layers were washed with water (2×200 mL) and brine (2×200 mL), dried over anhydrous sodium sulfate and filtered. The filtrate was concentrated under vacuum. The residue was purified by silica gel column chromatography, eluted with methanol/DCM (6/94) and concentrated under vacuum to afford the title compound as a solid: LCMS [M+1]$^+$954; $^1$H NMR (300 MHz, CDCl$_3$) δ 8.77 (brs, 1H), 7.95-7.86 (m, 2H), 7.01-6.89 (m, 7H), 6.77-6.55 (m, 10H), 5.39-5.38 (m, 1H), 4.99-4.89 (m, 1H), 4.76-4.52 (m, 2H), 4.37-3.08 (m, 5H), 3.72 (s, 6H), 3.71 (s, 3H), 3.68-3.65 (m, 2H), 1.45 (s, 9H).

Step H: 3-(2-amino-1H-benzo[d]imidazol-4-yl)-6-((R)-2-amino-3-hydroxypropylsulfonyl)-2-(2H-tetrazol-5-yl)benzenesulfonamide The title compound was prepared by removal of the PMB and Boc protective groups in the same fashion as described for EXAMPLES 271-272, Steps D-E. LC/MS [M+H]$^+$494.

EXAMPLE 274

3-(2-amino-1H-benzo[d]imidazol-4-yl)-6-((S)-2-amino-3-hydroxypropylsulfonyl)-2-(2H-tetrazol-5-yl)benzenesulfonamide

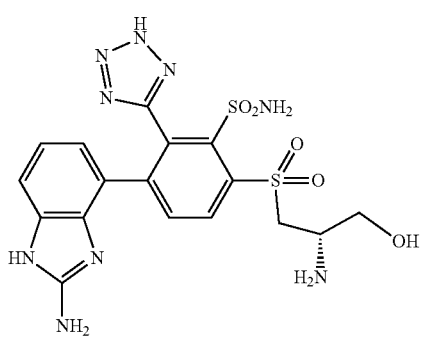 [SMILES: Nc1nc2c(-c3ccc(S(=O)(=O)C[C@@H](N)CO)c(S(N)(=O)=O)c3-c3nn[nH]n3)cccc2[nH]1]

Step A: (R)-methyl-2-((tert-butoxycarbonyl)amino)-3-((methylsulfonyl)oxy)propanoate To a solution of (R)-methyl-2-((tert-butoxycarbonyl)amino)-3-hydroxypropanoate (15.00 g, 68.40 mmol) in DCM (80 mL) was added methanesulfonyl chloride (15.68 g, 137.00 mmol) and Et$_3$N (20.73 g, 205.00 mmol) at 0° C., and the mixture was stirred at RT for 4 hours. The reaction mixture was concentrated in vacuum and dissolved in EA (100 mL). The EA mixture was washed with brine (3×100 mL) and dried over brine and anhydrous Na$_2$SO$_4$. The organic layer was evaporated in vacuum to afford the title compound as an oil: LCMS [M+Na]$^+$320; $^1$HNMR (400 MHz, CDCl$_3$) δ 5.41 (brs, 1H), 4.62-4.60 (m, 2H), 4.55-4.52 (m, 1H), 3.83 (s, 3H), 3.04 (s, 3H), 1.48 (s, 9H).

Step B: (S)-methyl-3-(acetylthio)-2-((tert-butoxycarbonyl)amino)propanoate

To a solution of (R)-methyl-2-((tert-butoxycarbonyl)amino)-3-((methylsulfonyl)oxy)propanoate (13.00 g, 43.77 mmol) in DMF (80 mL) was added potassium ethanethioate (9.98 g, 87.54 mmol) and the mixture was stirred at RT overnight. The reaction mixture was diluted with water (100 mL) and extracted by EA (3×100 mL). The combined organic layer was washed with water (2×150 mL) and brine (2×150 mL), dried over anhydrous Na$_2$SO$_4$ and filtered. The filtrate was concentrated in vacuum and purified by silica gel chromatography, eluted with 5%-10% EA in PE to afford the title compound as an oil: LCMS [M+Na]$^+$300; $^1$HNMR (400 MHz, DMSO-d$_6$) δ 5.24 (brs, 1H), 4.53-4.51 (m, 1H), 3.76 (s, 3H), 3.36-3.31 (m, 2H), 2.35 (s, 3H), 1.45 (s, 9H).

Step C: (S)-methyl-2-((tert-butoxycarbonyl)amino)-3-mercaptopropanoate

To a solution of (S)-methyl-3-(acetylthio)-2-((tert-butoxycarbonyl)amino)propanoate (1.50 g, 5.41 mmol) in MeOH (15 mL) was added K$_2$CO$_3$ (1.15 g, 10.82 mmol). The mixture was stirred at RT for 30 min. The reaction mixture was poured into ice water (50 mL) and neutralized with conc. HCl to pH 6-7. The solution was extracted with EA (3×50 mL). The organic layer was washed with water (3×50 mL) and brine (3×50 mL), dried over anhydrous Na$_2$SO$_4$ and filtered. The filtrate was concentrated under reduced pressure to afford the title compound as an oil: LCMS [2M+1]$^+$471; $^1$H NMR (400 MHz, DMSO-d$_6$) δ 7.29 (brs, 1H), 4.15-4.13 (m, 1H), 3.32 (s, 3H), 2.84-2.79 (m, 1H), 2.73-2.68 (m, 1H), 2.66-2.57 (m, 1H), 1.39 (s, 9H).

Step D: (S)-tert-butyl-(1-hydroxy-3-mercaptopropan-2-yl)carbamate

To a solution of (S)-methyl-2-((tert-butoxycarbonyl)amino)-3-mercaptopropanoate (1.50 g, 6.37 mmol) in THF (15 mL), was added LiAlH$_4$ (0.77 g, 20.40 mmol) at 0° C. The mixture was stirred at 0° C. for 1 hour. The reaction mixture was quenched with water (0.8 mL) by slow dropwise addition followed by the dropwise addition of a NaOH solution (15%, 2.4 mL). Then water (0.8 mL) was added. The mixture was filtered through CELITE and washed with THF several times. The filtrate was concentrated in vacuum. The residue was purified by silica gel chromatography, eluted with ethyl acetate/petroleum ether (1/2) to afford the title compound: LCMS [M+1]$^+$208.

Step E: (S)-tert-butyl-(1-((2-(N,N-bis(4-methoxybenzyl)sulfamoyl)-4-iodo-3-(2-(4-methoxybenzyl)-2H-tetrazol-5-yl)phenyl)thio)-3-hydroxypropan-2-yl)carbamate To a stirred solution of (S)-tert-butyl-(1-hydroxy-3-mercaptopropan-2-yl)carbamate (0.90 g, 4.34 mmol) in DMF (10 mL) was added 6-bromo-3-iodo-N,N-bis(4-methoxybenzyl)-2-(2-(4-methoxybenzyl)-2H-tetrazol-5-yl)benzenesulfonamide (0.86 g, 1.09 mmol) and sodium hydride (0.10 g, 4.34 mmol) under nitrogen atmosphere at RT. The resulting mixture was stirred at RT for 3 hours. The mixture was diluted with water (50 mL) and extracted with EA (3×50 mL). The combined organic layer was washed with water (3×60 mL) and brine (3×60 mL), dried over anhydrous $Na_2SO_4$ and filtered. The filtrate was concentrated in vacuum and purified by silica gel chromatography, eluting with 17%-20% EA in DCM to afford the title compound as a solid: LCMS [M+1]$^+$917; $^1$H NMR (300 MHz, $CDCl_3$) δ 8.02-7.99 (m, 2H), 7.23-7.21 (m, 2H), 6.94-6.87 (m, 4H), 6.81-6.75 (m, 6H), 5.52-5.47 (m, 1H), 5.15-5.10 (m, 2H), 4.71-4.61 (m, 2H), 3.98-3.87 (m, 3H), 3.79 (s, 3H), 3.78 (s, 6H), 3.77-3.73 (m, 4H), 1.45 (s, 9H).

Step F: (S)-tert-butyl(1-((2-(N,N-bis(4-methoxybenzyl)sulfamoyl)-4-iodo-3-(2-(4-methoxybenzyl)-2H-tetrazol-5-yl)phenyl)-sulfonyl)-3-hydroxypropan-2-yl)carbamate To a solution of (S)-tert-butyl(1-((2-(N,N-bis(4-methoxybenzyl)sulfamoyl)-4-iodo-3-(2-(4-methoxybenzyl)-2H-tetrazol-5-yl)phenyl)thio)-3-hydroxypropan-2-yl)carbamate (0.50 g, 0.55 mmol) in DCM (8 mL) was added 3-chlorobenzoperoxoic acid (0.38 g, 2.18 mmol) and the mixture was stirred at RT for 18 hours. The reaction mixture was diluted with EA (100 mL) and washed with a $Na_2SO_3$ aqueous solution (3×50 mL) and a $NaHCO_3$ aqueous solution (3×50 mL). The organic layer was washed with brine (2×50 mL) and dried over anhydrous $Na_2SO_4$ and filtered. The filtrate was concentrated under reduced pressure. The residue was purified by silica gel chromatography, eluted with 35%-40% EA in PE to afford the title compound as a solid: LCMS [M+1]$^+$949; $^1$H NMR (300 MHz, DMSO-$d_6$) δ 8.65-8.62 (m, 1H), 8.26-8.23 (m, 1H), 7.33-7.28 (m, 2H), 6.92-6.88 (m, 4H), 6.87-6.78 (m, 6H), 5.45-5.37 (m, 1H), 5.17-5.12 (m, 1H), 5.00 (brs, 1H), 4.57-4.45 (m, 2H), 4.15-3.83 (m, 7H), 3.73 (s, 3H), 3.72 (s, 6H), 1.39 (s, 9H).

Step G: (S)-tert-butyl(1-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)-3-hydroxypropan-2-yl)carbamates To a stirred solution of (S)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)-3-hydroxypropan-2-yl)carbamate (0.18 g, 0.19 mmol) in 1,4-dioxane (0.8 mL) and water (0.2 mL) was added (2-amino-1H-benzo[d]imidazol-4-yl)boronic acid (67 mg, 0.38 mmol), $Na_2CO_3$ (60 mg, 0.57 mmol) and Pd(dppf)$Cl_2$ (31 mg, 0.04 mmol) under nitrogen atmosphere at RT. The resulting mixture was stirred at 80° C. for 3 hours. The resulting mixture was diluted with water (100 mL) and extracted with ethyl acetate (3×200 mL). The combined organic layers were washed with water (2×200 mL) and brine (2×200 mL), dried over anhydrous sodium sulfate and filtered. The filtrate was concentrated under vacuum. The residue was purified by silica gel chromatography, eluting with 4%-10% MeOH in DCM to afford the title compound as a solid: LCMS [M+1]$^+$954.

Step H: (S)-3-(2-amino-1H-benzo[d]imidazol-4-yl)-6-((2-amino-3-hydroxypropyl)sulfon)-N-(4-methoyxbenzyl-2-(2-(4-methoxybenzyl)-2H-tetrazol-5-yl)benzenesulfonamide A solution of (S)-tert-butyl(1-((4-(2-amino-1H-benzo[d]imidazol-4-yl)-2-(N,N-bis(4-methoxybenzyl)-sulfamoyl)-3-(2-(4-methoxybenzyl)-2H-tetrazol-5-yl)phenyl)sulfonyl)-3-hydroxypropan-2-yl)carbamate (0.11 g, 0.12 mmol) in TFA (5 mL) was stirred at RT for 30 min. The reaction mixture was evaporated in vacuum and redissolved in DCM and concentrated again three times to afford the title compound as an oil: LCMS [M+1]$^+$734.

Step I: (S)-3-(2-amino-1H-benzo[d]imidazol-4-yl)-6-((2-amino-3-hydroxypropyl)sulfonyl)-2-(2H-tetrazol-5-yl)benzenesulfonamide A solution of (S)-3-(2-amino-1H-benzo[d]imidazol-4-yl)-6-((2-amino-3-hydroxypropyl)sulfonyl)-N-(4-methoxybenzyl)-2-(2-(4-methoxybenzyl)-2H-tetrazol-5-yl)benzenesulfonamide (80 mg, 0.11 mmol) in TFA (4 mL) was stirred at 80° C. for 1 hour. The reaction mixture was purified by Prep-HPLC with following condition: Column, Xbridge C18, 19×150 mm; mobile phase: acetonitrile in water (0.05% $NH_4HCO_3$), 5%-20% in 8 min; Detector, UV 254 nm. The collected fractions were combined and concentrated under reduced pressure to afford the title compound as a solid: LCMS [M+1]$^+$494; $^1$H NMR (300 MHz, DMSO-$d_6$) δ 8.32 (d, J=8.1 Hz, 1H), 7.97 (d, J=8.4 Hz, 1H), 6.98 (d, J=7.8 Hz, 1H), 6.63-6.61 (m, 1H), 6.18 (d, J=7.5 Hz, 1H), 4.24-4.17 (m, 1H), 3.99-3.91 (m, 1H), 3.63-3.61 (m, 3H).

EXAMPLE 275

3-(2-amino-1-methyl-1H-benzo[d]imidazol-4-yl)-6-((R)-2-aminopropylsulfonyl)-2-(2H-tetrazol-5-yl)benzenesulfonamide

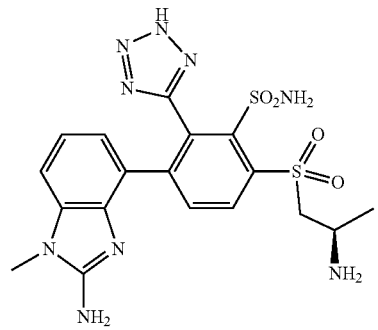 [SMILES: C[C@@H](N)CS(=O)(=O)c1ccc(-c2cccc3c2nc(N)n3C)c(-c2nn[nH]n2)c1S(N)(=O)=O]

Step A: (R)-tert-butyl(1-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate To a stirred solution of (R)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (0.25 g, 0.27 mmol) in 1,4-dioxane (0.8 ml) and water (0.2 ml) was added (2-amino-1-methyl-1H-benzo[d]imidazol-4-yl)boronic acid (154 mg, 0.804 mmol), Na$_2$CO$_3$ (85 mg, 0.80 mmol) and Pd(dppf)Cl$_2$ (44 mg, 0.05 mmol) under nitrogen atmosphere at RT. The resulting mixture was stirred at 80° C. overnight. The reaction was cooled to 20° C. and quenched with water (50 mL) and extracted with EA (3×50 mL). The combined organic layers were washed with brine (2×100 mL), dried over anhydrous sodium sulfate and filtered. The filtrate was evaporated. The crude product was purified by silica gel chromatography, eluting with 45% EA in DCM to afford the title compound as a solid: LCMS [M+H]$^+$: 952.

Step B: (R)-3-(2-amino-1-methyl-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide A solution of (R)-tert-butyl(1-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carba-mate (0.13 g, 0.14 mmol) in TFA (4 mL) was stirred at RT for 30 min. The reaction mixture was evaporated in vacuum to afford the title compound as an oil: LCMS [M+H]$^+$: 732.

Step C: (R)-3-(2-amino-1-methyl-1H-benzo[d]imidazol-4-yl)-6-((2-aminopropyl)sulfonyl)-2-(2H-tetrazol-5-yl)benzenesulfonamide A solution of (R)-3-(2-amino-1-methyl-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide (90 mg, 0.12 mmol) in TFA (4 mL) was stirred at 80° C. for 1 hour. The reaction mixture was concentrated under reduced pressure. The residue was purified by Prep-HPLC. Column, Xbridge C18, 19×150 mm; mobile phase: acetonitrile in water (0.05% NH$_4$HCO$_3$), 5%-30% in 10 min; Detector, UV 254 nm. The collected fractions were combined and concentrated under reduced pressure to afford the title compound as a solid: LCMS [M+H]$^+$: 492; $^1$H NMR (300 MHz, DMSO-d$_6$) δ 8.27 (d, J=8.4 Hz, 1H), 8.07 (d, J=8.4 Hz, 1H), 7.68 (brs, 4H), 6.95 (d, J=7.5 Hz, 1H), 6.56 (t, J=7.8 Hz, 1H), 6.50 (brs, 2H), 6.12 (d, J=7.8 Hz, 1H), 4.16-4.01 (m, 2H), 3.82-3.73 (m, 1H), 3.49 (s, 3H), 1.36 (d, J=6.6 Hz, 3H).

EXAMPLE 276

3-(2-amino-1-methyl-1H-benzo[d]imidazol-4-yl)-6-((S)-2-aminopropylsulfonyl)-2-(2H-tetrazol-5-yl)benzenesulfonamide

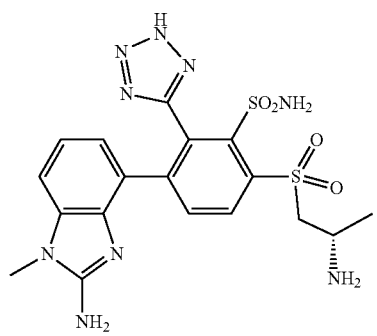 [SMILES: C[C@H](N)CS(=O)(=O)c1ccc(-c2cccc3c2nc(N)n3C)c(-c2nn[nH]n2)c1S(N)(=O)=O]

Step A: (S)-tert-butyl(1-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate To a stirred solution of (S)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (0.18 g, 0.19 mmol) in 1,4-dioxane (0.8 mL) and water (0.2 mL) was added (2-amino-1-methyl-1H-benzo[d]imidazol-4-yl)boronic acid (0.11 g, 0.579 mmol), Na$_2$CO$_3$ (61 mg, 0.58 mmol) and Pd(dppf)Cl$_2$ (35 mg, 0.04 mmol) under nitrogen atmosphere at RT. After the resulting mixture was stirred at 80° C. overnight, it was cooled to 20° C. and quenched with water (50 mL) and extracted with EA (3×50 mL). The combined organic layers were washed with brine (2×100 mL), dried over anhydrous sodium sulfate and filtered. The filtrate was evaporated and the residue was purified by silica gel chromatography, eluted with 50% EA in DCM to afford the title compound as a solid: LCMS [M+H]$^+$: 952.

Step B: (S)-3-(2-amino-1-methyl-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide A solution of (S)-tert-butyl(1-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propan-2-yl)carbamate (0.12 g, 0.13 mmol) in TFA (3 mL) was stirred at RT for 30 minutes. The reaction mixture was evaporated in vacuum to afford the title compound as an oil: LCMS [M+H]$^+$ 732.

Step C: (S)-3-(2-amino-1-methyl-1H-benzo[d]imidazol-4-yl)-6-((2-aminopropyl)sulfonyl)-2-(2H-tetrazol-5-yl)benzenesulfonamide A solution of (S)-3-(2-amino-1-methyl-1H-benzo[d]imidazol-4-yl)-6-((2-aminopropyl)sulfonyl)-N-(4-methoxybenzyl)-2-(2-(4-methoxybenzyl)-2H-tetrazol-5-yl)benzenesulfonamide (80 mg, 0.11 mmol) in TFA (4 mL) was stirred at 80° C. for 1 hour. The reaction mixture was concentrated in vacuum. The residue was purified by Prep-HPLC. Column, Xbridge C18, 19×150 mm; mobile phase: acetonitrile in water (0.05% NH$_4$HCO$_3$), 3%-30% in 8 min; Detector, UV 254 nm. RT: 4.5 min. The collected fractions were combined and concentrated under reducing pressure to afford the title compound as a solid: LCMS [M+H]$^+$: 492; $^1$H NMR (300 MHz, DMSO-d$_6$) δ 8.27 (d, J=8.4 Hz, 1H), 8.07 (d, J=8.4 Hz, 1H), 7.58 (brs, 4H), 6.95 (d, J=7.5 Hz, 1H), 6.54 (t, J=7.5 Hz, 1H), 6.51 (brs, 2H), 6.12 (d, J=7.5 Hz, 1H), 4.16-4.00 (m, 2H), 3.84-3.82 (m, 1H), 3.49 (s, 3H), 1.36 (d, J=6.6 Hz, 3H).

EXAMPLE 277

3-(2-amino-3H-benzo[d]imidazol-4-yl)-6-((R)-1-aminopropan-2-ylsulfonyl)-2-(2H-tetrazol-5-yl)benzenesulfonamide

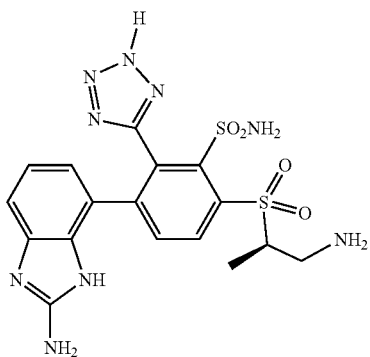 [SMILES: C[C@H](CN)S(=O)(=O)c1ccc(-c2cccc3nc(N)[nH]c23)c(-c2nn[nH]n2)c1S(N)(=O)=O]

Step A: tert-butyl (R)-2-(4-(2-amino-3H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)propylcarbamate Into a mixture of (R)-tert-butyl 2-(2-(N,N-bis(4-methoxybenzyl)sulfamoyl)-4-iodo-3-(2-(4-methoxybenzyl)-2H-tetrazol-5-yl)phenylsulfonyl)propylcarbamate (300 mg, 0.3 mmol), Pd(PPh₃)₄ (37 mg, 0.03 mmol) and 2-amino-1H-benzo[d]imidazol-4-ylboronic acid (142 mg, 0.8 mmol) in dioxane (8 mL), sodium carbonate (102 mg, 1.0 mmol) in water (2 mL) was added at room temperature. The resulting mixture was stirred at 80° C. for 12 hours under argon and then cooled to room temperature. The resulting mixture was quenched with water (10 mL) and extracted with ethyl acetate (3×10 mL). The combined organic layers were washed with brine (3×5 mL), dried over anhydrous sodium sulfate and filtered. The filtrate was evaporated under reduced pressure and the residue was purified by silica gel chromatography, eluting with 0-20% MeOH in DCM to give the title compound as a solid: LCMS [M+H]⁺: 938.

Step B: 3-(2-amino-3H-benzo[d]imidazol-4-yl)-6-((R)-1-aminopropan-2-ylsulfonyl)-N-(4-methoxybenzyl)-2-(2-(4-methoxybenzyl-2H-tetrazol-5-yl)benzenesulfonamide tert-butyl (R)-2-(4-(2-amino-3H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)propylcarbamate (200 mg, 0.21 mmol) was dissolved in DCM (3 mL) and treated with TFA (1.5 mL) at 0° C. The resulting mixture was stirred at RT for 0.5 hour. The solvent was evaporated to give the title compound as a solid: LCMS [M+H]⁺ 718.

Step C: 3-(2-amino-3H-benzo[d]imidazol-4-yl)-6-((R)-1-aminopropan-2-ylsulfonyl)-2-(2H-tetrazol-5-yl)benzenesulfonamide After the solution of 3-(2-amino-3H-benzo[d]imidazol-4-yl)-6-((R)-1-aminopropan-2-ylsulfonyl)-N-(4-methoxybenzyl)-2-(2-(4-methoxybenzyl)-2H-tetrazol-5-yl)benzenesulfonamide (140 mg, 0.2 mmol) in TFA (4 mL) was stirred at 80° C. for 1 hour, the solvent was evaporated and the residue was purified by Prep-HPLC with the following conditions: Column: XBridge BEH130 Prep C18 OBD Column 19×150 mm 5 μM 13 nm; Mobile Phase A: water with 10 mmol of NH₄HCO₃, Mobile Phase B: ACN; Flow rate: 20 mL/min; Gradient: 5% B to 23% B in 8 min; 254 nm. The collected fractions were combined and concentrated under reduced pressure to afford the title compound as a solid: LCMS [M+H]⁺: 478.0. ¹H NMR (400 MHz, DMSO): δ 12.81-12.45 (brs, J=10 Hz, 2H), 8.63-8.26 (m, J=5.2 Hz, 6H), 8.12 (d, J=8.4 Hz, 1H), 7.59-7.41 (brs, 2H), 7.28 (d, J=8.0 Hz, 1H), 7.05 (t, J=8.0 Hz, 1H), 6.72-6.48 (brs, 1H), 4.68-4.52 (m, 1H), 3.19-3.09 (m, 1H), 1.45 (d, J=6.4 Hz, 3H).

EXAMPLE 278

3-(2-amino-3H-benzo[d]imidazol-4-yl)-6-((S)-1-aminopropan-2-ylsulfonyl)-2-(2H-tetrazol-5-yl)benzenesulfonamide

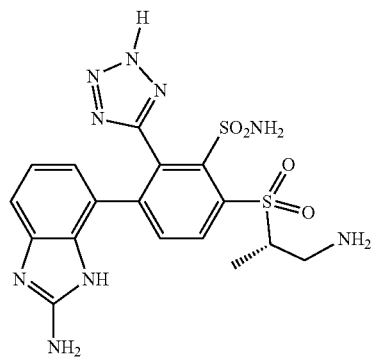 [SMILES: C[C@@H](CN)S(=O)(=O)c1ccc(-c2cccc3nc(N)[nH]c23)c(-c2nn[nH]n2)c1S(N)(=O)=O]

Step A: tert-butyl (S)-2-(4-(2-amino-3H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)propylcarbamate (S)-tert-butyl 2-(2-(N,N-bis(4-methoxybenzyl)sulfamoyl)-4-iodo-3-(2-(4-methoxybenzyl)-2H-tetrazol-5-yl)phenylsulfonyl)propylcarbamate (300 mg, 0.3 mmol) was combined with Pd(PPh₃)₄ (37 mg, 0.03 mmol) and 2-amino-1H-benzo[d]imidazol-4-ylboronic acid (142 mg, 0.8 mmol) in dioxane (8 mL). To the resulting mixture was added sodium carbonate (102 mg, 1.0 mmol) in water (2 mL) at room temperature. The resulting mixture was stirred at 80° C. for 12 hours under argon atmosphere. The reaction was cooled to room temperature and quenched with water (10 mL) and extracted with EA (3×10 mL). The combined organic layers were washed with brine (1×15 mL), dried over anhydrous sodium sulfate and filtered. The filtrate was evaporated under reduced pressure and the residue was purified by silica gel chromatography, eluting with 0~20% MeOH in DCM to give the title compound as a solid: LCMS [M+H]⁺: 938.

EXAMPLE 279

3-(2-amino-1-methyl-1H-benzo[d]imidazol-4-yl)-6-((R)-1-aminopropan-2-ylsulfonyl)-2-(2H-tetrazol-5-yl)benzenesulfonamide

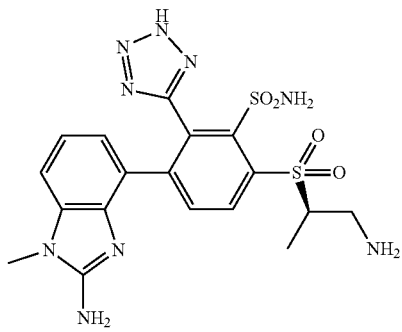 [SMILES: C[C@H](CN)S(=O)(=O)c1ccc(-c2cccc3c2nc(N)n3C)c(-c2nn[nH]n2)c1S(N)(=O)=O]

Step A: (R)-tert-butyl(2-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate To a stirred solution of (R)-tert-butyl(2-((2-(N,N-bis(4-methoxybenzyl)sulfamoyl)-3-(2-(4-methoxybenzyl)-2H-tetrazol-5-yl)phenyl)sulfonyl)propyl)carbamate (0.20 g, 0.25 mmol) in 1,4-dioxane (3 mL) and water (0.6 mL) was added (2-amino-1-methyl-1H-benzo[d]imidazol-4-yl)boronic acid (0.14 g, 0.74 mmol), $Na_2CO_3$ (79 mg, 0.74 mmol) and $Pd(PPh_3)_4$ (57 mg, 0.05 mmol) under nitrogen atmosphere at room temperature. The resulting mixture was stirred at 80° C. overnight. The reaction mixture was diluted with water (50 mL) and extracted with EA (3×80 mL). The organic layer was dried over brine (3×80 mL), anhydrous $Na_2SO_4$ and filtered. The filtrate was concentrated in vacuum. The residue was purified by silica gel chromatography, eluting with 4% MeOH in DCM to afford the title compound as a solid: LCMS [M+1]$^+$952

Step B: (R)-3-(2-amino-1-methyl-1H-benzo[d]imidazol-4-yl)-6-((1-aminopropan-2-yl)sulfonyl)-N-(4-methoxybenzyl)-2-(2-(4-methoxybenzyl)-2H-tetrazol-5-yl)benzenesulfonamide A solution of (R)-tert-butyl(2-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate (0.14 g, 0.15 mmol) in TFA (4 mL) was stirred at room temperature for 1 hour. The reaction mixture was evaporated in vacuum to afford the title compound as an oil: LCMS [M+1]$^+$ 732

Step C: (R)-3-(2-amino-1-methyl-1H-benzo[d]imidazol-4-yl)-6-((1-aminopropan-2-yl)sulfonyl)-2-(2H-tetrazol-5-yl)benzenesulfonamide A solution of (R)-3-(2-amino-1-methyl-1H-benzo[d]imidazol-4-yl)-6-((1-aminopropan-2-yl)sulfonyl)-N-(4-methoxybenzyl)-2-(2-(4-methoxybenzyl)-2H-tetrazol-5-yl)benzenesulfonamide (90 mg, 0.12 mmol) in TFA (5 mL) was stirred at 80° C. for 1 hour. The solvent was concentrated under reduced pressure. The residue was purified by Prep-HPLC. Column, Xbridge C18, 19×150 mm; mobile phase: acetonitrile in water (0.05% $NH_4HCO_3$), 5%-30% in 8 min; Detector, UV 254 nm. The collected fractions were combined and concentrated under vacuum to afford the title compound as a solid: LCMS [M+1]$^+$492; $^1$H NMR (300 MHz, DMSO-$d_6$) δ 8.21 (d, J=8.4 Hz, 1H), 8.03 (d, J=8.4 Hz, 1H), 6.97 (d, J=7.8 Hz, 1H), 6.54 (t, J=7.8 Hz, 1H), 6.11 (d, J=7.5 Hz, 1H), 4.62-4.57 (m, 1H), 3.50 (s, 3H), 3.35-3.31 (m, 1H), 3.10-3.07 (m, 1H), 1.41 (d, J=7.2 Hz, 3H).

EXAMPLE 280

3-(2-amino-1-methyl-1H-benzo[d]imidazol-4-yl)-6-((S)-1-aminopropan-2-ylsulfonyl)-2-(2H-tetrazol-5-yl)benzenesulfonamide

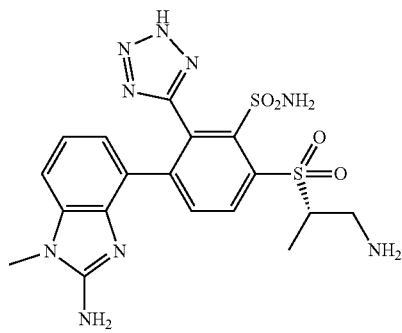 [SMILES: C[C@@H](CN)S(=O)(=O)c1ccc(-c2cccc3c2nc(N)n3C)c(-c2nn[nH]n2)c1S(N)(=O)=O]

Step A: (S)-tert-butyl (2-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate To a stirred solution of (S)-tert-butyl(2-((2-(N,N-bis(4-methoxybenzyl)sulfamoyl)-4-iodo-3-(2-(4-methoxybenzyl)-2H-tetrazol-5-yl)phenyl)sulfonyl)propyl)carbamate (0.20 g, 0.21 mmol) in 1,4-dioxane (3 mL) and water (0.5 mL) was added (2-amino-1-methyl-1H-benzo[d]imidazol-4-yl)boronic acid (0.12 g, 0.64 mmol), $Na_2CO_3$ (68 mg, 0.64 mmol) and $Pd(PPh_3)_4$ (49 mg, 0.04 mmol) under nitrogen atmosphere at room temperature. The resulting mixture was stirred at 80° C. overnight. The reaction mixture was diluted with water (50 mL) and extracted with EA (3×80 mL). The organic layer was dried over brine (3×80 mL), anhydrous $Na_2SO_4$ and filtered. The filtrate was concentrated in vacuum. The residue was purified by silica gel chromatography, eluting with 4% MeOH in DCM to afford the title compound as a solid: LCMS [M+1]$^+$952

Step B: (S)-3-(2-amino-1-methyl-1H-benzo[d]imidazol-4-yl)-6-((1-aminopropan-2-yl)sulfonyl)-N-(4-methoxybenzyl)-2-(2-(4-methoxybenzyl)-2H-tetrazol-5-yl)benzenesulfonamide A solution of (S)-tert-butyl(2-((4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propyl)carbamate (0.13 g, 0.13 mmol) in TFA (4 mL) was stirred at room temperature for 1 hour. The reaction mixture was evaporated in vacuum to afford the title compound as an oil: LCMS [M+1]$^+$732

Step C: (S)-3-(2-amino-1-methyl-1H-benzo[d]imidazol-4-yl)-6-((1-aminopropan-2-yl)sulfonyl)-2-(2H-tetrazol-5-yl)benzenesulfonamide A solution of (S)-3-(2-amino-1-methyl-1H-benzo[d]imidazol-4-yl)-6-((1-aminopropan-2-yl)sulfonyl)-N-(4-methoxybenzyl)-2-(2-(4-methoxybenzyl)-2H-tetrazol-5-yl)benzenesulfonamide (90 mg, 0.12 mmol) in TFA (4 mL) was stirred at 80° C. for 1 hour. The solvent was concentrated under reduced pressure. The residue was purified by Prep-HPLC. Column, Xbridge C18, 19×150 mm; mobile phase: acetonitrile in water (0.05% $NH_4HCO_3$), 5%-30% in 8 min; Detector, UV 254 nm. The collected fractions were combined and concentrated under vacuum to afford the title compound as a solid: LCMS [M+1]$^+$492; $^1$H NMR (300 MHz, DMSO-$d_6$) δ 8.23 (d, J=8.4 Hz, 1H), 8.04 (d, J=8.4 Hz, 1H), 6.99 (d, J=7.8 Hz, 1H), 6.57 (t, J=7.5 Hz, 1H), 6.14 (d, J=7.8 Hz, 1H), 4.63-4.58 (m, 1H), 3.50 (s, 3H), 3.34-3.32 (m, 1H), 3.14-3.12 (m, 1H), 1.42 (d, J=7.2 Hz, 3H).

EXAMPLE 281

6-((S)-3-amino-2-hydroxypropylsulfonyl)-3-(2-aminobenzo[d]thiazol-4-yl)-2-(2H-tetrazol-5-yl)benzenesulfonamide

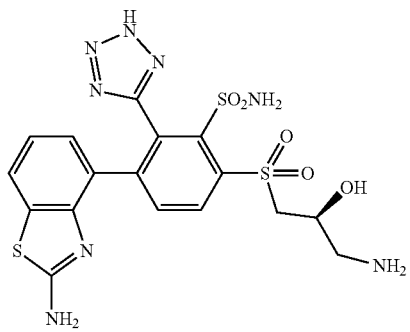 [SMILES: NC[C@H](O)CS(=O)(=O)c1ccc(-c2cccc3sc(N)nc23)c(-c2nn[nH]n2)c1S(N)(=O)=O]

Step A: (S)-tert-butyl (2,3-dihydroxypropyl)carbamate

In a 1000 mL RBF, di-tert-butyl dicarbonate (93 g, 428 mmol) was added to a stirred mixture of (S)-3-aminopropane-1,2-diol (30 g, 329 mmol), triethylamine (67 ml, 329 mmol) in MeOH (400 ml) at room temperature. The resulting mixture was stirred at RT for 2 hours and then concentrated under vacuum. The residue was purified by silica gel column chromatography, eluted with methanol/DCM (1/10) to give the title compound as a solid. $^1$H NMR (DMSOd-$_6$, 300 MHZ): 6.59 (br, 1H), 4.61 (d, J=4.5 Hz, 1H), 4.46 (t, J=5.7 Hz, 1H), 3.47-3.39 (m, 1H), 3.31-3.22 (m, 2H), 3.08-2.98 (m, 1H), 2.89-2.79 (m, 1H), 1.37 (s, 9H).

Step B: (S)-tert-butyl (2,3-bis((tert-butyldimethylsilyl)oxy)propyl)carbamate A solution of (S)-tert-butyl (2,3-dihydroxypropyl)carbamate (10 g, 52.3 mmol), tert-butylchlorodimethylsilane (17.34 g, 115 mmol) and 1H-imidazole (14.24 g, 209 mmol) in DCM (200 ml) was stirred at room temperature for 16 hours. The reaction mixture was filtered and filtrate was concentrated under vacuum. The residue was purified by silica gel chromatography, eluted with ethyl acetate/petroleum ether (1/3). The combined organic fractions were concentrated under reduced pressure to give the title compound as an oil. $^1$H NMR (CDCl$_3$, 300 MHZ): 4.81 (br, 1H), 3.77-3.65 (m, 1H), 3.53-3.36 (m, 2H), 3.23-3.05 (m, 2H), 1.38 (s, 9H), 0.86-0.81 (m, 18H), 0.04-0.00 (m, 12H).

Step C: (S)-tert-butyl (2-((tert-butyldimethylsilyl)oxy)-3-hydroxypropyl)carbamate (S)-tert-butyl (2,3-bis((tert-butyldimethylsilyl)oxy)propyl)carbamate (20 g, 47.6 mmol) was dissolved in DCM (20 ml), and acetic acid (100 ml, 47.6 mmol) was added. The reaction mixture was stirred at room temperature for 24 hours and then concentrated under vacuum. The residue was purified by silica gel chromatography, eluted with ethyl acetate/petroleum ether (30/70). The combined organic fractions were concentrated under reduced pressure to give the title compound as an oil.

Step D: (S)-3-(tert-butoxycarbonylamino)-2-(tert-butyldimethylsilyloxy)propyl methanesulfonate (S)-tert-butyl (2-((tert-butyldimethylsilyl)oxy)-3-hydroxypropyl)carbamate (2.0 g, 6.55 mmol) was dissolved in DCM (20 ml), then Et$_3$N (1.825 ml, 13.09 mmol) was added, and MsCl (0.765 ml, 9.82 mmol) was added at 0° C. The reaction mixture was stirred at room temperature for 1 hour, and then quenched with water (30 mL), extracted with ethyl acetate (3×30 mL). The combined organic layers were washed with water (2×30 mL) and brine (2×30 mL), dried over anhydrous magnesium sulfate and filtered. The filtrate was concentrated under vacuum to give (S)-3-(tert-butoxycarbonylamino)-2-(tert-butyldimethylsilyloxy)propyl methanesulfonate, which was used directly in next step. $^1$H NMR (300 MHz, DMSO-$d_6$) δ 6.87 (br, 1H), 4.18-4.05 (m, 1H), 4.03-3.83 (m, 2H), 3.12 (s, 3H), 2.95 (t, J=6.0 Hz, 2H), 1.34 (s, 9H), 0.81 (s, 9H), 0.08 (s, 6H).

Step E: (S)—S-(3-((tert-butoxycarbonyl)amino)-2-((tert-butyldimethylsilyl)oxy)propyl) ethanethioate A mixture of (S)-3-((tert-butoxycarbonyl)amino)-2-((tert-butyldimethylsilyl)oxy)propyl methanesulfonate (2.3 g, 6.00 mmol) and potassium ethanethioate (0.685 g, 6.00 mmol) in DMF (30 ml) was prepared. The reaction mixture was stirred at 50° C. overnight. The reaction mixture was diluted with water (100 mL) and extracted with ethyl acetate (3×100 mL). The combined organic layers were washed with brine (3×50 mL), dried over anhydrous sodium sulfate and filtered. The filtrate was concentrated under vacuum. The residue was purified by silica gel column chromatography, eluted with ethyl acetate/petroleum/ether (1/6) to give the title compound as an oil. LCMS [M+H]$^+$ 364; $^1$H NMR (300 MHz, Methanol-$d_4$) δ 3.85-3.81 (m, 1H), 3.04 (dd, J=5.9, 1.7 Hz, 2H), 2.96 (dd, J=5.6, 1.2 Hz, 2H), 2.30 (s, 3H), 1.41 (s, 9H), 0.87 (s, 9H), 0.08 (d, J=4.4 Hz, 6H).

Step F: (S)-tert-butyl (2-((tert-butyldimethylsilyl)oxy)-3-mercaptopropyl)carbamate A mixture of (S)—S-(3-((tert-butoxycarbonyl)amino)-2-((tert-butyldimethylsilyl)oxy)propyl) ethanethioate (1.9 g, 5.23 mmol) and Na$_2$CO$_3$ (1.385 g, 13.06 mmol) in methanol (20 ml) and water (4.0 ml) was prepared. The reaction mixture was stirred at room temperature for 1 hour. The reaction mixture was diluted with water (50 mL) and extracted with ethyl acetate (3×50 mL). The combined organic layers were washed with brine (3×50 mL), dried over anhydrous sodium sulfate and filtered. The filtrate was concentrated under vacuum to afford the title compound as an oil. LCMS [M+H]$^+$: 322

Step G: (S)-tert-butyl (3-((2-(N,N-bis(4-methoxybenzyl)sulfamoyl)-4-iodo-3-(2-(4-methoxybenzyl)-2H-tetrazol-5-yl)phenyl)thio)-2-((tert-butyldimethylsilyl)oxy)propyl)carbamate A mixture of 6-bromo-3-iodo-N,N-bis(4-methoxybenzyl)-2-(2-(4-methoxybenzyl)-2H-tetrazol-5-yl)benzenesulfonamide (1.3 g, 1.645 mmol), (S)-tert-butyl (2-((tert-butyldimethylsilyl)oxy)-3-mercaptopropyl)carbamate (1.322 g, 4.11 mmol) in DMF (15 ml) was prepared. NaH (0.145 g, 3.62 mmol) was added at 0° C. The reaction mixture was stirred at RT for 3 hours. The reaction mixture was diluted with water (100 mL) and extracted with ethyl acetate (3×100 mL). The combined organic layers were washed with brine (3×50 mL), dried over anhydrous sodium sulfate and filtered. The filtrate was concentrated under vacuum. The residue was purified by silica gel column chromatography, eluted with ethyl acetate/petroleum/ether (1/1) to give the title compound. LCMS [M+H]$^+$ 1031.

Step H: (S)-tert-butyl (3-((2-(N,N-bis(4-methoxybenzyl)sulfamoyl)-4-iodo-3-(2-(4-methoxybenzyl)-2H-tetrazol-5-yl)phenyl)thio)-2-hydroxypropyl)carbamate To a solution of (S)-tert-butyl (3-((2-(N,N-bis(4-methoxybenzyl)sulfamoyl)-4-iodo-3-(2-(4-methoxybenzyl)-2H-tetrazol-5-yl)phenyl)thio)-2-((tert-butyldimethylsilyl)oxy)propyl)carbamate (2.5 g, 2.425 mmol) was dissolved in THF (40 ml), TBAF (4.85 ml, 4.85 mmol) was added at 0° C. The reaction mixture was stirred at room temperature for 1 hour. The reaction mixture was quenched with water (50 mL), extracted with ethyl acetate (3×50 mL). The combined organic layers were washed with water (2×30 mL) and brine (2×30 mL), dried over anhydrous magnesium sulfate and filtered. The filtrate was concentrated under vacuum. The residue was purified by silica gel column chromatography, eluted with ethyl acetate/petroleum ether (2/1). The combined organic fractions were concentrated under reduced pressure to give the title compound as a solid. LCMS [M+H]$^+$: 917

Step I: (S)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate (S)-tert-butyl (3-((2-(N,N-bis(4-methoxybenzyl)sulfamoyl)-4-iodo-3-(2-(4-methoxybenzyl)-2H-tetrazol-5-yl)phenyl)thio)-2-hydroxypropyl)carbamate (1.3 g, 1.418 mmol) was dissolved in DCM (15 ml). 3-chlorobenzoperoxoic acid (0.979 g, 5.67 mmol) was added in portion. The reaction mixture was stirred at room temperature overnight. The residue was purified by silica gel column chromatography, eluted with ethyl acetate/petroleum ether (1/1). The combined organic fractions were concentrated under reduced pressure to give the title compound as a solid. LCMS [M+H]$^+$ 949.

Step J: (S)-tert-butyl (3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-2-hydroxypropyl)carbamate A mixture of (S)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate (500 mg, 0.527 mmol), (2-aminobenzo[d]thiazol-4-yl)boronic acid (204 mg, 1.054 mmol), Na$_2$CO$_3$ (168 mg, 1.581 mmol) and Pd(Ph$_3$P)$_4$ (91 mg, 0.079 mmol) in dioxane/H$_2$O=4/1 (5.0 ml) was prepared. The reaction mixture was stirred at 80° C. for 16 hours and then concentrated under vacuum. The residue was purified by silica gel chromatography, eluted with methanol/DCM (1/10). The combined organic fractions were concentrated under reduced pressure to give the title compound. LCMS [M+H]$^+$ 971.

Step K: 6-((S)-3-amino-2-hydroxypropylsulfonyl)-3-(2-aminobenzo[d]thiazol-4-yl)-N-(4-methoxybenzyl)-2-(2-(4-methoxybenzyl)-2H-tetrazol-5-yl)benzenesulfonamide (S)-tert-butyl (3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-2-hydroxypropyl)carbamate (330 mg, 0.340 mmol) was dissolved in DCM (8.0 ml). TFA (3.0 ml, 38.9 mmol) was added at 0° C. The reaction mixture was stirred at room temperature for 1 hour.

The reaction was concentrated under vacuum to give the title compound, which was used in next step directly without further purification. LCMS [M+H]$^+$ 751

Step L: (S)-6-((3-amino-2-hydroxypropyl)sulfonyl)-3-(2-aminobenzo[d]thiazol-4-yl)-2-(2H-tetrazol-5-yl)benzenesulfonamide (S)-6-((3-amino-2-hydroxypropyl)sulfonyl)-3-(2-aminobenzo[d]thiazol-4-yl)-N-(4-methoxybenzyl)-2-(2-(4-methoxybenzyl)-2H-tetrazol-5-yl)benzenesulfonamide (180 mg, 0.240 mmol) was dissolved in TFA (5 mL, 64.9 mmol). The reaction mixture was stirred at 80° C. for 1 hour. The solvent was removed under vacuum. The product was purified by Prep-HPLC with the following conditions: Column: XBridge Prep C18 OBD Column 19×250 mm 10 μM; Mobile Phase A: water with 10 mmol of NH$_4$HCO$_3$, Mobile Phase B: ACN; Flow rate: 25 mL/min; Gradient: 10% B to 30% B in 8 min; 254/220 nm. The collected fractions were combined and concentrated under vacuum to give the title compound as a solid. LCMS [M+H]$^+$ 511. $^1$H NMR (300 MHz, DMSO-d$_6$/D2O) δ 8.21 (d, J=8.4 Hz, 1H), 7.77 (d, J=8.4 Hz, 1H), 7.41 (d, J=7.8 Hz, 1H), 6.69 (t, J=7.7 Hz, 1H), 6.51 (d, J=7.5 Hz, 1H), 4.41-4.30 (m, 1H), 4.18-3.91 (m, 1H), 3.08-2.99 (m, 1H), 2.89-2.78 (m, 1H).

EXAMPLE 282

3-(2-amino-1H-benzo[d]imidazol-4-yl)-6-((S)-3-amino-2-hydroxypropyl sulfonyl)-2-(2H-tetrazol-5-yl)benzenesulfonamide

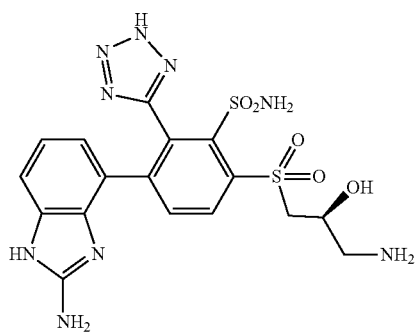 [SMILES: NC[C@H](O)CS(=O)(=O)c1ccc(-c2cccc3[nH]c(N)nc23)c(-c2nn[nH]n2)c1S(N)(=O)=O]

Step A: (S)-tert-butyl (3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)-2-hydroxypropyl)carbamate A mixture of (S)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate (prepared as described in EXAMPLE 281, Steps A-H, 200 mg, 0.211 mmol), (2-amino-1H-benzo[d]imidazol-4-yl)boronic acid (74.6 mg, 0.422 mmol), $Na_2CO_3$ (67.0 mg, 0.632 mmol) and $Pd(Ph_3P)_4$ (36.5 mg, 0.032 mmol) in dioxane/$H_2O$=4/1 (0.5 ml) was prepared. The reaction mixture was stirred at 80° C. for 8 hours. The solids were filtered out and the filtrate was concentrated. The residue was purified by silica gel column chromatography, eluted with methanol/DCM (1/10) to give the title compound as a solid. LCMS [M+H]$^+$: 954

Step B: 3-(2-amino-1H-benzo[d]imidazol-4-yl)-6-((S)-3-amino-2-hydroxypropylsulfonyl)-N-(4-methoxybenzyl)-2-(2-(4-methoxybenzyl)-2H-tetrazol-5-yl)benzenesulfonamide (S)-tert-butyl (3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)-2-hydroxypropyl)carbamate (152 mg, 0.159 mmol) was dissolved in DCM (3.0 ml), then TFA (1.5 ml, 19.47 mmol) was added at 0° C. The reaction mixture was stirred at room temperature for 1 hour and then concentrated under vacuum to give the title compound, which was used in the next step directly. LCMS [M+H]$^+$: 734.

Step C: (S)-3-(2-amino-1H-benzo[d]imidazol-4-yl)-6-((3-amino-2-hydroxypropyl)sulfonyl)-2-(2H-tetrazol-5-yl)benzenesulfonamide (S)-3-(2-amino-1H-benzo[d]imidazol-4-yl)-6-((3-amino-2-hydroxypropyl)sulfonyl)-N-(4-methoxybenzyl)-2-(2-(4-methoxybenzyl)-2H-tetrazol-5-yl)benzenesulfonamide (100 mg, 0.136 mmol) was dissolved in TFA (3.0 mL, 38.9 mmol). The reaction mixture was stirred at 80° C. for 1 hour. The solvent was removed under vacuum. The product was purified by Prep-HPLC with the following conditions: Column: XBridge C18 OBD Prep Column, 100 Å, 5 μm, 19 mm×250 mm; Mobile Phase A: water with 10 mmol of $NH_4HCO_3$, Mobile Phase B: ACN; Flow rate: 20 mL/min; Gradient: 5% B to 23% B in 8 min; 254 nm. The collected fractions were combined and concentrated under vacuum to give the title compound as a solid. LCMS [M+H]$^+$ 494; $^1$H NMR (300 MHz, DMSO-$d_6$/D2O): δ 8.24 (d, J=8.4 Hz, 1H), 7.85 (d, J=8.3 Hz, 1H), 6.91 (d, J=7.6 Hz, 1H), 6.63-6.60 (m, 1H), 6.23-6.19 (m, 1H), 4.28-4.19 (m, 1H), 4.11-3.98 (m, 2H), 3.01-2.83 (m, 1H), 2.86-2.71 (m, 1H).

EXAMPLE 283

3-(2-amino-1-ethyl-1H-benzo[d]imidazol-4-yl)-6-(azetidin-3-ylsulfonyl)-2-(2H-tetrazol-5-yl)benzenesulfonamide

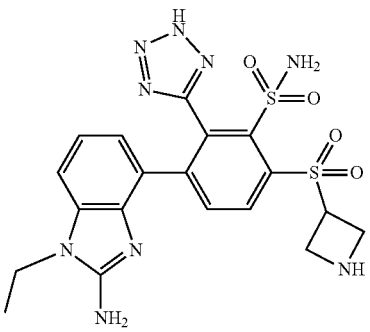 [SMILES: CCn1c(N)nc2c(-c3ccc(S(=O)(=O)C4CNC4)c(S(N)(=O)=O)c3-c3nn[nH]n3)cccc21]

Step A: 3-bromo-N-ethyl-2-nitrobenzenamine

To the solution of ethanamine in THF (2M) was added 1-bromo-3-fluoro-2-nitrobenzene (10 g, 54 mmol) at room temperature. The resulting solution was stirred in sealed tube at 80° C. for 2 hours and then concentrated under vacuum to give the title compound as a solid: LCMS [M+H]$^+$: 244; $^1$H NMR (400 MHz, CDCl$_3$) δ 7.26 (t, J=8.0 Hz, 1H), 689 (d, J=8.0 Hz, 1H), 6.71 (d, J=8.2 Hz, 1H), 3.39 (q, J=3.9 Hz, 2H), 1.45 (t, J=3.9 Hz, 3H).

Step B: 3-bromo-N1-ethylbenzene-1,2-diamine

To a stirred solution of 3-bromo-N-ethyl-2-nitrobenzenamine (10.5 g, 43 mmol) and Zn dust (14 g, 0.2 mmol) in MeOH (200 mL), HCl (12 M) was added dropwise at room temperature. After the resulting mixture was stirred at 50° C. for 1 hour, it was filtered. The filtrate was concentrated under vacuum to give the title compound as a solid. LCMS [M+H]$^+$: 215; $^1$H NMR (400 MHz, CD$_3$OD) δ 6.91-6.81 (m, 1H), 6.65-6.58 (m, 2H), 3.15 (q, J=7.1 Hz, 2H), 1.30 (t, J=7.1 Hz, 3H).

Step C: 4-bromo-1-ethyl-1H-benzo[d]imidazol-2-amine

A solution of 3-bromo-N1-ethylbenzene-1,2-diamine (8.3 g, 39 mmol) and BrCN (1.68 g, 16 mmol) in MeOH (100 mL) was stirred at room temperature for 4 hours. The reaction mixture was poured into the saturated NaHCO$_3$ solution. The precipitate was collected and dried under vacuum to give the title compound as a solid: LCMS [M+H]$^+$: 240; $^1$H NMR (400 MHz, DMSO-$d_6$): δ 7.14-7.10 (m, 2H), 6.81 (t, J=7.8 Hz, 1H), 6.73 (s, 2H), 4.01 (q, J=7.1 Hz, 2H), 1.20 (t, J=7.1 Hz, 3H).

Step D: 2-amino-1-ethyl-1H-benzo[d]imidazol-4-ylboronic Acid 100 ml of 1,4-dioxane solution of 4-bromo-1-ethyl-1H-benzo[d]imidazol-2-amine (1 g, 4 mmol), bis(pinacolato)diboron (4.7 g, 18.6 mmol) and potassium acetate (4.5 g, 46.5 mmol) was stirred at 80° C. for 4 hours under nitrogen. The reaction mixture was concentrated under vacuum and the residue was purified by Prep-HPLC with the following conditions: Column, Sunfire C18, 19×150 mm; mobile phase: water (0.05% TFA) and acetonitrile (Gradient time: 7 min. B %: 10%-20%); Detector, UV 220 and 254 nm. The collected fractions were combined and concentrated under vacuum to give the title compound as a solid. LCMS [M+H]⁺: 206; ¹H NMR (400 MHz, CDCl₃): δ 7.70-7.20 (m, 3H), 3.35-3.30 (m, 2H), 1.42-1.39 (m, 3H).

Step E: tert-butyl 3-(4-(2-amino-1-ethyl-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)azetidine-1-carboxylate A mixture of tert-butyl 3-(2-(N,N-bis(4-methoxybenzyl)sulfamoyl)-4-iodo-3-(2-(4-methoxybenzyl)-2H-tetrazol-5-yl)phenylsulfonyl)azetidine-1-carboxylate (200 mg, 0.215 mmol), 2-amino-1-ethyl-1H-benzo[d]imidazol-4-ylboronic acid (67 mg, 0.322 mmol), Na₂CO₃ (68 mg, 0.644 mmol) and tetrakis(triphenylphosphine)palladium (0) (50 mg, 0.043 mmol) in dioxane (4 mL) and water (1 mL) was stirred at 80° C. for 2 hours. The reaction mixture was concentrated under vacuum and the residue was purified by silica gel chromatography and eluted with methanol/DCM (1/10). The combined organic fractions were concentrated under reduced pressure to give the title compound as a solid. LCMS [M+H]⁺: 964.

Step F: 3-(2-amino-1-ethyl-1H-benzo[d]imidazol-4-yl)-6-(azetidin-3-ylsulfonyl)-N-(4-methoxybenzyl)-2-(2-(4-methoxybenzyl)-2H-tetrazol-5-yl)benzenesulfonamide A solution mixture of tert-butyl 3-(4-(2-amino-1-ethyl-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)azetidine-1-carboxylate (162 mg, 0.168 mmol) and TFA (1 mL, 12.98 mmol) in DCM (5 mL) was stirred at room temperature for 1 hour. The reaction mixture was concentrated under vacuum to give the title compound, which was used in the next step directly. LCMS [M+H]⁺: 744.

Step G: 3-(2-amino-1-ethyl-1H-benzo[d]imidazol-4-yl)-6-(azetidin-3-ylsulfonyl)-2-(2H-tetrazol-5-yl)benzenesulfonamide A solution of 3-(2-amino-1-ethyl-1H-benzo[d]imidazol-4-yl)-6-(azetidin-3-ylsulfonyl)-N-(4-methoxybenzyl)-2-(2-(4-methoxybenzyl)-2H-tetrazol-5-yl)benzenesulfonamide (119 mg, 0.117 mmol) in TFA (5 mL, 65 mmol) was stirred at 80° C. for 2 hours. The reaction mixture was concentrated under vacuum and the residue was purified by Prep-HPLC with the following conditions: Column: X Bridge C18, 19×150 mm, 5 μM; Mobile Phase A: water/0.05% ACOH Mobile Phase B: ACN; Flow rate: 20 mL/min; Gradient: 30% B to 70% B in 10 min; 254 nm. The collected fractions were combined and concentrated under vacuum to give the title compound as a solid. LCMS [M+H]⁺: 504. ¹H NMR (DMSO-d₆, 400 MHz): 8.26 (d, J=8.4 Hz, 1H), 8.11 (d, J=8.4 Hz, 1H), 7.80 (brs, 2H), 6.98 (d, J=7.8 Hz, 1H), 6.54-6.49 (m, 3H), 6.11 (d, J=7.8 Hz, 1H), 5.27-5.19 (m, 1H), 4.27-4.13 (m, 4H), 4.04-3.97 (m, 2H), 1.23-1.15 (m, 3H).

EXAMPLE 284

3-(2-amino-1-ethyl-1H-benzo[d]imidazol-4-yl)-6-(2-aminoethylsulfonyl)-2-(2H-tetrazol-5-yl)benzenesulfonamide

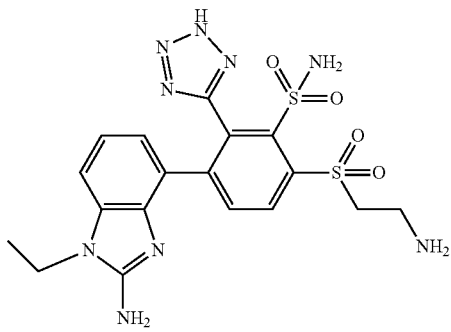 [SMILES: CCn1c(N)nc2c(-c3ccc(S(=O)(=O)CCN)c(S(N)(=O)=O)c3-c3nn[nH]n3)cccc21]

Step A: tert-butyl 2-(4-(2-amino-1-ethyl-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)ethylcarbamate A mixture of 6-(2-aminoethylsulfonyl)-3-iodo-N,N-bis(4-methoxybenzyl)-2-(2-(4-methoxybenzyl)-2H-tetrazol-5-yl)benzenesulfonamide (200 mg, 0.244 mmol), 2-amino-1-ethyl-1H-benzo[d]imidazol-4-yl boronic acid (100 mg, 0.488 mmol), Na₂CO₃ (77 mg, 0.732 mmol) and tetrakis(triphenylphosphine)palladium (0) (56 mg, 0.049 mmol) in dioxane (4 mL) and water (1 mL) was stirred at 80° C. for 2 hours. The reaction mixture was then concentrated under vacuum and the residue was purified by silica gel chromatography, eluted with methanol/DCM (1/10). The combined organic fractions were concentrated under reduced pressure to give the title compound as a solid: LCMS [M+H]⁺: 952.

Step B: 3-(2-amino-1-ethyl-1H-benzo[d]imidazol-4-yl)-6-(2-aminoethylsulfonyl)-N-(4-methoxybenzyl)-2-(2-(4-methoxybenzyl)-2H-tetrazol-5-yl)benzenesulfonamide To a solution of tert-butyl 2-(4-(2-amino-1-ethyl-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)ethylcarbamate (198 mg, 0.198 mmol) in DCM (5 mL), TFA (1 mL, 12.98 mmol) was added dropwise at 0° C. The resulting solution was stirred at room temperature for 1 hr and then concentrated under vacuum to give the title compound, which was used in the next step directly without further purification. LCMS [M+H]⁺: 732.

Step C: 3-(2-amino-1-ethyl-1H-benzo[d]imidazol-4-yl)-6-(2-aminoethylsulfonyl)-2-(2H-tetrazol-5-yl)benzenesulfonamide A solution of 3-(2-amino-1-ethyl-1H-benzo[d]imidazol-4-yl)-6-(2-aminoethylsulfonyl)-N-(4-methoxybenzyl)-2-(2-(4-methoxybenzyl)-2H-tetrazol-5-yl)benzenesulfonamide (139 mg, 0.190 mmol) in TFA (5 mL, 65 mmol) was stirred at 80° C. for 1 hr. The reaction mixture was concentrated under vacuum and the residue was purified by Prep-HPLC with the following conditions: Column: X Bridge C18, 19×150 mm, 5 μm; Mobile Phase A: water/0.05% of NH$_4$HCO$_3$, Mobile Phase B: ACN; Flow rate: 20 mL/min; Gradient: 30-70% B in 10 min; 254 nm. The collected fractions were combined and concentrated under vacuum to give the title compound as a solid: LCMS [M+H]$^+$: 492; $^1$H NMR (400 MHz, DMSO-d$_6$): δ 8.25 (d, J=8.4 Hz, 1H), 8.11 (d, J=8.4 Hz, 1H), 7.60 (brs, 4H), 6.98 (d, J=7.2 Hz, 1H), 6.66-6.49 (m, 3H), 6.09 (d, J=7.2 Hz, 1H), 4.14-4.09 (m, 2H), 4.04-3.95 (m, 2H), 3.32-3.23 (m, 2H), 1.23-1.16 (m, 3H).

EXAMPLE 285

3-(2-aminobenzo[d]thiazol-4-yl)-6-((R)-1-aminopropan-2-ylsulfonyl)-2-(2H-tetrazol-5-yl)benzenesulfonamide

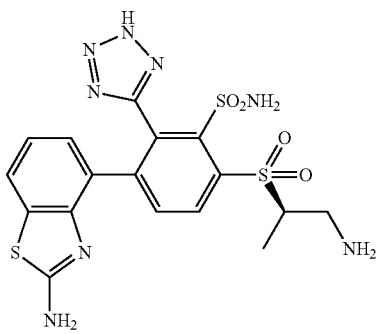 [SMILES: C[C@H](CN)S(=O)(=O)c1ccc(-c2cccc3sc(N)nc23)c(-c2nn[nH]n2)c1S(N)(=O)=O]

Step A: tert-butyl ((2R)-2-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonyl)propyl)carbamate In a 25 ml sealed tube was placed a solution of tert-butyl ((2R)-2-((2-(N,N-bis(4-methoxybenzyl)sulfamoyl)-4-iodo-3-(1-(4-methoxybenzyl)-1H-tetrazol-5-yl)phenyl)sulfonyl)propyl)carbamate (0.20 g, 0.21 mmol) in dioxane (10 mL) and water (2 mL), followed by the addition of Pd(PPh$_3$)$_4$ (50 mg, 0.04 mmol), (2-aminobenzo[d]thiazol-4-yl)boronic acid (92 mg, 0.47 mmol) and Na$_2$CO$_3$ (68 mg, 0.64 mmol). After the resulting mixture was degassed with nitrogen 3 times and stirred at 80° C. for 16 hours, it was diluted with water (50 mL) and extracted with ethyl acetate (3×50 mL). The combined organic layers were washed with water (2×50 mL), brine (2×50 mL), dried over anhydrous sodium sulfate, filtered and concentrated under vacuum. The residue was applied onto a silica gel column chromatography, eluted with methanol/DCM (1/10) to give the title compound as a solid: LCMS [M+H]$^+$: 955.

Step B: (R)-3-(2-aminobenzo[d]thiazol-4-yl)-6-((1-aminopropan-2-yl)sulfonyl)-N-(4-methoxybenzyl)-2-(2H-tetrazol-5-yl)benzenesulfonamide A solution of (R)-tert-butyl(2-((4-(2-aminobenzo[d]thiazol-4-yl)-2-(N,N-bis(4-methoxybenzyl)-sulfamoyl)-3-(2-(4-methoxybenzyl)-2H-tetrazol-5-yl)phenyl)sulfonyl)propyl)carbamate (0.13 g, 0.13 mmol) in TFA (4 mL) was stirred at room temperature for 1 hr. The reaction mixture was evaporated in vacuum to afford the title compound as an oil: LCMS [M+H]$^+$: 735.

Step C: (R)-3-(2-aminobenzo[d]thiazol-4-yl)-6-((1-aminopropan-2-yl)sulfonyl)-2-(2H-tetrazol-5-yl)benzenesulfonamide A solution of (R)-3-(2-aminobenzo[d]thiazol-4-yl)-6-((1-aminopropan-2-yl)sulfonyl)-N-(4-methoxybenzyl)-2-(2H-tetrazol-5-yl)benzenesulfonamide (75 mg, 0.12 mmol) in TFA (5 mL) as stirred at 80° C. for 1 hr. The reaction solvent was concentrated under vacuum and the residue was purified by Prep-HPLC. Column, Xbridge C18, 19×150 mm; mobile phase: acetonitrile in water (0.05% TFA), 5%-30% in 8 min; Detector, UV 254 nm to get the title compound as a solid: LCMS [M+H]$^+$: 495; $^1$H NMR (400 MHz, DMSO-d$_6$) δ 8.19 (d, J=8.0 Hz, 1H), 7.88 (d, J=8.4 Hz, 1H), 7.46 (d, J=8.0 Hz, 1H), 6.70 (t, J=8.0 Hz, 1H), 6.48 (d, J=6.8 Hz, 1H), 4.65-4.60 (m, 1H), 3.37-3.32 (m, 1H), 3.13-3.08 (m, 1H), 1.40 (d, J=6.8 Hz, 3H).

EXAMPLE 286

3-(2-aminobenzo[d]thiazol-4-yl)-6-((S)-1-aminopropan-2-ylsulfonyl)-2-(2H-tetrazol-5-yl)benzenesulfonamide

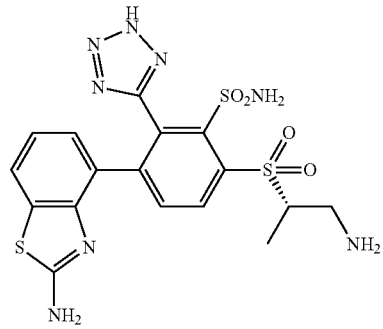 [SMILES: C[C@@H](CN)S(=O)(=O)c1ccc(-c2cccc3sc(N)nc23)c(-c2nn[nH]n2)c1S(N)(=O)=O]

Step A: (S)-tert-butyl(2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)-propyl)carbamate To a stirred solution of (S)-tert-butyl(2-((2-(N,N-bis(4-methoxybenzyl)sulfamoyl)-4-iodo-3-(2-(4-meth-oxybenzyl)-2H-tetrazol-5-yl)phenyl)sulfonyl)propyl)carbamate (0.20 g, 0.21 mmol) in 1,4-dioxane (3 mL) and water (0.5 mL) were added (2-aminobenzo[d]thiazol-4-yl)boronic acid (0.10 g, 0.54 mmol), Na$_2$CO$_3$ (68 mg, 0.64 mmol) and Pd(dppf)Cl$_2$ (35 mg, 0.04 mmol) under nitrogen atmosphere at room temperature. The resulting mixture was stirred at 80° C. overnight and then cooled to room temperature, diluted with water (50 mL) and extracted with ethyl acetate (3×50 mL). The combined organic layers were washed with water (2×50 mL), brine (2×50 mL), dried over sodium sulfate and filtered. The filtrate was concentrated under reduced pressure and the residue was purified by silica gel chromatography, eluted with 3% MeOH in DCM to afford the title compound as a solid: LCMS [M+H]$^+$: 955.

Step B: (S)-3-(2-aminobenzo[d]thiazol-4-yl)-6-((1-aminopropan-2-yl)sulfonyl)-N-(4-methoxybenzyl)-2-(2H-tetrazol-5-yl)benzenesulfonamide A solution of (S)-tert-butyl(2-((4-(2-aminobenzo[d]thiazol-4-yl)-2-(N,N-bis(4-methoxybenzyl)sulfamoyl)-3-(2-

(4-methoxybenzyl)-2H-tetrazol-5-yl)phenyl)sulfonyl)propyl)carbamate (0.12 g, 0.13 mmol) in TFA (4 mL) was stirred at room temperature for 1 hr and then evaporated in vacuum to afford the title compound as an oil, which was used in the next step directly without further purification: LCMS [M+H]+: 735.

Step C: (S)-3-(2-aminobenzo[d]thiazol-4-yl)-6-((1-aminopropan-2-yl)sulfonyl)-2-(2H-tetrazol-5-yl)benzenesulfonamide A solution of (S)-3-(2-aminobenzo[d]thiazol-4-yl)-6-((1-aminopropan-2-yl)sulfonyl)-N-(4-methoxybenzyl)-2-(2H-tetrazol-5-yl)benzenesulfonamide (80 mg, 0.13 mmol) in TFA (5 mL) was stirred at 80° C. for 1 hr. The reaction solvent was concentrated under vacuum. The residue was purified by Prep-HPLC. Column, Xbridge C18, 19×150 mm; mobile phase: acetonitrile in water (0.05% NH$_4$HCO$_3$), 5%-30% in 8 min; Detector, UV 254 nm. The collected fractions were combined and concentrated under reducing pressure to afford the title compound as a solid: LCMS [M+H]+: 495; $^1$H NMR (300 MHz, DMSO-d$_6$) δ 8.26 (d, J=9.0 Hz, 1H), 7.94 (d, J=8.4 Hz, 1H), 7.51 (d, J=7.5 Hz, 1H), 6.74 (t, J=8.0 Hz, 1H), 6.60 (d, J=6.8 Hz, 1H), 4.66-4.62 (m, 1H), 3.38-3.35 (m, 1H), 3.19-3.16 (m, 1H), 1.43 (d, J=6.9 Hz, 3H).

EXAMPLE 287

2'-amino-4-(azetidin-3-ylsulfonyl)-2-(2H-tetrazol-5-yl)biphenyl-3,3'-disulfonamide

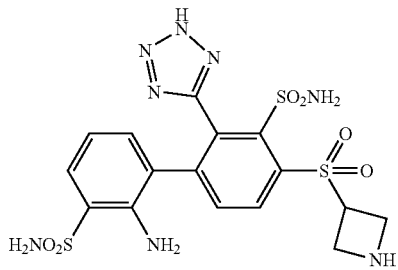 [SMILES: Nc1c(-c2ccc(S(=O)(=O)C3CNC3)c(S(N)(=O)=O)c2-c2nn[nH]n2)cccc1S(N)(=O)=O]

Step A: 5-bromo-2H-benzo[e][1,2,4]thiadiazin-3(4H)-one 1,1-dioxide

A solution of 2-bromoaniline (1 g, 5.81 mmol) in EtNO$_2$ (1 ml) was added to a stirred solution of sulfurisocyanatidic chloride (0.905 g, 6.39 mmol) in EtNO$_2$ (9.00 ml) at −40° C. during 5 minutes (the chlorosulphonylurea intermediates crystallised out). The reaction mixture was warmed to 0° C., and aluminum chloride (0.853 g, 6.39 mmol) was added. The resulting mixture was heated at 110° C. for 20 minutes, then cooled to room temperature and poured into ice-water. The precipitated solid was collected, washed with water, and dried to give the title compound as a solid: LCMS [M+H]+: 277, 279 (1:1); $^1$H NMR (400 MHz, DMSO-d$_6$): δ 10.16 (s, 1H), 7.94 (d, J=8.0 Hz, 1H), 7.80 (d, J=7.6 Hz, 1H), 7.30-7.21 (m, 1H).

Step B: 2-amino-3-bromobenzenesulfonamide 5-bromo-2H-benzo[e][1,2,4]thiadiazin-3(4H)-one 1,1-dioxide (100 mg, 0.361 mmol) was added to H$_2$SO$_4$ (3 ml, 28.1 mmol) and the mixture was stirred at 130° C. for 4 hours until a solution resulted. After dilution with ice-water and neutralizing with NaOH (40%), the product was precipitated out. The solid was collected, washed with water and dried to give the title compound as a solid: LCMS [M+H]+: 251, 253 (1:1); $^1$H NMR (400 MHz, DMSO-d$_6$): δ 7.70-7.61 (m, 2H), 7.48 (s, 2H), 6.63-6.59 (m, 1H), 5.86 (s, 2H).

Step C: 2-amino-3-(4,4,5,5-tetramethyl-1,3,2-dioxaborolan-2-yl)benzenesulfonamide To a solution of 2-amino-3-bromobenzenesulfonamide (500 mg, 1.991 mmol) in dioxane (5 ml) was added Pd(dppf)Cl$_2$ (353 mg, 0.597 mmol), 4,4,4',4',5,5,5',5'-octamethyl-2,2'-bi(1,3,2-dioxaborolane) (1011 mg, 3.98 mmol) and potassium acetate (586 mg, 5.97 mmol) with stirring at room temperature. The resulting mixture was degassed 3 times with N$_2$, then warmed to 80° C. and stirred for 16 hours. The reaction mixture was filtered; the filtrate was collected and concentrated under vacuum. The residue was purified by column chromatography on silica gel Isolute Flash Si; 20 g prepacked, eluting with EA/PE (0-10%) to give the title compound as a solid: LCMS [M+H]+: 299; $^1$H NMR (400 MHz, CDCl$_3$): δ 7.90-7.85 (m, 2H), 6.86-6.82 (m, 1H), 4.93 (s, 2H), 1.36 (s, 12H).

Step D: tert-butyl 3-((2'-amino-3-(N,N-bis(4-methoxybenzyl)sulfamoyl)-2-(2-(4-methoxybenzyl)-2H-tetrazol-5-yl)-3'-sulfamoyl-[1,1'-biphenyl]-4-yl)sulfonyl)azetidine-1-carboxylate Pd(dppf)Cl$_2$ (31.4 mg, 0.043 mmol), tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (200 mg, 0.215 mmol) and Na$_2$CO$_3$ (45.5 mg, 0.430 mmol) were added to a stirred mixture of 2-amino-3-(4,4,5,5-tetramethyl-1,3,2-dioxaborolan-2-yl)benzenesulfonamide (128 mg, 0.430 mmol) in 1,4-dioxane (0.3 ml) and water (0.1 ml). The resulting mixture was degassed 3 times with N$_2$, and stirred at 80° C. for 3 hours. The mixture was filtered, washing with ethyl acetate (30 mL). The organic layer was washed with brine (3×20 mL), dried over anhydrous Na$_2$SO$_4$ and concentrated. The residue was purified by column chromatography, eluted with EA/PE (0-60%) to give the title compound as a solid: LCMS ([M+H]+: 975

Step E: 2'-amino-4-(azetidin-3-ylsulfonyl)-2-(2H-tetrazol-5-yl)-[1,1'-biphenyl]-3,3'-disulfonamide tert-butyl 3-((2'-amino-3-(N,N-bis(4-methoxybenzyl)sulfamoyl)-2-(2-(4-methoxybenzyl)-2H-tetrazol-5-yl)-3'-sulfamoyl-[1,1'-biphenyl]-4-yl)sulfonyl)azetidine-1-carboxylate (130 mg, 0.133 mmol) was added to DCM (3 ml) and TFA (1 ml) at 0° C. and the resulting solution was stirred at room temperature for 1 hr. The reaction solution was evaporated under reduced pressure. To the residue was added TFA (4 ml) and the mixture was stirred at 80° C. for 1 hr. The reaction solution was evaporated under reduced pressure. The crude product was purified by Prep-HPLC with the following conditions: Column: XSelect CSH Prep C18 OBD Column, 19×150 mm; Mobile Phase A: water with 10 mmol NH$_4$HCO$_3$, Mobile Phase B: MeCN; Flow rate: 20 mL/min; Gradient: 8% B to 30% B in 8 min; 254/220 nm. The collected fractions were concentrated under vacuum to afford the title compound as a solid: LCMS [M+H]+: 515;

¹H NMR (400 MHz, DMSO-d₆): δ 8.30 (d, J=8.0 Hz, 1H), 7.77 (d, J=8.0 Hz, 1H), 7.45-7.43 (m, 1H), 7.35 (s, 2H), 6.55-6.53 (m, 1H), 6.44-6.30 (m, 1H), 5.33 (s, 2H), 5.23-5.19 (m, 1H), 4.30-4.22 (m, 4H).

EXAMPLE 288

2-amino-N-(2-aminoethyl)-4'-(azetidin-3-ylsulfonyl)-5'-sulfamoyl-6'-(2H-tetrazol-5-yl)biphenyl-3-carboxamide

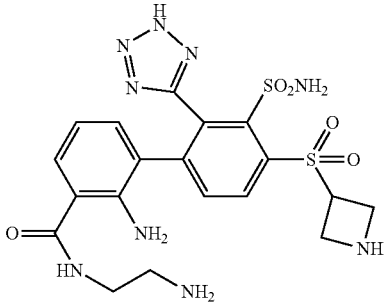 [SMILES: NCCNC(=O)c1cccc(-c2ccc(S(=O)(=O)C3CNC3)c(S(N)(=O)=O)c2-c2nn[nH]n2)c1N]

Step A: tert-butyl 3-((2'-amino-3-(N,N-bis(4-methoxybenzyl)sulfamoyl)-3'-((2-((tert-butoxycarbonyl)amino)ethoxy)(imino)methyl)-2-(2-(4-methoxybenzyl)-2H-tetrazol-5-yl)-[1,1'-biphenyl]-4-yl)sulfonyl)azetidine-1-carboxylate To a solution of 2-amino-3'-(N,N-bis(4-methoxybenzyl)sulfamoyl)-4'-((1-(tert-butoxycarbonyl)azetidin-3-yl)sulfonyl)-2'-(2-(4-methoxybenzyl)-2H-tetrazol-5-yl)-[1,1'-biphenyl]-3-carboxylic acid (160 mg, 0.170 mmol), HATU (97 mg, 0.255 mmol) and tert-butyl (2-aminoethyl)carbamate (109 mg, 0.681 mmol) in DMF (2 ml) was added DIEA (0.045 ml, 0.255 mmol) with stirring at 0° C. The reaction solution was degassed with nitrogen 3 times. The resulting solution was warmed to 0° C. and stirred for 4 hours. The reaction solution was cooled to room temperature, diluted with water (5 mL) and extracted with ethyl acetate (3×10 mL). The combined organic layers were washed with brine (3×20 mL), dried over anhydrous sodium sulfate and filtered. The filtrate was concentrated under vacuum to afford a solid. The residue was purified by silica gel column chromatography 20 g, eluted with EtOAc/petroleum ether (1/1) to afford the title compound as a solid: LCMS [M+H]⁺: 1082.

Step B: 2-amino-N-(2-aminoethyl)-4'-(azetidin-3-ylsulfonyl)-3'-sulfamoyl-2'-(2H-tetrazol-5-yl)-[1,1'-biphenyl]-3-carboxamide To a solution of tert-butyl (2-(2-amino-4'-(azetidin-3-ylsulfonyl)-3'-(N,N-bis(4-methoxybenzyl)sulfamoyl)-2'-(2-(4-methoxybenzyl)-2H-tetrazol-5-yl)-[1,1'-biphenyl]-3-ylcarboxamido)ethyl)carbamate (100 mg, 0.102 mmol) in DCM (2 ml) was added TFA (0.5 ml) with stirring at room temperature. The resulting solution was warmed to room temperature and stirred for 1 hr. The reaction solution was concentrated under vacuum to afford a residue. To the residue was added TFA (2 ml) with stirring at room temperature. The resulting solution was warmed to 80° C. and stirred for 1 hr. The resulting solution was concentrated under vacuum and the residue was purified by Prep-HPLC with the following conditions: Column: XBridge C18 OBD Prep Column, 100 Å, 5 μm, 19 mm×250 mm; Mobile Phase A: water with 10 mmol of NH₄HCO₃, Mobile Phase B: ACN; Flow rate: 20 mL/min; Gradient: 3% B to 30% B in 10 min; 254 nm. The collected fractions were combined and concentrated under vacuum to give the title compound as a solid: LCMS [M+H]⁺: 522; ¹H NMR (400 MHz, CD₃OD): δ 8.51 (d, J=8.4 Hz, 1H), 7.82-7.79 (m, 1H), 7.49-7.47 (m, 1H), 6.81 (d, J=6.4 Hz, 1H), 6.05 (d, J=6.4 Hz, 1H), 5.34-5.32 (m, 1H), 4.21-4.19 (m, 1H), 3.96-3.94 (m, 2H), 3.72-3.69 (m, 2H), 3.67-3.65 (m, 1H), 3.14-3.11 (m, 2H).

EXAMPLE 289

3-(2-amino-1-propyl-1H-benzo[d]imidazol-4-yl)-6-(azetidin-3-ylsulfonyl)-2-(2H-tetrazol-5-yl)benzenesulfonamide

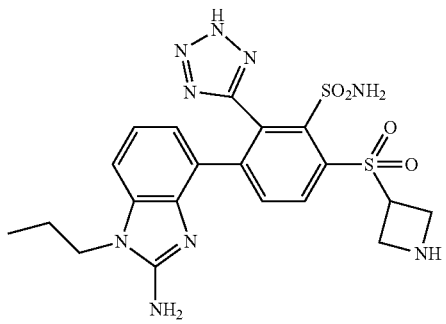 [SMILES: CCCn1c(N)nc2c(-c3ccc(S(=O)(=O)C4CNC4)c(S(N)(=O)=O)c3-c3nn[nH]n3)cccc21]

Step A: tert-butyl 3-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)azetidine-1-carboxylate To a solution of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (10 g, 10.74 mmol) in dioxane (100 ml) and water (25 ml) was added Na₂CO₃ (4.55 g, 43.0 mmol), 2-nitro-3-(4,4,5,5-tetramethyl-1,3,2-dioxaborolan-2-yl)aniline (5.67 g, 21.49 mmol) and Pd(PPh₃)₄ (2.483 g, 2.149 mmol) with stirring at room temperature. The reaction mixture was degassed with nitrogen 3 times. The resulting mixture was warmed to 80° C. and stirred overnight. The reaction mixture was cooled to room temperature, diluted with water (50 mL) and extracted with ethyl acetate (3×100 mL). The combined organic layers were washed with brine (3×100 mL), dried over anhydrous sodium sulfate and filtered. The filtrate was concentrated under vacuum to afford a residue. The residue was purified by silica gel column chromatography, eluting with EtOAc/isohexane (2/1) to afford the title compound as a solid: LCMS [M+H]⁺: 941.

Step B: tert-butyl 3-((3-(N,N-bis(4-methoxybenzyl)sulfamoyl)-3'-bromo-2-(2-(4-methoxybenzyl)-2H-tetrazol-5-yl)-2'-nitro-[1,1'-biphenyl]-4-yl)sulfonyl)azetidine-1-carboxylate To a solution of copper (II) bromide (28.5 mg, 0.128 mmol) in MeCN (1 ml) was added tert-butyl nitrite (17.53 mg, 0.170 mmol) with stirring at 0° C. The reaction solution was evacuated and backfilled with nitrogen 3 times. The resulting solution was added tert-butyl 3-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)azetidine-1-carboxylate (100 mg, 0.106 mmol) in MeCN (1 ml). The resulting solution was warmed to RT and stirred for 2 hours. The reaction solution was cooled to RT, diluted with water (30 mL) and extracted with ethyl acetate (3×10 mL). The combined organic layers were washed with brine (3×20 mL), dried over anhydrous sodium sulfate and filtered. The filtrate was concentrated under vacuum to afford a residue. The residue was purified by silica gel column chromatography 12 g, eluting with EtOAc/isohexane (1/1) to afford the title compound as a solid: LCMS [M+H]$^+$: 1004: 1006 (1:1).

Step C: tert-butyl 3-((3-(N,N-bis(4-methoxybenzyl)sulfamoyl)-2-(2-(4-methoxybenzyl)-2H-tetrazol-5-yl)-2'-nitro-3'-(propylamino)-[1,1'-biphenyl]-4-yl)sulfonyl)azetidine-1-carboxylate A mixture of tert-butyl 3-((3-(N,N-bis(4-methoxybenzyl)sulfamoyl)-3'-bromo-2-(2-(4-methoxybenzyl)-2H-tetrazol-5-yl)-2'-nitro-[1,1'-biphenyl]-4-yl)sulfonyl)azetidine-1-carboxylate (1 g, 0.995 mmol), BINAP (0.124 g, 0.199 mmol), Cs$_2$CO$_3$ (0.648 g, 1.990 mmol), diacetoxypalladium (0.022 g, 0.100 mmol) and propan-1-amine (0.118 g, 1.990 mmol) in dioxane (20 ml) was stirred at 80° C. for 16 hours. The reaction mixture was poured into water (50 mL), extracted with ethyl acetate (3×50 mL). The combined organic layers were washed with water (3×30 mL) and brine (3×30 mL), dried over anhydrous sodium sulfate and filtered. The filtrate was concentrated under vacuum. The residue was purified by silica gel column chromatography, eluting with ethyl acetate/petroleum ether (1/1) to give the title compound as a solid: LCMS [M+H]$^+$: 983.

Step D: tert-butyl 3-((2'-amino-3-(N,N-bis(4-methoxybenzyl)sulfamoyl)-2-(2-(4-methoxybenzyl)-2H-tetrazol-5-yl)-3'-(propylamino)-[1,1'-biphenyl]-4-yl)sulfonyl)azetidine-1-carboxylate Pd/C (43.3 mg, 0.407 mmol) was added to a mixture of tert-butyl 3-((3-(N,N-bis(4-methoxybenzyl)sulfamoyl)-2-(2-(4-methoxybenzyl)-2H-tetrazol-5-yl)-2'-nitro-3'-(propylamino)-[1,1'-biphenyl]-4-yl)sulfonyl)azetidine-1-carboxylate (400 mg, 0.407 mmol) in THF (2.500 ml) and MeOH (2.5 ml), and the resulting mixture was evacuated and backfilled 3 times with H$_2$. After the reaction mixture was stirred at RT overnight, it was filtered and concentrated under vacuum to give the title compound as a solid: LCMS [M+H]$^+$: 953.

Step E: tert-butyl 3-((4-(2-amino-1-propyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate Cyanic bromide (36.7 mg, 0.346 mmol) was added to a stirred mixture of tert-butyl 3-((2'-amino-3-(N,N-bis(4-methoxybenzyl)sulfamoyl)-2-(2-(4-methoxybenzyl)-2H-tetrazol-5-yl)-3'-(propylamino)-[1,1'-biphenyl]-4-yl)sulfonyl)azetidine-1-carboxylate (300 mg, 0.315 mmol) in EtOH (20 ml) and the mixture was stirred at 50° C. for 2 hours. After the mixture was cooled to RT, aqueous sodium hydrogen carbonate (saturated, 50 mL) was added and the mixture was extracted with ethyl acetate (3×30 mL). The combined organic fractions were washed with brine (3×30 mL), dried (Na$_2$SO$_4$), filtered and concentrated under reduced pressure. The residue was purified by column chromatography on silica gel chromatography, eluted with EA/PE (0-70%) to give the title compound as a solid: LCMS [M+H]$^+$: 978.

Step F: 3-(2-amino-1-propyl-1H-benzo[d]imidazol-4-yl)-6-(azetidin-3-ylsulfonyl)-2-(2H-tetrazol-5-yl)benzenesulfonamide To a solution of tert-butyl 3-((4-(2-amino-1-propyl-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate (100 mg, 0.102 mmol) in DCM (2 ml) was added TFA (0.5 ml) with stirring at room temperature. The resulting solution was warmed to room temperature and stirred for 1 hr. The reaction solution was concentrated under vacuum to afford an oil. To the oil was added TFA (2 ml) with stirring at room temperature. The resulting solution was warmed to 80° C. and stirred for 1 hour. The resulting solution was concentrated under vacuum to afford an oil. The product was purified by Prep-HPLC with the following conditions: Column: XBridge Prep C18 OBD Column, 5 μM, 19×150 mm; Mobile Phase A: water with 10 mmol of NH$_4$HCO$_3$, Mobile Phase B: MeCN; Flow rate: 20 mL/min; Gradient: 3% B to 40% B in 8 min; 254/220 nm. The collected fractions were combined and concentrated under vacuum to give the title compound as a solid: LCMS [M+H]$^+$: 518; $^1$H NMR (300 MHz, DMSO): δ 8.27 (d, J=8.7 Hz, 1H), 8.11 (d, J=8.7 Hz, 1H), 7.01-6.97 (m, 1H), 6.54-6.49 (m, 2H), 6.13-6.10 (m, 1H), 5.29-5.18 (m, 1H), 4.39-4.10 (m, 4H), 3.98-3.89 (m, 2H), 1.71-1.59 (m, 2H), 0.91-0.79 (m, 3H).

EXAMPLE 290

7-(4-((S)-pyrrolidin-3-ylsulfonyl)-3-sulfamoyl-2-(2H-tetrazol-5-yl)phenyl)-1H-benzo[d]imidazole-2-carboxylic Acid

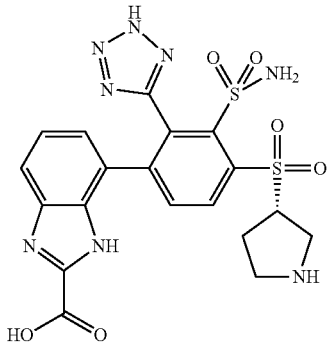 [SMILES: NS(=O)(=O)c1c(S(=O)(=O)[C@H]2CCNC2)ccc(-c2cccc3nc(C(=O)O)[nH]c23)c1-c1nn[nH]n1]

Step A: ethyl 7-(3-(N,N-bis(4-methoxybenzyl)sulfamoyl)-4-((S)-1-(tert-butoxycarbonyl)pyrrolidin-3-ylsulfonyl)-2-(2-(4-methoxybenzyl)-2H-tetrazol-5-yl)phenyl)-1H-benzo[d]imidazole-2-carboxylate To a solution of (S)-tert-butyl 3-(2-(N,N-bis(4-methoxybenzyl)sulfamoyl)-4-iodo-3-(2-(4-methoxybenzyl)-2H-tetrazol-5-yl)phenylsulfonyl)pyrrolidine-1-carboxylate (300 mg, 0.3 mmol) in dioxane (5 mL) and H$_2$O (1 mL), were added ethyl 7-(4,4,5,5-tetramethyl-1,3,2-dioxaborolan-2- yl)-1H-benzo[d]imidazole-2-carboxylate (202 mg, 0.6 mmol) and Na₂CO₃ (101 mg, 1.0 mmol). Under the atmosphere of N₂, the Pd(PPh₃)₄(37 mg, 0.03 mmol) was added to the mixture. The resulting mixture was stirred at 80° C. for 20 hours. After cooling to room temperature, the reaction mixture was quenched with water (8 mL). The resulting mixture was extracted with ethyl acetate (3×8 mL). The combined organic layers were washed with brine (2×8 mL), dried over anhydrous sodium sulfate and filtered. The filtrate was concentrated under reduced pressure. The residue was purified by column chromatography over silica gel using gradient of 0 ~70% ethyl acetate in petroleum ether as eluent to afford the title compound as a solid. LCMS [M+H]⁺ 1007.0

Step B: ethyl 7-(2-(2-(4-methoxybenzyl)-2H-tetrazol-5-yl)-3-(N-(4-methoxybenzyl)sulfamoyl)-4-((S)-pyrrolidin-3-yl sulfonyl)phenyl)-1H-benzo[d]imidazole-2-carboxylate A solution of ethyl 7-(3-(N,N-bis(4-methoxybenzyl)sulfamoyl)-4-((S)-1-(tert-butoxycarbonyl)pyrrolidin-3-ylsulfonyl)-2-(2-(4-methoxybenzyl)-2H-tetrazol-5-yl)phenyl)-1H-benzo[d]imidazole-2-carboxylate (300 mg, 0.3 mmol) and TFA (2 mL) in DCM (4 mL) was stirred at room temperature for 0.5 hr. The reaction mixture was concentrated under vacuum to give the title compound as an oil. LCMS [M+H]⁺ 787.0

Step C: ethyl 7-(4-((S)-pyrrolidin-3-ylsulfonyl)-3-sulfamoyl-2-(2H-tetrazol-5-yl)phenyl)-1H-benzo[d]imidazole-2-carboxylate A solution of ethyl 7-(2-(2-(4-methoxybenzyl)-2H-tetrazol-5-yl)-3-(N-(4-methoxybenzyl)sulfamoyl)-4-((S)-pyrrolidin-3-yl sulfonyl)phenyl)-1H-benzo[d]imidazole-2-carboxylate (200 mg, 0.25 mmol) in TFA (2 mL) was stirred at 80° C. for 1 hr. The reaction mixture was concentrated under vacuum to give the title compound as a solid. LCMS [M+H]⁺, 547.0. ¹H NMR (CD₃OD, 300 MHZ) δ: 8.61 (q, J=3.6 Hz, 1H), 7.97 (d, J=8.4 Hz, 1H), 7.15-6.95 (m, 2H), 6.75-6.61 (m, 1H), 5.27-5.09 (m, 1H), 4.05-3.35 (m, 6H), 2.79-2.37 (m, 2H), 1.51-1.09 (m, 3H).

Step D: 7-(4-((S)-pyrrolidin-3-ylsulfonyl)-3-sulfamoyl-2-(2H-tetrazol-5-yl)phenyl)-1H-benzo[d]imidazole-2-carboxylic Acid A solution of ethyl 7-(4-((S)-pyrrolidin-3-ylsulfonyl)-3-sulfamoyl-2-(2H-tetrazol-5-yl)phenyl)-1H-benzo[d]imidazole-2-carboxylate (180 mg, 0.32 mmol), LiOH (29 mg, 1.2 mmol) in methanol (3 mL) and H₂O (0.6 mL) was stirred for 4 hours at room temperature. The reaction mixture was concentrated under vacuum to give crude product. The product was purified by Prep-HPLC with the following conditions: Column: XBridge BEH130 Prep C18 OBD Column 19×150 mm 5 M 13 nm; Mobile Phase A: water with 10 mmol NH₄HCO₃, Mobile Phase B: ACN; Flow rate: 20 mL/min; Gradient: 3% B to 25% B in 8 min; 254 nm. The collected fractions were combined and concentrated under vacuum to give the title compound as a solid. LCMS [M+H]⁺ 519.0; ¹H NMR (DMSO-d₆, 300 MHZ) δ: 8.28 (q, J=2.7 Hz, 1H), 7.76 (q, J=3.0 Hz, 1H), 7.03 (d, J=1.2 Hz, 1H), 6.85 (t, J=1.8 Hz, 1H), 6.32 (t, J=1.2 Hz, 1H), 5.15-5.01 (m, J=3.9 Hz, 1H), 3.75-3.51 (m, 2H), 3.41-3.23 (m, 2H), 2.45-2.26 (m, 2H).

EXAMPLE 291

3-(2-amino-1H-benzo[d]imidazol-4-yl)-6-((3R,5S)-5-(hydroxymethyl)pyrrolidin-3-ylsulfonyl)-2-(2H-tetrazol-5-yl)benzenesulfonamide

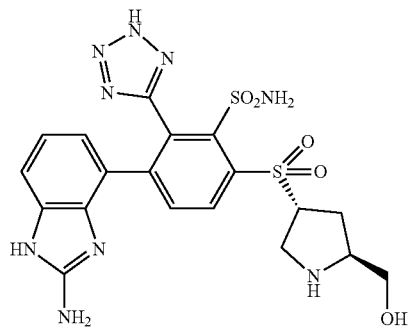 [SMILES: Nc1nc2c(-c3ccc(S(=O)(=O)[C@H]4CN[C@H](CO)C4)c(S(N)(=O)=O)c3-c3nn[nH]n3)cccc2[nH]1]

Step A: (2S,4R)-1-tert-butyl 2-methyl 4-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)pyrrolidine-1,2-dicarboxylate Into a solution of (2S,4R)-1-tert-butyl 2-methyl 4-(2-(N,N-bis(4-methoxybenzyl)sulfamoyl)-4-iodo-3-(2-(4-methoxybenzyl)-2H-tetrazol-5-yl)phenylsulfonyl)pyrrolidine-1,2-dicarboxylate (900 mg, 0.9 mmol), Pd(dppf)Cl₂ (70 mg, 0.1 mmol) and 2-amino-1H-benzo[d]imidazol-4-ylboronic acid (397 mg, 2.24 mmol) in dioxane (8 mL). This was followed by the addition of sodium carbonate (286 mg, 2.7 mmol) in water (2 mL) at room temperature. The resulting mixture was stirred at 80° C. for 12 hours under argon atmosphere. The reaction was cooled to room temperature and quenched with water (12 mL) and extracted with EA (3×12 mL). The combined organic layers were washed with brine (2×15 mL), dried over anhydrous sodium sulfate and filtered. The filtrate was evaporated under reduced pressure and the residue was purified by silica gel chromatography, eluting with DCM/MeOH (8/1) to give the title compound as a solid: LCMS [M+H]⁺: 1008; ¹H NMR (300 MHz, CD₃OD): δ 8.72-8.67 (m, 1H), 8.21-8.15 (m, 1H), 7.02-6.48 (m, 15H), 5.10-5.00 (m, 1H), 4.70-4.52 (m, 3H), 4.11-3.89 (m, 4H), 3.80-3.53 (m, 14H), 2.80-2.70 (m, 1H), 2.59-2.38 (m, 1H), 1.52 (s, 9H).

Step B: (2S,4R)-tert-butyl 4-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)-2-(hydroxymethyl)pyrrolidine-1-carboxylate A solution of (2S,4R)-1-tert-butyl 2-methyl 4-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)pyrrolidine-1,2-dicarboxylate (450 mg, 0.45 mmol) in THF (3 mL) was prepared. This was followed by the addition of LiBH₄ (29 mg, 1.32 mmol) at 0° C. The resulting mixture was stirred at room temperature for 2 hours under an argon atmosphere. The reaction mixture was quenched with water (8 ml) and extracted with EA (3×8 mL). The combined organic layers were washed with brine (1×10 mL), dried over anhydrous sodium sulfate and filtered. The filtrate was evaporated under reduced pressure and the residue was purified by silica gel chromatography, eluting with 0 ~20% MeOH in DCM to give the title compound as a solid: LCMS [M+H]$^+$: 980; $^1$H NMR (300 MHz, CD$_3$OD): δ 8.72-8.67 (m, 1H), 8.19-8.15 (m, 1H), 7.02-6.48 (m, 15H), 5.10-4.90 (m, 2H), 4.70-4.4.52 (m, 2H), 4.21-3.89 (m, 5H), 3.80-3.53 (m, 12H), 2.80-2.70 (m, 1H), 2.59-2.38 (m, 1H), 1.52 (s, 9H).

Step C: 3-(2-amino-1H-benzo[d]imidazol-4-yl)-6-((3R,5S)-5-(hydroxymethyl)pyrrolidin-3-ylsulfonyl)-N,N-bis(4-methoxybenzyl)-2-(2-(4-methoxybenzyl)-2H-tetrazol-5-yl)benzenesulfonamide A solution of (2S,4R)-tert-butyl 4-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonyl)-2-(hydroxymethyl)pyrrolidine-1-carboxylate (110 mg, 0.11 mmol) in DCM (2 mL) was prepared. This was followed by the addition of TFA (1 mL) at 0° C. The resulting mixture was stirred at room temperature for 0.5 hr. The solvent was evaporated to afford the title compound as a solid: LCMS [M+H]$^+$: 880.

Step D: 3-(2-amino-1H-benzo[d]imidazol-4-yl)-6-((3R,5S)-5-(hydroxymethyl)pyrrolidin-3-ylsulfonyl)-2-(2H-tetrazol-5-yl)benzenesulfonamide A solution of 3-(2-amino-1H-benzo[d]imidazol-4-yl)-6-((3R,5S)-5-(hydroxymethyl)pyrrolidin-3-ylsulfonyl)-N,N-bis(4-methoxybenzyl)-2-(2-(4-methoxybenzyl)-2H-tetrazol-5-yl)benzenesulfonamide (80 mg, 0.110 mmol) in TFA (2 mL, 26.0 mmol) was prepared. The resulting mixture was stirred at 80° C. for 1 hr. The solvent was evaporated and the residue was purified by Prep-HPLC with the following conditions: Column: SunFire C18 OBD Prep Column, 100 Å, 5 μm, 19 mm×250 mm; Mobile Phase A: water with 10 mmol NH$_4$HCO$_3$; Mobile Phase B: ACN; Flow rate: 25 mL/min; Gradient: 10% B to 40% B in 8 min; 254&220 nm. The collected fractions were combined and concentrated under reducing pressure to afford the title compound as a solid: LCMS [M+H]$^+$: 520; $^1$H NMR (400 MHz, DMSO-d$_6$): δ 8.31 (d, J=6.3 Hz, 1H), 8.02 (d, J=8.4 Hz, 1H), 7.88-7.21 (br, 1H), 6.97 (d, J=7.8 Hz, 1H), 6.65-6.37 (t, J=7.8 Hz, 1H), 6.55 (s, 2H), 6.15 (d, J=7.5 Hz, 1H), 5.05-4.88 (m, 1H), 3.68-3.37 (m, 5H), 2.59-2.38 (m, 1H), 2.12-1.99 (m, 1H).

EXAMPLE 292

3-(2-aminobenzo[d]thiazol-4-yl)-6-((3R,5S)-5-(hydroxymethyl)pyrrolidin-3-ylsulfonyl)-2-(2H-tetrazol-5-yl)benzenesulfonamide

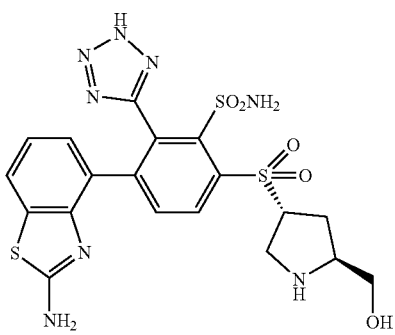 [SMILES: Nc1nc2c(-c3ccc(S(=O)(=O)[C@H]4CN[C@H](CO)C4)c(S(N)(=O)=O)c3-c3nn[nH]n3)cccc2s1]

Step A: (2S,4R)-1-tert-butyl 2-methyl 4-(2-(N,N-bis(4-methoxybenzyl)sulfamoyl)-4-iodo-3-(2-(4-methoxybenzyl)-2H-tetrazol-5-yl)phenylthio)pyrrolidine-1,2-dicarboxylate To a solution of 6-bromo-3-iodo-N,N-bis[(4-methoxyphenyl)methyl]-2-{2-[(4-methoxyphenyl)methyl]-2H-1,2,3,4-tetrazol-5-yl}benzene-1-sulfonamide (3.0 g, 0.004 mol) in DMF (15 mL) were added (2S,4R)-1-tert-butyl 2-methyl 4-mercaptopyrrolidine-1,2-dicarboxylate (2.0 g, 0.008 mol) and Cs$_2$CO$_3$ (4.0 g, 0.01 mol). The resulting mixture was stirred at 20° C. for 1 hr under argon atmosphere. The reaction was then quenched with water (20 mL) and extracted with EA (3×20 mL). The combined layers were washed with brine (2×20 mL), dried over anhydrous sodium sulfate and filtered. The filtrate was evaporated and the residue was purified by silica gel chromatography, eluted with 0-50% EA in PE to afford the title compound as a solid: LCMS [M+H]$^+$: 971; $^1$H NMR (300 MHz, CD$_3$OD): $^1$H NMR (400 MHz, DMSO-d$_6$): δ 8.06 (d, J=8.4 Hz, 1H), 7.61-7.55 (m, 1H), 7.21-7.11 (m, 2H), 6.92-6.68 (m, 10H), 5.54 (d, J=14.4 Hz, 1H), 5.22 (d, J=14.4 Hz, 1H), 4.68-4.56 (m, 2H), 4.18-4.01 (m, 3H), 3.91-3.48 (m, 3H), 3.73 (s, 12H), 2.54-2.15 (m, 2H), 1.51 (s, 9H).

Step B: (2S,4R)-1-tert-butyl 2-methyl 4-(2-(N,N-bis(4-methoxybenzyl)sulfamoyl)-4-iodo-3-(2-(4-methoxybenzyl)-2H-tetrazol-5-yl)phenylsulfonyl)pyrrolizidine-12-dicarboxylate Into a 50-mL RBF purged and maintained with an inert atmosphere of argon, was placed a solution of (2S,4R)-1-tert-butyl 2-methyl 4-(2-(N,N-bis(4-methoxybenzyl)sulfamoyl)-4-iodo-3-(2-(4-methoxybenzyl)-2H-tetrazol-5-yl)phenylthio)pyrrolidine-1,2-dicarboxylate (2.5 g, 2.58 mmol) in DCM (15 mL). This was followed by the addition of m-CPBA (1.77 g, 0.01 mol) at room temperature. The resulting mixture was stirred at room temperature for 16 hours under argon atmosphere. The reaction was quenched with aqueous Na$_2$SO$_3$ (10%, 50 mL) and extracted with EtOAc (3×50 mL). The combined layers were washed with saturated NaHCO$_3$ (3×40 mL), brine (3×40 mL), dried over anhydrous sodium sulfate and filtered. The filtrate was evaporated and the residue was purified by silica gel column chromatography, eluted with EtOAc in Pet. ether (2/1) to afford the title compound as a solid: LCMS {M+H]$^+$: 1003; $^1$H NMR (300 MHz, CD$_3$OD): δ 8.41-8.38 (m, 1H), 8.19-8.17 (m, 1H), 7.21-7.11 (m, 2H), 6.92-6.58 (m, 10H), 5.58-5.50 (m, 1H), 5.30-5.24 (m, 1H), 4.99-4.80 (m, 1H), 4.62-4.42 (m, 2H), 3.98-3.80 (m, 3H), 3.80-3.68 (m, 14H), 3.13-3.01 (m, 0.5H), 2.74-2.65 (m, 0.5H), 2.55-2.25 (m, 1H), 1.51 (s, 9H).

Step C: (2S,4R)-1-tert-butyl 2-methyl 4-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)pyrrolidine-1,2-dicarboxylate Into a 25-mL RBF purged and maintained with an inert atmosphere of argon, was placed a solution of (2S,4R)-1-tert-butyl 2-methyl 4-(2-(N,N-bis(4-methoxybenzyl)sulfamoyl)-4-iodo-3-(2-(4-methoxybenzyl)-2H-tetrazol-5-yl)phenylsulfonyl)pyrrolidine-1,2-dicarboxylate (700 mg, 0.7 mmol), Pd(dppf)Cl$_2$ (51 mg, 0.07 mmol) and 2-aminobenzo[d]thiazol-4-ylboronic acid (339 mg, 1.7 mmol) in dioxane (8 mL). This was followed by the addition of sodium carbonate (222 mg, 2.1 mmol) in water (1.5 mL) at room temperature. The resulting mixture was stirred at 80° C. for 12 hours under argon atmosphere. The reaction was cooled to room temperature and quenched with water (10 mL) and extracted with EA (3×10 mL). The combined organic layers were washed with brine (2×10 mL), dried over anhydrous sodium sulfate and filtered. The filtrate was evaporated under reduced pressure and the residue was purified by silica gel column chromatography, eluted with DCM/MeOH (10/1) to give the title compound as a solid: LCMS [M+H]$^+$: 1025; $^1$H NMR (300 MHz, CD$_3$OD): δ 8.68-8.65 (m, 1H), 8.15-8.12 (m, 1H), 7.53-7.50 (m, 1H), 6.99-6.95 (m, 4H), 6.85-6.69 (m, 10H), 5.03-4.90 (m, 3H), 4.70-4.61 (m, 2H), 4.58-4.39 (m, 1H), 4.08-3.92 (m, 2H), 3.88-3.80 (m, 2H), 3.72 (s, 12H), 3.13-3.01 (m, 0.5H), 2.74-2.65 (m, 0.5H), 2.55-2.25 (m, 1H), 1.51 (s, 9H).

Step D: (2S,4R)-tert-butyl 4-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)-2-(hydroxymethyl)pyrrolidine-1-carboxylate Into a 25-mL RBF, was placed a solution of (2S,4R)-1-tert-butyl 2-methyl 4-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)pyrrolidine-1,2-dicarboxylate (370 mg, 0.36 mmol) in THF (3 mL). This was followed by the addition of DIBAL-H (1.5 mL, 1.5 mmol) at 0° C. The resulting mixture was stirred at 0° C. for 2 hours under argon atmosphere. The reaction mixture was quenched with saturated ammonium chloride (5 mL) and extracted with EA (3×10 mL). The combined organic layers were washed with brine (2×20 mL), dried over anhydrous sodium sulfate and filtered. The filtrate was evaporated under reduced pressure and the residue was purified by silica gel column chromatography, eluted with 0 ~70% EA in PE to give the title compound as a solid: LCMS [M+H]$^+$: 997; $^1$H NMR (300 MHz, CD$_3$OD): δ 8.68-8.65 (m, 1H), 8.15-8.12 (m, 1H), 7.53-7.50 (m, 1H), 6.99-6.95 (m, 4H), 6.85-6.69 (m, 10H), 5.03-4.90 (m, 2H), 4.70-4.61 (m, 2H), 4.20-3.90 (m, 4H), 3.72 (s, 9H), 3.63-3.45 (m, 4H), 2.90-2.75 (m, 0.5H), 2.55-2.25 (m, 1.5H), 1.51 (s, 9H).

Step E: 3-(2-aminobenzo[d]thiazol-4-yl)-6-((3R,5S)-5-(hydroxymethyl)pyrrolidin-3-ylsulfonyl)-N,N-bis(4-methoxybenzyl)-2-(2-(4-methoxybenzyl)-2H-tetrazol-5-yl)benzenesulfonamide Into a 25-mL RBF was placed a solution of (2S,4R)-tert-butyl 4-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonyl)-2-(hydroxymethyl)pyrrolidine-1-carboxylate (145 mg, 0.15 mmol) in DCM (2 mL). This was followed by the addition of TFA (1 mL) at 0° C. The resulting mixture was stirred at room temperature for 0.5 hr. The solvent was evaporated to give the title compound as a solid: LCMS [M+H]$^+$: 897.

Step F: 3-(2-aminobenzo[d]thiazol-4-yl)-6-((3R,5S)-5-(hydroxymethyl)pyrrolidin-3-ylsulfonyl)-2-(2H-tetrazol-5-yl)benzenesulfonamide Into a 25-mL RBF was placed a solution of 3-(2-aminobenzo[d]thiazol-4-yl)-6-((3R,5 S)-5-(hydroxymethyl)pyrrolidin-3-ylsulfonyl)-N,N-bis(4-methoxybenzyl)-2-(2-(4-methoxybenzyl)-2H-tetrazol-5-yl)benzenesulfonamide (100 mg, 0.110 mmol) in TFA (2 mL, 26.0 mmol). The resulting mixture was stirred at 80° C. for 1 hr. The solvent was evaporated and the residue was purified by Prep-HPLC with the following conditions: Column: XBridge Prep C18 OBD Column 19×250 mm 10 µM; Mobile Phase A: water with 10 mmol NH$_4$HCO$_3$, Mobile Phase B: ACN; Flow rate: 25 mL/min; Gradient: 5% B to 35% B in 8 min; 254/220 nm. The collected fractions were combined and concentrated under reducing pressure to afford the title compound as a solid: LCMS [M+H]$^+$: 537; $^1$H NMR (400 MHz, DMSO-d$_6$): δ 8.30 (d, J=8.4 Hz, 1H), 7.93 (d, J=8.0 Hz, 1H), 7.69-7.49 (m, 4H), 6.72 (t, J=7.6 Hz, 1H), 6.50 (d, J=7.6 Hz, 1H), 5.34-5.26 (m, 1H), 5.12-5.01 (m, 1H), 3.81-3.48 (m, 5H), 2.50-2.48 (m, 1H), 2.19-2.05 (m, 1H).

EXAMPLE 293

3-(2-amino-1H-benzo[d]imidazol-4-yl)-6-((S)-2,3-diaminopropylsulfonyl)-2-(1H-tetrazol-5-yl)benzenesulfonamide

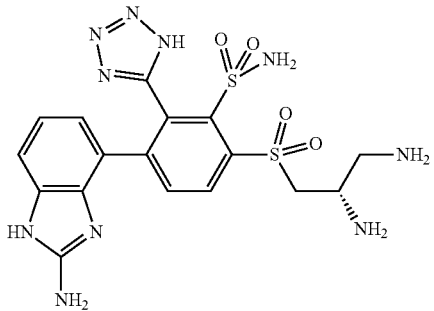 [SMILES: NC[C@H](N)CS(=O)(=O)c1ccc(-c2cccc3[nH]c(N)nc23)c(-c2nnn[nH]2)c1S(N)(=O)=O]

Step A: (isobutyl carbonic) (S)-10,10-dimethyl-3,8-dioxo-1-phenyl-2,9-dioxa-4,7-diazaundecane-6-carboxylic anhydride A solution of (S)-10,10-dimethyl-3,8-dioxo-1-phenyl-2,9-dioxa-4,7-diazaundecane-6-carboxylic acid (20 g, 59 mmol), isobutyl carbonochloridate (9.6 g, 71 mmol) and 4-methylmorpholine (7.2 g, 71 mmol) in THF (200 ml) was stirred at 0° C. for 6 hours. The reaction mixture was filtered, the filtrate was concentrated under vacuum to give the title compound as an oil.

Step B: benzyl tert-butyl (3-hydroxypropane-1,2-diyl)dicarbamate

A solution of (isobutyl carbonic) (S)-10,10-dimethyl-3,8-dioxo-1-phenyl-2,9-dioxa-4,7-diazaundecane-6-carboxylic anhydride (15 g, 34 mmol) and NaBH$_4$ (5 g, 136 mmol) in THF (100 ml) was stirred at room temperature for 2 hours. The reaction mixture was quenched with water (50 mL), and extracted with ethyl acetate (3×100 mL). The combined organic layers were washed with water (2×30 mL) and brine (2×30 mL), dried over anhydrous sodium sulfate and filtered. The filtrate was concentrated under vacuum to give crude product. The residue was purified by silica gel chromatography, eluted with methanol/DCM (1/20). The combined organic fractions were concentrated under reduced pressure to give the title compound as an oil. LCMS [M+H]$^+$: 325

Step C: (S)-3-(benzyloxycarbonylamino)-2-(tert-butoxycarbonylamino)propyl methanesulfonate MsCl (2.38 ml, 30 mmol) was added in dropwise to a stirred solution of benzyl tert-butyl (3-hydroxypropane-1,2-diyl)dicarbamate (8.2 g, 25 mmol) and TEA (10.4 ml, 75 mmol) in DCM (100 ml) at 0° C. and stirred at room temperature for 2 hours. The reaction mixture was quenched with water (50 mL), and extracted with ethyl acetate (3×100 mL). The combined organic layers were washed with water (2×30 mL) and brine (2×30 mL), dried over anhydrous sodium sulfate and filtered. The filtrate was concentrated under vacuum to give crude product. The residue was purified by silica gel column chromatography, eluting with methanol/DCM (1/25). The combined organic fractions were concentrated under reduced pressure to give the title compound as an oil. LCMS [M+H]$^+$: 403

Step D: (S)—S-3-(benzyloxycarbonylamino)-2-(tert-butoxycarbonylamino)propyl ethanethioate A solution of (S)-3-(benzyloxycarbonylamino)-2-(tert-butoxycarbonylamino)propyl methanesulfonate (8.0 g, 20 mmol) and potassium ethanethioate (9.1 g, 80 mmol) in DMF (80 ml) was stirred at 80° C. for 16 hours. The reaction mixture was quenched with water (100 mL), and extracted with ethyl acetate (3×100 mL). The combined organic layers were washed with water (2×30 mL) and brine (2×30 mL), dried over anhydrous sodium sulfate and filtered. The filtrate was concentrated under vacuum to give crude product. The residue was purified by silica gel column chromatography, eluting with ethyl acetate/petroleum ether (1/9). The combined organic fractions were concentrated under reduced pressure to give the title compound as an oil. LCMS [M+H]$^+$: 383

Step E: benzyl tert-butyl (3-mercaptopropane-1,2-diyl)dicarbamate

A solution of (S)—S-3-(benzyloxycarbonylamino)-2-(tert-butoxycarbonylamino)propyl ethanethioate (6.3 g, 16.4 mmol) and K$_2$CO$_3$ (4.5 g, 32.4 mmol) in Methanol (60 ml) was stirred at room temperature for 16 hours. The reaction mixture was quenched with water (100 mL), and extracted with ethyl acetate (3×25 mL). The combined organic layers were washed with water (2×20 mL) and brine (2×20 mL), dried over anhydrous sodium sulfate and filtered. The filtrate was concentrated under vacuum to give the title compound as an oil. LCMS [M+H]$^+$: 341

Step F: (S)-benzyl tert-butyl (3-((2-(N,N-bis(4-methoxybenzyl)sulfamoyl)-4-iodo-3-(2-(4-methoxybenzyl)-2H-tetrazol-5-yl)phenyl)thio)propane-1,2-diyl)dicarbamate A solution of 6-bromo-3-iodo-N,N-bis(4-methoxybenzyl)-2-(2-(4-methoxybenzyl)-2H-tetrazol-5-yl)benzenesulfonamide (4 g, 5 mmol), benzyl tert-butyl (3-mercaptopropane-1,2-diyl)dicarbamate (3.4 g, 10 mmol) and Cs$_2$CO$_3$ (4.8 g, 15 mmol) in DMF (40 ml) was stirred at room temperature for 16 hours. The reaction mixture was quenched with water (30 mL), diluted with water (80 mL) and extracted with ethyl acetate (3×50 mL). The combined organic layers were washed with water (2×30 mL) and brine (2×30 mL), dried over anhydrous sodium sulfate and fil-tered. The filtrate was concentrated under vacuum to give the title compound as a solid. LCMS [M+H]$^+$: 1050

Step G: (S)-benzyl tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propane-1,2-diyl)dicarbamate A solution of (S)-benzyl tert-butyl (3-((2-(N,N-bis(4-methoxybenzyl)sulfamoyl)-4-iodo-3-(2-(4-methoxybenzyl)-2H-tetrazol-5-yl)phenyl)thio)propane-1,2-diyl)dicarbamate (4.8 g, 4.5 mmol) and m-CPBA (3.1 g, 18 mmol) in DCM (50 ml) was stirred at room temperature for 16 hours. The reaction mixture was quenched with Na$_2$SO$_3$ (50 mL), diluted with water (50 mL) and extracted with DCM (3×50 mL). The combined organic layers were washed with water (2×20 mL) and brine (2×20 mL), dried over anhydrous sodium sulfate and filtered. The filtrate was concentrated under vacuum to give crude product. The residue was purified by silica gel Isolute Flash Si; 20 g prepacked column chromatography, eluting with EA/DCM (7/3). The combined organic fractions were concentrated under reduced pressure to give the title compound as a solid. LCMS [M+H]$^+$: 1082

Step H: (S)-benzyl tert-butyl (3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propane-1,2-diyl)dicarbamate A solution of (S)-benzyl tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)propane-1,2-diyl)dicarbamate (1 g, 0.9 mmol), 2-aminobenzo[d]thiazol-4-ylboronic acid (0.245 g, 1.4 mmol), Pd(PPh3)4 (0.491 g, 0.18 mmol) and Na$_2$CO$_3$ (0.286 g, 2.7 mmol) in 1,4-dioxane (15 ml) and water (3 ml) was stirred at 80° C. for 3 hours under argon. The reaction mixture was concentrated under vacuum to give crude product. The residue was purified by silica gel Isolute Flash Si; 50 g prepacked column chromatography, eluting with methanol/DCM (1/10). The combined organic fractions were concentrated under reduced pressure to give the title compound as a solid. LCMS [M+H]$^+$: 1087

Step I: methyl (S)-3-(2-amino-1H-benzo[d]imidazol-4-yl)-6-((2,3-diaminopropyl)sulfonyl)-2-(1H-tetrazol-5-yl)benzenesulfonamide A solution of (S)-benzyl tert-butyl (3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)propane-1,2-diyl)dicarbamate (200 mg, 0.184 mmol) in HCl (15 ml, 0.180 mol) was stirred at 70° C. for 6 hours. The reaction mixture was concentrated under vacuum to give crude product. The product was purified by Prep-HPLC with the following conditions: Column: X Bridge C18, 19*150 mm, 5 μM; Mobile Phase A: water/0.05% ACOH Mobile Phase B: ACN; Flow rate: 20 mL/min; Gradient: 30% B to 70% B in 10 min; 254 nm. The collected fractions were combined and concentrated under vacuum to give the title compound as a solid. LCMS [M+H]$^+$: 492

EXAMPLE 294

4-(4-((S)-2-aminopropylsulfonyl)-3-sulfamoyl-2-(2H-tetrazol-5-yl)phenyl)-1H-benzo[d]imidazole-2-carboxylic Acid

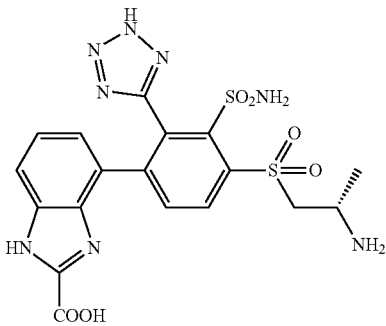 [SMILES: C[C@H](N)CS(=O)(=O)c1ccc(-c2cccc3[nH]c(C(=O)O)nc23)c(-c2nn[nH]n2)c1S(N)(=O)=O]

Step A: (S)-tert-butyl (1-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)propan-2-yl)carbamate Into a 25 mL RBF was placed (S)-tert-butyl (1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (400 mg, 0.429 mmol), 3-(4,4,5,5-tetramethyl-1,3,2-dioxaborolan-2-yl)benzene-1,2-diamine (201 mg, 0.858 mmol), Pd(PPh$_3$)$_4$ (99 mg, 0.086 mmol) and Na$_2$CO$_3$ (136 mg, 1.286 mmol) in 1,4-dioxane (1.2 ml) and water (0.40 ml). The resulting mixture was evacuated and backfilled with nitrogen 3 times and stirred at 80° C. for 16 hours. Then the mixture was diluted with EA (200 mL) and washed with water (3×50 mL). The organic layer was collected and washed with sat. NaCl (3×50 mL) and dried over anhydrous Na$_2$SO$_4$. Then the mixture was filtered with the filtrate collected and concentrated under vacuum. The residue was applied on a silica gel column with EA/PE(1/1) to give the title compound as a solid: LCMS [M+H]$^+$: 913;

Step B: (S)-ethyl 4-(3-(N,N-bis(4-methoxybenzyl)sulfamoyl)-4-((2-((tert-butoxycarbonyl)amino)propyl)sulfonyl)-2-(2-(4-methoxybenzyl)-2H-tetrazol-5-yl)phenyl)-1H-benzo[d]imidazole-2-carboxylate Ethyl 2,2,2-triethoxyacetate (221.9 mg, 1.02 mmol) was added dropwise to a solution of (s)-tert-butyl (1-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)propan-2-yl)carbamate (300 mg, 0.328 mmol) in EtOH (5 ml) at 0° C. The mixture was evacuated and backfilled with nitrogen 3 times and stirred at 80° C. for 16 hours. When the reaction was completed, it was concentrated under vacuum. The residue was applied on a silica gel column with EA/PE(1/1) to give the title compound as a solid.: LCMS (ESI) calc'd for C$_{49}$H$_{54}$N$_8$O$_{11}$S$_2$ [M+H]$^+$: 995. found 995.

Step C: ethyl 4-(4-((S)-2-aminopropylsulfonyl)-2-(2-(4-methoxybenzyl)-2H-tetrazol-5-yl)-3-(N-(4-methoxybenzyl)sulfamoyl)phenyl)-1H-benzo[d]imidazole-2-carboxylate Into a 25 mL RBF was placed ethyl 4-(3-(N,N-bis(4-methoxybenzyl)sulfamoyl)-4-((S)-2-(tert-butoxycarbonylamino)propylsulfonyl)-2-(2-(4-methoxybenzyl)-2H-tetrazol-5-yl)phenyl)-1H-benzo[d]imidazole-2-carboxylate (250 mg, 0.25 mmol) in DCM (3 mL) and TFA (1.5 mL). Then the mixture was stirred at RT for 1 hr. Then the solvent was removed under vacuum to give the title compound as an oil. The crude product was used for next step without purification. LCMS [M+H]$^+$: 775.

Step D: ethyl 4-(4-((S)-2-aminopropylsulfonyl)-3-sulfamoyl-2-(2H-tetrazol-5-yl)phenyl)-1H-benzo[d]imidazole-2-carboxylate Into a 25 mL RBF was placed ethyl 4-(4-((S)-2-aminopropylsulfonyl)-2-(2-(4-methoxybenzyl)-2H-tetrazol-5-yl)-3-(N-(4-methoxybenzyl)sulfamoyl)phenyl)-1H-benzo[d]imidazole-2-carboxylate (120 mg, 0.155 mmol) in TFA (2.0 mL). Then the mixture was stirred at 80° C. for 1 hr. Then the solvent was removed under vacuum to give the title compound as a solid. The crude product was used directly for next step. LCMS [M+H]$^+$: 535.

Step E: 4-(4-((S)-2-aminopropylsulfonyl)-3-sulfamoyl-2-(2H-tetrazol-5-yl)phenyl)-1H-benzo[d]imidazole-2-carboxylic Acid A solution of LiOH (16 mg, 0.67 mmol) in water (0.6 mL) was added dropwise to a stirred solution of ethyl 4-(4-((S)-2-aminopropylsulfonyl)-3-sulfamoyl-2-(2H-tetrazol-5-yl)phenyl)-1H-benzo[d]imidazole-2-carboxylate (90 mg, 0.17 mmol) in 1,4-dioxane (3 mL). Then the mixture was stirred for 4 hours. Then solvent was removed. The residue was dissolved in DMF (5 mL) and applied on Prep-HPLC (Condition: Column: XBridge BEH130 Prep C18 OBD Column 19×150 mm 5 M 13 nm; Mobile Phase A: water with 10 mmol NH$_4$HCO$_3$, Mobile Phase B: ACN; Flow rate: 20 mL/min; Gradient: 3% B to 25% B in 8 min; 254 nm) to give the title compound as a solid. LCMS [M+H]$^+$: 507; $^1$H NMR (300 MHz, d-CD$_3$OD): δ 8.42 (d, J=8.4 Hz, 1H), 7.95 (d, J=8.1 Hz, 1H), 7.46 (d, J=8.1 Hz, 1H), 7.05 (t, J=7.5 Hz, 1H), 6.72 (d, J=7.5 Hz, 1H), 4.27-4.01 (m, 3H), 1.49 (d, J=6.6 Hz, 3H).

EXAMPLE 295

3-(2-amino-4-cyano-1H-benzo[d]imidazol-7-yl)-6-((2-aminoethyl)sulfonyl)-2-(1H-tetrazol-5-yl)benzenesulfonamide

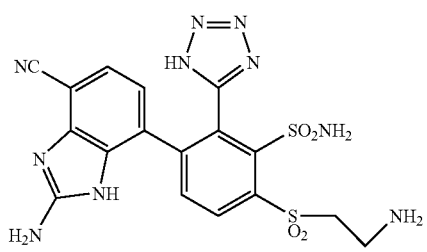 [SMILES: N#Cc1ccc(-c2ccc(S(=O)(=O)CCN)c(S(N)(=O)=O)c2-c2nnn[nH]2)c2[nH]c(N)nc12]

Step A: tert-butyl (2-((2',3'-diamino-3-(N,N-bis(4-methoxybenzyl)sulfamoyl)-4'-cyano-2-(2-(4-methoxybenzyl)-2H-tetrazol-5-yl)-[1,1'-biphenyl]-4-yl)sulfonyl)ethyl)carbamate A suspension of tert-butyl (2-((2-(N,N-bis(4-methoxybenzyl)sulfamoyl)-4-(5,5-dimethyl-1,3,2-dioxaborinan-2- yl)-3-(2-(4-methoxybenzyl)-2H-tetrazol-5-yl)phenyl)sulfonyl)ethyl)carbamate (200 mg, 0.221 mmol), cesium carbonate (216 mg, 0.663 mmol), 2,3-diamino-4-bromobenzonitrile (56.2 mg, 0.265 mmol) and 2nd generation Xphos precatalyst (34.8 mg, 0.044 mmol) in dioxane (4 ml) and water (1.0 ml) was degassed and heated at 80° C. for 17 hours. The mixture was diluted with EtOAc, then washed with brine. The organic layer was dried (MgSO$_4$) and concentrated. The crude product was chromatographed via silica gel (ISCO, 40 g column, 0-20% MeOH in DCM) to give the desired product. LC/MS (M+H)+: 924.54.

Step B: tert-butyl (2-((4-(2-amino-7-cyano-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)ethyl)-carbamate To a 5 mL microwave tube was added a solution of tert-butyl (2-((2',3'-diamino-3-(N,N-bis(4-methoxybenzyl)sulfamoyl)-4'-cyano-2-(2-(4-methoxybenzyl)-2H-tetrazol-5-yl)-[1,1'-biphenyl]-4-yl)sulfonyl)ethyl)carbamate (100 mg, 0.108 mmol) and cyanic bromide (11.46 mg, 0.108 mmol) in methanol (5 ml) and water (1.00 ml). The mixture was stirred at 80° C. for 2 hours. The solvent was removed in vacuum and the residue was purified by column chromatography (ISCO RediSep Gold column 24 g) using 0-20% methanol/DCM as mobile phase to get the desired product. LC/MS (M+H)+: 949.31.

Step C: 3-(2-amino-4-cyano-1H-benzo[d]imidazol-7-yl)-6-((2-aminoethyl)sulfonyl)-2-(1H-tetrazol-5-yl)benzenesulfonamide A solution of tert-butyl (2-((4-(2-amino-7-cyano-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)ethyl)-carbamate (20 mg, 0.021 mmol) in DCM (200 µl) was concentrated in vacuum. The residue was dissolved in anisole (22.9 µl, 0.211 mmol) and TFA (160 µl, 2.11 mmol) at 0° C. After stirring at rt for 0.5 hr, the volatile was removed in vacuo. The residue was dissolved in 0.5 mL of TFA and stirred at 80° C. for 1.0 hr. After removing the volatile, the residue was dissolved in 1 mL of DMSO and purified by reverse phase HPLC directly (3-60% acetonitrile in water) to give the product. LC/MS (M+H)+: 489.22.

EXAMPLE 296

3-(2-amino-5-fluoro-1H-benzo[d]imidazol-7-yl)-6-(azetidin-3-ylsulfonyl)-2-(1H-tetrazol-5-yl)benzenesulfonamide

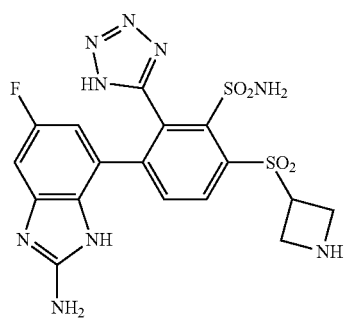 [SMILES: Nc1nc2cc(F)cc(-c3ccc(S(=O)(=O)C4CNC4)c(S(N)(=O)=O)c3-c3nnn[nH]3)c2[nH]1]

The title compound was prepared according to the general procedure described above for EXAMPLE 295 using (3-(N,N-Bis(4-methoxybenzyl)sulfamoyl)-4-((1-(tert-butoxycarbonyl)azetidin-3-yl)sulfonyl)-2-(2-(4-methoxybenzyl)-2H-tetrazol-5-yl)phenyl)boronic acid and (3-(N,N-Bis(4-methoxybenzyl)sulfamoyl)-4-((1-(tert-butoxycarbonyl)azetidin-3-yl)sulfonyl)-2-(1-(4-methoxybenzyl)-1H-tetrazol-5-yl)phenyl)boronic acid (REFERENCE EXAMPLE 7) and 7-bromo-5-fluoro-1H-benzo[d]imidazol-2-amine (REFERENCE EXAMPLE 49). LC/MS [M+H]$^+$ 482.08.

EXAMPLE 297

6-(azetidin-3-ylsulfonyl)-3-(1H-indazol-7-yl)-2-(1H-tetrazol-5-yl)benzenesulfonamide

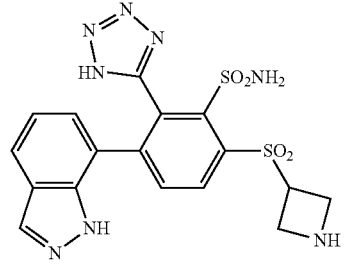 [SMILES: NS(=O)(=O)c1c(S(=O)(=O)C2CNC2)ccc(-c2cccc3cn[nH]c23)c1-c1nnn[nH]1]

Step A: tert-butyl 3-((2-(N,N-bis(4-methoxybenzyl)sulfamoyl)-4-(1H-indazol-7-yl)-3-(2-(4-methoxybenzyl)-2H-tetrazol-5-yl)phenyl)sulfonyl)azetidine-1-carboxylate A suspension of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (500 mg, 0.537 mmol), sodium carbonate (171 mg, 1.61 mmol), 7-(4,4,5,5-tetramethyl-1,3,2-dioxaborolan-2-yl)-1H-indazole (262 mg, 1.074 mmol) and tetrakis(triphenylphosphine)Pd(0) (62 mg, 0.054 mmol) in dioxane (4 ml) and water (1.0 ml) was degassed and heated at 120° C. for 17 hours. The mixture was diluted with EtOAc, then washed with brine. The organic layer was dried (MgSO$_4$) and concentrated. The crude product was chromatographed via silica gel chromatography 40 g column, 0-20% MeOH in DCM) to give the desired product. LC/MS (M+H)+: 921.60.

Step B: 6-(azetidin-3-ylsulfonyl)-3-(1H-indazol-7-yl)-2-(1H-tetrazol-5-yl)benzenesulfonamide A solution of tert-butyl 3-((2-(N,N-bis(4-methoxybenzyl)sulfamoyl)-4-(1H-indazol-7-yl)-3-(2-(4-methoxybenzyl)-2H-tetrazol-5-yl)phenyl)sulfonyl)azetidine-1-carboxylate (240 mg, 0.261 mmol) in DCM (200 µl) was concentrated in vacuum. The residue was dissolved in anisole (280 µl, 2.6 mmol) and TFA (2 ml, 26.1 mmol) at 0° C. After stirring at rt for 0.5 hr, the volatile was removed in vacuo. The residue was dissolved in 2 mL of TFA and stirred at 80° C. for 1.0 hr. After removing the volatile, the residue was dissolved in 1 mL of DMSO and purified by reverse phase HPLC directly (3-60% acetonitrile in water) to give the product. LC/MS (M+H)+: 461.22.

EXAMPLES 298-300 were prepared according to the general procedure described for EXAMPLE 297 using tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate or tert-Butyl 3-((2-(N,N-bis(4-methoxybenzyl)sulfamoyl)-4-iodo-3-(2-(4-methoxybenzyl)-2H-tetrazol-5-yl)phenyl)sulfonyl) azetidine-1-carboxylate and tert-butyl 3-((2-(N,N-bis(4-methoxybenzyl)sulfamoyl)-4-iodo-3-(1-(4-methoxybenzyl)-1H-tetrazol-5-yl)phenyl)sulfonyl) azetidine-1-carboxylate and boronic acids or boronic esters that are commercially available, known, or prepared as described herein.

| Ex. No. | Structure | Name | LC/MS m/e [M + H]$^+$ |
|---|---|---|---|
| 298 | 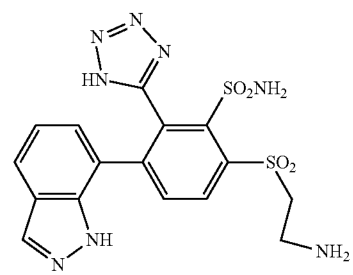 [SMILES: NCCS(=O)(=O)c1ccc(-c2cccc3cn[nH]c23)c(-c2nnn[nH]2)c1S(N)(=O)=O] | 6-((2-aminoethyl)sulfonyl)-3-(1H-indazol-7-yl)-2-(1H-tetrazol-5-yl)benzenesulfonamide | 449.23 |
| 299 | 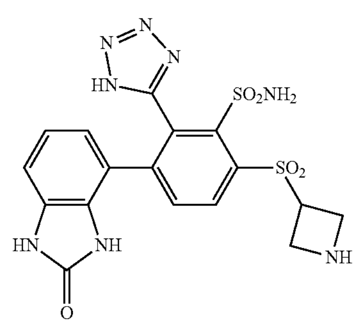 [SMILES: NS(=O)(=O)c1c(S(=O)(=O)C2CNC2)ccc(-c2cccc3[nH]c(=O)[nH]c23)c1-c1nnn[nH]1] | 6-(azetidin-3-ylsulfonyl)-3-(2-oxo-2,3-dihydro-1H-benzo[d]imidazol-4-yl)-2-(1H-tetrazol-5-yl)benzenesulfonamide | 477.20 |
| 300 | 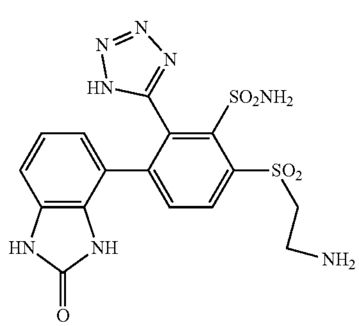 [SMILES: NCCS(=O)(=O)c1ccc(-c2cccc3[nH]c(=O)[nH]c23)c(-c2nnn[nH]2)c1S(N)(=O)=O] | 6-((2-aminoethyl)sulfonyl)-3-(2-oxo-2,3-dihydro-1H-benzo[d]imidazol-4-yl)-2-(1H-tetrazol-5-yl)benzenesulfonamide | 465.19 |

EXAMPLE 301

6-(azetidin-3-ylsulfonyl)-3-(2-oxo-2,3-dihydro-1H-imidazo[4,5-c]pyridin-7-yl)-2-(1H-tetrazol-5-yl)benzenesulfonamide

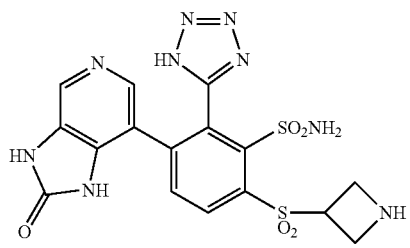 [SMILES: NS(=O)(=O)c1c(S(=O)(=O)C2CNC2)ccc(-c2cncc3[nH]c(=O)[nH]c23)c1-c1nnn[nH]1]

Step A: tert-butyl 3-((2-(N,N-bis(4-methoxybenzyl)sulfamoyl)-4-(4,5-diaminopyridin-3-yl)-3-(2-(4-methoxybenzyl)-2H-tetrazol-5-yl)phenyl)sulfonyl)azetidine-1-carboxylate A suspension of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (200 mg, 0.215 mmol), sodium carbonate (68.3 mg, 0.645 mmol), (4,5-diaminopyridin-3-yl)boronic acid (65.7 mg, 0.430 mmol) and tetrakis(triphenylphosphine)Pd(0) (24.83 mg, 0.021 mmol) in dioxane (4 ml) and water (1.0 ml) was degassed and heated at 80° C. for 17 hours. The mixture was diluted with EtOAc, then washed with brine. The organic layer was dried (MgSO$_4$) and concentrated. The crude product was chromatographed via silica gel (ISCO, 40 g column, 0-20% MeOH in DCM) to give the desired product. LC/MS (M+H)+: 912.60.

Step B: tert-butyl 3-((2-(N,N-bis(4-methoxybenzyl)sulfamoyl)-3-(2-(4-methoxybenzyl)-2H-tetrazol-5-yl)-4-(2-oxo-2,3-dihydro-1H-imidazo[4,5-c]pyridin-7-yl)phenyl)sulfonyl)-azetidine-1-carboxylate To a 5 mL microwave tube added a solution of tert-butyl 3-((2-(N,N-bis(4-methoxybenzyl)sulfamoyl)-4-(4,5-diaminopyridin-3-yl)-3-(2-(4-methoxybenzyl)-2H-tetrazol-5-yl)phenyl)sulfonyl)azetidine-1-carboxylate (18 mg, 0.020 mmol) and di(1H-imidazol-1-yl)methanone (3.20 mg, 0.020 mmol) in toluene (5 ml). The mixture was stirred at 80° C. for 2 hours. The solvent was removed in vacuum and the residue was purified by column chromatography (ISCO RediSep Gold column 24 g) using 0-20% methanol/DCM as mobile phase to obtain the desired product. LC/MS (M+H)+: 938.68.

Step C: 6-(azetidin-3-ylsulfonyl)-3-(2-oxo-2,3-dihydro-1H-imidazo[4,5-c]pyridin-7-yl)-2-(1H-tetrazol-5-yl)benzenesulfonamide A solution of tert-butyl 3-((2-(N,N-bis(4-methoxybenzyl)sulfamoyl)-3-(2-(4-methoxybenzyl)-2H-tetrazol-5-yl)-4-(2-oxo-2,3-dihydro-1H-imidazo[4,5-c]pyridin-7-yl)phenyl)sulfonyl)-azetidine-1-carboxylate (15 mg, 0.016 mmol) in DCM (200 μl) was concentrated in vacuum. The residue was dissolved in anisole (17.38 μl, 0.160 mmol) and TFA (123 μl, 1.6 mmol) at 0° C. After stirring at RT for 0.5 hr, the volatile was removed in vacuo. The residue was dissolved in 0.5 mL of TFA and stirred at 80° C. for 1.0 hr. After removing the volatile, the residue was dissolved in 1 mL of DMSO and purified by reverse phase HPLC directly (3-60% acetonitrile in water) to give the product. LC/MS (M+H)+: 478.25.

EXAMPLE 302

3-(2-amino-1H-benzo[d]imidazol-7-yl)-6-(azetidin-3-ylsulfonyl)-2-(1H-tetrazol-5-yl)benzenesulfonamide

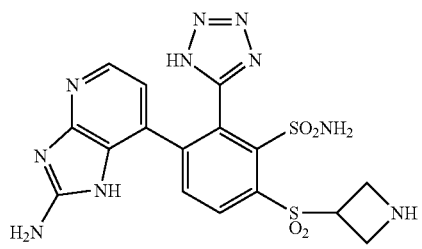 [SMILES: Nc1nc2nccc(-c3ccc(S(=O)(=O)C4CNC4)c(S(N)(=O)=O)c3-c3nnn[nH]3)c2[nH]1]

Step A: tert-butyl 3-((2-(N,N-bis(4-methoxybenzyl)sulfamoyl)-4-(2,3-diaminopyridin-4-yl)-3-(2-(4-methoxybenzyl)-2H-tetrazol-5-yl)phenyl)sulfonyl)azetidine-1-carboxylate A suspension of tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (200 mg, 0.215 mmol), sodium carbonate (68.3 mg, 0.645 mmol), (2,3-diaminopyridin-4-yl)boronic acid (65.7 mg, 0.430 mmol) and tetrakis(triphenylphosphine)Pd(0) (24.83 mg, 0.021 mmol) in dioxane (4 ml) and water (1.0 ml) was degassed and heated at 80° C. for 17 hours. The mixture was diluted with EtOAc, then washed with brine. The organic layer was dried (MgSO$_4$) and concentrated. The crude product was chromatographed via silica gel (ISCO, 40 g column, 0-20% MeOH in DCM) to give the desired product. LC/MS (M+H)$^+$: 912.72.

Step B: tert-butyl 3-((2-(N,N-bis(4-methoxybenzyl)sulfamoyl)-4-(2,3-diaminopyridin-4-yl)-3-(2-(4-methoxybenzyl)-2H-tetrazol-5-yl)phenyl)sulfonyl)azetidine-1-carboxylate To a 5 mL microwave tube was added a solution of tert-butyl 3-((2-(N,N-bis(4-methoxybenzyl)sulfamoyl)-4-(2,3-diaminopyridin-4-yl)-3-(2-(4-methoxybenzyl)-2H-tetrazol-5-yl)phenyl)sulfonyl)azetidine-1-carboxylate (82 mg, 0.090 mmol) and di(1H-imidazol-1-yl)methanimine (14.5 mg, 0.090 mmol) in toluene (5 ml). The mixture was stirred at 100° C. for 2 hours. The solvent was removed in vacuum and the residue was purified by column chromatography (ISCO RediSep Gold column 24 g) using 0-20% methanol/DCM as mobile phase to get the desired product. LC/MS (M+H)+: 938.60.

Step C: 3-(2-amino-3H-imidazo[4,5-b]pyridin-7-yl)-6-(azetidin-3-ylsulfonyl)-2-(2H-tetrazol-5-yl)benzenesulfonamide A solution of tert-butyl 3-((4-(2-amino-3H-imidazo[4,5-b]pyridin-7-yl)-2-(N,N-bis(4-methoxybenzyl)sulfamoyl)-3-

(2-(4-methoxybenzyl)-2H-tetrazol-5-yl)phenyl)sulfonyl) azetidine-1-carboxylate (40 mg, 0.043 mmol) in DCM (200 µl) was concentrated in vacuum. The residue was dissolved in anisole (46.4 µl, 0.427 mmol) and TFA (329 µl, 4.27 mmol) at 0° C. After stirring at RT for 0.5 hr, the volatile was removed in vacuo. The residue was dissolved in 0.5 mL of TFA and stirred at 80° C. for 1.0 hr. After removing the volatile, the residue was dissolved in 1 mL of DMSO and purified by reverse phase HPLC directly (3-60% acetonitrile in water) to give the product. LC/MS (M+H)+: 478.19.

EXAMPLE 303

3-(2-amino-1H-imidazo[4,5-b]pyridin-7-yl)-6-((2-aminoethyl)sulfonyl)-2-(1H-tetrazol-5-yl)benzenesulfonamide

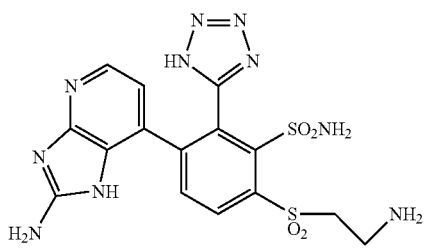 [SMILES: NCCS(=O)(=O)c1ccc(-c2ccnc3nc(N)[nH]c23)c(-c2nnn[nH]2)c1S(N)(=O)=O]

The title compound was prepared in an analogous fashion to that described for EXAMPLE 302 starting from tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl) carbamate and (2,3-diaminopyridin-4-yl)boronic acid. LC/MS [M+H]$^+$466.28.

EXAMPLE 304

5-(4-((2-aminoethyl)sulfonyl)-3-sulfamoyl-2-(1H-tetrazol-5-yl)phenyl)-[1,2,4]triazolo [1,5-a]pyridine-2-carb oxylic Acid

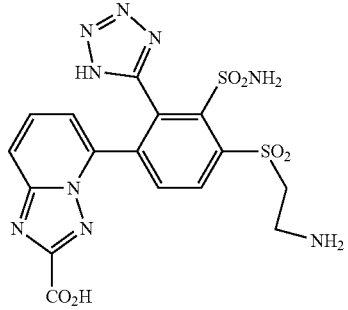 [SMILES: NCCS(=O)(=O)c1ccc(-c2cccc3nc(C(=O)O)nn23)c(-c2nnn[nH]2)c1S(N)(=O)=O]

Step A: methyl 5-(3-(N,N-bis(4-methoxybenzyl) sulfamoyl)-4-((2-((tert-butoxycarbon)amino)ethyl) sulfon-2-(2-(4-meth benz)-2H-tetrazol-5-yl)phenyl)-[1,2,4]triazolo[1,5-a]pyridine-2-carboxylate A suspension of tert-butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate (200 mg, 0.221 mmol), cesium carbonate (216 mg, 0.663 mmol), 2$^{nd}$ generation Xphos precatalyst (34.8 mg, 0.044 mmol), and 5-bromo-[1,2,4] triazolo[1,5-a]pyridine-2-carboxylic acid (64.2 mg, 0.265 mmol) in dioxane (4.0 ml) and water (1.0 ml) was degassed and heated at 120° C. for 17 hours. The mixture was diluted with EtOAc, washed with brine. The organic layer was dried (MgSO$_4$) and concentrated. The crude product was chromatographed via silica gel (ISCO, 40 g column, 0-20% MeOH in DCM) to give the desired product. LC/MS (M+H)+: 968.52.

Step B: 5-(4-((2-aminoethyl)sulfonyl)-3-sulfamoyl-2-(2H-tetrazol-5-yl)phenyl)-[1,2,4]triazolo[1,5-a] pyridine-2-carboxylic Acid A solution of methyl 5-(3-(N,N-bis(4-methoxybenzyl) sulfamoyl)-4-((2-((tert-butoxycarbonyl)amino)ethyl)sulfonyl)-2-(2-(4-methoxybenzyl)-2H-tetrazol-5-yl)phenyl)-[1,2, 4]triazolo[1,5-a]pyridine-2-carboxylate (38 mg, 0.039 mmol) in DCM (200 µL) was concentrated in vacuum. The residue was dissolved in anisole (43 µl, 0.39 mmol) and TFA (0.3 ml, 4 mmol) at 0° C. After stirring at RT for 0.5 hr, the volatile was removed in vacuo. The residue was dissolved in 1 mL of TFA and stirred at 80° C. for 1 hr. After removing the volatile, the residue was dissolved in 1 mL of methanol and purified by reverse phase HPLC directly (3-60% acetonitrile in water) to give the product methyl 5-(4-((2-aminoethyl)sulfonyl)-3-sulfamoyl-2-(2H-tetrazol-5-yl)phenyl)-[1,2,4]triazolo[1,5-a]pyridine-2-carboxylate, which was dissolved in dioxane (2 mL) and water (1 mL), and treated with LiOH (0.385 mg, 0.016 mmol) at RT overnight to give the product. LC/MS (M+H)$^+$: 494.16.

EXAMPLE 305

6-((2-aminoethyl)sulfonyl)-3-(2-(aminomethyl)-1H-benzo[d]imidazol-4-yl)-2-(2H-tetrazol-5-yl)benzenesulfonamide

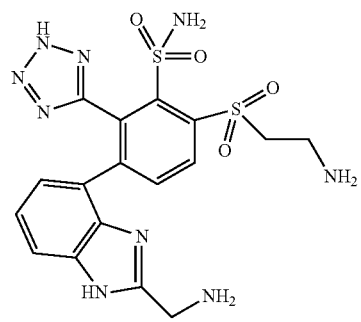 [SMILES: NCCS(=O)(=O)c1ccc(-c2cccc3[nH]c(CN)nc23)c(-c2nn[nH]n2)c1S(N)(=O)=O]

Step A: tert-butyl (2-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)ethyl)carbamate and tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate A suspension of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (11.5 g, 12.52 mmol), 2-nitro-3-(4,4,5,5-tetramethyl-1,3,2-dioxaborolan-2-yl)aniline (9.92 g, 37.5 mmol), tetrakis(triphenylphosphine)palladium(0) (1.446 g, 1.252 mmol) and sodium carbonate (3.98 g, 37.5 mmol) in a mixture solvent of dioxane (100 ml) and water (30 ml) was degassed and heated at 80° C. for 17 hours. The mixture was diluted with AcOEt, then washed with brine. The organic layer was dried (MgSO$_4$) and concentrated. The residue was purified by silica gel chromatography (0-60% the 60% EtOAc in Hexane) to give a mixture of tert-butyl (2-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)ethyl)carbamate and tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate. LCMS[M+1]$^+$: 899.59, 929.57.

Step B: tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate A mixture of tert-butyl (2-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)ethyl)carbamate and tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (3.5 g, 3.77 mmol) and platinum(iv) oxide (0.086 g, 0.377 mmol) in MeOH (50 ml) was hydrogenated at room temperature on a shaker at 50 Psi H$_2$ overnight. The catalyst was filtered off through a CELITE pad and the filtrate was concentrated. LCMS [M+1]$^+$: 899.60

Step C: tert-butyl (2-((2'-amino-3'-(2-(((benzyloxy)carbonyl)amino)acetamido)-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate To a solution of tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (0.3 g, 0.334 mmol), 2-(((benzyloxy)carbonyl)amino)acetic acid (0.070 g, 0.334 mmol) and EDC (0.096 g, 0.501 mmol) in DCM (25 ml) was added DMAP (0.045 g, 0.367 mmol) at room temperature. The mixture was stirred at room temperature overnight, washed with KHSO$_4$ aqueous and brine, dried (MgSO4) and concentrated. The crude material was directly used in the next step. LCMS [M+1]$^+$: 1090.66.

Step D: tert-butyl (2-((4-(2-((((benzyloxy)carbonyl)amino)methyl)-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate tert-butyl (2-((2'-amino-3'-(2-(((benzyloxy)carbonyl)amino)acetamido)-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (0.36 g, 0.33 mmol) in AcOH (20 ml) was heated at 80° C. for 1 hr. The mixture was concentrated. The crude material was directly used in the next step. LCMS [M+1]$^+$: 1072.70.

Step E: 6-((2-aminoethyl)sulfonyl)-3-(2-(aminomethyl)-1H-benzo[d]imidazol-4-yl)-2-(2H-tetrazol-5-yl)benzenesulfonamide tert-Butyl (2-((4-(2-((((benzyloxy)carbonyl)amino)methyl)-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate was dissolved in DCM (10 ml), and stirred with TFA (3 ml) at room temperature for 1 hr. The solution was concentrated under vacuum, and the residue was heated at 80° C. in TFA (5 ml) for 1 hr. Volatiles were evaporated under reduced pressure, and the crude material was purified by reverse phase HPLC (3-37% water in acetonitrile with 0.05% TFA). LCMS [M+1]$^+$: 478.26.

EXAMPLES 306-307 were synthesized using the procedure described for EXAMPLE 305, starting from tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (Step B) and commercially available carboxylic acids.

| Ex. No. | Starting Acid | Structure | Name | LC/MS m/e [M + H]$^+$ |
|---|---|---|---|---|
| 306 | HOOC-CH$_2$CH$_2$-NHBoc | (structure) | 3-(2-(2-aminoethyl)-1H-benzo[d]imidazol-4-yl)-6-((2-aminoethyl)sulfonyl)-2-(2H-tetrazol-5-yl)benzenesulfonamide | 492.39 |

| Ex. No. | Starting Acid | Structure | Name | LC/MS m/e [M + H]+ |
|---|---|---|---|---|
| 307 | HO-C(=O)-CF2-CH2-N(Bn)(Bn) (two Bn groups were removed by Hydrogenation over Pd(OH)2) | 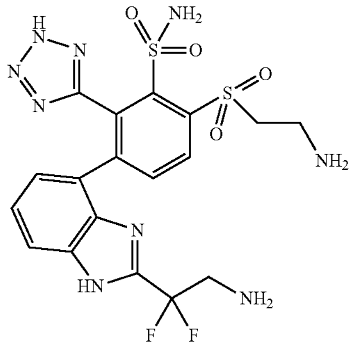 [SMILES: NCCS(=O)(=O)c1ccc(-c2cccc3[nH]c(C(F)(F)CN)nc23)c(-c2nn[nH]n2)c1S(N)(=O)=O] | 3-(2-(2-amino-1,1-difluoroethyl)-1H-benzo[d]imidazol-4-yl)-6-((2-aminoethyl)sulfonyl)-2-(2H-tetrazol-5-yl)benzenesulfonamide | 528.34 |

EXAMPLE 308

6-((2-aminoethyl)sulfonyl)-2-(2H-tetrazol-5-yl)-3-(2-(trifluoromethyl)-1H-benzo[d]imidazol-4-yl)benzenesulfonamide

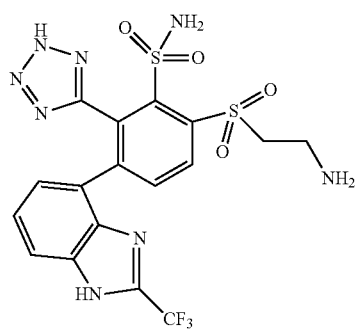 [SMILES: NCCS(=O)(=O)c1ccc(-c2cccc3[nH]c(C(F)(F)F)nc23)c(-c2nn[nH]n2)c1S(N)(=O)=O]

tert-Butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (0.17 g, 0.189 mmol) and TFA (0.029 ml, 0.378 mmol) in 4 N HCl (15 ml) were heated at 90° C. overnight. The mixture was concentrated, and the residue was purified by reverse phase HPLC (10-50% water in acetonitrile with 0.05% TFA). LCMS 517.25.

EXAMPLE 309

6-(azetidin-3-ylsulfonyl)-3-(2-hydroxybenzo[d]thiazol-4-yl)-2-(2H-tetrazol-5-yl)benzenesulfonamide

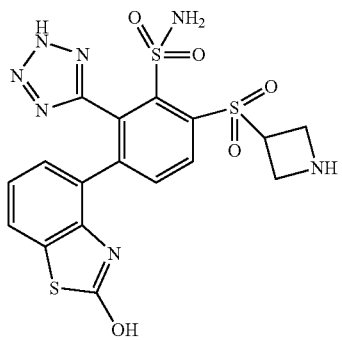 [SMILES: NS(=O)(=O)c1c(S(=O)(=O)C2CNC2)ccc(-c2cccc3sc(O)nc23)c1-c1nn[nH]n1]

A mixture of sodium hydroxide (0.181 ml, 0.181 mmol), tert-butyl 3-((2-(N,N-bis(4-methoxybenzyl)sulfamoyl)-3-(2-(4-methoxybenzyl)-2H-tetrazol-5-yl)-4-(2-((2-(trimethylsilyl)ethyl)sulfonyl)benzo[d]thiazol-4-yl)phenyl)sulfonyl)azetidine-1-carboxylate (0.1 g, 0.091 mmol) and methyl 2-aminoacetate (0.024 g, 0.272 mmol) in MeOH (3 ml) was heated in microwave oven at 150° C. for 1 hr. The mixture was cooled to RT, diluted with EtOAc, and washed with KHSO4. The organic layer was dried over MgSO4 and concentrated. LCMS [M+1]+: 954.49.mm. The residue was dissolved in DCM (4 ml), and stirred at RT for 1 hr with 2 ml TFA and two drops anisole, and concentrated under reduced pressure. The residue was heated at 80° C. in 2 ml TFA for 60 min. Volatiles were removed under vacuum, and the crude material was purified by reverse phase HPLC (10-50% AcCN in water with 0.05% TFA). LCMS 494.15.

EXAMPLE 310

3-(2'-Amino-[2,3'-bipyridin]-4-yl)-6-(azetidin-3-ylsulfonyl)-2-(1H-tetrazol-5-yl)benzenesulfonamide

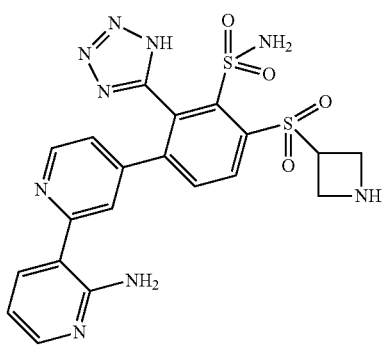 [SMILES: Nc1ncccc1-c1cc(-c2ccc(S(=O)(=O)C3CNC3)c(S(N)(=O)=O)c2-c2nnn[nH]2)ccn1]

Step A: tert-Butyl 3-((2-(N,N-bis(4-methoxybenzyl)sulfamoyl)-4-(2-chloropyridin-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-chloropyridin-4-yl)-3-(2-(4-methoxybenzyl)-2H-tetrazol-5-yl)phenyl)sulfonyl)azetidine-1-carboxylate 2-Chloro-4-(4,4,5,5-tetramethyl-1,3,2-dioxaborolan-2-yl)pyridine (425 mg, 1.773 mmol), tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (1500 mg, 1.611 mmol), sodium carbonate (342 mg, 3.22 mmol), Pd(dppf)Cl$_2$ (118 mg, 0.161 mmol) were placed in a reaction vial. Dioxane (12.1 mL) and water (4.0 mL) were added. The reaction mixture was degassed and then heated at 80° C. for 12 hours. The reaction mixture was then purified by column chromatography (0-75% EtOAc/hexane) to give tert-butyl 3-((2-(N,N-bis(4-methoxybenzyl)sulfamoyl)-4-(2-chloropyridin-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-chloropyridin-4-yl)-3-(2-(4-methoxybenzyl)-2H-tetrazol-5-yl)phenyl)sulfonyl)azetidine-1-carboxylate. LC-MS [M+H]$^+$: 916.6.

Step B: tert-Butyl 3-((4-(2'-amino-[2,3'-bipyridin]-4-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2'-amino-[2,3'-bipyridin]-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate tert-butyl (3-(4,4,5,5-tetramethyl-1,3,2-dioxaborolan-2-yl)pyridin-2-yl)carbamate (57.6 mg, 0.180 mmol), tert-butyl 3-((2-(N,N-bis(4-methoxybenzyl)sulfamoyl)-4-(2-chloropyridin-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-chloropyridin-4-yl)-3-(2-(4-methoxybenzyl)-2H-tetrazol-5-yl)phenyl)sulfonyl)azetidine-1-carboxylate (150 mg, 0.164 mmol), sodium carbonate (34.7 mg, 0.327 mmol), Pd(dppf)Cl$_2$ (11.98 mg, 0.016 mmol) were placed in a reaction vial and dioxane (1228 μl) and water (409 μl) were added. The reaction was degassed and then heated at 80° C. for 12 hours. The reaction mixture was purified by silica gel column chromatography (0-10% MeOH/EtOAc) to give tert-butyl 3-((4-(2'-amino-[2,3'-bipyridin]-4-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2'-amino-[2,3'-bipyridin]-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate. LC-MS [M+H]$^+$: 974.7

Step C: 3-(2'-Amino-[2,3'-bipyridin]-4-yl)-6-(azetidin-3-ylsulfonyl)-2-(1H-tetrazol-5-yl)benzenesulfonamide 3-(2'-Amino-[2,3'-bipyridin]-4-yl)-6-(azetidin-3-ylsulfonyl)-2-(1H-tetrazol-5-yl)benzenesulfonamide was prepared in a similar fashion to the synthesis of 6-(azetidin-3-ylsulfonyl)-3-(imidazo[1,2-a]pyridin-8-yl)-2-(1H-tetrazol-5-yl)benzenesulfonamide (Example 1, Step C and D) from tert-butyl 3-((4-(2'-amino-[2,3'-bipyridin]-4-yl)-2-(N,N-bis(4-methoxybenzyl)sulfamoyl)-3-(1-(4-methoxybenzyl)-1H-tetrazol-5-yl)phenyl)sulfonyl)azetidine-1-carboxylate and tert-butyl 3-((4-(2'-amino-[2,3'-bipyridin]-4-yl)-2-(N,N-bis(4-methoxybenzyl)sulfamoyl)-3-(2-(4-methoxybenzyl)-2H-tetrazol-5-yl)phenyl)sulfonyl)azetidine-1-carboxylate. LC-MS [M+H]$^+$: 514.4.

EXAMPLE 311

3-(2'-amino-[2,4'-bipyridin]-4-yl)-6-(azetidin-3-ylsulfonyl)-2-(1H-tetrazol-5-yl)benzenesulfonamide

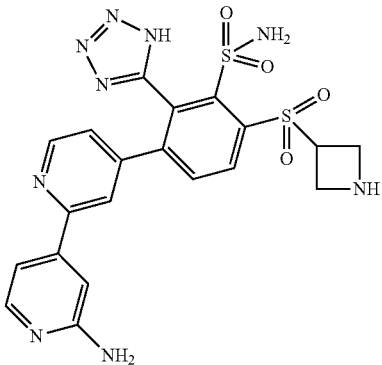 [SMILES: Nc1cc(-c2cc(-c3ccc(S(=O)(=O)C4CNC4)c(S(N)(=O)=O)c3-c3nnn[nH]3)ccn2)ccn1]

Step A: tert-Butyl 3-((2-(N,N-bis(4-methoxybenzyl)sulfamoyl)-4-(2'-((tert-butoxycarbonyl)amino)-[2,4'-bipyridin]-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2'-((tert-butoxycarbonyl)amino)-[2,4'-bipyridin]-4-yl)-3-(2-(4-methoxybenzyl)-2H-tetrazol-5-yl)phenyl)sulfonyl)azetidine-1-carboxylate tert-Butyl (4-(4,4,5,5-tetramethyl-1,3,2-dioxaborolan-2-yl)pyridin-2-yl)carbamate (57.6 mg, 0.180 mmol), tert-butyl 3-((2-(N,N-bis(4-methoxybenzyl)sulfamoyl)-4-(2-chloropyridin-4-yl)-3-(1-(4-methoxybenzyl)-1H-tetrazol-5-yl) phenyl)sulfonyl)azetidine-1-carboxylate and tert-butyl 3-((2-(N,N-bis(4-methoxybenzyl)sulfamoyl)-4-(2-chloropyridin-4-yl)-3-(2-(4-methoxybenzyl)-2H-tetrazol-5-yl) phenyl)sulfonyl)azetidine-1-carboxylate (Example 10, Step A) (150 mg, 0.164 mmol), sodium carbonate (34.7 mg, 0.327 mmol), Pd(dppf)₂Cl₂ (11.98 mg, 0.016 mmol) were placed in a reaction vial. Dioxane (1228 µl) and water (409 µl) were added. The reaction mixture was degassed and heated at 80° C. for 1 hr. The reaction mixture was cooled and purified by silica gel column chromatography (0-75% EtOAc/hexane) to give tert-butyl 3-((2-(N,N-bis(4-methoxybenzyl)sulfamoyl)-4-(2'-((tert-butoxycarbonyl)amino)-[2,4'-bipyridin]-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2'-((tert-butoxycarbonyl)amino)-[2,4'-bipyridin]-4-yl)-3-(2-(4-methoxybenzyl)-2H-tetrazol-5-yl)phenyl)sulfonyl) azetidine-1-carboxylate. LC-MS [M+H]⁺: 1074.7.

Step B: 3-(2'-Amino-[2,4'-bipyridin]-4-yl)-6-(azetidin-3-ylsulfonyl)-2-(1H-tetrazol-5-yl)benzenesulfonamide 3-(2'-Amino-[2,4'-bipyridin]-4-yl)-6-(azetidin-3-ylsulfonyl)-2-(1H-tetrazol-5-yl)benzenesulfonamide was prepared in a similar fashion to the synthesis of 6-(azetidin-3-ylsulfonyl)-3-(imidazo[1,2-a]pyridin-8-yl)-2-(1H-tetrazol-5-yl) benzenesulfonamide (Example 1, Steps C and D) from tert-butyl 3-((2-(N,N-bis(4-methoxybenzyl)sulfamoyl)-4-(2'-((tert-butoxycarbonyl)amino)-[2,4'-bipyridin]-4-yl)-3-(1-(4-methoxybenzyl)-1H-tetrazol-5-yl)phenyl)sulfonyl) azetidine-1-carboxylate and tert-butyl 3-((2-(N,N-bis(4-methoxybenzyl)sulfamoyl)-4-(2'-((tert-butoxycarbonyl)amino)-[2,4'-bipyridin]-4-yl)-3-(2-(4-methoxybenzyl)-2H-tetrazol-5-yl)phenyl)sulfonyl)azetidine-1-carboxylate. LC-MS [M+H]⁺: 514.3.

EXAMPLE 312

3-(2-amino-1H-benzo[d]imidazol-4-yl)-6-((R)-3-amino-2-hydroxypropylsulfonyl)-2-(2H-tetrazol-5-yl)benzenesulfonamide

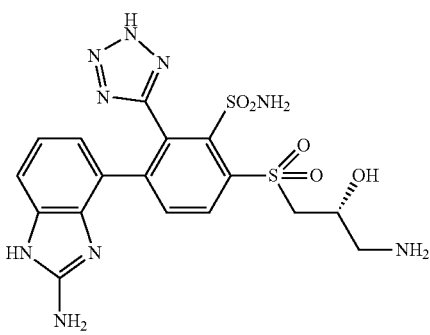 [SMILES: NC[C@@H](O)CS(=O)(=O)c1ccc(-c2cccc3[nH]c(N)nc23)c(-c2nn[nH]n2)c1S(N)(=O)=O]

The title compound was prepared in an analogous fashion as described for EXAMPLE 282 starting from (R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate, prepared as described in EXAMPLES 281 and 282, Steps A-H, except starting from (R)-3-aminopropane-1,2-diol. LC/MS [M+H]⁺ 494.

EXAMPLE 313

3-(2-aminobenzo[d]thiazol-4-yl)-6-((2-aminoethyl) sulfonyl)-2-(2H-tetrazol-5-yl)benzenesulfonamide

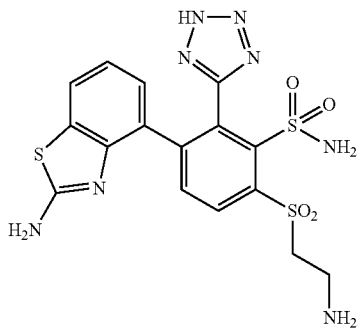 [SMILES: NCCS(=O)(=O)c1ccc(-c2cccc3sc(N)nc23)c(-c2nn[nH]n2)c1S(N)(=O)=O]

Step A: tert-butyl (2-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonyl) ethyl)carbamate and tert-butyl (2-((4-(2-aminobenzo [d]thiazol-4-yl)-2-(N,N-bis(4-methoxybenzyl) sulfamoyl)-3-(2-(4-methoxybenzyl)-2H-tetrazol-5-yl)phenyl)sulfonyl)ethyl)carbamate To a suspension of tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl) carbamate (0.55 g, 0.599 mmol), (2-aminobenzo[d]thiazol-4-yl)boronic acid (0.348 g, 1.796 mmol), was added tetrakis (triphenylphosphine)palladium(0) (0.069 g, 0.060 mmol) and sodium carbonate (0.190 g, 1.796 mmol) in dioxane (9 ml) and water (3 ml). The solution was thoroughly degassed and was heated at 80° C. for 17 hours. The mixture was diluted with EtOAc (200 mL), washed with brine (2×75 mL). The organic layer was dried (MgSO₄) and concentrated to isolate the title compound as an oil. LC/MS [M+H]⁺: 941.

Step B: 3-(2-aminobenzo[d]thiazol-4-yl)-6-((2-aminoethyl)sulfonyl)-2-(2H-tetrazol-5-yl)benzenesulfonamide tert-butyl (2-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonyl)ethyl)carbamate and tert-butyl (2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)ethyl)carbamate was treated with TFA (100 equiv) and p-anisole (10 equiv) and stirred at 80° C. for 30 min. The mixture was concentrated and purified by reverse phase HPLC to isolate the title compound. LC/MS[M+H]⁺: 481.18.

The compounds below were prepared using the same general procedure as EXAMPLE 313, substituting the appropriate reactants and reagents, which were commercially available or prepared as described herein.

| Ex. No. | Structure | Name | LC/MS m/e [M + H]+ |
|---|---|---|---|
| 321 | 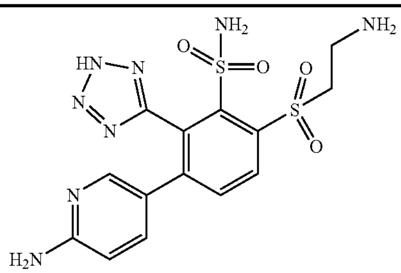 | 6-((2-aminoethyl)sulfonyl)-3-(6-aminopyridin-3-yl)-2-(2H-tetrazol-5-yl)benzenesulfonamide | 425.31 |
| 324 | 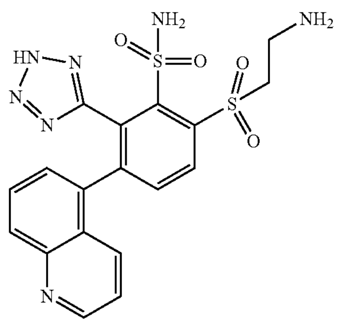 [SMILES: NCCS(=O)(=O)c1ccc(-c2cccc3ncccc23)c(-c2nn[nH]n2)c1S(N)(=O)=O] | 6-((2-aminoethyl)sulfonyl)-3-(quinolin-5-yl)-2-(2H-tetrazol-5-yl)benzenesulfonamide | 460.29 |

EXAMPLE 314

3-(2-aminobenzo[d]thiazol-4-yl)-6-((2-hydroxyethyl)sulfonyl)-2-(2H-tetrazol-5-yl)benzenesulfonamide

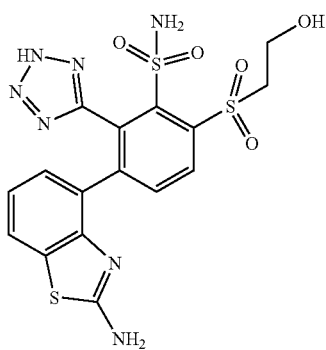 [SMILES: Nc1nc2c(-c3ccc(S(=O)(=O)CCO)c(S(N)(=O)=O)c3-c3nn[nH]n3)cccc2s1]

Step A: 3-(2-aminobenzo[d]thiazol-4-yl)-6-((2-hydroxyethyl)thio)-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-((2-hydroxyethyl)thio)-N,N-bis(4-methoxybenzyl)-2-(2-(4-methoxybenzyl)-2H-tetrazol-5-yl)benzenesulfonamide 3-(2-aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide (REFERENCE EXAMPLE 40, 300 mg, 0.369 mmol) was taken in dioxane (3691 µl) and the solution was degassed with nitrogen was added N-ethyl-N-isopropylpropan-2-amine (193 µl, 1.107 mmol), Pd$_2$dba$_3$ (33.8 mg, 0.037 mmol), and 4,5-bis(diphenylphosphino)-9,9-dimethylxanthene (42.7 mg, 0.074 mmol). The solution was degassed and 2-mercaptoethanol (57.7 mg, 0.738 mmol) was added and the reaction heated at 150° C. for 30 min under microwave irradiation. The solution was brought to room temperature and diluted with EtOAc. The organic was filtered through CELITE and the resulting filter cake was washed with EtOAc. The combined organic were concentrated in vacuo and purified on flash chromatography to isolate the title compound as an oil. LC/MS [M+H]+: 810

Step B: 3-(2-aminobenzo[d]thiazol-4-yl)-6-((2-hydroxyethyl)sulfonyl)-2-(2H-tetrazol-5-yl)benzenesulfonamide To a solution of 3-(2-aminobenzo[d]thiazol-4-yl)-6-((2-hydroxyethyl)thio)-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-((2-hydroxyethyl)thio)-N,N-bis(4-methoxybenzyl)-2-(2-(4-methoxybenzyl)-2H-tetrazol-5-yl)benzenesulfonamide dissolved in CH$_2$Cl$_2$ was added mCPBA (5 equivalents) and the mixture was stirred for 16 hours. The solution was extracted with 10% sodium thiosulfate. The resulting organic was concentrated and purified by flash silica gel chromatography to isolate the sulfone intermediate. The intermediate was heated in a mixture of TFA (100 equiv) and p-anisole (10 equiv) at 80° C. for thirty minutes. After this time the solution was concentrated and purified on reverse phase chromatography to isolate the title compound. LC/MS$_{calc}$ [M+H]+: 481.52 LC/MS$_{obs}$ [M+H]+: 482.30.

EXAMPLES 315 and 316

3-(2-aminobenzo[d]thiazol-4-yl)-6-(piperidin-4-yl-sulfonyl)-2-(2H-tetrazol-5-yl)benzenesulfonamide and 3-(2-amino-1-oxidobenzo[d]thiazol-4-yl)-6-(piperidin-4-ylsulfonyl)-2-(2H-tetrazol-5-yl)benzenesulfonamide

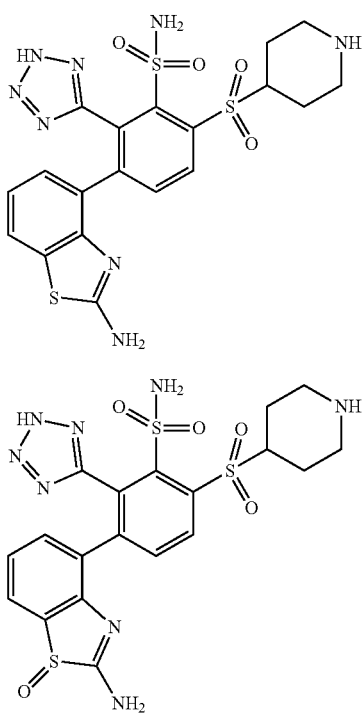

Step A: tert-butyl 4-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)thio)piperidine-1-carboxylate and tert-butyl 4-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)thio)piperidine-1-carboxylate 3-(2-aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide and t-butyl 4-mercaptopiperidine-mercaptopiperidine 1-carboxylate was treated with tert-butyl 4-mercaptopiperidine-1-carboxylate in the same fashion as in EXAMPLE 314, Step A to isolate the title compound as an oil. LC/MS [M+H]+: 949.

Step B: 3-(2-aminobenzo[d]thiazol-4-yl)-6-(piperidin-4-ylsulfonyl)-2-(2H-tetrazol-5-yl)benzenesulfonamide A solution of tert-butyl 4-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)thio)piperidine-1-carboxylate and tert-butyl 4-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)thio)piperidine-1-carboxylate dissolved in $CH_2Cl_2$ was treated with mCPBA (5 equivalents) and the mixture was stirred for 16 hours. The solution was extracted with 10% sodium thiosulfate. The resulting organic phase was concentrated and purified by flash silica gel chromatography to afford the sulfone intermediate along with the S-oxide intermediate. The resulting two intermediates were each dissolved in TFA (100 equiv) and p-anisole (10 equiv) and stirred at 80° C. for thirty minutes. After this time, the solutions were concentrated and purified on reverse phase chromatography to isolate the title compounds. EXAMPLE 315: LC/MS [M+H]+: 521.42; EXAMPLE 316: LC/MS [M+H]+: 537.45.

EXAMPLE 317

3-(2-aminobenzo[d]thiazol-4-yl)-6-(azetidin-3-ylsulfonyl)-2-(2H-tetrazol-5-yl)benzenesulfonamide

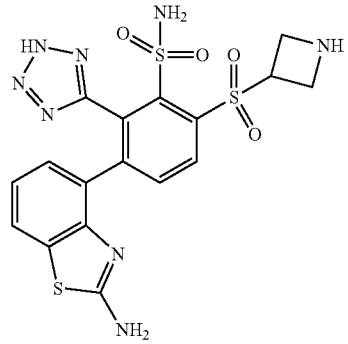 [SMILES: Nc1nc2c(-c3ccc(S(=O)(=O)C4CNC4)c(S(N)(=O)=O)c3-c3nn[nH]n3)cccc2s1]

Step A: tert-butyl 3-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)thio)azetidine-1-carboxylate and tert-butyl 3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)thio)azetidine-1-carboxylate 3-(2-aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide (REFERENCE EXAMPLE 40), was treated with tert-butyl 3-mercaptoazetidine-1-carboxylate in the same fashion as in EXAMPLE 314, Step A to isolate the title compound. LC/MS [M+H]+: 921.

Step B: 3-(2-aminobenzo[d]thiazol-4-yl)-6-(azetidin-3-ylsulfonyl)-2-(2H-tetrazol-5-yl)benzenesulfonamide A solution of tert-butyl 3-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)thio)azetidine-1-carboxylate and tert-butyl 3-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)thio)azetidine-1-carboxylate dissolved in $CH_2Cl_2$ was treated with mCPBA (5 equivalents) and the mixture was stirred for 16 hours. The solution was extracted with 10% sodium thiosulfate. The resulting organic was concentrated and purified on flash chromatography to isolate the sulfone intermediate. The resulting residue was dissolved in TFA (100 equiv) and p-anisole (10 equiv) and stirred at 80° C. for thirty minutes. After this time the solution was concentrated and purified on reverse phase chromatography to isolate the title compound. LC/MS [M+H]⁺: 493.34.

EXAMPLE 318

3-(1-oxoisoindolin-4-yl)-6-(piperidin-4-ylsulfonyl)-2-(2H-tetrazol-5-yl)benzenesulfonamide

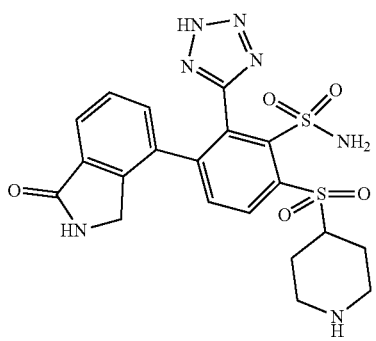 [SMILES: NS(=O)(=O)c1c(S(=O)(=O)C2CCNCC2)ccc(-c2cccc3c2CNC3=O)c1-c1nn[nH]n1]

Step A: 6-bromo-N,N-bis(4-methoxybenzyl)-2-(1-(4-methoxybenzyl)-1H-tetrazol-5-yl)-3-(1-oxoisoindolin-4-yl)benzenesulfonamide and 6-bromo-N,N-bis(4-methoxybenzyl)-2-(2-(4-methoxybenzyl)-2H-tetrazol-5-yl)-3-(1-oxoisoindolin-4-yl)benzenesulfonamide A microwave vial was charged with 6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide (2.2 g, 2.78 mmol), 4-(4,4,5,5-tetramethyl-1,3,2-dioxaborolan-2-yl)isoindolin-1-one (772 mg, 2.98 mmol), Na₂CO₃ (1475 mg, 13.92 mmol) and PdCl₂(dppf)-CH₂Cl₂ adduct (227 mg, 0.278 mmol). The vial was sealed, degassed, and filled with dioxane (10 mL) and water (3.5 mL). The resulting suspension was heated for 16 hours at 90° C. The reaction mixture was filtered over CELITE to removed palladium. The filtrate was diluted with EtOAc (200 mL) and washed with water (2×75 mL). The organic layer was dried over anhydrous MgSO₄, filtered, concentrated and purified by silica gel column chromatography to isolate the title compound. LC/MS [M+H]⁺:795, 797.

Step B: tert-butyl 4-((2-(N,N-bis(4-methoxybenzyl)sulfamoyl)-3-(1-(4-methoxybenzyl)-1H-tetrazol-5-yl)-4-(1-oxoisoindolin-4-yl)phenyl)thio)piperidine-1-carboxylate and tert-butyl 4-((2-(N,N-bis(4-methoxybenzyl)sulfamoyl)-3-(2-(4-methoxybenzyl)-2H-tetrazol-5-yl)-4-(1-oxoisoindolin-4-yl)phenyl)thio)piperidine-1-carboxylate To a mixture of 6-bromo-N,N-bis(4-methoxybenzyl)-2-(1-(4-methoxybenzyl)-1H-tetrazol-5-yl)-3-(1-oxoisoindolin-4-yl)benzenesulfonamide and 6-bromo-N,N-bis(4-methoxybenzyl)-2-(2-(4-methoxybenzyl)-2H-tetrazol-5-yl)-3-(1-oxoisoindolin-4-yl)benzenesulfonamide with t-butyl 4-mercaptopiperidine-mercaptopiperidine 1-carboxylate was treated with tert-butyl 4-mercaptopiperidine-1-carboxylate in the same fashion as in EXAMPLE 314, Step A to isolate the title compound as an oil. LC/MS [M+H]⁺:933.

Step C: 3-(1-oxoisoindolin-4-yl)-6-(piperidin-4-ylsulfonyl)-2-(2H-tetrazol-5-yl)benzenesulfonamide A mixture of tert-butyl 4-((2-(N,N-bis(4-methoxybenzyl)sulfamoyl)-3-(1-(4-methoxybenzyl)-1H-tetrazol-5-yl)-4-(1-oxoisoindolin-4-yl)phenyl)thio)piperidine-1-carboxylate and tert-butyl 4-((2-(N,N-bis(4-methoxybenzyl)sulfamoyl)-3-(2-(4-methoxybenzyl)-2H-tetrazol-5-yl)-4-(1-oxoisoindolin-4-yl)phenyl)thio)piperidine-1-carboxylate dissolved in CH₂Cl₂ was treated with mCPBA (5 equivalents) and the mixture was stirred for 16 hours. The solution was extracted with 10% sodium thiosulfate. The resulting organic was concentrated and purified on flash chromatography to isolate the sulfone intermediate. The resulting residue was dissolved in TFA (100 equiv) and p-anisole (10 equiv) at 80° C. for thirty minutes. After this time the solution was concentrated and purified on reverse phase chromatography to isolate the title compound. LC/MS [M+H]⁺: 504.45.

EXAMPLE 319

2-amino-8-(4-((2-hydroxyethyl)sulfonyl)-3-sulfamoyl-2-(2H-tetrazol-5-yl)phenyl)quinazoline 3-oxide

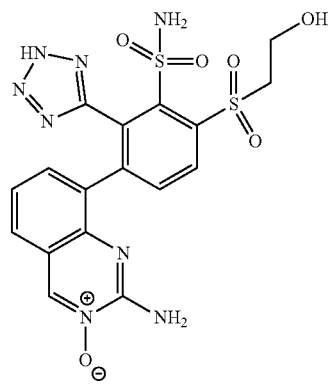 [SMILES: Nc1nc2c(-c3ccc(S(=O)(=O)CCO)c(S(N)(=O)=O)c3-c3nn[nH]n3)cccc2c[n+]1[O-]]

Step A: 3-(2-aminoquinazolin-8-yl)-6-bromo-N,N-bis(4-methoxybenzyl)-2-(1-(4-methoxybenzyl)-1H-tetrazol-5-yl)benzenesulfonamide and 3-(2-aminoquinazolin-8-yl)-6-bromo-N,N-bis(4-methoxybenzyl)-2-(2-(4-methoxybenzyl)-2H-tetrazol-5-yl)benzenesulfonamide The title compound was prepared starting from 6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide and (2-aminoquinazolin-8-yl)boronic acid using the same method as described in EXAMPLE 318, Step A. LC/MS [M+H]⁺: 807, 809.

Step B: 3-(2-aminoquinazolin-8-yl)-6-((2-hydroxyethyl)thio)-N,N-bis(4-methoxybenzyl)-2-(1-(4-methoxybenzyl)-1H-tetrazol-5-yl)benzenesulfonamide and 3-(2-aminoquinazolin-8-yl)-6-((2-hydroxyethyl)thio)-N,N-bis(4-methoxybenzyl)-2-(2-(4-methoxybenzyl)-2H-tetrazol-5-yl)benzenesulfonamide A mixture of 3-(2-aminoquinazolin-8-yl)-6-bromo-N,N-bis(4-methoxybenzyl)-2-(1-(4-methoxybenzyl)-1H-tetrazol-5-yl)benzenesulfonamide and 3-(2-aminoquinazolin-8-yl)-6-bromo-N,N-bis(4-methoxybenzyl)-2-(2-(4-methoxybenzyl)-2H-tetrazol-5-yl)benzenesulfonamide and 2-mercaptoethan-1-ol was treated as in EXAMPLE 314, Step A to isolate the title compound as an oil. LC/MS [M+H]$^+$: 805.

Step C: 2-amino-8-(4-((2-hydroxyethyl)sulfonyl)-3-sulfamoyl-2-(2H-tetrazol-5-yl)phenyl)quinazoline 3-oxide A mixture of 3-(2-aminoquinazolin-8-yl)-6-((2-hydroxyethyl)thio)-N,N-bis(4-methoxybenzyl)-2-(1-(4-methoxybenzyl)-1H-tetrazol-5-yl)benzenesulfonamide compound with 3-(2-aminoquinazolin-8-yl)-6-((2-hydroxyethyl)thio)-N,N-bis(4-methoxybenzyl)-2-(2-(4-methoxybenzyl)-2H-tetrazol-5-yl)benzenesulfonamide was dissolved in $CH_2Cl_2$ and treated with mCPBA (5 equivalents), and the mixture was stirred for 16 hours. The solution was extracted with 10% sodium thiosulfate. The resulting organic was concentrated and purified on flash chromatography to isolate the sulfone intermediate. The resulting sulfone was dissolved in TFA (100 equiv) and p-anisole (10 equiv) at 80° C. for thirty minutes. After this time the solution was concentrated and purified on reverse phase chromatography to isolate the title compound. LC/MS [M+H]$^+$: 493.45.

EXAMPLE 320

5-(4-((2-hydroxyethyl)sulfonyl)-3-sulfamoyl-2-(2H-tetrazol-5-yl)phenyl)quinoline 1-oxide

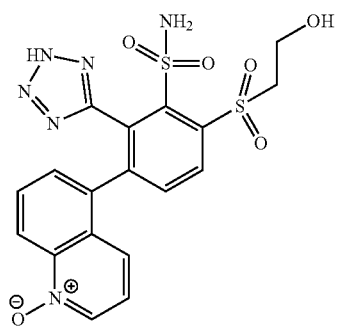 [SMILES: NS(=O)(=O)c1c(S(=O)(=O)CCO)ccc(-c2cccc3c2ccc[n+]3[O-])c1-c1nn[nH]n1]

Step A: 6-bromo-N,N-bis(4-methoxybenzyl)-2-(1-(4-methoxybenzyl)-1H-tetrazol-5-yl)-3-(quinolin-5-yl)benzenesulfonamide and 6-bromo-N,N-bis(4-methoxybenzyl)-2-(2-(4-methoxybenzyl)-2H-tetrazol-5-yl)-3-(quinolin-5-yl)benzenesulfonamide The title compound was prepared starting from a mixture of 6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide and quinoline-5-boronic acid using the same method as described in EXAMPLE 318, Step A. LC/MS [M+H]$^+$: 791,793.

Step B: 6-((2-hydroxyethyl)thio)-N,N-bis(4-methoxybenzyl)-2-(1-(4-methoxybenzyl)-1H-tetrazol-5-yl)-3-(quinolin-5-yl)benzenesulfonamide and 6-((2-hydroxyethyl)thio)-N,N-bis(4-methoxybenzyl)-2-(2-(4-methoxybenzyl)-2H-tetrazol-5-yl)-3-(quinolin-5-yl)benzenesulfonamide A mixture of 6-bromo-N,N-bis(4-methoxybenzyl)-2-(1-(4-methoxybenzyl)-1H-tetrazol-5-yl)-3-(quinolin-5-yl)benzenesulfonamide and 6-bromo-N,N-bis(4-methoxybenzyl)-2-(2-(4-methoxybenzyl)-2H-tetrazol-5-yl)-3-(quinolin-5-yl)benzenesulfonamide and 2-mercaptoethan-1-ol was treated as in EXAMPLE 314, Step A to isolate the tile compound. LC/MS [M+H]$^+$: 789.

Step C: 5-(4-((2-hydroxyethyl)sulfonyl)-3-sulfamoyl-2-(2H-tetrazol-5-yl)phenyl)quinoline 1-oxide A mixture of 6-((2-hydroxyethyl)thio)-N,N-bis(4-methoxybenzyl)-2-(1-(4-methoxybenzyl)-1H-tetrazol-5-yl)-3-(quinolin-5-yl)benzenesulfonamide and 6-((2-hydroxyethyl)thio)-N,N-bis(4-methoxybenzyl)-2-(2-(4-methoxybenzyl)-2H-tetrazol-5-yl)-3-(quinolin-5-yl)benzenesulfonamide was dissolved in $CH_2Cl_2$ and treated with mCPBA (5 equivalents), and the mixture was stirred for 16 hours. The solution was extracted with 10% sodium thiosulfate. The resulting organic was concentrated and purified on flash chromatography to isolate the sulfone intermediate. The resulting sulfone was dissolved in TFA (100 equiv) and p-anisole (10 equiv) at 80° C. for thirty minutes, then the solution was concentrated and purified on reverse phase chromatography to isolate the title compound. LC/MS [M+H]$^+$: 477.37.

EXAMPLE 322

4-((2-aminoethyl)sulfonyl)-4'-(piperidin-4-yl)-2-(2H-tetrazol-5-yl)-[1,1'-biphenyl]-3-sulfonamide

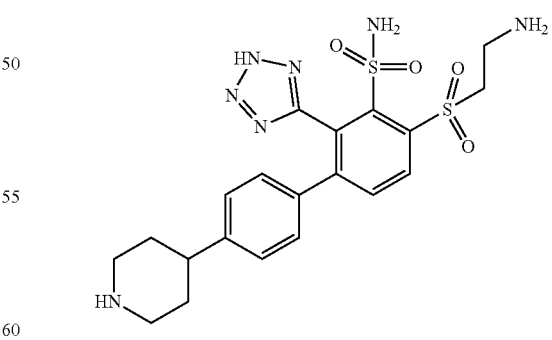

A suspension tert-butyl (2-((2-(N,N-bis(4-methoxybenzyl)sulfamoyl)-4-iodo-3-(1-(4-methoxybenzyl)-1H-tetrazol-5-yl)phenyl)thio)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)thio)ethyl) carbamate (100 mg, 0.109 mmol), tert-butyl 4-(4-(4,4,5,5- tetramethyl-1,3,2-dioxaborolan-2-yl)phenyl)piperidine-1-carboxylate (54.8 mg, 0.141 mmol), [1,1'-bis(diphenylphosphino)ferrocene]dichloropalladium (II) (7.96 mg, 10.88 μmol) and sodium carbonate (34.6 mg, 0.327 mmol) in dioxane (816 μl) and water (272 μl) was heated at 80° C. for 4 hours. The solution was poured into EtOAc (50 mL) and washed with water (20 mL), brine (20 mL), dried (MgSO$_4$) and concentrated and the resulting oil was dissolved in DCM (5 mL) and treated with TFA (100 equiv) and p-anisole (10 equiv). The solution was stirred at 80° C. for 30 min. The solution was then concentrated to isolate an oil which was purified on reverse phase chromatography to isolate the title compound. LC/MS [M+H]$^+$: 492.45.

EXAMPLE 323

7-(4-((2-aminoethyl)sulfonyl)-3-sulfamoyl-2-(2H-tetrazol-5-yl)phenyl)-1H-indole-2-carboxamide

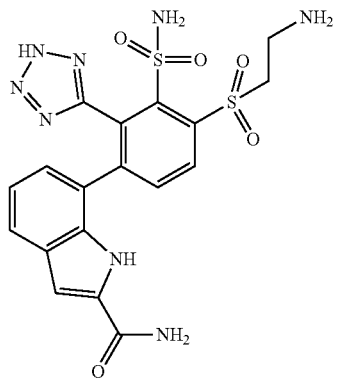 [SMILES: NCCS(=O)(=O)c1ccc(-c2cccc3cc(C(N)=O)[nH]c23)c(-c2nn[nH]n2)c1S(N)(=O)=O]

Step A: ethyl 7-(3-(N,N-bis(4-methoxybenzyl)sulfamoyl)-4-((2-((tert-butoxycarbonyl)amino)ethyl)sulfonyl)-2-(1-(4-methoxybenzyl)-1H-tetrazol-5-yl)phenyl)-1H-indole-2-carboxylate and ethyl 7-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-indole-2-carboxylate The title compound was prepared from tert-butyl (2-((2-(N,N-bis(4-methoxybenzyl)sulfamoyl)-4-iodo-3-(1-(4-methoxybenzyl)-1H-tetrazol-5-yl)phenyl)thio)ethyl)carbamate compound with tert-butyl (2-((2-(N,N-bis(4-methoxybenzyl)sulfamoyl)-4-iodo-3-(2-(4-methoxybenzyl)-2H-tetrazol-5-yl)phenyl)thio)ethyl)carbamate and ethyl 7-(4,4,5,5-tetramethyl-1,3,2-dioxaborolan-2-yl)indoline-2-carboxylate using the same method as in EXAMPLE 313, Step A. LC/MS [M+H]$^+$: 980.

Step B: 7-(3-(N,N-bis(4-methoxybenzyl)sulfamoyl)-4-((2-((tert-butoxycarbonyl)amino)ethyl)sulfonyl)-2-(1-(4-methoxybenzyl)-1H-tetrazol-5-yl)phenyl)-1H-indole-2-carboxylic acid and 7-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-indole-2-carboxylic Acid A suspension of ethyl 7-(3-(N,N-bis(4-methoxybenzyl)sulfamoyl)-4-((2-((tert-butoxycarbonyl)amino)ethyl)sulfo-nyl)-2-(1-(4-methoxybenzyl)-1H-tetrazol-5-yl)phenyl)-1H-indole-2-carboxylate and ethyl 7-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-indole-2-carboxylate (139 mg, 0.142 mmol), lithium hydroxide (16.98 mg, 0.709 mmol) in dioxane (1064 μl) and water (355 μl) and was stirred overnight. The solution was adjusted to pH 7 and the solution was added to EtOAc (50 mL) and the organic was extracted with water (2×5 mL). The organic was concentrated to isolate the title compound. LC/MS [M+H]$^+$: 952.

Step C: 7-(4-((2-aminoethyl)sulfonyl)-3-sulfamoyl-2-(2H-tetrazol-5-yl)phenyl)-1H-indole-2-carboxamide 7-(3-(N,N-bis(4-methoxybenzyl)sulfamoyl)-4-((2-((tert-butoxycarbonyl)amino)ethyl)sulfonyl)-2-(1-(4-methoxybenzyl)-1H-tetrazol-5-yl)phenyl)-1H-indole-2-carboxylic acid and 7-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-indole-2-carboxylic acid (135 mg, 0.142 mmol) was dissolved in DMF (3 mL) and EDC (68.0 mg, 0.354 mmol), HOAt (1.930 mg, 0.014 mmol), and Hunig's Base (0.099 mL, 0.567 mmol) was added. This was stirred for 5 minutes before the addition of bis(4-methoxybenzyl)amine (109 mg, 0.425 mmol). The solution was stirred at room temperature for 16 hours. The reaction was concentrated and the oil was purified on flash chromatography to isolate an oil. The resulting oil was dissolved in TFA (100 equiv) and p-anisole (10 equiv) at 80° C. for thirty minutes. After this time the solution was concentrated and purified on reverse phase chromatography to isolate the title compound. LC/MS [M+H]$^+$: 491.37.

EXAMPLE 325

3-(2-(methylsulfonamido)benzo[d]thiazol-4-yl)-6-(piperidin-4-ylsulfonyl)-2-(2H-tetrazol-5-yl)benzenesulfonamide

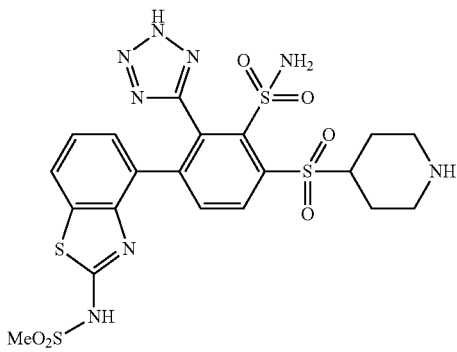 [SMILES: CS(=O)(=O)Nc1nc2c(-c3ccc(S(=O)(=O)C4CCNCC4)c(S(N)(=O)=O)c3-c3nn[nH]n3)cccc2s1]

A solution of tert-butyl 4-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonyl)piperidine-1-carboxylate and tert-butyl 4-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonyl)piperidine-1-carboxylate (200 mg, 0.204 mmol) in DCM (1019 μl) at room temperature was treated with DMAP (24.90 mg, 0.204 mmol) and methanesulfonyl chloride (31.8

μl, 0.408 mmol). The mixture was stirred for 16 hours and concentrated to isolate an oil. The oil was dissolved in EtOAc and extracted with water to isolate the protected intermediate. Purification on flash chromatography provided the intermediate compound. The resulting foam was dissolved in TFA (100 equiv) and p-anisole (10 equiv) at 80° C. for thirty minutes. After this time the solution was concentrated and purified on reverse phase chromatography to isolate the title compound. LC/MS [M+H]+: 599.32.

EXAMPLE 326

3-(2-aminobenzo[d]thiazol-4-yl)-6-((2-(dimethylamino)ethyl)sulfonyl)-2-(2H-tetrazol-5-yl)benzenesulfonamide

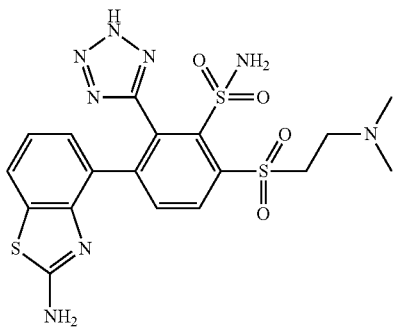 [SMILES: CN(C)CCS(=O)(=O)c1ccc(-c2cccc3sc(N)nc23)c(-c2nn[nH]n2)c1S(N)(=O)=O]

To a solution of 3-(2-aminobenzo[d]thiazol-4-yl)-6-((2-aminoethyl)sulfonyl)-2-(2H-tetrazol-5-yl)benzenesulfonamide was dissolved in THF (1249 μl) and chilled to 0° C. in an ice bath. Formaldehyde (37.2 μl, 0.499 mmol) was added and the solution was stirred for 5 min. Sodium cyanoborohydride (39.2 mg, 0.624 mmol) was added stirred for 90 min at 0° C. The solution was brought to neutral pH and concentrated. The resulting oil was purified by reverse phase chromatography to isolate the title compound. LC/MS [M+H]+: 509.20.

EXAMPLES 327 and 328

(R)-6-((2-Aminoethyl)sulfonyl)-3-(2-(1,2-diaminoethyl)-1H-benzo[d]imidazol-4-yl)-2-(2H-tetrazol-5-yl)benzenesulfonamide and (R)—N-(2-Amino-2-(4-(4-((2-aminoethyl)sulfonyl)-3-sulfamoyl-2-(2H-tetrazol-5-yl)phenyl)-1H-benzo[d]imidazol-2-yl)ethyl)-2,2,2-trifluoroacetamide

327

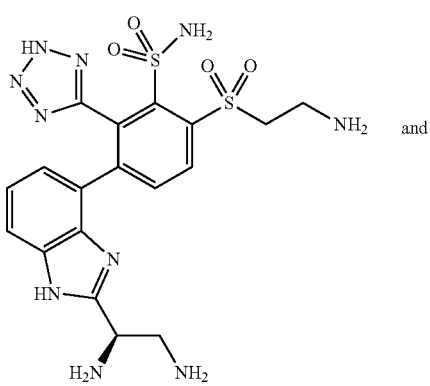

and

328

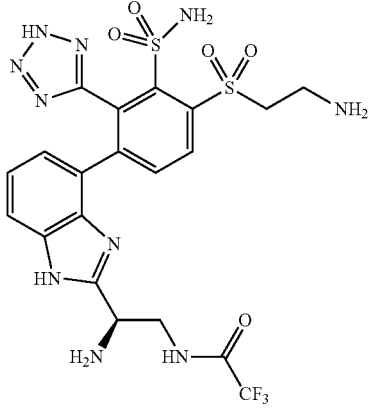

Step A: tert-Butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl) carbamate and tert-butyl (2-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)ethyl)carbamate A suspension of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (11.5 g, 12.52 mmol), 2-nitro-3-(4,4,5,5-tetramethyl-1,3,2-dioxaborolan-2-yl)aniline (9.92 g, 37.5 mmol), tetrakis(triphenylphosphine)palladium(0) (1.446 g, 1.252 mmol) and sodium carbonate (3.98 g, 37.5 mmol) in dioxane (100 ml) and water (30 ml) was degassed and heated at 80° C. for 17 hours. The mixture was diluted with AcOEt. The organic layer was separated, washed with brine, dried (MgSO4) and concentrated. The residue was purified by ISCO column (220 g, 0-60% the 60% EtOAc in Hexane) to give a mixture of 1:1 mixture of tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate and tert-butyl (2-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)ethyl)carbamate. The mixture was purified by column (EtOAc-Hexane). LC/MS [M+H]+: 899.59 and 929.57.

Step B: tert-Butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl) carbamate A mixture of tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate and tert-butyl (2-((3'-amino-3-(N,N-bis(4-methoxybenzyl)sulfamoyl)-2-(2-(4-methoxybenzyl)-2H-tetrazol-5-yl)-2'-nitro-[1,1'-biphenyl]-4-yl)sulfonyl)ethyl)carbamate (3.5 g, 3.77 mmol) and platinum(iv) oxide (0.856 g, 3.77 mmol) in MeOH (50 ml) was hydrogenated on a shaker at 50 Psi H2 overnight. The catalyst was filtered off through a CELITE pad and the filtrate was concentrated to give a solid which was directly used in the next step.

Step C: di-tert-Butyl (3-((2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-yl)amino)-3-oxopropane-1,2-diyl)(R)-dicarbamate tert-Butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (0.2 g, 0.222 mmol), (R)-2,3-bis((tert-butoxycarbonyl)amino)propanoic acid (0.169 g, 0.556 mmol), N1-((ethylimino)methylene)-N3,N3-dimethylpropane-1,3-diamine (0.086 g, 0.556 mmol) and N,N-dimethylpyridin-4-amine (0.04 g, 0.334 mmol) were added to a 50 ml flask with 25 ml of DCM with the exception of N,N-dimethylpyridin-4-amine which was added after one minute of stirring. The solution was stirred at room temperature for 3 hours. Then the reaction mixture was washed with KSO₄H, brine, and dried with magnesium sulfate. The solvent was removed under vacuum to give the product which was carried forward for the next step. LC/MS [M+H]⁺: 1186

Step D: di-tert-Butyl (1-(4-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-benzo[d]imidazol-2-yl)ethane-1,2-diyl)(S)-dicarbamate di-tert-Butyl (3-((2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-yl)amino)-3-oxopropane-1,2-diyl)(R)-dicarbamate (0.264 g, 0.222 mmol) was dissolved in 15 ml of acetic acid and stirred for one hour at 60°. The acetic acid was removed to give a sludge foam that was carried forward in the next step. LC/MS [M+H]⁺: 1168

Step E: (R)-6-((2-Aminoethyl)sulfonyl)-3-(2-(1,2-diaminoethyl)-1H-benzo[d]imidazol-4-yl)-2-(2H-tetrazol-5-yl)benzenesulfonamide and (R)—N-(2-amino-2-(4-(4-((2-aminoethyl)sulfonyl)-3-sulfamoyl-2-(2H-tetrazol-5-yl)phenyl)-1H-benzo[d]imidazol-2-yl)ethyl)-2,2,2-trifluoroacetamide di-tert-Butyl (1-(4-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-benzo[d]imidazol-2-yl)ethane-1,2-diyl)(S)-dicarbamate (0.257 g, 0.22 mmol) was dissolved in 10 ml of DCM to which 3 drops of anisole were added. After this 2 ml of TFA were added with bubbling for two hours. The solvent was removed and toluene was added and the solvent was removed again. Then 5 ml of TFA were added and the reaction was stirred at 80° C. for 1 hour. The solvent was removed to give the crude product. LC/MS [M+H]⁺: 507 and 254 (2 protonated amines) and 603, 302. Two products were separated via HPLC (2-37% acetonitrile in water with 0.05% NH₄OH).

The compounds below were synthesized following the same general procedure as described for EXAMPLE 327, substituting the appropriate reactants and reagents.

| EX NO | Starting Acid | Structure | Name | LC/MS [M + H]⁺ |
|---|---|---|---|---|
| 329 | (structure of Boc-serine) | (structure) | (S)-3-(2-(1-amino-2-hydroxyethyl)-1H-benzo[d]imidazol-4-yl)-6-((2-aminoethyl)sulfonyl)-2-(2H-tetrazol-5-yl)benzenesulfonamide | 508 |
| 330 | (structure of N-Boc aspartate methyl ester) | (structure) | 2-amino-3-(4-(4-((2-aminoethyl)sulfonyl)-3-sulfamoyl-2-(2H-tetrazol-5-yl)phenyl)-1H-benzo[d]imidazol-2-yl)propanoic acid | 536 |

-continued

| EX NO | Starting Acid | Structure | Name | LC/MS [M + H]+ |
|---|---|---|---|---|
| 331 | HO-acetic acid | (structure shown) | 6-((2-aminoethyl)sulfonyl)-3-(2-methyl-1H-benzo[d]imidazol-4-yl)-2-(2H-tetrazol-5-yl)benzenesulfonamide | 463 |

EXAMPLE 332

6-(Azetidin-3-ylsulfonyl)-3-(1H-benzo[d]imidazol-4-yl)-2-(2H-tetrazol-5-yl)benzenesulfonamide

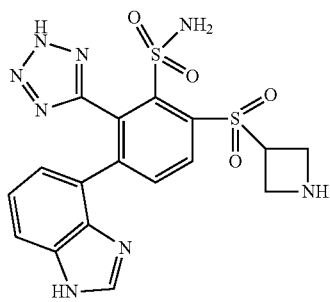 [SMILES: NS(=O)(=O)c1c(S(=O)(=O)C2CNC2)ccc(-c2cccc3[nH]cnc23)c1-c1nn[nH]n1]

The title compound was synthesized from tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate following the same procedure for 2'-amino-4-(azetidin-3-ylsulfonyl)-3'-cyano-2-(2H-tetrazol-5-yl)-[1,1'-biphenyl]-3-sulfonamide (EXAMPLE 196)

EXAMPLE 333

2-Amino-N-(4'-((2-aminoethyl)sulfonyl)-3'-sulfamoyl-2'-(2H-tetrazol-5-yl)-[1,1'-biphenyl]-3-yl)acetamide

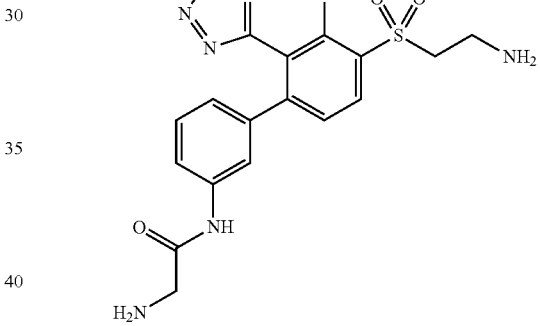

Step A: tert-butyl (2-((3'-amino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate Sodium carbonate (0.954 g, 9 mmol), tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (2.76 g, 3 mmol), (3-aminophenyl)boronic acid (1.23 g, 9 mmol), tetrakis(triphenylphosphine)palladium(0) (0.005 g, 0.005 mmol) were added to a 250 ml flask equipped with a stir bar and a reflux condenser. The flask was then put under nitrogen and solvent was added. The reaction was stirred overnight at 80° C. The reaction was diluted with ethyl acetate and washed with water. The organic layer was dried with magnesium sulfate and the solvent removed to give a foam which was purified via column (ethyl acetate in hexane 0-30 hold 30-100%) LC/MS [M+H]+: 884.

Step B: tert-Butyl (2-((3-(N,N-bis(4-methoxybenzyl)sulfamoyl)-3'-(2-((tert-butoxycarbonyl)amino)acetamido)-2-(2-(4-methoxybenzyl)-2H-tetrazol-5-yl)-[1,1'-biphenyl]-4-yl)sulfonyl)ethyl)carbamate (R)-2,3-bis((tert-butoxycarbonyl)amino)propanoic acid (0.172 g, 0,566 mmol), N,N-dimethylpyridin-4-amine (0.041 g, 0.556), N1-((ethylimino)methylene)-N3,N3-dimethylpropane-1,3-diamine (0.088 g, 0.226 mmol) and tert-butyl (2-((3'-amino-3-(N,N-bis(4-met hoxybenzyl)sulfamoyl)-2-(2-(4-methoxybenzyl)-2H-tetrazol-5-yl)-[1,1'-biphenyl]-4-yl)sulfonyl)ethyl)carbamate (0.2 g, 0.226 mmol) were added to a 50 ml flask with 25 ml of DCM with the exception of N,N-dimethylpyridin-4-amine which was added after one minute of stirring. The solution was stirred at RT for 2 hours. Then the reaction solution was washed with KSO₄H and dried with magnesium sulfate. The solvent was removed under vacuum to give the product as a solid which was used directly in the next step. LC/MS [M+H]⁺: 1042.

Step C: tert-Butyl (2-((3-(N,N-bis(4-methoxybenzyl)sulfamoyl)-3'-(2-((tert-butoxycarbonyl)amino)acetamido)-2-(2-(4-methoxybenzyl)-2H-tetrazol-5-yl)-[1,1'-biphenyl]-4-yl)sulfonyl)ethyl)carbamate tert-Butyl (2-((3-(N,N-bis(4-methoxybenzyl)sulfamoyl)-3'-(2-((tert-butoxycarbonyl)amino)acetamido)-2-(2-(4-methoxybenzyl)-2H-tetrazol-5-yl)-[1,1'-biphenyl]-4-yl)sulfonyl)ethyl)carbamate (0.235 g, 0.226 mmol) was dissolved in 10 ml of DCM to which 3 drops of anisole were added. After this, 2 ml of TFA were added. The solvent was removed and toluene was added and the solvent was removed again. Then 5 ml of TFA were added and the reaction was stirred at 80° C. for 1 hour. The solvent was removed to give the crude product as a sludge. LC/MS [M+H]⁺: 241 (dication). The product was purified via HPLC to give the pure product as a solid.

The EXAMPLE below was prepared using the same general procedure as described for EXAMPLE 333 using the corresponding Acid

EXAMPLE 335

2-Amino-5-(4-((2-aminoethyl)sulfonyl)-3-sulfamoyl-2-(2H-tetrazol-5-yl)phenyl)nicotinamide

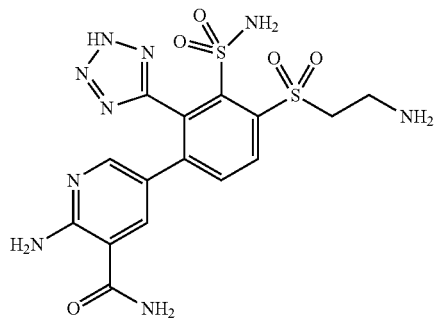 [SMILES: NCCS(=O)(=O)c1ccc(-c2cnc(N)c(C(N)=O)c2)c(-c2nn[nH]n2)c1S(N)(=O)=O]

Step A: 2-Amino-5-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)nicotinic Acid A suspension of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (2 g, 2.177 mmol), tetrakis(triphenylphosphine)palladium(0) (0.252 g, 0.218 mmol) and sodium carbonate (0.807 g, 7.62 mmol) in 1,4-dioxane (80 ml) and water (24.00 ml) was degassed and heated at 80° C. for 17 hours. The mixture was diluted with AcOEt. The organic layer was washed with brine, dried (MgSO4) and concentrated. The residue was purified by ISCO column (120 g, 0-30%, 30%, 30-100% EtOAc in Hexane). The desired was eluted out at 100% EtOAc). LC/MS [M+H]⁺: 929.78, 943.84. The ester isolated (LC/MS [M+H]⁺: 943.84) was hydrolyzed by LiOH (1 M 5 ml) in a mixture solvent of THF (20 ml) and MeOH (20 ml) at RT overnight. The mixture was acidified with KHSO₄ solution, extracted with AcOEt, dried over MgSO₄ and concentrated. This was combined with the isolated acid by column above for use in the next step.

| EX NO | Structure | Name | MW | LC/MS [M + H]⁺ |
|---|---|---|---|---|
| 334 | ![structure] | (R)-2-amino-N-(4'-((2-aminoethyl)sulfonyl)-3'-sulfamoyl-2'-(2H-tetrazol-5-yl)-[1,1'-biphenyl]-3-yl)-3-hydroxypropanamide | 510 | 511 |

Step B: tert-Butyl (2-((4-(6-amino-5-((4-methoxybenzyl)carbamoyl)pyridin-3-yl)-2-(N,N-bis(4-methoxybenzyl)sulfamoyl)-3-(2-(4-methoxybenzyl)-2H-tetrazol-5-yl)phenyl)sulfonyl)ethyl)carbamate N,N-dimethylpyridin-4-amine (0.026 g, 0.215 mmol), N1-((ethylimino)methylene)-N3,N3-dimethylpropane-1,3-diamine (0.083 g, 0.431 mmol), (4-methoxyphenyl)methanamine (0.059 g, 0.431 mmol), 2-amino-5-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)nicotinic acid (0.2 g, 0.215 mmol) were added to a 50 ml flask with 25 ml of DCM with the exception of N,N-dimethylpyridin-4-amine which was added after one minute of stirring. The solution was stirred at room temperature for 2 hours. Then the reaction solution was washed with KHSO$_4$ and brine, and dried with magnesium sulfate. The solvent was removed under vacuum to give the product as a solid which was carried forward for the next step. LC/MS [M+H]$^+$: 1049.

Step C: 2-amino-5-(4-((2-aminoethyl)sulfonyl)-3-sulfamoyl-2-(2H-tetrazol-5-yl)phenyl)nicotinamide tert-Butyl (2-((4-(6-amino-5-((4-methoxybenzyl)carbamoyl)pyridin-3-yl)-2-(N,N-bis(4-methoxybenzyl)sulfamoyl)-3-(2-(4-methoxybenzyl)-2H-tetrazol-5-yl)phenyl)sulfonyl)ethyl)carbamate (0.225 g, 0.215 mmol) was dissolved in 10 ml of DCM to which 3 drops of anisole were added. After this 2 ml of TFA were added. The solvent was removed and toluene was added and the solvent was removed again. Then 5 ml of TFA were added and the reaction was stirred at 80° C. for 1 hour then at 100° C. overnight. The solvent was removed to give the crude product as a sludge. LC/MS [M+H]$^+$: 234 (dication), 468. The product was purified via HPLC (AcCN in water with 0.1% NH$_4$OH) to give the pure product.

EXAMPLE 336

(S)-2-Amino-5-(4-((2-aminoethyl)sulfonyl)-3-sulfamoyl-2-(2H-tetrazol-5-yl)phenyl)-N-(pyrrolidin-3-yl)nicotinamide

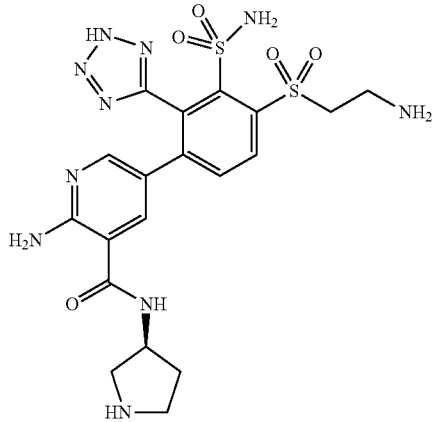 [SMILES: NCCS(=O)(=O)c1ccc(-c2cnc(N)c(C(=O)N[C@H]3CCNC3)c2)c(-c2nn[nH]n2)c1S(N)(=O)=O]

Step A: tert-Butyl (S)-3-(2-amino-5-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)nicotinamido)pyrrolidine-1-carboxylate N,N-dimethylpyridin-4-amine (0.026 g, 0.215 mmol), N1-((ethylimino)methylene)-N3,N3-dimethylpropane-1,3-diamine, HCl (0.083 g, 0.431), (S)-tert-butyl 3-aminopyrrolidine-1-carboxylate (0.08 g, 0.31 mmol), 2-amino-5-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)nicotinic acid (0.2 g, 0.215 mmol) were added to a 50 ml flask with 25 ml of DCM with the exception of N,N-dimethylpyridin-4-amine which was added after one minute of stirring. The suspension was stirred overnight at room temperature. The DCM was removed under vacuum and the solid was dissolved in ethyl acetate, washed with KHSO$_4$, and brine. The organic layer was dried with magnesium sulfate and the solvent was removed under vacuum to give the crude product as a foam. LC/MS [M+H]$^+$: 1098.

Step B: (S)-2-amino-5-(4-((2-aminoethyl)sulfonyl)-3-sulfamoyl-2-(2H-tetrazol-5-yl)phenyl)-N-(pyrrolidin-3-yl)nicotinamide tert-Butyl (S)-3-(2-amino-5-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)nicotinamido)pyrrolidine-1-carboxylate (0.236 g, 0.215 mmol) was dissolved in 10 ml of DCM to which 3 drops of anisole were added. After this 2 ml of TFA were added with concomitant bubbling for three hours. The solvent was removed and toluene was added and the solvent was removed again. Then 5 ml of TFA were added and the reaction was stirred at 80 C for 1 hour. The solvent was removed to give the crude product as a sludge. LC/MS [M+H]$^+$: 269 (2 protonated amines). The product was purified via HPLC to give the pure product as a solid EXAMPLE 337 below was prepared in an analogous fashion to that described for EXAMPLE 336 using the corresponding Boc-protected amine.

| EX NO | Structure | Name | MW | LC/MS [M + H]+ |
|---|---|---|---|---|
| 337 | 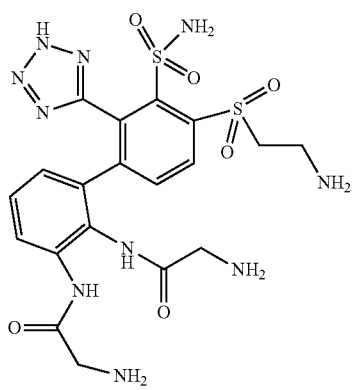 [SMILES: NCCS(=O)(=O)c1ccc(-c2cccc(NC(=O)CN)c2NC(=O)CN)c(-c2nn[nH]n2)c1S(N)(=O)=O] | 2-amino-N-(2-aminoethyl)-5-(4-((2-aminoethyl)sulfonyl)-3-sulfamoyl-2-(2H-tetrazol-5-yl)phenyl)nicotinamide | 510 | 511 |

EXAMPLE 338

N,N'-(4'-((2-Aminoethyl)sulfonyl)-3'-sulfamoyl-2'-(2H-tetrazol-5-yl)-[1,1'-biphenyl]-2,3-diyl)bis(2-aminoacetamide)

Step A: Diethyl 3,3'-((3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-2,3-diyl)bis(azanediyl))bis(2-((tert-butoxycarbonyl)amino)-3-oxopropanoate)

To a solution of tert-butyl (2-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (0.55 g, 0.612 mmol), 2-((tert-butoxycarbonyl)amino)-3-ethoxy-3-oxopropanoic acid (0.303 g, 1.224 mmol) and EDC (0.235 g, 1.224 mmol) in DCM (25 ml) was added DMAP (0.082 g, 0.673 mmol) at RT. The mixture was stirred at RT overnight, washed with KHSO₄ aqueous and brine, dried (MgSO4) and concentrated. LC/MS [M+H]+: 1358.

Step B: N,N'-(4'-((2-Aminoethyl)sulfonyl)-3'-sulfamoyl-2'-(2H-tetrazol-5-yl)-[1,1'-biphenyl]-2,3-diyl)bis(2-aminoacetamide)

A solution of ethyl 2-(4-(3-(N,N-bis(4-methoxybenzyl)sulfamoyl)-4-((2-((tert-butoxycarbonyl)amino)ethyl)sulfonyl)-2-(2-(4-methoxybenzyl)-2H-tetrazol-5-yl)phenyl)-1H-benzo[d]imidazol-2-yl)-2-((tert-butoxycarbonyl)amino)acetate (0.6 g, 0.540 mmol) and diethyl 3,3'-((3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-2,3-diyl)bis(azanediyl))bis(2-((tert-butoxycarbonyl)amino)-3-oxopropanoate) (0.734 g, 0.540 mmol) in a mixture solvents of THF (20.00 ml) and MeOH (20 ml) was stirred with LiOH (8.11 ml, 8.11 mmol) at RT overnight. The mixture was diluted with EtOAc, washed with KHSO₄ aqueous and brine, dried (MgSO₄) and concentrated. LC/MS [M+H]+: 1039.02, 1302.23. The two peaks were separated by ISCO (0-30%, 30%, 30-100% EtOAc in Hexane). The material with LC/MS [M+H]+ 1302 obtained above was dissolved in DCM (20 ml), and was stirred at RT for 2 hours with 4 ml TFA and two drops anisole, and concentrated. The residue was heated at 80° C. in 10 ml TFA for 40 min. TFA was removed, and the crude material was purified by Gilson (3-37% AcCN in water with 0.05% NH₄OH, 17 N). LC/MS [M+H]+: 553.63.

EXAMPLE 339

2'-Amino-4-((2-aminoethyl)sulfonyl)-2-(2H-tetrazol-5-yl)-[1,1'-biphenyl]-3-sulfonamide

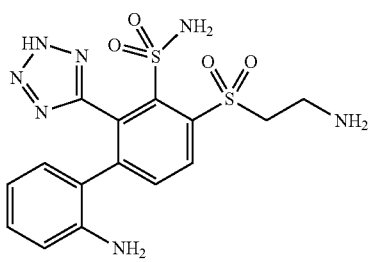 [SMILES: NCCS(=O)(=O)c1ccc(-c2ccccc2N)c(-c2nn[nH]n2)c1S(N)(=O)=O]

Step A: tert-Butyl (2-((2'-amino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate A suspension of 2-(4,4,5,5-tetramethyl-1,3,2-dioxaborolan-2-yl)aniline (2.146 g, 9.80 mmol), tert-butyl (2-((2-(N, N-bis(4-methoxybenzyl)sulfamoyl)-4-iodo-3-(2-(4-methoxybenzyl)-2H-tetrazol-5-yl)phenyl)sulfonyl)ethyl)carbamate (3 g, 3.27 mmol), tetrakis(triphenylphosphine)palladium(0) (0.377 g, 0.327 mmol) and sodium carbonate (1.211 g, 11.43 mmol) in 1,4-dioxane (80 ml) and water (24.00 ml) was degassed and heated at 80° C. for 17 hours. The mixture was diluted with AcOEt. The organic layer was washed with brine, dried (MgSO$_4$) and concentrated. The crude material was purified by column (80 g, 0-30% EtOAc, then 30% EtOAc and 30-100% EtOAc in Hexane).

Step B: 2'-Amino-4-((2-aminoethyl)sulfonyl)-2-(2H-tetrazol-5-yl)-[1,1'-biphenyl]-3-sulfonamide tert-Butyl (2-((2'-amino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (0.235 g, 0.226 mmol) was dissolved in DCM (20 ml), and was stirred at rt for 2 hours with 4 ml TFA and two drops anisole, and concentrated. The residue was heated at 80° C. in 10 ml TFA for 40 min. TFA was removed, and the crude material was purified by Gilson (3-37% AcCN in water with 0.05% NH$_4$OH, 17N). LC/MS [M+H]$^+$: 424 (dication).

Example 340

2-Amino-N-(4'-((2-aminoethyl)sulfonyl)-3'-sulfamoyl-2'-(2H-tetrazol-5-yl)-[1,1'-biphenyl]-2-yl)acetamide

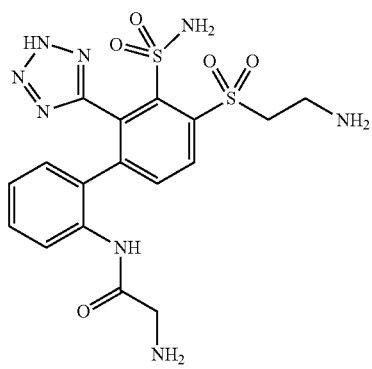 [SMILES: NCCS(=O)(=O)c1ccc(-c2ccccc2NC(=O)CN)c(-c2nn[nH]n2)c1S(N)(=O)=O]

Step A: tert-Butyl (2-((3-(N,N-bis(4-methoxybenzyl)sulfamoyl)-2'-(2-((tert-butoxycarbonyl)amino)acetamido)-2-(2-(4-methoxybenzyl)-2H-tetrazol-5-yl)-[1,1'-biphenyl]-4-yl)sulfonyl)ethyl)carbamate tert-Butyl (2-((2'-amino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate tert-butyl (2-aminoethyl)carbamate (0.2 g, 0.226 mmol), 2-((tert-butoxycarbonyl)amino)acetic acid (0.099 g, 0.566 mmol), N,N-dimethylpyridin-4-amine (0.041 g, 0.399 mmol), and N1-((ethylimino)methylene)-N3,N3-dimethylpropane-1,3-diamine (0.088 g, 0.566 mmol) were added to a 50 ml flask with 25 ml of DCM with the exception of N,N-dimethylpyridin-4-amine which was added after one minute of stirring. The solution was stirred at room temperature for 2 hours. Then the reaction solution was washed with KHSO$_4$ and brine, and dried with magnesium sulfate. The solvent was removed under vacuum to give the crude product which was purified via column chromatography (EtOac-Hexane). LC/MS [M+H]$^+$: 1042.

Step B: 2-Amino-N-(4'-((2-aminoethyl)sulfonyl-3'-sulfamoyl-2'-(2H-tetrazol-5-yl)-[1,1'-biphenyl]-2-yl)acetamide tert-Butyl (2-((3-(N,N-bis(4-methoxybenzyl)sulfamoyl)-2'-(2-((tert-butoxycarbonyl)amino)acetamido)-2-(2-(4-methoxybenzyl)-2H-tetrazol-5-yl)-[1,1'-biphenyl]-4-yl)sulfonyl)ethyl)carbamate (0.235 gm 0.236 mmol) was dissolved in 10 ml of DCM to which 3 drops of anisole were added. After this 2 ml of TFA were added. The solvent was removed and toluene was added and the solvent was removed again. Then 5 ml of TFA were added and the reaction was stirred at 80° C. for 1 hour. The solvent was removed to give the crude product as a sludge. LC/MS [M+H]$^+$: 241(dication). The product was purified via HPLC (3-37% AcCN in water with 0.05% NH4OH, 17N).

EXAMPLE 341

Methyl 2-((2-aminoethyl)amino)-4'-((2-aminoethyl)sulfonyl)-3'-sulfamoyl-2'-(2H-tetrazol-5-yl)-[1,1'-biphenyl]-3-carboxylate

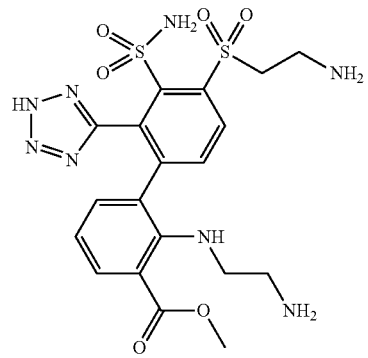 [SMILES: COC(=O)c1cccc(-c2ccc(S(=O)(=O)CCN)c(S(N)(=O)=O)c2-c2nn[nH]n2)c1NCCN]

Step A: methyl 2-((2-aminoethyl)amino)-4'-((2-aminoethyl)sulfonyl)-3'-sulfamoyl-2'-(2H-tetrazol-5-yl)-[1,1'-biphenyl]-3-carboxylate A suspension of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (1 g, 1.088 mmol), (2-((2-((tert-butoxycarbonyl)amino)ethyl)amino)-3-(methoxycarbonyl)phenyl)boronic acid (0.791 g, 2.340 mmol), tetrakis(triphenylphosphine)palladium(0) (0.126 g, 0.109 mmol) and sodium carbonate (0.346 g, 3.27 mmol) in dioxane (50 ml) and water (15 ml) was degassed and heated at 80° C. for 17 hours. The mixture was diluted with AcOEt, washed with brine. The organic layer was dried (MgSO$_4$) and concentrated. The crude material was purified by ISCO column (80 g, 0-30%, 30%, 30-100% EtOAc in hexane. The desired was eluted out at 100% EtOAc). LC/MS [M+H]$^+$: 1085.78

Step B: methyl 2-((2-aminoethyl)amino)-4'-((2-aminoethyl)sulfonyl)-3'-sulfamoyl-2'-(2H-tetrazol-5-yl)-[1,1'-biphenyl]-3-carboxylate Methyl 3'-(N,N-bis(4-methoxybenzyl)sulfamoyl)-2-((2-((tert-butoxycarbonyl)amino)ethyl)amino)-4'-((2-((tert-butoxycarbonyl)amino)ethyl)sulfonyl)-2'-(2-(4-methoxybenzyl)-2H-tetrazol-5-yl)-[1,1'-biphenyl]-3-carboxylate (0.08 g, 0.074 mmol) was dissolved in DCM (3 ml), stirred at RT for 2 hours with 2 ml TFA and two drops anisole, and concentrated. The residue was heated at 80° C. in 2 ml TFA for 40 min. TFA was removed. The crude material was purified by Gilson (3-42% water in acetonitrile with 0.05% TFA). LC/MS [M+H]$^+$: 525.43.

EXAMPLE 342

N-(2-Aminoethyl)-4'-((2-aminoethyl)sulfonyl)-3'-sulfamoyl-2'-(2H-tetrazol-5-yl)-[1,1'-biphenyl]-2-carboxamide

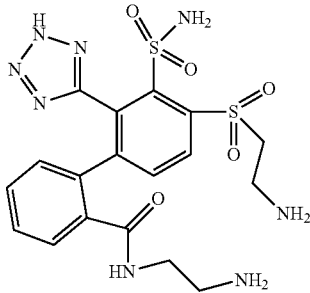 [SMILES: NCCNC(=O)c1ccccc1-c1ccc(S(=O)(=O)CCN)c(S(N)(=O)=O)c1-c1nn[nH]n1]

Step A: methyl 3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-2-carboxylate A suspension of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (from outsourcing) (2 g, 2.177 mmol), (2-(methoxycarbonyl)phenyl)boronic acid (0.783 g, 4.35 mmol), tetrakis(triphenylphosphine)palladium(0) (0.252 g, 0.218 mmol) and sodium carbonate (0.692 g, 6.53 mmol) in Dioxane (50 ml) and water (15 ml) was degassed and heated at 80° C. for 17 hours. The mixture was diluted with AcOEt, washed with brine. The organic layer was dried (MgSO4) and concentrated. The residue was purified by ISCO column (80 g, 0-30%, 30%, 30-100% EtOAc in Hexane). LC/MS [M+H]$^+$: 927.76

Step B: 3'-(N,N-bis(4-Methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-2-carboxylic Acid To a solution of methyl 3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-2-carboxylate (0.85 g, 0.917 mmol) in THF (10.0 ml) and MeOH (10 ml) was added lithium hydroxide (4.58 ml, 4.58 mmol) with stirring at room temperature. The resulting solution was stirred overnight and diluted with EtOAc (100 ml), washed with KHSO4 aqueous and brine. The organic layer was dried (MgSO$_4$) and concentrated. The crude material was directly used in the next step LC/MS [M+H]$^+$: 913.78.

Step C: tert-Butyl (2-((3-(N,N-bis(4-methoxybenzyl)sulfamoyl)-2'-((2-((tert-butoxycarbonyl)amino)ethyl)carbamoyl)-2-(2-(4-methoxybenzyl)-2H-tetrazol-5-yl)-[1,1'-biphenyl]-4-yl)sulfonyl)ethyl)carbamate To a solution of N1-((ethylimino)methylene)-N3,N3-dimethylpropane-1,3-diamine hydrochloride (0.042 g, 0.219 mmol), 3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-2-carboxylic acid (0.1 g, 0.110 mmol) and tert-butyl (2-aminoethyl)carbamate (0.035 g, 0.219 mmol) in DCM (15 ml) was added N,N-dimethylpyridin-4-amine (0.013 g, 0.110 mmol) at RT. The mixture was stirred at RT for 3 hours, diluted with ether (80 ml), washed with KHSO$_4$ aqueous and brine, dried (MgSO$_4$) and concentrated. The crude material was used directly in the next step. LC/MS [M+H]$^+$: 1055.90.

Step D: N-(2-Aminoethyl)-4'-((2-aminoethyl)sulfonyl)-3'-sulfamoyl-2'-2-tetra-5-yl)-[1,1'-biphenyl]-2-carboxamide tert-Butyl (2-((3-(N,N-bis(4-methoxybenzyl)sulfamoyl)-2'-((2-((tert-butoxycarbonyl)amino)ethyl)carbamoyl)-2-(2-(4-methoxybenzyl)-2H-tetrazol-5-yl)-[1,1'-biphenyl]-4-yl)sulfonyl)ethyl)carbamate (0.116 g, 0.110 mmol) was dissolved in DCM (10 ml), and was stirred at RT for 2 hours with 2 ml TFA and two drops anisole, and concentrated. The residue was heated at 80° C. in 5 ml TFA for 40 min. TFA was removed, and the crude material was purified by Gilson (5-42% AcCN in water with 0.05% NH$_4$OH, 17N). LC/MS [M+H]$^+$: 495.31.

EXAMPLE 343

6-(Azetidin-3-ylsulfonyl)-3-(2-(2-oxoimidazolidin-1-yl)pyridin-4-yl)-2-(1H-tetrazol-5-yl)benzenesulfonamide

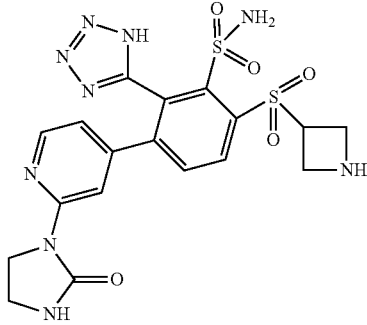 [SMILES: NS(=O)(=O)c1c(S(=O)(=O)C2CNC2)ccc(-c2ccnc(N3CCNC3=O)c2)c1-c1nnn[nH]1]

Step A: tert-Butyl 3-((2-(N,N-bis(4-methoxybenzyl)sulfamoyl)-4-(2-chloropyridin-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-chloropyridin-4-yl)-3-(2-(4-methoxybenzyl)-2H-tetrazol-5-yl)phenyl)sulfonyl)azetidine-1-carboxylate 2-Chloro-4-(4,4,5,5-tetramethyl-1,3,2-dioxaborolan-2-yl)pyridine (154 mg, 0.645 mmol), tert-butyl 3-((2-(N,N-bis (4-methoxybenzyl)sulfamoyl)-4-iodo-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (500 mg, 0.537 mmol), sodium carbonate (114 mg, 1.074 mmol), Pd(dppf)Cl₂ (39.3 mg, 0.054 mmol) were placed in a reaction vial. Dioxane (4029 µl) and water (1343 µl) were added. The reaction was degassed and heated at 80° C. for 12 hours. The reaction was purified by column chromatography (0-75% hexane/EtOAc) to give the title compound. LC/MS [M+H]⁺: 916.6.

Step B: tert-Butyl 3-((2-(N,N-bis(4-methoxybenzyl)sulfamoyl)-3-(1-(4-methoxybenzyl)-1H-tetrazol-5-yl)-4-(2-(2-oxoimidazolidin-1-yl)pyridin-4-yl)phenyl)sulfonyl)azetidine-1-carboxylate and tert-butyl 3-((2-(N,N-bis(4-methoxybenzyl)sulfamoyl)-3-(2-(4-methoxybenzyl)-2H-tetrazol-5-yl)-4-(2-(2-oxoimidazolidin-1-yl)pyridin-4-yl)phenyl)sulfonyl)azetidine-1-carboxylate tert-Butyl 3-((2-(N,N-bis(4-methoxybenzyl)sulfamoyl)-4-(2-chloropyridin-4-yl)-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-(2-chloropyridin-4-yl)-3-(2-(4-methoxybenzyl)-2H-tetrazol-5-yl)phenyl)sulfonyl)azetidine-1-carboxylate (50 mg, 0.055 mmol), XANTPHOS (6.31 mg, 10.91 µmol), Palladium(II) acetate (1.225 mg, 5.46 µmol), cesium carbonate (26.7 mg, 0.082 mmol), imidazolidin-2-one (23.49 mg, 0.273 mmol) were placed in a reaction vial. Dioxane (800 µl) was added. The reaction was degassed and heated at 100° C. for 2.5 h. The reaction was purified with chromatography to give the title compound. LC/MS [M+H]⁺: 966.6.

Step C: 6-(Azetidin-3-ylsulfonyl)-3-(2-(2-oxoimidazolidin-1-yl)pyridin-4-yl)-2-(1H-tetrazol-5-yl)benzenesulfonamide tert-Butyl 3-((2-(N,N-bis(4-methoxybenzyl)sulfamoyl)-3-(1-(4-methoxybenzyl)-1H-tetrazol-5-yl)-4-(2-(2-oxoimidazolidin-1-yl)pyridin-4-yl)phenyl)sulfonyl)azetidine-1-carboxylate and tert-butyl 3-((2-(N,N-bis(4-methoxybenzyl)sulfamoyl)-3-(2-(4-methoxybenzyl)-2H-tetrazol-5-yl)-4-(2-(2-oxoimidazolidin-1-yl)pyridin-4-yl)phenyl)sulfonyl)azetidine-1-carboxylate (54 mg, 0.056 mmol) was stirred in TFA/DCM (1/1, 2 mL) for 1 h at room temperature. LC-MS showed Boc and one of the PMBs was removed. The reaction was concentrated and co-evaporated with toluene 3 times. The residue was dissolved in TFA (2 mL) and heated at 60° C. for 2 h. The reaction was concentrated and the residue was purified with Gilson (3-40% CH₃CN/water with 0.05% TFA). The correct fractions were combined and concentrated. 1.2 M HCl in MeOH (0.1 mL) was added. The product was lyophilized from CH₃CN/water to give the HCl salt of the title compound. LC/MS [M+H]+: 506.4.

EXAMPLE 344

3'-(5-Amino-1,3,4-oxadiazol-2-yl)-4-(azetidin-3-ylsulfonyl)-2-(1H-tetrazol-5-yl)-[1,1'-biphenyl]-3-sulfonamide

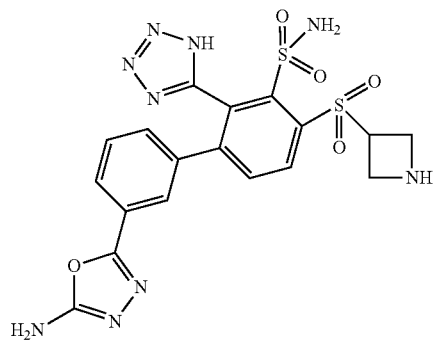 [SMILES: Nc1nnc(-c2cccc(-c3ccc(S(=O)(=O)C4CNC4)c(S(N)(=O)=O)c3-c3nnn[nH]3)c2)o1]

Step A: tert-Butyl 3-((3-(N,N-bis(4-methoxybenzyl)sulfamoyl)-3'-formyl-2-(1-(4-methoxybenzyl)-1H-tetrazol-5-yl)-[1,1'-biphenyl]-4-yl)sulfonyl)azetidine-1-carboxylate and tert-butyl 3-((3-(N,N-bis(4-methoxybenzyl)sulfamoyl)-3'-formyl-2-(2-(4-methoxybenzyl)-2H-tetrazol-5-yl)-[1,1'-biphenyl]-4-yl)sulfonyl)azetidine-1-carboxylate 3-(4,4,5,5-Tetramethyl-1,3,2-dioxaborolan-2-yl)benzaldehyde (299 mg, 1.289 mmol), tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate and tert-butyl 3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (1000 mg, 1.074 mmol), sodium carbonate (228 mg, 2.149 mmol), Pd(dppf)Cl₂ (79 mg, 0.107 mmol) were placed in a reaction vial. Dioxane (8057 µl) and Water (2686 µl) were added. The reaction was degassed and heated at 80° C. for 5 hours. The reaction was purified by column chromatography (0-75% Hexane/EtOAc) to give the title compound. LC/MS [M+H]⁺: 909.5.

Step B: tert-Butyl (E)-3-((3-(N,N-bis(4-methoxybenzyl)sulfamoyl)-3'-((2-carbamoylhydrazono)methyl)-2-(1-(4-methoxybenzyl)-1H-tetrazol-5-yl)-[1,1'-biphenyl]-4-yl)sulfonyl)azetidine-1-carboxylate and tert-butyl (E)-3-((3-(N,N-bis(4-methoxybenzyl)sulfamoyl)-3'-((2-carbamoylhydrazono)methyl)-2-(2-(4-methoxybenzyl)-2H-tetrazol-5-yl)-[1,1'-biphenyl]-4-yl)sulfonyl)azetidine-1-carboxylate Sodium acetate (90 mg, 1.100 mmol) and hydrazinecarboxamide hydrochloride (24.54 mg, 0.220 mmol) were dissolved in 0.5 mL of water. tert-Butyl 3-((3-(N,N-bis(4-methoxybenzyl)sulfamoyl)-3'-formyl-2-(1-(4-methoxybenzyl)-1H-tetrazol-5-yl)-[1,1'-biphenyl]-4-yl)sulfonyl)azetidine-1-carboxylate and tert-butyl 3-((3-(N,N-bis(4-methoxybenzyl)sulfamoyl)-3'-formyl-2-(2-(4-methoxybenzyl)-2H-tetrazol-5-yl)-[1,1'-biphenyl]-4-yl)sulfonyl)azetidine-1-carboxylate (200 mg, 0.220 mmol) in EtOH (2 mL) were added. A small amount of THF and DCM were added to help to dissolve the starting material. The reaction was stirred at room temp. for 12 hours. The reaction was purified to give the title compound. LC/MS [M+H]+: 966.7.

Step C: tert-Butyl 3-((3'-(5-amino-1,3,4-oxadiazol-2-yl)-3-(N,N-bis(4-methoxybenzyl)sulfamoyl)-2-(1-(4-methoxybenzyl)-1H-tetrazol-5-yl)-[1,1'-biphenyl]-4-yl)sulfonyl)azetidine-1-carboxylate and tert-butyl 3-((3'-(5-amino-1,3,4-oxadiazol-2-yl)-3-(N,N-bis(4-methoxybenzyl)sulfamoyl)-2-(2-(4-methoxybenzyl)-2H-tetrazol-5-yl)-[1,1'-biphenyl]-4-yl)sulfonyl)azetidine-1-carboxylate (E)-tert-Butyl 3-((3-(N,N-bis(4-methoxybenzyl)sulfamoyl)-3'-((2-carbamoylhydrazono)methyl)-2-(1-(4-methoxybenzyl)-1H-tetrazol-5-yl)-[1,1'-biphenyl]-4-yl)sulfonyl)azetidine-1-carboxylate and tert-butyl (E)-3-((3-(N,N-bis(4-methoxybenzyl)sulfamoyl)-3'-((2-carbamoylhydrazono)methyl)-2-(2-(4-methoxybenzyl)-2H-tetrazol-5-yl)-[1,1'-biphenyl]-4-yl)sulfonyl)azetidine-1-carboxylate (186 mg, 0.193 mmol) was dissolved in HOAc (1.4 mL). Sodium acetate (237 mg, 2.89 mmol) was added. Bromine (31.7 µl, 0.616 mmol) in HOAc (100 uL) was then added to the resulting mixture. The reaction mixture was stirred at room temp. for 1 hour. The reaction was diluted with EtOAc and washed with water. The organic layer was separated and concentrated. The residue was purified by column chromatography (100% hexane to 100% EtOAc/Hexane) to give the title compound. LC/MS [M+H]+: 964.6.

Step D: 3'-(5-Amino-1,3,4-oxadiazol-2-yl)-4-(azetidin-3-ylsulfonyl)-2-(1H-tetrazol-5-yl)-[1,1'-biphenyl]-3-sulfonamide tert-Butyl 3-((3'-(5-amino-1,3,4-oxadiazol-2-yl)-3-(N,N-bis(4-methoxybenzyl)sulfamoyl)-2-(1-(4-methoxybenzyl)-1H-tetrazol-5-yl)-[1,1'-biphenyl]-4-yl)sulfonyl)azetidine-1-carboxylate and tert-butyl 3-((3'-(5-amino-1,3,4-oxadiazol-2-yl)-3-(N,N-bis(4-methoxybenzyl)sulfamoyl)-2-(2-(4-methoxybenzyl)-2H-tetrazol-5-yl)-[1,1'-biphenyl]-4-yl)sulfonyl)azetidine-1-carboxylate (197 mg, 0.204 mmol) was dissolved in DCM (1.5 mL), TFA (1 mL) was added. The mixture was stirred at RT for 1 h. The reaction was concentrated and co-evaporated with toluene 3 times. The resulting residue was dissolved in TFA (2 mL) and heated at 80° C. for 1 h. The reaction was concentrated and purified with Gilson (3-55% CH$_3$CN/water with 0.05% TFA). The correct fractions were concentrated and lyophilized from CH$_3$CN/water with the addition of 0.2 mL of HCl (1.2 M in MeOH). LC/MS [M+H]+: 504.5.

EXAMPLE 345

4-((2-Aminoethyl)sulfonyl)-3'-(1H-imidazol-1-yl)-2-(1H-tetrazol-5-yl)-[1,1'-biphenyl]-3-sulfonamide

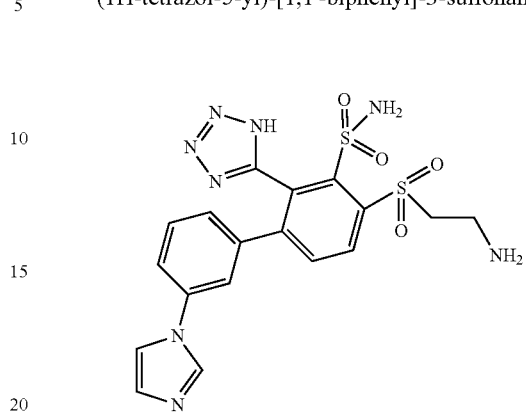

Step A: tert-Butyl (2-((3-(N,N-bis(4-methoxybenzyl)sulfamoyl)-3'-(1H-imidazol-1-yl)-2-(1-(4-methoxybenzyl)-1H-tetrazol-5-yl)-[1,1'-biphenyl]-4-yl)sulfonyl)ethyl)carbamate and tert-butyl (2-((3-(N,N-bis(4-methoxybenzyl)sulfamoyl)-3'-(1H-imidazol-1-yl)-2-(2-(4-methoxybenzyl)-2H-tetrazol-5-yl)-[1,1'-biphenyl]-4-yl)sulfonyl)ethyl)carbamate XphosPdG2 (43.5 mg, 0.055 mmol), sodium carbonate (58.6 mg, 0.553 mmol), 1-(3-bromophenyl)-1H-imidazole (74.0 mg, 0.332 mmol), and tert-butyl (2-((2-(N,N-bis(4-methoxybenzyl)sulfamoyl)-4-(5,5-dimethyl-1,3,2-dioxaborinan-2-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate (250 mg, 0.276 mmol) were placed in a vial. Dioxane (1036 µl) and Water (345 µl) were added. The mixture was degassed and heated at 80° C. for 1 h. The reaction was purified by column chromatography (100% hexane to 100% EtOAc/EtOH (3/1)) to give the title compound. LC/MS [M+H]+: 935.8.

Step B: 4-((2-Aminoethyl)sulfonyl)-3'-(1H-imidazol-1-yl)-2-(1H-tetrazol-5-yl)-[1,1'-biphenyl]-3-sulfonamide The title compound was prepared from tert-butyl (2-((3-(N,N-bis(4-methoxybenzyl)sulfamoyl)-3'-(1H-imidazol-1-yl)-2-(1-(4-methoxybenzyl)-1H-tetrazol-5-yl)-[1,1'-biphenyl]-4-yl)sulfonyl)ethyl)carbamate and tert-butyl (2-((3-(N,N-bis(4-methoxybenzyl)sulfamoyl)-3'-(1H-imidazol-1-yl)-2-(2-(4-methoxybenzyl)-2H-tetrazol-5-yl)-[1,1'-biphenyl]-4-yl)sulfonyl)ethyl)carbamate (Step A) in a similar fashion to the synthesis of 3'-(5-Amino-1,3,4-oxadiazol-2-yl)-4-(azetidin-3-ylsulfonyl)-2-(1H-tetrazol-5-yl)-[1,1'-biphenyl]-3-sulfonamide (Example 2, Step D). LC/MS [M+H]+: 475.6.

EXAMPLE 346

3'-(2-Amino-1H-imidazol-4-yl)-4-((2-aminoethyl)sulfonyl)-2-(1H-tetrazol-5-yl)-[1,1'-biphenyl]-3-sulfonamide

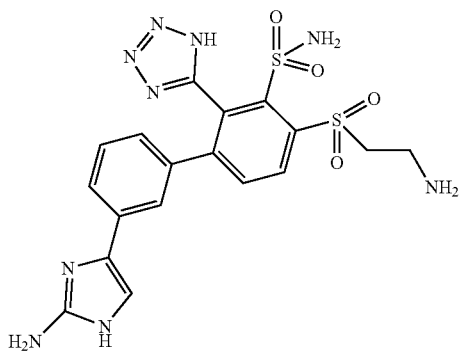 [SMILES: NCCS(=O)(=O)c1ccc(-c2cccc(-c3c[nH]c(N)n3)c2)c(-c2nnn[nH]2)c1S(N)(=O)=O]

Step A: N-(4-(3-bromophenyl)-1H-imidazol-2-yl)acetamide

2-Bromo-1-(3-bromophenyl)ethanone (1000 mg, 3.60 mmol) was stirred with N-carbamimidoylacetamide (1091 mg, 10.79 mmol) in DMF (2998 μl) at room temperature for 48 h. The reaction mixture was diluted with EtOAc and washed with saturated NH$_4$Cl aqueous solution and brine. The organic layer was separated and concentrated. The residue was purified by column chromatography (100% hexane to 100% (EtOAc/EtOH) (3/1) to give the title compound. LC/MS [M+H]$^+$: 280.1, 282.1.

Step B: 4-(3-Bromophenyl)-1H-imidazol-2-amine

N-(4-(3-bromophenyl)-1H-imidazol-2-yl)acetamide was dissolved in MeOH (2 mL), to which HCl in dioxane (4 N, 2 mL) and water (2 mL) were added. The mixture was heated at 100° C. for 1 h. LC-MS showed that the acyl group was removed. The reaction mixture was cooled to room temperature and concentrated to remove the solvents. The product was free based with a SCX cartridge and lyophilized from CH$_3$CN/water. LC/MS [M+H]$^+$: 238.2, 240.2.

Step C: tert-Butyl (2-((3'-(2-amino-1H-imidazol-4-yl)-3-(N,N-bis(4-methoxybenzyl)sulfamoyl)-2-(1-(4-methoxybenzyl)-1H-tetrazol-5-yl)-[1,1'-biphenyl]-4-yl)sulfonyl)ethyl)carbamate and tert-butyl (2-((3'-(2-amino-1H-imidazol-4-yl)-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl) carbamate XPhos Pd G2 (87 mg, 0.111 mmol), sodium carbonate (117 mg, 1.105 mmol), 4-(3-bromophenyl)-1H-imidazol-2-amine (158 mg, 0.663 mmol), and tert-butyl (2-((2-(N,N-bis(4-methoxybenzyl)sulfamoyl)-4-(5,5-dimethyl-1,3,2-dioxaborinan-2-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(5,5-dimethyl-1,3,2-dioxaborinan-2-yl)-3-(2-(4-methoxybenzyl)-2H-tetrazol-5-yl)phenyl)sulfonyl)ethyl)carbamate (500 mg, 0.553 mmol) were placed in a vial. Dioxane (2072 μl) and water (691 μl) were added. The mixture was degassed and heated at 80° C. for 1 hour. LC-MS showed the consumption of starting material and formation of the desired product along with deboronation product. The mixture was purified by column chromatography (100% hexane to 100% EtOAc/EtOH (3/1)/hexane) to give the title compound. LC/MS [M+H]$^+$: 950.8.

Step D: 3'-(2-Amino-1H-imidazol-4-yl)-4-((2-aminoethyl)sulfonyl)-2-(1H-tetrazol-5-yl)-[1,1'-biphenyl]-3-sulfonamide The title compound was prepared from tert-butyl (2-((3'-(2-amino-1H-imidazol-4-yl)-3-(N,N-bis(4-methoxybenzyl)sulfamoyl)-2-(1-(4-methoxybenzyl)-1H-tetrazol-5-yl)-[1,1'-biphenyl]-4-yl)sulfonyl)ethyl)carbamate and tert-butyl (2-((3'-(2-amino-1H-imidazol-4-yl)-3-(N,N-bis(4-methoxybenzyl)sulfamoyl)-2-(2-(4-methoxybenzyl)-2H-tetrazol-5-yl)-[1,1'-biphenyl]-4-yl)sulfonyl)ethyl)carbamate (Step C, above) in a similar fashion to the synthesis of 3'-(5-Amino-1,3,4-oxadiazol-2-yl)-4-(azetidin-3-ylsulfonyl)-2-(1H-tetrazol-5-yl)-[1,1'-biphenyl]-3-sulfonamide (Example 2, Step D). LC/MS [M+H]+: 490.5

EXAMPLE 347

6-((2-Aminoethyl)sulfonyl)-3-(3-hydroxy-2-oxoindolin-7-yl)-2-(1H-tetrazol-5-yl)benzenesulfonamide

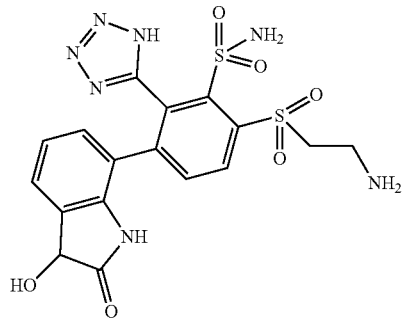 [SMILES: NCCS(=O)(=O)c1ccc(-c2cccc3c2NC(=O)C3O)c(-c2nnn[nH]2)c1S(N)(=O)=O]

Step A: (2,3-Dioxoindolin-7-yl)boronic Acid

7-Bromoindoline-2,3-dione (150 mg, 0.664 mmol), 5,5,5',5'-tetramethyl-2,2'-bi(1,3,2-dioxaborinane) (375 mg, 1.659 mmol), Ph$_3$PdG2 (57.0 mg, 0.100 mmol), and potassium acetate (261 mg, 2.65 mmol) were placed in a reaction vial. Dioxane (135 ml) was added. The reaction was degassed and heated at 90° C. for 4 hours. The reaction mixture was used directly in the next step. LC/MS [M+H]$^+$: 192.0

Step B: tert-Butyl (2-((2-(N,N-bis(4-methoxybenzyl)sulfamoyl)-4-(3-hydroxy-2-oxoindolin-7-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(3-hydroxy-2-oxoindolin-7-yl)-3-(2-(4-methoxybenzyl)-2H-tetrazol-5-yl)phenyl)sulfonyl)ethyl)carbamate Pd (dppf)Cl$_2$ (29.9 mg, 0.041 mmol), sodium carbonate (57.7 mg, 0.544 mmol), tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (250 mg, 0.272 mmol), and water (1.1 mL) were added to (2,3-dioxoindolin-7-yl)boronic acid (above, step A). The reaction mixture was degassed and heated at 80° C. for 12 h. LC-MS showed the coupled product with ketone reduced to alcohol. The reaction was purified by column chromatography (100% hexane to 100% EtOAc/Hexane) to give the title compound. LC/MS [M+H]⁺: 940.7.

Step C: 6-((2-Aminoethyl)sulfonyl)-3-(3-hydroxy-2-oxoindolin-7-yl)-2-(1H-tetrazol-5-yl)benzenesulfonamide The title compound was prepared from tert-butyl (2-((2-(N,N-bis(4-methoxybenzyl)sulfamoyl)-4-(3-hydroxy-2-oxoindolin-7-yl)-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-(3-hydroxy-2-oxoindolin-7-yl)-3-(2-(4-methoxybenzyl)-2H-tetrazol-5-yl)phenyl)sulfonyl)ethyl)carbamate (Step B, above) in a similar fashion to the synthesis of 3'-(5-amino-1,3,4-oxadiazol-2-yl)-4-(azetidin-3-ylsulfonyl)-2-(1H-tetrazol-5-yl)-[1,1'-biphenyl]-3-sulfonamide (Example 2, Step D). LC/MS [M+H]+: 480.2

EXAMPLE 348

Ammonium (R)-4-(4-((2-aminopropyl)sulfonyl)-3-sulfamoyl-2-(2H-tetrazol-5-yl) phenyl)-1H-benzo[d]imidazole-2-carboxylate

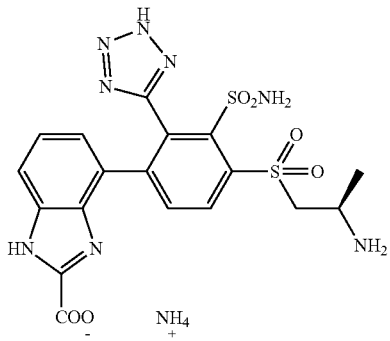

Step A: (R)-tert-butyl(1-((2',3'-diamino-3-(N,N-bis(4-methoxybenzyl)sulfamoyl)-2-(2-(4-methoxybenzyl)-2H-tetrazol-5-yl)-[1,1'-biphenyl]-4-yl)sulfonyl)propan-2-yl) carbamate To a solution of (R)-tert-butyl(1-((2-(N,N-bis(4-methoxybenzyl)sulfamoyl)-4-iodo-3-(2-(4-methoxybenzyl)-2H-tetrazol-5-yl)phenyl)sulfonyl)propan-2-yl)carbamate (0.40 g, 0.43 mmol) in 1,4-dioxane (4 mL) and water (1 mL) were added 3-(4,4,5,5-tetramethyl-1,3,2-dioxaborolan-2-yl)benzene-1,2-diamine (0.20 g, 0.86 mmol), Pd(PPh₃)₄(99 mg, 0.09 mmol) and Na₂CO₃ (0.14 g, 1.27 mmol) at room temperature. The reaction mixture was degassed with nitrogen three times. The reaction mixture was irradiated with microwave radiation at 80° C. for 1 h under nitrogen. The resulting mixture was diluted with water (50 mL) and extracted with EA (3×100 mL). The combined organic layers were washed with water (3×100 mL) and brine (3×150 mL), dried over anhydrous Na₂SO₄ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]⁺: 913.

Step B: (R)-ethyl-4-(3-(N,N-bis(4-methoxybenzyl)sulfamoyl)-4-((2-((tert-butoxycarbonyl) amino)propyl)sulfonyl)-2-(2-(4-methoxybenzyl)-2H-tetrazol-5-yl)phenyl)-1H-benzo[d]imidazole-2-carboxylate To a solution of (R)-tert-butyl(1-((2',3'-diamino-3-(N,N-bis(4-methoxybenzyl) sulfamoyl)-2-(2-(4-methoxybenzyl)-2H-tetrazol-5-yl)-[1,1'-biphenyl]-4-yl)sulfonyl) propan-2-yl)carbamate (0.32 g, 0.35 mmol) in EtOH (8 mL) was added ethyl 2,2,2-triethoxyacetate (0.39 g, 1.75 mmol) at 0° C. The reaction mixture was degassed with nitrogen three times and stirred at 80° C. for 16 hours under nitrogen. The resulting mixture was concentrated under vacuum. The residue was purified by silica gel column chromatography, eluted with 50% EA in PE. The fractions containing desired product were combined and concentrated under vacuum to afford the title compound: LCMS [M+1]⁺: 995.

Step C: (R)-ethyl-4-(4-((2-aminopropyl)sulfonyl)-3-sulfamoyl-2-(2H-tetrazol-5-yl)phenyl)-1H-benzo[d]imidazole-2-carboxylate To a stirred solution of (R)-ethyl 4-(3-(N,N-bis(4-methoxybenzyl)sulfamoyl)-4-((2-((tert-butoxycarbonyl)amino)propyl)sulfonyl)-2-(2-(4-methoxybenzyl)-2H-tetrazol-5-yl)phenyl)-1H-benzo[d]imidazole-2-carboxylate (0.20 g, 0.20 mmol) in DCM (2 mL) was added TFA (2 mL) at 0° C. The solution was warmed to room temperature and stirred for 1 h. The resulting solution was concentrated under vacuum. The residue was co-evaporated with anisole (3×3 mL) under vacuum and used directly in the next step without further purification. The crude product was dissolved in TFA (4 mL). The solution was stirred at 80° C. for 1 hour. The resulting solution was concentrated under vacuum to afford the title compound, which was used in the next step directly without further purification: LCMS [M+1]⁺: 535.

Step D: Ammonium (R)-4-(4-((2-aminopropyl)sulfonyl)-3-sulfamoyl-2-(2H-tetrazol-5-yl) phenyl)-1H-benzo[d]imidazole-2-carboxylate To a stirred solution of (R)-ethyl-4-(4-((2-aminopropyl)sulfonyl)-3-sulfamoyl-2-(2H-tetrazol-5-yl)phenyl)-1H-benzo[d]imidazole-2-carboxylate (100 mg, 0.19 mmol) in 1,4-dioxane (1 mL) was added a solution of LiOH (17.9 mg, 0.748 mmol) in water (1 mL) dropwise at 0° C. The reaction mixture was stirred for 2 hours. The resulting mixture was concentrated under vacuum. The crude product was purified by Prep-HPLC with the following conditions: Column: XBridge BEH130 Prep C18 OBD Column 19×150 mm, 5 μm, 13 nm; Mobile Phase A: water with 10 mmol/L NH₄HCO₃, Mobile Phase B: ACN; Flow rate: 20 mL/min; Gradient: 3% B to 19% B in 8 min; Detector: 254 and 220 nm; Retention time: 6.71 min. The fractions containing desired product were combined and concentrated under vacuum to afford the title compound: LCMS [M+1-17]⁺: 507; ¹H NMR (300 MHz, CD₃OD+DCl): δ 8.46 (d, J=8.1

Hz, 1H), 8.00 (d, J=8.1 Hz, 1H), 7.49 (d, J=7.5 Hz, 1H), 7.10 (t, J=8.1 Hz, 1H), 6.76 (d, J=7.5 Hz, 1H), 4.30-3.99 (m, 3H), 1.53 (d, J=6.3 Hz, 3H).

EXAMPLE 349

3-(2-Aminobenzo[d]thiazol-4-yl)-6-(((3 S,5S)-5-(hydroxymethyl)pyrrolidin-3-yl) sulfonyl)-2-(2H-tetrazol-5-yl)benzenesulfonamide

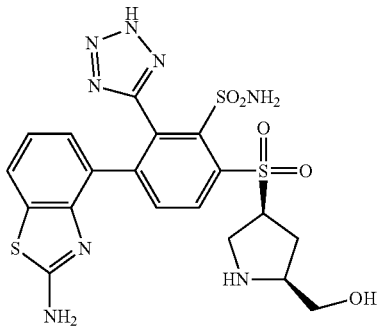 [SMILES: Nc1nc2c(-c3ccc(S(=O)(=O)[C@@H]4CN[C@H](CO)C4)c(S(N)(=O)=O)c3-c3nn[nH]n3)cccc2s1]

Step A: (2S,4S)-1-tert-butyl-2-methyl-4-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl) sulfonyl)pyrrolidine-1,2-dicarboxylate To a solution of (2S,4S)-1-tert-butyl-2-methyl-4-((2-(N,N-bis(4-methoxybenzyl) sulfamoyl)-4-iodo-3-(2-(4-methoxybenzyl)-2H-tetrazol-5-yl)phenyl)sulfonyl) pyrrolidine-1,2-dicarboxylate (1.50 g, 1.50 mmol) in 1,4-dioxane (15 mL) and water (3 mL) were added (2-aminobenzo[d]thiazol-4-yl)boronic acid (0.44 g, 2.20 mmol), Pd(PPh$_3$)$_4$ (0.35 g, 0.18 mmol) and Na$_2$CO$_3$ (0.48 g, 4.50 mmol) at room temperature. The reaction mixture was degassed with nitrogen three times. The reaction mixture was stirred at 60° C. for 16 h under nitrogen. The resulting mixture was diluted with water (50 mL) and extracted with EA (3×100 mL). The combined organic layers was washed with water (3×100 mL) and brine (3×50 mL), dried over anhydrous Na$_2$SO$_4$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]$^+$: 1025.

Step B: (2S,4S)-tert-butyl-4-((4-(2-aminobenzo[d]thiazol-4-yl)-2-(N,N-bis(4-methoxybenzyl) sulfamoyl)-3-(2-(4-methoxybenzyl)-2H-tetrazol-5-yl) phenyl)sulfonyl)-2-(hydroxymethyl)pyrrolidine-1-carboxylate To a stirred solution of (2S,4S)-1-tert-butyl-2-methyl 4-((4-(2-aminobenzo [d]thiazol-4-yl)-2-(N,N-bis(4-methoxybenzyl)sulfamoyl)-3-(2-(4-methoxybenzyl)-2H-tetrazol-5-yl)phenyl)sulfonyl)pyrrolidine-1,2-dicarboxylate (0.52 g, 0.5 mmol) in THF (5 mL) was added LiBH$_4$ (1 M, 2.5 mL, 2.5 mmol) dropwise at 0° C. The reaction mixture was stirred at room temperature for 2 h under nitrogen. The resulting mixture was quenched with ice-water (50 mL) and extracted with EA (3×50 mL). The combined organic layers were washed with water (3×50 mL) and brine (3×50 mL), dried over anhydrous Na$_2$SO$_4$ and filtered. The filtrate was concentrated under vacuum to afford the title compound, which was used directly in the next step, LCMS [M+1]$^+$: 997.

Step C: 3-(2-Aminobenzo[d]thiazol-4-yl)-6-(((3S,5S)-5-(hydroxymethyl)pyrrolidin-3-yl) sulfonyl)-2-(2H-tetrazol-5-yl)benzenesulfonamide To a solution of (2S,4S)-tert-butyl-4-((4-(2-aminobenzo[d]thiazol-4-yl)-2-(N,N-bis (4-methoxybenzyl)sulfamoyl)-3-(2-(4-methoxybenzyl)-2H-tetrazol-5-yl)phenyl) sulfonyl)-2-(hydroxymethyl)pyrrolidine-1-carboxylate (0.22 g, 0.22 mmol) in DCM (4 mL) was added TFA (2 mL) at 0° C. The solution was warmed to RT and stirred for 1 hour. The resulting solution was concentrated under vacuum. The residue was co-evaporated with anisole (3×3 mL) under vacuum. The crude product was dissolved in TFA (4 mL). The solution was stirred at 80° C. for 1 hour. The resulting solution was concentrated under vacuum. The crude product was purified by Prep-HPLC with the following conditions: Column: X Bridge Prep C18 OBD Column 19×250 mm, 10 m; Mobile Phase A: water with 10 mmol/L NH$_4$HCO$_3$, Mobile Phase B: ACN; Flow rate: 25 mL/min; Gradient: 10% B to 20% B in 10 min; Detector: 254 and 220 nm; Retention time: 8.12 min. The fractions containing desired product were combined and concentrated under vacuum to afford the title compound: LCMS [M+1]$^+$: 537; $^1$H NMR (400 MHz, DMSO-d$_6$): δ 8.25 (d, J=8.0 Hz, 1H), 7.93 (d, J=8.0 Hz, 1H), 7.71-7.49 (m, 5H), 6.73-6.69 (m, 1H), 6.54-6.48 (m, 1H), 5.28-5.24 (m, 1H), 5.08-5.04 (m, 1H), 3.63-3.44 (m, 5H), 2.38-2.27 (m, 1H), 2.18-2.07 (m, 1H).

EXAMPLE 350

3-(2-Aminobenzo[d]thiazol-4-yl)-6-(((3 S,5S)-5-(hydroxymethyl)pyrrolidin-3-yl) sulfonyl)-2-(2H-tetrazol-5-yl)benzenesulfonamide

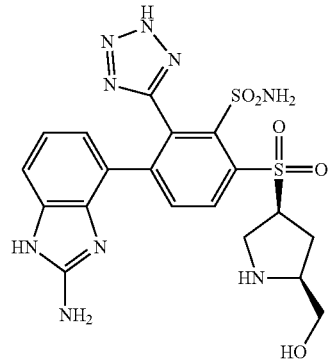 [SMILES: Nc1nc2c(-c3ccc(S(=O)(=O)[C@@H]4CN[C@H](CO)C4)c(S(N)(=O)=O)c3-c3nn[nH]n3)cccc2[nH]1]

Step A: (2S,4S)-benzyl-4-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl) phenyl)sulfonyl)-2-(hydroxymethyl)pyrrolidine-1-carboxylate The title compound was prepared as described for EXAMPLE 349, step A using (2S,4S)-benzyl-4-((2-(N,N-bis(4-methoxybenzyl)sulfamoyl)-4-iodo-3-(2-(4-methoxybenzyl)-2H-tetrazol-5-yl)phenyl)sulfonyl)-2-(hydroxymethyl)pyrrolidine-1-carboxylate (200 mg, 0.2 mmol) and 2-amino-3H-benzo[d]imidazol-4-ylboronic acid (71 mg, 0.4 mmol) to afford the title compound as a solid: LCMS [M+1]$^+$: 1014.

Step B: 3-(2-Amino-1H-benzo[d]imidazol-4-yl)-6-(((3S,5S)-5-(hydroxymethyl)pyrrolidin-3-yl)sulfonyl)-2-(2H-tetrazol-5-yl)benzenesulfonamide To (2S,4S)-benzyl-4-(4-(2-amino-1H-benzo[d]imidazol-4-yl)-2-(N,N-bis (4-methoxybenzyl)sulfamoyl)-3-(2-(4-methoxybenzyl)-2H-tetrazol-5-yl)phenylsulfonyl)-2-(hydroxymethyl)pyrrolidine-1-carboxylate (0.3 g, 0.30 mmol) was added aqueous HCl (2 N, 20 mL, 24.0 mmol). The mixture was stirred at 70° C. for 3 hours. The resulting solution was concentrated under vacuum. The crude product was purified by Prep-HPLC with the following conditions: Column: X Bridge Prep Phenyl OBD Column 19×150 mm, 5 μm, 13 nm; Mobile Phase A: water with 10 mmol/L NH$_4$HCO$_3$, Mobile Phase B: ACN; Flow rate: 20 mL/min; Gradient: 5% B to 20% B in 8 min; Detector: 254 nm and 220 nm; Retention time: 5.89 min. The fractions containing desired product were combined and concentrated under vacuum to afford the title compound: LCMS [M+1]$^+$: 520; $^1$H NMR (400 MHz, DMSO-d$_6$): δ 8.29 (d, J=8.0 Hz, 1H), 8.03 (d, J=8.0 Hz, 1H), 7.65 (brs, 2H), 6.99 (d, J=7.6 Hz, 1H), 6.62-6.59 (m, 3H), 6.17 (d, J=7.2 Hz, 1H), 5.08-5.00 (m, 1H), 3.15-3.77 (m, 5H), 2.44-2.27 (m, 1H), 2.14-2.06 (m, 1H).

EXAMPLE 351

(S)-3-(2-amino-1H-benzo[d]imidazol-7-yl)-6-((1-amino-3-hydroxypropan-2-yl) sulfonyl)-2-(1H-tetrazol-5-yl)benzenesulfonamide

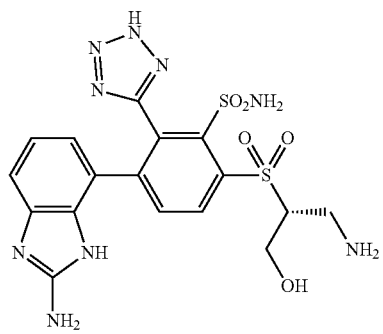 [SMILES: NC[C@H](CO)S(=O)(=O)c1ccc(-c2cccc3nc(N)[nH]c23)c(-c2nn[nH]n2)c1S(N)(=O)=O]

Step A: (R)-tert-butyl(2-((4-(2-amino-1H-benzo[d]imidazol-7-yl)-2-(N,N-bis(4-methoxy benzyl)sulfamoyl)-3-(2-(4-methoxybenzyl)-2H-tetrazol-5-yl) phenyl)sulfonyl)-3-hydroxypropyl)carbamate To a solution of (R)-tert-butyl(2-((2-(N,N-bis(4-methoxybenzyl)sulfamoyl)-4-iodo-3-(2-(4-methoxybenzyl)-2H-tetrazol-5-yl)phenyl)sulfonyl)-3-hydroxypropyl)carbamate (0.60 g, 0.63 mmol), in 1,4-dioxane (6.0 mL) and water (1.2 mL) were added (2-amino-1H-benzo[d]imidazol-4-yl)boronic acid (0.22 g, 1.26 mmol), Pd(dppf)Cl$_2$ adduct CH$_2$Cl$_2$ (46 mg, 0.063 mmol) and Na$_2$CO$_3$ (0.2 g, 1.89 mmol). The reaction mixture was degassed with nitrogen three times. The reaction mixture was stirred for 6 h at 80° C. The resulting reaction mixture was diluted with water (50 mL), extracted with DCM (3×60 mL). The combined organic layers were washed with brine (3×50 mL), dried over anhydrous Na$_2$SO$_4$ and filtered. The filtrate was concentrated under vacuum. The residue was purified by silica gel column chromatography, eluted with 5% MeOH in EA. The fractions containing desired product were combined and concentrated under vacuum to afford the title compound: LCMS [M+1]$^+$: 954.

Step B: (R)-3-(2-amino-1H-benzo[d]imidazol-7-yl)-6-((1-amino-3-hydroxypropan-2-yl)sulfonyl)-2-(1H-tetrazol-5-yl)benzenesulfonamide To a solution of (R)-tert-butyl(2-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl) phenyl)sulfonyl)-3-hydroxypropyl)carbamate (0.26 g, 0.27 mmol) in DCM (3 mL) was added TFA (1 mL) at 0° C. The solution was warmed to room temperature, stirred for 1 hour, and concentrated under vacuum. The residue was co-evaporated with anisole (3×3 mL) under vacuum and used directly in the next step without further purification. The crude product was dissolved in TFA (4 mL). The solution was stirred at 80° C. for 1 hour. The resulting solution was concentrated under vacuum. The crude product was purified by Prep-HPLC with the following conditions: Column: X Bridge C18, 19×150 mm, 5 m; Mobile Phase A: water with 0.05% NH$_4$HCO$_3$, Mobile Phase B: ACN; Flow rate: 20 mL/min; Gradient: 15 B to 48% B in 8 min; 254 nm; Retention time: 6.85 min. The collected fractions containing desired product were combined and concentrated under vacuum to afford the title compound: LCMS [M+1]$^+$: 494; $^1$H NMR (300 MHz, DMSO-d$_6$): δ 8.21 (d, J=8.4 Hz, 1H), 8.00 (d, J=8.4 Hz, 1H), 6.95 (d, J=8.1 Hz, 1H), 6.47-6.42 (m, 1H), 6.40-6.34 (brs, 2H), 6.16 (d, J=8.1 Hz, 1H), 4.55 (t, J=6.0 Hz, 1H), 3.96-3.84 (m, 2H), 3.38-3.19 (m, 2H).

EXAMPLES 352-372 below were prepared in an analogous fashion to EXAMPLE 351 using the corresponding iodide and boronic acids or esters prepared as described herein or commercially available.

| EX. No. | Structure | Chemical Name | LC/MS [M + H] |
|---|---|---|---|
| 352 | 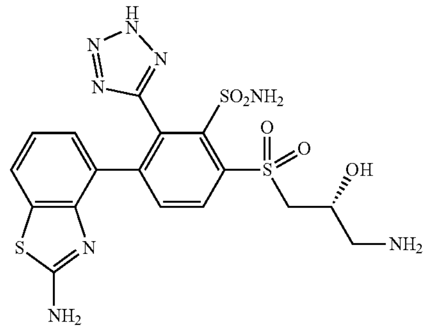 [SMILES: NC[C@@H](O)CS(=O)(=O)c1ccc(-c2cccc3sc(N)nc23)c(-c2nn[nH]n2)c1S(N)(=O)=O] | (R)-6-((3-amino-2-hydroxypropyl)sulfonyl)-3-(2-aminobenzo[d]thiazol-4-yl)-2-(2H-tetrazol-5-yl)benzenesulfonamide | 511 |
| 353 | 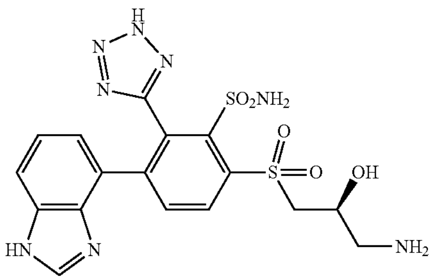 [SMILES: NC[C@H](O)CS(=O)(=O)c1ccc(-c2cccc3[nH]cnc23)c(-c2nn[nH]n2)c1S(N)(=O)=O] | (S)-6-((3-amino-2-hydroxypropyl)sulfonyl)-3-(1H-benzo[d]imidazol-4-yl)-2-(2H-tetrazol-5-yl)benzenesulfonamide | 479 |
| 354 | 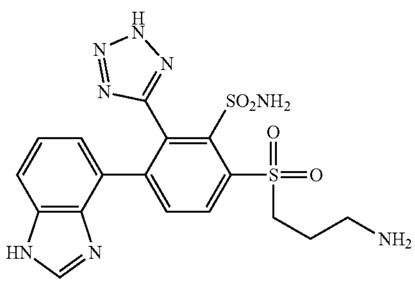 [SMILES: NCCCS(=O)(=O)c1ccc(-c2cccc3[nH]cnc23)c(-c2nn[nH]n2)c1S(N)(=O)=O] | 6-((3-aminopropyl)sulfonyl)-3-(1H-benzo[d]imidazol-7-yl)-2-(1H-tetrazol-5-yl)benzenesulfonamide | 463 |
| 355 | 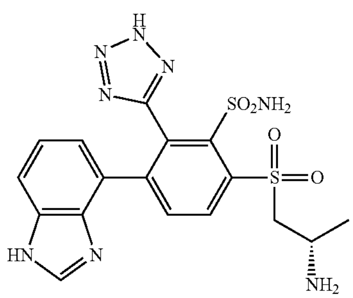 [SMILES: C[C@H](N)CS(=O)(=O)c1ccc(-c2cccc3[nH]cnc23)c(-c2nn[nH]n2)c1S(N)(=O)=O] | (S)-6-((2-aminopropyl)sulfonyl)-3-(1H-benzo[d]imidazol-4-yl)-2-(2H-tetrazol-5-yl)benzenesulfonamide | 463 |
| 356 | 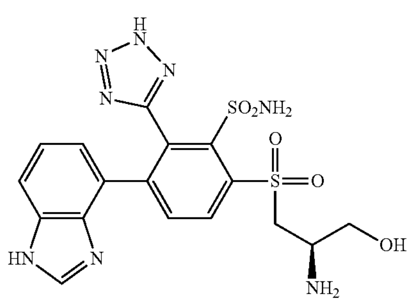 [SMILES: N[C@H](CO)CS(=O)(=O)c1ccc(-c2cccc3[nH]cnc23)c(-c2nn[nH]n2)c1S(N)(=O)=O] | (R)-6-((2-amino-3-hydroxypropyl)sulfonyl)-3-(1H-benzo[d]imidazol-4-yl)-2-(2H-tetrazol-5-yl)benzenesulfonamide | 479 |

| EX. No. | Structure | Chemical Name | LC/MS [M + H] |
|---|---|---|---|
| 357 | 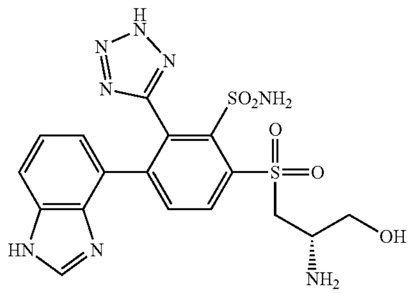 [SMILES: N[C@@H](CO)CS(=O)(=O)c1ccc(-c2cccc3[nH]cnc23)c(-c2nn[nH]n2)c1S(N)(=O)=O] | (S)-6-((2-amino-3-hydroxypropyl)sulfonyl)-3-(1H-benzo[d]imidazol-4-yl)-2-(2H-tetrazol-5-yl)benzenesulfonamide | 479 |
| 358 | 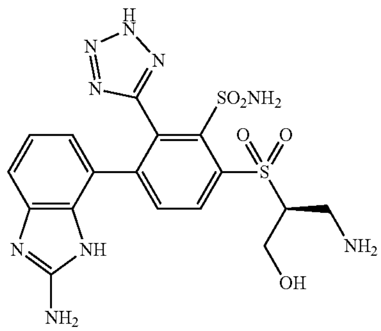 [SMILES: NC[C@@H](CO)S(=O)(=O)c1ccc(-c2cccc3nc(N)[nH]c23)c(-c2nn[nH]n2)c1S(N)(=O)=O] | (S)-3-(2-amino-1H-benzo[d]imidazol-7-yl)-6-((1-amino-3-hydroxypropan-2-yl)sulfonyl)-2-(1H-tetrazol-5-yl)benzenesulfonamide | 494 |
| 359 | 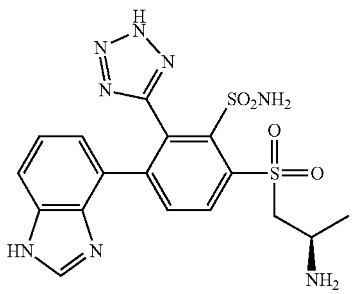 [SMILES: C[C@@H](N)CS(=O)(=O)c1ccc(-c2cccc3[nH]cnc23)c(-c2nn[nH]n2)c1S(N)(=O)=O] | (S)-4-(2-amino-1H-benzo[d]imidazol-7-yl)-N1-methyl-N1-(pyrrolidin-3-yl)-3-(1H-tetrazol-5-yl)benzene-1,2-disulfonamide | 463 |
| 360 | 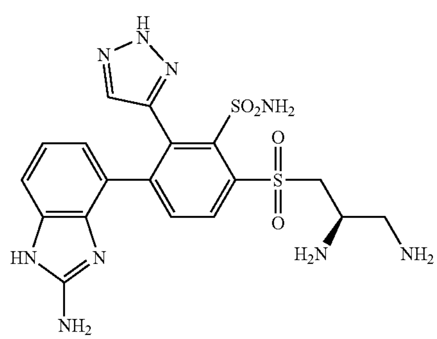 [SMILES: NC[C@@H](N)CS(=O)(=O)c1ccc(-c2cccc3[nH]c(N)nc23)c(-c2cn[nH]n2)c1S(N)(=O)=O] | (R)-3-(2-amino-1H-benzo[d]imidazol-4-yl)-6-((2,3-diaminopropyl)sulfonyl)-2-(2H-tetrazol-5-yl)benzenesulfonamide | 493 |
| 361 | 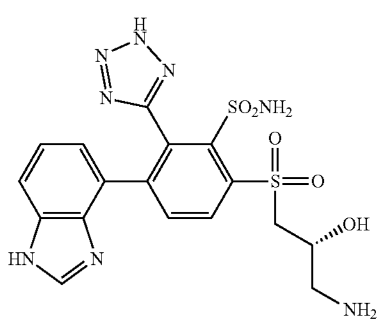 [SMILES: NC[C@@H](O)CS(=O)(=O)c1ccc(-c2cccc3[nH]cnc23)c(-c2nn[nH]n2)c1S(N)(=O)=O] | (R)-6-((3-amino-2-hydroxypropyl)sulfonyl)-3-(1H-benzo[d]imidazol-4-yl)-2-(2H-tetrazol-5-yl)benzenesulfonamide | 479 |

| EX. No. | Structure | Chemical Name | LC/MS [M + H] |
|---|---|---|---|
| 362 | 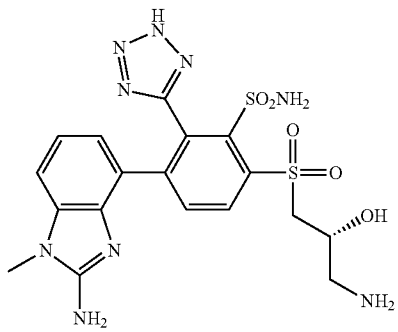 [SMILES: Cn1c(N)nc2c(-c3ccc(S(=O)(=O)C[C@H](O)CN)c(S(N)(=O)=O)c3-c3nn[nH]n3)cccc21] | (R)-3-(2-amino-1-methyl-1H-benzo[d]imidazol-4-yl)-6-((3-amino-2-hydroxypropyl)sulfonyl)-2-(2H-tetrazol-5-yl)benzenesulfonamide | 508 |
| 363 | 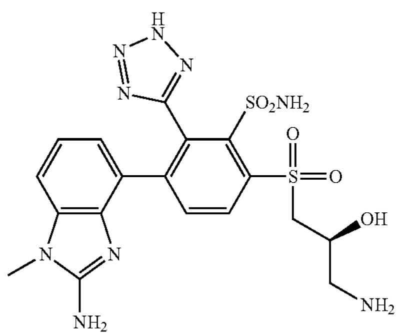 [SMILES: Cn1c(N)nc2c(-c3ccc(S(=O)(=O)C[C@@H](O)CN)c(S(N)(=O)=O)c3-c3nn[nH]n3)cccc21] | (S)-3-(2-amino-1-methyl-1H-benzo[d]imidazol-4-yl)-6-((3-amino-2-hydroxypropyl)sulfonyl)-2-(2H-tetrazol-5-yl)benzenesulfonamide | 508 |
| 364 | 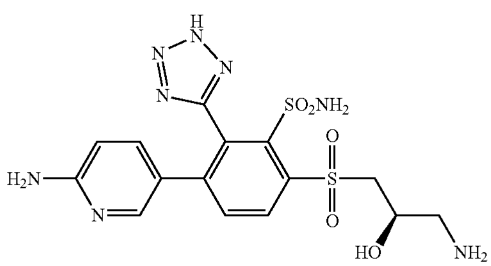 [SMILES: NC[C@@H](O)CS(=O)(=O)c1ccc(-c2ccc(N)nc2)c(-c2nn[nH]n2)c1S(N)(=O)=O] | (R)-6-((3-amino-2-hydroxypropyl)sulfonyl)-3-(6-aminopyridin-3-yl)-2-(2H-tetrazol-5-yl)benzenesulfonamide | 455 |
| 365 | 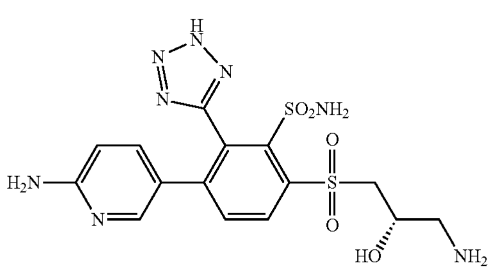 [SMILES: NC[C@H](O)CS(=O)(=O)c1ccc(-c2ccc(N)nc2)c(-c2nn[nH]n2)c1S(N)(=O)=O] | (S)-6-((3-amino-2-hydroxypropyl)sulfonyl)-3-(6-aminopyridin-3-yl)-2-(2H-tetrazol-5-yl)benzenesulfonamide | 455 |

-continued

| EX. No. | Structure | Chemical Name | LC/MS [M + H] |
|---|---|---|---|
| 366 | 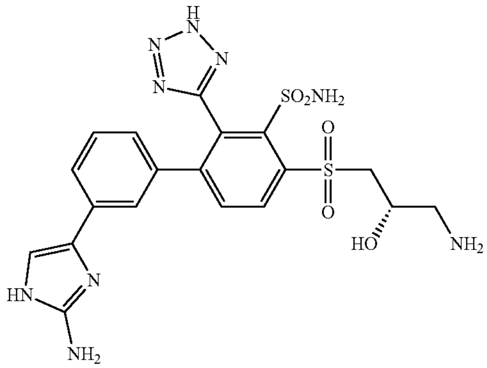 [SMILES: NC[C@H](O)CS(=O)(=O)c1ccc(-c2cccc(-c3c[nH]c(N)n3)c2)c(-c2nn[nH]n2)c1S(N)(=O)=O] | (S)-3'-(2-amino-1H-imidazol-4-yl)-4-((3-amino-2-hydroxypropyl)sulfonyl)-2-(2H-tetrazol-5-yl)-[1,1'-biphenyl]-3-sulfonamide | 520 |
| 367 | 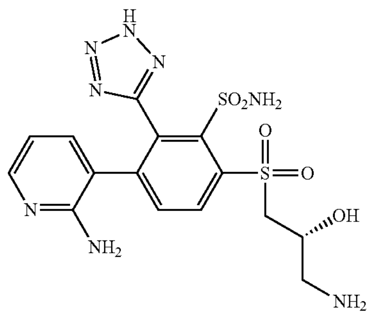 [SMILES: NC[C@@H](O)CS(=O)(=O)c1ccc(-c2cccnc2N)c(-c2nn[nH]n2)c1S(N)(=O)=O] | (R)-6-((3-amino-2-hydroxypropyl)sulfonyl)-3-(2-aminopyridin-3-yl)-2-(2H-tetrazol-5-yl)benzenesulfonamide | 453 |
| 368 | 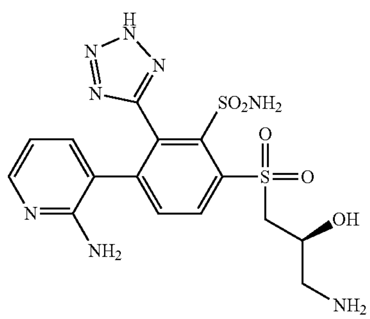 [SMILES: NC[C@H](O)CS(=O)(=O)c1ccc(-c2cccnc2N)c(-c2nn[nH]n2)c1S(N)(=O)=O] | (S)-6-((3-amino-2-hydroxypropyl)sulfonyl)-3-(2-aminopyridin-3-yl)-2-(2H-tetrazol-5-yl)benzenesulfonamide | 453 |
| 369 | 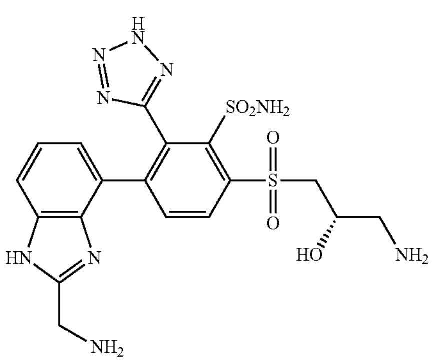 [SMILES: NCc1nc2c(-c3ccc(S(=O)(=O)C[C@@H](O)CN)c(S(N)(=O)=O)c3-c3nn[nH]n3)cccc2[nH]1] | (S)-6-((3-amino-2-hydroxypropyl)sulfonyl)-3-(2-(aminomethyl)-1H-benzo[d]imidazol-4-yl)-2-(2H-tetrazol-5-yl)benzenesulfonamide | 508 |

| EX. No. | Structure | Chemical Name | LC/MS [M + H] |
|---|---|---|---|
| 370 | 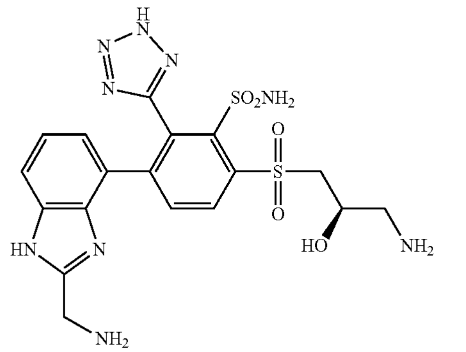 [SMILES: NCc1nc2c(-c3ccc(S(=O)(=O)C[C@H](O)CN)c(S(N)(=O)=O)c3-c3nn[nH]n3)cccc2[nH]1] | (R)-6-((3-amino-2-hydroxypropyl)sulfonyl)-3-(2-(aminomethyl)-1H-benzo[d]imidazol-4-yl)-2-(2H-tetrazol-5-yl)benzenesulfonamide | 508 |
| 371 | 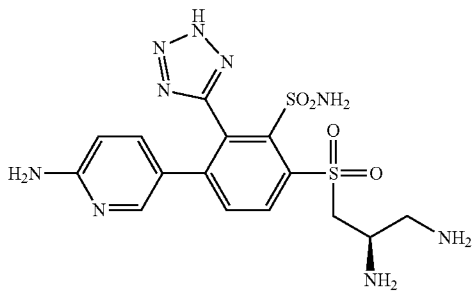 [SMILES: NC[C@@H](N)CS(=O)(=O)c1ccc(-c2ccc(N)nc2)c(-c2nn[nH]n2)c1S(N)(=O)=O] | (R)-3-(6-aminopyridin-3-yl)-6-((2,3-diaminopropyl)sulfonyl)-2-(2H-tetrazol-5-yl)benzenesulfonamide | 454 |
| 372 | 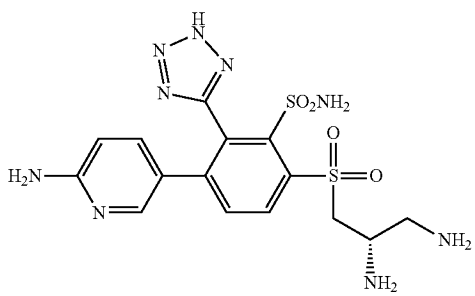 [SMILES: NC[C@H](N)CS(=O)(=O)c1ccc(-c2ccc(N)nc2)c(-c2nn[nH]n2)c1S(N)(=O)=O] | (S)-3-(6-aminopyridin-3-yl)-6-((2,3-diaminopropyl)sulfonyl)-2-(2H-tetrazol-5-yl)benzenesulfonamide | 454 |

EXAMPLE 373

3-(2-Amino-1-(2-hydroxyethyl)-1H-benzo[d]imidazol-4-yl)-6-(azetidin-3-ylsulfonyl)-2-(2H-tetrazol-5-yl)benzenesulfonamide

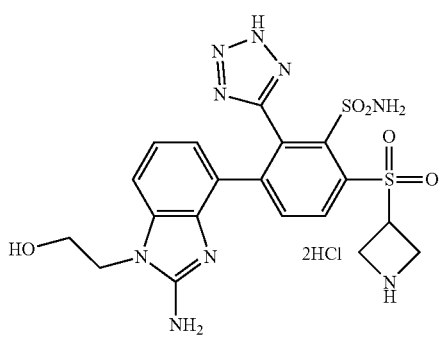 [SMILES: Nc1nc2c(-c3ccc(S(=O)(=O)C4CNC4)c(S(N)(=O)=O)c3-c3nn[nH]n3)cccc2n1CCO]

Step A: Tert-butyl-3-((3-(N,N-bis(4-methoxybenzyl)sulfamoyl)-3'-((2-hydroxyethyl)amino)-2-(2-(4-methoxybenzyl)-2H-tetrazol-5-yl)-2'-nitro-[1,1'-biphenyl]-4-yl)sulfonyl) azetidine-1-carboxylate To a solution of tert-butyl-3-((2-(N,N-bis(4-methoxybenzyl)sulfamoyl)-4-iodo-3-(2-(4-methoxybenzyl)-2H-tetrazol-5-yl)phenyl)sulfonyl)azetidine-1-carboxylate (2.0 g, 2.15 mmol) in 1,4-dioxane (20 mL) and water (7 mL) were added Pd(PPh$_3$)$_4$(0.50 g, 0.43 mmol), 2-((2-nitro-3-(4,4,5,5-tetramethyl-1,3,2-dioxaborolan-2-yl) phenyl)amino)ethanol (1.3 g, 4.30 mmol) and Na$_2$CO$_3$ (0.68 g, 6.45 mmol) at room temperature. The reaction mixture was degassed with nitrogen three times. The reaction mixture was stirred for 16 hours at 80° C. The resulting mixture was diluted with water (100 mL) and extracted with EA (3×100 mL). The combined organic layers was washed with brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 985.

Step B: Tert-butyl-3-((2'-amino-3-(N,N-bis(4-methoxybenzyl)sulfamoyl)-3'-((2-hydroxyethyl)amino)-2-(2-(4-methoxybenzyl)-2H-tetrazol-5-yl)-[1,1'-biphenyl]-4-yl)sulfonyl) azetidine-1-carboxylate To a solution of tert-butyl 3-((3-(N,N-bis(4-methoxybenzyl)sulfamoyl)-3'-((2-hydroxyethyl)amino)-2-(2-(4-methoxybenzyl)-2H-tetrazol-5-yl)-2'-nitro-[1,1'-biphenyl]-4-yl)sulfonyl)azetidine-1-carboxylate (1.40 g, 1.42 mmol) in MeOH (15 mL) was added Pd—C (10%, 1.51 g, 1.42 mmol) at room temperature under mitrogen. The reaction mixture was degassed with hydrogen three times. The mixture was stirred at room temperature for 16 hours. The resulting mixture was filtered. The filtrate was concentrated under vacuum to afford the title compound, which was used in the next step without further purification: LCMS [M+1]$^+$: 955.

Step C: Tert-butyl-3-((4-(2-amino-1-(2-hydroxyethyl)-1H-benzo[d]imidazol-4-yl)-2-(N,N-bis(4-methoxybenzyl)sulfamoyl)-3-(2-(4-methoxybenzyl)-2H-tetrazol-5-yl)phenyl) sulfonyl)azetidine-1-carboxylate To a solution of tert-butyl-3-((2'-amino-3-(N,N-bis(4-methoxybenzyl) sulfamoyl)-3'-((2-hydroxyethyl)amino)-2-(2-(4-methoxybenzyl)-2H-tetrazol-5-yl)-[1,1'-biphenyl]-4-yl)sulfonyl)azetidine-1-carboxylate (0.20 g, 0.21 mmol) in MeOH (2 mL) was added cyanic bromide (44.4 mg, 0.42 mmol) at room temperature. The reaction solution was warmed to 50° C. and stirred for 2 h. The resulting solution was diluted with water (50 mL) and extracted with EA (3×50 mL). The combined organic layers was washed with brine (3×50 mL), dried over anhydrous Na$_2$SO$_4$ and filtered. The filtrate was concentrated under vacuum. The residue was purified by silica gel column chromatography, eluted with 10% MeOH in DCM. The fractions containing desired product were combined and concentrated vacuum to afford the title compound: LCMS [M+1]$^+$: 980.

Step D: 3-(2-Amino-1-(2-hydroxyethyl)-1H-benzo[d]imidazol-4-yl)-6-(azetidin-3-ylsulfonyl)-2-(2H-tetrazol-5-yl)benzenesulfonamide To a solution of tert-butyl-3-((4-(2-amino-1-(2-hydroxyethyl)-1H-benzo[d]imidazol-4-yl)-2-(N,N-bis(4-methoxybenzyl)sulfamoyl)-3-(2-(4-methoxybenzyl)-2H-tetrazol-5-yl)phenyl) sulfonyl)azetidine-1-carboxylate (0.15 g, 0.15 mmol) was added to conc. HCl (5 mL). The solution was stirred for 5 hours at 80° C. The resulting solution was concentrated under vacuum. The crude product was purified by Prep-HPLC with the following conditions: Column: X Bridge BEH130 Prep C18 OBD Column 19×150 mm, 5 µm, 13 nm; Mobile Phase A: water with 10 mmol/L NH$_4$HCO$_3$, Mobile Phase B: ACN; Flow rate: 20 mL/min; Gradient: 5% B to 30% B in 8 min; 254 nm/220 nm; Retention time: 6.03 min. The fractions containing desired product were combined and concentrated under vacuum to afford the title compound: LCMS [M+1-72]$^+$: 520; $^1$H NMR (400 MHz, CD$_3$OD+DCl): δ 8.73 (d, J=8.4 Hz, 1H), 8.10 (d, J=8.4 Hz, 1H), 7.51-7.49 (m, 1H), 7.24-7.20 (m, 1H), 6.88-6.86 (m, 1H), 5.38-5.30 (m, 1H), 4.65-4.62 (m, 2H), 4.57-4.51 (m, 2H), 4.31-4.28 (m, 2H), 3.93-3.86 (m, 2H).

EXAMPLE 374

2'-Amino-4-(azetidin-3-ylsulfonyl)-3'-((2-hydroxyethyl)amino)-2-(2H-tetrazol-5-yl)-[1,1'-biphenyl]-3-sulfonamide

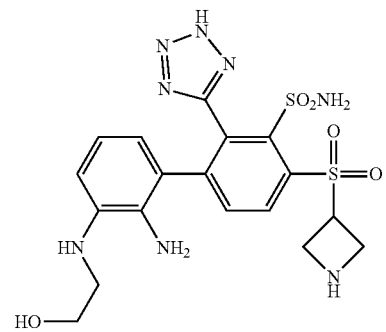 [SMILES: Nc1c(NCCO)cccc1-c1ccc(S(=O)(=O)C2CNC2)c(S(N)(=O)=O)c1-c1nn[nH]n1]

Step A: 2'-Amino-4-(azetidin-3-ylsulfonyl)-3'-((2-hydroxyethyl)amino)-2-(2H-tetrazol-5-yl)-[1,1'-biphenyl]-3-sulfonamide To a solution of tert-butyl3-((2'-amino-3-(N,N-bis(4-methoxybenzyl)sulfamoyl)-3'-((2-hydroxyethyl)amino)-2-(2-(4-methoxybenzyl)-2H-tetrazol-5-yl)-[1,1'-biphenyl]-4-yl)sulfonyl)azetidine-1-carboxylate (0.20 g, 0.21 mmol) was added aqueous conc. HCl (5 mL) at room temperature. The reaction solution was stirred for 4 hours at 80° C. The resulting solution was concentrated under vacuum. The crude product was purified by Prep-HPLC with the following conditions: Column: X Bridge Prep C18 OBD Column 19×250 mm, 10 µm; Mobile Phase A: water with 10 mmol/L NH$_4$HCO$_3$, Mobile Phase B: ACN; Flow rate: 25 mL/min; Gradient: 5% B to 35% B in 5 min; Detector: 254/220 nm; Retention time: 4.01 min. The fractions containing desired product were combined and concentrated under vacuum to afford the title compound: LCMS [M+1]$^+$: 495; $^1$H NMR (300 MHz, CD$_3$OD+DCl): δ 8.45 (d, J=8.1 Hz, 1H), 7.80 (d, J=8.1 Hz, 1H), 6.49-6.47 (m, 2H), 6.18-6.15 (m, 1H), 5.29-5.27 (m, 1H), 4.31-4.09 (m, 4H), 3.86-3.84 (m, 2H), 3.20-3.11 (m, 2H).

EXAMPLE 375

2-Amino-4'-((2-aminoethyl)sulfonyl)-N-(3-aminopropyl)-3'-sulfamoyl-2'-(2H-tetrazol-5-yl)-[1,1'-biphenyl]-3-carboxamide

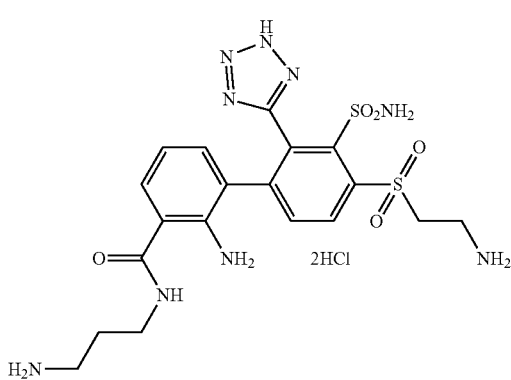 [SMILES: NCCCNC(=O)c1cccc(-c2ccc(S(=O)(=O)CCN)c(S(N)(=O)=O)c2-c2nn[nH]n2)c1N]

Step A: Methyl-2-amino-3'-(N,N-bis(4-methoxybenzyl)sulfamoyl)-4'-((2-((tert-butoxy carbonyl)amino)ethyl)sulfonyl)-2'-(2-(4-methoxybenzyl)-2H-tetrazol-5-yl)-[1,1'-biphenyl]-3-carboxylate To a solution of tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate (4.0 g, 4.35 mmol) in 1,4-dioxane (30 mL) m and water (6 mL) were added Pd(PPh$_3$)$_4$ (0.50 g, 0.44 mmol), methyl 2-amino-3-(4,4,5,5-tetramethyl-1,3,2-dioxaborolan-2-yl) benzoate (1.21 g, 4.35 mmol, prepared as described in *Bioorganic and Medicinal Chemistry Letters*, 2012, 22(9): 3327-3331) and Na$_2$CO$_3$ (0.69 g, 6.53 mmol) at room temperature. The reaction mixture was degassed with nitrogen three times. The reaction mixture was stirred at 80° C. for 16 hours under nitrogen. The resulting mixture was diluted with water (200 mL) and extracted with EA (3×200 mL). The combined organic layers was washed with water (3×200 mL) and brine (3×200 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 942.

Step B: 2-Amino-3'-(N,N-bis(4-methoxybenzyl)sulfamoyl)-4'-((2-((tert-butoxycarbonyl) amino)ethyl)sulfonyl)-2'-(2-(4-methoxybenzyl)-2H-tetrazol-5-yl)-[1,1'-biphenyl]-3-carboxylic acid To a solution of methyl-2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-carboxylate (0.80 g, 0.85 mmol) in THF (3 mL) and MeOH (3 mL) was added 2M aqueous LiOH (8.5 mL, 16.98 mmol) at room temperature. The resulting solution was stirred for 16 h at room temperature. The pH of the solution was adjusted to 4 with aqueous HCl (20%). The resulting mixture was filtered. The filter cake was washed with water (2×10 mL) to afford the title compound, which was used directly in the next step, LCMS [M+1]$^+$: 928.

Step C: Tert-butyl-N-{2-[(4-{2-amino-3-[(3-{[(tert-butoxy)carbonyl]amino}propyl)carbamoyl]phenyl}-2-{bis [(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene)sulfonyl]ethyl}carbamate To a solution of 2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-carboxylic acid (0.20 g, 0.22 mmol) in DMF (2 mL) were added HATU (0.12 g, 0.32 mmol) and tert-butyl (3-aminopropyl)carbamate (0.15 g, 0.86 mmol) and DIEA (0.06 mL, 0.32 mmol) at 0° C. The reaction mixture was stirred at 0° C. for 4 h under nitrogen. The resulting mixture was diluted with water (50 mL) and extracted with EA (3×50 mL). The combined organic layers was washed with brine (3×50 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1084.

Step D: 2-Amino-4'-((2-aminoethyl)sulfonyl)-N-(3-aminopropyl)-3'-sulfamoyl-2'-(2H-tetrazol-5-yl)-[1,1'-biphenyl]-3-carboxamide To a solution of tert-butyl-N-{2-[(4-{2-amino-3-[(3-{[(tert-butoxy)carbonyl]amino}propyl)carbamoyl]phenyl}-2-{bis [(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene)sulfonyl]ethyl}carbamate (0.18 g, 0.17 mmol) in DCM (6 mL) was added TFA (2 mL) at 0° C. The solution was warmed to room temperature and stirred for 1 h. The resulting solution was concentrated under vacuum. The residue was co-evaporated with anisole (3×3 mL) under vacuum and used directly in the next step without further purification. The crude product was added to TFA (4 mL). The solution was stirred at 80° C. for 1 h. The resulting solution was concentrated under vacuum. The crude product was purified by Prep-HPLC with the following conditions: Column: Sunfire Prep C18 OBD Column, 10 μm, 19×250 mm; Mobile Phase A: water with 10 mmol/L NH$_4$HCO$_3$, Mobile Phase B: ACN; Flow rate: 20 mL/min; Gradient: 5% B to 35% B in 8 min; Detector: 254/220 nm. The fractions containing desired product were combined and concentrated under vacuum to afford the title compound: LCMS [M+1-72]$^+$: 524; $^1$H NMR (400 MHz, CD$_3$OD+DCl): δ 8.69 (d, J=8.4 Hz, 1H), 7.99 (d, J=8.4 Hz, 1H), 7.55-7.52 (m, 1H), 6.96-6.93 (m, 1H), 6.77-6.72 (m, 1H), 4.22-4.12 (m, 2H), 3.57-3.45 (m, 4H), 2.99-2.89 (m, 2H), 1.94-1.84 (m, 2H).

EXAMPLE 376

(S)-2-Amino-4'-((2-aminoethyl)sulfonyl)-N-(pyrrolidin-3-yl)-3'-sulfamoyl-2'-(2H-tetrazol-5-yl)-[1,1'-biphenyl]-3-carboxamide

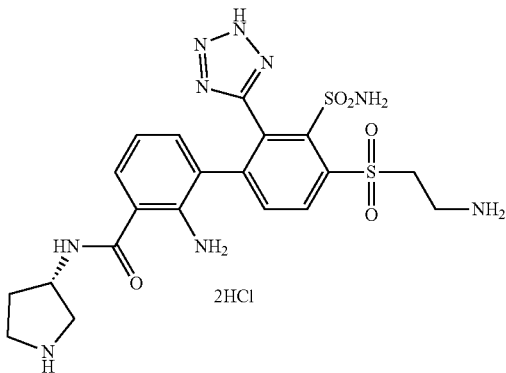 [SMILES: NCCS(=O)(=O)c1ccc(-c2cccc(C(=O)N[C@H]3CCNC3)c2N)c(-c2nn[nH]n2)c1S(N)(=O)=O]

Step A: (S)-tert-butyl-3-(2-amino-3'-(N,N-bis(4-methoxybenzyl)sulfamoyl)-4'-((2-((tert-butoxycarbonyl)amino)ethyl)sulfonyl)-2'-(2-(4-methoxybenzyl-2'H-tetrazol-5-yl)-[1,1'-biphenyl]-3-ylcarboxamido)pyrrolidine-1-carboxylate To a solution of 2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-carboxylic acid (0.20 g, 0.22 mmol) in DMF (2 mL) were added HATU (0.12 g, 0.32 mmol), (S)-tert-butyl 3-aminopyrrolidine-1-carboxylate (0.16 g, 0.86 mmol) and DIEA (0.06 mL, 0.32 mmol) at 0° C. The reaction mixture was degassed with nitrogen three times. The mixture was stirred for 4 hours at RT under nitrogen. The resulting mixture was diluted with water (50 mL) and extracted with EA (3×50 mL). The combined organic layers was washed with water (3×50 mL) and brine (3×50 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1096.

Step B: (S)-2-amino-4'-((2-aminoethyl)sulfonyl)-N-(pyrrolidin-3-yl)-3'-sulfamoyl-2'-(2H-tetrazol-5-yl)-[1,1'-biphenyl]-3-carboxamide A solution of (S)-tert-butyl-3-(2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-ylcarboxamido)pyrrolidine-1-carboxylate (0.12 g, 0.11 mmol) in TFA (3 mL) was stirred at room temperature for 1 h. The resulting solution was concentrated under vacuum. The residue was co-evaporated with anisole (3×3 mL) under vacuum and used directly in the next step without further purification. The crude product was dissolved in TFA (4 mL). The solution was stirred at 80° C. for 1 h. The resulting solution was concentrated under vacuum. The crude product was purified by Prep-HPLC with the following conditions: Column: X Bridge BEH130 Prep C18 OBD Column 19×150 mm, 5 m, 13 nm; Mobile Phase A: waters with 0.05% TFA, Mobile Phase B: ACN; Flow rate: 20 mL/min; Gradient: 5% B to 30% B in 8 min; 254 nm; Retention time: 6.78 min. The fractions containing desired product were combined and concentrated under vacuum to afford the title compound: LCMS [M+1-72]$^+$: 536; $^1$H NMR (300 MHz, CD$_3$OD+DCl): δ 8.73 (d, J=8.1 Hz, 1H), 8.04 (d, J=8.1 Hz, 1H), 7.80-7.78 (m, 1H), 7.09-7.01 (m, 2H), 4.65-4.61 (m, 1H), 4.33-4.26 (m, 2H), 3.65-3.44 (m, 4H), 3.40-3.33 (m, 2H), 2.47-2.38 (m, 1H), 2.26-2.18 (m, 1H).

EXAMPLES 377-378 below were prepared in an analogous fashion to EXAMPLE 376 using 2-amino-3'-(N,N-bis(4-methoxybenzyl)sulfamoyl)-4'-((2-((tert-butoxycarbonyl)amino)ethyl)sulfonyl)-2'-(2-(4-methoxybenzyl)-2H-tetrazol-5-yl)-[1,1'-biphenyl]-3-carboxylic acid and the Boc protected amines which are commercially available.

| EX. No. | Structure | Chemical Name | MW | LC/MS [M + H] |
|---|---|---|---|---|
| 377 | 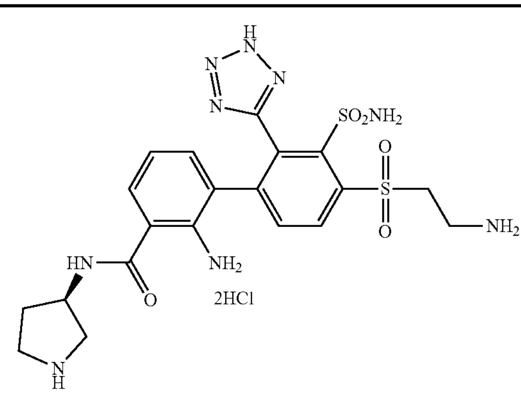 | (R)-2-amino-4'-((2-aminoethyl)sulfonyl)-N-(pyrrolidin-3-yl)-3'-sulfamoyl-2'-(2H-tetrazol-5-yl)-[1,1'-biphenyl]-3-carboxamide | 535 | 536 |

| EX. No. | Structure | Chemical Name | MW | LC/MS [M + H] |
|---|---|---|---|---|
| 378 | 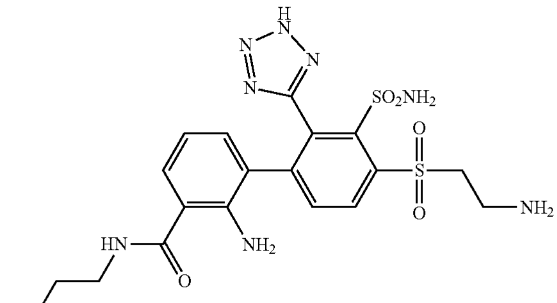 | 2-amino-N-(2-aminoethyl)-4'-((2-aminoethyl)sulfonyl)-3'-sulfamoyl-2'-(2H-tetrazol-5-yl)-[1,1'-biphenyl]-3-carboxamide | 509 | 510 |

EXAMPLE 379

(R)-6-((3-amino-2-hydroxypropyl)sulfonyl)-3-(2-amino-6-iodo-1H-benzo[d]imidazol-4-yl)-2-(2H-tetrazol-5-yl)benzenesulfonamide

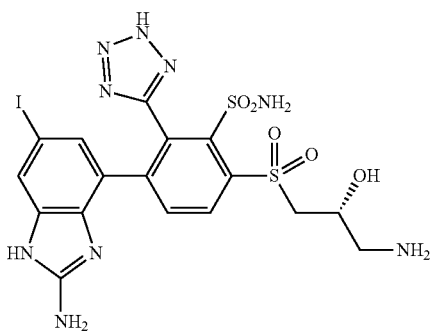 [SMILES: NC[C@@H](O)CS(=O)(=O)c1ccc(-c2cc(I)cc3[nH]c(N)nc23)c(-c2nn[nH]n2)c1S(N)(=O)=O]

Step A: (R)-tert-butyl(3-((4-(2-amino-1H-benzo[d]imidazol-4-yl)-2-(N,N-bis(4-methoxy benzyl)sulfamoyl)-3-(2-(4-methoxybenzyl)-2H-tetrazol-5-yl)phenyl)sulfonyl)-2-hydroxypropyl)carbamate To a solution of (R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate (11 g, 12 mmol) in 1,4-dioxane (150 mL) and water (30 mL) were added (2-amino-1H-benzo[d]imidazol-4-yl)boronic acid (5.13 g, 30 mmol), Na$_2$CO$_3$ (3.69 g, 35 mmol) and Pd(dppf)Cl$_2$ adduct CH$_2$Cl$_2$ (1.9 g, 2 mmol). The reaction mixture was degassed with nitrogen three times. The reaction mixture was stirred at 80° C. for 12 hours under nitrogen. The resulting mixture was diluted with water (500 mL) and extracted with EA (3×500 mL). The combined organic layers was washed with brine (2×400 mL), dried over anhydrous Na$_2$SO$_4$ and filtered. The residue was purified by silica gel column chromatography, eluted with 10% MeOH in DCM. The fractions containing desired product were combined and concentrated under vacuum to afford the title compound: LCMS [M+1]$^+$: 954.

Step B: (R)-3-(2-amino-1H-benzo[d]imidazol-4-yl)-6-((3-amino-2-hydroxypropyl)sulfonyl)-2-(2H-tetrazol-5-yl)benzenesulfonamide To a solution of (R)-tert-butyl(3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonyl)-2-hydroxypropyl)carbamate (7.2 g, 7.56 mmol) in DCM (10 mL) was added TFA (5 mL) at 0° C. The solution was warmed to room temperature and stirred for 0.5 h. The resulting mixture was concentrated under vacuum. The residue was co-evaporated with anisole (3×10 mL) under vacuum and used directly in the next step. The crude product was dissolved in TFA (8 mL). The solution was stirred at 80° C. for 1 h. The resulting mixture was concentrated under vacuum. The crude product was purified by Prep-HPLC with the following conditions: Column: X Bridge BEH130 Prep C18 OBD Column 19×150 mm, 5 μm, 13 nm; Mobile Phase A: water with 10 mmol/L NH$_4$HCO$_3$, Mobile Phase B: ACN; Flow rate: 20 mL/min; Gradient: 5% B to 17% B in 7 min; 254 nm; Retention time: 5.80 min. The fractions containing desired product were combined and concentrated under vacuum to afford the title compound: LCMS [M+1]$^+$: 494; $^1$H NMR (300 MHz, DMSO-d$_6$): δ 8.20 (d, J=7.2 Hz, 1H), 7.97 (d, J=8.4 Hz, 1H), 7.65 (brs, 2H), 6.87 (d, J=7.2 Hz, 1H), 6.46-6.42 (m, 1H), 6.10 (brs, 2H), 6.08-6.03 (m, 1H), 4.25-4.19 (m, 1H), 4.10-3.82 (m, 2H), 3.09-2.91 (m, 1H), 2.89-2.75 (m, 1H).

Step C: (R)-6-((3-amino-2-hydroxypropyl)sulfonyl)-3-(2-amino-6-iodo-1H-benzo[d]imidazol-4-yl)-2-(2H-tetrazol-5-yl)benzenesulfonamide To a solution of (R)-3-(2-amino-1H-benzo[d]imidazol-4-yl)-6-((3-amino-2-hydroxypropyl)sulfonyl)-2-(2H-tetrazol-5-yl)benzenesulfonamide (0.17 g, 0.34 mmol) in TFA (4 mL) was added NIS (0.12 g, 0.55 mmol) at 0° C. The reaction mixture was stirred at room temperature for 5 hours. The reaction mixture was concentrated under vacuum at room temperature. The residue was purified by Column: X Bridge C18 OBD Prep Column 100 Å, 10 μm, 19 mm×250 mm; Mobile Phase A: waters with 10 mmol/L NH$_4$HCO$_3$, Mobile Phase B: ACN; Flow rate: 20 mL/min; Gradient: 10% B to 20% B in 8 min; Detector: 254/220 nm; Retention time: 6.23 min. The collected fractions containing desired product were combined and concentrated under vacuum to afford the title compound: LCMS [M+1]$^+$: 620; $^1$H NMR (400 MHz, DMSO-d$_6$): δ 10.85 (brs, 1H), 8.26 (d, J=8.4 Hz, 1H), 7.97 (d, J=8.8 Hz, 1H), 7.60 (brs, 2H), 7.22 (s, 1H), 6.45-6.41 (s, 1H), 6.40 (brs, 2H), 5.85 (brs, 1H), 4.42-4.29 (m, 1H), 4.15-4.11 (m, 1H), 4.01-3.97 (m, 1H), 3.09-3.07 (m, 1H), 2.92-2.81 (m, 1H).

Biological Assays

Enzyme Activity: Determination of IC$_{50}$

The Class B enzyme activities were measured in the presence of the test inhibitor in a fluorescence assay against a commercially available substrate consisting of a cephalosporin core linking 7-hydroxycoumarin to fluorescein (CCF2-FA). The enzyme (NDM-1, IMP-1 or VIM-1; for a review, see: Meine, M.-R.; Llarrull, L. I.; Vila, A. J. *Antibiotics*, 2014, 3, 285-316) and the substrate were diluted in 100 mM KH$_2$PO$_4$ buffer (pH 7) containing 0.005% Tween-20 and 10 μM ZnSO$_4$. In the assay, the final concentration of enzyme was 1 pM, 2 pM and 30 pM for NDM-1, IMP-1 and VIM-1, respectively, and the final concentration of CCF2-FA was 1.25 μM. The test inhibitor was dissolved in dimethylsulfoxide and diluted 1:50 in the assay, resulting in a final concentration range of 20 μM to 0.00063 μM. In a 384-well microplate, the test inhibitor was incubated with the metallo-β-lactamase enzyme and the substrate for 2 hours at 25° C. Fluorescence at 460 nm following excitation at 405 nm was measured. The IC$_{50}$ value was determined from semi-logarithmic plots of enzyme inhibition versus inhibitor concentration, with a curve generated using a 4-parameter fit.

Representative compounds of the present invention exhibit inhibition of Class B β-lactamases in this assay. For example, the compounds of Examples 1-379 were tested in this assay and were found to have the IC$_{50}$ values shown in Table 1.

Antibiotic Potentiation Activity: Determination of Synergistic Concentration

The concentrations of metallo-β-lactamase inhibitors required to restore the susceptibility of various strains of bacteria to inactive concentrations of antibiotics were determined in an assay that assessed bacterial growth by measuring the optical density at 600 nm (OD$_{600}$). The bacterial strains tested included the clinical strains *Escherichia coli* expressing NDM-1 (CLB30005, CLB30016), *Serratia marcescens* expressing IMP-1 (CL5741), and *Klebsiella pneumoniae* expressing VIM-1 (IHMA599644). Inhibitor activity was measured in the presence and absence of imipenem in a 384-well microplate.

The clinical strains CLB30016, CL5741 and IHMA599644 were grown on trypticase soy agar containing 5% sheep's blood. The bacteria on agar plates were incubated at 35° C. with humidity overnight. The following day, individual colonies from each clinical strain were picked and resuspended in 5 ml saline to attain an OD$_{600}$ of 0.14, 0.11, 0.15 and 0.13, for CLB30016, CL5741 and IHMA599644, respectively. These were further diluted 1:100 into 1.1× CAMHB and used to inoculate the test wells as described below.

Imipenem in 10 mM 3-(N-morpholino)propanesulfonic acid (MOPS, pH 7) was stored in single use aliquots at −80° C. Test inhibitors were dissolved in dimethylsulfoxide and diluted 1:50 in the assay, resulting in a final concentration range of 200 μM to 0.195 μM. On the day of the assay, 4 μl of antibiotic was added to 45 ul of bacteria followed by 1 μl of test compound and mixed by pipetting and with an orbital shaker. The concentration of antibiotic used in the assay was 1 μg/ml. Microplates were covered and incubated at 35° C. for 22 hours to 24 hours. At the end of the incubation, absorbance was determined using a spectrophotometer. The synergistic concentration of MBLI was determined by identifying the lowest concentration of test compound in the presence of a given concentration of antibiotic that was required to inhibit 95% of the growth of the bacteria. The results for Examples 1-380 are reported in Table 1, expressed as the concentration of compound that potentiated the action of antibiotic (imipenem) affecting 95% inhibition of bacterial growth (MITC95).

Representative compounds of the present invention do not have any or have minimal intrinsic antibacterial activity but display a synergistic effect when used in combination with a beta-lactam antibiotic. For example, in general, the compounds of Examples 1-379 were determined to restore susceptibility to imipenem for one or more of the test organisms at concentrations of 100 μM or less.

TABLE 1

Inhibition of metallo-β-lactamases (IMP-1, NDM-1, VIM-1) and antibiotic potentiation vs. MBL-expressing bacteria by Examples 1-379.

| Ex. No. | IMP-1 IC50 nM | NDM-1 IC50 nM | VIM-1 IC50 nM | *Serratia marcescens* expressing IMP-1 (CL5741) MITC95 μM | *Escherichia coli* expressing NDM-1 (CLB30016) MITC95 μM | *Klebsiella pneumoniae* expressing VIM-1 (IHMA599644) MITC95 μM |
|---|---|---|---|---|---|---|
| 1 | 422.4 | 20.77 | 140.7 | 6.25 | 0.3906 | 6.25 |
| 2 | 75.76 | 2.242 | 73.66 | 1.781 | 0.5 | 6.25 |
| 3 | 108.7 | 3.272 | 79.49 | 6.25 | 0.125 | 25 |
| 4 | 15.12 | 11.48 | 53.49 | 1.563 | 0.7813 | 3.125 |
| 5 | 6.884 | 1.982 | 2.022 | 3.125 | 3.125 | 3.125 |
| 6 | 0.2116 | 0.307 | 0.1953 | 1.563 | 0.7813 | 1.563 |
| 7 | 50.37 | 7.553 | 25.59 | 3.125 | 0.3906 | 6.25 |
| 8 | 37.7 | 2.615 | 6.918 | 12.5 | 3.125 | 12.5 |
| 9 | 0.9132 | 0.3319 | 0.3751 | 1.563 | 0.7813 | 3.125 |
| 10 | 27.31 | 3.196 | 6.458 | 6.25 | 6.25 | 6.25 |
| 11 | 41.33 | 1.148 | 1.856 | 0.7813 | 0.3906 | 0.3906 |
| 12 | 130.3 | 4.059 | 4.36 | 6.25 | 6.25 | 6.25 |
| 13 | 50.75 | 0.6192 | 6.61 | 3.125 | 0.3906 | 1.563 |
| 14 | 23.87 | 0.2923 | 0.8681 | 3.125 | 6.25 | 3.125 |
| 15 | 0.6125 | 0.08973 | 0.2065 | 0.3906 | 0.3906 | 0.7813 |
| 16 | 2.368 | 0.4902 | 0.6531 | 0.7813 | 0.3906 | 3.125 |
| 17 | 0.9593 | 0.2067 | 0.7068 | 3.125 | 3.125 | 6.25 |
| 18 | 0.2271 | 0.4416 | 0.3613 | 3.125 | 1.563 | 3.125 |

TABLE 1-continued

Inhibition of metallo-β-lactamases (IMP-1, NDM-1, VIM-1) and antibiotic potentiation vs. MBL-expressing bacteria by Examples 1-379.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 19 | 2.496 | 0.1085 | 0.1528 | 1.563 | 0.7813 | 1.563 |
| 20 | 1.192 | 0.2911 | 0.168 | 1.563 | 3.125 | 3.125 |
| 21 | 0.6394 | 0.1499 | 0.4498 | 3.125 | 1.563 | 3.125 |
| 22 | 0.4316 | 0.164 | 0.2133 | 0.7813 | 0.3906 | 1.563 |
| 23 | 0.3524 | 0.1228 | 0.09862 | 0.7813 | 0.3906 | 0.7813 |
| 24 | 0.5282 | 0.382 | 0.2178 | 3.125 | 3.125 | 3.125 |
| 25 | 0.8618 | 0.5322 | 0.4411 | 0.6719 | 0.5156 | 2.135 |
| 26 | 0.6603 | 0.02857 | 0.16 | 3.125 | 1.563 | 3.125 |
| 27 | 1.748 | 0.185 | 0.33 | 3.125 | 6.25 | 3.125 |
| 28 | 1.334 | 0.0489 | 0.1725 | 3.125 | 1.563 | 3.125 |
| 29 | 0.3132 | 0.2402 | 0.3277 | 1.563 | 1.563 | 3.125 |
| 30 | 0.5847 | 0.0846 | 0.409 | 1.563 | 0.7813 | 3.125 |
| 31 | 1.373 | 0.3365 | 0.3729 | 1.563 | 1.563 | 3.125 |
| 32 | 0.1379 | 0.03308 | 0.1064 | 0.7813 | 0.3906 | 1.563 |
| 33 | 0.2961 | 0.02391 | 0.1196 | 1.563 | 1.563 | 3.125 |
| 34 | 0.2288 | 0.07135 | 0.1749 | 0.7813 | 0.7813 | 1.563 |
| 35 | 0.5029 | 0.06953 | 0.2433 | 1.563 | 1.563 | 6.25 |
| 36 | 0.3573 | 0.1042 | 0.2825 | 0.7813 | 3.125 | 1.563 |
| 37 | 1.904 | 0.08102 | 0.3479 | 3.125 | 25 | 6.25 |
| 38 | 0.1263 | 0.0286 | 0.3412 | 12.5 | 31.25 | 25 |
| 39 | 0.2759 | 0.03031 | 0.1289 | 3.125 | 1.563 | 3.125 |
| 40 | 1.987 | 0.4086 | 0.3479 | 0.5573 | 0.4453 | 1.375 |
| 41 | 3.509 | 0.5355 | 0.1707 | 1.563 | 1.563 | 1.563 |
| 42 | 1.188 | 0.1766 | 0.3062 | 1.563 | 0.5859 | 1.563 |
| 43 | 0.8284 | 0.08347 | 0.2575 | 0.7982 | 0.2902 | 1.151 |
| 44 | 1.979 | 0.4465 | 0.2988 | 6.25 | 6.25 | 25 |
| 45 | 1.685 | 0.2899 | 0.135 | 6.25 | 25 | 6.25 |
| 46 | 2.147 | 0.445 | 0.3783 | 25 | 6.25 | 25 |
| 47 | 0.8463 | 0.2137 | 0.3613 | 3.125 | 1.563 | 3.125 |
| 48 | 2.296 | 0.3915 | 0.4041 | 3.125 | 1.563 | 3.125 |
| 49 | 1.373 | 0.2778 | 0.3076 | 6.25 | 6.25 | 6.25 |
| 50 | 1.437 | 0.2425 | 0.5852 | 3.125 | 3.125 | 6.25 |
| 51 | 1.315 | 0.1451 | 0.4265 | 0.7813 | 0.3906 | 1.563 |
| 52 | 1.333 | 0.2215 | 0.6277 | 1.563 | 0.3906 | 3.125 |
| 53 | 6.116 | 0.4583 | 1.543 | 6.25 | 12.5 | 12.5 |
| 54 | 2.383 | 0.1779 | 0.4352 | 6.25 | 6.25 | 12.5 |
| 55 | 1.423 | 0.08175 | 0.3115 | 3.125 | 3.125 | 6.25 |
| 56 | 2.824 | 0.1799 | 0.3501 | 3.125 | 6.25 | 6.25 |
| 57 | 1.979 | 0.2641 | 0.4458 | 6.25 | 6.25 | 12.5 |
| 58 | 0.5967 | 0.3784 | 0.3416 | 1.563 | 0.7813 | 3.125 |
| 59 | 1.435 | 0.1306 | 0.1866 | 3.125 | 3.125 | 3.125 |
| 60 | 2.349 | 0.8111 | 0.4081 | 3.125 | 1.563 | 6.25 |
| 61 | 2.219 | 0.2542 | 0.6775 | 6.25 | 12.5 | 25 |
| 62 | 2.629 | 0.3455 | 0.3962 | 1.563 | 0.3906 | 1.563 |
| 63 | 125.1 | 5.906 | 30.55 | 3.125 | 1 | 3.125 |
| 64 | 0.3586 | 1.06 | 0.3393 | 1.563 | 1.563 | 3.125 |
| 65 | 2.501 | 0.7844 | 0.627 | 6.25 | 1.563 | 12.5 |
| 66 | 9.674 | 0.5908 | 0.5692 | 6.25 | 3.125 | 12.5 |
| 67 | 1.317 | 0.3756 | 0.3327 | 3.125 | 1.563 | 3.125 |
| 68 | 0.3557 | 0.07087 | 0.2555 | 6.25 | 6.25 | 12.5 |
| 69 | 2.769 | 1.253 | 0.485 | 0.4453 | 0.25 | 0.8906 |
| 70 | 0.7963 | 0.2511 | 0.3703 | 0.6406 | 0.25 | 0.8906 |
| 71 | 0.1292 | 0.1148 | 0.315 | 0.7813 | 0.3906 | 1.563 |
| 72 | 0.3219 | 0.1532 | 0.286 | 1.563 | 0.7813 | 1.563 |
| 73 | 0.2141 | 0.1089 | 0.2414 | 3.125 | 0.7813 | 3.125 |
| 74 | 0.9891 | 0.09601 | 0.1723 | 1.563 | 0.7813 | 3.125 |
| 75 | 0.4333 | 0.4998 | 0.2829 | 1.563 | 1.563 | 1.563 |
| 76 | 0.2579 | 0.1481 | 0.2404 | 0.7813 | 0.7813 | 1.563 |
| 77 | 1.129 | 1.046 | 0.3845 | 1.563 | 0.7813 | 1.563 |
| 78 | 0.4412 | 0.05759 | 0.1358 | 1.172 | 0.7813 | 2.344 |
| 79 | 0.241 | 0.3537 | 0.3269 | 0.8906 | 0.25 | 1.281 |
| 80 | 0.08501 | 0.05082 | 0.1095 | 0.7813 | 1.172 | 1.563 |
| 81 | 0.2663 | 0.2898 | 0.3561 | 1.563 | 0.7813 | 3.125 |
| 82 | 0.1938 | 0.08706 | 0.131 | 1.563 | 1.563 | 3.125 |
| 83 | 0.3411 | 0.1171 | 0.2633 | 6.25 | 6.25 | 12.5 |
| 84 | 0.1455 | 0.07808 | 0.1396 | 1.563 | 1.563 | 3.125 |
| 85 | 0.1437 | 0.05112 | 0.08585 | 0.7813 | 0.3906 | 1.563 |
| 86 | 0.8692 | 0.2953 | 0.1415 | 0.7813 | 0.7813 | 0.7813 |
| 87 | 0.562 | 0.4755 | 0.1329 | 0.7813 | 0.7813 | 0.7813 |
| 88 | 0.1444 | 0.05215 | 0.158 | 6.25 | 1.563 | 12.5 |
| 89 | 0.6009 | 0.277 | 0.1522 | 1.563 | 1.563 | 3.125 |

TABLE 1-continued

Inhibition of metallo-β-lactamases (IMP-1, NDM-1, VIM-1) and antibiotic potentiation vs. MBL-expressing bacteria by Examples 1-379.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 90 | 0.09947 | 0.07456 | 0.1463 | 1.563 | 0.7813 | 1.563 |
| 91 | 0.3863 | 0.1886 | 0.2391 | 1.563 | 1.172 | 2.344 |
| 92 | 0.6122 | 0.1409 | 0.2232 | 0.6406 | 0.2969 | 0.8542 |
| 93 | 0.1299 | 0.07321 | 0.1298 | 0.7813 | 1.172 | 3.125 |
| 94 | 0.5042 | 0.2058 | 0.2222 | 1.563 | 0.7813 | 3.125 |
| 95 | 0.2209 | 0.1378 | 0.2929 | 1.563 | 1.563 | 6.25 |
| 96 | 0.2647 | 0.1217 | 0.1849 | 1.563 | 1.563 | 3.125 |
| 97 | 0.1709 | 0.06447 | 0.2489 | 1.563 | 0.7813 | 1.563 |
| 98 | 1.974 | 0.4 | 0.2407 | 3.125 | 3.125 | 3.125 |
| 99 | 13.67 | 3.945 | 0.5355 | 12.5 | 6.25 | 6.25 |
| 100 | 1.609 | 0.3578 | 0.3309 | 3.125 | 6.25 | 3.125 |
| 101 | 1.479 | 0.9049 | 0.3988 | 3.125 | 3.125 | 6.25 |
| 102 | 0.9095 | 0.4066 | 0.4567 | 3.125 | 3.125 | 3.125 |
| 103 | 1.854 | 0.9538 | 0.5814 | 3.125 | 12.5 | 6.25 |
| 104 | 3.527 | 2.091 | 0.6989 | 6.25 | 3.125 | 3.125 |
| 105 | 1.695 | 1.063 | 0.7592 | 1.563 | 3.125 | 3.125 |
| 106 | 3.267 | 1.507 | 1.593 | 3.125 | 12.5 | 6.25 |
| 107 | 120.7 | 50.3 | 28.34 | 6.25 | 1.563 | 3.125 |
| 108 | 3.713 | 1.062 | 0.6123 | 3.125 | 6.25 | 6.25 |
| 109 | 9.131 | 3.932 | 1.437 | 1.563 | 0.7813 | 3.125 |
| 110 | 13.15 | 4.791 | 3.468 | 1.563 | 1.563 | 3.125 |
| 111 | 4.423 | 1.384 | 0.9596 | 3.125 | 3.125 | 6.25 |
| 112 | 8.682 | 2.512 | 1.794 | 3.125 | 3.125 | 6.25 |
| 113 | 6.061 | 0.1368 | 0.1642 | 3.125 | 1.563 | 6.25 |
| 114 | 0.2605 | 0.1497 | 0.1157 | 0.7813 | 0.3906 | 1.563 |
| 115 | 0.7931 | 0.2365 | 0.2761 | 3.125 | 3.125 | 3.125 |
| 116 | 0.7223 | 0.1987 | 0.1767 | 3.125 | 1.563 | 3.125 |
| 117 | 1.411 | 0.9297 | 0.4314 | 3.125 | 6.25 | 6.25 |
| 118 | 1.42 | 0.1446 | 0.3881 | 6.25 | 3.125 | 6.25 |
| 119 | 5.736 | 1.801 | 0.5064 | 6.25 | 6.25 | 6.25 |
| 120 | 0.5526 | 0.7555 | 1.42 | 3.125 | 3.125 | 6.25 |
| 121 | 3.568 | 0.7404 | 1.442 | 3.125 | 0.7813 | 6.25 |
| 122 | 0.5697 | 0.1546 | 0.3236 | 3.125 | 3.125 | 6.25 |
| 123 | 1.136 | 0.1683 | 0.2152 | 3.125 | 1.563 | 3.125 |
| 124 | 6.097 | 1.495 | 4.949 | 6.25 | 3.125 | 12.5 |
| 125 | 5.232 | 4.023 | 2.535 | 6.25 | 6.25 | 6.25 |
| 126 | 0.7146 | 0.4277 | 0.4773 | 6.25 | 3.125 | 6.25 |
| 127 | 3.013 | 0.4295 | 0.4279 | 3.125 | 0.7813 | 3.125 |
| 128 | 0.5237 | 0.1337 | 0.3141 | 3.125 | 1.563 | 3.125 |
| 129 | 2.633 | 0.6472 | 1.238 | 6.25 | 6.25 | 6.25 |
| 130 | 1.692 | 0.2296 | 0.2477 | 6.25 | 1.563 | 6.25 |
| 131 | 0.5101 | 0.345 | 0.1303 | 3.125 | 0.7813 | 3.125 |
| 132 | 1.49 | 3.498 | 1.547 | 1.563 | 0.7813 | 3.125 |
| 133 | 29.42 | 15.56 | 0.9678 | 6.25 | 6.25 | 6.25 |
| 134 | 2.471 | 2.655 | 0.9908 | 3.125 | 6.25 | 6.25 |
| 135 | 1.65 | 0.2647 | 1.216 | 3.125 | 0.7813 | 6.25 |
| 136 | 1.715 | 2.143 | 1.188 | 1.563 | 1.563 | 3.125 |
| 137 | 32.62 | 16.84 | 23.53 | 1.563 | 0.7813 | 3.125 |
| 138 | 1.282 | 0.8004 | 0.4102 | 3.125 | 1.563 | 6.25 |
| 139 | 3.317 | 3.96 | 2.038 | 3.125 | 1.563 | 6.25 |
| 140 | 0.4883 | 0.8436 | 0.2227 | 1.563 | 1.563 | 1.563 |
| 141 | 4.886 | 4.323 | 1.009 | 0.8906 | 0.25 | 1.781 |
| 142 | 0.517 | 0.5185 | 0.1535 | 1.563 | 1.563 | 3.125 |
| 143 | 8.828 | 11.25 | 2.021 | 3.125 | 1.563 | 3.125 |
| 144 | 5.589 | 7.205 | 3.04 | 3.125 | 0.7813 | 3.125 |
| 145 | 4.842 | 4.308 | 1.25 | 3.125 | 1.563 | 6.25 |
| 146 | 44.36 | 20.59 | 1.322 | 3.125 | 0.7813 | 6.25 |
| 147 | 4.096 | 3.117 | 0.519 | 6.25 | 6.25 | 6.25 |
| 148 | 0.9832 | 0.6084 | 0.4336 | 3.125 | 3.125 | 3.125 |
| 149 | 0.8561 | 0.5344 | 0.1851 | 3.125 | 1.563 | 3.125 |
| 150 | 0.9309 | 0.4973 | 0.4404 | 3.125 | 3.125 | 3.125 |
| 151 | 0.1912 | 0.2705 | 0.5438 | 12.5 | 12.5 | 25 |
| 152 | 4.787 | 5.826 | 2.006 | 6.25 | 3.125 | 6.25 |
| 153 | 0.4573 | 0.5931 | 0.3087 | 3.125 | 1.563 | 3.125 |
| 154 | 0.6763 | 1.129 | 0.4301 | 3.125 | 3.125 | 6.25 |
| 155 | 0.2255 | 0.8141 | 0.289 | 1.563 | 0.7813 | 1.563 |
| 156 | 0.9807 | 1.076 | 0.7428 | 1.563 | 0.7813 | 6.25 |
| 157 | 1.889 | 1.942 | 0.2947 | 1.563 | 1.563 | 3.125 |
| 158 | 6.269 | 16.64 | 7.082 | 12.5 | 12.5 | 25 |
| 159 | 0.4866 | 1.099 | 0.2644 | 3.125 | 1.563 | 3.125 |
| 160 | 0.568 | 1.022 | 0.3746 | 3.125 | 1.563 | 6.25 |

TABLE 1-continued

Inhibition of metallo-β-lactamases (IMP-1, NDM-1, VIM-1) and antibiotic potentiation vs. MBL-expressing bacteria by Examples 1-379.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 161 | 1.691 | 3.474 | 3.037 | 6.25 | 6.25 | 12.5 |
| 162 | 2.815 | 2.782 | 0.3203 | 3.125 | 3.125 | 6.25 |
| 163 | 1.22 | 0.9798 | 0.1198 | 3.125 | 1.563 | 3.125 |
| 164 | 0.2328 | 0.1468 | 0.1434 | 3.125 | 6.25 | 6.25 |
| 165 | 1.604 | 2.48 | 0.5711 | 3.125 | 3.125 | 6.25 |
| 166 | 1.512 | 2.794 | 0.3265 | 3.125 | 1.563 | 6.25 |
| 167 | 1.073 | 0.8818 | 0.3427 | 3.125 | 6.25 | 3.125 |
| 168 | 2.02 | 2.503 | 0.5146 | 3.125 | 1.563 | 6.25 |
| 169 | 5.274 | 5.995 | 1.028 | 3.125 | 0.7813 | 6.25 |
| 170 | 2.865 | 3.48 | 1.007 | 0.7813 | 0.3906 | 3.125 |
| 171 | 1.025 | 0.3064 | 0.2719 | 3.125 | 1.563 | 6.25 |
| 172 | 4.901 | 2.983 | 0.1932 | 1.281 | 0.25 | 3.125 |
| 173 | 0.1603 | 0.3383 | 0.2636 | 0.8906 | 0.25 | 0.8906 |
| 174 | 0.2203 | 0.3921 | 0.1403 | 0.7813 | 0.3906 | 1.563 |
| 175 | 2.198 | 0.1492 | 0.4782 | 1.563 | 0.7813 | 1.563 |
| 176 | 1.088 | 0.2497 | 0.8309 | 0.7813 | 0.7813 | 1.563 |
| 177 | 1.351 | 0.2638 | 0.2933 | 0.7813 | 0.7813 | 1.563 |
| 178 | 0.9904 | 0.2753 | 0.6603 | 0.7813 | 0.3906 | 1.563 |
| 179 | 0.1346 | 0.1061 | 0.3218 | 1.563 | 0.7813 | 1.563 |
| 180 | 0.2603 | 0.08325 | 0.1955 | 1.563 | 3.125 | 3.125 |
| 181 | 0.8074 | 0.1491 | 0.4197 | 0.6875 | 0.3203 | 0.8542 |
| 182 | 0.9793 | 0.1537 | 0.2099 | 0.6406 | 0.25 | 0.8906 |
| 183 | 0.1574 | 0.1218 | 0.2936 | 1.563 | 0.7813 | 1.563 |
| 184 | 0.243 | 0.09248 | 0.2618 | 0.7813 | 0.7813 | 1.563 |
| 185 | 0.4656 | 0.6572 | 0.5496 | 1.563 | 0.7813 | 3.125 |
| 186 | 0.5408 | 0.2465 | 0.2276 | 1.563 | 1.563 | 1.563 |
| 187 | 0.07567 | 0.0691 | 0.1585 | 0.7813 | 0.7813 | 1.563 |
| 188 | 0.109 | 0.04354 | 0.1131 | 0.7813 | 1.563 | 1.563 |
| 189 | 0.3321 | 0.2186 | 0.4195 | 1.563 | 1.563 | 1.563 |
| 190 | 0.3525 | 0.1135 | 0.1689 | 1.563 | 1.563 | 3.125 |
| 191 | 0.2104 | 0.436 | 0.298 | 3.125 | 3.125 | 6.25 |
| 192 | 0.5523 | 1.004 | 0.1943 | 1.563 | 0.7813 | 3.125 |
| 193 | 0.09413 | 0.1365 | 0.1064 | 1.563 | 3.125 | 6.25 |
| 194 | 0.1537 | 0.09084 | 0.2084 | 0.7813 | 0.7813 | 1.563 |
| 195 | 0.2505 | 0.2603 | 0.1551 | 0.7813 | 0.3906 | 1.563 |
| 196 | 1.545 | 0.3153 | 0.2334 | 1.563 | 0.7813 | 1.563 |
| 197 | 0.5541 | 0.5562 | 0.2624 | 1.563 | 0.7813 | 3.125 |
| 198 | 0.3737 | 0.2385 | 0.2055 | 1.563 | 0.7813 | 1.563 |
| 199 | 1.836 | 0.1973 | 0.646 | 12.5 | 6.25 | 25 |
| 200 | 13.7 | 5.652 | 21.57 | 25 | 25 | 100 |
| 201 | 0.1531 | 0.09563 | 0.176 | 1.563 | 0.7813 | 3.125 |
| 202 | 0.8585 | 2.918 | 1.098 | 3.125 | 1.563 | 3.125 |
| 203 | 22.95 | 11.24 | 0.5906 | 1.563 | 3.125 | 1.563 |
| 204 | 37.5 | 16.22 | 1.04 | 1.563 | 0.7813 | 1.563 |
| 205 | 82.49 | 44.62 | 6.639 | 3.125 | 1.563 | 3.125 |
| 206 | 23.52 | 20.27 | 0.857 | 3.125 | 6.25 | 3.125 |
| 207 | 24.59 | 15.95 | 0.7102 | 3.125 | 2.344 | 3.125 |
| 208 | 123.7 | 20.55 | 18.63 | 3.125 | 1.563 | 6.25 |
| 209 | 65.26 | 16.42 | 52.12 | 6.25 | 3.125 | 25 |
| 210 | 7.758 | 32.16 | 0.5656 | 1.563 | 3.125 | 3.125 |
| 211 | 6.315 | 24.33 | 0.7848 | 6.25 | 12.5 | 25 |
| 212 | 30.24 | 11.32 | 0.8642 | 1.563 | 0.7813 | 1.563 |
| 213 | 68.27 | 12.91 | 7.039 | 1.563 | 1.563 | 3.125 |
| 214 | 3.321 | 0.1392 | 0.2206 | 3.125 | 3.125 | 6.25 |
| 215 | 2.188 | 0.2388 | 0.2978 | 3.125 | 3.125 | 6.25 |
| 216 | 1.661 | 0.1015 | 0.1514 | 3.125 | 12.5 | 6.25 |
| 217 | 3.807 | 1.492 | 0.3127 | 3.125 | 6.25 | 6.25 |
| 218 | 3.554 | 1.752 | 2.228 | 1.563 | 0.3906 | 3.125 |
| 219 | 5.655 | 0.6469 | 0.5204 | 0.6406 | 0.125 | 1.281 |
| 220 | 14.88 | 0.9014 | 0.3366 | 12.5 | 6.25 | 12.5 |
| 221 | 43.97 | 5.131 | 6.949 | 12.5 | 6.25 | 12.5 |
| 222 | 4.298 | 1.488 | 2.45 | 3.125 | 3.125 | 3.125 |
| 223 | 10.22 | 2.511 | 3.159 | 3.125 | 0.7813 | 6.25 |
| 224 | 2.581 | 0.6181 | 1.292 | 3.125 | 0.7813 | 3.125 |
| 225 | 1.965 | 0.1635 | 0.2285 | 1.563 | 1.563 | 3.125 |
| 226 | 35.68 | 15.05 | 48.5 | 3.125 | 1.563 | 6.25 |
| 227 | 5.902 | 1.946 | 1.177 | 6.25 | 3.125 | 6.25 |
| 228 | 0.5211 | 0.9851 | 0.3142 | 3.125 | 1.563 | 3.125 |
| 229 | 1.735 | 0.1389 | 0.4741 | 6.25 | 6.25 | 12.5 |
| 230 | 0.4363 | 0.1101 | 0.3562 | 6.25 | 6.25 | 25 |
| 231 | 0.7172 | 0.1021 | 0.5579 | 6.25 | 6.25 | 12.5 |

TABLE 1-continued

Inhibition of metallo-β-lactamases (IMP-1, NDM-1, VIM-1) and antibiotic potentiation vs. MBL-expressing bacteria by Examples 1-379.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 232 | 0.5855 | 0.5831 | 0.5387 | 3.125 | 6.25 | 12.5 |
| 233 | 0.2032 | 0.03239 | 0.1133 | 3.125 | 3.125 | 12.5 |
| 234 | 4.366 | 15.65 | 13.92 | 3.125 | 3.125 | 12.5 |
| 235 | 23.61 | 31.89 | 8.183 | 12.5 | 12.5 | 50 |
| 236 | 0.1035 | 2.118 | 0.1267 | 3.125 | 3.125 | 3.125 |
| 237 | 0.6302 | 5.808 | 0.7545 | 1.563 | 0.3906 | 6.25 |
| 238 | 0.3325 | 0.8615 | 0.2009 | 3.125 | 3.125 | 6.25 |
| 239 | 0.09091 | 0.1285 | 0.108 | 3.125 | 12.5 | 6.25 |
| 240 | 7.464 | 4.77 | 2.598 | 12.5 | 3.125 | 25 |
| 241 | 0.04443 | 0.6576 | 0.08682 | 3.125 | 6.25 | 12.5 |
| 242 | 3.34 | 4.014 | 7.469 | 6.25 | 12.5 | 50 |
| 243 | 11.26 | 5.881 | 9.861 | 3.125 | 3.125 | 12.5 |
| 244 | 0.1438 | 0.1562 | 0.1121 | 3.125 | 3.125 | 6.25 |
| 245 | 0.126 | 0.3859 | 0.2182 | 25 | 25 | 50 |
| 246 | 0.1034 | 0.3266 | 0.139 | 12.5 | 50 | 25 |
| 247 | 3.238 | 2.012 | 1.832 | 1.563 | 1.563 | 3.125 |
| 248 | 2.091 | 0.5656 | 0.5564 | 1.563 | 3.125 | 3.125 |
| 249 | 0.2632 | 0.1442 | 0.3222 | 6.25 | 6.25 | 25 |
| 250 | 0.8195 | 0.2452 | 0.6811 | 6.25 | 6.25 | 100 |
| 251 | 0.7476 | 0.07266 | 0.2506 | 1.563 | 0.3906 | 1.563 |
| 252 | 0.4227 | 0.04643 | 0.2087 | 3.125 | 1.563 | 6.25 |
| 253 | 0.6641 | 0.1727 | 0.2942 | 1.563 | 1.563 | 3.125 |
| 254 | 0.7478 | 0.08251 | 0.2178 | 3.125 | 1.563 | 6.25 |
| 255 | 1.662 | 0.151 | 0.4187 | 6.25 | 6.25 | 12.5 |
| 256 | 0.9989 | 0.1081 | 0.3499 | 6.25 | 6.25 | 12.5 |
| 257 | 1.201 | 0.1226 | 0.4278 | 25 | 25 | 50 |
| 258 | 0.4687 | 0.2283 | 0.454 | 12.5 | 25 | 25 |
| 259 | 0.3493 | 0.1674 | 0.2453 | 12.5 | 25 | 25 |
| 260 | 1.989 | 0.5978 | 0.8126 | 6.25 | 6.25 | 12.5 |
| 261 | 1.153 | 0.3997 | 0.7343 | 6.25 | 6.25 | 12.5 |
| 262 | 0.5062 | 0.08026 | 0.3216 | 1.563 | 0.7813 | 3.125 |
| 263 | 4.592 | 0.4311 | 0.5939 | 1.563 | 1.563 | 6.25 |
| 264 | 1.821 | 0.3639 | 0.175 | 1.563 | 3.125 | 3.125 |
| 265 | 1.486 | 0.168 | 0.2386 | 1.563 | 3.125 | 6.25 |
| 266 | 0.6431 | 0.1984 | 0.2323 | 3.125 | 6.25 | 6.25 |
| 267 | 0.964 | 0.2132 | 0.5172 | 0.7813 | 0.3906 | 1.563 |
| 268 | 0.3627 | 0.1766 | 0.329 | 1.563 | 1.563 | 3.125 |
| 269 | 0.1522 | 0.1164 | 0.1757 | 1.563 | 1.563 | 3.125 |
| 270 | 0.6253 | 0.1429 | 0.2279 | 0.6406 | 0.125 | 0.8906 |
| 271 | 0.6874 | 1.333 | 0.1771 | 3.125 | 3.125 | 3.125 |
| 272 | 6.063 | 1.845 | 0.6404 | 6.25 | 3.125 | 6.25 |
| 273 | 0.7089 | 0.1469 | 0.2543 | 1.563 | 0.3906 | 1.563 |
| 274 | 0.431 | 0.1128 | 0.2055 | 1.563 | 0.7813 | 1.563 |
| 275 | 0.8402 | 0.5821 | 0.6957 | 0.8906 | 0.5 | 1.781 |
| 276 | 0.2854 | 0.2397 | 0.2141 | 0.7813 | 0.7813 | 3.125 |
| 277 | 1.374 | 0.5269 | 0.3623 | 0.7813 | 0.3906 | 1.563 |
| 278 | 1.42 | 0.1452 | 0.3647 | 0.7813 | 0.3906 | 1.563 |
| 279 | 0.6948 | 0.806 | 0.4705 | 1.563 | 0.3906 | 1.563 |
| 280 | 0.9543 | 0.2236 | 0.445 | 0.7813 | 0.3906 | 1.563 |
| 281 | 0.1256 | 0.05608 | 0.1335 | 0.7813 | 0.7813 | 1.563 |
| 282 | 0.7772 | 0.1572 | 0.2802 | 0.5156 | 0.3438 | 0.8359 |
| 283 | 0.4957 | 0.1162 | 0.3484 | 1.563 | 0.3906 | 1.563 |
| 284 | 0.3267 | 0.2891 | 0.5072 | 1.563 | 0.3906 | 1.563 |
| 285 | 0.5343 | 0.3699 | 0.3635 | 1.563 | 3.125 | 1.563 |
| 286 | 0.3228 | 0.09338 | 0.2652 | 0.7813 | 0.7813 | 1.563 |
| 287 | 2.921 | 0.3863 | 0.6069 | 3.125 | 3.125 | 3.125 |
| 288 | 9.827 | 1.666 | 0.8606 | 3.125 | 3.125 | 1.563 |
| 289 | 0.2992 | 0.1204 | 0.4069 | 1.563 | 0.3906 | 3.125 |
| 290 | 2.958 | 0.4722 | 0.5004 | 3.125 | 3.125 | 3.125 |
| 291 | 0.9587 | 0.1946 | 0.5404 | 0.7813 | 0.7813 | 1.563 |
| 292 | 0.2701 | 0.161 | 0.3315 | 1.563 | 3.125 | 3.125 |
| 293 | 1.314 | 0.1573 | 0.4652 | 1.563 | 0.3906 | 1.563 |
| 294 | 0.3502 | 0.08274 | 0.1845 | 3.125 | 1.563 | 3.125 |
| 295 | 1.218 | 0.1155 | 0.1052 | 3.125 | 1.563 | 3.125 |
| 296 | 0.2968 | 0.1226 | 0.2269 | 0.7813 | 0.5859 | 1.172 |
| 297 | 0.5956 | 0.2173 | 0.282 | 1.563 | 1.563 | 3.125 |
| 298 | 0.3005 | 0.4253 | 0.2569 | 1.563 | 0.7813 | 1.563 |
| 299 | 1.446 | 0.1882 | 0.3018 | 3.125 | 3.125 | 6.25 |
| 300 | 0.4151 | 0.2537 | 0.1624 | 1.563 | 0.7813 | 3.125 |
| 301 | 2.874 | 0.5359 | 0.9602 | 3.125 | 0.7813 | 6.25 |
| 302 | 104.9 | 22.52 | 9.989 | 12.5 | 3.125 | 6.25 |

TABLE 1-continued

Inhibition of metallo-β-lactamases (IMP-1, NDM-1, VIM-1) and antibiotic potentiation vs. MBL-expressing bacteria by Examples 1-379.

| Ex. No. | IMP-1 IC50 nM | NDM-1 IC50 nM | VIM-1 IC50 nM | *Serratia marcescens* expressing IMP-1 (CL5741) MITC95 µM | *Escherichia coli* expressing NDM-1 (CLB30016) MITC95 µM | *Klebsiella pneumoniae* expressing VIM-1 (IHMA599644) MITC95 µM |
|---|---|---|---|---|---|---|
| 303 | 111.1 | 97.27 | 11.26 | 6.25 | 3.125 | 3.125 |
| 304 | 5.362 | 0.2144 | 0.4777 | 6.25 | 6.25 | 50 |
| 305 | 1.909 | 0.6435 | 0.4935 | 0.7813 | 1.563 | 1.563 |
| 306 | 2.843 | 0.8482 | 0.3742 | 0.7813 | 0.7813 | 1.563 |
| 307 | 0.08676 | 0.03721 | 0.03064 | 0.7813 | 0.7813 | 0.7813 |
| 308 | 0.56 | 0.1698 | 0.2191 | 3.125 | 3.125 | 3.125 |
| 309 | 0.256 | 0.08851 | 0.1449 | 3.125 | 0.7813 | 3.125 |
| 310 | 2.304 | 1.042 | 0.3191 | 1.563 | 1.563 | 3.125 |
| 311 | 2.324 | 0.9215 | 0.3146 | 1.563 | 3.125 | 3.125 |
| 312 | 0.4301 | 0.1199 | 0.3888 | 0.5573 | 0.3477 | 0.8542 |
| 313 | 0.2566 | 0.1552 | 0.2317 | 1.228 | 1.618 | 2.009 |
| 314 | 0.4453 | 0.3788 | 0.7265 | 6.25 | 12.5 | 12.5 |
| 315 | 0.2492 | 0.1133 | 0.2509 | 1.563 | 1.563 | 3.125 |
| 316 | 0.8353 | 0.2836 | 0.779 | 12.5 | 6.25 | 12.5 |
| 317 | 0.2272 | 0.03116 | 0.1893 | 0.7813 | 1.172 | 1.563 |
| 318 | 27.1 | 1.946 | 0.5172 | 25 | 12.5 | 12.5 |
| 319 | 1.919 | 0.1942 | 0.4066 | 25 | 100 | 50 |
| 320 | 1.061 | 0.9387 | 0.2083 | 25 | 50 | 12.5 |
| 321 | 0.9486 | 1.365 | 1.011 | 0.4453 | 0.125 | 1.281 |
| 322 | 0.1699 | 0.7314 | 0.205 | 1.563 | 3.125 | 3.125 |
| 323 | 0.1456 | 0.05127 | 0.214 | 1.563 | 3.125 | 1.563 |
| 324 | 0.5505 | 0.2219 | 0.1386 | 1.563 | 1.563 | 3.125 |
| 325 | 0.2389 | 0.07229 | 0.3464 | 12.5 | 12.5 | 25 |
| 326 | 0.2484 | 0.07611 | 0.1672 | 3.125 | 3.125 | 6.25 |
| 327 | 2.233 | 1.018 | 0.4554 | 3.125 | 1.563 | 3.125 |
| 328 | 3.423 | 1.305 | 0.4744 | 3.125 | 1.563 | 3.125 |
| 329 | 1.928 | 0.4043 | 0.2823 | 3.125 | 1.563 | 6.25 |
| 330 | 3.611 | 0.6747 | 0.6387 | 1.563 | 3.125 | 6.25 |
| 331 | 0.302 | 0.1649 | 0.1827 | 1.563 | 3.125 | 6.25 |
| 332 | 0.5575 | 0.1241 | 0.2745 | 1.563 | 0.7813 | 3.125 |
| 333 | 10.32 | 3.445 | 0.3118 | 1.563 | 0.3906 | 1.563 |
| 334 | 4.537 | 2.53 | 0.5042 | 3.125 | 1.563 | 3.125 |
| 335 | 8.904 | 3.223 | 1.233 | 1.563 | 1.563 | 3.125 |
| 336 | 9.512 | 6.303 | 3.567 | 1.563 | 0.7813 | 3.125 |
| 337 | 12.27 | 5.654 | 4.385 | 1.563 | 0.7813 | 1.563 |
| 338 | 74.93 | 20.43 | 15.05 | 3.125 | 1.563 | 6.25 |
| 339 | 3.417 | 2.524 | 1.783 | 3.125 | 1.563 | 3.125 |
| 340 | 107.4 | 24.82 | 8.162 | 3.125 | 1.563 | 3.125 |
| 341 | 16.1 | 4.008 | 4.46 | 3.125 | 1.563 | 3.125 |
| 342 | 34.22 | 15.34 | 2.84 | 3.125 | 1.563 | 1.563 |
| 343 | 1.889 | 0.5097 | 0.198 | 3.125 | 3.125 | 6.25 |
| 344 | 1.704 | 0.4698 | 0.2679 | 3.125 | 3.125 | 6.25 |
| 345 | 0.857 | 1.963 | 0.434 | 1.563 | 0.7813 | 3.125 |
| 346 | 1.974 | 0.5185 | 0.9313 | 1.563 | 0.3906 | 1.563 |
| 347 | 1.339 | 1.729 | 0.9328 | 1.563 | 3.125 | 6.25 |
| 348 | 0.8468 | 0.163 | 0.4784 | 3.125 | 3.125 | 6.25 |
| 349 | 0.2198 | 0.06588 | 0.4521 | 1.563 | 3.125 | 3.125 |
| 350 | 0.9816 | 0.2502 | 0.6736 | 1.563 | 0.7813 | 3.125 |
| 351 | 1.361 | 0.1997 | 0.7112 | 0.7813 | 0.7813 | 1.563 |
| 352 | 0.1447 | 0.06577 | 0.2548 | 0.7813 | 0.7813 | 1.563 |
| 353 | 0.3919 | 0.1849 | 0.2022 | 1.563 | 1.563 | 3.125 |
| 354 | 0.2746 | 0.2255 | 0.1623 | 0.7813 | 0.7813 | 1.563 |
| 355 | 0.3267 | 0.1645 | 0.1647 | 1.563 | 1.563 | 3.125 |
| 356 | 0.4964 | 0.2703 | 0.3438 | 1.563 | 1.563 | 3.125 |
| 357 | 0.2938 | 0.1627 | 0.2491 | 1.563 | 1.563 | 3.125 |
| 358 | 1.146 | 0.2212 | 0.7888 | 0.7813 | 0.7813 | 1.563 |
| 359 | 0.454 | 0.2858 | 0.316 | 1.563 | 1.563 | 1.563 |
| 360 | 0.5441 | 0.06538 | 0.2867 | 1.391 | 0.25 | 1.781 |
| 361 | 0.1736 | 0.09046 | 0.2527 | 0.7813 | 0.7813 | 1.563 |
| 362 | 0.4077 | 0.295 | 0.6048 | 0.7813 | 0.3906 | 1.563 |
| 363 | 0.425 | 0.2748 | 0.3557 | 0.7813 | 0.3906 | 1.563 |
| 364 | 0.4862 | 0.7955 | 0.8754 | 0.9766 | 0.3418 | 1.563 |
| 365 | 1.206 | 1.529 | 0.6321 | 0.7813 | 0.293 | 2.344 |
| 366 | 1.809 | 0.6229 | 1.174 | 1.563 | 0.7813 | 1.563 |
| 367 | 3.162 | 0.8594 | 0.7027 | 0.7813 | 0.1953 | 1.563 |
| 368 | 5.545 | 1.09 | 0.561 | 0.7813 | 0.1953 | 2.344 |
| 369 | 3.571 | 0.9728 | 0.4006 | 0.7813 | 0.7813 | 1.563 |
| 370 | 1.247 | 0.3613 | 0.3926 | 0.7813 | 0.7813 | 1.563 |
| 371 | 1.375 | 1.16 | 1.077 | 1.563 | 1.563 | 3.125 |
| 372 | 1.425 | 1.171 | 0.9921 | 1.563 | 0.7813 | 3.125 |
| 373 | 0.4089 | 0.1385 | 0.2478 | 1.563 | 0.7813 | 3.125 |

TABLE 1-continued

Inhibition of metallo-β-lactamases (IMP-1, NDM-1, VIM-1) and antibiotic potentiation vs. MBL-expressing bacteria by Examples 1-379.

| Ex. No. | IMP-1 IC50 nM | NDM-1 IC50 nM | VIM-1 IC50 nM | Serratia marcescens expressing IMP-1 (CL5741) MITC95 µM | Escherichia coli expressing NDM-1 (CLB30016) MITC95 µM | Klebsiella pneumoniae expressing VIM-1 (IHMA599644) MITC95 µM |
|---|---|---|---|---|---|---|
| 374 | 2.71 | 1.421 | 2.568 | 3.125 | 3.125 | 6.25 |
| 375 | 1.705 | 2.106 | 0.5296 | 1.563 | 1.563 | 1.563 |
| 376 | 2.58 | 2.92 | 0.5389 | 1.563 | 3.125 | 1.563 |
| 377 | 1.883 | 1.768 | 0.6712 | 1.563 | 1.563 | 3.125 |
| 378 | 5.104 | 3.721 | 0.5441 | 0.7813 | 0.7813 | 1.563 |
| 379 | 0.1697 | 0.08087 | 0.123 | 0.7813 | 0.7813 | 1.563 |

Efflux

In order to assess the contribution of efflux to lack of whole cell inhibition of metallo-beta-lactamase inhibitors of formula I, tool strains were constructed. The strain background is Pseudomonas aeruginosa PAO1. A wild-type (MB5919) and an isogenic strain in which multiple efflux pumps have been disrupted genetically were used. The MBL IMP-1, obtained from a clinical isolate was introduced into the strain pair by the following process:

Plasmid DNA (encoding IMP-1) was extracted from CL 5673 (IMP-1, P. aeruginosa clinical strain) by standard techniques. The plasmid DNA was transformed into parental MB5919 (oprD+, efflux+, inducible AmpC) and MB5890 (oprD+, efflux-, inducible AmpC) isogenic strains by electroporation. These transformed strains were plated onto cation-adjusted Muller-Hinton agar plates containing ceftazidime at 32 µg/ml (MB5919) and 16 µg/ml (MB5890) to select for those cells in which the IMP-1-expressing plasmid was introduced successfully, resulting in resistance to ceftazidime. Agarose-gel electrophoresis of PCR product for IMP-1 from the successful transformants was used to compare to control and to the original strain from which the plasmid was obtained, confirming transfer of the IMP-1 gene (data not shown).

Minimum inhibitory concentrations of sentinel antibiotics were performed to quality control the new strains. The imipenem MIC went up dramatically, as expected, due to presence of the IMP-1, also meropenem (MEM) and ceftazidime (CAZ). The efflux +/− set behaved similarly with non-BL antibiotics as they should with the efflux-strain exhibiting increased sensitivity to chloramphenicol (CAM) and ciprofloxacin (Cipro).

| | MIC [ug/ml] | | | | | | | |
|---|---|---|---|---|---|---|---|---|
| | | | CL 5673 (IMP-1) plasmid | | pFIp-Vim1 plasmid | | | |
| | MB 5919 | MB 5890 | MB 9798 | MB 9799 | MB 9861 | MB 9862 | pFIp-Vim2 plasmid | |
| OprD efflux | OprD+ efflux+ | OprD+ efflux- | OprD+ efflux+ | OprD+ efflux- | OprD+ efflux+ | OprD+ efflux- | OprD+ efflux+ | OprD+ efflux- |
| | MB 5919 | MB 5890 | MB 5919 Trans IMP1 plasmid | MB 5890 Trans IMP1 plasmid | MB 5919 Trans pFIp-Vim1 plasmid | MB 5890 Trans pFIp-Vim1 | MB 5919 Trans pFIp-Vim2 plasd | MB 5890 Trans pFIp-Vim2 plasd |
| Imipenem | 4 | 2 | 64 | 32 | >64 | 64 | >64 | 32 |
| Meropenem | 2 | 0.5 | >64 | 64 | >64 | 64 | >64 | 32 |
| Pipercillin | 2 | 1 | 4 | 4 | >256 | 128 | >256 | 128 |
| Chloramphenicol | >64 | 1 | >64 | 1 | >64 | 2 | >64 | 1 |
| Ciprofloxicin | 0.5 | 0.008 | 0.5 | 0.008 | 1 | 0.008 | 1 | 0.008 |
| CAZ | 1 | 0.5 | 256 | 256 | >256 | >256 | 128 | 64 |
| Azithromycin | 16 | 1 | 16 | 2 | 32 | 1 | 32 | 1 |

The strain set was then used as a pair to determine the effect of metallo-β-lactamase inhibitors of Formula I on the MIC of imipenem and/or ceftazidime. A fixed concentration of antibiotic is included in standard microbroth MIC tests, usually at the CLSI breakpoint concentration. A fixed amount of a class A/C beta-lactamase inhibitor is also included to inhibit the resident Pseudomonas AmpC enzyme. A serial titration of the metallo-β-lactamase inhibitor was included and the concentration of metallo-β-lactamase inhibitor which restores susceptibility of the strain to the included antibiotic was recorded. That concentration of metallo-β-lactamase inhibitor was then compared between the two strains to determine the fold difference between the efflux+(MB9798) and efflux−(MB9799) strains. This is taken as an indication of the extent to which the MBLi is subject to efflux.

TABLE 2

Concentration of metallo-β-lactamase inhibitors of Formula I which restores susceptibility of efflux+ (MB9798) and efflux– (MB9799) strains to imipenem at 2 μg/mL in the presence of a class A, C, D serine β-lactamase inhibitor closely related to relebactam. Efflux ratio is in the Table below is the ratio MITC95 PA_9798/MITC95 PA_9799

| EX. No. | P. aeruginosa expressing IMP-1, efflux+ (MB9798) MITC95 μM | P. aeruginosa expressing IMP-1, efflux– (MB9799) MITC95 μM | Efflux ratio |
|---|---|---|---|
| 1 | 50 | 6.25 | 8.00 |
| 2 | 6.25 | 1.281 | 4.88 |
| 3 | 25 | 2.563 | 9.75 |
| 4 | 1.563 | 0.3906 | 4.00 |
| 5 | 3.125 | 1.563 | 2.00 |
| 6 | 0.7813 | 0.7813 | 1.00 |
| 7 | 25 | 3.125 | 8.00 |
| 8 | 50 | 6.25 | 8.00 |
| 9 | 6.25 | 1.563 | 4.00 |
| 10 | 6.25 | 3.125 | 2.00 |
| 11 | 3.125 | 0.3906 | 8.00 |
| 12 | 25 | 3.125 | 8.00 |
| 13 | 6.25 | 1.563 | 4.00 |
| 14 | 6.25 | 1.563 | 4.00 |
| 15 | 0.3906 | 0.3906 | 1.00 |
| 16 | 6.25 | 1.563 | 4.00 |
| 17 | 3.125 | 1.563 | 2.00 |
| 18 | 3.125 | 1.563 | 2.00 |
| 19 | 6.25 | 1.563 | 4.00 |
| 20 | 3.125 | 1.563 | 2.00 |
| 21 | 1.563 | 1.563 | 1.00 |
| 22 | 1.563 | 0.7813 | 2.00 |
| 23 | 0.7813 | 0.3906 | 2.00 |
| 24 | 3.125 | 1.563 | 2.00 |
| 25 | 2.302 | 1.058 | 2.18 |
| 26 | 3.125 | 1.563 | 2.00 |
| 27 | 6.25 | 1.563 | 4.00 |
| 28 | 6.25 | 1.563 | 4.00 |
| 29 | 3.125 | 1.563 | 2.00 |
| 30 | 1.563 | 1.563 | 1.00 |
| 31 | 6.25 | 1.563 | 4.00 |
| 32 | 1.563 | 0.7813 | 2.00 |
| 33 | 3.125 | 1.563 | 2.00 |
| 34 | 6.25 | 0.7813 | 8.00 |
| 35 | 1.563 | 1.563 | 1.00 |
| 36 | 0.7813 | 0.7813 | 1.00 |
| 37 | 3.125 | 1.563 | 2.00 |
| 38 | 9.375 | 6.25 | 1.50 |
| 39 | 0.7813 | 1.563 | 0.50 |
| 40 | 3.125 | 0.5573 | 5.61 |
| 41 | 3.125 | 0.7813 | 4.00 |
| 42 | 0.7813 | 0.7813 | 1.00 |
| 43 | 0.6081 | 0.6406 | 0.95 |
| 44 | 100 | 3.125 | 32.00 |
| 45 | 50 | 3.125 | 16.00 |
| 46 | 200 | 3.125 | 64.00 |
| 47 | 6.25 | 1.563 | 4.00 |
| 48 | 3.125 | 1.563 | 2.00 |
| 49 | 12.5 | 3.125 | 4.00 |
| 50 | 3.125 | 3.125 | 1.00 |
| 51 | 0.7813 | 0.7813 | 1.00 |
| 52 | 6.25 | 1.563 | 4.00 |
| 53 | 12.5 | 6.25 | 2.00 |
| 54 | 50 | 3.125 | 16.00 |
| 55 | 50 | 1.563 | 31.99 |
| 56 | 3.125 | 3.125 | 1.00 |
| 57 | 200 | 3.125 | 64.00 |
| 58 | 1.563 | 1.563 | 1.00 |
| 59 | 3.125 | 1.563 | 2.00 |
| 60 | 12.5 | 3.125 | 4.00 |
| 61 | 12.5 | 12.5 | 1.00 |
| 62 | 1.563 | 0.7813 | 2.00 |
| 63 | 50 | 1.781 | 28.07 |
| 64 | 1.563 | 1.563 | 1.00 |
| 65 | 25 | 6.25 | 4.00 |
| 66 | 50 | 6.25 | 8.00 |
| 67 | 3.125 | 1.563 | 2.00 |
| 68 | 6.25 | 3.125 | 2.00 |
| 69 | 3.125 | 0.4453 | 7.02 |
| 70 | 0.4453 | 0.4453 | 1.00 |
| 71 | 0.7813 | 0.7813 | 1.00 |
| 72 | 3.125 | 0.7813 | 4.00 |
| 73 | 1.563 | 1.563 | 1.00 |
| 74 | 3.125 | 0.7813 | 4.00 |
| 75 | 6.25 | 0.7813 | 8.00 |
| 76 | 0.7813 | 0.7813 | 1.00 |
| 77 | 6.25 | 0.7813 | 8.00 |
| 78 | 1.172 | 0.7813 | 1.50 |
| 79 | 0.8906 | 0.6406 | 1.39 |
| 80 | 0.7813 | 0.7813 | 1.00 |
| 81 | 0.7813 | 0.7813 | 1.00 |
| 82 | 3.125 | 1.563 | 2.00 |
| 83 | 12.5 | 6.25 | 2.00 |
| 84 | 6.25 | 1.563 | 4.00 |
| 85 | 1.563 | 0.7813 | 2.00 |
| 86 | 1.563 | 0.3906 | 4.00 |
| 87 | 0.7813 | 0.3906 | 2.00 |
| 88 | 6.25 | 3.125 | 2.00 |
| 89 | 3.125 | 1.563 | 2.00 |
| 90 | 1.563 | 0.7813 | 2.00 |
| 91 | 0.7813 | 0.7813 | 1.00 |
| 92 | 0.4777 | 0.5893 | 0.81 |
| 93 | 0.7813 | 0.7813 | 1.00 |
| 94 | 3.125 | 1.563 | 2.00 |
| 95 | 3.125 | 1.563 | 2.00 |
| 96 | 0.7813 | 1.563 | 0.50 |
| 97 | 0.3906 | 0.7813 | 0.50 |
| 98 | 25 | 1.563 | 15.99 |
| 99 | 200 | 1.563 | 127.96 |
| 100 | 6.25 | 1.563 | 4.00 |
| 101 | 12.5 | 1.563 | 8.00 |
| 102 | 3.125 | 1.563 | 2.00 |
| 103 | 12.5 | 1.563 | 8.00 |
| 104 | 12.5 | 1.563 | 8.00 |
| 105 | 3.125 | 1.563 | 2.00 |
| 106 | 6.25 | 1.563 | 4.00 |
| 107 | 12.5 | 3.125 | 4.00 |
| 108 | 25 | 1.563 | 15.99 |
| 109 | 12.5 | 1.563 | 8.00 |
| 110 | 25 | 1.563 | 15.99 |
| 111 | 6.25 | 1.563 | 4.00 |
| 112 | 12.5 | 3.125 | 4.00 |
| 113 | 12.5 | 1.563 | 8.00 |
| 114 | 6.25 | 0.7813 | 8.00 |
| 115 | 12.5 | 1.563 | 8.00 |
| 116 | 25 | 1.563 | 15.99 |
| 117 | 25 | 1.563 | 15.99 |
| 118 | 12.5 | 3.125 | 4.00 |
| 119 | 100 | 1.563 | 63.98 |
| 120 | 25 | 1.563 | 15.99 |
| 121 | 200 | 1.563 | 127.96 |
| 122 | 6.25 | 1.563 | 4.00 |
| 123 | 25 | 1.563 | 15.99 |
| 124 | 200 | 1.563 | 127.96 |
| 125 | 50 | 3.125 | 16.00 |
| 126 | 12.5 | 1.563 | 8.00 |
| 127 | 25 | 1.563 | 15.99 |
| 128 | 3.125 | 1.563 | 2.00 |
| 129 | 25 | 1.563 | 15.99 |
| 130 | 12.5 | 3.125 | 4.00 |
| 131 | 25 | 1.563 | 15.99 |
| 132 | 6.25 | 1.563 | 4.00 |
| 133 | 200 | 3.125 | 64.00 |
| 134 | 25 | 1.563 | 15.99 |

TABLE 2-continued

Concentration of metallo-β-lactamase inhibitors of Formula I which restores susceptibility of efflux+ (MB9798) and efflux− (MB9799) strains to imipenem at 2 μg/mL in the presence of a class A, C, D serine β-lactamase inhibitor closely related to relebactam. Efflux ratio is in the Table below is the ratio MITC95 PA_9798/MITC95 PA_9799

| EX. No. | P. aeruginosa expressing IMP-1, efflux+ (MB9798) MITC95 μM | P. aeruginosa expressing IMP-1, efflux− (MB9799) MITC95 μM | Efflux ratio |
|---|---|---|---|
| 135 | 3.125 | 1.563 | 2.00 |
| 136 | 12.5 | 0.7813 | 16.00 |
| 137 | 25 | 1.563 | 15.99 |
| 138 | 6.25 | 1.563 | 4.00 |
| 139 | 12.5 | 1.563 | 8.00 |
| 140 | 3.125 | 0.7813 | 4.00 |
| 141 | 6.25 | 0.8906 | 7.02 |
| 142 | 3.125 | 0.7813 | 4.00 |
| 143 | 12.5 | 1.563 | 8.00 |
| 144 | 50 | 1.563 | 31.99 |
| 145 | 12.5 | 1.563 | 8.00 |
| 146 | 100 | 1.563 | 63.98 |
| 147 | 100 | 1.563 | 63.98 |
| 148 | 3.125 | 1.563 | 2.00 |
| 149 | 6.25 | 0.7813 | 8.00 |
| 150 | 1.563 | 1.563 | 1.00 |
| 151 | 12.5 | 3.125 | 4.00 |
| 152 | 50 | 1.563 | 31.99 |
| 153 | 6.25 | 1.563 | 4.00 |
| 154 | 12.5 | 1.563 | 8.00 |
| 155 | 3.125 | 0.7813 | 4.00 |
| 156 | 50 | 1.563 | 31.99 |
| 157 | 12.5 | 0.7813 | 16.00 |
| 158 | 200 | 3.125 | 64.00 |
| 159 | 12.5 | 1.563 | 8.00 |
| 160 | 12.5 | 1.563 | 8.00 |
| 161 | 50 | 1.563 | 31.99 |
| 162 | 100 | 1.563 | 63.98 |
| 163 | 100 | 0.7813 | 127.99 |
| 164 | 6.25 | 3.125 | 2.00 |
| 165 | 12.5 | 3.125 | 4.00 |
| 166 | 12.5 | 1.563 | 8.00 |
| 167 | 6.25 | 0.7813 | 8.00 |
| 168 | 6.25 | 1.563 | 4.00 |
| 169 | 25 | 1.563 | 15.99 |
| 170 | 6.25 | 1.563 | 4.00 |
| 171 | 12.5 | 1.563 | 8.00 |
| 172 | 6.25 | 1.781 | 3.51 |
| 173 | 0.8906 | 0.4453 | 2.00 |
| 174 | 3.125 | 0.3906 | 8.00 |
| 175 | 0.7813 | 0.7813 | 1.00 |
| 176 | 0.7813 | 0.7813 | 1.00 |
| 177 | 0.7813 | 0.7813 | 1.00 |
| 178 | 0.7813 | 0.7813 | 1.00 |
| 179 | 0.7813 | 1.563 | 0.50 |
| 180 | 0.7813 | 0.7813 | 1.00 |
| 181 | 0.6875 | 0.6875 | 1.00 |
| 182 | 0.6406 | 0.6406 | 1.00 |
| 183 | 0.7813 | 0.7813 | 1.00 |
| 184 | 0.7813 | 0.7813 | 1.00 |
| 185 | 1.563 | 0.7813 | 2.00 |
| 186 | 1.563 | 0.7813 | 2.00 |
| 187 | 1.563 | 0.7813 | 2.00 |
| 188 | 1.563 | 0.7813 | 2.00 |
| 189 | 0.7813 | 0.7813 | 1.00 |
| 190 | 1.563 | 1.563 | 1.00 |
| 191 | 25 | 1.563 | 15.99 |
| 192 | 3.125 | 0.7813 | 4.00 |
| 193 | 6.25 | 1.563 | 4.00 |
| 194 | 0.3906 | 0.7813 | 0.50 |
| 195 | 0.7813 | 0.7813 | 1.00 |
| 196 | 12.5 | 0.7813 | 16.00 |
| 197 | 12.5 | 1.563 | 8.00 |
| 198 | 0.7813 | 0.7813 | 1.00 |
| 199 | 12.5 | 6.25 | 2.00 |
| 200 | 100 | 25 | 4.00 |
| 201 | 1.563 | 0.7813 | 2.00 |
| 202 | 6.25 | 1.563 | 4.00 |
| 203 | 3.125 | 0.7813 | 4.00 |
| 204 | 1.563 | 0.7813 | 2.00 |
| 205 | 6.25 | 3.125 | 2.00 |
| 206 | 3.125 | 1.563 | 2.00 |
| 207 | 3.125 | 1.563 | 2.00 |
| 208 | 6.25 | 3.125 | 2.00 |
| 209 | 50 | 3.125 | 16.00 |
| 210 | 12.5 | 0.7813 | 16.00 |
| 211 | 50 | 1.563 | 31.99 |
| 212 | 1.563 | 0.7813 | 2.00 |
| 213 | 6.25 | 1.563 | 4.00 |
| 214 | 3.125 | 1.563 | 2.00 |
| 215 | 6.25 | 3.125 | 2.00 |
| 216 | 6.25 | 1.563 | 4.00 |
| 217 | 12.5 | 1.563 | 8.00 |
| 218 | 12.5 | 1.563 | 8.00 |
| 219 | 6.25 | 1.281 | 4.88 |
| 220 | 100 | 3.125 | 32.00 |
| 221 | 50 | 3.125 | 16.00 |
| 222 | 100 | 1.563 | 63.98 |
| 223 | 6.25 | 3.125 | 2.00 |
| 224 | 3.125 | 1.563 | 2.00 |
| 225 | 3.125 | 1.563 | 2.00 |
| 226 | 25 | 0.7813 | 32.00 |
| 227 | 3.125 | 1.563 | 2.00 |
| 228 | 0.7813 | 0.7813 | 1.00 |
| 229 | 25 | 6.25 | 4.00 |
| 230 | 100 | 3.125 | 32.00 |
| 231 | 25 | 3.125 | 8.00 |
| 232 | 12.5 | 1.563 | 8.00 |
| 233 | 12.5 | 1.563 | 8.00 |
| 234 | 50 | 0.7813 | 64.00 |
| 235 | 50 | 6.25 | 8.00 |
| 236 | 6.25 | 0.7813 | 8.00 |
| 237 | 25 | 1.563 | 15.99 |
| 238 | 50 | 1.563 | 31.99 |
| 239 | 1.563 | 1.563 | 1.00 |
| 240 | 50 | 12.5 | 4.00 |
| 241 | 12.5 | 1.563 | 8.00 |
| 242 | 50 | 1.563 | 31.99 |
| 243 | 100 | 0.7813 | 127.99 |
| 244 | 6.25 | 1.563 | 4.00 |
| 245 | 50 | 6.25 | 8.00 |
| 246 | 12.5 | 3.125 | 4.00 |
| 247 | 25 | 1.563 | 15.99 |
| 248 | 6.25 | 1.563 | 4.00 |
| 249 | 12.5 | 6.25 | 2.00 |
| 250 | 200 | 3.125 | 64.00 |
| 251 | 1.563 | 0.7813 | 2.00 |
| 252 | 3.125 | 3.125 | 1.00 |
| 253 | 1.563 | 1.563 | 1.00 |
| 254 | 3.125 | 1.563 | 2.00 |
| 255 | 12.5 | 3.125 | 4.00 |
| 256 | 6.25 | 6.25 | 1.00 |
| 257 | 25 | 12.5 | 2.00 |
| 258 | 12.5 | 6.25 | 2.00 |
| 259 | 12.5 | 6.25 | 2.00 |
| 260 | 6.25 | 6.25 | 1.00 |
| 261 | 6.25 | 6.25 | 1.00 |
| 262 | 0.7813 | 0.7813 | 1.00 |
| 263 | 6.25 | 3.125 | 2.00 |
| 264 | 6.25 | 0.7813 | 8.00 |
| 265 | 6.25 | 1.563 | 4.00 |
| 266 | 6.25 | 3.125 | 2.00 |
| 267 | 0.7813 | 0.7813 | 1.00 |
| 268 | 1.563 | 1.563 | 1.00 |

TABLE 2-continued

Concentration of metallo-β-lactamase inhibitors of Formula I which restores susceptibility of efflux+ (MB9798) and efflux− (MB9799) strains to imipenem at 2 µg/mL in the presence of a class A, C, D serine β-lactamase inhibitor closely related to relebactam. Efflux ratio is in the Table below is the ratio MITC95 PA_9798/MITC95 PA_9799

| EX. No. | P. aeruginosa expressing IMP-1, efflux+ (MB9798) MITC95 µM | P. aeruginosa expressing IMP-1, efflux− (MB9799) MITC95 µM | Efflux ratio |
| --- | --- | --- | --- |
| 269 | 0.7813 | 0.7813 | 1.00 |
| 270 | 0.4453 | 0.4453 | 1.00 |
| 271 | 12.5 | 1.563 | 8.00 |
| 272 | 100 | 1.563 | 63.98 |
| 273 | 0.7813 | 0.7813 | 1.00 |
| 274 | 0.7813 | 0.7813 | 1.00 |
| 275 | 2.563 | 0.8906 | 2.88 |
| 276 | 1.563 | 0.7813 | 2.00 |
| 277 | 1.563 | 0.7813 | 2.00 |
| 278 | 1.563 | 0.7813 | 2.00 |
| 279 | 3.125 | 0.7813 | 4.00 |
| 280 | 3.125 | 0.7813 | 4.00 |
| 281 | 0.3906 | 0.7813 | 0.50 |
| 282 | 0.418 | 0.418 | 1.00 |
| 283 | 6.25 | 1.563 | 4.00 |
| 284 | 3.125 | 0.7813 | 4.00 |
| 285 | 3.125 | 0.7813 | 4.00 |
| 286 | 1.563 | 0.7813 | 2.00 |
| 287 | 6.25 | 3.125 | 2.00 |
| 288 | 3.125 | 0.7813 | 4.00 |
| 289 | 12.5 | 1.563 | 8.00 |
| 290 | 6.25 | 1.563 | 4.00 |
| 291 | 0.7813 | 0.7813 | 1.00 |
| 292 | 1.563 | 1.563 | 1.00 |
| 293 | 0.7813 | 0.7813 | 1.00 |
| 294 | 1.563 | 1.563 | 1.00 |
| 295 | 1.563 | 1.563 | 1.00 |
| 296 | 0.7813 | 0.7813 | 1.00 |
| 297 | 1.563 | 0.7813 | 2.00 |
| 298 | 1.563 | 0.7813 | 2.00 |
| 299 | 3.125 | 3.125 | 1.00 |
| 300 | 1.563 | 0.7813 | 2.00 |
| 301 | 3.125 | 1.563 | 2.00 |
| 302 | 200 | 12.5 | 16.00 |
| 303 | 100 | 3.125 | 32.00 |
| 304 | 25 | 12.5 | 2.00 |
| 305 | 1.563 | 0.7813 | 2.00 |
| 306 | 1.563 | 0.7813 | 2.00 |
| 307 | 0.3906 | 0.3906 | 1.00 |
| 308 | 6.25 | 1.563 | 4.00 |
| 309 | 3.125 | 1.563 | 2.00 |
| 310 | 25 | 1.563 | 15.99 |
| 311 | 50 | 1.563 | 31.99 |
| 312 | 0.2786 | 0.5573 | 0.50 |
| 313 | 0.6138 | 0.8929 | 0.69 |
| 314 | 12.5 | 6.25 | 2.00 |
| 315 | 0.7813 | 0.7813 | 1.00 |
| 316 | 6.25 | 6.25 | 1.00 |
| 317 | 0.7813 | 0.7813 | 1.00 |
| 318 | 25 | 6.25 | 4.00 |
| 319 | 25 | 12.5 | 2.00 |
| 320 | 25 | 6.25 | 4.00 |
| 321 | 1.781 | 0.6406 | 2.78 |
| 322 | 1.563 | 0.7813 | 2.00 |
| 323 | 0.7813 | 0.7813 | 1.00 |
| 324 | 6.25 | 0.7813 | 8.00 |
| 325 | 6.25 | 6.25 | 1.00 |
| 326 | 1.563 | 1.563 | 1.00 |
| 327 | 3.125 | 1.563 | 2.00 |
| 328 | 3.125 | 1.563 | 2.00 |
| 329 | 3.125 | 1.563 | 2.00 |
| 330 | 6.25 | 3.125 | 2.00 |
| 331 | 1.563 | 1.563 | 1.00 |
| 332 | 6.25 | 1.563 | 4.00 |
| 333 | 6.25 | 0.7813 | 8.00 |
| 334 | 12.5 | 1.563 | 8.00 |
| 335 | 12.5 | 1.563 | 8.00 |
| 336 | 12.5 | 1.563 | 8.00 |
| 337 | 6.25 | 0.7813 | 8.00 |
| 338 | 25 | 6.25 | 4.00 |
| 339 | 6.25 | 1.563 | 4.00 |
| 340 | 12.5 | 3.125 | 4.00 |
| 341 | 25 | 1.563 | 15.99 |
| 342 | 12.5 | 3.125 | 4.00 |
| 343 | 25 | 1.563 | 15.99 |
| 344 | 25 | 1.563 | 15.99 |
| 345 | 25 | 0.7813 | 32.00 |
| 346 | 6.25 | 0.7813 | 8.00 |
| 347 | 12.5 | 3.125 | 4.00 |
| 348 | 25 | 3.125 | 8.00 |
| 349 | 1.563 | 1.563 | 1.00 |
| 350 | 1.563 | 1.563 | 1.00 |
| 351 | 0.7813 | 0.7813 | 1.00 |
| 352 | 0.3906 | 0.7813 | 0.50 |
| 353 | 0.7813 | 0.7813 | 1.00 |
| 354 | 0.7813 | 0.7813 | 1.00 |
| 355 | 3.125 | 1.563 | 2.00 |
| 356 | 1.563 | 1.563 | 1.00 |
| 357 | 0.7813 | 1.563 | 0.50 |
| 358 | 0.7813 | 0.7813 | 1.00 |
| 359 | 1.563 | 0.7813 | 2.00 |
| 360 | 0.8906 | 1.281 | 0.70 |
| 361 | 0.7813 | 0.7813 | 1.00 |
| 362 | 0.7813 | 0.7813 | 1.00 |
| 363 | 0.7813 | 0.7813 | 1.00 |
| 364 | 0.7813 | 0.7813 | 1.00 |
| 365 | 1.172 | 0.7813 | 1.50 |
| 366 | 3.125 | 1.563 | 2.00 |
| 367 | 1.563 | 1.563 | 1.00 |
| 368 | 1.563 | 1.172 | 1.33 |
| 369 | 0.7813 | 0.7813 | 1.00 |
| 370 | 0.7813 | 0.7813 | 1.00 |
| 371 | 3.125 | 1.563 | 2.00 |
| 372 | 3.125 | 1.563 | 2.00 |
| 373 | 1.563 | 1.563 | 1.00 |
| 374 | 6.25 | 3.125 | 2.00 |
| 375 | 1.563 | 0.7813 | 2.00 |
| 376 | 3.125 | 1.563 | 2.00 |
| 377 | 3.125 | 1.563 | 2.00 |
| 378 | 1.563 | 0.7813 | 2.00 |
| 379 | 0.3906 | 0.7813 | 0.50 |

Representative compounds of Formula I of the instant invention generally have a lower efflux ratio than compounds in which the atom or linker at the C-6 position is a carbon or hydrogen instead of —SO$_2^-$.

What is claimed is:

1. A compound of Formula I

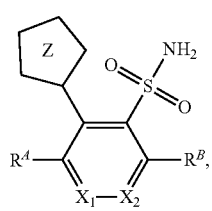

(I)

or a pharmaceutically acceptable salt thereof, wherein:

$X^1$ is N or CH;

$X^2$ is N or CH;

Z is tetrazolyl, wherein Z is linked through a carbon to carbon bond to the six-membered core ring having $X_1$ and $X_2$;

$R^A$ is —$(CH_2)_n$-AryA1, —$(CH_2)_n$-HetA1, —$(CH_2)_n$—$C_4$-$C_6$cycloalkyl, or —$(CH_2)_n$—$C_4$-$C_6$cycloalkenyl, wherein said —$(CH_2)_n$—$C_4$-$C_6$cycloalkyl and —$(CH_2)_n$—$C_4$-$C_6$cycloalkenyl are optionally substituted with 1, 2, or 3 substituents independently selected from —$NH_2$, —OH, —F, and —$NR^aC(O)C_1$-$C_6$alkyl optionally substituted with 1 or 2 substituents independently selected from —F, —$CF_3$, —$NR^aR^b$, and —$OR^a$;

$R^B$ is —$SR^1$, —$SOR^2$ or —$SO_2R^3$;

$R^1$ is HetB1, AryB1, or —$CH_3$;

$R^2$ is HetB1 or —$CH_3$;

$R^3$ is
1) $C_1$-$C_6$alkyl optionally substituted with 1, 2 or 3 substituents independently selected from F, —$NR^aR^b$, —$N^+R^aR^bH$, —$N^+R^aR^bCH_3$, —OH, and cyclopropyl;
2) $C_4$-$C_6$cycloalkyl optionally substituted with 1 or 2 substituents independently selected from F, —$NR^aR^b$, and —OH;
3) —OH;
4) —$(CH_2)_kAryB1$;
5) —$(CH_2)_kHetB1$;

AryA1 is an aromatic ring system selected from:
1) a 5-6 membered monocyclic ring with 0, 1, 2, or 3 heteroatom ring atoms independently selected from N, O, and S, optionally substituted with 1, 2, or 3 substituents independently selected from:
   a) halogen,
   b) —$C_1$-$C_6$alkyl,
   c) —CN,
   d) —$CH_2OH$,
   e) —$C(O)NR^aR^b$,
   f) —$C(O)NH(CH_2)_{2-4}NH_2$ optionally substituted with one or two substituents independently selected from —$NR^aR^b$ and —$(CH_2)_nOR^a$,
   g) —$C(O)OR^a$,
   h) —$(CH_2)_pNHR^a$ optionally substituted with one or two substituents independently selected from —$NR^aR^b$ or —$OR^a$,
   i) —$(CH_2)_pNR^aC(=NH)NH_2$,
   j) —$NR^aC(O)C_1$-$C_6$ alkyl optionally substituted with one or two substituents independently selected from —$NR^aR^b$ or —$OR^a$,
   k) —$NR^aSO_2$—$C_1$-$C_6$alkyl,
   l) —$NR^aSO_2$-cyclopropyl,
   m) —$OR^a$,
   n) oxo,
   o) —$SC_1$-$C_6$ alkyl optionally substituted with one or two substituents independently selected from —$NR^aR^b$ or —$OR^a$;
   p) —$SO_2R^a$,
   q) —$SO_2NR^aR^b$,
   r) —$SO_2NH$-cyclopropyl,
   s) -AryA2,
   t) —$(CH_2)_nNR^aAryA2$,
   u) —$C(O)NR^aHetA2$ and
   v) -HetA2, and
2) an 8- to 10-membered bicyclic ring with 1, 2, 3 or 4 heteroatom ring atoms selected from N, O and S, wherein an S atom optionally has one or two oxo substituents and a N atom is optionally in the form of an N-oxide, and wherein the ring is optionally substituted with 1 or 2 substituents independently selected from
   a) halogen;
   b) $C_1$-$C_6$alkyl optionally substituted with one to three substituents independently selected from —$NR^aR^b$, —$C(O)OR^a$, —$NR^aC(O)CF_3$, —F and —$OR^a$;
   c) —$(CH_2)_nCF_3$;
   d) —$C(=NH)NH_2$;
   e) —CN;
   f) —$C(O)CF_3$;
   g) —$C(O)NR^aR^b$;
   h) —$C(O)NHCH_2C(O)OR^a$;
   i) —$C(O)NH$—$C_2$-$C_4$alkyl-$NH_2$,
   j) —$C(O)OR^a$;
   k) —$NR^aR^b$;
   l) —$NHCH_2SO_3H$;
   m) —$(CH_2)_nNHC(=NH)NH_2$;
   n) —$NHC(O)C_1$-$C_6$alkyl;
   o) —$NHC(O)NH_2$;
   p) —$NHC(O)OR^a$;
   q) —$NHSO_2CH_3$;
   r) —$OR^a$;
   s) oxo;
   t) —$SO_2R^a$,
   u) —$CH_2$-phenyl-$OCH_3$; and
   v) -HetA2;

HetA1 is dihydrothiopyranyl, wherein the S atom is optionally substituted with 2 oxo, or tetrahydropyranyl;

AryA2 is a 5-6-membered aromatic monocyclic ring with 1, 2, 3, or 4 heteroatom ring atoms independently selected from N, N as a quaternary salt, and S, or 4 N ring atoms, optionally substituted with one or two substituents independently selected from: —$CH_2OH$, —COOH, —$CONH_2$, —$C(O)OC_1$-$C_6$alkyl, and —$(CH_2)_pNHR^a$ optionally substituted with one or two substituents independently selected from —$NR^aR^b$ and —$OR^a$;

HetA2 is a 4-6-membered saturated monocyclic ring with 1 or 2 heteroatom ring atoms independently selected from N, O and S, wherein the S is optionally substituted with two oxo groups, and wherein the ring is optionally substituted with 1 or 2 substituents independently selected from $C_1$-$C_6$alkyl, —CN, —OH, and oxo;

AryB1 is an aromatic ring selected from:
1) a 5-6 membered monocyclic aromatic ring with 0, 1, 2, or 3 N ring atoms, optionally substituted with 1 substituent selected from —$CF_3$, $C_1$-$C_6$ alkyl, —$(CH_2)_nNH_2$ and —$OCH_3$; and
2) a 9-membered bicyclic ring with 2 N ring atoms;

HetB1 is a saturated ring selected from:
1) a carbon-linked 4-6-membered saturated monocyclic ring with 1 or 2 heteroatom ring atoms independently selected from N, O and S, wherein the S is optionally substituted with one or two oxo groups, and wherein the ring is optionally substituted with 1 or 2 substituents independently selected from F, $C_1$-$C_6$ alkyl, $C_1$-$C_6$ hydroxyalkyl, —CN, —$C(O)C_1$-$C_6$ alkyl, —$(C_1$-$C_4$alkyl$)_n$-$NR^aR^b$, —$(CH_2)_nC(O)NR^aR^b$, —$C(O)NH$-cyclopropyl, —$C(O)OR^a$, —OH, oxo, and —$SO_2$—$C_1$-$C_6$ alkyl; and
2) a carbon-linked 6-10-membered bicyclic ring with 1, 2, 3 or 4 heteroatom ring atoms selected from N, O and S, optionally substituted with one to three substituents, independently selected from: —F, —$C_1$-

$C_6$alkyl, —NR$^a$R$^b$, oxo, —(CH$_2$)$_{1-2}$OH, —CH$_2$NH$_2$, —SO$_2$CH$_3$, —CH$_2$C$_3$-C$_6$cycloalkyl or —NH$_2$, wherein a ring sulfur atom is optionally substituted with one or two oxo groups, wherein the bicyclic ring may be bridged, fused or spirocyclic, and wherein the C$_3$-C$_6$cycloalkyl is optionally substituted with —CH$_2$OH;

R$^a$ and R$^b$ are independently H or C$_1$-C$_6$ alkyl;

k is 0, 1, 2, 3, or 4;

each n is independently 0 or 1; and each p is independently 0, 1, 2, or 3.

2. The compound of claim 1, or a pharmaceutically acceptable salt thereof, wherein X$^1$ and X$^2$ are CH.

3. The compound of claim 1, or a pharmaceutically acceptable salt thereof, having the Formula IA:

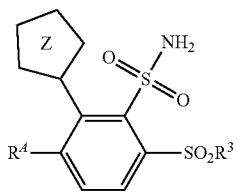

(IA)

wherein:
R$^A$ is AryA1; HetA1; C$_4$-C$_6$cycloalkyl; or C$_4$-C$_6$cycloalkenyl wherein said C$_4$-C$_6$cycloalkyl and C$_4$-C$_6$cycloalkenyl are optionally substituted with —NH$_2$ or NHC(O)(CH$_2$)$_{1-3}$NH$_2$;

R$^3$ is
1) —(CH$_2$)$_k$HetB1;
2) C$_1$-C$_6$alkyl optionally substituted with 1 or 2 substituents independently selected from —NR$^a$R$^b$, —OH, and cyclopropyl;
3) C$_4$-C$_6$cycloalkyl optionally substituted with —NH$_2$;
4) —OH; or
5) -AryB1;

AryA1 is an aromatic ring system selected from:
1) a 5-6 membered monocyclic ring with 0, 1, or 2 heteroatom ring atoms independently selected from N and S, substituted with 1 or 2 substituents independently selected from:
a) —F,
b) —C$_1$-C$_6$ alkyl,
c) —CN,
d) —CH$_2$OH,
e) —C(O)NR$^a$R$^b$,
f) —C(O)NH(CH$_2$)$_{2-4}$NH$_2$,
g) —C(O)OR$^a$,
h) —(CH$_2$)NHR$^a$,
i) —NHC(=NH)NH$_2$,
j) —NHC(O)CH$_3$;
k) —NR$^a$SO$_2$—C$_1$-C$_6$alkyl,
l) —NHSO$_2$-cyclopropyl,
m) —OR$^a$,
n) —SO$_2$NR$^a$R$^b$,
o) —SO$_2$NH-cyclopropyl,
p) -AryA2, and
q) -HetA2, and
2) an 8- to 10-membered bicyclic ring with 1, 2, 3 or 4 heteroatom ring atoms selected from N, O and S, wherein an S atom optionally has one or two oxo substituents and wherein the ring is optionally substituted with 1 or 2 substituents independently selected from —F, —C$_1$-C$_6$ alkyl, —CH$_2$CF$_3$, —CF$_2$CH$_2$NH$_2$, —CF$_3$, —C(=NH)NH$_2$, —CN, —C(O)CF$_3$, —C(O)NR$^a$R$^b$, —C(O)NHCH$_2$C(O)OR$^a$, —C(O)OR$^a$, —(CH$_2$)$_{0-2}$NR$^a$R$^b$, —NHC(O)CH$_3$, —NHC(O)NH$_2$, —NHC(O)OR$^a$, —NHCH$_2$SO$_3$H, —NHSO$_2$CH$_3$, —OR$^a$, oxo, —CH$_2$-phenyl-OCH$_3$, and -HetA2;

AryB1 is an aromatic ring system selected from:
1) a 5-6 membered monocyclic aromatic ring with 0, 1, 2, or 3 N ring atoms, optionally substituted with 1 substituent selected from C$_1$-C$_6$ alkyl, —CF$_3$, and —OCH$_3$; or
2) a 9-membered bicyclic ring with 2 N ring atoms;

HetB1 is a saturated ring system selected from:
1) a carbon-linked 4-6-membered saturated monocyclic ring with 1 or 2 heteroatom ring atoms independently selected from N, O and S, wherein the S is optionally substituted with an oxo group, and wherein the ring is optionally substituted with 1 or 2 substituents independently selected from
a) —F,
b) —C$_1$-C$_6$ alkyl,
c) —C$_1$-C$_6$ hydroxyalkyl,
d) —CN,
e) —C(O)CH$_3$,
f) —(CH$_2$)$_n$C(O)NR$^a$R$^b$,
g) —C(O)NH-cyclopropyl,
h) —C(O)OR$^a$,
i) —(C$_1$-C$_4$alkyl)$_n$-NR$^a$R$^b$,
j) —SO$_2$—C$_1$-C$_6$ alkyl, and
k) oxo; and
2) a carbon-linked 6-10-membered bicyclic ring with 1 to 2 heteroatom ring atoms selected from N and S, optionally substituted with C$_1$-C$_6$alkyl, —CH$_2$C$_3$-C$_6$cycloalkyl or —NH$_2$, wherein the S is optionally substituted with two oxo groups, wherein the bicyclic ring may be bridged, fused or spirocyclic, and wherein the C$_3$-C$_6$cycloalkyl is optionally substituted with —CH$_2$OH; and R$^a$ and R$^b$ are independently H or C$_1$-C$_6$ alkyl.

4. The compound of claim 1, or a pharmaceutically acceptable salt thereof, wherein R$^A$ is AryA1.

5. The compound of claim 4, or a pharmaceutically acceptable salt thereof, wherein R$^A$ is:

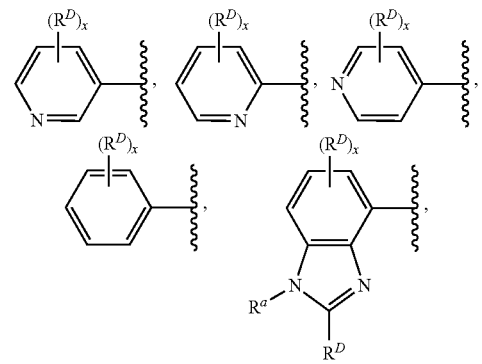

487

-continued

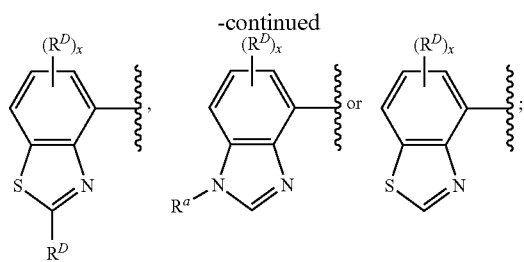

wherein:

~~~ indicates the point of attachment to the rest of the compound, and
each $R^D$ is independently F, —$C_1$-$C_6$ alkyl, —CONH—$C_2$-$C_4$alkyl-$NH_2$, —$NHR^a$, —$C(O)OC_1$-$C_6$alkyl, or —$(CH_2)_xNHR^a$,
each x is independently 0, 1, or 2, and
n is 0 or 1.

6. The compound of claim 4, or a pharmaceutically acceptable salt thereof, wherein AryA1 is 1) pyridyl optionally substituted with —$NH_2$, 2) benzoimidazolyl optionally substituted with 1 or 2 substituents independently selected from F, —$CH_3$ and —$(CH_2)_nNH_2$; or 3) benzothiazolyl optionally substituted with 1 or 2 substituents independently selected from —$CH_3$ and —$(CH_2)_nNH_2$.

7. The compound of claim 1, wherein $R^3$ is: HetB1 or $C_1$-$C_6$alkyl optionally substituted with 1 or 2 substituents independently selected from —$NR^aR^b$, —OH, and cyclopropyl.

8. The compound of claim 1, or a pharmaceutically acceptable salt thereof, having the Formula IB:

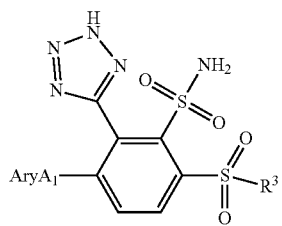

(IB)

wherein:
AryA1 is an aromatic ring system selected from:
1) a 5-6 membered monocyclic ring with 0 or 1 N ring atoms optionally substituted with 1 or 2 substituents independently selected from F, —$C_1$-$C_6$ alkyl, —CONH—$C_{2-4}$alkyl-$NH_2$, or —$NHR^a$; and
2) a 9-membered bicyclic ring with 2 or 3 heteroatom ring atoms selected from N and S, wherein the ring is optionally substituted with 1 or 2 substituents independently selected from —F, —$C_1$-$C_6$ alkyl, —$C(O)OC_1$-$C_6$alkyl, and —$(CH_2)_xNR^aR^b$;
$R^3$ is:
1) $C_1$-$C_6$alkyl optionally substituted with 1, 2 or 3 substituents independently selected from F, —$NR^aR^b$, —$N^+R^aR^bH$, —$N^+R^aR^bCH_3$, —OH, and cyclopropyl;

488

2) $C_4$-$C_6$cycloalkyl optionally substituted with 1 or 2 substituents independently selected from F, —$NR^aR^b$, and —OH;
3) -AryB1; or
4) HetB1; and
x is 0, 1 or 2.

9. A compound of claim 1 having the structure:

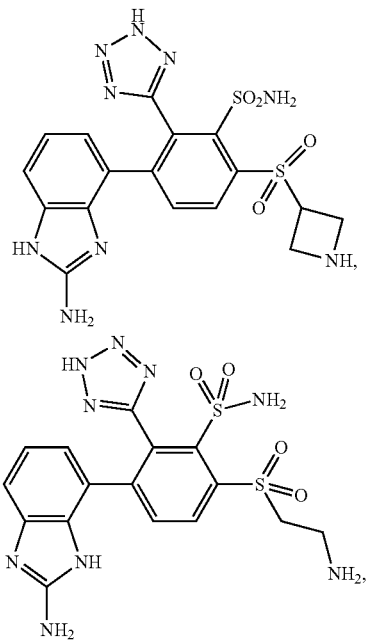

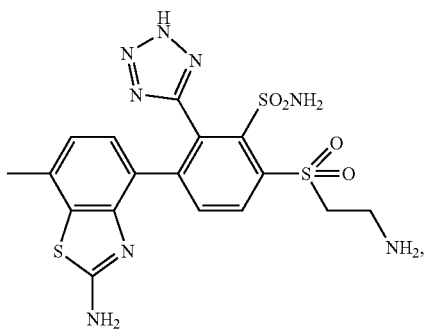

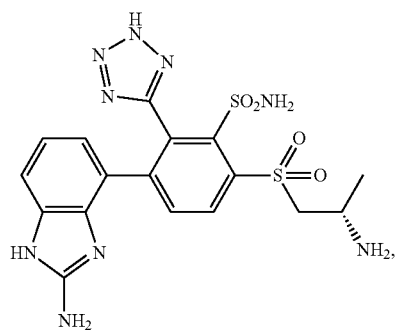

489
-continued
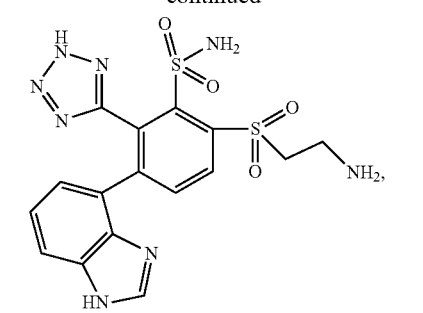
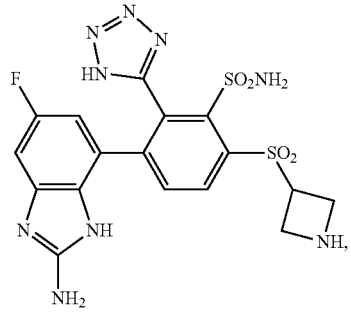
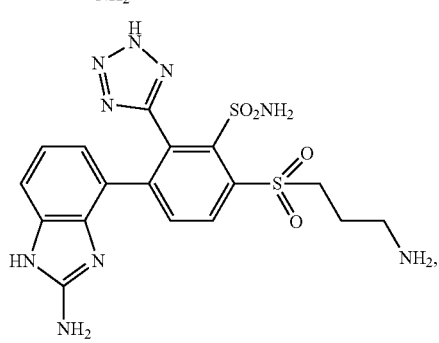
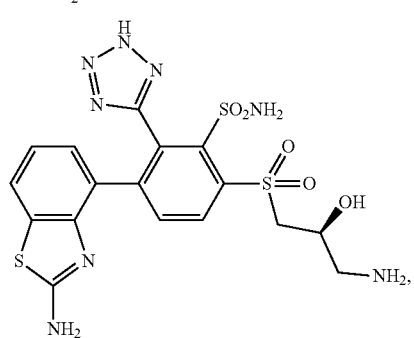
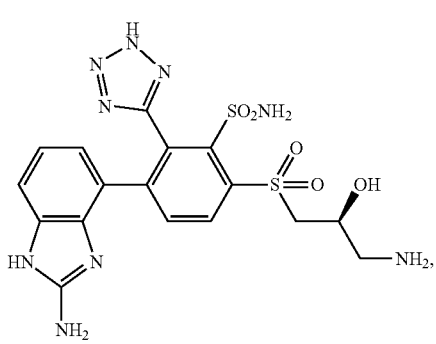
490
-continued
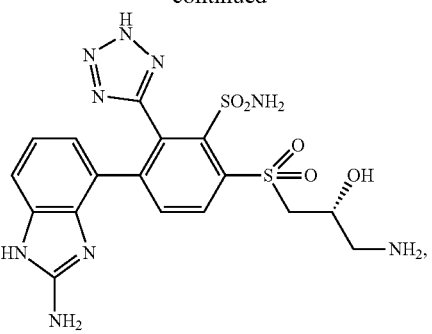
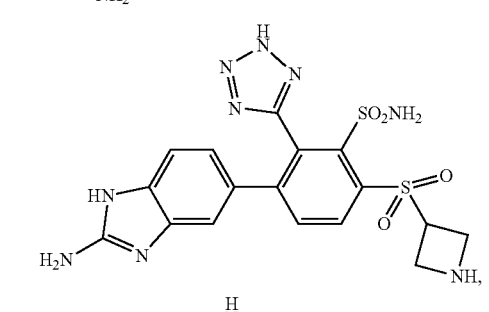
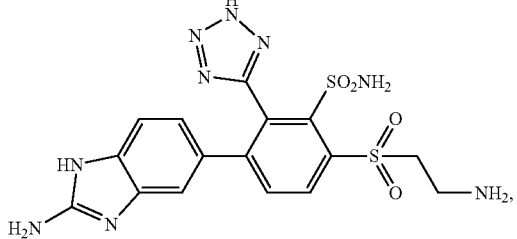
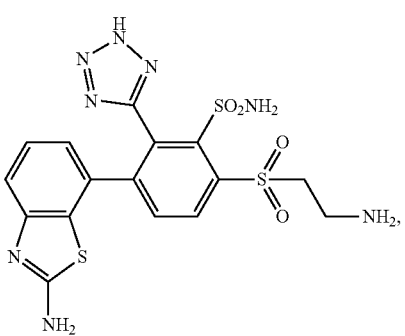
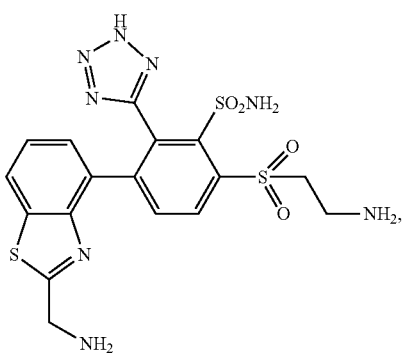

491
-continued
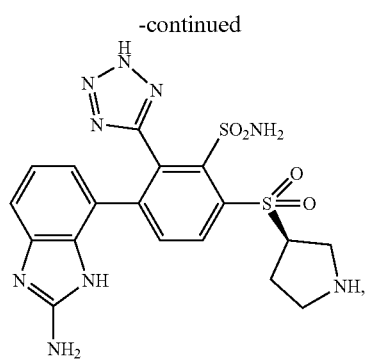
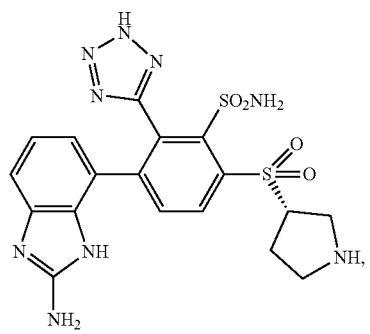
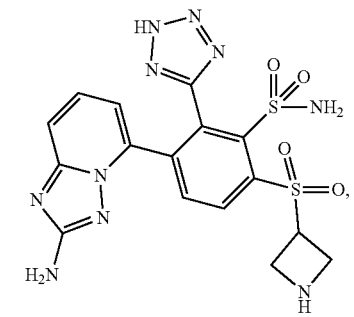
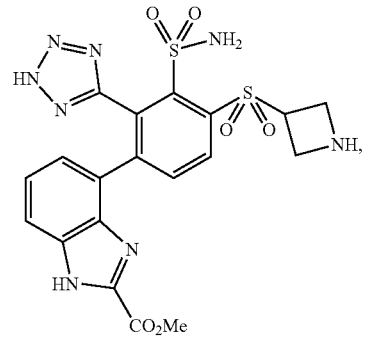
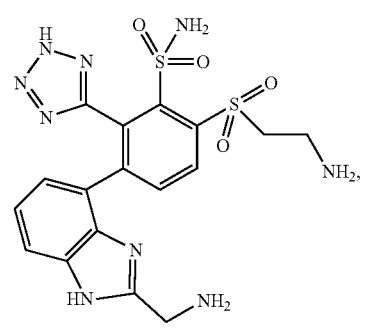
492
-continued
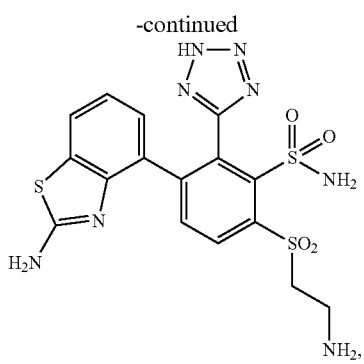
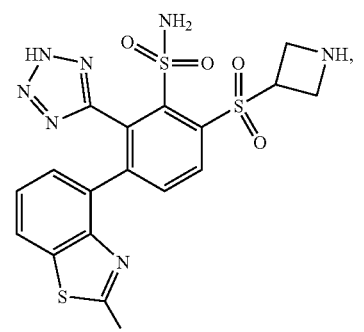
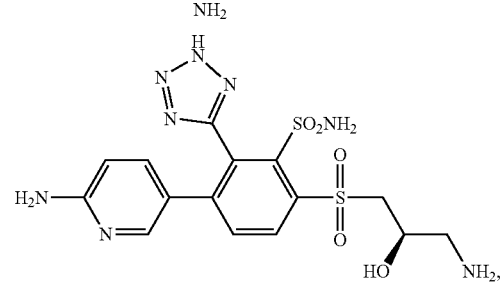
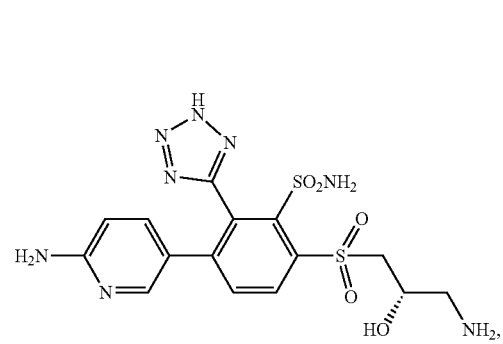
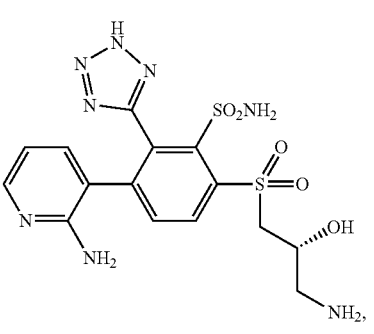

-continued

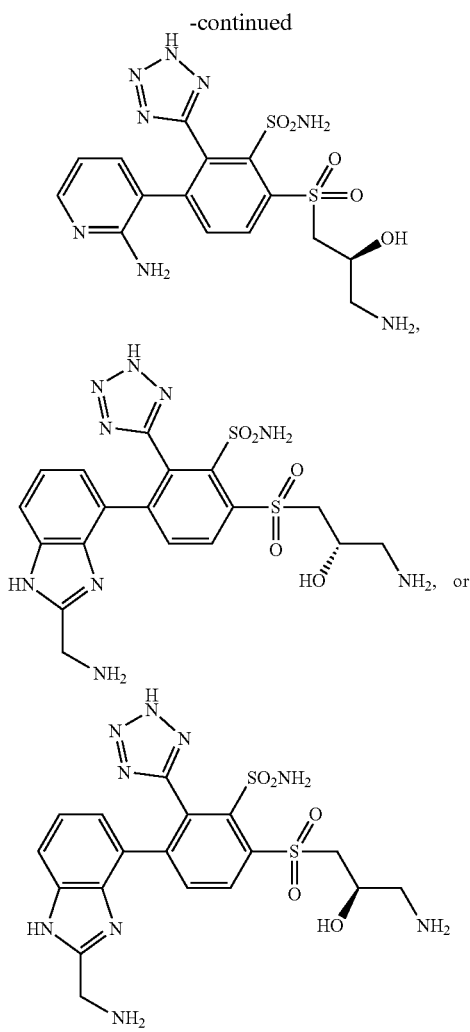

or a pharmaceutically acceptable salt thereof.

10. A zwitterion of the compound of claim 9.

11. A pharmaceutical composition which comprises a compound according to claim 1, or a pharmaceutically acceptable salt thereof, and a pharmaceutically acceptable carrier.

12. The pharmaceutical composition according to claim 11, which further comprises an effective amount of a beta-lactam antibiotic.

13. The pharmaceutical composition according to claim 12, which further comprises an effective amount of one or more beta-lactamase inhibitor compounds.

14. The pharmaceutical composition according to claim 13, wherein the composition comprises a beta-lactamase inhibitor compound selected from the group consisting of: relebactam, avibactam, vaborbactam, tazobactam, sulbactam, and clavulanic acid.

15. The pharmaceutical composition according to claim 14, wherein the beta-lactamase inhibitor compound is tazobactam and the beta-lactam antibiotic is ceftolozane.

16. The pharmaceutical composition according to claim 14, wherein the beta-lactamase inhibitor compound is relebactam.

17. The pharmaceutical composition according to claim 12, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, cefoperazone, cefotaxime, ceftriaxone, cefipime, ceftolozane, and ceftazidime.

18. The pharmaceutical composition according to claim 17, wherein the beta-lactam antibiotic is imipenem.

19. The pharmaceutical composition according to claim 18, further comprising cilastatin or a pharmaceutically acceptable salt thereof.

20. A method for inhibiting a bacterial beta-lactamase in a subject which comprises administering to the subject (i) an effective amount of a compound according to claim 1, or a pharmaceutically acceptable salt thereof, optionally in combination with a beta-lactam antibiotic.

21. A method for treating a bacterial infection which comprises administering to a subject in need of such treatment a therapeutically effective amount of a compound according to claim 1, or a pharmaceutically acceptable salt thereof, in combination with a beta-lactam antibiotic.

22. The method of claim 20, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, cefoperazone, cefotaxime, ceftriaxone, cefipime, ceftolozane, and ceftazidime.

23. The method of claim 20, wherein the beta-lactam antibiotic is imipenem.

24. A method for treating a bacterial infection which comprises administering to a subject in need of such treatment a therapeutically effective amount of a compound according to claim 1, or a pharmaceutically acceptable salt thereof, and a therapeutically effective amount of imipenem, cilastatin, and relebactam.

25. The method of claim 21, wherein the bacterial infection is due to *Pseudomonas* spp., *Klebsiella* spp., *Enterobacter* spp., *Escherichi* spp., *Morganella* spp., *Citrobacter* spp., *Serratia*, spp. or *Acintetobacter* spp.

26. The compound of claim 9, having the structure:

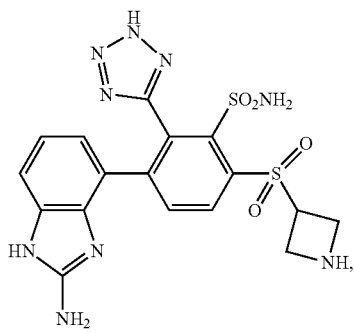

or a pharmaceutically acceptable salt thereof.

* * * * *